US007611713B2

(12) United States Patent
Sette et al.

(10) Patent No.: US 7,611,713 B2
(45) Date of Patent: Nov. 3, 2009

(54) INDUCING CELLULAR IMMUNE RESPONSES TO HEPATITIS B VIRUS USING PEPTIDE COMPOSITIONS

(75) Inventors: Alessandro Sette, La Jolla, CA (US); John Sidney, San Diego, CA (US); Scott Southwood, Santee, CA (US); Maria Vitiello, La Jolla, CA (US); Brian Livingston, San Diego, CA (US); Esteban Celis, Rochester, MN (US); Ralph Kubo, Carlsbad, CA (US); Howard Grey, La Jolla, CA (US); Robert Chesnut, Cardiff-by-the-Sea, CA (US)

(73) Assignee: Pharmexa Inc., San Diego, CA (US)

( * ) Notice: Subject to any disclaimer, the term of this patent is extended or adjusted under 35 U.S.C. 154(b) by 0 days.

(21) Appl. No.: 10/654,601

(22) Filed: Sep. 4, 2003

(65) Prior Publication Data
US 2005/0063983 A1    Mar. 24, 2005

Related U.S. Application Data

(62) Division of application No. 09/239,043, filed on Jan. 27, 1999, now Pat. No. 6,689,363.

(51) Int. Cl.
A61K 38/00    (2006.01)
A61K 39/00    (2006.01)
A61K 39/12    (2006.01)
A61K 39/29    (2006.01)

(52) U.S. Cl. .............. 424/189.1; 424/184.1; 424/192.1; 424/228.1; 530/300; 530/328

(58) Field of Classification Search .............. 424/184.1, 424/185.1, 186.1, 189.1, 204.1, 227.1; 514/2; 530/300, 326, 327, 328, 350
See application file for complete search history.

(56) References Cited

U.S. PATENT DOCUMENTS

| | | | |
|---|---|---|---|
| 4,235,877 A | 11/1980 | Fullerton | |
| 4,428,941 A | 1/1984 | Galibert et al. | |
| 4,487,715 A | 12/1984 | Nitecki et al. | |
| 4,599,230 A | 7/1986 | Milich et al. | |
| 4,599,231 A | 7/1986 | Milich et al. | |
| 4,818,527 A | 4/1989 | Thornton et al. | |
| 4,837,028 A | 6/1989 | Allen | |
| 4,882,145 A | 11/1989 | Thornton et al. | |
| 5,013,548 A | 5/1991 | Haynes et al. | |
| 5,017,558 A | 5/1991 | Vyas | |
| 5,019,386 A | 5/1991 | Machida et al. | |
| 5,039,522 A | 8/1991 | Neurath | |
| 5,128,319 A | 7/1992 | Arlinghaus | |
| 5,143,726 A | 9/1992 | Thornton et al. | |
| 5,196,194 A | 3/1993 | Rutter et al. | |
| 5,200,320 A | 4/1993 | Sette et al. | |
| 5,360,714 A | 11/1994 | Seeger | |
| 5,503,829 A | 4/1996 | Ladant et al. | |
| 5,662,907 A | 9/1997 | Kubo et al. | |
| 5,736,142 A | 4/1998 | Sette et al. | |
| 5,780,036 A | 7/1998 | Chisari | |
| 5,783,567 A | 7/1998 | Hedley et al. | |
| 5,788,969 A | 8/1998 | Chisari | |
| 5,821,048 A | 10/1998 | Howley et al. | |
| 5,840,303 A | 11/1998 | Chisari et al. | |
| 5,932,224 A | 8/1999 | Chisari | |
| 6,034,214 A | 3/2000 | Boon et al. | |
| 6,037,135 A | 3/2000 | Kubo et al. | |
| 6,235,288 B1 | 5/2001 | Chisari | |
| 6,322,789 B1 | 11/2001 | Vitiello et al. | |
| 6,365,160 B1 | 4/2002 | Webb et al. | |
| 6,413,935 B1 | 7/2002 | Sette et al. | |
| 6,419,931 B1 | 7/2002 | Vitiello et al. | |
| 6,534,482 B1 * | 3/2003 | Fikes et al. .................. 514/44 |
| 6,602,510 B1 | 8/2003 | Fikes et al. | |
| 6,607,727 B1 | 8/2003 | Chisari et al. | |
| 6,689,363 B1 | 2/2004 | Sette et al. | |
| 2002/0098197 A1 | 7/2002 | Sette et al. | |
| 2002/0160960 A1 | 10/2002 | Sette et al. | |
| 2002/0168374 A1 | 11/2002 | Kubo et al. | |
| 2002/0177694 A1 | 11/2002 | Sette et al. | |
| 2003/0021809 A1 | 1/2003 | Chisari et al. | |
| 2003/0143672 A1 | 7/2003 | Tangri et al. | |
| 2003/0216342 A1 | 11/2003 | Fikes et al. | |
| 2003/0216343 A1 | 11/2003 | Fikes et al. | |
| 2004/0096445 A1 | 5/2004 | Sidney et al. | |
| 2004/0157273 A1 | 8/2004 | Sidney et al. | |
| 2005/0049197 A1 | 3/2005 | Sette et al. | |
| 2005/0063983 A1 | 3/2005 | Sette et al. | |

FOREIGN PATENT DOCUMENTS

EP    0 044 710 A1    1/1982

(Continued)

OTHER PUBLICATIONS

GenPept Accession AP 671816, core protein, NCBI printout, May 4, 1994.*

(Continued)

*Primary Examiner*—Zachariah Lucas
(74) *Attorney, Agent, or Firm*—Sterne, Kessler, Goldstein & Fox P.L.L.C.

(57) ABSTRACT

This invention uses our knowledge of the mechanisms by which antigen is recognized by T cells to develop epitope-based vaccines directed towards HBV. More specifically, this application communicates our discovery of pharmaceutical compositions and methods of use in the prevention and treatment of HBV infection.

5 Claims, 1 Drawing Sheet

FOREIGN PATENT DOCUMENTS

Figure 1:
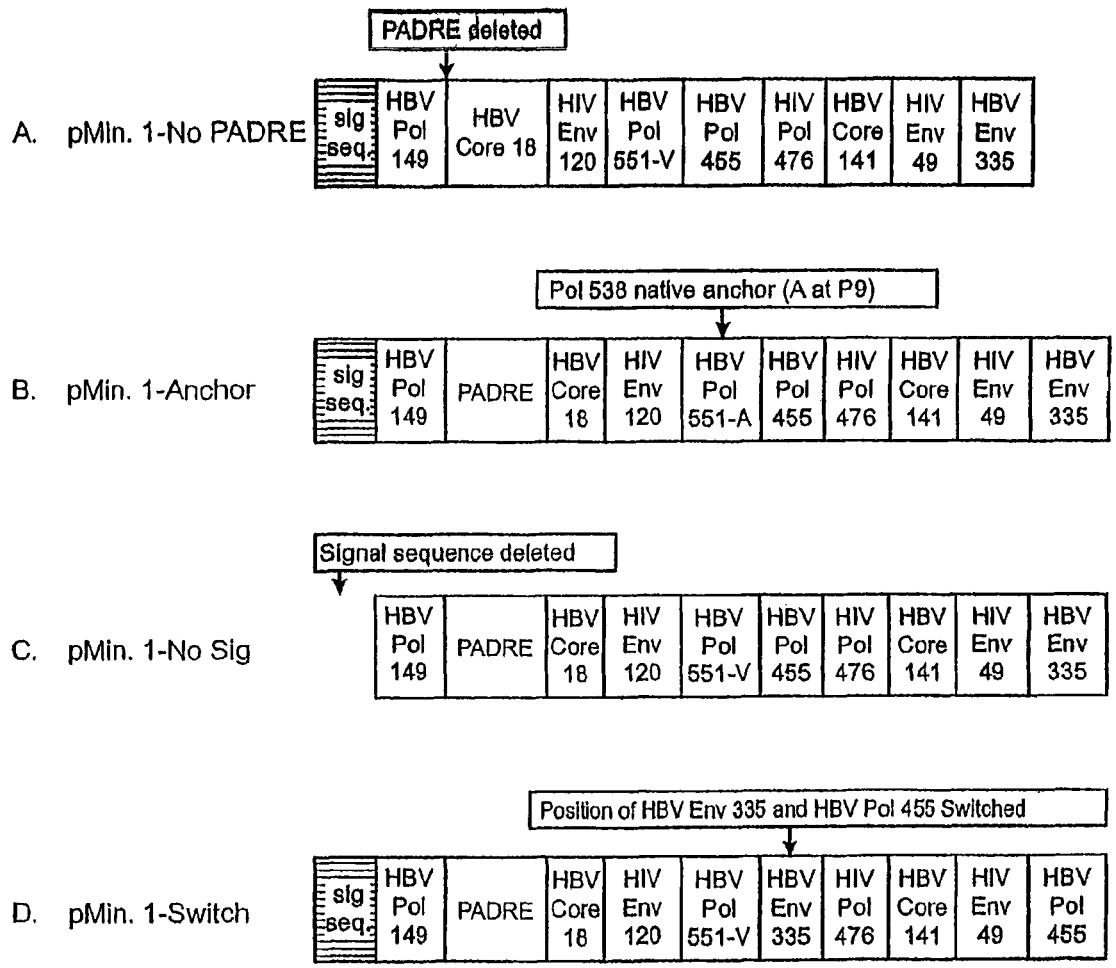

| | | |
|---|---|---|
| EP | 0 226 513 A1 | 6/1987 |
| EP | 0 271 302 | 6/1988 |
| EP | 0 429 816 | 6/1991 |
| EP | 0 433 242 | 6/1991 |
| EP | 0 469 281 | 2/1992 |
| EP | 0 491 077 | 6/1992 |
| EP | 0 534 615 | 3/1993 |
| EP | 0 378 881 | 6/1993 |
| EP | 1 018 558 A2 | 7/2000 |
| WO | WO 81/00577 | 3/1981 |
| WO | WO 92/02543 A1 | 2/1992 |
| WO | WO 92/12996 A2 | 8/1992 |
| WO | WO 92/21033 A1 | 11/1992 |
| WO | WO 93/03753 | 3/1993 |
| WO | WO 93/03764 A1 | 3/1993 |
| WO | WO 94/03205 A1 | 2/1994 |
| WO | WO 94/11738 A1 | 5/1994 |
| WO | WO 94/19011 | 9/1994 |
| WO | WO 94/20127 A1 | 9/1994 |
| WO | WO 95/03777 | 2/1995 |
| WO | WO 95/07707 | 3/1995 |
| WO | WO 95/22317 | 8/1995 |
| WO | WO 96/03140 A1 | 2/1996 |
| WO | WO 96/22067 | 7/1996 |
| WO | WO 97/34617 | 9/1997 |
| WO | WO 97/34621 | 9/1997 |
| WO | WO 97/41440 | 11/1997 |
| WO | WO 98/32456 A1 | 7/1998 |
| WO | WO 99/45954 | 9/1999 |
| WO | WO 99/58658 A2 | 11/1999 |
| WO | WO 01/00225 | 1/2001 |
| WO | WO 02/19986 A1 | 3/2002 |

OTHER PUBLICATIONS

Hosono et al., Virology, vol. 212 No. 1, pp. 151-162 (Sep. 1995).*

Menne et al., Journal of Virology, vol. 75 No. 1, pp. 65-74 (Jan 1997).*

Kast et al., Journal of Immunology, vol. 152 No. 8, pp. 3904-3912 (Apr. 1994).*

Pinilla et al., Molecular Immunology, vol. 30 No. 6, pp. 577-585 (Apr. 1993).*

Riffkin et al., Gene, vol. 167 No. 1-2, pp. 279-283 (Dec. 1995).*

Bowie et al., Science, vol. 247 No. 4948, pp. 1306-1310 (Mar. 1990).*

Sarobe et al., Journal of Clincial Investigation, vol. 10 No. 6, pp. 1239-1248 (Sep. 1998).*

Bertoletti et al., Journal of Experimental Medicine, vol. 180 No. 3, pp. 933-943 (Sep. 1994).*

Hasegawa et al., "Enhanced replication of a hepatitis B virus mutant associated with an epidemic of fulminant hepatitis," Journal of Virology, vol. 68 No. 3, pp. 1651-1659 (Mar. 1994).*

GenPept AAA18580, "core antigen [Hepatitis B virus]", first available Apr. 1994.*

Alberti, A., et al., "Antibody Response to Pre-S2 and Hepatitis B Virus Induced Liver Damage," Lancet 1:1421-1424, Lancet Publishing Group (1988).

Barnaba, V., et al., "Recognition of Hepatitis B Virus Envelope Proteins by Liver-Infiltrating T Lymphocytes in Chronic HBV Infection," J. Immunol. 143:2650-2655, American Association of Immunologists (1989).

Bertoletti, A., et al., "Molecular Features of the Hepatitis B Virus Nucleocapsid T-Cell Epitope 18-27: Interaction with HLA and T-Cell Receptor," Hepatology 26:1027-1034, Williams & Wilkins (1997).

Cerny, A., et al, "Induction in vitro of a primary human antiviral cytotoxic T cell response," Eur. J. Immunol. 25:627-630, VCH Verlagsgesellschaft (1995).

Jolivet, M., et al., "Polyvalent synthetic vaccines: relationship between T epitopes and immunogenicity," Vaccine 8:35-40, Butterworth & Co. (1990).

Kuhröber, A., et al., "DNA vaccination with plasmids encoding the intracellular (HBcAg) or secreted (HBeAg) form of the core protein of hepatitis B virus primes T cell responses to two overlapping $K^b$- and $K^d$-restricted epitopes," Int. Immunol. 9:1203-1212, Oxford University Press (1997).

Livingston, B.D., et al., "Immunization with the HBV Core 18-27 Epitope Elicits CTL Responses In Humans Expressing Different HLA-A2 Supertype Molecules," Hum. Immunol. 60:1013-1017, Elsevier Science (Nov. 1999).

Livingston, B.D., et al., "The Hepatitis B Virus-Specific CTL Responses Induced in Humans by Lipopeptide Vaccination are Comparable to Those Elicited by Acute Viral Infection," J. Immunol. 159:1383-1392, American Association of Immunologists (1997).

Milich, D.R., "T- and B-cell recognition of hepatitis B viral antigens," Immunol. Today 9:380-386, Elsevier Science (1988).

Milich, D.R., and Chisari, F.V., "Immunogenetics and Cellular Correlates of the Immune Response to Hepatitis B Surface Antigen Determinants," in Advances in Hepatitis Research, Chisari, F.V., ed., Masson Publishing Co., New York, NY, pp. 91-109 (1984).

Missale, G., et al., "HLA-A31- and HLA-Aw68-restricted Cytotoxic T Cell Responses to a Single Hepatitis B Virus Nucleocapsid Epitope during Acute Viral Hepatitis," J. Exp. Med. 177:751-762, Rockefeller University Press (1993).

Moriyama, T., et al., "Immunobiology and Pathogenesis of Hepatocellular Injury in Hepatitis B Virus Transgenic Mice," Science 248:361-364, American Association for the Advancement of Science (1990).

Neurath, A.R., et al., "Specificity of Antibodies Elicited by a Synthetic Peptide Having a Sequence in Common with a Fragment of a Virus Protein—The Hepatitis B Surface Antigen," Dev. Biol. Stand. 54:103-112, S. Karger (1983).

Oseroff, C., et al., "Pools of lipidated HTL-CTL constructs prime for multiple HBV and HCV CTL epitope responses," Vaccine 16:823-833, Elsevier Science (Apr. 1998).

Schulz, M., et al., "Peptide-induced antiviral protection by cytotoxic T cells," Proc. Natl. Acad. Sci. USA 88:991-993, National Academy of Sciences (1991).

Sidney, J., et al., "DRB1*0301 Molecules Recognize a Structural Motif Distinct from the One Recognized by Most DR $\beta_1$ Alleles," J. Immunol. 149:2634-2640, American Association of Immunologists (1992).

Sobao, Y., et al., "Identification of hepatitis B virus-specific CTL epitopes presented by HLA-A*2402, the most common HLA class I allele in East Asia," J. Hepatol. 34:922-929, Elsevier (2001).

van der Most, R.G., et al.; "Analysis of Cytotoxic T Cell Responses to Dominant and Subdominant Epitopes During Acute and Chronic Lymphocytic Choriomeningitis Virus Infection," J. Immunol. 157:5543-5554, American Association of Immunologists (1996).

Vitiello, A., et al., "Comparison of cytotoxic T lymphocyte responses induced by peptide or DNA immunization: implications on immunogenicity and immunodominance," Eur. J. Immunol. 27:671-678, VCH Verlagsgesellschaft (1997).

Alexander, J., et al., "Development of High Potency Universal DR-Restricted Helper Epitopes by Modification of High Affinity DR-Blocking Peptides," Immunity 1:751-761, Cell Press (1994).

Arndt, S.O., et al., "Selection of the MHC Class II-Associated Peptide Repertoire by HLA-DM," Immunol. Res. 16:261-272, Humana Press (Dec. 1997).

Barouch, D., et al., "HLA-A2 Subtypes Are Functionally Distinct in Peptide Binding and Presentation," J. Exp. Med. 182:1847-1856, Rockefeller University Press (1995).

Bender, A., et al., "Improved methods for the generation of dendritic cells from nonproliferating progenitors in human blood," J. Immunol. Methods 196:121-135, Elsevier Science (1996).

Ben-Yedidia, T., and Arnon. R., "Design of peptide and polypeptide vaccines," Curr. Opin. Biotechnol. 8:442-448, Current Biology. Ltd. (1997).

Carbone, F.R., and Bevan, M.J., "Induction of Ovalbumin-Specific Cytotoxic T Cells by In Vivo Peptide Immunization," J. Exp. Med. 169:603-612, Rockefeller University Press (1989).

Carbone, F.R., et al., "Induction of Cytotoxic T Lymphocytes by Primary In Vitro Stimulation with Peptides," J. Exp. Med. 167:1767-1779, Rockefeller University Press (1988).

Cassell, D., and Forman, J., "Linked Recognition of Helper and Cytotoxic Antigenic Determinants for the Generation of Cytotoxic T Lymphocytes," Ann. N.Y. Acad. Sci.532:51-60, New York Academy Of Sciences (1991).

Deres, K., et al., "In vivo priming of virus-specific cytotoxic T lymphocytes with synthetic lipopeptide vaccine," Nature 342:561-564, Nature Publishing Group (1989).

del Guercio, M-F., et al., "Potent immunogenic short linear peptide constructs composed of B cell epitopes and Pan DR T Helper Epitopes (PADRE) for antibody responses in vivo," Vaccine 15:441-448, Elsevier Science (Mar. 1997).

DiBrino, M., et al., "Endogenous Peptides with Distinct Amino Acid Anchor Residue Motifs Bind to HLA-A1 and HLA-BB," J. Immunol. 152:620-631, American Association of Immunologists (1994).

DiBrino, M., et al., "The HLA-B14 Peptide Binding Site Can Accommodate Peptides with Different Combinations of Anchor Residues," J. Biol. Chem. 269:32426-32434, American Society for Biochemistry and Molecular Biology (1994).

Donnelly, J.J., et al., "DNA Vaccines," Annu. Rev. Immunol. 15:617-648, Annual Reviews Inc. (Apr. 1997).

Francis. M.J., et al. "Non-responsiveness to a foot-and-mouth disease virus peptide overcome by addition of foreign helper T-cell determinants," Nature 330:168-170, Nature Publication Group (1987).

Fynan, E.F., et al., "DNA vaccines: Protective immunizations by parental. mucosal, and gene-gun inoculations," Proc. Natl. Acad. Sci. USA 90:11478-11482, National Academy of Sciences (1993).

Gileadi, U., et al., "Effect of epitope flanking residues on the presentation of N-terminal cytotoxic T lymphocyte epitopes," Eur. J. Immunol. 29:2213-2222, WILEY-VCH Verlag GmbH (Jul. 1999).

Golvano, J., et al., "Polarity of immunogens: implications for vaccine design," Eur. J. Immunol. 20:2363-2366, VCH Verlagsgesellschaft mbH (1990).

Gulukota, K., et al., "Two Complementary Methods for Predicting Peptides Binding Major Histocompatibility Complex Molecules," J. Mol. Biol. 267:1258-1267, Academic Press Limited (Apr. 1997).

Hahn, Y.S., et al., "CD8+ T Cell Recognition of an Endogenously Processed Epitope is Regulated Primarily by Residues within the Epitope," J. Exp. Med. 176:1335-1341, Rockefeller University Press (1992).

Hahn, Y.S., et al., "Presentation of Viral Antigen to Class I Major Histocompatibility Complex-Restricted Cytotoxic T Lymphocyte. Recognition of an Immunodominant Influenza Hemagglutinin Site by Cytotoxic T Lymphocyte is Independent of the Position of the Site in the Hemagglutinin Translation Product," J. Exp. Med. 174:733-736, Rockefeller University Press (1991).

Hammer, J., et al., "Precise Prediction of Major Histocompatibility Complex Class II-Peptide Interaction Based on Peptide Side Chain Scanning," J. Exp. Med. 180:2353-2358, Rockefeller University Press (1994).

Hill, C.M., et al., "Exploration of Requirements for Peptide Binding to HLA DRB1*0101 and DRB1*0401," J. Immunol. 152:2890-2898, American Association of Immunologists (1994).

Huczko. E.L.. et al., "Characteristics of Endogenous Peptides Eluted from the Class I MHC Molecule HLA-B7 Determined by Mass Spectrometry and Computer Modeling," J. Immunol. 151:2572-2587, American Association of Immunologists (1993).

Ishioka, G.Y., et al., "Class I MHC-restricted, peptide specific cytotoxic T lymphocytes generated by peptide priming in vivo," in Vaccines90: Modern Approaches to New Vaccines Including Prevention of AIDS, Brown, F., et al., eds., Cold Spring harbor Laboratory Press, Cold Spring Harbor, NY, pp. 7-11 (1990).

Ishioka, G.Y., et al., "Induction of Class I MHC-Restricted, Peptide-Specific Cytolytic T Lymphocytes by Peptide Priming in Vivo," J. Immunol. 143:1094-1100, American Association of Immunologists (1989).

Jardetzky, T.S., et al., "Peptide binding to HLA-DR1: a peptide with most residues substituted to alanine retains MHC binding," EMBO J. 9:1797-1803, Oxford University Press (1990).

Kondo, A., et al., "Two distinct HLA-A*0101-specific submotifs illustrate alternative peptide binding modes," Immunogenetics 45:249-258, Springer-Verlag (Jan. 1997).

Kubitscheck, U., et al., "Peptide Binding to Class I Molecules of the Major Histocompatibility Complex on the Surface of Living Target Cells," Scand. J. Immunol. 36:341-348, Blackwell Scientific Publications (1992).

Kubo, R.T., et al., "Definition of Specific Peptide Motifs for Four Major HLA-A Alleles," J. Immunol. 152:3913-3924, American Association of Immunologists (1994).

Kumar, A., et al., "Universal T Helper Cell Determinants Enhance Immunogenicity of a Plasmodium falciparum Merozoite Surface Antigen Peptide," J. Immunol. 148:1499-1505, American Association of Immunologists (1992).

Lasarte, J-J., et al., "Induction of Cytotoxic T Lymphocytes in Mice against the Principal Neutralizing Domain of HIV-1 by Immunization with an Engineered T-Cytotoxic-T-Helper Synthetic Helper Peptide Construct," Cell. Immunol. 141:211-218, Academic Press Inc. (1992).

Madden. D.R., et al., "The structure of HLA-B27 reveals nonamer self-peptides bound in an extended conformation," Nature 353:321-325, Nature Publishing Group (1991).

Maier, R., et al., "Peptide motifs of HLA-A3, -A24, and -B7 molecules as determined by pool sequencing," Immunogenetics 40:306-308, Springer-Verlag (1994).

Martinon, F., et al., "Immunization of Mice with Lipopeptides Bypasses the Prerequisite for Adjuvant," J. Immunol. 149:3416-3422, American Association of Immunologists (1992).

Niedermann, G., et al., "Contribution of Proteasome-Mediated Proteolysis to the Hierarchy of Epitopes Presented by Major Histocompatibility Complex Class I Molecules," Immunity 2:289-299, Cell Press (1995).

Niedermann, G., et al., "The specificity of proteasomes: impact on MHC class I processing and presentation of antigens," Immunol. Rev. 172:29-48, Munksgaard (Dec. 1999).

Nikolić-Žugić, J., and Carbone, F.R., "Peptide Presentation by Class-I Major Histocompatibility Complex Molecules," Immunol. Res. 10:54-65, S. Karger AG (1991).

O'Sullivan, D., et al., "Characterization of the Specificity of Peptide Binding to Four DR Haplotypes," J. Immunol. 145:1799-1808, American Association of Immunologists (1990).

O'Sullivan, D., et al., "On the Interaction of Promiscuous Antigenic Peptides with Different DR Alleles," J. Immunol. 147:2663-2669, American Association of Immunologists (1991).

Panina-Bordignon, P., et al., "Universally immunogenic T cell eptiopes: promiscuous binding to human MHC class II and promiscuous recognition by T cells," Eur. J. Immunol. 19:2237-2242, VCH Verlagsgesellschaft mbH (1989).

Paz, P., et al., "Discrete Proteolytic Intermediates in the MHC Class I Antigen Processing Pathway and MHC I-Dependent Peptide Trimming in the ER," Immunity 11:241-251, Cell Press (Aug. 1999).

Penna, A., et al., "Cytotoxic T Lymphocytes Recognize an HLA-A2-Restricted Epitope Within the Hepatitis B Virus Nucleocapsid Antigen," J. Exp. Med. 174:1565-1570. Rockefeller University Press (1991).

Pryjma, J., et al., "Induction and Suppression of Immunoglobulin Synthesis in Cultures of Human Lymphocytes: Effects of Pokeweed Mitogen and Staphylococcus Aureus Cowan I," J. Immunol. 124:656-661, Williams & Wilkins Co. (1980).

Rahemtulla, A., et al., "Normal development and function of CD8+ cells but markedly decreased helper cell activity in mice lacking CD4," Nature 353:180-183, Nature Publishing Group (1991).

Rammensee, H-G., et al., "SYFPEITHI: database for MHC ligands and peptide motifs," Immunogenetics 50:213-219, Springer-Verlag (Nov. 1999).

Reitermann, A., et al., "Lipopeptide Derivatives of Bacterial Lipoprotein Constitute Potent Immune Adjuvants Combined with or Covalently Coupled to Antigen or Hapten," Biol. Chem. Hoppe Seyler 370:343-352, Walter De Gruyter (1989).

Restifo, N.P., et al., "Antigen Processing in Vivo and the Elicitation of Primary CTL Responses," J. Immunol. 154:4414-4422, American Association of Immunologists (1995).

Saper, M.A., et al., "Refined Structure of the Human Histocompatibility Antigen HLA-A2 at 2.6 A Resolution," J. Mol. Biol. 219:277-319, Academic Press Ltd. (1991).

Schaeffer, E.B., et al., "Relative contribution of 'determinant selection' and 'holes in the T-cell repertoire' to T-cell responses," Proc. Natl. Acad. Sci. USA 86:4649-4653, National Academy of Sciences (1989).

Schumacher, T.N.M., et al., "Peptide selection by MHC class I molecules," Nature 350:703-706, Nature Publishing Group (1991).

Sette, A., and Sidney, J., "HLA supertypes and supermotifs: a functional perspective on HLA polymorphism," Curr. Opin. Immunol. 10:478-482, Current Biology Publications (Aug. 1998).

Sette, A., et al., "A Novel Approach to the Generation of High Affinity Class II-Binding Peptides," J. Immunol. 145:1809-1813, American Association of Immunologists (1990).

Sette, A., et al., "Effect of Conformational Propensity of Peptide Antigens in Their Interaction with MHC Class II Molecules," J. Immunol. 143:1268-1273, American Association of Immunologists (1989).

Sette, A., et al., "Peptide Binding to the Most Frequent HLA-A Class I Alleles Measured by Quantitative Molecular Binding Assays," Mol. Immunol. 31:813-822, Pergamon Press (1994).

Sidney, J., et al., "Definition of an HLA-A3-Like Supermotif Demonstrates the Overlapping Peptide-Binding Repertoires of Common HLA Molecules," Hum. Immunol. 45:79-93, Elsevier Science Inc. (1996).

Sidney, J., et al., "Practical, biochemical and evolutionary implications of the discovery of HLA class I supermotifs;" Immunol. Today 17:261-266, Elsevier Science (1996).

Sidney, J., et al., "The HLA-A*0207 Peptide Binding Repertoire is Limited to a Subset of the A*0201 Repertoire," Hum. Immunol. 58:12-20, Elsevier Science Inc. (Nov. 1997).

Sinigaglia, F., and Hammer, J., "Defining rules for the peptide-MHC class II interaction," Curr. Opin. Immunol. 6:52-56, Current Biology Ltd. (1994).

Southwood, S., et al., "Several Common HLA-DR Types Share Largely Overlapping Peptide Binding Repertoires," J. Immunol. 160:3363-3373, American Association of Immunologists (Apr. 1998).

Sprent, J., and Schaefer, M., "Properties of Purified T Cell Subsets. 1. In Vitro Responses to Class I vs. Class II H-2 Alloantigens," *J. Exp. Med.* 162:2068-2088, Rockefeller University Press (1985).

Stark, J.M., et al., "Immunogenicity of lipid-conjugated antigens. I. The Influence of Chain Length and Degree of Conjugation on Induction of Antibody in Mice," Immunology 39:345-352, Blackwell Scientific Publications (1980).

Steinman, R.M., "Dendritic cells and immune-based therapies," Exp. Hematol. 24:859-862, Elsevier Science Inc. (1996).

Sudo, T., et al., "Differences in MHC Class I Self Peptide Repertoires Among HLA-A2 Subtypes," *J. Immunol.* 155:4749-4756, American Association of Immunologists (1995).

Sugawara, S., et al., "A simple method to eliminate the antigenicity of surface class I MHC molecules from the membrane of viable cells by acid treatment at pH 3," J. Immunol. Methods 100:83-90, Elsevier Science (1987).

Tam, J.P., and Lu, Y-A., "Vaccine engineering: Enhancement of immunogenicity of synthetic peptide vaccines related to hepatitis in chemically defined models consisting of T- and B-cell epitopes," Proc. Natl. Acad. Sci. USA 86:9084-9088, National Academy of Sciences (1989).

Townsend, A., and Bodmer, H., "Antigen Recognition by Class I-Restricted T Lymphocytes," Ann. Rev. Immunol. 7:601-624, Annual Reviews, Inc. (1989).

von Boehmer, H., and Haas, W., "Distinct Ir Genes for Helper and Killer Cells in the Cytotoxic Response to H-Y Antigen," J. Exp. Med. 150:1134-1142, Rockefeller University Press (1979).

Watari, E., et al., "A Synthetic Peptide Induces Long-Term Protection from Lethal Infection with Herpes Simplex Virus 2," J. Exp. Med. 165:459-470, Rockefeller University Press (1987).

Wentworth, P.A., et al., "In Vitro Induction of Primary, Antigen-Specific CTL from Human Peripheral Blood Mononuclear Cells Stimulated with Synthetic Peptides," Mol. Immunol. 32:603-612, Elsevier Science Ltd. (1995).

Wherry, E.J., et al., "The Induction of Virus-Specific CTL as a Function of Increasing Epitope Expression: Responses Rise Steadily Until Excessively High Levels of Epitope Are Attained," J. Immunol. 163:3735-3745, American Association of Immunologists (Oct. 1999).

Widmann, C., et al., "T helper epitopes enhance the cytotoxic response of mice immunized with MHC class I-restricted malaria peptides," J. Immunol. Meth. 155:95-99, Elsevier Science Publishers B.V. (1992).

Wiesmüller, K-H., et al., "Lipopeptide-Helper-T-Cell Epitope-CTL Epitope Conjugate Induces Antibodies Against the CTL Epitope," Innovation Perspective Solid Phase Synthesis Collect. Papers, Int. Symp. 2nd, pp. 499-502 (1991).

Wiesmüller, K-H., et al., "Novel low-molecular-weight synthetic vaccine against foot-and mouth disease containing a potent B cell and macrophage activator," Vaccine 7:29-33, Butterworth & Co. (1989).

Yewdell, J.W., and Bennink. J.R., "Immunodominance in Major Histocompatibility Complex Class I-Restricted T Lymphocyte Responses," Annu. Rev. Immunol. 17:51-88, Annual Reviews Inc. (Apr. 1999).

Zhou, X., et al., "In vivo primary Induction of virus-specific CTL by immunization with 9-mer synthetic peptides," J. Immunol. Methods 153:193-200, Elsevier Science Publishers B.V. (1992).

Zinkernagel, R.M., et al., "The Lymphoreticular System in Triggering Virus Plus Self-Specific Cytotoxic T Cells: Evidence for T Help," J. Exp. Med. 147:897-911, Rockefeller University Press (1978).

Altuvia, Y. et al., "A Structure-Based Algorithm to Predict Potential Binding Peptides to MHC Molecules with Hydrophobic Binding Pockets," Human Immunol. 58:1-11, Elsevier Science Inc. (1997).

U.S. Appl. No. 10/817,970, Grey at al., filed Apr. 6, 2004.

Alexander, J., et al., "The Optimization of Helper T Lymphocyte (HTL) Function in Vaccine Development," *Immunol. Res.* 18:79-92, Humana Press (1998).

Ando, K., et al., "Mechanisms of class I restricted immunopathology. A transgenic mouse model of fulminant hepatitis," *J. Exp. Med.* 178:1541-1554, Rockefeller University Press (1993).

Barber, L.D., et al., "Overlap in the repertoires of peptides bound in vivo by a group of related class I HLA-B allotypes," *Curr. Biol.* 5:179-190, Current Biology Ltd. (1995).

Barnaba, V., et al., "Selective killing of hepatitis B envelope antigen-specific B cells by class I-restricted, exogenous antigen-specific T lymphocytes," Nature 345:258-260, Nature Pub. Co. (1990).

Battegay, M., et al., "Patients with Chronic Hepatitis C Have Circulating Cytotoxic T Cells Which Recognize Hepatitis C Virus-Encoded Peptides Binding to HLA-A2.1 Molecules," *J. Virol.* 69:2462-2470, American Society for Microbiology (1995).

Bertoletti, A., et al., "Definition of a minimal optimal cytotoxic T-cell epitope within the hepatitis B virus nucleocapsid protein," *J. Virology* 67:2376-2380, American Society for Microbiology (1993).

Bertoletti, A., et al., "HLA class I-restricted human cytotoxic T cells recognize endogenously synthesized hepatitis B virus nucleocapsid antigen," *Proc. Natl. Acad. Sci. USA* 88:10445-10449, National Academy of Sciences (1991).

Bertoletti, A., et al., "Natural variants of cytotoxic epitopes are T-cell receptor antagonists for antiviral cytotoxic T cells," *Nature* 369:407-410, Nature Pub. Co. (1994).

Bhatnagar, P.K., et al., "Immune response to synthetic peptide analogues of hepatitis B surface antigen specific for the a determinant," *Proc. Natl. Acad. Sci. USA* 79:4400-4404, National Academy of Sciences (1982).

Borras-Cuesta, F., et al., "Engineering of immunogenic peptides by co-linear synthesis of determinants recognized by B and T cells," *Eur. J. Immunol.* 17:1213-1215, VCH Verlagsgesellschaft (1987).

Bruss, V., "A Short Linear Sequence in the Pre-S Domain of the Large Hepatitis B Virus Envelope Protein Required for Virion Formation," *J. Virol.* 71:9350-9357, American Society for Microbiology (1997).

Celis, E., et al., "Recognition of hepatitis B surface antigen by human T lymphocytes. Proliferative and cytotoxic responses to a major antigenic determinant defined by synthetic peptides," *J. Immunol.* 140:1808-1815, American Association of Immunologists (1988).

Cerny, A., et al., "Cytotoxic T Lymphocyte Response to Hepatitis C Virus-derived Peptides Containing the HLA A2.1 Binding Motif," *J. Clin. Invest.* 95:521-530, The American Society for Clinical Investigation, Inc. (1995).

Chang, K.-M., et al., "Identification of HLA-A3 and -B7-Restricted CTL Response to Hepatitis C Virus in Patients with Acute and Chronic Hepatitis C," *J. Immunol.* 162:1156-1164, The American Association of Immunologists (1999).

Chisari, F.V., and Ferrari, C., "Hepatitis B virus immunopathogenesis," *Annu. Rev. Immunol.* 13:29-60, Annual Reviews Inc. (1995).

Cohen, J., "The Scientific Challenge of Hepatitis C," *Science* 285:26-30, American Association for the Advancement of Science (1999).

del Guercio, M.F., et al., "Binding of a peptide antigen to multiple HLA alleles allows definition of an A2-like supertype," *J. Immunol.* 154:685-693, American Association of Immunologists (1995).

Diepolder, H.M., et al., "Immunodominant CD4+ T-Cell Epitope within Nonstructural Protein 3 in Acute Hepatitis C Virus Infection," *J. Virol.* 71:6011-6019, American Society for Microbiology (1997).

Fayolle, C., et al., "In vivo induction of cytotoxic T cell response by a free synthetic peptide requires CD4+ T cell help," *J. Immunol.* 147:4069-4073, American Association of Immunologists (1991).

Ferrari, C., et al, "Identification of immunodominant T cell epitopes of the hepatitis B virus nucleocapsid antigen," *J. Clin. Invest.* 88:214-222, American Society for Clinical Investigation (1991).

Fujii, N., et al., "Synthesis of Peptide Fragments of Hepatitis B Virus Surface Antigen (HbsAg) and Their Immunogenicity," *Peptide Chemistry*, Munekata, E., ed., Protein Research Foundation, Osaka, JP, pp. 215-220 (1983).

Hayashi, Y., et al., "Studies on peptides. CLXVI. Solid-phase syntheses and immunological properties of fragment peptides related to human hepatitis B virus surface antigen (HBsAg) and its pre-S2 gene," *Chem. Pharm. Bull.* 36:4993-4999, Pharmaceutical Society of Japan (1988).

Henry, J.B., *Clinical & Laboratory Diagnosis & Management by Laboratory Methods, 18th edition*, W.B. Saunders Company, Philadelphia, PA, p. 785 (1991).

Hopp, T.P., "Immunogenicity of a synthetic HBsAg peptide: enhancement by conjugation to a fatty acid carrier," *Mol. Immunol.* 21:13-26, Pergamon Press (1984).

Ishioka, et al., "Class I MHC-restricted, Peptide-specific Cytotoxic T Lymphocytes Generated by Peptide Priming In Vivo," in *Vaccines 90*, Brown, F., et al., eds., Cold Springs Harbor Laboratory Press, Cold Springs Harbor, NY, pp. 7-11 (1990).

Kondo, A., et al., "Prominent roles of secondary anchor residues in peptide binding to HLA-A24 human class I molecules," *J. Immunol.* 155:4307-4312.A73, American Association of Immunologists (1995).

Lamonaca, V., et al., "Conserved Hepatitis C Virus Sequences Are Highly Immunogenic for CD4+ T Cells: Implications for Vaccine Development," *Hepatology* 30:1088-1098, American Association for the Study of Liver Diseases (1999).

Lerner, R.A., et al., "Chemically synthesized peptides predicted from the nucleotide sequence of the hepatitis B virus genome elicit antibodies reactive with the native envelope protein of Dane particles," *Proc. Natl. Acad. Sci. USA* 78:3403-3407, National Academy of Sciences (1981).

Milich, D.R., "Probing T cell antigen recognition: use of synthetic peptides," *Pept. Res.* 3:85-96, Eaton Publishing (1990).

Milich, D.R., et al., "Immune response to hepatitis B virus core antigen (HBcAg): localization of T cell recognition sites within HBcAg/HBeAg," *J. Immunol.* 139:1223-1231, American Association of Immunologists (1987).

Nayersina, R., et al., "HLA A2 restricted cytotoxic T lymphocyte responses to multiple hepatitis B surface antigen epitopes during hepatitis B virus infection," *J. Immunol.* 150:4659-4671, American Association of Immunologists (1993).

Penna, A., et al., "Cytotoxic T lymphocytes recognize an HLA-A2-restricted epitope within the hepatitis B virus nucleocapsid antigen," *J. Exp. Med.* 174:1565-2570, Rockefeller University Press (1991).

Penna, A., et al., "Hepatitis B virus (HBV)-specific cytotoxic T-cell (CTL) response in humans: characterization of HLA class II-restricted CTLs that recognize endogenously synthesized HBV envelope antigens," *J. Virol.* 66:1193-1198, American Society for Microbiology (1992).

Preisler-Adams, S., et al., "Complete nucleotide sequence of a hepatitis B virus, subtype adw2, and identification of three types of C open reading frame," *Nucl. Acids Res.* 21:2258, Oxford University Press (1993).

Prezzi, C., et al., "Virus-specific CD8+ T cells with type 1 or type 2 cytokine profile are related to different disease activity in chronic hepatitis C virus infection," *Eur. J. Immunol.* 31:894-906, Wiley-VCH Verlag GmbH (2001).

Rehermann, B., et al., "Cytotoxic T Lymphocyte Responsiveness after Resolution of Chronic Hepatitis B Virus Infection," *J. Clin. Invest.* 97:1655-1665, The American Society for Clinical Investigation, Inc. (1996).

Rehermann, B., et al., "The cytotoxic T lymphocyte response to multiple hepatitis B virus polymerase epitopes during and after acute viral hepatitis," *J. Exp. Med.* 181:1047-1058, Rockefeller University Press (1995).

Sällberg, M., et al., "Human and murine B-cells recognize the HBeAg/beta (or HBe2) epitope as a linear determinant," *Mol. Immunol.* 28:719-726, Pergamon Press (1991).

Scognamiglio, P., et al., "Presence of Effector CD8+ Cells in Hepatitis C Virus-Exposed Healthy Seronegative Donors," *J. Immunol.* 162:6681-6689, The American Association of Immunologists (1999).

Shimizu, Y., et al., "Dendritic cell immunization breaks cytotoxic T lymphocyte tolerance in hepatitis B virus transgenic mice," *J. Immunol.* 161:4520-4529, American Association of Immunologists (1998).

Shirai, M., et al., "CTL Responses of HLA-A2.1-Transgenic Mice Specific for Hepatitis C Viral Peptides Predict Epitopes for CTL of Humans Carrying HLA-A2.1," *J. Immunol.* 154:2733-2742, The American Association of Immunologists (1995).

Sidney, J., et al., "Definition of an HLA-A3-like supermotif demonstrates the overlapping peptide-binding repertoires of common HLA molecules," *Hum. Immunol.* 45:79-93, Elsevier Science (1996).

Sidney, J., et al., "Specificity and degeneracy in peptide binding to HLA-B7-like class I molecules," *J. Immunol.* 157:3480-3490, American Association of Immunologists (1996).

Toes, R.E., et al. "Enhancement of Tumor Outgrowth Through CTL Tolerization After Peptide VAccination is Avoided by Peptide Presentation on Dendritic Cells" *J. Immunology* 160:4449-4456, American Association of Immunologists (1998).

Vitiello, A., et al., "Development of a lipopeptide-based therapeutic vaccine to treat chronic HBV infection. I. Induction of a primary cytotoxic T lymphocyte response in humans," *J. Clin. Invest.*, 95:341-349, American Society for Clinical Investigation (Jan. 1995).

Wakita, T., et al., "Gamma-interferon production in response to hepatitis B core protein and its synthetic peptides in patients with chronic hepatitis B virus infection," *Digestion* 47:149-155, Karger (1990).

Wentworth, P.A., et al., "Identification of A2-restricted hepatitis C virus-specific cytotoxic T lymphocyte epitopes from conserved regions of the viral genome," *Int. Immunol.* 8:651-659, Oxford University press (1996).

Wong, D.K.H., et al., "Liver-Derived CTL in Hepatitis C Virus Infection: Breadth and Specificity of Responses in a Cohort of Persons with Chronic Infection," *J. Immunol.* 160:1479-1488, The American Association of Immunologists (1998).

U.S. Appl. No. 09/350,401, Sette et al., filed Jul. 8, 1999.

U.S. Appl. No. 10/363,990, Sette et al., filed Mar. 10, 2003 (Published as WO 02/19986 A1; see document AP4).

Compugen Ltd. Sequence Search Report, Database Issued Patents, Results #13 for SEQ ID No. 2524, Mar. 2001.

Basalp, A., et al., "Enhancement of the immune response to hepatitis B virus vaccine by antigen specific IgM," *Immunol. Ltrs.* 73:1-6, Elsevier Science B.V. (Jul. 2000).

Pasek, M., et al., "Hepatitis B virus genes and their expression in *E. coli*," *Nature* 282:575-579, Macmillan Publishers (1979).

Vitiello, A., et al., "Comparison of cytotoxic T lymphocyte responses induced by peptide or DNA immunization: implications on immunogenicity and immunodominance," *Europ. J. Immunol.* 27:671-678, VCH Verlagsgesellschaft mbH (Mar. 1997).

Supplementary Partial European Search Report for European Application No. 00 96 8348 (Sep. 2004).

Altuvia Y., et al., "A structure-Based Algorithm to Predict Potential Binding Peptides to MHC Molecules with Hydrophobic Binding Pockets," *Human Immunology*, 58:1, 1997, pp. 1-11.

Geisbill, Jochen et al., "Detection and Characterization of Human Papillomavirus Type 45 DNA in the Cervical Carcinoma Cell Line MS751," *Journal of General Virology*, 78:3, 1997, pp. 655-658.

Aichele, P., et al., "Antiviral cytotoxic T cell response induced by in vivo priming with a free synthetic peptide," *J. Exp. Med.* 171:1815-1820, Rockefeller University Press (1990).

Alexander, J., et al., "Derivation of HLA-A11/K$^b$ Transgenic Mice. Functional CTL Repertoire and Recognition of Human A11-Restricted CTL Epitopes," *J. Immunol.* 159:4753-4761, The American Association of Immunologists (Nov. 1997).

Bergmann, C.C., et al., "Differential Effects of Flanking Residues on Presentation of Epitopes from Chimeric Peptides," *J. Virol.* 68:5306-5310, American Society for Microbiology (Aug. 1994).

Bertoni, R., et al., "Human Histocompatibility Leukocyte Antigen-binding Supermotifs Predict Broadly Cross-reactive Cytotoxic T Lymphocyte Responses in Patients with Acute Hepatitis," *J. Clin. Invest.* 100:503-513, The American Society for Clinical Investigation, Inc. (Aug. 1997).

Bertoni, R., et al., "Human Class I Supertypes and CTL Repertoires Extend to Chimpanzees," *J. Immunol.* 161:4447-4455, American Association of Immunologists (Oct. 1998).

Bjorkman, P.J., et al., "Structure of the human class I histocompatibility antigen, HLA-A2," *Nature* 329:506-512, Macmillan Publishers, Ltd. (1987).

Bjorkman, P.J., et al., "The foreign antigen binding site and T cell recognition regions of class I histocompatibility antigens," *Nature* 329:512-518, Macmillan Publishers, Ltd. (1987).

Buus, S., et al., "Autologous Peptides Constitutively Occupy the Antigen Binding Site on Ia," *Science* 242:1045-1047, American Association for the Advancement of Science (1988).

Carreno, B.M., et al., "HLA-B37 and HLA-A2.1 molecules bind largely nonoverlapping sets of peptides," *Proc. Natl. Acad. Sci. USA* 87:3420-3424, National Academy Press (1990).

Corr, M., et al., "Endogenous Peptides of a Soluble Major Histocompatibility Complex Class I Molecule, H-2L$^d_s$: Sequence Motif, Quantitative Binding, and Molecular Modeling of the Complex," *J. Exp. Med.* 176:1681-1692, Rockefeller University Press (Dec. 1992).

De Bruijn, M.L.H., et al., "Peptide loading of empty major histocompatibility complex molecules on RMA-S cells allows the induction of primary cytotoxic T lymphocyte responses," *Eur. J. Immunol.* 21:2963-2970, VCH Verlagsgesellschaft mbH (1991).

Del Val, M., et al., "Efficient Processing of an Antigenic Sequence for Presentation by MHC Class I Molecules Depends on Its Neighboring Residues in the Protein," *Cell* 66:1145-1153, Cell Press (1991).

Deres, K., et al., "In vivo priming of virus-specific cytotoxic T lymphocytes with synthetic lipopeptide vaccine," *Nature* 342:561-564, Macmillan Publishers, Ltd. (1989).

DiBrino, M., et al., "HLA-A1 and HLA-A3 T Cell Epitopes Derived from Influenza Virus Proteins Predicted from Peptide Binding Motifs," *J. Immunol.* 151:5930-5935, The Association of Immunologists (Dec. 1993).

DiBrino, M., et al., "Endogenous peptides bound to HLA-A3 possess a specific combination of anchor residues that permit identification of potential antigenic peptides," *Proc. Natl. Acad. Sci. USA* 90:1508-1512, National Academy Press (Feb. 1993).

Ding, Y.-H., et al., "Two Human T Cell Receptors Bind in a Similar Diagonal Mode to the HLA-A2/Tax Peptide Complex Using Different TCR Amino Acids," *Immunity* 8:403-11, Cell Press (Apr. 1998).

Eisenlohr, L.C., et al., "Flanking Sequences Influence the Presentation of an Endogenously Synthesized Peptide to Cytotoxic T Lymphocytes," *J. Exp. Med.* 175:481-487, The Rockefeller University Press (Feb. 1992).

Engelhard, V.H., "Structure of peptides associated with MHC Class I molecules," *Curr. Opin. Immunol.* 6:13-23, Current Biology, Ltd. (Feb. 1994).

Falk, K., et al., "Allele-specific motifs revealed by sequencing of self-peptides eluted from MHC molecules," *Nature* 351:290-296, Macmillan Publishers, Ltd. (1991).

Falk, K., et al., "MHC peptide motif register. Peptide motifs of HLA-B35 and -B37 molecules," *Immunogenetics* 38:161-162, Springer-Verlag (Apr. 1993).

Falk, K., et al., "Allele-specific peptide ligand motifs of HLA-C molecules," *Proc. Natl. Acad. Sci. USA* 90:12005-12009, National Academy Press (Dec. 1993).

Falk, K., et al., "Pool sequencing of natural HLA-DR, DQ, and DP ligands reveals detailed peptide motifs, constraints of processing, and general rules," *Immunogenetics* 39:230-242, Springer-Verlag (Feb. 1994).

Falk, K., et al., "Peptide motifs of HLA-A1, -A11, -A31, and -A33 molecules," *Immunogenetics* 40:238-241, Springer-Verlag (Jul. 1994).

Foon, K.A., "Biological Response Modifiers: The New Immunotherapy," *Cancer Res.* 49:1621-1639, American Association for Cancer Research (1989).

Geysen, H.M., et al., "Cognitive Features of Continuous Antigenic Determinants," *J. Mol. Recognit.* 1:32-41, Heyden & Sons, Ltd. (1988).

Guo, H.-C., et al., "Different length peptides bind to HLA-Aw68 similarly at their ends but bulge out in the middle," *Nature* 360:364-366, Macmillan Publishers, Ltd. (Nov. 1992).

Henderson, R.A., et al., "HLA-A2.1-Associated Peptides from a Mutant Cell Line: A Second Pathway of Antigen Presentation," *Science* 255:1264-1266, American Association for the Advancement of Science (Mar. 1992).

Hill, A., et al., "Characterization of two Epstein-Barr virus epitopes restricted by HLA-B7," *Eur. J. Immunol.* 25:18-24, VCH Verlagsgesellschaft mbH (Jan. 1995).

Hunt, D.F., et al., "Characterization of Peptides Bound to the Class I MHC Molecule HLA-A2.1 by Mass Spectrometry," *Science* 255:1261-1263, American Association for the Advancement of Science (Mar. 1992).

Ishioka, G.Y., et al., "Utilization of MHC Class I Transgenic Mice for Development of Minigene DNA Vaccines Encoding Multiple HLA-Restricted CTL Epitopes," *J. Immunol.* 162:3915-3925, The American Association of Immunologists (Apr. 1999).

Jameson, S.C., and Bevan, M.J., "Dissection of major histocompatibility complex (MHC) and T cell receptor contact residues in a K$^b$-restricted ovalbumin peptide and an assessment of the predictive power of MHC-binding motifs," *Eur. J. Immunol.* 22:2663-2667, VCH Verlagsgesellschaft mbH (Oct. 1992).

Jardetzky, T.S., et al., "Identification of self peptides bound to purified HLA-B27," *Nature* 353:326-329, Macmillan Publishers, Ltd. (1991).

Kannagi, M., et al., "Target Epitope in the Tax Protein of Human T-Cell Leukemia Virus Type I Recognized by Class I Major Histocompatibility Complex-Restricted Cells," *J. Virol.* 66:2928-2933, American Society for Microbiology (May 1992).

Kast, W.M., et al., "Protection against lethal Sendai virus infection by in vivo priming of virus-specific cytotoxic T lymphocytes with a free synthetic peptide," *Proc. Natl. Acad. Sci. USA* 88:2283-2287, National Academy Press (1991).

Kast, W.M., et al., "Strict peptide length is not required for the induction of cytotoxic T lymphocyte-mediated antiviral protection by peptide vaccination," *Eur. J. Immunol.* 23:1189-1192, VCH Verlagsgesellschaft mbH (May 1993).

Krieger, J.I., et al., "Single amino acid changes in DR and antigen define residues critical for peptide-MHC binding and T cell recognition," *J. Immunol.* 146:2331-2340, American Association of Immunologists (1991).

Lipford, G.B., et al., "Primary in Vivo Responses to Ovalbumin. Probing the Predictive Value of the K$^b$ Binding Motif," *J. Immunol.* 150:1212-1222, The American Association of Immunologists (Feb. 1993).

Maryanski, J.L., et al., "Synthetic peptides as antigens and competitors in recognition by H-2-restricted cytolytic T cells specific for HLA," *J. Exp. Med.* 167:1391-1405, Rockefeller University Press (1988).

Maryanski, J.L., et al., "Competitor Analogs for Defined T Cell Antigens: Peptides Incorporating a Putative Binding Motif and Polyproline or Polyglycine Spacers," *Cell* 60:63-72, Cell Press (1990).

Morrison, J., et al., "Identification of the nonamer peptide from influenza A matrix protein and the role of pockets of HLA-A2 in its recognition by cytotoxic T lymphocytes," *Eur. J. Immunol.* 22:903-907, VCH Verlagsgesellschaft mbH (Apr. 1992).

Niedermann, G., et al., "The proteolytic fragments generated by vertebrate proteosomes: Structural relationships to major histocompatibility complex class I binding peptides," *Proc. Natl. Acad. Sci. USA* 93:8572-8577, National Academy Press (Aug. 1996).

Ochoa-Garay, J., et al., "The ability of peptides to induce cytotoxic T cells in vitro does not strongly correlate with their affinity for the $H-2L^d$ molecule: implications for vaccine design and immunotherapy," *Mol. Immunol.* 34:273-281, Elsevier Science, Ltd. (Feb. 1997).

Pamer, E.G., et al., "Precise prediction of a dominant class I MHC-restricted epitome of *Listeria monocytogenes*," *Nature* 353:852-855, Macmillan Publishers, Ltd. (1991).

Parham, P., et al., "The Origins of HLA-A,B,C Polymorphism," *Immunol. Rev.* 143:141-180, Munksgaard (Feb. 1995).

Parker, K.C., et al., "Peptide Binding to HLA-A2 and HLA-B27 Isolated from *Escherichia coli*," *J. Biol. Chem.* 267:5451-5459, American Society for Biochemistry and Molecular Biology, Inc. (Mar. 1992).

Parker, K.C., et al., "Sequence motifs important for peptide binding to the human MHC class I molecule, HLA-A2," *J. Immunol.* 149:3580-3587, American Association of Immunologists (Dec. 1992).

Rammensee, H.-G., et al., "Peptides Naturally Presented by MHC Class I Molecules," *Annu. Rev. Immunol.* 11:213-244, Annual Reviews, Inc. (Jan. 1993).

Rammensee, H.-G., et al., "MHC ligands and peptide motifs: first listing," *Immunogenetics* 41:178-228, Springer-Verlag (Feb. 1995).

Reddehase, M.J., et al., "A pentapeptide as minimal antigenic determinant for MHC class I-restricted T lymphocytes," *Nature* 337:651-653, Macmillan Publishers, Ltd. (1989).

Romero, P., et al., "$H-2K^d$-restricted Antigenic Peptides Share a Simple Binding Motif," *J. Exp. Med.* 174:603-612, Rockefeller University Press (1991).

Rothbard, J.B., "Major histocompatibility complex-peptide interactions," *Curr. Opin. Immunol.* 2:99-105, Current Biology, Ltd. (1989).

Rötzschke, O., et al., "Isolation and analysis of naturally processed viral peptides as recognized by cytotoxic T cells," *Nature* 348:252-254, Macmillan Publishers, Ltd. (1990).

Rötzschke, O., et al., "Characterization of Naturally Occurring Minor Histocompatibility Peptides Including H-4 and H-Y," *Science* 249:283-287, American Association for the Advancement of Science (1990).

Rötzschke, O., and Falk, K., "Naturally-occurring peptide antigens derived from the MHC class-I-restricted processing pathway," *Immunol. Today* 12:447-455, Elsevier Science Publishers, Ltd. (1991).

Rötzschke, O., et al., "Peptide motifs of closely related HLA class I molecules encompass substantial differences," *Eur. J. Immunol.* 22:2453-2456, VCH Verlagsgesellschaft mbH (Sep. 1992).

Rötzschke, O., and Falk, K., "Origin, structure and motifs of naturally processed MHC class II ligands," *Curr. Opin. Immunol.* 6:45-51, Current Biology, Ltd. (Feb. 1994).

Rudinger, J., "Characteristics of the amino acids as components of a peptide hormone sequence," in *Peptide Hormones*, Parsons, J.A., ed., University Park Press, Baltimore, MD, pp. 1-7 (1976).

Ruppert, J., et al., "Prominent Role of Secondary Anchor Residues in Peptide Binding to HLA-A2.1 Molecules," *Cell* 74:929-937, Cell Press (Sep. 1993).

Schulz, M., et al., "Major histocompatibility complex binding and T cell recognition of a viral nonapeptide containing a minimal tetrapeptide," *Eur. J. Immunol.* 21:1181-1185, VCH Verlagsgesellschaft mbH (1991).

Sette, A., et al., "Prediction of major histocompatibility complex binding regions of protein antigens by sequence pattern analysis," *Proc. Natl. Acad. Sci. USA* 86:3296-3300, National Academy Press (1989).

Sette, A., et al., "Random association between the peptide repertoire of A2.1 class I and several different DR class II molecules," *J. Immunol.* 147:3893-3900, The American Association of Immunologists (1991).

Sette, A., et al., "The Relationship Between Class I Binding Affinity and Immunogenicity of Potential Cytotoxic T Cell Epitopes," *J. Immunol.* 153:5586-5592, The American Association of Immunologists (Dec. 1994).

Shastri, N., et al., "Presentation of Endogenous Peptide/MHC Class I Complexes Is Profoundly Influenced by Specific C-Terminal Flanking Residues," *J. Immunol.* 155: 4339-4346, The American Association of Immunologists (Nov. 1995).

Sherman, L.A., et al., "Extracellular Processing of Peptide Antigens That Bind Class I Major Histocompatibility Molecules," *J. Exp. Med.* 175:1221-1226, The Rockefeller University Press (May 1992).

Shimojo, N., et al., "Specificity of peptide binding by the HLA-A2.1 molecule," *J. Immunol.* 143:2939-2947, The American Association of Immunologists (1989).

Sidney, J., et al., "Several HLA Alleles Share Overlapping Peptide Specificities," *J. Immunol.* 154:247-259, The American Association of Immunologists (Jan. 1995).

Threlkeld, S.C., et al., "Degenerate and Promiscuous Recognition by CTL of Peptides Presented by the MHC Class I A3-like Superfamily. Implications for Vaccine Development," *J. Immunol.* 159:1648-1657, The American Association of Immunologists (Aug. 1997).

Wentworth, P.A., et al., "Differences and similarities in the A2.1-restricted cytotoxic T cell repertoire in humans and human leukocyte antigen-transgenic mice," *Eur. J. Immunol.* 26:97-101, VCH Verlagsgesellschaft mbH (Jan. 1996).

Whitton, J.L., et al., "Molecular Analyses of a Five-Amino-Acid Cytotoxic T-Lymphocyte (CTL) Epitope: an Immunodominant Region Which Induces Nonreciprocal CTL Cross-Reactivity," *J. Virol.* 63:4303-4310, American Society for Microbiology (1989).

Yewdell, J.W., and Bennink, J.R., "Cell Biology of Antigen Processing and Presentation to Major Histocompatibility Complex Class I Molecule-Restricted T Lymphocytes," *Adv. Immunol.* 52:1-123, Academic Press (Jul. 1992).

York, I.A., and Rock, K.L., "Antigen processing and presentation by the class I major histocompatibility complex," *Annu. Rev. Immunol.* 14:369-396, Annual Reviews, Inc. (Apr. 1996).

Zhang, Q-J., et al., "An HLA-A11-specific motif in nonamer peptides derived from viral and cellular proteins," *Proc. Natl. Acad. Sci. USA* 90:2217-2221, National Academy Press (Mar. 1993).

Parker, K.C., et al., "Scheme for Ranking Potential HLA-A2 Binding Peptides Based on Independent Binding of Individual Peptide Side-Chains," *J. Immunol.* 152:163-175, The American Association of Immunologists (Jan. 1994).

Dialog File 351, Accession No. 7180926, Derwent WPI English language abstract for EP 0 226 513, Jun. 1987.

Dialog File 351, Accession No. 9263567, Derwent WPI English language abstract for WO 92/21033, Nov. 1992.

Dialog File 351, Accession No. 9888606, Derwent WPI English language abstract for WO 94/11738, May 1994.

\* cited by examiner

SEQUENCE LISTING

```
<160> NUMBER OF SEQ ID NOS: 2579

<210> SEQ ID NO 1
<211> LENGTH: 10
<212> TYPE: PRT
<213> ORGANISM: Orthohepadnaviridae hepatitis B virus

<400> SEQUENCE: 1

Ala Ile Cys Ser Val Val Arg Arg Ala Phe
 1               5                  10

<210> SEQ ID NO 2
<211> LENGTH: 9
<212> TYPE: PRT
<213> ORGANISM: Orthohepadnaviridae hepatitis B virus

<400> SEQUENCE: 2

Ala Leu Arg Gln Ala Ile Leu Cys Trp
 1               5

<210> SEQ ID NO 3
<211> LENGTH: 9
<212> TYPE: PRT
<213> ORGANISM: Orthohepadnaviridae hepatitis B virus

<400> SEQUENCE: 3

Ala Met Gln Trp Asn Ser Thr Thr Phe
 1               5

<210> SEQ ID NO 4
<211> LENGTH: 8
<212> TYPE: PRT
<213> ORGANISM: Orthohepadnaviridae hepatitis B virus

<400> SEQUENCE: 4

Ala Ser Phe Cys Gly Ser Pro Tyr
 1               5

<210> SEQ ID NO 5
<211> LENGTH: 10
<212> TYPE: PRT
```

-continued

<213> ORGANISM: Orthohepadnaviridae hepatitis B virus

<400> SEQUENCE: 5

Ala Ser Phe Cys Gly Ser Pro Tyr Ser Trp
1               5                   10

<210> SEQ ID NO 6
<211> LENGTH: 8
<212> TYPE: PRT
<213> ORGANISM: Orthohepadnaviridae hepatitis B virus

<400> SEQUENCE: 6

Ala Ser Lys Leu Cys Leu Gly Trp
1               5

<210> SEQ ID NO 7
<211> LENGTH: 10
<212> TYPE: PRT
<213> ORGANISM: Orthohepadnaviridae hepatitis B virus

<400> SEQUENCE: 7

Ala Ser Lys Leu Cys Leu Gly Trp Leu Trp
1               5                   10

<210> SEQ ID NO 8
<211> LENGTH: 8
<212> TYPE: PRT
<213> ORGANISM: Orthohepadnaviridae hepatitis B virus

<400> SEQUENCE: 8

Ala Ser Pro Leu His Val Ala Trp
1               5

<210> SEQ ID NO 9
<211> LENGTH: 8
<212> TYPE: PRT
<213> ORGANISM: Orthohepadnaviridae hepatitis B virus

<400> SEQUENCE: 9

Cys Ile Pro Ile Pro Ser Ser Trp
1               5

<210> SEQ ID NO 10
<211> LENGTH: 10
<212> TYPE: PRT
<213> ORGANISM: Orthohepadnaviridae hepatitis B virus

<400> SEQUENCE: 10

Cys Ile Pro Ile Pro Ser Ser Trp Ala Phe
1               5                   10

<210> SEQ ID NO 11
<211> LENGTH: 11
<212> TYPE: PRT
<213> ORGANISM: Orthohepadnaviridae hepatitis B virus

<400> SEQUENCE: 11

Cys Leu Ile Phe Leu Leu Val Leu Leu Asp Tyr
1               5                   10

<210> SEQ ID NO 12
<211> LENGTH: 8
<212> TYPE: PRT
<213> ORGANISM: Orthohepadnaviridae hepatitis B virus -continued

```
<400> SEQUENCE: 12

Cys Leu Arg Arg Phe Ile Ile Phe
1               5

<210> SEQ ID NO 13
<211> LENGTH: 10
<212> TYPE: PRT
<213> ORGANISM: Orthohepadnaviridae hepatitis B virus

<400> SEQUENCE: 13

Cys Leu Arg Arg Phe Ile Ile Phe Leu Phe
1               5                   10

<210> SEQ ID NO 14
<211> LENGTH: 8
<212> TYPE: PRT
<213> ORGANISM: Orthohepadnaviridae hepatitis B virus

<400> SEQUENCE: 14

Cys Ser Val Val Arg Arg Ala Phe
1               5

<210> SEQ ID NO 15
<211> LENGTH: 10
<212> TYPE: PRT
<213> ORGANISM: Orthohepadnaviridae hepatitis B virus

<400> SEQUENCE: 15

Cys Thr Cys Ile Pro Ile Pro Ser Ser Trp
1               5                   10

<210> SEQ ID NO 16
<211> LENGTH: 8
<212> TYPE: PRT
<213> ORGANISM: Orthohepadnaviridae hepatitis B virus

<400> SEQUENCE: 16

Asp Ile Asp Pro Tyr Lys Glu Phe
1               5

<210> SEQ ID NO 17
<211> LENGTH: 10
<212> TYPE: PRT
<213> ORGANISM: Orthohepadnaviridae hepatitis B virus

<400> SEQUENCE: 17

Asp Leu Leu Asp Thr Ala Ser Ala Leu Tyr
1               5                   10

<210> SEQ ID NO 18
<211> LENGTH: 9
<212> TYPE: PRT
<213> ORGANISM: Orthohepadnaviridae hepatitis B virus

<400> SEQUENCE: 18

Asp Ser Trp Trp Thr Ser Leu Asn Phe
1               5

<210> SEQ ID NO 19
<211> LENGTH: 10
<212> TYPE: PRT
<213> ORGANISM: Orthohepadnaviridae hepatitis B virus

<400> SEQUENCE: 19
```

Glu Leu Leu Ser Phe Leu Pro Ser Asp Phe
1               5                   10

<210> SEQ ID NO 20
<211> LENGTH: 11
<212> TYPE: PRT
<213> ORGANISM: Orthohepadnaviridae hepatitis B virus

<400> SEQUENCE: 20

Glu Leu Leu Ser Phe Leu Pro Ser Asp Phe Phe
1               5                   10

<210> SEQ ID NO 21
<211> LENGTH: 8
<212> TYPE: PRT
<213> ORGANISM: Orthohepadnaviridae hepatitis B virus

<400> SEQUENCE: 21

Glu Ser Arg Leu Val Val Asp Phe
1               5

<210> SEQ ID NO 22
<211> LENGTH: 11
<212> TYPE: PRT
<213> ORGANISM: Orthohepadnaviridae hepatitis B virus

<400> SEQUENCE: 22

Glu Ser Arg Leu Val Val Asp Phe Ser Gln Phe
1               5                   10

<210> SEQ ID NO 23
<211> LENGTH: 9
<212> TYPE: PRT
<213> ORGANISM: Orthohepadnaviridae hepatitis B virus

<400> SEQUENCE: 23

Phe Ile Leu Leu Leu Cys Leu Ile Phe
1               5

<210> SEQ ID NO 24
<211> LENGTH: 11
<212> TYPE: PRT
<213> ORGANISM: Orthohepadnaviridae hepatitis B virus

<400> SEQUENCE: 24

Phe Leu Phe Ile Leu Leu Leu Cys Leu Ile Phe
1               5                   10

<210> SEQ ID NO 25
<211> LENGTH: 8
<212> TYPE: PRT
<213> ORGANISM: Orthohepadnaviridae hepatitis B virus

<400> SEQUENCE: 25

Phe Leu Leu Val Leu Leu Asp Tyr
1               5

<210> SEQ ID NO 26
<211> LENGTH: 8
<212> TYPE: PRT
<213> ORGANISM: Orthohepadnaviridae hepatitis B virus

<400> SEQUENCE: 26

Phe Ser Pro Thr Tyr Lys Ala Phe
1               5

<210> SEQ ID NO 27
<211> LENGTH: 11
<212> TYPE: PRT
<213> ORGANISM: Orthohepadnaviridae hepatitis B virus

<400> SEQUENCE: 27

Phe Ser Ser Ala Gly Pro Cys Ala Leu Arg Phe
 1               5                  10

<210> SEQ ID NO 28
<211> LENGTH: 10
<212> TYPE: PRT
<213> ORGANISM: Orthohepadnaviridae hepatitis B virus

<400> SEQUENCE: 28

Phe Ser Trp Leu Ser Leu Leu Val Pro Phe
 1               5                  10

<210> SEQ ID NO 29
<211> LENGTH: 10
<212> TYPE: PRT
<213> ORGANISM: Orthohepadnaviridae hepatitis B virus

<400> SEQUENCE: 29

Phe Thr Phe Ser Pro Thr Tyr Lys Ala Phe
 1               5                  10

<210> SEQ ID NO 30
<211> LENGTH: 9
<212> TYPE: PRT
<213> ORGANISM: Orthohepadnaviridae hepatitis B virus

<400> SEQUENCE: 30

Phe Val Gly Leu Ser Pro Thr Val Trp
 1               5

<210> SEQ ID NO 31
<211> LENGTH: 9
<212> TYPE: PRT
<213> ORGANISM: Orthohepadnaviridae hepatitis B virus

<400> SEQUENCE: 31

Gly Leu Leu Gly Phe Ala Ala Pro Phe
 1               5

<210> SEQ ID NO 32
<211> LENGTH: 10
<212> TYPE: PRT
<213> ORGANISM: Orthohepadnaviridae hepatitis B virus

<400> SEQUENCE: 32

Gly Leu Ser Pro Phe Leu Leu Ala Gln Phe
 1               5                  10

<210> SEQ ID NO 33
<211> LENGTH: 10
<212> TYPE: PRT
<213> ORGANISM: Orthohepadnaviridae hepatitis B virus

<400> SEQUENCE: 33

Gly Met Asp Ile Asp Pro Tyr Lys Glu Phe
 1               5                  10

```
<210> SEQ ID NO 34
<211> LENGTH: 10
<212> TYPE: PRT
<213> ORGANISM: Orthohepadnaviridae hepatitis B virus

<400> SEQUENCE: 34

Gly Val Trp Ile Arg Thr Pro Pro Ala Tyr
1               5                   10

<210> SEQ ID NO 35
<211> LENGTH: 10
<212> TYPE: PRT
<213> ORGANISM: Orthohepadnaviridae hepatitis B virus

<400> SEQUENCE: 35

His Leu Asn Pro Asn Lys Thr Lys Arg Trp
1               5                   10

<210> SEQ ID NO 36
<211> LENGTH: 11
<212> TYPE: PRT
<213> ORGANISM: Orthohepadnaviridae hepatitis B virus

<400> SEQUENCE: 36

His Leu Tyr Ser His Pro Ile Ile Leu Gly Phe
1               5                   10

<210> SEQ ID NO 37
<211> LENGTH: 10
<212> TYPE: PRT
<213> ORGANISM: Orthohepadnaviridae hepatitis B virus

<400> SEQUENCE: 37

His Thr Ala Glu Leu Leu Ala Ala Cys Phe
1               5                   10

<210> SEQ ID NO 38
<211> LENGTH: 11
<212> TYPE: PRT
<213> ORGANISM: Orthohepadnaviridae hepatitis B virus

<400> SEQUENCE: 38

His Thr Ala Leu Arg Gln Ala Ile Leu Cys Trp
1               5                   10

<210> SEQ ID NO 39
<211> LENGTH: 10
<212> TYPE: PRT
<213> ORGANISM: Orthohepadnaviridae hepatitis B virus

<400> SEQUENCE: 39

His Thr Leu Trp Lys Ala Gly Ile Leu Tyr
1               5                   10

<210> SEQ ID NO 40
<211> LENGTH: 8
<212> TYPE: PRT
<213> ORGANISM: Orthohepadnaviridae hepatitis B virus

<400> SEQUENCE: 40

Ile Leu Leu Leu Cys Leu Ile Phe
1               5

<210> SEQ ID NO 41
<211> LENGTH: 9
```

```
<212> TYPE: PRT
<213> ORGANISM: Orthohepadnaviridae hepatitis B virus

<400> SEQUENCE: 41

Ile Leu Arg Gly Thr Ser Phe Val Tyr
 1               5

<210> SEQ ID NO 42
<211> LENGTH: 11
<212> TYPE: PRT
<213> ORGANISM: Orthohepadnaviridae hepatitis B virus

<400> SEQUENCE: 42

Ile Leu Thr Ile Pro Gln Ser Leu Asp Ser Trp
 1               5                  10

<210> SEQ ID NO 43
<211> LENGTH: 11
<212> TYPE: PRT
<213> ORGANISM: Orthohepadnaviridae hepatitis B virus

<400> SEQUENCE: 43

Ile Val Gly Leu Leu Gly Phe Ala Ala Pro Phe
 1               5                  10

<210> SEQ ID NO 44
<211> LENGTH: 11
<212> TYPE: PRT
<213> ORGANISM: Orthohepadnaviridae hepatitis B virus

<400> SEQUENCE: 44

Lys Ile Pro Met Gly Val Gly Leu Ser Pro Phe
 1               5                  10

<210> SEQ ID NO 45
<211> LENGTH: 8
<212> TYPE: PRT
<213> ORGANISM: Orthohepadnaviridae hepatitis B virus

<400> SEQUENCE: 45

Lys Leu Cys Leu Gly Trp Leu Trp
 1               5

<210> SEQ ID NO 46
<211> LENGTH: 8
<212> TYPE: PRT
<213> ORGANISM: Orthohepadnaviridae hepatitis B virus

<400> SEQUENCE: 46

Lys Leu Ile Met Pro Ala Arg Phe
 1               5

<210> SEQ ID NO 47
<211> LENGTH: 9
<212> TYPE: PRT
<213> ORGANISM: Orthohepadnaviridae hepatitis B virus

<400> SEQUENCE: 47

Lys Leu Ile Met Pro Ala Arg Phe Tyr
 1               5

<210> SEQ ID NO 48
<211> LENGTH: 10
<212> TYPE: PRT
<213> ORGANISM: Orthohepadnaviridae hepatitis B virus
```

```
<400> SEQUENCE: 48

Lys Leu Pro Val Asn Arg Pro Ile Asp Trp
1               5                   10

<210> SEQ ID NO 49
<211> LENGTH: 11
<212> TYPE: PRT
<213> ORGANISM: Orthohepadnaviridae hepatitis B virus

<400> SEQUENCE: 49

Lys Thr Lys Arg Trp Gly Tyr Ser Leu Asn Phe
1               5                   10

<210> SEQ ID NO 50
<211> LENGTH: 9
<212> TYPE: PRT
<213> ORGANISM: Orthohepadnaviridae hepatitis B virus

<400> SEQUENCE: 50

Lys Val Gly Asn Phe Thr Gly Leu Tyr
1               5

<210> SEQ ID NO 51
<211> LENGTH: 10
<212> TYPE: PRT
<213> ORGANISM: Orthohepadnaviridae hepatitis B virus

<400> SEQUENCE: 51

Leu Ile Phe Leu Leu Val Leu Leu Asp Tyr
1               5                   10

<210> SEQ ID NO 52
<211> LENGTH: 8
<212> TYPE: PRT
<213> ORGANISM: Orthohepadnaviridae hepatitis B virus

<400> SEQUENCE: 52

Leu Ile Met Pro Ala Arg Phe Tyr
1               5

<210> SEQ ID NO 53
<211> LENGTH: 9
<212> TYPE: PRT
<213> ORGANISM: Orthohepadnaviridae hepatitis B virus

<400> SEQUENCE: 53

Leu Leu Asp Thr Ala Ser Ala Leu Tyr
1               5

<210> SEQ ID NO 54
<211> LENGTH: 8
<212> TYPE: PRT
<213> ORGANISM: Orthohepadnaviridae hepatitis B virus

<400> SEQUENCE: 54

Leu Leu Gly Cys Ala Ala Asn Trp
1               5

<210> SEQ ID NO 55
<211> LENGTH: 8
<212> TYPE: PRT
<213> ORGANISM: Orthohepadnaviridae hepatitis B virus

<400> SEQUENCE: 55
```

```
Leu Leu Gly Phe Ala Ala Pro Phe
 1               5
```

<210> SEQ ID NO 56
<211> LENGTH: 9
<212> TYPE: PRT
<213> ORGANISM: Orthohepadnaviridae hepatitis B virus

<400> SEQUENCE: 56

```
Leu Leu Pro Ile Phe Phe Cys Leu Trp
 1               5
```

<210> SEQ ID NO 57
<211> LENGTH: 11
<212> TYPE: PRT
<213> ORGANISM: Orthohepadnaviridae hepatitis B virus

<400> SEQUENCE: 57

```
Leu Leu Pro Ile Phe Phe Cys Leu Trp Val Tyr
 1               5                   10
```

<210> SEQ ID NO 58
<211> LENGTH: 9
<212> TYPE: PRT
<213> ORGANISM: Orthohepadnaviridae hepatitis B virus

<400> SEQUENCE: 58

```
Leu Leu Ser Phe Leu Pro Ser Asp Phe
 1               5
```

<210> SEQ ID NO 59
<211> LENGTH: 10
<212> TYPE: PRT
<213> ORGANISM: Orthohepadnaviridae hepatitis B virus

<400> SEQUENCE: 59

```
Leu Leu Ser Phe Leu Pro Ser Asp Phe Phe
 1               5                   10
```

<210> SEQ ID NO 60
<211> LENGTH: 8
<212> TYPE: PRT
<213> ORGANISM: Orthohepadnaviridae hepatitis B virus

<400> SEQUENCE: 60

```
Leu Leu Ser Ser Asn Leu Ser Trp
 1               5
```

<210> SEQ ID NO 61
<211> LENGTH: 8
<212> TYPE: PRT
<213> ORGANISM: Orthohepadnaviridae hepatitis B virus

<400> SEQUENCE: 61

```
Leu Leu Val Leu Gln Ala Gly Phe
 1               5
```

<210> SEQ ID NO 62
<211> LENGTH: 9
<212> TYPE: PRT
<213> ORGANISM: Orthohepadnaviridae hepatitis B virus

<400> SEQUENCE: 62

```
Leu Leu Val Leu Gln Ala Gly Phe Phe
```

```
                1               5

<210> SEQ ID NO 63
<211> LENGTH: 8
<212> TYPE: PRT
<213> ORGANISM: Orthohepadnaviridae hepatitis B virus

<400> SEQUENCE: 63

Leu Leu Val Pro Phe Val Gln Trp
1               5

<210> SEQ ID NO 64
<211> LENGTH: 9
<212> TYPE: PRT
<213> ORGANISM: Orthohepadnaviridae hepatitis B virus

<400> SEQUENCE: 64

Leu Leu Val Pro Phe Val Gln Trp Phe
1               5

<210> SEQ ID NO 65
<211> LENGTH: 11
<212> TYPE: PRT
<213> ORGANISM: Orthohepadnaviridae hepatitis B virus

<400> SEQUENCE: 65

Leu Leu Trp Phe His Ile Ser Cys Leu Thr Phe
1               5                   10

<210> SEQ ID NO 66
<211> LENGTH: 8
<212> TYPE: PRT
<213> ORGANISM: Orthohepadnaviridae hepatitis B virus

<400> SEQUENCE: 66

Leu Ser Phe Leu Pro Ser Asp Phe
1               5

<210> SEQ ID NO 67
<211> LENGTH: 9
<212> TYPE: PRT
<213> ORGANISM: Orthohepadnaviridae hepatitis B virus

<400> SEQUENCE: 67

Leu Ser Phe Leu Pro Ser Asp Phe Phe
1               5

<210> SEQ ID NO 68
<211> LENGTH: 9
<212> TYPE: PRT
<213> ORGANISM: Orthohepadnaviridae hepatitis B virus

<400> SEQUENCE: 68

Leu Ser Leu Asp Val Ser Ala Ala Phe
1               5

<210> SEQ ID NO 69
<211> LENGTH: 10
<212> TYPE: PRT
<213> ORGANISM: Orthohepadnaviridae hepatitis B virus

<400> SEQUENCE: 69

Leu Ser Leu Asp Val Ser Ala Ala Phe Tyr
1               5                   10
```

```
<210> SEQ ID NO 70
<211> LENGTH: 10
<212> TYPE: PRT
<213> ORGANISM: Orthohepadnaviridae h

```
<211> LENGTH: 9
<212> TYPE: PRT
<213> ORGANISM: Orthohepadnaviridae hepatitis B virus

<400> SEQUENCE: 77

Leu Ser Val Pro Asn Pro Leu Gly Phe
 1               5

<210> SEQ ID NO 78
<211> LENGTH: 11
<212> TYPE: PRT
<213> ORGANISM: Orthohepadnaviridae hepatitis B virus

<400> SEQUENCE: 78

Leu Thr Phe Gly Arg Glu Thr Val Leu Glu Tyr
 1               5                  10

<210> SEQ ID NO 79
<211> LENGTH: 10
<212> TYPE: PRT
<213> ORGANISM: Orthohepadnaviridae hepatitis B virus

<400> SEQUENCE: 79

Leu Thr Ile Pro Gln Ser Leu Asp Ser Trp
 1               5                  10

<210> SEQ ID NO 80
<211> LENGTH: 11
<212> TYPE: PRT
<213> ORGANISM: Orthohepadnaviridae hepatitis B virus

<400> SEQUENCE: 80

Leu Thr Ile Pro Gln Ser Leu Asp Ser Trp Trp
 1               5                  10

<210> SEQ ID NO 81
<211> LENGTH: 11
<212> TYPE: PRT
<213> ORGANISM: Orthohepadnaviridae hepatitis B virus

<400> SEQUENCE: 81

Leu Thr Asn Leu Leu Ser Ser Asn Leu Ser Trp
 1               5                  10

<210> SEQ ID NO 82
<211> LENGTH: 8
<212> TYPE: PRT
<213> ORGANISM: Orthohepadnaviridae hepatitis B virus

<400> SEQUENCE: 82

Leu Val Leu Gln Ala Gly Phe Phe
 1               5

<210> SEQ ID NO 83
<211> LENGTH: 8
<212> TYPE: PRT
<213> ORGANISM: Orthohepadnaviridae hepatitis B virus

<400> SEQUENCE: 83

Leu Val Pro Phe Val Gln Trp Phe
 1               5

<210> SEQ ID NO 84
<211> LENGTH: 8
<212> TYPE: PRT
```

-continued

<213> ORGANISM: Orthohepadnaviridae hepatitis B virus

<400> SEQUENCE: 84

Leu Val Val Asp Phe Ser Gln Phe
1 5

<210> SEQ ID NO 85
<211> LENGTH: 10
<212> TYPE: PRT
<213> ORGANISM: Orthohepadnaviridae hepatitis B virus

<400> SEQUENCE: 85

Met Met Trp Tyr Trp Gly Pro Ser Leu Tyr
1 5 10

<210> SEQ ID NO 86
<211> LENGTH: 9
<212> TYPE: PRT
<213> ORGANISM: Orthohepadnaviridae hepatitis B virus

<400> SEQUENCE: 86

Met Ser Thr Thr Asp Leu Glu Ala Tyr
1 5

<210> SEQ ID NO 87
<211> LENGTH: 10
<212> TYPE: PRT
<213> ORGANISM: Orthohepadnaviridae hepatitis B virus

<400> SEQUENCE: 87

Met Ser Thr Thr Asp Leu Glu Ala Tyr Phe
1 5 10

<210> SEQ ID NO 88
<211> LENGTH: 11
<212> TYPE: PRT
<213> ORGANISM: Orthohepadnaviridae hepatitis B virus

<400> SEQUENCE: 88

Asn Leu Gly Asn Leu Asn Val Ser Ile Pro Trp
1 5 10

<210> SEQ ID NO 89
<211> LENGTH: 9
<212> TYPE: PRT
<213> ORGANISM: Orthohepadnaviridae hepatitis B virus

<400> SEQUENCE: 89

Asn Leu Leu Ser Ser Asn Leu Ser Trp
1 5

<210> SEQ ID NO 90
<211> LENGTH: 8
<212> TYPE: PRT
<213> ORGANISM: Orthohepadnaviridae hepatitis B virus

<400> SEQUENCE: 90

Asn Leu Asn Val Ser Ile Pro Trp
1 5

<210> SEQ ID NO 91
<211> LENGTH: 10
<212> TYPE: PRT
<213> ORGANISM: Orthohepadnaviridae hepatitis B virus

```
<400> SEQUENCE: 91

Asn Leu Ser Val Pro Asn Pro Leu Gly Phe
1               5                   10

<210> SEQ ID NO 92
<211> LENGTH: 9
<212> TYPE: PRT
<213> ORGANISM: Orthohepadnaviridae hepatitis B virus

<400> SEQUENCE: 92

Asn Ser Val Val Leu Ser Arg Lys Tyr
1               5

<210> SEQ ID NO 93
<211> LENGTH: 9
<212> TYPE: PRT
<213> ORGANISM: Orthohepadnaviridae hepatitis B virus

<400> SEQUENCE: 93

Pro Ile Phe Phe Cys Leu Trp Val Tyr
1               5

<210> SEQ ID NO 94
<211> LENGTH: 8
<212> TYPE: PRT
<213> ORGANISM: Orthohepadnaviridae hepatitis B virus

<400> SEQUENCE: 94

Pro Ile Pro Ser Ser Trp Ala Phe
1               5

<210> SEQ ID NO 95
<211> LENGTH: 9
<212> TYPE: PRT
<213> ORGANISM: Orthohepadnaviridae hepatitis B virus

<400> SEQUENCE: 95

Pro Leu Asp Lys Gly Ile Lys Pro Tyr
1               5

<210> SEQ ID NO 96
<211> LENGTH: 10
<212> TYPE: PRT
<213> ORGANISM: Orthohepadnaviridae hepatitis B virus

<400> SEQUENCE: 96

Pro Leu Asp Lys Gly Ile Lys Pro Tyr Tyr
1               5                   10

<210> SEQ ID NO 97
<211> LENGTH: 10
<212> TYPE: PRT
<213> ORGANISM: Orthohepadnaviridae hepatitis B virus

<400> SEQUENCE: 97

Pro Leu Leu Pro Ile Phe Phe Cys Leu Trp
1               5                   10

<210> SEQ ID NO 98
<211> LENGTH: 9
<212> TYPE: PRT
<213> ORGANISM: Orthohepadnaviridae hepatitis B virus

<400> SEQUENCE: 98
```

-continued

Pro Leu Leu Val Leu Gln Ala Gly Phe
1               5

<210> SEQ ID NO 99
<211> LENGTH: 10
<212> TYPE: PRT
<213> ORGANISM: Orthohepadnaviridae hepatitis B virus

<400> SEQUENCE: 99

Pro Leu Leu Val Leu Gln Ala Gly Phe Phe
1               5                   10

<210> SEQ ID NO 100
<211> LENGTH: 9
<212> TYPE: PRT
<213> ORGANISM: Orthohepadnaviridae hepatitis B virus

<400> SEQUENCE: 100

Pro Met Gly Val Gly Leu Ser Pro Phe
1               5

<210> SEQ ID NO 101
<211> LENGTH: 9
<212> TYPE: PRT
<213> ORGANISM: Orthohepadnaviridae hepatitis B virus

<400> SEQUENCE: 101

Pro Thr Thr Gly Arg Thr Ser Leu Tyr
1               5

<210> SEQ ID NO 102
<211> LENGTH: 9
<212> TYPE: PRT
<213> ORGANISM: Orthohepadnaviridae hepatitis B virus

<400> SEQUENCE: 102

Pro Thr Val Trp Leu Ser Val Ile Trp
1               5

<210> SEQ ID NO 103
<211> LENGTH: 8
<212> TYPE: PRT
<213> ORGANISM: Orthohepadnaviridae hepatitis B virus

<400> SEQUENCE: 103

Pro Val Asn Arg Pro Ile Asp Trp
1               5

<210> SEQ ID NO 104
<211> LENGTH: 11
<212> TYPE: PRT
<213> ORGANISM: Orthohepadnaviridae hepatitis B virus

<400> SEQUENCE: 104

Gln Val Phe Ala Asp Ala Thr Pro Thr Gly Trp
1               5                   10

<210> SEQ ID NO 105
<211> LENGTH: 8
<212> TYPE: PRT
<213> ORGANISM: Orthohepadnaviridae hepatitis B virus

<400> SEQUENCE: 105

Arg Ile Val Gly Leu Leu Gly Phe
1               5

<210> SEQ ID NO 106
<211> LENGTH: 10
<212> TYPE: PRT
<213> ORGANISM: Orthohepadnaviridae hepatitis B virus

<400> SEQUENCE: 106

Arg Leu Lys Leu Ile Met Pro Ala Arg Phe
 1               5                  10

<210> SEQ ID NO 107
<211> LENGTH: 11
<212> TYPE: PRT
<213> ORGANISM: Orthohepadnaviridae hepatitis B virus

<400> SEQUENCE: 107

Arg Leu Lys Leu Ile Met Pro Ala Arg Phe Tyr
 1               5                  10

<210> SEQ ID NO 108
<211> LENGTH: 9
<212> TYPE: PRT
<213> ORGANISM: Orthohepadnaviridae hepatitis B virus

<400> SEQUENCE: 108

Arg Leu Val Val Asp Phe Ser Gln Phe
 1               5

<210> SEQ ID NO 109
<211> LENGTH: 11
<212> TYPE: PRT
<213> ORGANISM: Orthohepadnaviridae hepatitis B virus

<400> SEQUENCE: 109

Arg Thr Pro Ala Arg Val Thr Gly Gly Val Phe
 1               5                  10

<210> SEQ ID NO 110
<211> LENGTH: 11
<212> TYPE: PRT
<213> ORGANISM: Orthohepadnaviridae hepatitis B virus

<400> SEQUENCE: 110

Ser Ile Pro Trp Thr His Lys Val Gly Asn Phe
 1               5                  10

<210> SEQ ID NO 111
<211> LENGTH: 11
<212> TYPE: PRT
<213> ORGANISM: Orthohepadnaviridae hepatitis B virus

<400> SEQUENCE: 111

Ser Leu Asp Ser Trp Trp Thr Ser Leu Asn Phe
 1               5                  10

<210> SEQ ID NO 112
<211> LENGTH: 8
<212> TYPE: PRT
<213> ORGANISM: Orthohepadnaviridae hepatitis B virus

<400> SEQUENCE: 112

Ser Leu Asp Val Ser Ala Ala Phe
 1               5

<210> SEQ ID NO 113
<211> LENGTH: 9
<212> TYPE: PRT
<213> ORGANISM: Orthohepadnaviridae hepatitis B virus

<400> SEQUENCE: 113

Ser Leu Asp Val Ser Ala Ala Phe Tyr
1               5

<210> SEQ ID NO 114
<211> LENGTH: 9
<212> TYPE: PRT
<213> ORGANISM: Orthohepadnaviridae hepatitis B virus

<400> SEQUENCE: 114

Ser Leu Leu Val Pro Phe Val Gln Trp
1               5

<210> SEQ ID NO 115
<211> LENGTH: 10
<212> TYPE: PRT
<213> ORGANISM: Orthohepadnaviridae hepatitis B virus

<400> SEQUENCE: 115

Ser Leu Leu Val Pro Phe Val Gln Trp Phe
1               5                   10

<210> SEQ ID NO 116
<211> LENGTH: 10
<212> TYPE: PRT
<213> ORGANISM: Orthohepadnaviridae hepatitis B virus

<400> SEQUENCE: 116

Ser Leu Arg Gly Leu Pro Val Cys Ala Phe
1               5                   10

<210> SEQ ID NO 117
<211> LENGTH: 10
<212> TYPE: PRT
<213> ORGANISM: Orthohepadnaviridae hepatitis B virus

<400> SEQUENCE: 117

Ser Ser Ala Gly Pro Cys Ala Leu Arg Phe
1               5                   10

<210> SEQ ID NO 118
<211> LENGTH: 8
<212> TYPE: PRT
<213> ORGANISM: Orthohepadnaviridae hepatitis B virus

<400> SEQUENCE: 118

Ser Thr Thr Asp Leu Glu Ala Tyr
1               5

<210> SEQ ID NO 119
<211> LENGTH: 9
<212> TYPE: PRT
<213> ORGANISM: Orthohepadnaviridae hepatitis B virus

<400> SEQUENCE: 119

Ser Thr Thr Asp Leu Glu Ala Tyr Phe
1               5

<210> SEQ ID NO 120
<211> LENGTH: 8

<212> TYPE: PRT
<213> ORGANISM: Orthohepadnaviridae hepatitis B virus

<400> SEQUENCE: 120

Ser Val Pro Asn Pro Leu Gly Phe
1               5

<210> SEQ ID NO 121
<211> LENGTH: 8
<212> TYPE: PRT
<213> ORGANISM: Orthohepadnaviridae hepatitis B virus

<400> SEQUENCE: 121

Ser Val Val Leu Ser Arg Lys Tyr
1               5

<210> SEQ ID NO 122
<211> LENGTH: 11
<212> TYPE: PRT
<213> ORGANISM: Orthohepadnaviridae hepatitis B virus

<400> SEQUENCE: 122

Ser Val Val Leu Ser Arg Lys Tyr Thr Ser Phe
1               5                   10

<210> SEQ ID NO 123
<211> LENGTH: 9
<212> TYPE: PRT
<213> ORGANISM: Orthohepadnaviridae hepatitis B virus

<400> SEQUENCE: 123

Thr Ile Pro Gln Ser Leu Asp Ser Trp
1               5

<210> SEQ ID NO 124
<211> LENGTH: 10
<212> TYPE: PRT
<213> ORGANISM: Orthohepadnaviridae hepatitis B virus

<400> SEQUENCE: 124

Thr Ile Pro Gln Ser Leu Asp Ser Trp Trp
1               5                   10

<210> SEQ ID NO 125
<211> LENGTH: 9
<212> TYPE: PRT
<213> ORGANISM: Orthohepadnaviridae hepatitis B virus

<400> SEQUENCE: 125

Thr Leu Trp Lys Ala Gly Ile Leu Tyr
1               5

<210> SEQ ID NO 126
<211> LENGTH: 8
<212> TYPE: PRT
<213> ORGANISM: Orthohepadnaviridae hepatitis B virus

<400> SEQUENCE: 126

Thr Thr Asp Leu Glu Ala Tyr Phe
1               5

<210> SEQ ID NO 127
<211> LENGTH: 8
<212> TYPE: PRT
<213> ORGANISM: Orthohepadnaviridae hepatitis B virus

<400> SEQUENCE: 127

Thr Thr Gly Arg Thr Ser Leu Tyr
1               5

<210> SEQ ID NO 128
<211> LENGTH: 11
<212> TYPE: PRT
<213> ORGANISM: Orthohepadnaviridae hepatitis B virus

<400> SEQUENCE: 128

Thr Val Gln Ala Ser Lys Leu Cys Leu Gly Trp
1 5 10

<210> SEQ ID NO 129
<211> LENGTH: 8
<212> TYPE: PRT
<213> ORGANISM: Orthohepadnaviridae hepatitis B virus

<400> SEQUENCE: 129

Thr Val Trp Leu Ser Val Ile Trp
1 5

<210> SEQ ID NO 130
<211> LENGTH: 9
<212> TYPE: PRT
<213> ORGANISM: Orthohepadnaviridae hepatitis B virus

<400> SEQUENCE: 130

Val Leu Ser Arg Lys Tyr Thr Ser Phe
1 5

<210> SEQ ID NO 131
<211> LENGTH: 11
<212> TYPE: PRT
<213> ORGANISM: Orthohepadnaviridae hepatitis B virus

<400> SEQUENCE: 131

Val Leu Ser Arg Lys Tyr Thr Ser Phe Pro Trp
1 5 10

<210> SEQ ID NO 132
<211> LENGTH: 10
<212> TYPE: PRT
<213> ORGANISM: Orthohepadnaviridae hepatitis B virus

<400> SEQUENCE: 132

Val Val Leu Ser Arg Lys Tyr Thr Ser Phe
1 5 10

<210> SEQ ID NO 133
<211> LENGTH: 8
<212> TYPE: PRT
<213> ORGANISM: Orthohepadnaviridae hepatitis B virus

<400> SEQUENCE: 133

Trp Ile Leu Arg Gly Thr Ser Phe
1 5

<210> SEQ ID NO 134
<211> LENGTH: 10
<212> TYPE: PRT
<213> ORGANISM: Orthohepadnaviridae hepatitis B virus

<400> SEQUENCE: 134

```
Trp Ile Leu Arg Gly Thr Ser Phe Val Tyr
 1               5                  10

<210> SEQ ID NO 135
<211> LENGTH: 8
<212> TYPE: PRT
<213> ORGANISM: Orthohepadnaviridae hepatitis B virus

<400> SEQUENCE: 135

Trp Ile Arg Thr Pro Pro Ala Tyr
 1               5

<210> SEQ ID NO 136
<211> LENGTH: 9
<212> TYPE: PRT
<213> ORGANISM: Orthohepadnaviridae hepatitis B virus

<400> SEQUENCE: 136

Trp Leu Leu Gly Cys Ala Ala Asn Trp
 1               5

<210> SEQ ID NO 137
<211> LENGTH: 10
<212> TYPE: PRT
<213> ORGANISM: Orthohepadnaviridae hepatitis B virus

<400> SEQUENCE: 137

Trp Leu Ser Leu Asp Val Ser Ala Ala Phe
 1               5                  10

<210> SEQ ID NO 138
<211> LENGTH: 11
<212> TYPE: PRT
<213> ORGANISM: Orthohepadnaviridae hepatitis B virus

<400> SEQUENCE: 138

Trp Leu Ser Leu Asp Val Ser Ala Ala Phe Tyr
 1               5                  10

<210> SEQ ID NO 139
<211> LENGTH: 8
<212> TYPE: PRT
<213> ORGANISM: Orthohepadnaviridae hepatitis B virus

<400> SEQUENCE: 139

Trp Leu Ser Leu Leu Val Pro Phe
 1               5

<210> SEQ ID NO 140
<211> LENGTH: 11
<212> TYPE: PRT
<213> ORGANISM: Orthohepadnaviridae hepatitis B virus

<400> SEQUENCE: 140

Trp Leu Ser Leu Leu Val Pro Phe Val Gln Trp
 1               5                  10

<210> SEQ ID NO 141
<211> LENGTH: 10
<212> TYPE: PRT
<213> ORGANISM: Orthohepadnaviridae hepatitis B virus

<400> SEQUENCE: 141

Trp Leu Trp Gly Met Asp Ile Asp Pro Tyr
```

```
<210> SEQ ID NO 142
<211> LENGTH: 10
<212> TYPE: PRT
<213> ORGANISM: Orthohepadnaviridae hepatitis B virus

<400> SEQUENCE: 142

Trp Met Cys Leu Arg Arg Phe Ile Ile Phe
 1               5                  10

<210> SEQ ID NO 143
<211> LENGTH: 11
<212> TYPE: PRT
<213> ORGANISM: Orthohepadnaviridae hepatitis B virus

<400> SEQUENCE: 143

Trp Met Met Trp Tyr Trp Gly Pro Ser Leu Tyr
 1               5                  10

<210> SEQ ID NO 144
<211> LENGTH: 8
<212> TYPE: PRT
<213> ORGANISM: Orthohepadnaviridae hepatitis B virus

<400> SEQUENCE: 144

Trp Thr His Lys Val Gly Asn Phe
 1               5

<210> SEQ ID NO 145
<211> LENGTH: 11
<212> TYPE: PRT
<213> ORGANISM: Orthohepadnaviridae hepatitis B virus

<400> SEQUENCE: 145

Tyr Leu Pro Leu Asp Lys Gly Ile Lys Pro Tyr
 1               5                  10

<210> SEQ ID NO 146
<211> LENGTH: 8
<212> TYPE: PRT
<213> ORGANISM: Orthohepadnaviridae hepatitis B virus

<400> SEQUENCE: 146

Tyr Leu Val Ser Phe Gly Val Trp
 1               5

<210> SEQ ID NO 147
<211> LENGTH: 9
<212> TYPE: PRT
<213> ORGANISM: Orthohepadnaviridae hepatitis B virus

<400> SEQUENCE: 147

Tyr Ser His Pro Ile Ile Leu Gly Phe
 1               5

<210> SEQ ID NO 148
<211> LENGTH: 8
<212> TYPE: PRT
<213> ORGANISM: Orthohepadnaviridae hepatitis B virus

<400> SEQUENCE: 148

Tyr Ser Leu Asn Phe Met Gly Tyr
 1               5
```

```
<210> SEQ ID NO 149
<211> LENGTH: 11
<212> TYPE: PRT
<213> ORGANISM: Orthohepadnaviridae hepatitis B virus

<400> SEQUENCE: 149

Ala Ala Cys Phe Ala Arg Ser Arg Ser Gly Ala
1               5                   10

<210> SEQ ID NO 150
<211> LENGTH: 8
<212> TYPE: PRT
<213> ORGANISM: Orthohepadnaviridae hepatitis B virus

<400> SEQUENCE: 150

Ala Ala Met Pro His Leu Leu Val
1               5

<210> SEQ ID NO 151
<211> LENGTH: 9
<212> TYPE: PRT
<213> ORGANISM: Orthohepadnaviridae hepatitis B virus

<400> SEQUENCE: 151

Ala Ala Asn Trp Ile Leu Arg Gly Thr
1               5

<210> SEQ ID NO 152
<211> LENGTH: 11
<212> TYPE: PRT
<213> ORGANISM: Orthohepadnaviridae hepatitis B virus

<400> SEQUENCE: 152

Ala Ala Pro Phe Thr Gln Cys Gly Tyr Pro Ala
1               5                   10

<210> SEQ ID NO 153
<211> LENGTH: 9
<212> TYPE: PRT
<213> ORGANISM: Orthohepadnaviridae hepatitis B virus

<400> SEQUENCE: 153

Ala Ile Cys Ser Val Val Arg Arg Ala
1               5

<210> SEQ ID NO 154
<211> LENGTH: 8
<212> TYPE: PRT
<213> ORGANISM: Orthohepadnaviridae hepatitis B virus

<400> SEQUENCE: 154

Ala Ile Leu Cys Trp Gly Glu Leu
1               5

<210> SEQ ID NO 155
<211> LENGTH: 9
<212> TYPE: PRT
<213> ORGANISM: Orthohepadnaviridae hepatitis B virus

<400> SEQUENCE: 155

Ala Ile Leu Cys Trp Gly Glu Leu Met
1               5

<210> SEQ ID NO 156
```

```
<211> LENGTH: 9
<212> TYPE: PRT
<213> ORGANISM: Orthohepadnaviridae hepatitis B virus

<400> SEQUENCE: 156

Ala Leu Met Pro Leu Tyr Ala Cys Ile
1               5

<210> SEQ ID NO 157
<211> LENGTH: 8
<212> TYPE: PRT
<213> ORGANISM: Orthohepadnaviridae hepatitis B virus

<400> SEQUENCE: 157

Ala Met Gln Trp Asn Ser Thr Thr
1               5

<210> SEQ ID NO 158
<211> LENGTH: 9
<212> TYPE: PRT
<213> ORGANISM: Orthohepadnaviridae hepatitis B virus

<400> SEQUENCE: 158

Ala Met Ser Thr Thr Asp Leu Glu Ala
1               5

<210> SEQ ID NO 159
<211> LENGTH: 8
<212> TYPE: PRT
<213> ORGANISM: Orthohepadnaviridae hepatitis B virus

<400> SEQUENCE: 159

Ala Thr Pro Thr Gly Trp Gly Leu
1               5

<210> SEQ ID NO 160
<211> LENGTH: 9
<212> TYPE: PRT
<213> ORGANISM: Orthohepadnaviridae hepatitis B virus

<400> SEQUENCE: 160

Ala Thr Pro Thr Gly Trp Gly Leu Ala
1               5

<210> SEQ ID NO 161
<211> LENGTH: 10
<212> TYPE: PRT
<213> ORGANISM: Orthohepadnaviridae hepatitis B virus

<400> SEQUENCE: 161

Ala Thr Pro Thr Gly Trp Gly Leu Ala Ile
1               5                   10

<210> SEQ ID NO 162
<211> LENGTH: 8
<212> TYPE: PRT
<213> ORGANISM: Orthohepadnaviridae hepatitis B virus

<400> SEQUENCE: 162

Ala Val Pro Asn Leu Gln Ser Leu
1               5

<210> SEQ ID NO 163
<211> LENGTH: 9
<212> TYPE: PRT
```

-continued

<213> ORGANISM: Orthohepadnaviridae hepatitis B virus

<400> SEQUENCE: 163

Ala Val Pro Asn Leu Gln Ser Leu Thr
1               5

<210> SEQ ID NO 164
<211> LENGTH: 11
<212> TYPE: PRT
<213> ORGANISM: Orthohepadnaviridae hepatitis B virus

<400> SEQUENCE: 164

Ala Val Pro Asn Leu Gln Ser Leu Thr Asn Leu
1               5                   10

<210> SEQ ID NO 165
<211> LENGTH: 10
<212> TYPE: PRT
<213> ORGANISM: Orthohepadnaviridae hepatitis B virus

<400> SEQUENCE: 165

Cys Ala Ala Asn Trp Ile Leu Arg Gly Thr
1               5                   10

<210> SEQ ID NO 166
<211> LENGTH: 10
<212> TYPE: PRT
<213> ORGANISM: Orthohepadnaviridae hepatitis B virus

<400> SEQUENCE: 166

Cys Ala Phe Ser Ser Ala Gly Pro Cys Ala
1               5                   10

<210> SEQ ID NO 167
<211> LENGTH: 11
<212> TYPE: PRT
<213> ORGANISM: Orthohepadnaviridae hepatitis B virus

<400> SEQUENCE: 167

Cys Ala Phe Ser Ser Ala Gly Pro Cys Ala Leu
1               5                   10

<210> SEQ ID NO 168
<211> LENGTH: 8
<212> TYPE: PRT
<213> ORGANISM: Orthohepadnaviridae hepatitis B virus

<400> SEQUENCE: 168

Cys Ala Leu Arg Phe Thr Ser Ala
1               5

<210> SEQ ID NO 169
<211> LENGTH: 9
<212> TYPE: PRT
<213> ORGANISM: Orthohepadnaviridae hepatitis B virus

<400> SEQUENCE: 169

Cys Ile Pro Ile Pro Ser Ser Trp Ala
1               5

<210> SEQ ID NO 170
<211> LENGTH: 11
<212> TYPE: PRT
<213> ORGANISM: Orthohepadnaviridae hepatitis B virus

```
<400> SEQUENCE: 170

Cys Ile Pro Ile Pro Ser Ser Trp Ala Phe Ala
1               5                   10

<210> SEQ ID NO 171

Cys Leu Arg Arg Phe Ile Ile Phe Leu
1               5

<210> SEQ ID NO 178
<211> LENGTH: 11
<212> TYPE: PRT
<213> ORGANISM: Orthohepadnaviridae hepatitis B virus

<400> SEQUENCE: 178

Cys Leu Arg Arg Phe Ile Ile Phe Leu Phe Ile
1               5                   10

<210> SEQ ID NO 179
<211> LENGTH: 8
<212> TYPE: PRT
<213> ORGANISM: Orthohepadnaviridae hepatitis B virus

<400> SEQUENCE: 179

Cys Leu Thr Phe Gly Arg Glu Thr
1               5

<210> SEQ ID NO 180
<211> LENGTH: 9
<212> TYPE: PRT
<213> ORGANISM: Orthohepadnaviridae hepatitis B virus

<400> SEQUENCE: 180

Cys Leu Thr Phe Gly Arg Glu Thr Val
1               5

<210> SEQ ID NO 181
<211> LENGTH: 11
<212> TYPE: PRT
<213> ORGANISM: Orthohepadnaviridae hepatitis B virus

<400> SEQUENCE: 181

Cys Thr Cys Ile Pro Ile Pro Ser Ser Trp Ala
1               5                   10

<210> SEQ ID NO 182
<211> LENGTH: 9
<212> TYPE: PRT
<213> ORGANISM: Orthohepadnaviridae hepatitis B virus

<400> SEQUENCE: 182

Asp Ala Thr Pro Thr Gly Trp Gly Leu
1               5

<210> SEQ ID NO 183
<211> LENGTH: 10
<212> TYPE: PRT
<213> ORGANISM: Orthohepadnaviridae hepatitis B virus

<400> SEQUENCE: 183

Asp Ala Thr Pro Thr Gly Trp Gly Leu Ala
1               5                   10

<210> SEQ ID NO 184
<211> LENGTH: 11
<212> TYPE: PRT
<213> ORGANISM: Orthohepadnaviridae hepatitis B virus

<400> SEQUENCE: 184

Asp Ala Thr Pro Thr Gly Trp Gly Leu Ala Ile
1               5                   10

<210> SEQ ID NO 185
<211> LENGTH: 10
<212> TYPE: PRT
<213> ORGANISM: Orthohepadnaviridae hepatitis B virus

<400> SEQUENCE: 185

Asp Ile Asp Pro Tyr Lys Glu Phe Gly Ala
1               5                   10

<210> SEQ ID NO 186
<211> LENGTH: 8
<212> TYPE: PRT
<213> ORGANISM: Orthohepadnaviridae hepatitis B virus

<400> SEQUENCE: 186

Asp Leu Leu Asp Thr Ala Ser Ala
1               5

<210> SEQ ID NO 187
<211> LENGTH: 9
<212> TYPE: PRT
<213> ORGANISM: Orthohepadnaviridae hepatitis B virus

<400> SEQUENCE: 187

Asp Leu Leu Asp Thr Ala Ser Ala Leu
1               5

<210> SEQ ID NO 188
<211> LENGTH: 9
<212> TYPE: PRT
<213> ORGANISM: Orthohepadnaviridae hepatitis B virus

<400> SEQUENCE: 188

Asp Leu Asn Leu Gly Asn Leu Asn Val
1               5

<210> SEQ ID NO 189
<211> LENGTH: 11
<212> TYPE: PRT
<213> ORGANISM: Orthohepadnaviridae hepatitis B virus

<400> SEQUENCE: 189

Asp Leu Asn Leu Gly Asn Leu Asn Val Ser Ile
1               5                   10

<210> SEQ ID NO 190
<211> LENGTH: 10
<212> TYPE: PRT
<213> ORGANISM: Orthohepadnaviridae hepatitis B virus

<400> SEQUENCE: 190

Asp Thr Ala Ser Ala Leu Tyr Arg Glu Ala
1               5                   10

<210> SEQ ID NO 191
<211> LENGTH: 11
<212> TYPE: PRT
<213> ORGANISM: Orthohepadnaviridae hepatitis B virus

<400> SEQUENCE: 191

Asp Thr Ala Ser Ala Leu Tyr Arg Glu Ala Leu
1               5                   10

<210> SEQ ID NO 192
<211> LENGTH: 8
<212> TYPE: PRT
<213> ORGANISM: Orthohepadnaviridae hepatitis B virus

<400> SEQUENCE: 192

Asp Val Leu Cys Leu Arg Pro Val
1               5

<210> SEQ ID NO 193
<211> LENGTH: 10
<212> TYPE: PRT
<213> ORGANISM: Orthohepadnaviridae hepatitis B virus

<400> SEQUENCE: 193

Asp Val Leu Cys Leu Arg Pro Val Gly Ala
1               5                   10

<210> SEQ ID NO 194
<211> LENGTH: 9
<212> TYPE: PRT
<213> ORGANISM: Orthohepadnaviridae hepatitis B virus

<400> SEQUENCE: 194

Asp Val Val Leu Gly Ala Lys Ser Val
1               5

<210> SEQ ID NO 195
<211> LENGTH: 9
<212> TYPE: PRT
<213> ORGANISM: Orthohepadnaviridae hepatitis B virus

<400> SEQUENCE: 195

Glu Ala Gly Pro Leu Glu Glu Glu Leu
1               5

<210> SEQ ID NO 196
<211> LENGTH: 8
<212> TYPE: PRT
<213> ORGANISM: Orthohepadnaviridae hepatitis B virus

<400> SEQUENCE: 196

Glu Leu Gly Glu Glu Ile Arg Leu
1               5

<210> SEQ ID NO 197
<211> LENGTH: 8
<212> TYPE: PRT
<213> ORGANISM: Orthohepadnaviridae hepatitis B virus

<400> SEQUENCE: 197

Glu Leu Leu Ala Ala Cys Phe Ala
1               5

<210> SEQ ID NO 198
<211> LENGTH: 8
<212> TYPE: PRT
<213> ORGANISM: Orthohepadnaviridae hepatitis B virus

<400> SEQUENCE: 198

Glu Thr Val Leu Glu Tyr Leu Val
1               5

<210> SEQ ID NO 199
<211> LENGTH: 11

```
<212> TYPE: PRT
<213> ORGANISM: Orthohepadnaviridae hepatitis B virus

<400> SEQUENCE: 199

Phe Ala Asp Ala Thr Pro Thr Gly Trp Gly Leu
 1               5                  10

<210> SEQ ID NO 200
<211> LENGTH: 8
<212> TYPE: PRT
<213> ORGANISM: Orthohepadnaviridae hepatitis B virus

<400> SEQUENCE: 200

Phe Ala Arg Ser Arg Ser Gly Ala
 1               5

<210> SEQ ID NO 201
<211> LENGTH: 8
<212> TYPE: PRT
<213> ORGANISM: Orthohepadnaviridae hepatitis B virus

<400> SEQUENCE: 201

Phe Ala Ser Pro Leu His Val Ala
 1               5

<210> SEQ ID NO 202
<211> LENGTH: 9
<212> TYPE: PRT
<213> ORGANISM: Orthohepadnaviridae hepatitis B virus

<400> SEQUENCE: 202

Phe Ala Val Pro Asn Leu Gln Ser Leu
 1               5

<210> SEQ ID NO 203
<211> LENGTH: 10
<212> TYPE: PRT
<213> ORGANISM: Orthohepadnaviridae hepatitis B virus

<400> SEQUENCE: 203

Phe Ala Val Pro Asn Leu Gln Ser Leu Thr
 1               5                  10

<210> SEQ ID NO 204
<211> LENGTH: 8
<212> TYPE: PRT
<213> ORGANISM: Orthohepadnaviridae hepatitis B virus

<400> SEQUENCE: 204

Phe Ile Ile Phe Leu Phe Ile Leu
 1               5

<210> SEQ ID NO 205
<211> LENGTH: 9
<212> TYPE: PRT
<213> ORGANISM: Orthohepadnaviridae hepatitis B virus

<400> SEQUENCE: 205

Phe Ile Ile Phe Leu Phe Ile Leu Leu
 1               5

<210> SEQ ID NO 206
<211> LENGTH: 10
<212> TYPE: PRT
<213> ORGANISM: Orthohepadnaviridae hepatitis B virus
```

<400> SEQUENCE: 206

Phe Ile Ile Phe Leu Phe Ile Leu Leu Leu
1               5                   10

<210> SEQ ID NO 207
<211> LENGTH: 8
<212> TYPE: PRT
<213> ORGANISM: Orthohepadnaviridae hepatitis B virus

<400> SEQUENCE: 207

Phe Ile Leu Leu Leu Cys Leu Ile
1               5

<210> SEQ ID NO 208
<211> LENGTH: 10
<212> TYPE: PRT
<213> ORGANISM: Orthohepadnaviridae hepatitis B virus

<400> SEQUENCE: 208

Phe Ile Leu Leu Leu Cys Leu Ile Phe Leu
1               5                   10

<210> SEQ ID NO 209
<211> LENGTH: 11
<212> TYPE: PRT
<213> ORGANISM: Orthohepadnaviridae hepatitis B virus

<400> SEQUENCE: 209

Phe Ile Leu Leu Leu Cys Leu Ile Phe Leu Leu
1               5                   10

<210> SEQ ID NO 210
<211> LENGTH: 9
<212> TYPE: PRT
<213> ORGANISM: Orthohepadnaviridae hepatitis B virus

<400> SEQUENCE: 210

Phe Leu Phe Ile Leu Leu Leu Cys Leu
1               5

<210> SEQ ID NO 211
<211> LENGTH: 10
<212> TYPE: PRT
<213> ORGANISM: Orthohepadnaviridae hepatitis B virus

<400> SEQUENCE: 211

Phe Leu Phe Ile Leu Leu Leu Cys Leu Ile
1               5                   10

<210> SEQ ID NO 212
<211> LENGTH: 8
<212> TYPE: PRT
<213> ORGANISM: Orthohepadnaviridae hepatitis B virus

<400> SEQUENCE: 212

Phe Leu Gly Pro Leu Leu Val Leu
1               5

<210> SEQ ID NO 213
<211> LENGTH: 10
<212> TYPE: PRT
<213> ORGANISM: Orthohepadnaviridae hepatitis B virus

<400> SEQUENCE: 213

```
Phe Leu Gly Pro Leu Leu Val Leu Gln Ala
1               5                   10

<210> SEQ ID NO 214
<211> LENGTH: 9
<212> TYPE: PRT
<213> ORGANISM: Orthohepadnaviridae hepatitis B virus

<400> SEQUENCE: 214

Phe Leu Leu Ala Gln Phe Thr Ser Ala
1               5

<210> SEQ ID NO 215
<211> LENGTH: 10
<212> TYPE: PRT
<213> ORGANISM: Orthohepadnaviridae hepatitis B virus

<400> SEQUENCE: 215

Phe Leu Leu Ala Gln Phe Thr Ser Ala Ile
1               5                   10

<210> SEQ ID NO 216
<211> LENGTH: 9
<212> TYPE: PRT
<213> ORGANISM: Orthohepadnaviridae hepatitis B virus

<400> SEQUENCE: 216

Phe Leu Leu Ser Leu Gly Ile His Leu
1               5

<210> SEQ ID NO 217
<211> LENGTH: 8
<212> TYPE: PRT
<213> ORGANISM: Orthohepadnaviridae hepatitis B virus

<400> SEQUENCE: 217

Phe Leu Leu Thr Arg Ile Leu Thr
1               5

<210> SEQ ID NO 218
<211> LENGTH: 9
<212> TYPE: PRT
<213> ORGANISM: Orthohepadnaviridae hepatitis B virus

<400> SEQUENCE: 218

Phe Leu Leu Thr Arg Ile Leu Thr Ile
1               5

<210> SEQ ID NO 219
<211> LENGTH: 11
<212> TYPE: PRT
<213> ORGANISM: Orthohepadnaviridae hepatitis B virus

<400> SEQUENCE: 219

Phe Leu Leu Val Leu Leu Asp Tyr Gln Gly Met
1               5                   10

<210> SEQ ID NO 220
<211> LENGTH: 10
<212> TYPE: PRT
<213> ORGANISM: Orthohepadnaviridae hepatitis B virus

<400> SEQUENCE: 220

Phe Leu Val Asp Lys Asn Pro His Asn Thr
```

-continued

<210> SEQ ID NO 221
<211> LENGTH: 9
<212> TYPE: PRT
<213> ORGANISM: Orthohepadnaviridae hepatitis B virus

<400> SEQUENCE: 221

Phe Thr Phe Ser Pro Thr Tyr Lys Ala
1               5

<210> SEQ ID NO 222
<211> LENGTH: 11
<212> TYPE: PRT
<213> ORGANISM: Orthohepadnaviridae hepatitis B virus

<400> SEQUENCE: 222

Phe Thr Phe Ser Pro Thr Tyr Lys Ala Phe Leu
1               5                   10

<210> SEQ ID NO 223
<211> LENGTH: 8
<212> TYPE: PRT
<213> ORGANISM: Orthohepadnaviridae hepatitis B virus

<400> SEQUENCE: 223

Phe Thr Gly Leu Tyr Ser Ser Thr
1               5

<210> SEQ ID NO 224
<211> LENGTH: 9
<212> TYPE: PRT
<213> ORGANISM: Orthohepadnaviridae hepatitis B virus

<400> SEQUENCE: 224

Phe Thr Gly Leu Tyr Ser Ser Thr Val
1               5

<210> SEQ ID NO 225
<211> LENGTH: 8
<212> TYPE: PRT
<213> ORGANISM: Orthohepadnaviridae hepatitis B virus

<400> SEQUENCE: 225

Phe Thr Gln Cys Gly Tyr Pro Ala
1               5

<210> SEQ ID NO 226
<211> LENGTH: 9
<212> TYPE: PRT
<213> ORGANISM: Orthohepadnaviridae hepatitis B virus

<400> SEQUENCE: 226

Phe Thr Gln Cys Gly Tyr Pro Ala Leu
1               5

<210> SEQ ID NO 227
<211> LENGTH: 10
<212> TYPE: PRT
<213> ORGANISM: Orthohepadnaviridae hepatitis B virus

<400> SEQUENCE: 227

Phe Thr Gln Cys Gly Tyr Pro Ala Leu Met
1               5                   10

<210> SEQ ID NO 228
<211> LENGTH: 8
<212> TYPE: PRT
<213> ORGANISM: Orthohepadnaviridae hepatitis B virus

<400> SEQUENCE: 228

Phe Thr Ser Ala Ile Cys Ser Val
 1               5

<210> SEQ ID NO 229
<211> LENGTH: 9
<212> TYPE: PRT
<213> ORGANISM: Orthohepadnaviridae hepatitis B virus

<400> SEQUENCE: 229

Phe Thr Ser Ala Ile Cys Ser Val Val
 1               5

<210> SEQ ID NO 230
<211> LENGTH: 8
<212> TYPE: PRT
<213> ORGANISM: Orthohepadnaviridae hepatitis B virus

<400> SEQUENCE: 230

Phe Val Gly Leu Ser Pro Thr Val
 1               5

<210> SEQ ID NO 231
<211> LENGTH: 10
<212> TYPE: PRT
<213> ORGANISM: Orthohepadnaviridae hepatitis B virus

<400> SEQUENCE: 231

Phe Val Gly Leu Ser Pro Thr Val Trp Leu
 1               5                  10

<210> SEQ ID NO 232
<211> LENGTH: 10
<212> TYPE: PRT
<213> ORGANISM: Orthohepadnaviridae hepatitis B virus

<400> SEQUENCE: 232

Phe Val Leu Gly Gly Cys Arg His Lys Leu
 1               5                  10

<210> SEQ ID NO 233
<211> LENGTH: 11
<212> TYPE: PRT
<213> ORGANISM: Orthohepadnaviridae hepatitis B virus

<400> SEQUENCE: 233

Phe Val Leu Gly Gly Cys Arg His Lys Leu Val
 1               5                  10

<210> SEQ ID NO 234
<211> LENGTH: 8
<212> TYPE: PRT
<213> ORGANISM: Orthohepadnaviridae hepatitis B virus

<400> SEQUENCE: 234

Phe Val Gln Trp Phe Val Gly Leu
 1               5

<210> SEQ ID NO 235

-continued

<211> LENGTH: 11
<212> TYPE: PRT
<213> ORGANISM: Orthohepadnaviridae hepatitis B virus

<400> SEQUENCE: 235

Phe Val Gln Trp Phe Val Gly Leu Ser Pro Thr
1               5                   10

<210> SEQ ID NO 236
<211> LENGTH: 8
<212> TYPE: PRT
<213> ORGANISM: Orthohepadnaviridae hepatitis B virus

<400> SEQUENCE: 236

Phe Val Tyr Val Pro Ser Ala Leu
1               5

<210> SEQ ID NO 237
<211> LENGTH: 11
<212> TYPE: PRT
<213> ORGANISM: Orthohepadnaviridae hepatitis B virus

<400> SEQUENCE: 237

Phe Val Tyr Val Pro Ser Ala Leu Asn Pro Ala
1               5                   10

<210> SEQ ID NO 238
<211> LENGTH: 9
<212> TYPE: PRT
<213> ORGANISM: Orthohepadnaviridae hepatitis B virus

<400> SEQUENCE: 238

Gly Ala His Leu Ser Leu Arg Gly Leu
1               5

<210> SEQ ID NO 239
<211> LENGTH: 11
<212> TYPE: PRT
<213> ORGANISM: Orthohepadnaviridae hepatitis B virus

<400> SEQUENCE: 239

Gly Ala His Leu Ser Leu Arg Gly Leu Pro Val
1               5                   10

<210> SEQ ID NO 240
<211> LENGTH: 8
<212> TYPE: PRT
<213> ORGANISM: Orthohepadnaviridae hepatitis B virus

<400> SEQUENCE: 240

Gly Ala Lys Ser Val Gln His Leu
1               5

<210> SEQ ID NO 241
<211> LENGTH: 11
<212> TYPE: PRT
<213> ORGANISM: Orthohepadnaviridae hepatitis B virus

<400> SEQUENCE: 241

Gly Ala Lys Ser Val Gln His Leu Glu Ser Leu
1               5                   10

<210> SEQ ID NO 242
<211> LENGTH: 9
<212> TYPE: PRT

<213> ORGANISM: Orthohepadnaviridae hepatitis B virus

<400> SEQUENCE: 242

Gly Ile His Leu Asn Pro Asn Lys Thr
1 5

<210> SEQ ID NO 243
<211> LENGTH: 8
<212> TYPE: PRT
<213> ORGANISM: Orthohepadnaviridae hepatitis B virus

<400> SEQUENCE: 243

Gly Ile Leu Tyr Lys Arg Glu Thr
1 5

<210> SEQ ID NO 244
<211> LENGTH: 9
<212> TYPE: PRT
<213> ORGANISM: Orthohepadnaviridae hepatitis B virus

<400> SEQUENCE: 244

Gly Ile Leu Tyr Lys Arg Glu Thr Thr
1 5

<210> SEQ ID NO 245
<211> LENGTH: 9
<212> TYPE: PRT
<213> ORGANISM: Orthohepadnaviridae hepatitis B virus

<400> SEQUENCE: 245

Gly Leu Cys Gln Val Phe Ala Asp Ala
1 5

<210> SEQ ID NO 246
<211> LENGTH: 10
<212> TYPE: PRT
<213> ORGANISM: Orthohepadnaviridae hepatitis B virus

<400> SEQUENCE: 246

Gly Leu Cys Gln Val Phe Ala Asp Ala Thr
1 5 10

<210> SEQ ID NO 247
<211> LENGTH: 10
<212> TYPE: PRT
<213> ORGANISM: Orthohepadnaviridae hepatitis B virus

<400> SEQUENCE: 247

Gly Leu Leu Gly Phe Ala Ala Pro Phe Thr
1 5 10

<210> SEQ ID NO 248
<211> LENGTH: 9
<212> TYPE: PRT
<213> ORGANISM: Orthohepadnaviridae hepatitis B virus

<400> SEQUENCE: 248

Gly Leu Leu Gly Trp Ser Pro Gln Ala
1 5

<210> SEQ ID NO 249
<211> LENGTH: 10
<212> TYPE: PRT
<213> ORGANISM: Orthohepadnaviridae hepatitis B virus

```
<400> SEQUENCE: 249

Gly Leu Pro Val Cys Ala Phe Ser Ser Ala
1               5                   10

<210> SEQ ID NO 250
<211> LENGTH: 8
<212> TYPE: PRT
<213> ORGANISM: Orthohepadnaviridae hepatitis B virus

<400> SEQUENCE: 250

Gly Leu Ser Pro Phe Leu Leu Ala
1               5

<210> SEQ ID NO 251
<211> LENGTH: 11
<212> TYPE: PRT
<213> ORGANISM: Orthohepadnaviridae hepatitis B virus

<400> SEQUENCE: 251

Gly Leu Ser Pro Phe Leu Leu Ala Gln Phe Thr
1               5                   10

<210> SEQ ID NO 252
<211> LENGTH: 8
<212> TYPE: PRT
<213> ORGANISM: Orthohepadnaviridae hepatitis B virus

<400> SEQUENCE: 252

Gly Leu Ser Pro Thr Val Trp Leu
1               5

<210> SEQ ID NO 253
<211> LENGTH: 10
<212> TYPE: PRT
<213> ORGANISM: Orthohepadnaviridae hepatitis B virus

<400> SEQUENCE: 253

Gly Leu Ser Pro Thr Val Trp Leu Ser Val
1               5                   10

<210> SEQ ID NO 254
<211> LENGTH: 11
<212> TYPE: PRT
<213> ORGANISM: Orthohepadnaviridae hepatitis B virus

<400> SEQUENCE: 254

Gly Leu Ser Pro Thr Val Trp Leu Ser Val Ile
1               5                   10

<210> SEQ ID NO 255
<211> LENGTH: 8
<212> TYPE: PRT
<213> ORGANISM: Orthohepadnaviridae hepatitis B virus

<400> SEQUENCE: 255

Gly Met Leu Pro Val Cys Pro Leu
1               5

<210> SEQ ID NO 256
<211> LENGTH: 8
<212> TYPE: PRT
<213> ORGANISM: Orthohepadnaviridae hepatitis B virus

<400> SEQUENCE: 256
```

Gly Thr Asp Asn Ser Val Val Leu
1               5

<210> SEQ ID NO 257
<211> LENGTH: 10
<212> TYPE: PRT
<213> ORGANISM: Orthohepadnaviridae hepatitis B virus

<400> SEQUENCE: 257

Gly Thr Asn Leu Ser Val Pro Asn Pro Leu
1               5                   10

<210> SEQ ID NO 258
<211> LENGTH: 10
<212> TYPE: PRT
<213> ORGANISM: Orthohepadnaviridae hepatitis B virus

<400> SEQUENCE: 258

Gly Thr Ser Phe Val Tyr Val Pro Ser Ala
1               5                   10

<210> SEQ ID NO 259
<211> LENGTH: 11
<212> TYPE: PRT
<213> ORGANISM: Orthohepadnaviridae hepatitis B virus

<400> SEQUENCE: 259

Gly Thr Ser Phe Val Tyr Val Pro Ser Ala Leu
1               5                   10

<210> SEQ ID NO 260
<211> LENGTH: 8
<212> TYPE: PRT
<213> ORGANISM: Orthohepadnaviridae hepatitis B virus

<400> SEQUENCE: 260

Gly Val Gly Leu Ser Pro Phe Leu
1               5

<210> SEQ ID NO 261
<211> LENGTH: 9
<212> TYPE: PRT
<213> ORGANISM: Orthohepadnaviridae hepatitis B virus

<400> SEQUENCE: 261

Gly Val Gly Leu Ser Pro Phe Leu Leu
1               5

<210> SEQ ID NO 262
<211> LENGTH: 10
<212> TYPE: PRT
<213> ORGANISM: Orthohepadnaviridae hepatitis B virus

<400> SEQUENCE: 262

Gly Val Gly Leu Ser Pro Phe Leu Leu Ala
1               5                   10

<210> SEQ ID NO 263
<211> LENGTH: 9
<212> TYPE: PRT
<213> ORGANISM: Orthohepadnaviridae hepatitis B virus

<400> SEQUENCE: 263

Gly Val Trp Ile Arg Thr Pro Pro Ala
1               5

```
<210> SEQ ID NO 264
<211> LENGTH: 11
<212> TYPE: PRT
<213> ORGANISM: Orthohepadnaviridae hepatitis B virus

<400> SEQUENCE: 264

His Ile Ser Cys Leu Thr Phe Gly Arg Glu Thr
 1               5                  10

<210> SEQ ID NO 265
<211> LENGTH: 9
<212> TYPE: PRT
<213> ORGANISM: Orthohepadnaviridae hepatitis B virus

<400> SEQUENCE: 265

His Leu Leu Val Gly Ser Ser Gly Leu
 1               5

<210> SEQ ID NO 266
<211> LENGTH: 9
<212> TYPE: PRT
<213> ORGANISM: Orthohepadnaviridae hepatitis B virus

<400> SEQUENCE: 266

His Leu Ser Leu Arg Gly Leu Pro Val
 1               5

<210> SEQ ID NO 267
<211> LENGTH: 11
<212> TYPE: PRT
<213> ORGANISM: Orthohepadnaviridae hepatitis B virus

<400> SEQUENCE: 267

His Leu Ser Leu Arg Gly Leu Pro Val Cys Ala
 1               5                  10

<210> SEQ ID NO 268
<211> LENGTH: 8
<212> TYPE: PRT
<213> ORGANISM: Orthohepadnaviridae hepatitis B virus

<400> SEQUENCE: 268

His Leu Tyr Ser His Pro Ile Ile
 1               5

<210> SEQ ID NO 269
<211> LENGTH: 9
<212> TYPE: PRT
<213> ORGANISM: Orthohepadnaviridae hepatitis B virus

<400> SEQUENCE: 269

His Leu Tyr Ser His Pro Ile Ile Leu
 1               5

<210> SEQ ID NO 270
<211> LENGTH: 8
<212> TYPE: PRT
<213> ORGANISM: Orthohepadnaviridae hepatitis B virus

<400> SEQUENCE: 270

His Thr Ala Glu Leu Leu Ala Ala
 1               5
```

-continued

<210> SEQ ID NO 271
<211> LENGTH: 11
<212> TYPE: PRT
<213> ORGANISM: Orthohepadnaviridae hepatitis B virus

<400> SEQUENCE: 271

His Thr Ala Glu Leu Leu Ala Ala Cys Phe Ala
1 5 10

<210> SEQ ID NO 272
<211> LENGTH: 8
<212> TYPE: PRT
<213> ORGANISM: Orthohepadnaviridae hepatitis B virus

<400> SEQUENCE: 272

His Thr Ala Leu Arg Gln Ala Ile
1 5

<210> SEQ ID NO 273
<211> LENGTH: 9
<212> TYPE: PRT
<213> ORGANISM: Orthohepadnaviridae hepatitis B virus

<400> SEQUENCE: 273

His Thr Ala Leu Arg Gln Ala Ile Leu
1 5

<210> SEQ ID NO 274
<211> LENGTH: 8
<212> TYPE: PRT
<213> ORGANISM: Orthohepadnaviridae hepatitis B virus

<400> SEQUENCE: 274

His Thr Leu Trp Lys Ala Gly Ile
1 5

<210> SEQ ID NO 275
<211> LENGTH: 9
<212> TYPE: PRT
<213> ORGANISM: Orthohepadnaviridae hepatitis B virus

<400> SEQUENCE: 275

His Thr Leu Trp Lys Ala Gly Ile Leu
1 5

<210> SEQ ID NO 276
<211> LENGTH: 8
<212> TYPE: PRT
<213> ORGANISM: Orthohepadnaviridae hepatitis B virus

<400> SEQUENCE: 276

Ile Ile Phe Leu Phe Ile Leu Leu
1 5

<210> SEQ ID NO 277
<211> LENGTH: 9
<212> TYPE: PRT
<213> ORGANISM: Orthohepadnaviridae hepatitis B virus

<400> SEQUENCE: 277

Ile Ile Phe Leu Phe Ile Leu Leu Leu
1 5

<210> SEQ ID NO 278
<211> LENGTH: 11

```
<212> TYPE: PRT
<213> ORGANISM: Orthohepadnaviridae hepatitis B virus

<400> SEQUENCE: 278

Ile Ile Phe Leu Phe Ile Leu Leu Leu Cys Leu
1               5                   10

<210> SEQ ID NO 279
<211> LENGTH: 8
<212> TYPE: PRT
<213> ORGANISM: Orthohepadnaviridae hepatitis B virus

<400> SEQUENCE: 279

Ile Ile Leu Gly Phe Arg Lys Ile
1               5

<210> SEQ ID NO 280
<211> LENGTH: 10
<212> TYPE: PRT
<213> ORGANISM: Orthohepadnaviridae hepatitis B virus

<400> SEQUENCE: 280

Ile Ile Leu Gly Phe Arg Lys Ile Pro Met
1               5                   10

<210> SEQ ID NO 281
<211> LENGTH: 8
<212> TYPE: PRT
<213> ORGANISM: Orthohepadnaviridae hepatitis B virus

<400> SEQUENCE: 281

Ile Leu Cys Trp Gly Glu Leu Met
1               5

<210> SEQ ID NO 282
<211> LENGTH: 9
<212> TYPE: PRT
<213> ORGANISM: Orthohepadnaviridae hepatitis B virus

<400> SEQUENCE: 282

Ile Leu Gly Phe Arg Lys Ile Pro Met
1               5

<210> SEQ ID NO 283
<211> LENGTH: 9
<212> TYPE: PRT
<213> ORGANISM: Orthohepadnaviridae hepatitis B virus

<400> SEQUENCE: 283

Ile Leu Leu Leu Cys Leu Ile Phe Leu
1               5

<210> SEQ ID NO 284
<211> LENGTH: 10
<212> TYPE: PRT
<213> ORGANISM: Orthohepadnaviridae hepatitis B virus

<400> SEQUENCE: 284

Ile Leu Leu Leu Cys Leu Ile Phe Leu Leu
1               5                   10

<210> SEQ ID NO 285
<211> LENGTH: 11
<212> TYPE: PRT
<213> ORGANISM: Orthohepadnaviridae hepatitis B virus
```

```
<400> SEQUENCE: 285

Ile Leu Leu Leu Cys Leu Ile Phe Leu Leu Val
1               5                   10

<210> SEQ ID NO 286
<211> LENGTH: 8
<212> TYPE: PRT
<213> ORGANISM: Orthohepadnaviridae hepatitis B virus

<400> SEQUENCE: 286

Ile Leu Arg Gly Thr Ser Phe Val
1               5

<210> SEQ ID NO 287
<211> LENGTH: 10
<212> TYPE: PRT
<213> ORGANISM: Orthohepadnaviridae hepatitis B virus

<400> SEQUENCE: 287

Ile Leu Arg Gly Thr Ser Phe Val Tyr Val
1               5                   10

<210> SEQ ID NO 288
<211> LENGTH: 8
<212> TYPE: PRT
<213> ORGANISM: Orthohepadnaviridae hepatitis B virus

<400> SEQUENCE: 288

Ile Leu Ser Thr Leu Pro Glu Thr
1               5

<210> SEQ ID NO 289
<211> LENGTH: 9
<212> TYPE: PRT
<213> ORGANISM: Orthohepadnaviridae hepatitis B virus

<400> SEQUENCE: 289

Ile Leu Ser Thr Leu Pro Glu Thr Thr
1               5

<210> SEQ ID NO 290
<211> LENGTH: 10
<212> TYPE: PRT
<213> ORGANISM: Orthohepadnaviridae hepatitis B virus

<400> SEQUENCE: 290

Ile Leu Ser Thr Leu Pro Glu Thr Thr Val
1               5                   10

<210> SEQ ID NO 291
<211> LENGTH: 11
<212> TYPE: PRT
<213> ORGANISM: Orthohepadnaviridae hepatitis B virus

<400> SEQUENCE: 291

Ile Leu Ser Thr Leu Pro Glu Thr Thr Val Val
1               5                   10

<210> SEQ ID NO 292
<211> LENGTH: 8
<212> TYPE: PRT
<213> ORGANISM: Orthohepadnaviridae hepatitis B virus

<400> SEQUENCE: 292
```

Ile Leu Thr Ile Pro Gln Ser Leu
1               5

<210> SEQ ID NO 293
<211> LENGTH: 8
<212> TYPE: PRT
<213> ORGANISM: Orthohepadnaviridae hepatitis B virus

<400> SEQUENCE: 293

Ile Leu Tyr Lys Arg Glu Thr Thr
1               5

<210> SEQ ID NO 294
<211> LENGTH: 8
<212> TYPE: PRT
<213> ORGANISM: Orthohepadnaviridae hepatitis B virus

<400> SEQUENCE: 294

Ile Val Gly Leu Leu Gly Phe Ala
1               5

<210> SEQ ID NO 295
<211> LENGTH: 9
<212> TYPE: PRT
<213> ORGANISM: Orthohepadnaviridae hepatitis B virus

<400> SEQUENCE: 295

Ile Val Gly Leu Leu Gly Phe Ala Ala
1               5

<210> SEQ ID NO 296
<211> LENGTH: 10
<212> TYPE: PRT
<213> ORGANISM: Orthohepadnaviridae hepatitis B virus

<400> SEQUENCE: 296

Lys Ala Gly Ile Leu Tyr Lys Arg Glu Thr
1               5                   10

<210> SEQ ID NO 297
<211> LENGTH: 11
<212> TYPE: PRT
<213> ORGANISM: Orthohepadnaviridae hepatitis B virus

<400> SEQUENCE: 297

Lys Ala Gly Ile Leu Tyr Lys Arg Glu Thr Thr
1               5                   10

<210> SEQ ID NO 298
<211> LENGTH: 8
<212> TYPE: PRT
<213> ORGANISM: Orthohepadnaviridae hepatitis B virus

<400> SEQUENCE: 298

Lys Ile Pro Met Gly Val Gly Leu
1               5

<210> SEQ ID NO 299
<211> LENGTH: 10
<212> TYPE: PRT
<213> ORGANISM: Orthohepadnaviridae hepatitis B virus

<400> SEQUENCE: 299

Lys Leu Cys Leu Gly Trp Leu Trp Gly Met

-continued

```
<210> SEQ ID NO 300
<211> LENGTH: 9
<212> TYPE: PRT
<213> ORGANISM: Orthohepadnaviridae hepatitis B virus

<400> SEQUENCE: 300

Lys Leu His Leu Tyr Ser His Pro Ile
1               5

<210> SEQ ID NO 301
<211> LENGTH: 10
<212> TYPE: PRT
<213> ORGANISM: Orthohepadnaviridae hepatitis B virus

<400> SEQUENCE: 301

Lys Leu His Leu Tyr Ser His Pro Ile Ile
1               5                   10

<210> SEQ ID NO 302
<211> LENGTH: 11
<212> TYPE: PRT
<213> ORGANISM: Orthohepadnaviridae hepatitis B virus

<400> SEQUENCE: 302

Lys Leu His Leu Tyr Ser His Pro Ile Ile Leu
1               5                   10

<210> SEQ ID NO 303
<211> LENGTH: 8
<212> TYPE: PRT
<213> ORGANISM: Orthohepadnaviridae hepatitis B virus

<400> SEQUENCE: 303

Lys Leu Pro Val Asn Arg Pro Ile
1               5

<210> SEQ ID NO 304
<211> LENGTH: 9
<212> TYPE: PRT
<213> ORGANISM: Orthohepadnaviridae hepatitis B virus

<400> SEQUENCE: 304

Lys Thr Lys Arg Trp Gly Tyr Ser Leu
1               5

<210> SEQ ID NO 305
<211> LENGTH: 9
<212> TYPE: PRT
<213> ORGANISM: Orthohepadnaviridae hepatitis B virus

<400> SEQUENCE: 305

Lys Val Cys Gln Arg Ile Val Gly Leu
1               5

<210> SEQ ID NO 306
<211> LENGTH: 10
<212> TYPE: PRT
<213> ORGANISM: Orthohepadnaviridae hepatitis B virus

<400> SEQUENCE: 306

Lys Val Cys Gln Arg Ile Val Gly Leu Leu
1               5                   10
```

<210> SEQ ID NO 307
<211> LENGTH: 8
<212> TYPE: PRT
<213> ORGANISM: Orthohepadnaviridae hepatitis B virus

<400> SEQUENCE: 307

Lys Val Gly Asn Phe Thr Gly Leu
1               5

<210> SEQ ID NO 308
<211> LENGTH: 8
<212> TYPE: PRT
<213> ORGANISM: Orthohepadnaviridae hepatitis B virus

<400> SEQUENCE: 308

Lys Val Leu His Lys Arg Thr Leu
1               5

<210> SEQ ID NO 309
<211> LENGTH: 10
<212> TYPE: PRT
<213> ORGANISM: Orthohepadnaviridae hepatitis B virus

<400> SEQUENCE: 309

Lys Val Leu His Lys Arg Thr Leu Gly Leu
1               5                   10

<210> SEQ ID NO 310
<211> LENGTH: 9
<212> TYPE: PRT
<213> ORGANISM: Orthohepadnaviridae hepatitis B virus

<400> SEQUENCE: 310

Leu Ala Phe Ser Tyr Met Asp Asp Val
1               5

<210> SEQ ID NO 311
<211> LENGTH: 10
<212> TYPE: PRT
<213> ORGANISM: Orthohepadnaviridae hepatitis B virus

<400> SEQUENCE: 311

Leu Ala Phe Ser Tyr Met Asp Asp Val Val
1               5                   10

<210> SEQ ID NO 312
<211> LENGTH: 11
<212> TYPE: PRT
<213> ORGANISM: Orthohepadnaviridae hepatitis B virus

<400> SEQUENCE: 312

Leu Ala Phe Ser Tyr Met Asp Asp Val Val Leu
1               5                   10

<210> SEQ ID NO 313
<211> LENGTH: 8
<212> TYPE: PRT
<213> ORGANISM: Orthohepadnaviridae hepatitis B virus

<400> SEQUENCE: 313

Leu Ala Gln Phe Thr Ser Ala Ile
1               5

<210> SEQ ID NO 314

```
<211> LENGTH: 11
<212> TYPE: PRT
<213> ORGANISM: Orthohepadnaviridae hepatitis B virus

<400> SEQUENCE: 314

Leu Ala Gln Phe Thr Ser Ala Ile Cys Ser Val
1               5                   10

<210> SEQ ID NO 315
<211> LENGTH: 8
<212> TYPE: PRT
<213> ORGANISM: Orthohepadnaviridae hepatitis B virus

<400> SEQUENCE: 315

Leu Ile Phe Leu Leu Val Leu Leu
1               5

<210> SEQ ID NO 316
<211> LENGTH: 8
<212> TYPE: PRT
<213> ORGANISM: Orthohepadnaviridae hepatitis B virus

<400> SEQUENCE: 316

Leu Leu Ala Gln Phe Thr Ser Ala
1               5

<210> SEQ ID NO 317
<211> LENGTH: 9
<212> TYPE: PRT
<213> ORGANISM: Orthohepadnaviridae hepatitis B virus

<400> SEQUENCE: 317

Leu Leu Ala Gln Phe Thr Ser Ala Ile
1               5

<210> SEQ ID NO 318
<211> LENGTH: 8
<212> TYPE: PRT
<213> ORGANISM: Orthohepadnaviridae hepatitis B virus

<400> SEQUENCE: 318

Leu Leu Cys Leu Ile Phe Leu Leu
1               5

<210> SEQ ID NO 319
<211> LENGTH: 9
<212> TYPE: PRT
<213> ORGANISM: Orthohepadnaviridae hepatitis B virus

<400> SEQUENCE: 319

Leu Leu Cys Leu Ile Phe Leu Leu Val
1               5

<210> SEQ ID NO 320
<211> LENGTH: 10
<212> TYPE: PRT
<213> ORGANISM: Orthohepadnaviridae hepatitis B virus

<400> SEQUENCE: 320

Leu Leu Cys Leu Ile Phe Leu Leu Val Leu
1               5                   10

<210> SEQ ID NO 321
<211> LENGTH: 11
<212> TYPE: PRT
```

<213> ORGANISM: Orthohepadnaviridae hepatitis B virus

<400> SEQUENCE: 321

Leu Leu Cys Leu Ile Phe Leu Leu Val Leu Leu
1 5 10

<210> SEQ ID NO 322
<211> LENGTH: 8
<212> TYPE: PRT
<213> ORGANISM: Orthohepadnaviridae hepatitis B virus

<400> SEQUENCE: 322

Leu Leu Asp Thr Ala Ser Ala Leu
1 5

<210> SEQ ID NO 323
<211> LENGTH: 8
<212> TYPE: PRT
<213> ORGANISM: Orthohepadnaviridae hepatitis B virus

<400> SEQUENCE: 323

Leu Leu Asp Tyr Gln Gly Met Leu
1 5

<210> SEQ ID NO 324
<211> LENGTH: 10
<212> TYPE: PRT
<213> ORGANISM: Orthohepadnaviridae hepatitis B virus

<400> SEQUENCE: 324

Leu Leu Asp Tyr Gln Gly Met Leu Pro Val
1 5 10

<210> SEQ ID NO 325
<211> LENGTH: 9
<212> TYPE: PRT
<213> ORGANISM: Orthohepadnaviridae hepatitis B virus

<400> SEQUENCE: 325

Leu Leu Gly Cys Ala Ala Asn Trp Ile
1 5

<210> SEQ ID NO 326
<211> LENGTH: 10
<212> TYPE: PRT
<213> ORGANISM: Orthohepadnaviridae hepatitis B virus

<400> SEQUENCE: 326

Leu Leu Gly Cys Ala Ala Asn Trp Ile Leu
1 5 10

<210> SEQ ID NO 327
<211> LENGTH: 9
<212> TYPE: PRT
<213> ORGANISM: Orthohepadnaviridae hepatitis B virus

<400> SEQUENCE: 327

Leu Leu Gly Phe Ala Ala Pro Phe Thr
1 5

<210> SEQ ID NO 328
<211> LENGTH: 8
<212> TYPE: PRT
<213> ORGANISM: Orthohepadnaviridae hepatitis B virus -continued

```
<400> SEQUENCE: 328

Leu Leu Gly Trp Ser Pro Gln Ala
1               5

<210> SEQ ID NO 329
<211> LENGTH: 11
<212> TYPE: PRT
<213> ORGANISM: Orthohepadnaviridae hepatitis B virus

<400> SEQUENCE: 329

Leu Leu Gly Trp Ser Pro Gln Ala Gln Gly Ile
1               5                   10

<210> SEQ ID NO 330
<211> LENGTH: 8
<212> TYPE: PRT
<213> ORGANISM: Orthohepadnaviridae hepatitis B virus

<400> SEQUENCE: 330

Leu Leu Leu Cys Leu Ile Phe Leu
1               5

<210> SEQ ID NO 331
<211> LENGTH: 9
<212> TYPE: PRT
<213> ORGANISM: Orthohepadnaviridae hepatitis B virus

<400> SEQUENCE: 331

Leu Leu Leu Cys Leu Ile Phe Leu Leu
1               5

<210> SEQ ID NO 332
<211> LENGTH: 10
<212> TYPE: PRT
<213> ORGANISM: Orthohepadnaviridae hepatitis B virus

<400> SEQUENCE: 332

Leu Leu Leu Cys Leu Ile Phe Leu Leu Val
1               5                   10

<210> SEQ ID NO 333
<211> LENGTH: 11
<212> TYPE: PRT
<213> ORGANISM: Orthohepadnaviridae hepatitis B virus

<400> SEQUENCE: 333

Leu Leu Leu Cys Leu Ile Phe Leu Leu Val Leu
1               5                   10

<210> SEQ ID NO 334
<211> LENGTH: 8
<212> TYPE: PRT
<213> ORGANISM: Orthohepadnaviridae hepatitis B virus

<400> SEQUENCE: 334

Leu Leu Pro Ile Phe Phe Cys Leu
1               5

<210> SEQ ID NO 335
<211> LENGTH: 10
<212> TYPE: PRT
<213> ORGANISM: Orthohepadnaviridae hepatitis B virus

<400> SEQUENCE: 335
```

-continued

Leu Leu Pro Ile Phe Phe Cys Leu Trp Val
1               5                   10

<210> SEQ ID NO 336
<211> LENGTH: 8
<212> TYPE: PRT
<213> ORGANISM: Orthohepadnaviridae hepatitis B virus

<400> SEQUENCE: 336

Leu Leu Ser Leu Gly Ile His Leu
1               5

<210> SEQ ID NO 337
<211> LENGTH: 9
<212> TYPE: PRT
<213> ORGANISM: Orthohepadnaviridae hepatitis B virus

<400> SEQUENCE: 337

Leu Leu Ser Ser Asn Leu Ser Trp Leu
1               5

<210> SEQ ID NO 338
<211> LENGTH: 11
<212> TYPE: PRT
<213> ORGANISM: Orthohepadnaviridae hepatitis B virus

<400> SEQUENCE: 338

Leu Leu Ser Ser Asn Leu Ser Trp Leu Ser Leu
1               5                   10

<210> SEQ ID NO 339
<211> LENGTH: 8
<212> TYPE: PRT
<213> ORGANISM: Orthohepadnaviridae hepatitis B virus

<400> SEQUENCE: 339

Leu Leu Thr Arg Ile Leu Thr Ile
1               5

<210> SEQ ID NO 340
<211> LENGTH: 8
<212> TYPE: PRT
<213> ORGANISM: Orthohepadnaviridae hepatitis B virus

<400> SEQUENCE: 340

Leu Leu Val Gly Ser Ser Gly Leu
1               5

<210> SEQ ID NO 341
<211> LENGTH: 10
<212> TYPE: PRT
<213> ORGANISM: Orthohepadnaviridae hepatitis B virus

<400> SEQUENCE: 341

Leu Leu Val Leu Leu Asp Tyr Gln Gly Met
1               5                   10

<210> SEQ ID NO 342
<211> LENGTH: 11
<212> TYPE: PRT
<213> ORGANISM: Orthohepadnaviridae hepatitis B virus

<400> SEQUENCE: 342

Leu Leu Val Leu Leu Asp Tyr Gln Gly Met Leu
1               5                   10

```
<210> SEQ ID NO 343
<211> LENGTH: 10
<212> TYPE: PRT
<213> ORGANISM: Orthohepadnaviridae hepatitis B virus

<400> SEQUENCE: 343

Leu Leu Val Leu Gln Ala Gly Phe Phe Leu
1               5                   10

<210> SEQ ID NO 344
<211> LENGTH: 11
<212> TYPE: PRT
<213> ORGANISM: Orthohepadnaviridae hepatitis B virus

<400> SEQUENCE: 344

Leu Leu Val Leu Gln Ala Gly Phe Phe Leu Leu
1               5                   10

<210> SEQ ID NO 345
<211> LENGTH: 10
<212> TYPE: PRT
<213> ORGANISM: Orthohepadnaviridae hepatitis B virus

<400> SEQUENCE: 345

Leu Leu Val Pro Phe Val Gln Trp Phe Val
1               5                   10

<210> SEQ ID NO 346
<211> LENGTH: 9
<212> TYPE: PRT
<213> ORGANISM: Orthohepadnaviridae hepatitis B virus

<400> SEQUENCE: 346

Leu Leu Trp Phe His Ile Ser Cys Leu
1               5

<210> SEQ ID NO 347
<211> LENGTH: 10
<212> TYPE: PRT
<213> ORGANISM: Orthohepadnaviridae hepatitis B virus

<400> SEQUENCE: 347

Leu Leu Trp Phe His Ile Ser Cys Leu Thr
1               5                   10

<210> SEQ ID NO 348
<211> LENGTH: 8
<212> TYPE: PRT
<213> ORGANISM: Orthohepadnaviridae hepatitis B virus

<400> SEQUENCE: 348

Leu Met Pro Leu Tyr Ala Cys Ile
1               5

<210> SEQ ID NO 349
<211> LENGTH: 8
<212> TYPE: PRT
<213> ORGANISM: Orthohepadnaviridae hepatitis B virus

<400> SEQUENCE: 349

Leu Thr Phe Gly Arg Glu Thr Val
1               5
```

<210> SEQ ID NO 350
<211> LENGTH: 9
<212> TYPE: PRT
<213> ORGANISM: Orthohepadnaviridae hepatitis B virus

<400> SEQUENCE: 350

Leu Thr Phe Gly Arg Glu Thr Val Leu
 1               5

<210> SEQ ID NO 351
<211> LENGTH: 9
<212> TYPE: PRT
<213> ORGANISM: Orthohepadnaviridae hepatitis B virus

<400> SEQUENCE: 351

Leu Thr Asn Leu Leu Ser Ser Asn Leu
 1               5

<210> SEQ ID NO 352
<211> LENGTH: 11
<212> TYPE: PRT
<213> ORGANISM: Orthohepadnaviridae hepatitis B virus

<400> SEQUENCE: 352

Leu Thr Arg Ile Leu Thr Ile Pro Gln Ser Leu
 1               5                  10

<210> SEQ ID NO 353
<211> LENGTH: 9
<212> TYPE: PRT
<213> ORGANISM: Orthohepadnaviridae hepatitis B virus

<400> SEQUENCE: 353

Leu Thr Val Asn Glu Lys Arg Arg Leu
 1               5

<210> SEQ ID NO 354
<211> LENGTH: 9
<212> TYPE: PRT
<213> ORGANISM: Orthohepadnaviridae hepatitis B virus

<400> SEQUENCE: 354

Leu Val Asp Lys Asn Pro His Asn Thr
 1               5

<210> SEQ ID NO 355
<211> LENGTH: 9
<212> TYPE: PRT
<213> ORGANISM: Orthohepadnaviridae hepatitis B virus

<400> SEQUENCE: 355

Leu Val Leu Leu Asp Tyr Gln Gly Met
 1               5

<210> SEQ ID NO 356
<211> LENGTH: 10
<212> TYPE: PRT
<213> ORGANISM: Orthohepadnaviridae hepatitis B virus

<400> SEQUENCE: 356

Leu Val Leu Leu Asp Tyr Gln Gly Met Leu
 1               5                  10

<210> SEQ ID NO 357
<211> LENGTH: 9

<212> TYPE: PRT
<213> ORGANISM: Orthohepadnaviridae hepatitis B virus

<400> SEQUENCE: 357

Leu Val Leu Gln Ala Gly Phe Phe Leu
 1               5

<210> SEQ ID NO 358
<211> LENGTH: 10
<212> TYPE: PRT
<213> ORGANISM: Orthohepadnaviridae hepatitis B virus

<400> SEQUENCE: 358

Leu Val Leu Gln Ala Gly Phe Phe Leu Leu
 1               5                  10

<210> SEQ ID NO 359
<211> LENGTH: 11
<212> TYPE: PRT
<213> ORGANISM: Orthohepadnaviridae hepatitis B virus

<400> SEQUENCE: 359

Leu Val Leu Gln Ala Gly Phe Phe Leu Leu Thr
 1               5                  10

<210> SEQ ID NO 360
<211> LENGTH: 9
<212> TYPE: PRT
<213> ORGANISM: Orthohepadnaviridae hepatitis B virus

<400> SEQUENCE: 360

Leu Val Pro Phe Val Gln Trp Phe Val
 1               5

<210> SEQ ID NO 361
<211> LENGTH: 11
<212> TYPE: PRT
<213> ORGANISM: Orthohepadnaviridae hepatitis B virus

<400> SEQUENCE: 361

Leu Val Pro Phe Val Gln Trp Phe Val Gly Leu
 1               5                  10

<210> SEQ ID NO 362
<211> LENGTH: 8
<212> TYPE: PRT
<213> ORGANISM: Orthohepadnaviridae hepatitis B virus

<400> SEQUENCE: 362

Leu Val Ser Phe Gly Val Trp Ile
 1               5

<210> SEQ ID NO 363
<211> LENGTH: 10
<212> TYPE: PRT
<213> ORGANISM: Orthohepadnaviridae hepatitis B virus

<400> SEQUENCE: 363

Leu Val Ser Phe Gly Val Trp Ile Arg Thr
 1               5                  10

<210> SEQ ID NO 364
<211> LENGTH: 9
<212> TYPE: PRT
<213> ORGANISM: Orthohepadnaviridae hepatitis B virus

<400> SEQUENCE: 364

Met Met Trp Tyr Trp Gly Pro Ser Leu
1               5

<210> SEQ ID NO 365
<211> LENGTH: 8
<212> TYPE: PRT
<213> ORGANISM: Orthohepadnaviridae hepatitis B virus

<400> SEQUENCE: 365

Asn Ala Pro Ile Leu Ser Thr Leu
1               5

<210> SEQ ID NO 366
<211> LENGTH: 11
<212> TYPE: PRT
<213> ORGANISM: Orthohepadnaviridae hepatitis B virus

<400> SEQUENCE: 366

Asn Ala Pro Ile Leu Ser Thr Leu Pro Glu Thr
1               5                   10

<210> SEQ ID NO 367
<211> LENGTH: 9
<212> TYPE: PRT
<213> ORGANISM: Orthohepadnaviridae hepatitis B virus

<400> SEQUENCE: 367

Asn Leu Gly Asn Leu Asn Val Ser Ile
1               5

<210> SEQ ID NO 368
<211> LENGTH: 10
<212> TYPE: PRT
<213> ORGANISM: Orthohepadnaviridae hepatitis B virus

<400> SEQUENCE: 368

Asn Leu Leu Ser Ser Asn Leu Ser Trp Leu
1               5                   10

<210> SEQ ID NO 369
<211> LENGTH: 9
<212> TYPE: PRT
<213> ORGANISM: Orthohepadnaviridae hepatitis B virus

<400> SEQUENCE: 369

Asn Leu Asn Val Ser Ile Pro Trp Thr
1               5

<210> SEQ ID NO 370
<211> LENGTH: 8
<212> TYPE: PRT
<213> ORGANISM: Orthohepadnaviridae hepatitis B virus

<400> SEQUENCE: 370

Asn Leu Gln Ser Leu Thr Asn Leu
1               5

<210> SEQ ID NO 371
<211> LENGTH: 9
<212> TYPE: PRT
<213> ORGANISM: Orthohepadnaviridae hepatitis B virus

<400> SEQUENCE: 371

Asn Leu Gln Ser Leu Thr Asn Leu Leu
1               5

<210> SEQ ID NO 372
<211> LENGTH: 8
<212> TYPE: PRT
<213> ORGANISM: Orthohepadnaviridae hepatitis B virus

<400> SEQUENCE: 372

Asn Leu Ser Val Pro Asn Pro Leu
1               5

<210> SEQ ID NO 373
<211> LENGTH: 9
<212> TYPE: PRT
<213> ORGANISM: Orthohepadnaviridae hepatitis B virus

<400> SEQUENCE: 373

Asn Leu Ser Trp Leu Ser Leu Asp Val
1               5

<210> SEQ ID NO 374
<211> LENGTH: 11
<212> TYPE: PRT
<213> ORGANISM: Orthohepadnaviridae hepatitis B virus

<400> SEQUENCE: 374

Asn Leu Ser Trp Leu Ser Leu Asp Val Ser Ala
1               5                   10

<210> SEQ ID NO 375
<211> LENGTH: 10
<212> TYPE: PRT
<213> ORGANISM: Orthohepadnaviridae hepatitis B virus

<400> SEQUENCE: 375

Asn Val Ser Ile Pro Trp Thr His Lys Val
1               5                   10

<210> SEQ ID NO 376
<211> LENGTH: 8
<212> TYPE: PRT
<213> ORGANISM: Orthohepadnaviridae hepatitis B virus

<400> SEQUENCE: 376

Pro Ala Ala Met Pro His Leu Leu
1               5

<210> SEQ ID NO 377
<211> LENGTH: 9
<212> TYPE: PRT
<213> ORGANISM: Orthohepadnaviridae hepatitis B virus

<400> SEQUENCE: 377

Pro Ala Ala Met Pro His Leu Leu Val
1               5

<210> SEQ ID NO 378
<211> LENGTH: 10
<212> TYPE: PRT
<213> ORGANISM: Orthohepadnaviridae hepatitis B virus

<400> SEQUENCE: 378

Pro Ala Asp Asp Pro Ser Arg Gly Arg Leu

-continued

<210> SEQ ID NO 379
<211> LENGTH: 9
<212> TYPE: PRT
<213> ORGANISM: Orthohepadnaviridae hepatitis B virus

<400> SEQUENCE: 379

Pro Ala Gly Gly Ser Ser Ser Gly Thr
 1               5

<210> SEQ ID NO 380
<211> LENGTH: 10
<212> TYPE: PRT
<213> ORGANISM: Orthohepadnaviridae hepatitis B virus

<400> SEQUENCE: 380

Pro Ala Gly Gly Ser Ser Ser Gly Thr Val
 1               5                  10

<210> SEQ ID NO 381
<211> LENGTH: 8
<212> TYPE: PRT
<213> ORGANISM: Orthohepadnaviridae hepatitis B virus

<400> SEQUENCE: 381

Pro Ala Leu Met Pro Leu Tyr Ala
 1               5

<210> SEQ ID NO 382
<211> LENGTH: 10
<212> TYPE: PRT
<213> ORGANISM: Orthohepadnaviridae hepatitis B virus

<400> SEQUENCE: 382

Pro Ala Leu Met Pro Leu Tyr Ala Cys Ile
 1               5                  10

<210> SEQ ID NO 383
<211> LENGTH: 8
<212> TYPE: PRT
<213> ORGANISM: Orthohepadnaviridae hepatitis B virus

<400> SEQUENCE: 383

Pro Ala Pro Cys Asn Phe Phe Thr
 1               5

<210> SEQ ID NO 384
<211> LENGTH: 10
<212> TYPE: PRT
<213> ORGANISM: Orthohepadnaviridae hepatitis B virus

<400> SEQUENCE: 384

Pro Ala Pro Cys Asn Phe Phe Thr Ser Ala
 1               5                  10

<210> SEQ ID NO 385
<211> LENGTH: 8
<212> TYPE: PRT
<213> ORGANISM: Orthohepadnaviridae hepatitis B virus

<400> SEQUENCE: 385

Pro Ala Arg Asp Val Leu Cys Leu
 1               5

```
<210> SEQ ID NO 386
<211> LENGTH: 11
<212> TYPE: PRT
<213> ORGANISM: Orthohepadnaviridae hepatitis B virus

<400> SEQUENCE: 386

Pro Ala Arg Asp Val Leu Cys Leu Arg Pro Val
1               5                   10

<210> SEQ ID NO 387
<211> LENGTH: 8
<212> TYPE: PRT
<213> ORGANISM: Orthohepadnaviridae hepatitis B virus

<400> SEQUENCE: 387

Pro Ala Arg Val Thr Gly Gly Val
1               5

<210> SEQ ID NO 388
<211> LENGTH: 10
<212> TYPE: PRT
<213> ORGANISM: Orthohepadnaviridae hepatitis B virus

<400> SEQUENCE: 388

Pro Ala Arg Val Thr Gly Gly Val Phe Leu
1               5                   10

<210> SEQ ID NO 389
<211> LENGTH: 11
<212> TYPE: PRT
<213> ORGANISM: Orthohepadnaviridae hepatitis B virus

<400> SEQUENCE: 389

Pro Ala Arg Val Thr Gly Gly Val Phe Leu Val
1               5                   10

<210> SEQ ID NO 390
<211> LENGTH: 8
<212> TYPE: PRT
<213> ORGANISM: Orthohepadnaviridae hepatitis B virus

<400> SEQUENCE: 390

Pro Ala Tyr Arg Pro Pro Asn Ala
1               5

<210> SEQ ID NO 391
<211> LENGTH: 10
<212> TYPE: PRT
<213> ORGANISM: Orthohepadnaviridae hepatitis B virus

<400> SEQUENCE: 391

Pro Ala Tyr Arg Pro Pro Asn Ala Pro Ile
1               5                   10

<210> SEQ ID NO 392
<211> LENGTH: 11
<212> TYPE: PRT
<213> ORGANISM: Orthohepadnaviridae hepatitis B virus

<400> SEQUENCE: 392

Pro Ala Tyr Arg Pro Pro Asn Ala Pro Ile Leu
1               5                   10

<210> SEQ ID NO 393
```

-continued

<211> LENGTH: 10
<212> TYPE: PRT
<213> ORGANISM: Orthohepadnaviridae hepatitis B virus

<400> SEQUENCE: 393

Pro Ile Asp Trp Lys Val Cys Gln Arg Ile
1 5 10

<210> SEQ ID NO 394
<211> LENGTH: 11
<212> TYPE: PRT
<213> ORGANISM: Orthohepadnaviridae hepatitis B virus

<400> SEQUENCE: 394

Pro Ile Asp Trp Lys Val Cys Gln Arg Ile Val
1 5 10

<210> SEQ ID NO 395
<211> LENGTH: 8
<212> TYPE: PRT
<213> ORGANISM: Orthohepadnaviridae hepatitis B virus

<400> SEQUENCE: 395

Pro Ile Phe Phe Cys Leu Trp Val
1 5

<210> SEQ ID NO 396
<211> LENGTH: 10
<212> TYPE: PRT
<213> ORGANISM: Orthohepadnaviridae hepatitis B virus

<400> SEQUENCE: 396

Pro Ile Phe Phe Cys Leu Trp Val Tyr Ile
1 5 10

<210> SEQ ID NO 397
<211> LENGTH: 8
<212> TYPE: PRT
<213> ORGANISM: Orthohepadnaviridae hepatitis B virus

<400> SEQUENCE: 397

Pro Ile His Thr Ala Glu Leu Leu
1 5

<210> SEQ ID NO 398
<211> LENGTH: 9
<212> TYPE: PRT
<213> ORGANISM: Orthohepadnaviridae hepatitis B virus

<400> SEQUENCE: 398

Pro Ile His Thr Ala Glu Leu Leu Ala
1 5

<210> SEQ ID NO 399
<211> LENGTH: 10
<212> TYPE: PRT
<213> ORGANISM: Orthohepadnaviridae hepatitis B virus

<400> SEQUENCE: 399

Pro Ile His Thr Ala Glu Leu Leu Ala Ala
1 5 10

<210> SEQ ID NO 400
<211> LENGTH: 9
<212> TYPE: PRT

<213> ORGANISM: Orthohepadnaviridae hepatitis B virus

<400> SEQUENCE: 400

Pro Ile Ile Leu Gly Phe Arg Lys Ile
1               5

<210> SEQ ID NO 401
<211> LENGTH: 11
<212> TYPE: PRT
<213> ORGANISM: Orthohepadnaviridae hepatitis B virus

<400> SEQUENCE: 401

Pro Ile Ile Leu Gly Phe Arg Lys Ile Pro Met
1               5                   10

<210> SEQ ID NO 402
<211> LENGTH: 9
<212> TYPE: PRT
<213> ORGANISM: Orthohepadnaviridae hepatitis B virus

<400> SEQUENCE: 402

Pro Ile Leu Ser Thr Leu Pro Glu Thr
1               5

<210> SEQ ID NO 403
<211> LENGTH: 10
<212> TYPE: PRT
<213> ORGANISM: Orthohepadnaviridae hepatitis B virus

<400> SEQUENCE: 403

Pro Ile Leu Ser Thr Leu Pro Glu Thr Thr
1               5                   10

<210> SEQ ID NO 404
<211> LENGTH: 11
<212> TYPE: PRT
<213> ORGANISM: Orthohepadnaviridae hepatitis B virus

<400> SEQUENCE: 404

Pro Ile Leu Ser Thr Leu Pro Glu Thr Thr Val
1               5                   10

<210> SEQ ID NO 405
<211> LENGTH: 9
<212> TYPE: PRT
<213> ORGANISM: Orthohepadnaviridae hepatitis B virus

<400> SEQUENCE: 405

Pro Ile Pro Ser Ser Trp Ala Phe Ala
1               5

<210> SEQ ID NO 406
<211> LENGTH: 9
<212> TYPE: PRT
<213> ORGANISM: Orthohepadnaviridae hepatitis B virus

<400> SEQUENCE: 406

Pro Leu Glu Glu Glu Leu Pro Arg Leu
1               5

<210> SEQ ID NO 407
<211> LENGTH: 10
<212> TYPE: PRT
<213> ORGANISM: Orthohepadnaviridae hepatitis B virus

```
<400> SEQUENCE: 407

Pro Leu Glu Glu Glu Leu Pro Arg Leu Ala
1               5                   10

<210> SEQ ID NO 408
<211> LENGTH: 10
<212> TYPE: PRT
<213> ORGANISM: Orthohepadnaviridae hepatitis B virus

<400> SEQUENCE: 408

Pro Leu Gly Phe Phe Pro Asp His Gln Leu
1               5                   10

<210> SEQ ID NO 409
<211> LENGTH: 10
<212> TYPE: PRT
<213> ORGANISM: Orthohepadnaviridae hepatitis B virus

<400> SEQUENCE: 409

Pro Leu His Pro Ala Ala Met Pro His Leu
1               5                   10

<210> SEQ ID NO 410
<211> LENGTH: 11
<212> TYPE: PRT
<213> ORGANISM: Orthohepadnaviridae hepatitis B virus

<400> SEQUENCE: 410

Pro Leu His Pro Ala Ala Met Pro His Leu Leu
1               5                   10

<210> SEQ ID NO 411
<211> LENGTH: 9
<212> TYPE: PRT
<213> ORGANISM: Orthohepadnaviridae hepatitis B virus

<400> SEQUENCE: 411

Pro Leu Leu Pro Ile Phe Phe Cys Leu
1               5

<210> SEQ ID NO 412
<211> LENGTH: 11
<212> TYPE: PRT
<213> ORGANISM: Orthohepadnaviridae hepatitis B virus

<400> SEQUENCE: 412

Pro Leu Leu Pro Ile Phe Phe Cys Leu Trp Val
1               5                   10

<210> SEQ ID NO 413
<211> LENGTH: 11
<212> TYPE: PRT
<213> ORGANISM: Orthohepadnaviridae hepatitis B virus

<400> SEQUENCE: 413

Pro Leu Leu Val Leu Gln Ala Gly Phe Phe Leu
1               5                   10

<210> SEQ ID NO 414
<211> LENGTH: 9
<212> TYPE: PRT
<213> ORGANISM: Orthohepadnaviridae hepatitis B virus

<400> SEQUENCE: 414
```

```
Pro Leu Pro Ile His Thr Ala Glu Leu
1               5
```

<210> SEQ ID NO 415
<211> LENGTH: 10
<212> TYPE: PRT
<213> ORGANISM: Orthohepadnaviridae hepatitis B virus

<400> SEQUENCE: 415

```
Pro Leu Pro Ile His Thr Ala Glu Leu Leu
1               5                   10
```

<210> SEQ ID NO 416
<211> LENGTH: 11
<212> TYPE: PRT
<213> ORGANISM: Orthohepadnaviridae hepatitis B virus

<400> SEQUENCE: 416

```
Pro Leu Pro Ile His Thr Ala Glu Leu Leu Ala
1               5                   10
```

<210> SEQ ID NO 417
<211> LENGTH: 10
<212> TYPE: PRT
<213> ORGANISM: Orthohepadnaviridae hepatitis B virus

<400> SEQUENCE: 417

```
Pro Leu Ser Tyr Gln His Phe Arg Lys Leu
1               5                   10
```

<210> SEQ ID NO 418
<211> LENGTH: 11
<212> TYPE: PRT
<213> ORGANISM: Orthohepadnaviridae hepatitis B virus

<400> SEQUENCE: 418

```
Pro Leu Ser Tyr Gln His Phe Arg Lys Leu Leu
1               5                   10
```

<210> SEQ ID NO 419
<211> LENGTH: 10
<212> TYPE: PRT
<213> ORGANISM: Orthohepadnaviridae hepatitis B virus

<400> SEQUENCE: 419

```
Pro Leu Thr Val Asn Glu Lys Arg Arg Leu
1               5                   10
```

<210> SEQ ID NO 420
<211> LENGTH: 10
<212> TYPE: PRT
<213> ORGANISM: Orthohepadnaviridae hepatitis B virus

<400> SEQUENCE: 420

```
Pro Met Gly Val Gly Leu Ser Pro Phe Leu
1               5                   10
```

<210> SEQ ID NO 421
<211> LENGTH: 11
<212> TYPE: PRT
<213> ORGANISM: Orthohepadnaviridae hepatitis B virus

<400> SEQUENCE: 421

```
Pro Met Gly Val Gly Leu Ser Pro Phe Leu Leu
1               5                   10
```

```
<210> SEQ ID NO 422
<211> LENGTH: 8
<212> TYPE: PRT
<213> ORGANISM: Orthohepadnaviridae hepatitis B virus

<400> SEQUENCE: 422

Pro Thr Gly Trp Gly Leu Ala Ile
1               5

<210> SEQ ID NO 423
<211> LENGTH: 8
<212> TYPE: PRT
<213> ORGANISM: Orthohepadnaviridae hepatitis B virus

<400> SEQUENCE: 423

Pro Thr Ser Asn His Ser Pro Thr
1               5

<210> SEQ ID NO 424
<211> LENGTH: 8
<212> TYPE: PRT
<213> ORGANISM: Orthohepadnaviridae hepatitis B virus

<400> SEQUENCE: 424

Pro Thr Thr Gly Arg Thr Ser Leu
1               5

<210> SEQ ID NO 425
<211> LENGTH: 10
<212> TYPE: PRT
<213> ORGANISM: Orthohepadnaviridae hepatitis B virus

<400> SEQUENCE: 425

Pro Thr Thr Gly Arg Thr Ser Leu Tyr Ala
1               5                   10

<210> SEQ ID NO 426
<211> LENGTH: 8
<212> TYPE: PRT
<213> ORGANISM: Orthohepadnaviridae hepatitis B virus

<400> SEQUENCE: 426

Pro Thr Val Gln Ala Ser Lys Leu
1               5

<210> SEQ ID NO 427
<211> LENGTH: 10
<212> TYPE: PRT
<213> ORGANISM: Orthohepadnaviridae hepatitis B virus

<400> SEQUENCE: 427

Pro Thr Val Gln Ala Ser Lys Leu Cys Leu
1               5                   10

<210> SEQ ID NO 428
<211> LENGTH: 8
<212> TYPE: PRT
<213> ORGANISM: Orthohepadnaviridae hepatitis B virus

<400> SEQUENCE: 428

Pro Thr Val Trp Leu Ser Val Ile
1               5
```

<210> SEQ ID NO 429
<211> LENGTH: 10
<212> TYPE: PRT
<213> ORGANISM: Orthohepadnaviridae hepatitis B virus

<400> SEQUENCE: 429

Pro Thr Val Trp Leu Ser Val Ile Trp Met
1               5                   10

<210> SEQ ID NO 430
<211> LENGTH: 8
<212> TYPE: PRT
<213> ORGANISM: Orthohepadnaviridae hepatitis B virus

<400> SEQUENCE: 430

Pro Val Cys Ala Phe Ser Ser Ala
1               5

<210> SEQ ID NO 431
<211> LENGTH: 10
<212> TYPE: PRT
<213> ORGANISM: Orthohepadnaviridae hepatitis B virus

<400> SEQUENCE: 431

Pro Val Asn Arg Pro Ile Asp Trp Lys Val
1               5                   10

<210> SEQ ID NO 432
<211> LENGTH: 8
<212> TYPE: PRT
<213> ORGANISM: Orthohepadnaviridae hepatitis B virus

<400> SEQUENCE: 432

Gln Ala Phe Thr Phe Ser Pro Thr
1               5

<210> SEQ ID NO 433
<211> LENGTH: 11
<212> TYPE: PRT
<213> ORGANISM: Orthohepadnaviridae hepatitis B virus

<400> SEQUENCE: 433

Gln Ala Phe Thr Phe Ser Pro Thr Tyr Lys Ala
1               5                   10

<210> SEQ ID NO 434
<211> LENGTH: 8
<212> TYPE: PRT
<213> ORGANISM: Orthohepadnaviridae hepatitis B virus

<400> SEQUENCE: 434

Gln Ala Gly Phe Phe Leu Leu Thr
1               5

<210> SEQ ID NO 435
<211> LENGTH: 10
<212> TYPE: PRT
<213> ORGANISM: Orthohepadnaviridae hepatitis B virus

<400> SEQUENCE: 435

Gln Ala Gly Phe Phe Leu Leu Thr Arg Ile
1               5                   10

<210> SEQ ID NO 436
<211> LENGTH: 11

```
<212> TYPE: PRT
<213> ORGANISM: Orthohepadnaviridae hepatitis B virus

<400> SEQUENCE: 436

Gln Ala Gly Phe Phe Leu Leu Thr Arg Ile Leu
1               5                   10

<210> SEQ ID NO 437
<211> LENGTH: 9
<212> TYPE: PRT
<213> ORGANISM: Orthohepadnaviridae hepatitis B virus

<400> SEQUENCE: 437

Gln Ala Ile Leu Cys Trp Gly Glu Leu
1               5

<210> SEQ ID NO 438
<211> LENGTH: 10
<212> TYPE: PRT
<213> ORGANISM: Orthohepadnaviridae hepatitis B virus

<400> SEQUENCE: 438

Gln Ala Ile Leu Cys Trp Gly Glu Leu Met
1               5                   10

<210> SEQ ID NO 439
<211> LENGTH: 8
<212> TYPE: PRT
<213> ORGANISM: Orthohepadnaviridae hepatitis B virus

<400> SEQUENCE: 439

Gln Ala Met Gln Trp Asn Ser Thr
1               5

<210> SEQ ID NO 440
<211> LENGTH: 9
<212> TYPE: PRT
<213> ORGANISM: Orthohepadnaviridae hepatitis B virus

<400> SEQUENCE: 440

Gln Ala Met Gln Trp Asn Ser Thr Thr
1               5

<210> SEQ ID NO 441
<211> LENGTH: 10
<212> TYPE: PRT
<213> ORGANISM: Orthohepadnaviridae hepatitis B virus

<400> SEQUENCE: 441

Gln Ala Ser Lys Leu Cys Leu Gly Trp Leu
1               5                   10

<210> SEQ ID NO 442
<211> LENGTH: 8
<212> TYPE: PRT
<213> ORGANISM: Orthohepadnaviridae hepatitis B virus

<400> SEQUENCE: 442

Gln Leu Asp Pro Ala Arg Asp Val
1               5

<210> SEQ ID NO 443
<211> LENGTH: 9
<212> TYPE: PRT
<213> ORGANISM: Orthohepadnaviridae hepatitis B virus
```

```
<400> SEQUENCE: 443

Gln Leu Asp Pro Ala Arg Asp Val Leu
1               5

<210> SEQ ID NO 444
<211> LENGTH: 11
<212> TYPE: PRT
<213> ORGANISM: Orthohepadnaviridae hepatitis B virus

<400> SEQUENCE: 444

Gln Leu Asp Pro Ala Arg Asp Val Leu Cys Leu
1               5                   10

<210> SEQ ID NO 445
<211> LENGTH: 10
<212> TYPE: PRT
<213> ORGANISM: Orthohepadnaviridae hepatitis B virus

<400> SEQUENCE: 445

Gln Leu Leu Trp Phe His Ile Ser Cys Leu
1               5                   10

<210> SEQ ID NO 446
<211> LENGTH: 11
<212> TYPE: PRT
<213> ORGANISM: Orthohepadnaviridae hepatitis B virus

<400> SEQUENCE: 446

Gln Leu Leu Trp Phe His Ile Ser Cys Leu Thr
1               5                   10

<210> SEQ ID NO 447
<211> LENGTH: 9
<212> TYPE: PRT
<213> ORGANISM: Orthohepadnaviridae hepatitis B virus

<400> SEQUENCE: 447

Gln Val Phe Ala Asp Ala Thr Pro Thr
1               5

<210> SEQ ID NO 448
<211> LENGTH: 8
<212> TYPE: PRT
<213> ORGANISM: Orthohepadnaviridae hepatitis B virus

<400> SEQUENCE: 448

Arg Ala Phe Pro His Cys Leu Ala
1               5

<210> SEQ ID NO 449
<211> LENGTH: 9
<212> TYPE: PRT
<213> ORGANISM: Orthohepadnaviridae hepatitis B virus

<400> SEQUENCE: 449

Arg Ile Leu Thr Ile Pro Gln Ser Leu
1               5

<210> SEQ ID NO 450
<211> LENGTH: 9
<212> TYPE: PRT
<213> ORGANISM: Orthohepadnaviridae hepatitis B virus

<400> SEQUENCE: 450
```

```
Arg Ile Val Gly Leu Leu Gly Phe Ala
 1               5

<210> SEQ ID NO 451
<211> LENGTH: 10
<212> TYPE: PRT
<213> ORGANISM: Orthohepadnaviridae hepatitis B virus

<400> SEQUENCE: 451

Arg Ile Val Gly Leu Leu Gly Phe Ala Ala
 1               5                  10

<210> SEQ ID NO 452
<211> LENGTH: 8
<212> TYPE: PRT
<213> ORGANISM: Orthohepadnaviridae hepatitis B virus

<400> SEQUENCE: 452

Arg Leu Lys Leu Ile Met Pro Ala
 1               5

<210> SEQ ID NO 453
<211> LENGTH: 10
<212> TYPE: PRT
<213> ORGANISM: Orthohepadnaviridae hepatitis B virus

<400> SEQUENCE: 453

Arg Thr Pro Ala Arg Val Thr Gly Gly Val
 1               5                  10

<210> SEQ ID NO 454
<211> LENGTH: 11
<212> TYPE: PRT
<213> ORGANISM: Orthohepadnaviridae hepatitis B virus

<400> SEQUENCE: 454

Arg Thr Pro Pro Ala Tyr Arg Pro Pro Asn Ala
 1               5                  10

<210> SEQ ID NO 455
<211> LENGTH: 8
<212> TYPE: PRT
<213> ORGANISM: Orthohepadnaviridae hepatitis B virus

<400> SEQUENCE: 455

Arg Val Ala Glu Asp Leu Asn Leu
 1               5

<210> SEQ ID NO 456
<211> LENGTH: 11
<212> TYPE: PRT
<213> ORGANISM: Orthohepadnaviridae hepatitis B virus

<400> SEQUENCE: 456

Arg Val Ala Glu Asp Leu Asn Leu Gly Asn Leu
 1               5                  10

<210> SEQ ID NO 457
<211> LENGTH: 8
<212> TYPE: PRT
<213> ORGANISM: Orthohepadnaviridae hepatitis B virus

<400> SEQUENCE: 457

Arg Val His Phe Ala Ser Pro Leu
```

-continued

```
1               5

<210> SEQ ID NO 458
<211> LENGTH: 10
<212> TYPE: PRT
<213> ORGANISM: Orthohepadnaviridae hepatitis B virus

<400> SEQUENCE: 458

Arg Val His Phe Ala Ser Pro Leu His Val
1               5                   10

<210> SEQ ID NO 459
<211> LENGTH: 11
<212> TYPE: PRT
<213> ORGANISM: Orthohepadnaviridae hepatitis B virus

<400> SEQUENCE: 459

Arg Val His Phe Ala Ser Pro Leu His Val Ala
1               5                   10

<210> SEQ ID NO 460
<211> LENGTH: 8
<212> TYPE: PRT
<213> ORGANISM: Orthohepadnaviridae hepatitis B virus

<400> SEQUENCE: 460

Arg Val Thr Gly Gly Val Phe Leu
1               5

<210> SEQ ID NO 461
<211> LENGTH: 9
<212> TYPE: PRT
<213> ORGANISM: Orthohepadnaviridae hepatitis B virus

<400> SEQUENCE: 461

Arg Val Thr Gly Gly Val Phe Leu Val
1               5

<210> SEQ ID NO 462
<211> LENGTH: 10
<212> TYPE: PRT
<213> ORGANISM: Orthohepadnaviridae hepatitis B virus

<400> SEQUENCE: 462

Ser Ala Gly Pro Cys Ala Leu Arg Phe Thr
1               5                   10

<210> SEQ ID NO 463
<211> LENGTH: 10
<212> TYPE: PRT
<213> ORGANISM: Orthohepadnaviridae hepatitis B virus

<400> SEQUENCE: 463

Ser Ala Ile Cys Ser Val Val Arg Arg Ala
1               5                   10

<210> SEQ ID NO 464
<211> LENGTH: 8
<212> TYPE: PRT
<213> ORGANISM: Orthohepadnaviridae hepatitis B virus

<400> SEQUENCE: 464

Ser Ala Leu Tyr Arg Glu Ala Leu
1               5
```

<210> SEQ ID NO 465
<211> LENGTH: 8
<212> TYPE: PRT
<213> ORGANISM: Orthohepadnaviridae hepatitis B virus

<400> SEQUENCE: 465

Ser Ile Pro Trp Thr His Lys Val
1               5

<210> SEQ ID NO 466
<211> LENGTH: 9
<212> TYPE: PRT
<213> ORGANISM: Orthohepadnaviridae hepatitis B virus

<400> SEQUENCE: 466

Ser Leu Asp Ser Trp Trp Thr Ser Leu
1               5

<210> SEQ ID NO 467
<211> LENGTH: 11
<212> TYPE: PRT
<213> ORGANISM: Orthohepadnaviridae hepatitis B virus

<400> SEQUENCE: 467

Ser Leu Gly Ile His Leu Asn Pro Asn Lys Thr
1               5                   10

<210> SEQ ID NO 468
<211> LENGTH: 11
<212> TYPE: PRT
<213> ORGANISM: Orthohepadnaviridae hepatitis B virus

<400> SEQUENCE: 468

Ser Leu Leu Val Pro Phe Val Gln Trp Phe Val
1               5                   10

<210> SEQ ID NO 469
<211> LENGTH: 8
<212> TYPE: PRT
<213> ORGANISM: Orthohepadnaviridae hepatitis B virus

<400> SEQUENCE: 469

Ser Leu Asn Phe Met Gly Tyr Val
1               5

<210> SEQ ID NO 470
<211> LENGTH: 9
<212> TYPE: PRT
<213> ORGANISM: Orthohepadnaviridae hepatitis B virus

<400> SEQUENCE: 470

Ser Leu Asn Phe Met Gly Tyr Val Ile
1               5

<210> SEQ ID NO 471
<211> LENGTH: 9
<212> TYPE: PRT
<213> ORGANISM: Orthohepadnaviridae hepatitis B virus

<400> SEQUENCE: 471

Ser Leu Arg Gly Leu Pro Val Cys Ala
1               5

<210> SEQ ID NO 472

```
<211> LENGTH: 10
<212> TYPE: PRT
<213> ORGANISM: Orthohepadnaviridae hepatitis B virus

<400> SEQUENCE: 472

Ser Leu Thr Asn Leu Leu Ser Ser Asn Leu
1               5                   10

<210> SEQ ID NO 473
<211> LENGTH: 9
<212> TYPE: PRT
<213> ORGANISM: Orthohepadnaviridae hepatitis B virus

<400> SEQUENCE: 473

Ser Thr Gly Pro Cys Lys Thr Cys Thr
1               5

<210> SEQ ID NO 474
<211> LENGTH: 8
<212> TYPE: PRT
<213> ORGANISM: Orthohepadnaviridae hepatitis B virus

<400> SEQUENCE: 474

Ser Thr Leu Pro Glu Thr Thr Val
1               5

<210> SEQ ID NO 475
<211> LENGTH: 9
<212> TYPE: PRT
<213> ORGANISM: Orthohepadnaviridae hepatitis B virus

<400> SEQUENCE: 475

Ser Thr Leu Pro Glu Thr Thr Val Val
1               5

<210> SEQ ID NO 476
<211> LENGTH: 11
<212> TYPE: PRT
<213> ORGANISM: Orthohepadnaviridae hepatitis B virus

<400> SEQUENCE: 476

Ser Thr Asn Arg Gln Ser Gly Arg Gln Pro Thr
1               5                   10

<210> SEQ ID NO 477
<211> LENGTH: 8
<212> TYPE: PRT
<213> ORGANISM: Orthohepadnaviridae hepatitis B virus

<400> SEQUENCE: 477

Ser Val Gln His Leu Glu Ser Leu
1               5

<210> SEQ ID NO 478
<211> LENGTH: 9
<212> TYPE: PRT
<213> ORGANISM: Orthohepadnaviridae hepatitis B virus

<400> SEQUENCE: 478

Ser Val Arg Phe Ser Trp Leu Ser Leu
1               5

<210> SEQ ID NO 479
<211> LENGTH: 10
<212> TYPE: PRT
```

<213> ORGANISM: Orthohepadnaviridae hepatitis B virus

<400> SEQUENCE: 479

Ser Val Arg Phe Ser Trp Leu Ser Leu Leu
1               5                   10

<210> SEQ ID NO 480
<211> LENGTH: 11
<212> TYPE: PRT
<213> ORGANISM: Orthohepadnaviridae hepatitis B virus

<400> SEQUENCE: 480

Ser Val Arg Phe Ser Trp Leu Ser Leu Leu Val
1               5                   10

<210> SEQ ID NO 481
<211> LENGTH: 9
<212> TYPE: PRT
<213> ORGANISM: Orthohepadnaviridae hepatitis B virus

<400> SEQUENCE: 481

Ser Val Val Leu Ser Arg Lys Tyr Thr
1               5

<210> SEQ ID NO 482
<211> LENGTH: 11
<212> TYPE: PRT
<213> ORGANISM: Orthohepadnaviridae hepatitis B virus

<400> SEQUENCE: 482

Ser Val Val Arg Arg Ala Phe Pro His Cys Leu
1               5                   10

<210> SEQ ID NO 483
<211> LENGTH: 10
<212> TYPE: PRT
<213> ORGANISM: Orthohepadnaviridae hepatitis B virus

<400> SEQUENCE: 483

Thr Ala Glu Leu Leu Ala Ala Cys Phe Ala
1               5                   10

<210> SEQ ID NO 484
<211> LENGTH: 8
<212> TYPE: PRT
<213> ORGANISM: Orthohepadnaviridae hepatitis B virus

<400> SEQUENCE: 484

Thr Ala Leu Arg Gln Ala Ile Leu
1               5

<210> SEQ ID NO 485
<211> LENGTH: 9
<212> TYPE: PRT
<213> ORGANISM: Orthohepadnaviridae hepatitis B virus

<400> SEQUENCE: 485

Thr Ala Ser Ala Leu Tyr Arg Glu Ala
1               5

<210> SEQ ID NO 486
<211> LENGTH: 10
<212> TYPE: PRT
<213> ORGANISM: Orthohepadnaviridae hepatitis B virus

```
<400> SEQUENCE: 486

Thr Ala Ser Ala Leu Tyr Arg Glu Ala Leu
1               5                   10

<210> SEQ ID NO 487
<211> LENGTH: 11
<212> TYPE: PRT
<213> ORGANISM: Orthohepadnaviridae hepatitis B virus

<400> SEQUENCE: 487

Thr Ile Pro Gln Ser Leu Asp Ser Trp Trp Thr
1               5                   10

<210> SEQ ID NO 488
<211> LENGTH: 8
<212> TYPE: PRT
<213> ORGANISM: Orthohepadnaviridae hepatitis B virus

<400> SEQUENCE: 488

Thr Leu Pro Glu Thr Thr Val Val
1               5

<210> SEQ ID NO 489
<211> LENGTH: 8
<212> TYPE: PRT
<213> ORGANISM: Orthohepadnaviridae hepatitis B virus

<400> SEQUENCE: 489

Thr Leu Trp Lys Ala Gly Ile Leu
1               5

<210> SEQ ID NO 490
<211> LENGTH: 9
<212> TYPE: PRT
<213> ORGANISM: Orthohepadnaviridae hepatitis B virus

<400> SEQUENCE: 490

Thr Thr Gly Arg Thr Ser Leu Tyr Ala
1               5

<210> SEQ ID NO 491
<211> LENGTH: 9
<212> TYPE: PRT
<213> ORGANISM: Orthohepadnaviridae hepatitis B virus

<400> SEQUENCE: 491

Thr Thr Ser Thr Gly Pro Cys Lys Thr
1               5

<210> SEQ ID NO 492
<211> LENGTH: 11
<212> TYPE: PRT
<213> ORGANISM: Orthohepadnaviridae hepatitis B virus

<400> SEQUENCE: 492

Thr Thr Ser Thr Gly Pro Cys Lys Thr Cys Thr
1               5                   10

<210> SEQ ID NO 493
<211> LENGTH: 8
<212> TYPE: PRT
<213> ORGANISM: Orthohepadnaviridae hepatitis B virus

<400> SEQUENCE: 493
```

Thr Val Asn Glu Lys Arg Arg Leu
1               5

<210> SEQ ID NO 494
<211> LENGTH: 9
<212> TYPE: PRT
<213> ORGANISM: Orthohepadnaviridae hepatitis B virus

<400> SEQUENCE: 494

Thr Val Gln Ala Ser Lys Leu Cys Leu
1               5

<210> SEQ ID NO 495
<211> LENGTH: 9
<212> TYPE: PRT
<213> ORGANISM: Orthohepadnaviridae hepatitis B virus

<400> SEQUENCE: 495

Thr Val Trp Leu Ser Val Ile Trp Met
1               5

<210> SEQ ID NO 496
<211> LENGTH: 10
<212> TYPE: PRT
<213> ORGANISM: Orthohepadnaviridae hepatitis B virus

<400> SEQUENCE: 496

Val Ala Glu Asp Leu Asn Leu Gly Asn Leu
1               5                   10

<210> SEQ ID NO 497
<211> LENGTH: 9
<212> TYPE: PRT
<213> ORGANISM: Orthohepadnaviridae hepatitis B virus

<400> SEQUENCE: 497

Val Leu Cys Leu Arg Pro Val Gly Ala
1               5

<210> SEQ ID NO 498
<211> LENGTH: 10
<212> TYPE: PRT
<213> ORGANISM: Orthohepadnaviridae hepatitis B virus

<400> SEQUENCE: 498

Val Leu Gly Ala Lys Ser Val Gln His Leu
1               5                   10

<210> SEQ ID NO 499
<211> LENGTH: 9
<212> TYPE: PRT
<213> ORGANISM: Orthohepadnaviridae hepatitis B virus

<400> SEQUENCE: 499

Val Leu Gly Gly Cys Arg His Lys Leu
1               5

<210> SEQ ID NO 500
<211> LENGTH: 10
<212> TYPE: PRT
<213> ORGANISM: Orthohepadnaviridae hepatitis B virus

<400> SEQUENCE: 500

Val Leu Gly Gly Cys Arg His Lys Leu Val
1               5                   10

<210> SEQ ID NO 501
<211> LENGTH: 9
<212> TYPE: PRT
<213> ORGANISM: Orthohepadnaviridae hepatitis B virus

<400> SEQUENCE: 501

Val Leu His Lys Arg Thr Leu Gly Leu
 1               5

<210> SEQ ID NO 502
<211> LENGTH: 8
<212> TYPE: PRT
<213> ORGANISM: Orthohepadnaviridae hepatitis B virus

<400> SEQUENCE: 502

Val Leu Leu Asp Tyr Gln Gly Met
 1               5

<210> SEQ ID NO 503
<211> LENGTH: 9
<212> TYPE: PRT
<213> ORGANISM: Orthohepadnaviridae hepatitis B virus

<400> SEQUENCE: 503

Val Leu Leu Asp Tyr Gln Gly Met Leu
 1               5

<210> SEQ ID NO 504
<211> LENGTH: 11
<212> TYPE: PRT
<213> ORGANISM: Orthohepadnaviridae hepatitis B virus

<400> SEQUENCE: 504

Val Leu Leu Asp Tyr Gln Gly Met Leu Pro Val
 1               5                   10

<210> SEQ ID NO 505
<211> LENGTH: 8
<212> TYPE: PRT
<213> ORGANISM: Orthohepadnaviridae hepatitis B virus

<400> SEQUENCE: 505

Val Leu Gln Ala Gly Phe Phe Leu
 1               5

<210> SEQ ID NO 506
<211> LENGTH: 9
<212> TYPE: PRT
<213> ORGANISM: Orthohepadnaviridae hepatitis B virus

<400> SEQUENCE: 506

Val Leu Gln Ala Gly Phe Phe Leu Leu
 1               5

<210> SEQ ID NO 507
<211> LENGTH: 10
<212> TYPE: PRT
<213> ORGANISM: Orthohepadnaviridae hepatitis B virus

<400> SEQUENCE: 507

Val Leu Gln Ala Gly Phe Phe Leu Leu Thr
 1               5                   10

<210> SEQ ID NO 508
<211> LENGTH: 8
<212> TYPE: PRT
<213> ORGANISM: Orthohepadnaviridae hepatitis B virus

<400> SEQUENCE: 508

Val Thr Gly Gly Val Phe Leu Val
1               5

<210> SEQ ID NO 509
<211> LENGTH: 8
<212> TYPE: PRT
<213> ORGANISM: Orthohepadnaviridae hepatitis B virus

<400> SEQUENCE: 509

Val Val Leu Gly Ala Lys Ser Val
1               5

<210> SEQ ID NO 510
<211> LENGTH: 11
<212> TYPE: PRT
<213> ORGANISM: Orthohepadnaviridae hepatitis B virus

<400> SEQUENCE: 510

Val Val Leu Gly Ala Lys Ser Val Gln His Leu
1               5                   10

<210> SEQ ID NO 511
<211> LENGTH: 8
<212> TYPE: PRT
<213> ORGANISM: Orthohepadnaviridae hepatitis B virus

<400> SEQUENCE: 511

Val Val Leu Ser Arg Lys Tyr Thr
1               5

<210> SEQ ID NO 512
<211> LENGTH: 10
<212> TYPE: PRT
<213> ORGANISM: Orthohepadnaviridae hepatitis B virus

<400> SEQUENCE: 512

Val Val Arg Arg Ala Phe Pro His Cys Leu
1               5                   10

<210> SEQ ID NO 513
<211> LENGTH: 11
<212> TYPE: PRT
<213> ORGANISM: Orthohepadnaviridae hepatitis B virus

<400> SEQUENCE: 513

Val Val Arg Arg Ala Phe Pro His Cys Leu Ala
1               5                   10

<210> SEQ ID NO 514
<211> LENGTH: 9
<212> TYPE: PRT
<213> ORGANISM: Orthohepadnaviridae hepatitis B virus

<400> SEQUENCE: 514

Trp Ile Leu Arg Gly Thr Ser Phe Val
1               5

<210> SEQ ID NO 515
<211> LENGTH: 11

```
<212> TYPE: PRT
<213> ORGANISM: Orthohepadnaviridae hepatitis B virus

<400> SEQUENCE: 515

Trp Ile Leu Arg Gly Thr Ser Phe Val Tyr Val
1               5                   10

<210> SEQ ID NO 516
<211> LENGTH: 10
<212> TYPE: PRT
<213> ORGANISM: Orthohepadnaviridae hepatitis B virus

<400> SEQUENCE: 516

Trp Leu Leu Gly Cys Ala Ala Asn Trp Ile
1               5                   10

<210> SEQ ID NO 517
<211> LENGTH: 11
<212> TYPE: PRT
<213> ORGANISM: Orthohepadnaviridae hepatitis B virus

<400> SEQUENCE: 517

Trp Leu Leu Gly Cys Ala Ala Asn Trp Ile Leu
1               5                   10

<210> SEQ ID NO 518
<211> LENGTH: 8
<212> TYPE: PRT
<213> ORGANISM: Orthohepadnaviridae hepatitis B virus

<400> SEQUENCE: 518

Trp Leu Ser Leu Asp Val Ser Ala
1               5

<210> SEQ ID NO 519
<211> LENGTH: 9
<212> TYPE: PRT
<213> ORGANISM: Orthohepadnaviridae hepatitis B virus

<400> SEQUENCE: 519

Trp Leu Ser Leu Asp Val Ser Ala Ala
1               5

<210> SEQ ID NO 520
<211> LENGTH: 9
<212> TYPE: PRT
<213> ORGANISM: Orthohepadnaviridae hepatitis B virus

<400> SEQUENCE: 520

Trp Leu Ser Leu Leu Val Pro Phe Val
1               5

<210> SEQ ID NO 521
<211> LENGTH: 8
<212> TYPE: PRT
<213> ORGANISM: Orthohepadnaviridae hepatitis B virus

<400> SEQUENCE: 521

Trp Met Cys Leu Arg Arg Phe Ile
1               5

<210> SEQ ID NO 522
<211> LENGTH: 9
<212> TYPE: PRT
<213> ORGANISM: Orthohepadnaviridae hepatitis B virus
```

```
<400> SEQUENCE: 522

Trp Met Cys Leu Arg Arg Phe Ile Ile
 1               5

<210> SEQ ID NO 523
<211> LENGTH: 11
<212> TYPE: PRT
<213> ORGANISM: Orthohepadnaviridae hepatitis B virus

<400> SEQUENCE: 523

Trp Met Cys Leu Arg Arg Phe Ile Ile Phe Leu
 1               5                  10

<210> SEQ ID NO 524
<211> LENGTH: 10
<212> TYPE: PRT
<213> ORGANISM: Orthohepadnaviridae hepatitis B virus

<400> SEQUENCE: 524

Trp Met Met Trp Tyr Trp Gly Pro Ser Leu
 1               5                  10

<210> SEQ ID NO 525
<211> LENGTH: 9
<212> TYPE: PRT
<213> ORGANISM: Orthohepadnaviridae hepatitis B virus

<400> SEQUENCE: 525

Trp Thr His Lys Val Gly Asn Phe Thr
 1               5

<210> SEQ ID NO 526
<211> LENGTH: 11
<212> TYPE: PRT
<213> ORGANISM: Orthohepadnaviridae hepatitis B virus

<400> SEQUENCE: 526

Trp Thr His Lys Val Gly Asn Phe Thr Gly Leu
 1               5                  10

<210> SEQ ID NO 527
<211> LENGTH: 8
<212> TYPE: PRT
<213> ORGANISM: Orthohepadnaviridae hepatitis B virus

<400> SEQUENCE: 527

Tyr Leu His Thr Leu Trp Lys Ala
 1               5

<210> SEQ ID NO 528
<211> LENGTH: 10
<212> TYPE: PRT
<213> ORGANISM: Orthohepadnaviridae hepatitis B virus

<400> SEQUENCE: 528

Tyr Leu His Thr Leu Trp Lys Ala Gly Ile
 1               5                  10

<210> SEQ ID NO 529
<211> LENGTH: 11
<212> TYPE: PRT
<213> ORGANISM: Orthohepadnaviridae hepatitis B virus

<400> SEQUENCE: 529
```

```
Tyr Leu His Thr Leu Trp Lys Ala Gly Ile Leu
 1               5                  10

<210> SEQ ID NO 530
<211> LENGTH: 8
<212> TYPE: PRT
<213> ORGANISM: Orthohepadnaviridae hepatitis B virus

<400> SEQUENCE: 530

Tyr Leu Pro Leu Asp Lys Gly Ile
 1               5

<210> SEQ ID NO 531
<211> LENGTH: 9
<212> TYPE: PRT
<213> ORGANISM: Orthohepadnaviridae hepatitis B virus

<400> SEQUENCE: 531

Tyr Leu Val Ser Phe Gly Val Trp Ile
 1               5

<210> SEQ ID NO 532
<211> LENGTH: 11
<212> TYPE: PRT
<213> ORGANISM: Orthohepadnaviridae hepatitis B virus

<400> SEQUENCE: 532

Tyr Leu Val Ser Phe Gly Val Trp Ile Arg Thr
 1               5                  10

<210> SEQ ID NO 533
<211> LENGTH: 9
<212> TYPE: PRT
<213> ORGANISM: Orthohepadnaviridae hepatitis B virus

<400> SEQUENCE: 533

Tyr Met Asp Asp Val Val Leu Gly Ala
 1               5

<210> SEQ ID NO 534
<211> LENGTH: 8
<212> TYPE: PRT
<213> ORGANISM: Orthohepadnaviridae hepatitis B virus

<400> SEQUENCE: 534

Tyr Thr Ser Phe Pro Trp Leu Leu
 1               5

<210> SEQ ID NO 535
<211> LENGTH: 11
<212> TYPE: PRT
<213> ORGANISM: Orthohepadnaviridae hepatitis B virus

<400> SEQUENCE: 535

Tyr Thr Ser Phe Pro Trp Leu Leu Gly Cys Ala
 1               5                  10

<210> SEQ ID NO 536
<211> LENGTH: 9
<212> TYPE: PRT
<213> ORGANISM: Orthohepadnaviridae hepatitis B virus

<400> SEQUENCE: 536

Tyr Val Pro Ser Ala Leu Asn Pro Ala
```

```
<210> SEQ ID NO 537
<211> LENGTH: 8
<212> TYPE: PRT
<213> ORGANISM: Orthohepadnaviridae hepatitis B virus

<400> SEQUENCE: 537

Ala Ala Cys Phe Ala Arg Ser Arg
1               5

<210> SEQ ID NO 538
<211> LENGTH: 8
<212> TYPE: PRT
<213> ORGANISM: Orthohepadnaviridae hepatitis B virus

<400> SEQUENCE: 538

Ala Ile Cys Ser Val Val Arg Arg
1               5

<210> SEQ ID NO 539
<211> LENGTH: 10
<212> TYPE: PRT
<213> ORGANISM: Orthohepadnaviridae hepatitis B virus

<400> SEQUENCE: 539

Ala Leu Asn Pro Ala Asp Asp Pro Ser Arg
1               5                   10

<210> SEQ ID NO 540
<211> LENGTH: 8
<212> TYPE: PRT
<213> ORGANISM: Orthohepadnaviridae hepatitis B virus

<400> SEQUENCE: 540

Ala Leu Arg Phe Thr Ser Ala Arg
1               5

<210> SEQ ID NO 541
<211> LENGTH: 9
<212> TYPE: PRT
<213> ORGANISM: Orthohepadnaviridae hepatitis B virus

<400> SEQUENCE: 541

Ala Ser Pro Leu His Val Ala Trp Arg
1               5

<210> SEQ ID NO 542
<211> LENGTH: 9
<212> TYPE: PRT
<213> ORGANISM: Orthohepadnaviridae hepatitis B virus

<400> SEQUENCE: 542

Ala Ser Thr Asn Arg Gln Ser Gly Arg
1               5

<210> SEQ ID NO 543
<211> LENGTH: 8
<212> TYPE: PRT
<213> ORGANISM: Orthohepadnaviridae hepatitis B virus

<400> SEQUENCE: 543

Cys Ala Ala Asn Trp Ile Leu Arg
1               5
```

<210> SEQ ID NO 544
<211> LENGTH: 9
<212> TYPE: PRT
<213> ORGANISM: Orthohepadnaviridae hepatitis B virus

<400> SEQUENCE: 544

Cys Ala Leu Arg Phe Thr Ser Ala Arg
1               5

<210> SEQ ID NO 545
<211> LENGTH: 10
<212> TYPE: PRT
<213> ORGANISM: Orthohepadnaviridae hepatitis B virus

<400> SEQUENCE: 545

Cys Leu Arg Pro Val Gly Ala Glu Ser Arg
1               5                   10

<210> SEQ ID NO 546
<211> LENGTH: 9
<212> TYPE: PRT
<213> ORGANISM: Orthohepadnaviridae hepatitis B virus

<400> SEQUENCE: 546

Cys Ser Pro His His Thr Ala Leu Arg
1               5

<210> SEQ ID NO 547
<211> LENGTH: 11
<212> TYPE: PRT
<213> ORGANISM: Orthohepadnaviridae hepatitis B virus

<400> SEQUENCE: 547

Asp Leu Leu Asp Thr Ala Ser Ala Leu Tyr Arg
1               5                   10

<210> SEQ ID NO 548
<211> LENGTH: 8
<212> TYPE: PRT
<213> ORGANISM: Orthohepadnaviridae hepatitis B virus

<400> SEQUENCE: 548

Asp Thr Ala Ser Ala Leu Tyr Arg
1               5

<210> SEQ ID NO 549
<211> LENGTH: 11
<212> TYPE: PRT
<213> ORGANISM: Orthohepadnaviridae hepatitis B virus

<400> SEQUENCE: 549

Glu Ala Gly Pro Leu Glu Glu Glu Leu Pro Arg
1               5                   10

<210> SEQ ID NO 550
<211> LENGTH: 9
<212> TYPE: PRT
<213> ORGANISM: Orthohepadnaviridae hepatitis B virus

<400> SEQUENCE: 550

Glu Leu Leu Ala Ala Cys Phe Ala Arg
1               5

<210> SEQ ID NO 551

-continued

```
<211> LENGTH: 11
<212> TYPE: PRT
<213> ORGANISM: Orthohepadnaviridae hepatitis B virus

<400> SEQUENCE: 551

Glu Leu Leu Ala Ala Cys Phe Ala Arg Ser Arg
1               5                   10

<210> SEQ ID NO 552
<211> LENGTH: 8
<212> TYPE: PRT
<213> ORGANISM: Orthohepadnaviridae hepatitis B virus

<400> SEQUENCE: 552

Glu Thr Thr Val Val Arg Arg Arg
1               5

<210> SEQ ID NO 553
<211> LENGTH: 10
<212> TYPE: PRT
<213> ORGANISM: Orthohepadnaviridae hepatitis B virus

<400> SEQUENCE: 553

Glu Thr Thr Val Val Arg Arg Arg Gly Arg
1               5                   10

<210> SEQ ID NO 554
<211> LENGTH: 10
<212> TYPE: PRT
<213> ORGANISM: Orthohepadnaviridae hepatitis B virus

<400> SEQUENCE: 554

Phe Ala Ser Pro Leu His Val Ala Trp Arg
1               5                   10

<210> SEQ ID NO 555
<211> LENGTH: 10
<212> TYPE: PRT
<213> ORGANISM: Orthohepadnaviridae hepatitis B virus

<400> SEQUENCE: 555

Phe Ser Ser Ala Gly Pro Cys Ala Leu Arg
1               5                   10

<210> SEQ ID NO 556
<211> LENGTH: 8
<212> TYPE: PRT
<213> ORGANISM: Orthohepadnaviridae hepatitis B virus

<400> SEQUENCE: 556

Phe Thr Phe Ser Pro Thr Tyr Lys
1               5

<210> SEQ ID NO 557
<211> LENGTH: 10
<212> TYPE: PRT
<213> ORGANISM: Orthohepadnaviridae hepatitis B virus

<400> SEQUENCE: 557

Phe Thr Ser Ala Ile Cys Ser Val Val Arg
1               5                   10

<210> SEQ ID NO 558
<211> LENGTH: 11
<212> TYPE: PRT
```

<213> ORGANISM: Orthohepadnaviridae hepatitis B virus

<400> SEQUENCE: 558

Phe Thr Ser Ala Ile Cys Ser Val Val Arg Arg
1               5                   10

<210> SEQ ID NO 559
<211> LENGTH: 9
<212> TYPE: PRT
<213> ORGANISM: Orthohepadnaviridae hepatitis B virus

<400> SEQUENCE: 559

Phe Val Leu Gly Gly Cys Arg His Lys
1               5

<210> SEQ ID NO 560
<211> LENGTH: 8
<212> TYPE: PRT
<213> ORGANISM: Orthohepadnaviridae hepatitis B virus

<400> SEQUENCE: 560

Gly Ile His Leu Asn Pro Asn Lys
1               5

<210> SEQ ID NO 561
<211> LENGTH: 10
<212> TYPE: PRT
<213> ORGANISM: Orthohepadnaviridae hepatitis B virus

<400> SEQUENCE: 561

Gly Ile His Leu Asn Pro Asn Lys Thr Lys
1               5                   10

<210> SEQ ID NO 562
<211> LENGTH: 11
<212> TYPE: PRT
<213> ORGANISM: Orthohepadnaviridae hepatitis B virus

<400> SEQUENCE: 562

Gly Ile His Leu Asn Pro Asn Lys Thr Lys Arg
1               5                   10

<210> SEQ ID NO 563
<211> LENGTH: 8
<212> TYPE: PRT
<213> ORGANISM: Orthohepadnaviridae hepatitis B virus

<400> SEQUENCE: 563

Gly Met Asp Ile Asp Pro Tyr Lys
1               5

<210> SEQ ID NO 564
<211> LENGTH: 10
<212> TYPE: PRT
<213> ORGANISM: Orthohepadnaviridae hepatitis B virus

<400> SEQUENCE: 564

Gly Thr Asp Asn Ser Val Val Leu Ser Arg
1               5                   10

<210> SEQ ID NO 565
<211> LENGTH: 11
<212> TYPE: PRT
<213> ORGANISM: Orthohepadnaviridae hepatitis B virus

```
<400> SEQUENCE: 565

Gly Thr Asp Asn Ser Val Val Leu Ser Arg Lys
 1               5                  10

<210> SEQ ID NO 566
<211> LENGTH: 11
<212> TYPE: PRT
<213> ORGANISM: Orthohepadnaviridae hepatitis B virus

<400> SEQUENCE: 566

Gly Val Trp Ile Arg Thr Pro Pro Ala Tyr Arg
 1               5                  10

<210> SEQ ID NO 567
<211> LENGTH: 9
<212> TYPE: PRT
<213> ORGANISM: Orthohepadnaviridae hepatitis B virus

<400> SEQUENCE: 567

His Ile Ser Cys Leu Thr Phe Gly Arg
 1               5

<210> SEQ ID NO 568
<211> LENGTH: 8
<212> TYPE: PRT
<213> ORGANISM: Orthohepadnaviridae hepatitis B virus

<400> SEQUENCE: 568

His Leu Asn Pro Asn Lys Thr Lys
 1               5

<210> SEQ ID NO 569
<211> LENGTH: 9
<212> TYPE: PRT
<213> ORGANISM: Orthohepadnaviridae hepatitis B virus

<400> SEQUENCE: 569

His Leu Asn Pro Asn Lys Thr Lys Arg
 1               5

<210> SEQ ID NO 570
<211> LENGTH: 11
<212> TYPE: PRT
<213> ORGANISM: Orthohepadnaviridae hepatitis B virus

<400> SEQUENCE: 570

His Thr Leu Trp Lys Ala Gly Ile Leu Tyr Lys
 1               5                  10

<210> SEQ ID NO 571
<211> LENGTH: 8
<212> TYPE: PRT
<213> ORGANISM: Orthohepadnaviridae hepatitis B virus

<400> SEQUENCE: 571

Ile Ser Cys Leu Thr Phe Gly Arg
 1               5

<210> SEQ ID NO 572
<211> LENGTH: 8
<212> TYPE: PRT
<213> ORGANISM: Orthohepadnaviridae hepatitis B virus

<400> SEQUENCE: 572
```

```
Lys Ala Gly Ile Leu Tyr Lys Arg
 1               5
```

<210> SEQ ID NO 573
<211> LENGTH: 11
<212> TYPE: PRT
<213> ORGANISM: Orthohepadnaviridae hepatitis B virus

<400> SEQUENCE: 573

```
Lys Leu Pro Val Asn Arg Pro Ile Asp Trp Lys
 1               5                  10
```

<210> SEQ ID NO 574
<211> LENGTH: 9
<212> TYPE: PRT
<213> ORGANISM: Orthohepadnaviridae hepatitis B virus

<400> SEQUENCE: 574

```
Lys Val Phe Val Leu Gly Gly Cys Arg
 1               5
```

<210> SEQ ID NO 575
<211> LENGTH: 9
<212> TYPE: PRT
<213> ORGANISM: Orthohepadnaviridae hepatitis B virus

<400> SEQUENCE: 575

```
Leu Ala Ala Cys Phe Ala Arg Ser Arg
 1               5
```

<210> SEQ ID NO 576
<211> LENGTH: 8
<212> TYPE: PRT
<213> ORGANISM: Orthohepadnaviridae hepatitis B virus

<400> SEQUENCE: 576

```
Leu Leu Ala Ala Cys Phe Ala Arg
 1               5
```

<210> SEQ ID NO 577
<211> LENGTH: 10
<212> TYPE: PRT
<213> ORGANISM: Orthohepadnaviridae hepatitis B virus

<400> SEQUENCE: 577

```
Leu Leu Ala Ala Cys Phe Ala Arg Ser Arg
 1               5                  10
```

<210> SEQ ID NO 578
<211> LENGTH: 10
<212> TYPE: PRT
<213> ORGANISM: Orthohepadnaviridae hepatitis B virus

<400> SEQUENCE: 578

```
Leu Leu Asp Thr Ala Ser Ala Leu Tyr Arg
 1               5                  10
```

<210> SEQ ID NO 579
<211> LENGTH: 11
<212> TYPE: PRT
<213> ORGANISM: Orthohepadnaviridae hepatitis B virus

<400> SEQUENCE: 579

```
Leu Leu Gly Cys Ala Ala Asn Trp Ile Leu Arg
 1               5                  10
```

```
<210> SEQ ID NO 580
<211> LENGTH: 11
<212> TYPE: PRT
<213> ORGANISM: Orthohepadnaviridae hepatitis B virus

<400> SEQUENCE: 580

Leu Ser Leu Gly Ile His Leu Asn Pro Asn Lys
 1               5                  10

<210> SEQ ID NO 581
<211> LENGTH: 11
<212> TYPE: PRT
<213> ORGANISM: Orthohepadnaviridae hepatitis B virus

<400> SEQUENCE: 581

Leu Ser Thr Leu Pro Glu Thr Thr Val Val Arg
 1               5                  10

<210> SEQ ID NO 582
<211> LENGTH: 8
<212> TYPE: PRT
<213> ORGANISM: Orthohepadnaviridae hepatitis B virus

<400> SEQUENCE: 582

Leu Ser Tyr Gln His Phe Arg Lys
 1               5

<210> SEQ ID NO 583
<211> LENGTH: 8
<212> TYPE: PRT
<213> ORGANISM: Orthohepadnaviridae hepatitis B virus

<400> SEQUENCE: 583

Leu Thr Val Asn Glu Lys Arg Arg
 1               5

<210> SEQ ID NO 584
<211> LENGTH: 9
<212> TYPE: PRT
<213> ORGANISM: Orthohepadnaviridae hepatitis B virus

<400> SEQUENCE: 584

Leu Val Ser Phe Gly Val Trp Ile Arg
 1               5

<210> SEQ ID NO 585
<211> LENGTH: 10
<212> TYPE: PRT
<213> ORGANISM: Orthohepadnaviridae hepatitis B virus

<400> SEQUENCE: 585

Leu Val Val Asp Phe Ser Gln Phe Ser Arg
 1               5                  10

<210> SEQ ID NO 586
<211> LENGTH: 11
<212> TYPE: PRT
<213> ORGANISM: Orthohepadnaviridae hepatitis B virus

<400> SEQUENCE: 586

Met Ser Thr Thr Asp Leu Glu Ala Tyr Phe Lys
 1               5                  10
```

```
<210> SEQ ID NO 587
<211> LENGTH: 8
<212> TYPE: PRT
<213> ORGANISM: Orthohepadnaviridae hepatitis B virus

<400> SEQUENCE: 587

Asn Leu Glu Asp Pro Ala Ser Arg
1               5

<210> SEQ ID NO 588
<211> LENGTH: 11
<212> TYPE: PRT
<213> ORGANISM: Orthohepadnaviridae hepatitis B virus

<400> SEQUENCE: 588

Asn Leu Asn Val Ser Ile Pro Trp Thr His Lys
1               5                   10

<210> SEQ ID NO 589
<211> LENGTH: 8
<212> TYPE: PRT
<213> ORGANISM: Orthohepadnaviridae hepatitis B virus

<400> SEQUENCE: 589

Asn Ser Val Val Leu Ser Arg Lys
1               5

<210> SEQ ID NO 590
<211> LENGTH: 9
<212> TYPE: PRT
<213> ORGANISM: Orthohepadnaviridae hepatitis B virus

<400> SEQUENCE: 590

Asn Val Ser Ile Pro Trp Thr His Lys
1               5

<210> SEQ ID NO 591
<211> LENGTH: 9
<212> TYPE: PRT
<213> ORGANISM: Orthohepadnaviridae hepatitis B virus

<400> SEQUENCE: 591

Pro Ala Asp Asp Pro Ser Arg Gly Arg
1               5

<210> SEQ ID NO 592
<211> LENGTH: 9
<212> TYPE: PRT
<213> ORGANISM: Orthohepadnaviridae hepatitis B virus

<400> SEQUENCE: 592

Pro Ala Arg Asp Val Leu Cys Leu Arg
1               5

<210> SEQ ID NO 593
<211> LENGTH: 10
<212> TYPE: PRT
<213> ORGANISM: Orthohepadnaviridae hepatitis B virus

<400> SEQUENCE: 593

Pro Ala Ser Thr Asn Arg Gln Ser Gly Arg
1               5                   10

<210> SEQ ID NO 594
<211> LENGTH: 9
```

```
<212> TYPE: PRT
<213> ORGANISM: Orthohepadnaviridae hepatitis B virus

<400> SEQUENCE: 594

Pro Ile Asp Trp Lys Val Cys Gln Arg
1               5

<210> SEQ ID NO 595
<211> LENGTH: 8
<212> TYPE: PRT
<213> ORGANISM: Orthohepadnaviridae hepatitis B virus

<400> SEQUENCE: 595

Pro Ile Ile Leu Gly Phe Arg Lys
1               5

<210> SEQ ID NO 596
<211> LENGTH: 8
<212> TYPE: PRT
<213> ORGANISM: Orthohepadnaviridae hepatitis B virus

<400> SEQUENCE: 596

Pro Leu Glu Glu Glu Leu Pro Arg
1               5

<210> SEQ ID NO 597
<211> LENGTH: 8
<212> TYPE: PRT
<213> ORGANISM: Orthohepadnaviridae hepatitis B virus

<400> SEQUENCE: 597

Pro Leu Ser Tyr Gln His Phe Arg
1               5

<210> SEQ ID NO 598
<211> LENGTH: 9
<212> TYPE: PRT
<213> ORGANISM: Orthohepadnaviridae hepatitis B virus

<400> SEQUENCE: 598

Pro Leu Ser Tyr Gln His Phe Arg Lys
1               5

<210> SEQ ID NO 599
<211> LENGTH: 8
<212> TYPE: PRT
<213> ORGANISM: Orthohepadnaviridae hepatitis B virus

<400> SEQUENCE: 599

Pro Leu Thr Val Asn Glu Lys Arg
1               5

<210> SEQ ID NO 600
<211> LENGTH: 9
<212> TYPE: PRT
<213> ORGANISM: Orthohepadnaviridae hepatitis B virus

<400> SEQUENCE: 600

Pro Leu Thr Val Asn Glu Lys Arg Arg
1               5

<210> SEQ ID NO 601
<211> LENGTH: 9
<212> TYPE: PRT
<213> ORGANISM: Orthohepadnaviridae hepatitis B virus
```

-continued

<400> SEQUENCE: 601

Pro Val Gly Ala Glu Ser Arg Gly Arg
1               5

<210> SEQ ID NO 602
<211> LENGTH: 9
<212> TYPE: PRT
<213> ORGANISM: Orthohepadnaviridae hepatitis B virus

<400> SEQUENCE: 602

Pro Val Asn Arg Pro Ile Asp Trp Lys
1               5

<210> SEQ ID NO 603
<211> LENGTH: 10
<212> TYPE: PRT
<213> ORGANISM: Orthohepadnaviridae hepatitis B virus

<400> SEQUENCE: 603

Gln Ala Phe Thr Phe Ser Pro Thr Tyr Lys
1               5                   10

<210> SEQ ID NO 604
<211> LENGTH: 9
<212> TYPE: PRT
<213> ORGANISM: Orthohepadnaviridae hepatitis B virus

<400> SEQUENCE: 604

Gln Ala Gly Phe Phe Leu Leu Thr Arg
1               5

<210> SEQ ID NO 605
<211> LENGTH: 11
<212> TYPE: PRT
<213> ORGANISM: Orthohepadnaviridae hepatitis B virus

<400> SEQUENCE: 605

Gln Ser Pro Arg Arg Arg Arg Ser Gln Ser Arg
1               5                   10

<210> SEQ ID NO 606
<211> LENGTH: 8
<212> TYPE: PRT
<213> ORGANISM: Orthohepadnaviridae hepatitis B virus

<400> SEQUENCE: 606

Gln Ser Ser Gly Ile Leu Ser Arg
1               5

<210> SEQ ID NO 607
<211> LENGTH: 9
<212> TYPE: PRT
<213> ORGANISM: Orthohepadnaviridae hepatitis B virus

<400> SEQUENCE: 607

Arg Leu Lys Leu Ile Met Pro Ala Arg
1               5

<210> SEQ ID NO 608
<211> LENGTH: 11
<212> TYPE: PRT
<213> ORGANISM: Orthohepadnaviridae hepatitis B virus

<400> SEQUENCE: 608

-continued

Arg Leu Lys Val Phe Val Leu Gly Gly Cys Arg
1               5                   10

<210> SEQ ID NO 609
<211> LENGTH: 11
<212> TYPE: PRT
<213> ORGANISM: Orthohepadnaviridae hepatitis B virus

<400> SEQUENCE: 609

Arg Leu Val Val Asp Phe Ser Gln Phe Ser Arg
1               5                   10

<210> SEQ ID NO 610
<211> LENGTH: 11
<212> TYPE: PRT
<213> ORGANISM: Orthohepadnaviridae hepatitis B virus

<400> SEQUENCE: 610

Arg Ser Pro Arg Arg Arg Thr Pro Ser Pro Arg
1               5                   10

<210> SEQ ID NO 611
<211> LENGTH: 8
<212> TYPE: PRT
<213> ORGANISM: Orthohepadnaviridae hepatitis B virus

<400> SEQUENCE: 611

Arg Ser Gln Ser Pro Arg Arg Arg
1               5

<210> SEQ ID NO 612
<211> LENGTH: 9
<212> TYPE: PRT
<213> ORGANISM: Orthohepadnaviridae hepatitis B virus

<400> SEQUENCE: 612

Arg Ser Gln Ser Pro Arg Arg Arg Arg
1               5

<210> SEQ ID NO 613
<211> LENGTH: 8
<212> TYPE: PRT
<213> ORGANISM: Orthohepadnaviridae hepatitis B virus

<400> SEQUENCE: 613

Arg Thr Pro Ser Pro Arg Arg Arg
1               5

<210> SEQ ID NO 614
<211> LENGTH: 9
<212> TYPE: PRT
<213> ORGANISM: Orthohepadnaviridae hepatitis B virus

<400> SEQUENCE: 614

Arg Thr Pro Ser Pro Arg Arg Arg Arg
1               5

<210> SEQ ID NO 615
<211> LENGTH: 11
<212> TYPE: PRT
<213> ORGANISM: Orthohepadnaviridae hepatitis B virus

<400> SEQUENCE: 615

Arg Val Thr Gly Gly Val Phe Leu Val Asp Lys

-continued

```
<210> SEQ ID NO 616
<211> LENGTH: 8
<212> TYPE: PRT
<213> ORGANISM: Orthohepadnaviridae hepatitis B virus

<400> SEQUENCE: 616

Ser Ala Gly Pro Cys Ala Leu Arg
1               5

<210> SEQ ID NO 617
<211> LENGTH: 8
<212> TYPE: PRT
<213> ORGANISM: Orthohepadnaviridae hepatitis B virus

<400> SEQUENCE: 617

Ser Ala Ile Cys Ser Val Val Arg
1               5

<210> SEQ ID NO 618
<211> LENGTH: 9
<212> TYPE: PRT
<213> ORGANISM: Orthohepadnaviridae hepatitis B virus

<400> SEQUENCE: 618

Ser Ala Ile Cys Ser Val Val Arg Arg
1               5

<210> SEQ ID NO 619
<211> LENGTH: 11
<212> TYPE: PRT
<213> ORGANISM: Orthohepadnaviridae hepatitis B virus

<400> SEQUENCE: 619

Ser Ala Leu Asn Pro Ala Asp Asp Pro Ser Arg
1               5                   10

<210> SEQ ID NO 620
<211> LENGTH: 10
<212> TYPE: PRT
<213> ORGANISM: Orthohepadnaviridae hepatitis B virus

<400> SEQUENCE: 620

Ser Leu Gly Ile His Leu Asn Pro Asn Lys
1               5                   10

<210> SEQ ID NO 621
<211> LENGTH: 9
<212> TYPE: PRT
<213> ORGANISM: Orthohepadnaviridae hepatitis B virus

<400> SEQUENCE: 621

Ser Ser Ala Gly Pro Cys Ala Leu Arg
1               5

<210> SEQ ID NO 622
<211> LENGTH: 10
<212> TYPE: PRT
<213> ORGANISM: Orthohepadnaviridae hepatitis B virus

<400> SEQUENCE: 622

Ser Thr Leu Pro Glu Thr Thr Val Val Arg
1               5                   10
```

-continued

```
<210> SEQ ID NO 623
<211> LENGTH: 11
<212> TYPE: PRT
<213> ORGANISM: Orthohepadnaviridae hepatitis B virus

<400> SEQUENCE: 623

Ser Thr Leu Pro Glu Thr Thr Val Val Arg Arg
1               5                   10

<210> SEQ ID NO 624
<211> LENGTH: 8
<212> TYPE: PRT
<213> ORGANISM: Orthohepadnaviridae hepatitis B virus

<400> SEQUENCE: 624

Ser Thr Asn Arg Gln Ser Gly Arg
1               5

<210> SEQ ID NO 625
<211> LENGTH: 10
<212> TYPE: PRT
<213> ORGANISM: Orthohepadnaviridae hepatitis B virus

<400> SEQUENCE: 625

Ser Thr Thr Asp Leu Glu Ala Tyr Phe Lys
1               5                   10

<210> SEQ ID NO 626
<211> LENGTH: 11
<212> TYPE: PRT
<213> ORGANISM: Orthohepadnaviridae hepatitis B virus

<400> SEQUENCE: 626

Thr Ala Glu Leu Leu Ala Ala Cys Phe Ala Arg
1               5                   10

<210> SEQ ID NO 627
<211> LENGTH: 9
<212> TYPE: PRT
<213> ORGANISM: Orthohepadnaviridae hepatitis B virus

<400> SEQUENCE: 627

Thr Leu Pro Glu Thr Thr Val Val Arg
1               5

<210> SEQ ID NO 628
<211> LENGTH: 10
<212> TYPE: PRT
<213> ORGANISM: Orthohepadnaviridae hepatitis B virus

<400> SEQUENCE: 628

Thr Leu Pro Glu Thr Thr Val Val Arg Arg
1               5                   10

<210> SEQ ID NO 629
<211> LENGTH: 11
<212> TYPE: PRT
<213> ORGANISM: Orthohepadnaviridae hepatitis B virus

<400> SEQUENCE: 629

Thr Leu Pro Glu Thr Thr Val Val Arg Arg Arg
1               5                   10

<210> SEQ ID NO 630
```

```
<211> LENGTH: 10
<212> TYPE: PRT
<213> ORGANISM: Orthohepadnaviridae hepatitis B virus

<400> SEQUENCE: 630

Thr Leu Trp Lys Ala Gly Ile Leu Tyr Lys
1               5                   10

<210> SEQ ID NO 631
<211> LENGTH: 11
<212> TYPE: PRT
<213> ORGANISM: Orthohepadnaviridae hepatitis B virus

<400> SEQUENCE: 631

Thr Leu Trp Lys Ala Gly Ile Leu Tyr Lys Arg
1               5                   10

<210> SEQ ID NO 632
<211> LENGTH: 9
<212> TYPE: PRT
<213> ORGANISM: Orthohepadnaviridae hepatitis B virus

<400> SEQUENCE: 632

Thr Ser Ala Ile Cys Ser Val Val Arg
1               5

<210> SEQ ID NO 633
<211> LENGTH: 10
<212> TYPE: PRT
<213> ORGANISM: Orthohepadnaviridae hepatitis B virus

<400> SEQUENCE: 633

Thr Ser Ala Ile Cys Ser Val Val Arg Arg
1               5                   10

<210> SEQ ID NO 634
<211> LENGTH: 9
<212> TYPE: PRT
<213> ORGANISM: Orthohepadnaviridae hepatitis B virus

<400> SEQUENCE: 634

Thr Thr Asp Leu Glu Ala Tyr Phe Lys
1               5

<210> SEQ ID NO 635
<211> LENGTH: 8
<212> TYPE: PRT
<213> ORGANISM: Orthohepadnaviridae hepatitis B virus

<400> SEQUENCE: 635

Thr Thr Ser Thr Gly Pro Cys Lys
1               5

<210> SEQ ID NO 636
<211> LENGTH: 9
<212> TYPE: PRT
<213> ORGANISM: Orthohepadnaviridae hepatitis B virus

<400> SEQUENCE: 636

Thr Thr Val Val Arg Arg Arg Gly Arg
1               5

<210> SEQ ID NO 637
<211> LENGTH: 8
<212> TYPE: PRT
```

<213> ORGANISM: Orthohepadnaviridae hepatitis B virus

<400> SEQUENCE: 637

Thr Val Val Arg Arg Arg Gly Arg
 1               5

<210> SEQ ID NO 638
<211> LENGTH: 11
<212> TYPE: PRT
<213> ORGANISM: Orthohepadnaviridae hepatitis B virus

<400> SEQUENCE: 638

Thr Val Val Arg Arg Arg Gly Arg Ser Pro Arg
 1               5                  10

<210> SEQ ID NO 639
<211> LENGTH: 8
<212> TYPE: PRT
<213> ORGANISM: Orthohepadnaviridae hepatitis B virus

<400> SEQUENCE: 639

Val Leu Gly Gly Cys Arg His Lys
 1               5

<210> SEQ ID NO 640
<211> LENGTH: 11
<212> TYPE: PRT
<213> ORGANISM: Orthohepadnaviridae hepatitis B virus

<400> SEQUENCE: 640

Val Leu Gln Ala Gly Phe Phe Leu Leu Thr Arg
 1               5                  10

<210> SEQ ID NO 641
<211> LENGTH: 8
<212> TYPE: PRT
<213> ORGANISM: Orthohepadnaviridae hepatitis B virus

<400> SEQUENCE: 641

Val Ser Phe Gly Val Trp Ile Arg
 1               5

<210> SEQ ID NO 642
<211> LENGTH: 8
<212> TYPE: PRT
<213> ORGANISM: Orthohepadnaviridae hepatitis B virus

<400> SEQUENCE: 642

Val Ser Ile Pro Trp Thr His Lys
 1               5

<210> SEQ ID NO 643
<211> LENGTH: 10
<212> TYPE: PRT
<213> ORGANISM: Orthohepadnaviridae hepatitis B virus

<400> SEQUENCE: 643

Val Thr Gly Gly Val Phe Leu Val Asp Lys
 1               5                  10

<210> SEQ ID NO 644
<211> LENGTH: 9
<212> TYPE: PRT
<213> ORGANISM: Orthohepadnaviridae hepatitis B virus

<400> SEQUENCE: 644

Val Val Asp Phe Ser Gln Phe Ser Arg
1               5

<210> SEQ ID NO 645
<211> LENGTH: 10
<212> TYPE: PRT
<213> ORGANISM: Orthohepadnaviridae hepatitis B virus

<400> SEQUENCE: 645

Val Val Arg Arg Arg Gly Arg Ser Pro Arg
1               5                   10

<210> SEQ ID NO 646
<211> LENGTH: 11
<212> TYPE: PRT
<213> ORGANISM: Orthohepadnaviridae hepatitis B virus

<400> SEQUENCE: 646

Val Val Arg Arg Arg Gly Arg Ser Pro Arg Arg
1               5                   10

<210> SEQ ID NO 647
<211> LENGTH: 9
<212> TYPE: PRT
<213> ORGANISM: Orthohepadnaviridae hepatitis B virus

<400> SEQUENCE: 647

Trp Ile Arg Thr Pro Pro Ala Tyr Arg
1               5

<210> SEQ ID NO 648
<211> LENGTH: 8
<212> TYPE: PRT
<213> ORGANISM: Orthohepadnaviridae hepatitis B virus

<400> SEQUENCE: 648

Trp Leu Gln Phe Arg Asn Ser Lys
1               5

<210> SEQ ID NO 649
<211> LENGTH: 11
<212> TYPE: PRT
<213> ORGANISM: Orthohepadnaviridae hepatitis B virus

<400> SEQUENCE: 649

Trp Leu Trp Gly Met Asp Ile Asp Pro Tyr Lys
1               5                   10

<210> SEQ ID NO 650
<211> LENGTH: 9
<212> TYPE: PRT
<213> ORGANISM: Orthohepadnaviridae hepatitis B virus

<400> SEQUENCE: 650

Tyr Leu Pro Leu Asp Lys Gly Ile Lys
1               5

<210> SEQ ID NO 651
<211> LENGTH: 10
<212> TYPE: PRT
<213> ORGANISM: Orthohepadnaviridae hepatitis B virus

<400> SEQUENCE: 651

```
Tyr Leu Val Ser Phe Gly Val Trp Ile Arg
1               5                   10
```

<210> SEQ ID NO 652
<211> LENGTH: 10
<212> TYPE: PRT
<213> ORGANISM: Orthohepadnaviridae hepatitis B virus

<400> SEQUENCE: 652

```
Tyr Met Asp Asp Val Val Leu Gly Ala Lys
1               5                   10
```

<210> SEQ ID NO 653
<211> LENGTH: 10
<212> TYPE: PRT
<213> ORGANISM: Orthohepadnaviridae hepatitis B virus

<400> SEQUENCE: 653

```
Tyr Ser His Pro Ile Ile Leu Gly Phe Arg
1               5                   10
```

<210> SEQ ID NO 654
<211> LENGTH: 11
<212> TYPE: PRT
<213> ORGANISM: Orthohepadnaviridae hepatitis B virus

<400> SEQUENCE: 654

```
Tyr Ser His Pro Ile Ile Leu Gly Phe Arg Lys
1               5                   10
```

<210> SEQ ID NO 655
<211> LENGTH: 8
<212> TYPE: PRT
<213> ORGANISM: Orthohepadnaviridae hepatitis B virus

<400> SEQUENCE: 655

```
Ala Phe Pro His Cys Leu Ala Phe
1               5
```

<210> SEQ ID NO 656
<211> LENGTH: 10
<212> TYPE: PRT
<213> ORGANISM: Orthohepadnaviridae hepatitis B virus

<400> SEQUENCE: 656

```
Ala Phe Pro His Cys Leu Ala Phe Ser Tyr
1               5                   10
```

<210> SEQ ID NO 657
<211> LENGTH: 11
<212> TYPE: PRT
<213> ORGANISM: Orthohepadnaviridae hepatitis B virus

<400> SEQUENCE: 657

```
Ala Phe Pro His Cys Leu Ala Phe Ser Tyr Met
1               5                   10
```

<210> SEQ ID NO 658
<211> LENGTH: 10
<212> TYPE: PRT
<213> ORGANISM: Orthohepadnaviridae hepatitis B virus

<400> SEQUENCE: 658

```
Ala Phe Ser Ser Ala Gly Pro Cys Ala Leu
1               5                   10
```

```
<210> SEQ ID NO 659
<211> LENGTH: 10
<212> TYPE: PRT
<213> ORGANISM: Orthohepadnaviridae hepatitis B virus

<400> SEQUENCE: 659

Ala Phe Ser Tyr Met Asp Asp Val Val Leu
1               5                   10

<210> SEQ ID NO 660
<211> LENGTH: 8
<212> TYPE: PRT
<213> ORGANISM: Orthohepadnaviridae hepatitis B virus

<400> SEQUENCE: 660

Ala Phe Thr Phe Ser Pro Thr Tyr
1               5

<210> SEQ ID NO 661
<211> LENGTH: 11
<212> TYPE: PRT
<213> ORGANISM: Orthohepadnaviridae hepatitis B virus

<400> SEQUENCE: 661

Ala Phe Thr Phe Ser Pro Thr Tyr Lys Ala Phe
1               5                   10

<210> SEQ ID NO 662
<211> LENGTH: 10
<212> TYPE: PRT
<213> ORGANISM: Orthohepadnaviridae hepatitis B virus

<400> SEQUENCE: 662

Ala Ile Cys Ser Val Val Arg Arg Ala Phe
1               5                   10

<210> SEQ ID NO 663
<211> LENGTH: 8
<212> TYPE: PRT
<213> ORGANISM: Orthohepadnaviridae hepatitis B virus

<400> SEQUENCE: 663

Ala Ile Leu Cys Trp Gly Glu Leu
1               5

<210> SEQ ID NO 664
<211> LENGTH: 9
<212> TYPE: PRT
<213> ORGANISM: Orthohepadnaviridae hepatitis B virus

<400> SEQUENCE: 664

Ala Ile Leu Cys Trp Gly Glu Leu Met
1               5

<210> SEQ ID NO 665
<211> LENGTH: 9
<212> TYPE: PRT
<213> ORGANISM: Orthohepadnaviridae hepatitis B virus

<400> SEQUENCE: 665

Ala Leu Met Pro Leu Tyr Ala Cys Ile
1               5
```

-continued

<210> SEQ ID NO 666
<211> LENGTH: 9
<212> TYPE: PRT
<213> ORGANISM: Orthohepadnaviridae hepatitis B virus

<400> SEQUENCE: 666

Ala Leu Arg Gln Ala Ile Leu Cys Trp
 1               5

<210> SEQ ID NO 667
<211> LENGTH: 9
<212> TYPE: PRT
<213> ORGANISM: Orthohepadnaviridae hepatitis B virus

<400> SEQUENCE: 667

Ala Met Gln Trp Asn Ser Thr Thr Phe
 1               5

<210> SEQ ID NO 668
<211> LENGTH: 8
<212> TYPE: PRT
<213> ORGANISM: Orthohepadnaviridae hepatitis B virus

<400> SEQUENCE: 668

Ala Thr Pro Thr Gly Trp Gly Leu
 1               5

<210> SEQ ID NO 669
<211> LENGTH: 10
<212> TYPE: PRT
<213> ORGANISM: Orthohepadnaviridae hepatitis B virus

<400> SEQUENCE: 669

Ala Thr Pro Thr Gly Trp Gly Leu Ala Ile
 1               5                  10

<210> SEQ ID NO 670
<211> LENGTH: 8
<212> TYPE: PRT
<213> ORGANISM: Orthohepadnaviridae hepatitis B virus

<400> SEQUENCE: 670

Ala Val Pro Asn Leu Gln Ser Leu
 1               5

<210> SEQ ID NO 671
<211> LENGTH: 11
<212> TYPE: PRT
<213> ORGANISM: Orthohepadnaviridae hepatitis B virus

<400> SEQUENCE: 671

Ala Val Pro Asn Leu Gln Ser Leu Thr Asn Leu
 1               5                  10

<210> SEQ ID NO 672
<211> LENGTH: 9
<212> TYPE: PRT
<213> ORGANISM: Orthohepadnaviridae hepatitis B virus

<400> SEQUENCE: 672

Ala Tyr Arg Pro Pro Asn Ala Pro Ile
 1               5

<210> SEQ ID NO 673
<211> LENGTH: 10

-continued

<212> TYPE: PRT
<213> ORGANISM: Orthohepadnaviridae hepatitis B virus

<400> SEQUENCE: 673

Ala Tyr Arg Pro Pro Asn Ala Pro Ile Leu
1               5                   10

<210> SEQ ID NO 674
<211> LENGTH: 11
<212> TYPE: PRT
<213> ORGANISM: Orthohepadnaviridae hepatitis B virus

<400> SEQUENCE: 674

Cys Phe Arg Lys Leu Pro Val Asn Arg Pro Ile
1               5                   10

<210> SEQ ID NO 675
<211> LENGTH: 8
<212> TYPE: PRT
<213> ORGANISM: Orthohepadnaviridae hepatitis B virus

<400> SEQUENCE: 675

Cys Ile Pro Ile Pro Ser Ser Trp
1               5

<210> SEQ ID NO 676
<211> LENGTH: 10
<212> TYPE: PRT
<213> ORGANISM: Orthohepadnaviridae hepatitis B virus

<400> SEQUENCE: 676

Cys Ile Pro Ile Pro Ser Ser Trp Ala Phe
1               5                   10

<210> SEQ ID NO 677
<211> LENGTH: 8
<212> TYPE: PRT
<213> ORGANISM: Orthohepadnaviridae hepatitis B virus

<400> SEQUENCE: 677

Cys Leu Gly Trp Leu Trp Gly Met
1               5

<210> SEQ ID NO 678
<211> LENGTH: 10
<212> TYPE: PRT
<213> ORGANISM: Orthohepadnaviridae hepatitis B virus

<400> SEQUENCE: 678

Cys Leu Gly Trp Leu Trp Gly Met Asp Ile
1               5                   10

<210> SEQ ID NO 679
<211> LENGTH: 8
<212> TYPE: PRT
<213> ORGANISM: Orthohepadnaviridae hepatitis B virus

<400> SEQUENCE: 679

Cys Leu Ile Phe Leu Leu Val Leu
1               5

<210> SEQ ID NO 680
<211> LENGTH: 9
<212> TYPE: PRT
<213> ORGANISM: Orthohepadnaviridae hepatitis B virus

```
<400> SEQUENCE: 680

Cys Leu Ile Phe Leu Leu Val Leu Leu
1               5

<210> SEQ ID NO 681
<211> LENGTH: 11
<212> TYPE: PRT
<213> ORGANISM: Orthohepadnaviridae hepatitis B virus

<400> SEQUENCE: 681

Cys Leu Ile Phe Leu Leu Val Leu Leu Asp Tyr
1               5                   10

<210> SEQ ID NO 682
<211> LENGTH: 8
<212> TYPE: PRT
<213> ORGANISM: Orthohepadnaviridae hepatitis B virus

<400> SEQUENCE: 682

Cys Leu Arg Arg Phe Ile Ile Phe
1               5

<210> SEQ ID NO 683
<211> LENGTH: 9
<212> TYPE: PRT
<213> ORGANISM: Orthohepadnaviridae hepatitis B virus

<400> SEQUENCE: 683

Cys Leu Arg Arg Phe Ile Ile Phe Leu
1               5

<210> SEQ ID NO 684
<211> LENGTH: 10
<212> TYPE: PRT
<213> ORGANISM: Orthohepadnaviridae hepatitis B virus

<400> SEQUENCE: 684

Cys Leu Arg Arg Phe Ile Ile Phe Leu Phe
1               5                   10

<210> SEQ ID NO 685
<211> LENGTH: 11
<212> TYPE: PRT
<213> ORGANISM: Orthohepadnaviridae hepatitis B virus

<400> SEQUENCE: 685

Cys Leu Arg Arg Phe Ile Ile Phe Leu Phe Ile
1               5                   10

<210> SEQ ID NO 686
<211> LENGTH: 10
<212> TYPE: PRT
<213> ORGANISM: Orthohepadnaviridae hepatitis B virus

<400> SEQUENCE: 686

Cys Thr Cys Ile Pro Ile Pro Ser Ser Trp
1               5                   10

<210> SEQ ID NO 687
<211> LENGTH: 8
<212> TYPE: PRT
<213> ORGANISM: Orthohepadnaviridae hepatitis B virus

<400> SEQUENCE: 687
```

```
Asp Ile Asp Pro Tyr Lys Glu Phe
  1               5
```

<210> SEQ ID NO 688
<211> LENGTH: 9
<212> TYPE: PRT
<213> ORGANISM: Orthohepadnaviridae hepatitis B virus

<400> SEQUENCE: 688

```
Asp Leu Leu Asp Thr Ala Ser Ala Leu
  1               5
```

<210> SEQ ID NO 689
<211> LENGTH: 10
<212> TYPE: PRT
<213> ORGANISM: Orthohepadnaviridae hepatitis B virus

<400> SEQUENCE: 689

```
Asp Leu Leu Asp Thr Ala Ser Ala Leu Tyr
  1               5                  10
```

<210> SEQ ID NO 690
<211> LENGTH: 11
<212> TYPE: PRT
<213> ORGANISM: Orthohepadnaviridae hepatitis B virus

<400> SEQUENCE: 690

```
Asp Leu Asn Leu Gly Asn Leu Asn Val Ser Ile
  1               5                  10
```

<210> SEQ ID NO 691
<211> LENGTH: 11
<212> TYPE: PRT
<213> ORGANISM: Orthohepadnaviridae hepatitis B virus

<400> SEQUENCE: 691

```
Asp Thr Ala Ser Ala Leu Tyr Arg Glu Ala Leu
  1               5                  10
```

<210> SEQ ID NO 692
<211> LENGTH: 8
<212> TYPE: PRT
<213> ORGANISM: Orthohepadnaviridae hepatitis B virus

<400> SEQUENCE: 692

```
Asp Trp Lys Val Cys Gln Arg Ile
  1               5
```

<210> SEQ ID NO 693
<211> LENGTH: 11
<212> TYPE: PRT
<213> ORGANISM: Orthohepadnaviridae hepatitis B virus

<400> SEQUENCE: 693

```
Asp Trp Lys Val Cys Gln Arg Ile Val Gly Leu
  1               5                  10
```

<210> SEQ ID NO 694
<211> LENGTH: 11
<212> TYPE: PRT
<213> ORGANISM: Orthohepadnaviridae hepatitis B virus

<400> SEQUENCE: 694

```
Asp Tyr Gln Gly Met Leu Pro Val Cys Pro Leu
```

```
                1               5                   10
```

<210> SEQ ID NO 695
<211> LENGTH: 8
<212> TYPE: PRT
<213> ORGANISM: Orthohepadnaviridae hepatitis B virus

<400> SEQUENCE: 695

Glu Leu Gly Glu Glu Ile Arg Leu
1               5

<210> SEQ ID NO 696
<211> LENGTH: 10
<212> TYPE: PRT
<213> ORGANISM: Orthohepadnaviridae hepatitis B virus

<400> SEQUENCE: 696

Glu Leu Leu Ser Phe Leu Pro Ser Asp Phe
1               5                   10

<210> SEQ ID NO 697
<211> LENGTH: 11
<212> TYPE: PRT
<213> ORGANISM: Orthohepadnaviridae hepatitis B virus

<400> SEQUENCE: 697

Glu Leu Leu Ser Phe Leu Pro Ser Asp Phe Phe
1               5                   10

<210> SEQ ID NO 698
<211> LENGTH: 9
<212> TYPE: PRT
<213> ORGANISM: Orthohepadnaviridae hepatitis B virus

<400> SEQUENCE: 698

Glu Tyr Leu Val Ser Phe Gly Val Trp
1               5

<210> SEQ ID NO 699
<211> LENGTH: 10
<212> TYPE: PRT
<213> ORGANISM: Orthohepadnaviridae hepatitis B virus

<400> SEQUENCE: 699

Glu Tyr Leu Val Ser Phe Gly Val Trp Ile
1               5                   10

<210> SEQ ID NO 700
<211> LENGTH: 8
<212> TYPE: PRT
<213> ORGANISM: Orthohepadnaviridae hepatitis B virus

<400> SEQUENCE: 700

Phe Phe Cys Leu Trp Val Tyr Ile
1               5

<210> SEQ ID NO 701
<211> LENGTH: 8
<212> TYPE: PRT
<213> ORGANISM: Orthohepadnaviridae hepatitis B virus

<400> SEQUENCE: 701

Phe Phe Leu Leu Thr Arg Ile Leu
1               5

```
<210> SEQ ID NO 702
<211> LENGTH: 10
<212> TYPE: PRT
<213> ORGANISM: Orthohepadnaviridae hepatitis B virus

<400> SEQUENCE: 702

Phe Phe Leu Leu Thr Arg Ile Leu Thr Ile
1               5                   10

<210> SEQ ID NO 703
<211> LENGTH: 11
<212> TYPE: PRT
<213> ORGANISM: Orthohepadnaviridae hepatitis B virus

<400> SEQUENCE: 703

Phe Phe Pro Asp His Gln Leu Asp Pro Ala Phe
1               5                   10

<210> SEQ ID NO 704
<211> LENGTH: 8
<212> TYPE: PRT
<213> ORGANISM: Orthohepadnaviridae hepatitis B virus

<400> SEQUENCE: 704

Phe Ile Ile Phe Leu Phe Ile Leu
1               5

<210> SEQ ID NO 705
<211> LENGTH: 9
<212> TYPE: PRT
<213> ORGANISM: Orthohepadnaviridae hepatitis B virus

<400> SEQUENCE: 705

Phe Ile Ile Phe Leu Phe Ile Leu Leu
1               5

<210> SEQ ID NO 706
<211> LENGTH: 10
<212> TYPE: PRT
<213> ORGANISM: Orthohepadnaviridae hepatitis B virus

<400> SEQUENCE: 706

Phe Ile Ile Phe Leu Phe Ile Leu Leu Leu
1               5                   10

<210> SEQ ID NO 707
<211> LENGTH: 8
<212> TYPE: PRT
<213> ORGANISM: Orthohepadnaviridae hepatitis B virus

<400> SEQUENCE: 707

Phe Ile Leu Leu Leu Cys Leu Ile
1               5

<210> SEQ ID NO 708
<211> LENGTH: 9
<212> TYPE: PRT
<213> ORGANISM: Orthohepadnaviridae hepatitis B virus

<400> SEQUENCE: 708

Phe Ile Leu Leu Leu Cys Leu Ile Phe
1               5

<210> SEQ ID NO 709
```

```
<211> LENGTH: 10
<212> TYPE: PRT
<213> ORGANISM: Orthohepadnaviridae hepatitis B virus

<400> SEQUENCE: 709

Phe Ile Leu Leu Leu Cys Leu Ile Phe Leu
 1               5                  10

<210> SEQ ID NO 710
<211> LENGTH: 11
<212> TYPE: PRT
<213> ORGANISM: Orthohepadnaviridae hepatitis B virus

<400> SEQUENCE: 710

Phe Ile Leu Leu Leu Cys Leu Ile Phe Leu Leu
 1               5                  10

<210> SEQ ID NO 711
<211> LENGTH: 9
<212> TYPE: PRT
<213> ORGANISM: Orthohepadnaviridae hepatitis B virus

<400> SEQUENCE: 711

Phe Leu Phe Ile Leu Leu Leu Cys Leu
 1               5

<210> SEQ ID NO 712
<211> LENGTH: 10
<212> TYPE: PRT
<213> ORGANISM: Orthohepadnaviridae hepatitis B virus

<400> SEQUENCE: 712

Phe Leu Phe Ile Leu Leu Leu Cys Leu Ile
 1               5                  10

<210> SEQ ID NO 713
<211> LENGTH: 11
<212> TYPE: PRT
<213> ORGANISM: Orthohepadnaviridae hepatitis B virus

<400> SEQUENCE: 713

Phe Leu Phe Ile Leu Leu Leu Cys Leu Ile Phe
 1               5                  10

<210> SEQ ID NO 714
<211> LENGTH: 8
<212> TYPE: PRT
<213> ORGANISM: Orthohepadnaviridae hepatitis B virus

<400> SEQUENCE: 714

Phe Leu Gly Pro Leu Leu Val Leu
 1               5

<210> SEQ ID NO 715
<211> LENGTH: 10
<212> TYPE: PRT
<213> ORGANISM: Orthohepadnaviridae hepatitis B virus

<400> SEQUENCE: 715

Phe Leu Leu Ala Gln Phe Thr Ser Ala Ile
 1               5                  10

<210> SEQ ID NO 716
<211> LENGTH: 9
<212> TYPE: PRT
```

<213> ORGANISM: Orthohepadnaviridae hepatitis B virus

<400> SEQUENCE: 716

Phe Leu Leu Ser Leu Gly Ile His Leu
1               5

<210> SEQ ID NO 717
<211> LENGTH: 9
<212> TYPE: PRT
<213> ORGANISM: Orthohepadnaviridae hepatitis B virus

<400> SEQUENCE: 717

Phe Leu Leu Thr Arg Ile Leu Thr Ile
1               5

<210> SEQ ID NO 718
<211> LENGTH: 8
<212> TYPE: PRT
<213> ORGANISM: Orthohepadnaviridae hepatitis B virus

<400> SEQUENCE: 718

Phe Leu Leu Val Leu Leu Asp Tyr
1               5

<210> SEQ ID NO 719
<211> LENGTH: 11
<212> TYPE: PRT
<213> ORGANISM: Orthohepadnaviridae hepatitis B virus

<400> SEQUENCE: 719

Phe Leu Leu Val Leu Leu Asp Tyr Gln Gly Met
1               5                   10

<210> SEQ ID NO 720
<211> LENGTH: 10
<212> TYPE: PRT
<213> ORGANISM: Orthohepadnaviridae hepatitis B virus

<400> SEQUENCE: 720

Phe Thr Phe Ser Pro Thr Tyr Lys Ala Phe
1               5                   10

<210> SEQ ID NO 721
<211> LENGTH: 11
<212> TYPE: PRT
<213> ORGANISM: Orthohepadnaviridae hepatitis B virus

<400> SEQUENCE: 721

Phe Thr Phe Ser Pro Thr Tyr Lys Ala Phe Leu
1               5                   10

<210> SEQ ID NO 722
<211> LENGTH: 9
<212> TYPE: PRT
<213> ORGANISM: Orthohepadnaviridae hepatitis B virus

<400> SEQUENCE: 722

Phe Thr Gln Cys Gly Tyr Pro Ala Leu
1               5

<210> SEQ ID NO 723
<211> LENGTH: 10
<212> TYPE: PRT
<213> ORGANISM: Orthohepadnaviridae hepatitis B virus

<400> SEQUENCE: 723

Phe Thr Gln Cys Gly Tyr Pro Ala Leu Met
1               5                   10

<210> SEQ ID NO 724
<211> LENGTH: 9
<212> TYPE: PRT
<213> ORGANISM: Orthohepadnaviridae hepatitis B virus

<400> SEQUENCE: 724

Phe Val Gly Leu Ser Pro Thr Val Trp
1               5

<210> SEQ ID NO 725
<211> LENGTH: 10
<212> TYPE: PRT
<213> ORGANISM: Orthohepadnaviridae hepatitis B virus

<400> SEQUENCE: 725

Phe Val Gly Leu Ser Pro Thr Val Trp Leu
1               5                   10

<210> SEQ ID NO 726
<211> LENGTH: 10
<212> TYPE: PRT
<213> ORGANISM: Orthohepadnaviridae hepatitis B virus

<400> SEQUENCE: 726

Phe Val Leu Gly Gly Cys Arg His Lys Leu
1               5                   10

<210> SEQ ID NO 727
<211> LENGTH: 8
<212> TYPE: PRT
<213> ORGANISM: Orthohepadnaviridae hepatitis B virus

<400> SEQUENCE: 727

Phe Val Gln Trp Phe Val Gly Leu
1               5

<210> SEQ ID NO 728
<211> LENGTH: 8
<212> TYPE: PRT
<213> ORGANISM: Orthohepadnaviridae hepatitis B virus

<400> SEQUENCE: 728

Phe Val Tyr Val Pro Ser Ala Leu
1               5

<210> SEQ ID NO 729
<211> LENGTH: 11
<212> TYPE: PRT
<213> ORGANISM: Orthohepadnaviridae hepatitis B virus

<400> SEQUENCE: 729

Gly Phe Ala Ala Pro Phe Thr Gln Cys Gly Tyr
1               5                   10

<210> SEQ ID NO 730
<211> LENGTH: 8
<212> TYPE: PRT
<213> ORGANISM: Orthohepadnaviridae hepatitis B virus

<400> SEQUENCE: 730

```
Gly Phe Phe Leu Leu Thr Arg Ile
1               5
```

<210> SEQ ID NO 731
<211> LENGTH: 9
<212> TYPE: PRT
<213> ORGANISM: Orthohepadnaviridae hepatitis B virus

<400> SEQUENCE: 731

```
Gly Phe Phe Leu Leu Thr Arg Ile Leu
1               5
```

<210> SEQ ID NO 732
<211> LENGTH: 11
<212> TYPE: PRT
<213> ORGANISM: Orthohepadnaviridae hepatitis B virus

<400> SEQUENCE: 732

```
Gly Phe Phe Leu Leu Thr Arg Ile Leu Thr Ile
1               5                   10
```

<210> SEQ ID NO 733
<211> LENGTH: 8
<212> TYPE: PRT
<213> ORGANISM: Orthohepadnaviridae hepatitis B virus

<400> SEQUENCE: 733

```
Gly Phe Phe Pro Asp His Gln Leu
1               5
```

<210> SEQ ID NO 734
<211> LENGTH: 9
<212> TYPE: PRT
<213> ORGANISM: Orthohepadnaviridae hepatitis B virus

<400> SEQUENCE: 734

```
Gly Phe Leu Gly Pro Leu Leu Val Leu
1               5
```

<210> SEQ ID NO 735
<211> LENGTH: 11
<212> TYPE: PRT
<213> ORGANISM: Orthohepadnaviridae hepatitis B virus

<400> SEQUENCE: 735

```
Gly Phe Arg Lys Ile Pro Met Gly Val Gly Leu
1               5                   10
```

<210> SEQ ID NO 736
<211> LENGTH: 9
<212> TYPE: PRT
<213> ORGANISM: Orthohepadnaviridae hepatitis B virus

<400> SEQUENCE: 736

```
Gly Leu Leu Gly Phe Ala Ala Pro Phe
1               5
```

<210> SEQ ID NO 737
<211> LENGTH: 10
<212> TYPE: PRT
<213> ORGANISM: Orthohepadnaviridae hepatitis B virus

<400> SEQUENCE: 737

```
Gly Leu Ser Pro Phe Leu Leu Ala Gln Phe
1               5                   10
```

```
<210> SEQ ID NO 738
<211> LENGTH: 8
<212> TYPE: PRT
<213> ORGANISM: Orthohepadnaviridae hepatitis B virus

<400> SEQUENCE: 738

Gly Leu Ser Pro Thr Val Trp Leu
1               5

<210> SEQ ID NO 739
<211> LENGTH: 11
<212> TYPE: PRT
<213> ORGANISM: Orthohepadnaviridae hepatitis B virus

<400> SEQUENCE: 739

Gly Leu Ser Pro Thr Val Trp Leu Ser Val Ile
1               5                   10

<210> SEQ ID NO 740
<211> LENGTH: 10
<212> TYPE: PRT
<213> ORGANISM: Orthohepadnaviridae hepatitis B virus

<400> SEQUENCE: 740

Gly Met Asp Ile Asp Pro Tyr Lys Glu Phe
1               5                   10

<210> SEQ ID NO 741
<211> LENGTH: 8
<212> TYPE: PRT
<213> ORGANISM: Orthohepadnaviridae hepatitis B virus

<400> SEQUENCE: 741

Gly Met Leu Pro Val Cys Pro Leu
1               5

<210> SEQ ID NO 742
<211> LENGTH: 8
<212> TYPE: PRT
<213> ORGANISM: Orthohepadnaviridae hepatitis B virus

<400> SEQUENCE: 742

Gly Thr Asp Asn Ser Val Val Leu
1               5

<210> SEQ ID NO 743
<211> LENGTH: 10
<212> TYPE: PRT
<213> ORGANISM: Orthohepadnaviridae hepatitis B virus

<400> SEQUENCE: 743

Gly Thr Asn Leu Ser Val Pro Asn Pro Leu
1               5                   10

<210> SEQ ID NO 744
<211> LENGTH: 11
<212> TYPE: PRT
<213> ORGANISM: Orthohepadnaviridae hepatitis B virus

<400> SEQUENCE: 744

Gly Thr Ser Phe Val Tyr Val Pro Ser Ala Leu
1               5                   10
```

<210> SEQ ID NO 745
<211> LENGTH: 8
<212> TYPE: PRT
<213> ORGANISM: Orthohepadnaviridae hepatitis B virus

<400> SEQUENCE: 745

Gly Val Gly Leu Ser Pro Phe Leu
1               5

<210> SEQ ID NO 746
<211> LENGTH: 9
<212> TYPE: PRT
<213> ORGANISM: Orthohepadnaviridae hepatitis B virus

<400> SEQUENCE: 746

Gly Val Gly Leu Ser Pro Phe Leu Leu
1               5

<210> SEQ ID NO 747
<211> LENGTH: 10
<212> TYPE: PRT
<213> ORGANISM: Orthohepadnaviridae hepatitis B virus

<400> SEQUENCE: 747

Gly Val Trp Ile Arg Thr Pro Pro Ala Tyr
1               5                   10

<210> SEQ ID NO 748
<211> LENGTH: 8
<212> TYPE: PRT
<213> ORGANISM: Orthohepadnaviridae hepatitis B virus

<400> SEQUENCE: 748

Gly Trp Leu Trp Gly Met Asp Ile
1               5

<210> SEQ ID NO 749
<211> LENGTH: 11
<212> TYPE: PRT
<213> ORGANISM: Orthohepadnaviridae hepatitis B virus

<400> SEQUENCE: 749

Gly Trp Leu Trp Gly Met Asp Ile Asp Pro Tyr
1               5                   10

<210> SEQ ID NO 750
<211> LENGTH: 9
<212> TYPE: PRT
<213> ORGANISM: Orthohepadnaviridae hepatitis B virus

<400> SEQUENCE: 750

Gly Trp Ser Pro Gln Ala Gln Gly Ile
1               5

<210> SEQ ID NO 751
<211> LENGTH: 10
<212> TYPE: PRT
<213> ORGANISM: Orthohepadnaviridae hepatitis B virus

<400> SEQUENCE: 751

Gly Trp Ser Pro Gln Ala Gln Gly Ile Leu
1               5                   10

<210> SEQ ID NO 752
<211> LENGTH: 8

```
<212> TYPE: PRT
<213> ORGANISM: Orthohepadnaviridae hepatitis B virus

<400> SEQUENCE: 752

Gly Tyr Pro Ala Leu Met Pro Leu
 1               5

<210> SEQ ID NO 753
<211> LENGTH: 9
<212> TYPE: PRT
<213> ORGANISM: Orthohepadnaviridae hepatitis B virus

<400> SEQUENCE: 753

Gly Tyr Pro Ala Leu Met Pro Leu Tyr
 1               5

<210> SEQ ID NO 754
<211> LENGTH: 10
<212> TYPE: PRT
<213> ORGANISM: Orthohepadnaviridae hepatitis B virus

<400> SEQUENCE: 754

Gly Tyr Arg Trp Met Cys Leu Arg Arg Phe
 1               5                  10

<210> SEQ ID NO 755
<211> LENGTH: 11
<212> TYPE: PRT
<213> ORGANISM: Orthohepadnaviridae hepatitis B virus

<400> SEQUENCE: 755

Gly Tyr Arg Trp Met Cys Leu Arg Arg Phe Ile
 1               5                  10

<210> SEQ ID NO 756
<211> LENGTH: 9
<212> TYPE: PRT
<213> ORGANISM: Orthohepadnaviridae hepatitis B virus

<400> SEQUENCE: 756

Gly Tyr Ser Leu Asn Phe Met Gly Tyr
 1               5

<210> SEQ ID NO 757
<211> LENGTH: 11
<212> TYPE: PRT
<213> ORGANISM: Orthohepadnaviridae hepatitis B virus

<400> SEQUENCE: 757

Gly Tyr Ser Leu Asn Phe Met Gly Tyr Val Ile
 1               5                  10

<210> SEQ ID NO 758
<211> LENGTH: 10
<212> TYPE: PRT
<213> ORGANISM: Orthohepadnaviridae hepatitis B virus

<400> SEQUENCE: 758

His Phe Ala Ser Pro Leu His Val Ala Trp
 1               5                  10

<210> SEQ ID NO 759
<211> LENGTH: 8
<212> TYPE: PRT
<213> ORGANISM: Orthohepadnaviridae hepatitis B virus
```

```
<400> SEQUENCE: 759

His Phe Arg Lys Leu Leu Leu Leu
1               5

<210> SEQ ID NO 760
<211> LENGTH: 9
<212> TYPE: PRT
<213> ORGANISM: Orthohepadnaviridae hepatitis B virus

<400> SEQUENCE: 760

His Leu Leu Val Gly Ser Ser Gly Leu
1               5

<210> SEQ ID NO 761
<211> LENGTH: 10
<212> TYPE: PRT
<213> ORGANISM: Orthohepadnaviridae hepatitis B virus

<400> SEQUENCE: 761

His Leu Asn Pro Asn Lys Thr Lys Arg Trp
1               5                   10

<210> SEQ ID NO 762
<211> LENGTH: 8
<212> TYPE: PRT
<213> ORGANISM: Orthohepadnaviridae hepatitis B virus

<400> SEQUENCE: 762

His Leu Tyr Ser His Pro Ile Ile
1               5

<210> SEQ ID NO 763
<211> LENGTH: 9
<212> TYPE: PRT
<213> ORGANISM: Orthohepadnaviridae hepatitis B virus

<400> SEQUENCE: 763

His Leu Tyr Ser His Pro Ile Ile Leu
1               5

<210> SEQ ID NO 764
<211> LENGTH: 11
<212> TYPE: PRT
<213> ORGANISM: Orthohepadnaviridae hepatitis B virus

<400> SEQUENCE: 764

His Leu Tyr Ser His Pro Ile Ile Leu Gly Phe
1               5                   10

<210> SEQ ID NO 765
<211> LENGTH: 10
<212> TYPE: PRT
<213> ORGANISM: Orthohepadnaviridae hepatitis B virus

<400> SEQUENCE: 765

His Thr Ala Glu Leu Leu Ala Ala Cys Phe
1               5                   10

<210> SEQ ID NO 766
<211> LENGTH: 8
<212> TYPE: PRT
<213> ORGANISM: Orthohepadnaviridae hepatitis B virus

<400> SEQUENCE: 766
```

His Thr Ala Leu Arg Gln Ala Ile
1               5

<210> SEQ ID NO 767
<211> LENGTH: 9
<212> TYPE: PRT
<213> ORGANISM: Orthohepadnaviridae hepatitis B virus

<400> SEQUENCE: 767

His Thr Ala Leu Arg Gln Ala Ile Leu
1               5

<210> SEQ ID NO 768
<211> LENGTH: 11
<212> TYPE: PRT
<213> ORGANISM: Orthohepadnaviridae hepatitis B virus

<400> SEQUENCE: 768

His Thr Ala Leu Arg Gln Ala Ile Leu Cys Trp
1               5                   10

<210> SEQ ID NO 769
<211> LENGTH: 8
<212> TYPE: PRT
<213> ORGANISM: Orthohepadnaviridae hepatitis B virus

<400> SEQUENCE: 769

His Thr Leu Trp Lys Ala Gly Ile
1               5

<210> SEQ ID NO 770
<211> LENGTH: 9
<212> TYPE: PRT
<213> ORGANISM: Orthohepadnaviridae hepatitis B virus

<400> SEQUENCE: 770

His Thr Leu Trp Lys Ala Gly Ile Leu
1               5

<210> SEQ ID NO 771
<211> LENGTH: 10
<212> TYPE: PRT
<213> ORGANISM: Orthohepadnaviridae hepatitis B virus

<400> SEQUENCE: 771

His Thr Leu Trp Lys Ala Gly Ile Leu Tyr
1               5                   10

<210> SEQ ID NO 772
<211> LENGTH: 11
<212> TYPE: PRT
<213> ORGANISM: Orthohepadnaviridae hepatitis B virus

<400> SEQUENCE: 772

His Tyr Leu His Thr Leu Trp Lys Ala Gly Ile
1               5                   10

<210> SEQ ID NO 773
<211> LENGTH: 8
<212> TYPE: PRT
<213> ORGANISM: Orthohepadnaviridae hepatitis B virus

<400> SEQUENCE: 773

Ile Phe Phe Cys Leu Trp Val Tyr

```
<210> SEQ ID NO 774
<211> LENGTH: 9
<212> TYPE: PRT
<213> ORGANISM: Orthohepadnaviridae h -continued
<210> SEQ ID NO 781
<211> LENGTH: 11
<212> TYPE: PRT
<213> ORGANISM: Orthohepadnaviridae hepatitis B virus

<400> SEQUENCE: 781

Ile Ile Phe Leu Phe Ile Leu Leu Leu Cys Leu
1               5                   10

<210> SEQ ID NO 782
<211> LENGTH: 8
<212> TYPE: PRT
<213> ORGANISM: Orthohepadnaviridae hepatitis B virus

<400> SEQUENCE: 782

Ile Ile Leu Gly Phe Arg Lys Ile
1               5

<210> SEQ ID NO 783
<211> LENGTH: 10
<212> TYPE: PRT
<213> ORGANISM: Orthohepadnaviridae hepatitis B virus

<400> SEQUENCE: 783

Ile Ile Leu Gly Phe Arg Lys Ile Pro Met
1               5                   10

<210> SEQ ID NO 784
<211> LENGTH: 8
<212> TYPE: PRT
<213> ORGANISM: Orthohepadnaviridae hepatitis B virus

<400> SEQUENCE: 784

Ile Leu Cys Trp Gly Glu Leu Met
1               5

<210> SEQ ID NO 785
<211> LENGTH: 9
<212> TYPE: PRT
<213> ORGANISM: Orthohepadnaviridae hepatitis B virus

<400> SEQUENCE: 785

Ile Leu Gly Phe Arg Lys Ile Pro Met
1               5

<210> SEQ ID NO 786
<211> LENGTH: 8
<212> TYPE: PRT
<213> ORGANISM: Orthohepadnaviridae hepatitis B virus

<400> SEQUENCE: 786

Ile Leu Leu Leu Cys Leu Ile Phe
1               5

<210> SEQ ID NO 787
<211> LENGTH: 9
<212> TYPE: PRT
<213> ORGANISM: Orthohepadnaviridae hepatitis B virus

<400> SEQUENCE: 787

Ile Leu Leu Leu Cys Leu Ile Phe Leu
1               5

<210> SEQ ID NO 788

-continued

<211> LENGTH: 10
<212> TYPE: PRT
<213> ORGANISM: Orthohepadnaviridae hepatitis B virus

<400> SEQUENCE: 788

Ile Leu Leu Leu Cys Leu Ile Phe Leu Leu
1 5 10

<210> SEQ ID NO 789
<211> LENGTH: 9
<212> TYPE: PRT
<213> ORGANISM: Orthohepadnaviridae hepatitis B virus

<400> SEQUENCE: 789

Ile Leu Arg Gly Thr Ser Phe Val Tyr
1 5

<210> SEQ ID NO 790
<211> LENGTH: 8
<212> TYPE: PRT
<213> ORGANISM: Orthohepadnaviridae hepatitis B virus

<400> SEQUENCE: 790

Ile Leu Thr Ile Pro Gln Ser Leu
1 5

<210> SEQ ID NO 791
<211> LENGTH: 11
<212> TYPE: PRT
<213> ORGANISM: Orthohepadnaviridae hepatitis B virus

<400> SEQUENCE: 791

Ile Leu Thr Ile Pro Gln Ser Leu Asp Ser Trp
1 5 10

<210> SEQ ID NO 792
<211> LENGTH: 11
<212> TYPE: PRT
<213> ORGANISM: Orthohepadnaviridae hepatitis B virus

<400> SEQUENCE: 792

Ile Val Gly Leu Leu Gly Phe Ala Ala Pro Phe
1 5 10

<210> SEQ ID NO 793
<211> LENGTH: 11
<212> TYPE: PRT
<213> ORGANISM: Orthohepadnaviridae hepatitis B virus

<400> SEQUENCE: 793

Ile Trp Met Met Trp Tyr Trp Gly Pro Ser Leu
1 5 10

<210> SEQ ID NO 794
<211> LENGTH: 10
<212> TYPE: PRT
<213> ORGANISM: Orthohepadnaviridae hepatitis B virus

<400> SEQUENCE: 794

Lys Phe Ala Val Pro Asn Leu Gln Ser Leu
1 5 10

<210> SEQ ID NO 795
<211> LENGTH: 8
<212> TYPE: PRT

-continued

<210> SEQ ID NO 795
<211> LENGTH: 7
<212> TYPE: PRT
<213> ORGANISM: Orthohepadnaviridae hepatitis B virus

<400> SEQUENCE: 795

Lys Ile Pro Met Gly Val Gly Leu
1               5

<210> SEQ ID NO 796
<211> LENGTH: 11
<212> TYPE: PRT
<213> ORGANISM: Orthohepadnaviridae hepatitis B virus

<400> SEQUENCE: 796

Lys Ile Pro Met Gly Val Gly Leu Ser Pro Phe
1               5                   10

<210> SEQ ID NO 797
<211> LENGTH: 8
<212> TYPE: PRT
<213> ORGANISM: Orthohepadnaviridae hepatitis B virus

<400> SEQUENCE: 797

Lys Leu Cys Leu Gly Trp Leu Trp
1               5

<210> SEQ ID NO 798
<211> LENGTH: 10
<212> TYPE: PRT
<213> ORGANISM: Orthohepadnaviridae hepatitis B virus

<400> SEQUENCE: 798

Lys Leu Cys Leu Gly Trp Leu Trp Gly Met
1               5                   10

<210> SEQ ID NO 799
<211> LENGTH: 9
<212> TYPE: PRT
<213> ORGANISM: Orthohepadnaviridae hepatitis B virus

<400> SEQUENCE: 799

Lys Leu His Leu Tyr Ser His Pro Ile
1               5

<210> SEQ ID NO 800
<211> LENGTH: 10
<212> TYPE: PRT
<213> ORGANISM: Orthohepadnaviridae hepatitis B virus

<400> SEQUENCE: 800

Lys Leu His Leu Tyr Ser His Pro Ile Ile
1               5                   10

<210> SEQ ID NO 801
<211> LENGTH: 11
<212> TYPE: PRT
<213> ORGANISM: Orthohepadnaviridae hepatitis B virus

<400> SEQUENCE: 801

Lys Leu His Leu Tyr Ser His Pro Ile Ile Leu
1               5                   10

<210> SEQ ID NO 802
<211> LENGTH: 8
<212> TYPE: PRT
<213> ORGANISM: Orthohepadnaviridae hepatitis B virus

<400> SEQUENCE: 802

Lys Leu Ile Met Pro Ala Arg Phe
1               5

<210> SEQ ID NO 803
<211> LENGTH: 9
<212> TYPE: PRT
<213> ORGANISM: Orthohepadnaviridae hepatitis B virus

<400> SEQUENCE: 803

Lys Leu Ile Met Pro Ala Arg Phe Tyr
1               5

<210> SEQ ID NO 804
<211> LENGTH: 8
<212> TYPE: PRT
<213> ORGANISM: Orthohepadnaviridae hepatitis B virus

<400> SEQUENCE: 804

Lys Leu Pro Val Asn Arg Pro Ile
1               5

<210> SEQ ID NO 805
<211> LENGTH: 10
<212> TYPE: PRT
<213> ORGANISM: Orthohepadnaviridae hepatitis B virus

<400> SEQUENCE: 805

Lys Leu Pro Val Asn Arg Pro Ile Asp Trp
1               5                   10

<210> SEQ ID NO 806
<211> LENGTH: 9
<212> TYPE: PRT
<213> ORGANISM: Orthohepadnaviridae hepatitis B virus

<400> SEQUENCE: 806

Lys Thr Lys Arg Trp Gly Tyr Ser Leu
1               5

<210> SEQ ID NO 807
<211> LENGTH: 11
<212> TYPE: PRT
<213> ORGANISM: Orthohepadnaviridae hepatitis B virus

<400> SEQUENCE: 807

Lys Thr Lys Arg Trp Gly Tyr Ser Leu Asn Phe
1               5                   10

<210> SEQ ID NO 808
<211> LENGTH: 9
<212> TYPE: PRT
<213> ORGANISM: Orthohepadnaviridae hepatitis B virus

<400> SEQUENCE: 808

Lys Val Cys Gln Arg Ile Val Gly Leu
1               5

<210> SEQ ID NO 809
<211> LENGTH: 10
<212> TYPE: PRT
<213> ORGANISM: Orthohepadnaviridae hepatitis B virus

<400> SEQUENCE: 809

```
Lys Val Cys Gln Arg Ile Val Gly Leu Leu
1               5                   10
```

<210> SEQ ID NO 810
<211> LENGTH: 8
<212> TYPE: PRT
<213> ORGANISM: Orthohepadnaviridae hepatitis B virus

<400> SEQUENCE: 810

```
Lys Val Gly Asn Phe Thr Gly Leu
1               5
```

<210> SEQ ID NO 811
<211> LENGTH: 9
<212> TYPE: PRT
<213> ORGANISM: Orthohepadnaviridae hepatitis B virus

<400> SEQUENCE: 811

```
Lys Val Gly Asn Phe Thr Gly Leu Tyr
1               5
```

<210> SEQ ID NO 812
<211> LENGTH: 8
<212> TYPE: PRT
<213> ORGANISM: Orthohepadnaviridae hepatitis B virus

<400> SEQUENCE: 812

```
Lys Val Leu His Lys Arg Thr Leu
1               5
```

<210> SEQ ID NO 813
<211> LENGTH: 10
<212> TYPE: PRT
<213> ORGANISM: Orthohepadnaviridae hepatitis B virus

<400> SEQUENCE: 813

```
Lys Val Leu His Lys Arg Thr Leu Gly Leu
1               5                   10
```

<210> SEQ ID NO 814
<211> LENGTH: 9
<212> TYPE: PRT
<213> ORGANISM: Orthohepadnaviridae hepatitis B virus

<400> SEQUENCE: 814

```
Lys Tyr Leu Pro Leu Asp Lys Gly Ile
1               5
```

<210> SEQ ID NO 815
<211> LENGTH: 8
<212> TYPE: PRT
<213> ORGANISM: Orthohepadnaviridae hepatitis B virus

<400> SEQUENCE: 815

```
Lys Tyr Thr Ser Phe Pro Trp Leu
1               5
```

<210> SEQ ID NO 816
<211> LENGTH: 9
<212> TYPE: PRT
<213> ORGANISM: Orthohepadnaviridae hepatitis B virus

<400> SEQUENCE: 816

```
Lys Tyr Thr Ser Phe Pro Trp Leu Leu
1               5
```

<210> SEQ ID NO 817
<211> LENGTH: 8
<212> TYPE: PRT
<213> ORGANISM: Orthohepadnaviridae hepatitis B virus

<400> SEQUENCE: 817

Leu Phe Ile Leu Leu Leu Cys Leu
 1               5

<210> SEQ ID NO 818
<211> LENGTH: 9
<212> TYPE: PRT
<213> ORGANISM: Orthohepadnaviridae hepatitis B virus

<400> SEQUENCE: 818

Leu Phe Ile Leu Leu Leu Cys Leu Ile
 1               5

<210> SEQ ID NO 819
<211> LENGTH: 10
<212> TYPE: PRT
<213> ORGANISM: Orthohepadnaviridae hepatitis B virus

<400> SEQUENCE: 819

Leu Phe Ile Leu Leu Leu Cys Leu Ile Phe
 1               5                  10

<210> SEQ ID NO 820
<211> LENGTH: 11
<212> TYPE: PRT
<213> ORGANISM: Orthohepadnaviridae hepatitis B virus

<400> SEQUENCE: 820

Leu Phe Ile Leu Leu Leu Cys Leu Ile Phe Leu
 1               5                  10

<210> SEQ ID NO 821
<211> LENGTH: 8
<212> TYPE: PRT
<213> ORGANISM: Orthohepadnaviridae hepatitis B virus

<400> SEQUENCE: 821

Leu Ile Phe Leu Leu Val Leu Leu
 1               5

<210> SEQ ID NO 822
<211> LENGTH: 10
<212> TYPE: PRT
<213> ORGANISM: Orthohepadnaviridae hepatitis B virus

<400> SEQUENCE: 822

Leu Ile Phe Leu Leu Val Leu Leu Asp Tyr
 1               5                  10

<210> SEQ ID NO 823
<211> LENGTH: 8
<212> TYPE: PRT
<213> ORGANISM: Orthohepadnaviridae hepatitis B virus

<400> SEQUENCE: 823

Leu Ile Met Pro Ala Arg Phe Tyr
 1               5

```
<210> SEQ ID NO 824
<211> LENGTH: 9
<212> TYPE: PRT
<213> ORGANISM: Orthohepadnaviridae hepatitis B virus

<400> SEQUENCE: 824

Leu Leu Ala Gln Phe Thr Ser Ala Ile
1               5

<210> SEQ ID NO 825
<211> LENGTH: 8
<212> TYPE: PRT
<213> ORGANISM: Orthohepadnaviridae hepatitis B virus

<400> SEQUENCE: 825

Leu Leu Cys Leu Ile Phe Leu Leu
1               5

<210> SEQ ID NO 826
<211> LENGTH: 10
<212> TYPE: PRT
<213> ORGANISM: Orthohepadnaviridae hepatitis B virus

<400> SEQUENCE: 826

Leu Leu Cys Leu Ile Phe Leu Leu Val Leu
1               5                   10

<210> SEQ ID NO 827
<211> LENGTH: 11
<212> TYPE: PRT
<213> ORGANISM: Orthohepadnaviridae hepatitis B virus

<400> SEQUENCE: 827

Leu Leu Cys Leu Ile Phe Leu Leu Val Leu Leu
1               5                   10

<210> SEQ ID NO 828
<211> LENGTH: 8
<212> TYPE: PRT
<213> ORGANISM: Orthohepadnaviridae hepatitis B virus

<400> SEQUENCE: 828

Leu Leu Asp Thr Ala Ser Ala Leu
1               5

<210> SEQ ID NO 829
<211> LENGTH: 9
<212> TYPE: PRT
<213> ORGANISM: Orthohepadnaviridae hepatitis B virus

<400> SEQUENCE: 829

Leu Leu Asp Thr Ala Ser Ala Leu Tyr
1               5

<210> SEQ ID NO 830
<211> LENGTH: 8
<212> TYPE: PRT
<213> ORGANISM: Orthohepadnaviridae hepatitis B virus

<400> SEQUENCE: 830

Leu Leu Asp Tyr Gln Gly Met Leu
1               5

<210> SEQ ID NO 831
<211> LENGTH: 8
```

```
<212> TYPE: PRT
<213> ORGANISM: Orthohepadnaviridae hepatitis B virus

<400> SEQUENCE: 831

Leu Leu Gly Cys Ala Ala Asn Trp
 1               5

<210> SEQ ID NO 832
<211> LENGTH: 9
<212> TYPE: PRT
<213> ORGANISM: Orthohepadnaviridae hepatitis B virus

<400> SEQUENCE: 832

Leu Leu Gly Cys Ala Ala Asn Trp Ile
 1               5

<210> SEQ ID NO 833
<211> LENGTH: 10
<212> TYPE: PRT
<213> ORGANISM: Orthohepadnaviridae hepatitis B virus

<400> SEQUENCE: 833

Leu Leu Gly Cys Ala Ala Asn Trp Ile Leu
 1               5                  10

<210> SEQ ID NO 834
<211> LENGTH: 8
<212> TYPE: PRT
<213> ORGANISM: Orthohepadnaviridae hepatitis B virus

<400> SEQUENCE: 834

Leu Leu Gly Phe Ala Ala Pro Phe
 1               5

<210> SEQ ID NO 835
<211> LENGTH: 11
<212> TYPE: PRT
<213> ORGANISM: Orthohepadnaviridae hepatitis B virus

<400> SEQUENCE: 835

Leu Leu Gly Trp Ser Pro Gln Ala Gln Gly Ile
 1               5                  10

<210> SEQ ID NO 836
<211> LENGTH: 8
<212> TYPE: PRT
<213> ORGANISM: Orthohepadnaviridae hepatitis B virus

<400> SEQUENCE: 836

Leu Leu Leu Cys Leu Ile Phe Leu
 1               5

<210> SEQ ID NO 837
<211> LENGTH: 9
<212> TYPE: PRT
<213> ORGANISM: Orthohepadnaviridae hepatitis B virus

<400> SEQUENCE: 837

Leu Leu Leu Cys Leu Ile Phe Leu Leu
 1               5

<210> SEQ ID NO 838
<211> LENGTH: 11
<212> TYPE: PRT
<213> ORGANISM: Orthohepadnaviridae hepatitis B virus
```

```
<400> SEQUENCE: 838

Leu Leu Leu Cys Leu Ile Phe Leu Leu Val Leu
1               5                   10

<210> SEQ ID NO 839
<211> LENGTH: 8
<212> TYPE: PRT
<213> ORGANISM: Orthohepadnaviridae hepatitis B virus

<400> SEQUENCE: 839

Leu Leu Pro Ile Phe Phe Cys Leu
1               5

<210> SEQ ID NO 840
<211> LENGTH: 9
<212> TYPE: PRT
<213> ORGANISM: Orthohepadnaviridae hepatitis B virus

<400> SEQUENCE: 840

Leu Leu Pro Ile Phe Phe Cys Leu Trp
1               5

<210> SEQ ID NO 841
<211> LENGTH: 11
<212> TYPE: PRT
<213> ORGANISM: Orthohepadnaviridae hepatitis B virus

<400> SEQUENCE: 841

Leu Leu Pro Ile Phe Phe Cys Leu Trp Val Tyr
1               5                   10

<210> SEQ ID NO 842
<211> LENGTH: 9
<212> TYPE: PRT
<213> ORGANISM: Orthohepadnaviridae hepatitis B virus

<400> SEQUENCE: 842

Leu Leu Ser Phe Leu Pro Ser Asp Phe
1               5

<210> SEQ ID NO 843
<211> LENGTH: 10
<212> TYPE: PRT
<213> ORGANISM: Orthohepadnaviridae hepatitis B virus

<400> SEQUENCE: 843

Leu Leu Ser Phe Leu Pro Ser Asp Phe Phe
1               5                   10

<210> SEQ ID NO 844
<211> LENGTH: 8
<212> TYPE: PRT
<213> ORGANISM: Orthohepadnaviridae hepatitis B virus

<400> SEQUENCE: 844

Leu Leu Ser Leu Gly Ile His Leu
1               5

<210> SEQ ID NO 845
<211> LENGTH: 8
<212> TYPE: PRT
<213> ORGANISM: Orthohepadnaviridae hepatitis B virus

<400> SEQUENCE: 845
```

Leu Leu Ser Ser Asn Leu Ser Trp
1               5

<210> SEQ ID NO 846
<211> LENGTH: 9
<212> TYPE: PRT
<213> ORGANISM: Orthohepadnaviridae hepatitis B virus

<400> SEQUENCE: 846

Leu Leu Ser Ser Asn Leu Ser Trp Leu
1               5

<210> SEQ ID NO 847
<211> LENGTH: 11
<212> TYPE: PRT
<213> ORGANISM: Orthohepadnaviridae hepatitis B virus

<400> SEQUENCE: 847

Leu Leu Ser Ser Asn Leu Ser Trp Leu Ser Leu
1               5                   10

<210> SEQ ID NO 848
<211> LENGTH: 8
<212> TYPE: PRT
<213> ORGANISM: Orthohepadnaviridae hepatitis B virus

<400> SEQUENCE: 848

Leu Leu Thr Arg Ile Leu Thr Ile
1               5

<210> SEQ ID NO 849
<211> LENGTH: 8
<212> TYPE: PRT
<213> ORGANISM: Orthohepadnaviridae hepatitis B virus

<400> SEQUENCE: 849

Leu Leu Val Gly Ser Ser Gly Leu
1               5

<210> SEQ ID NO 850
<211> LENGTH: 10
<212> TYPE: PRT
<213> ORGANISM: Orthohepadnaviridae hepatitis B virus

<400> SEQUENCE: 850

Leu Leu Val Leu Leu Asp Tyr Gln Gly Met
1               5                   10

<210> SEQ ID NO 851
<211> LENGTH: 11
<212> TYPE: PRT
<213> ORGANISM: Orthohepadnaviridae hepatitis B virus

<400> SEQUENCE: 851

Leu Leu Val Leu Leu Asp Tyr Gln Gly Met Leu
1               5                   10

<210> SEQ ID NO 852
<211> LENGTH: 8
<212> TYPE: PRT
<213> ORGANISM: Orthohepadnaviridae hepatitis B virus

<400> SEQUENCE: 852

Leu Leu Val Leu Gln Ala Gly Phe

-continued

```
<210> SEQ ID NO 853
<211> LENGTH: 9
<212> TYPE: PRT
<213> ORGANISM: Orthohepadnaviridae hepatitis B virus

<400> SEQUENCE: 853

Leu Leu Val Leu Gln Ala Gly Phe Phe
  1               5

<210> SEQ ID NO 854
<211> LENGTH: 10
<212> TYPE: PRT
<213> ORGANISM: Orthohepadnaviridae hepatitis B virus

<400> SEQUENCE: 854

Leu Leu Val Leu Gln Ala Gly Phe Phe Leu
  1               5                  10

<210> SEQ ID NO 855
<211> LENGTH: 11
<212> TYPE: PRT
<213> ORGANISM: Orthohepadnaviridae hepatitis B virus

<400> SEQUENCE: 855

Leu Leu Val Leu Gln Ala Gly Phe Phe Leu Leu
  1               5                  10

<210> SEQ ID NO 856
<211> LENGTH: 8
<212> TYPE: PRT
<213> ORGANISM: Orthohepadnaviridae hepatitis B virus

<400> SEQUENCE: 856

Leu Leu Val Pro Phe Val Gln Trp
  1               5

<210> SEQ ID NO 857
<211> LENGTH: 9
<212> TYPE: PRT
<213> ORGANISM: Orthohepadnaviridae hepatitis B virus

<400> SEQUENCE: 857

Leu Leu Val Pro Phe Val Gln Trp Phe
  1               5

<210> SEQ ID NO 858
<211> LENGTH: 9
<212> TYPE: PRT
<213> ORGANISM: Orthohepadnaviridae hepatitis B virus

<400> SEQUENCE: 858

Leu Leu Trp Phe His Ile Ser Cys Leu
  1               5

<210> SEQ ID NO 859
<211> LENGTH: 11
<212> TYPE: PRT
<213> ORGANISM: Orthohepadnaviridae hepatitis B virus

<400> SEQUENCE: 859

Leu Leu Trp Phe His Ile Ser Cys Leu Thr Phe
  1               5                  10
```

<210> SEQ ID NO 860
<211> LENGTH: 8
<212> TYPE: PRT
<213> ORGANISM: Orthohepadnaviridae hepatitis B virus

<400> SEQUENCE: 860

Leu Met Pro Leu Tyr Ala Cys Ile
 1               5

<210> SEQ ID NO 861
<211> LENGTH: 9
<212> TYPE: PRT
<213> ORGANISM: Orthohepadnaviridae hepatitis B virus

<400> SEQUENCE: 861

Leu Thr Phe Gly Arg Glu Thr Val Leu
 1               5

<210> SEQ ID NO 862
<211> LENGTH: 11
<212> TYPE: PRT
<213> ORGANISM: Orthohepadnaviridae hepatitis B virus

<400> SEQUENCE: 862

Leu Thr Phe Gly Arg Glu Thr Val Leu Glu Tyr
 1               5                  10

<210> SEQ ID NO 863
<211> LENGTH: 10
<212> TYPE: PRT
<213> ORGANISM: Orthohepadnaviridae hepatitis B virus

<400> SEQUENCE: 863

Leu Thr Ile Pro Gln Ser Leu Asp Ser Trp
 1               5                  10

<210> SEQ ID NO 864
<211> LENGTH: 11
<212> TYPE: PRT
<213> ORGANISM: Orthohepadnaviridae hepatitis B virus

<400> SEQUENCE: 864

Leu Thr Ile Pro Gln Ser Leu Asp Ser Trp Trp
 1               5                  10

<210> SEQ ID NO 865
<211> LENGTH: 9
<212> TYPE: PRT
<213> ORGANISM: Orthohepadnaviridae hepatitis B virus

<400> SEQUENCE: 865

Leu Thr Asn Leu Leu Ser Ser Asn Leu
 1               5

<210> SEQ ID NO 866
<211> LENGTH: 11
<212> TYPE: PRT
<213> ORGANISM: Orthohepadnaviridae hepatitis B virus

<400> SEQUENCE: 866

Leu Thr Asn Leu Leu Ser Ser Asn Leu Ser Trp
 1               5                  10

<210> SEQ ID NO 867

```
<211> LENGTH: 11
<212> TYPE: PRT
<213> ORGANISM: Orthohepadnaviridae hepatitis B virus

<400> SEQUENCE: 867

Leu Thr Arg Ile Leu Thr Ile Pro Gln Ser Leu
 1               5                  10

<210> SEQ ID NO 868
<211> LENGTH: 9
<212> TYPE: PRT
<213> ORGANISM: Orthohepadnaviridae hepatitis B virus

<400> SEQUENCE: 868

Leu Thr Val Asn Glu Lys Arg Arg Leu
 1               5

<210> SEQ ID NO 869
<211> LENGTH: 9
<212> TYPE: PRT
<213> ORGANISM: Orthohepadnaviridae hepatitis B virus

<400> SEQUENCE: 869

Leu Val Leu Leu Asp Tyr Gln Gly Met
 1               5

<210> SEQ ID NO 870
<211> LENGTH: 10
<212> TYPE: PRT
<213> ORGANISM: Orthohepadnaviridae hepatitis B virus

<400> SEQUENCE: 870

Leu Val Leu Leu Asp Tyr Gln Gly Met Leu
 1               5                  10

<210> SEQ ID NO 871
<211> LENGTH: 8
<212> TYPE: PRT
<213> ORGANISM: Orthohepadnaviridae hepatitis B virus

<400> SEQUENCE: 871

Leu Val Leu Gln Ala Gly Phe Phe
 1               5

<210> SEQ ID NO 872
<211> LENGTH: 9
<212> TYPE: PRT
<213> ORGANISM: Orthohepadnaviridae hepatitis B virus

<400> SEQUENCE: 872

Leu Val Leu Gln Ala Gly Phe Phe Leu
 1               5

<210> SEQ ID NO 873
<211> LENGTH: 10
<212> TYPE: PRT
<213> ORGANISM: Orthohepadnaviridae hepatitis B virus

<400> SEQUENCE: 873

Leu Val Leu Gln Ala Gly Phe Phe Leu Leu
 1               5                  10

<210> SEQ ID NO 874
<211> LENGTH: 8
<212> TYPE: PRT
```

<210> SEQ ID NO 874
<211> LENGTH: 7
<212> TYPE: PRT
<213> ORGANISM: Orthohepadnaviridae hepatitis B virus

<400> SEQUENCE: 874

Leu Val Pro Phe Val Gln Trp Phe
1               5

<210> SEQ ID NO 875
<211> LENGTH: 11
<212> TYPE: PRT
<213> ORGANISM: Orthohepadnaviridae hepatitis B virus

<400> SEQUENCE: 875

Leu Val Pro Phe Val Gln Trp Phe Val Gly Leu
1               5                   10

<210> SEQ ID NO 876
<211> LENGTH: 8
<212> TYPE: PRT
<213> ORGANISM: Orthohepadnaviridae hepatitis B virus

<400> SEQUENCE: 876

Leu Val Ser Phe Gly Val Trp Ile
1               5

<210> SEQ ID NO 877
<211> LENGTH: 8
<212> TYPE: PRT
<213> ORGANISM: Orthohepadnaviridae hepatitis B virus

<400> SEQUENCE: 877

Leu Val Val Asp Phe Ser Gln Phe
1               5

<210> SEQ ID NO 878
<211> LENGTH: 8
<212> TYPE: PRT
<213> ORGANISM: Orthohepadnaviridae hepatitis B virus

<400> SEQUENCE: 878

Leu Trp Phe His Ile Ser Cys Leu
1               5

<210> SEQ ID NO 879
<211> LENGTH: 10
<212> TYPE: PRT
<213> ORGANISM: Orthohepadnaviridae hepatitis B virus

<400> SEQUENCE: 879

Leu Trp Phe His Ile Ser Cys Leu Thr Phe
1               5                   10

<210> SEQ ID NO 880
<211> LENGTH: 9
<212> TYPE: PRT
<213> ORGANISM: Orthohepadnaviridae hepatitis B virus

<400> SEQUENCE: 880

Leu Trp Gly Met Asp Ile Asp Pro Tyr
1               5

<210> SEQ ID NO 881
<211> LENGTH: 8
<212> TYPE: PRT
<213> ORGANISM: Orthohepadnaviridae hepatitis B virus -continued

```
<400> SEQUENCE: 881

Leu Trp Lys Ala Gly Ile Leu Tyr
 1               5

<210> SEQ ID NO 882
<211> LENGTH: 8
<212> TYPE: PRT
<213> ORGANISM: Orthohepadnaviridae hepatitis B virus

<400> SEQUENCE: 882

Leu Tyr Ser His Pro Ile Ile Leu
 1               5

<210> SEQ ID NO 883
<211> LENGTH: 10
<212> TYPE: PRT
<213> ORGANISM: Orthohepadnaviridae hepatitis B virus

<400> SEQUENCE: 883

Leu Tyr Ser His Pro Ile Ile Leu Gly Phe
 1               5                  10

<210> SEQ ID NO 884
<211> LENGTH: 9
<212> TYPE: PRT
<213> ORGANISM: Orthohepadnaviridae hepatitis B virus

<400> SEQUENCE: 884

Met Met Trp Tyr Trp Gly Pro Ser Leu
 1               5

<210> SEQ ID NO 885
<211> LENGTH: 10
<212> TYPE: PRT
<213> ORGANISM: Orthohepadnaviridae hepatitis B virus

<400> SEQUENCE: 885

Met Met Trp Tyr Trp Gly Pro Ser Leu Tyr
 1               5                  10

<210> SEQ ID NO 886
<211> LENGTH: 8
<212> TYPE: PRT
<213> ORGANISM: Orthohepadnaviridae hepatitis B virus

<400> SEQUENCE: 886

Met Trp Tyr Trp Gly Pro Ser Leu
 1               5

<210> SEQ ID NO 887
<211> LENGTH: 9
<212> TYPE: PRT
<213> ORGANISM: Orthohepadnaviridae hepatitis B virus

<400> SEQUENCE: 887

Met Trp Tyr Trp Gly Pro Ser Leu Tyr
 1               5

<210> SEQ ID NO 888
<211> LENGTH: 8
<212> TYPE: PRT
<213> ORGANISM: Orthohepadnaviridae hepatitis B virus

<400> SEQUENCE: 888
```

```
Asn Phe Leu Leu Ser Leu Gly Ile
1               5

<210> SEQ ID NO 889
<211> LENGTH: 10
<212> TYPE: PRT
<213> ORGANISM: Orthohepadnaviridae hepatitis B virus

<400> SEQUENCE: 889

Asn Phe Leu Leu Ser Leu Gly Ile His Leu
1               5                   10

<210> SEQ ID NO 890
<211> LENGTH: 9
<212> TYPE: PRT
<213> ORGANISM: Orthohepadnaviridae hepatitis B virus

<400> SEQUENCE: 890

Asn Leu Gly Asn Leu Asn Val Ser Ile
1               5

<210> SEQ ID NO 891
<211> LENGTH: 11
<212> TYPE: PRT
<213> ORGANISM: Orthohepadnaviridae hepatitis B virus

<400> SEQUENCE: 891

Asn Leu Gly Asn Leu Asn Val Ser Ile Pro Trp
1               5                   10

<210> SEQ ID NO 892
<211> LENGTH: 9
<212> TYPE: PRT
<213> ORGANISM: Orthohepadnaviridae hepatitis B virus

<400> SEQUENCE: 892

Asn Leu Leu Ser Ser Asn Leu Ser Trp
1               5

<210> SEQ ID NO 893
<211> LENGTH: 10
<212> TYPE: PRT
<213> ORGANISM: Orthohepadnaviridae hepatitis B virus

<400> SEQUENCE: 893

Asn Leu Leu Ser Ser Asn Leu Ser Trp Leu
1               5                   10

<210> SEQ ID NO 894
<211> LENGTH: 8
<212> TYPE: PRT
<213> ORGANISM: Orthohepadnaviridae hepatitis B virus

<400> SEQUENCE: 894

Asn Leu Asn Val Ser Ile Pro Trp
1               5

<210> SEQ ID NO 895
<211> LENGTH: 8
<212> TYPE: PRT
<213> ORGANISM: Orthohepadnaviridae hepatitis B virus

<400> SEQUENCE: 895

Asn Leu Gln Ser Leu Thr Asn Leu
1               5
```

<210> SEQ ID NO 896
<211> LENGTH: 9
<212> TYPE: PRT
<213> ORGANISM: Orthohepadnaviridae hepatitis B virus

<400> SEQUENCE: 896

Asn Leu Gln Ser Leu Thr Asn Leu Leu
1               5

<210> SEQ ID NO 897
<211> LENGTH: 8
<212> TYPE: PRT
<213> ORGANISM: Orthohepadnaviridae hepatitis B virus

<400> SEQUENCE: 897

Asn Leu Ser Val Pro Asn Pro Leu
1               5

<210> SEQ ID NO 898
<211> LENGTH: 10
<212> TYPE: PRT
<213> ORGANISM: Orthohepadnaviridae hepatitis B virus

<400> SEQUENCE: 898

Asn Leu Ser Val Pro Asn Pro Leu Gly Phe
1               5                   10

<210> SEQ ID NO 899
<211> LENGTH: 9
<212> TYPE: PRT
<213> ORGANISM: Orthohepadnaviridae hepatitis B virus

<400> SEQUENCE: 899

Asn Trp Ile Leu Arg Gly Thr Ser Phe
1               5

<210> SEQ ID NO 900
<211> LENGTH: 11
<212> TYPE: PRT
<213> ORGANISM: Orthohepadnaviridae hepatitis B virus

<400> SEQUENCE: 900

Asn Trp Ile Leu Arg Gly Thr Ser Phe Val Tyr
1               5                   10

<210> SEQ ID NO 901
<211> LENGTH: 11
<212> TYPE: PRT
<213> ORGANISM: Orthohepadnaviridae hepatitis B virus

<400> SEQUENCE: 901

Pro Phe Leu Leu Ala Gln Phe Thr Ser Ala Ile
1               5                   10

<210> SEQ ID NO 902
<211> LENGTH: 10
<212> TYPE: PRT
<213> ORGANISM: Orthohepadnaviridae hepatitis B virus

<400> SEQUENCE: 902

Pro Phe Thr Gln Cys Gly Tyr Pro Ala Leu
1               5                   10

<210> SEQ ID NO 903
<211> LENGTH: 11
<212> TYPE: PRT
<213> ORGANISM: Orthohepadnaviridae hepatitis B virus

<400> SEQUENCE: 903

Pro Phe Thr Gln Cys Gly Tyr Pro Ala Leu Met
1               5                   10

<210> SEQ ID NO 904
<211> LENGTH: 9
<212> TYPE: PRT
<213> ORGANISM: Orthohepadnaviridae hepatitis B virus

<400> SEQUENCE: 904

Pro Phe Val Gln Trp Phe Val Gly Leu
1               5

<210> SEQ ID NO 905
<211> LENGTH: 10
<212> TYPE: PRT
<213> ORGANISM: Orthohepadnaviridae hepatitis B virus

<400> SEQUENCE: 905

Pro Ile Asp Trp Lys Val Cys Gln Arg Ile
1               5                   10

<210> SEQ ID NO 906
<211> LENGTH: 9
<212> TYPE: PRT
<213> ORGANISM: Orthohepadnaviridae hepatitis B virus

<400> SEQUENCE: 906

Pro Ile Phe Phe Cys Leu Trp Val Tyr
1               5

<210> SEQ ID NO 907
<211> LENGTH: 10
<212> TYPE: PRT
<213> ORGANISM: Orthohepadnaviridae hepatitis B virus

<400> SEQUENCE: 907

Pro Ile Phe Phe Cys Leu Trp Val Tyr Ile
1               5                   10

<210> SEQ ID NO 908
<211> LENGTH: 8
<212> TYPE: PRT
<213> ORGANISM: Orthohepadnaviridae hepatitis B virus

<400> SEQUENCE: 908

Pro Ile His Thr Ala Glu Leu Leu
1               5

<210> SEQ ID NO 909
<211> LENGTH: 9
<212> TYPE: PRT
<213> ORGANISM: Orthohepadnaviridae hepatitis B virus

<400> SEQUENCE: 909

Pro Ile Ile Leu Gly Phe Arg Lys Ile
1               5

<210> SEQ ID NO 910
<211> LENGTH: 11

```
<212> TYPE: PRT
<213> ORGANISM: Orthohepadnaviridae hepatitis B virus

<400> SEQUENCE: 910

Pro Ile Ile Leu Gly Phe Arg Lys Ile Pro Met
1               5                   10

<210> SEQ ID NO 911
<211> LENGTH: 8
<212> TYPE: PRT
<213> ORGANISM: Orthohepadnaviridae hepatitis B virus

<400> SEQUENCE: 911

Pro Ile Pro Ser Ser Trp Ala Phe
1               5

<210> SEQ ID NO 912
<211> LENGTH: 9
<212> TYPE: PRT
<213> ORGANISM: Orthohepadnaviridae hepatitis B virus

<400> SEQUENCE: 912

Pro Leu Asp Lys Gly Ile Lys Pro Tyr
1               5

<210> SEQ ID NO 913
<211> LENGTH: 10
<212> TYPE: PRT
<213> ORGANISM: Orthohepadnaviridae hepatitis B virus

<400> SEQUENCE: 913

Pro Leu Asp Lys Gly Ile Lys Pro Tyr Tyr
1               5                   10

<210> SEQ ID NO 914
<211> LENGTH: 9
<212> TYPE: PRT
<213> ORGANISM: Orthohepadnaviridae hepatitis B virus

<400> SEQUENCE: 914

Pro Leu Glu Glu Glu Leu Pro Arg Leu
1               5

<210> SEQ ID NO 915
<211> LENGTH: 10
<212> TYPE: PRT
<213> ORGANISM: Orthohepadnaviridae hepatitis B virus

<400> SEQUENCE: 915

Pro Leu Gly Phe Phe Pro Asp His Gln Leu
1               5                   10

<210> SEQ ID NO 916
<211> LENGTH: 10
<212> TYPE: PRT
<213> ORGANISM: Orthohepadnaviridae hepatitis B virus

<400> SEQUENCE: 916

Pro Leu His Pro Ala Ala Met Pro His Leu
1               5                   10

<210> SEQ ID NO 917
<211> LENGTH: 11
<212> TYPE: PRT
<213> ORGANISM: Orthohepadnaviridae hepatitis B virus
```

```
<400> SEQUENCE: 917

Pro Leu His Pro Ala Met Pro His Leu Leu
1               5                   10

<210> SEQ ID NO 918
<211> LENGTH: 9
<212> TYPE: PRT
<213> ORGANISM: Orthohepadnaviridae hepatitis B virus

<400> SEQUENCE: 918

Pro Leu Leu Pro Ile Phe Phe Cys Leu
1               5

<210> SEQ ID NO 919
<211> LENGTH: 10
<212> TYPE: PRT
<213> ORGANISM: Orthohepadnaviridae hepatitis B virus

<400> SEQUENCE: 919

Pro Leu Leu Pro Ile Phe Phe Cys Leu Trp
1               5                   10

<210> SEQ ID NO 920
<211> LENGTH: 9
<212> TYPE: PRT
<213> ORGANISM: Orthohepadnaviridae hepatitis B virus

<400> SEQUENCE: 920

Pro Leu Leu Val Leu Gln Ala Gly Phe
1               5

<210> SEQ ID NO 921
<211> LENGTH: 10
<212> TYPE: PRT
<213> ORGANISM: Orthohepadnaviridae hepatitis B virus

<400> SEQUENCE: 921

Pro Leu Leu Val Leu Gln Ala Gly Phe Phe
1               5                   10

<210> SEQ ID NO 922
<211> LENGTH: 11
<212> TYPE: PRT
<213> ORGANISM: Orthohepadnaviridae hepatitis B virus

<400> SEQUENCE: 922

Pro Leu Leu Val Leu Gln Ala Gly Phe Phe Leu
1               5                   10

<210> SEQ ID NO 923
<211> LENGTH: 9
<212> TYPE: PRT
<213> ORGANISM: Orthohepadnaviridae hepatitis B virus

<400> SEQUENCE: 923

Pro Leu Pro Ile His Thr Ala Glu Leu
1               5

<210> SEQ ID NO 924
<211> LENGTH: 10
<212> TYPE: PRT
<213> ORGANISM: Orthohepadnaviridae hepatitis B virus

<400> SEQUENCE: 924
```

```
Pro Leu Pro Ile His Thr Ala Glu Leu Leu
1               5                   10

<210> SEQ ID NO 925
<211> LENGTH: 10
<212> TYPE: PRT
<213> ORGANISM: Orthohepadnaviridae hepatitis B virus

<400> SEQUENCE: 925

Pro Leu Ser Tyr Gln His Phe Arg Lys Leu
1               5                   10

<210> SEQ ID NO 926
<211> LENGTH: 11
<212> TYPE: PRT
<213> ORGANISM: Orthohepadnaviridae hepatitis B virus

<400> SEQUENCE: 926

Pro Leu Ser Tyr Gln His Phe Arg Lys Leu Leu
1               5                   10

<210> SEQ ID NO 927
<211> LENGTH: 10
<212> TYPE: PRT
<213> ORGANISM: Orthohepadnaviridae hepatitis B virus

<400> SEQUENCE: 927

Pro Leu Thr Val Asn Glu Lys Arg Arg Leu
1               5                   10

<210> SEQ ID NO 928
<211> LENGTH: 9
<212> TYPE: PRT
<213> ORGANISM: Orthohepadnaviridae hepatitis B virus

<400> SEQUENCE: 928

Pro Met Gly Val Gly Leu Ser Pro Phe
1               5

<210> SEQ ID NO 929
<211> LENGTH: 10
<212> TYPE: PRT
<213> ORGANISM: Orthohepadnaviridae hepatitis B virus

<400> SEQUENCE: 929

Pro Met Gly Val Gly Leu Ser Pro Phe Leu
1               5                   10

<210> SEQ ID NO 930
<211> LENGTH: 11
<212> TYPE: PRT
<213> ORGANISM: Orthohepadnaviridae hepatitis B virus

<400> SEQUENCE: 930

Pro Met Gly Val Gly Leu Ser Pro Phe Leu Leu
1               5                   10

<210> SEQ ID NO 931
<211> LENGTH: 8
<212> TYPE: PRT
<213> ORGANISM: Orthohepadnaviridae hepatitis B virus

<400> SEQUENCE: 931

Pro Thr Gly Trp Gly Leu Ala Ile
```

<210> SEQ ID NO 932
<211> LENGTH: 8
<212> TYPE: PRT
<213> ORGANISM: Orthohepadnaviridae hepatitis B virus

<400> SEQUENCE: 932

Pro Thr Thr Gly Arg Thr Ser Leu
1               5

<210> SEQ ID NO 933
<211> LENGTH: 9
<212> TYPE: PRT
<213> ORGANISM: Orthohepadnaviridae hepatitis B virus

<400> SEQUENCE: 933

Pro Thr Thr Gly Arg Thr Ser Leu Tyr
1               5

<210> SEQ ID NO 934
<211> LENGTH: 8
<212> TYPE: PRT
<213> ORGANISM: Orthohepadnaviridae hepatitis B virus

<400> SEQUENCE: 934

Pro Thr Val Gln Ala Ser Lys Leu
1               5

<210> SEQ ID NO 935
<211> LENGTH: 10
<212> TYPE: PRT
<213> ORGANISM: Orthohepadnaviridae hepatitis B virus

<400> SEQUENCE: 935

Pro Thr Val Gln Ala Ser Lys Leu Cys Leu
1               5                   10

<210> SEQ ID NO 936
<211> LENGTH: 8
<212> TYPE: PRT
<213> ORGANISM: Orthohepadnaviridae hepatitis B virus

<400> SEQUENCE: 936

Pro Thr Val Trp Leu Ser Val Ile
1               5

<210> SEQ ID NO 937
<211> LENGTH: 9
<212> TYPE: PRT
<213> ORGANISM: Orthohepadnaviridae hepatitis B virus

<400> SEQUENCE: 937

Pro Thr Val Trp Leu Ser Val Ile Trp
1               5

<210> SEQ ID NO 938
<211> LENGTH: 10
<212> TYPE: PRT
<213> ORGANISM: Orthohepadnaviridae hepatitis B virus

<400> SEQUENCE: 938

Pro Thr Val Trp Leu Ser Val Ile Trp Met
1               5                   10

<210> SEQ ID NO 939
<211> LENGTH: 8
<212> TYPE: PRT
<213> ORGANISM: Orthohepadnaviridae hepatitis B virus

<400> SEQUENCE: 939

Pro Val Asn Arg Pro Ile Asp Trp
1               5

<210> SEQ ID NO 940
<211> LENGTH: 10
<212> TYPE: PRT
<213> ORGANISM: Orthohepadnaviridae hepatitis B virus

<400> SEQUENCE: 940

Pro Trp Leu Leu Gly Cys Ala Ala Asn Trp
1               5                   10

<210> SEQ ID NO 941
<211> LENGTH: 11
<212> TYPE: PRT
<213> ORGANISM: Orthohepadnaviridae hepatitis B virus

<400> SEQUENCE: 941

Pro Trp Leu Leu Gly Cys Ala Ala Asn Trp Ile
1               5                   10

<210> SEQ ID NO 942
<211> LENGTH: 9
<212> TYPE: PRT
<213> ORGANISM: Orthohepadnaviridae hepatitis B virus

<400> SEQUENCE: 942

Pro Trp Thr His Lys Val Gly Asn Phe
1               5

<210> SEQ ID NO 943
<211> LENGTH: 9
<212> TYPE: PRT
<213> ORGANISM: Orthohepadnaviridae hepatitis B virus

<400> SEQUENCE: 943

Gln Leu Asp Pro Ala Arg Asp Val Leu
1               5

<210> SEQ ID NO 944
<211> LENGTH: 11
<212> TYPE: PRT
<213> ORGANISM: Orthohepadnaviridae hepatitis B virus

<400> SEQUENCE: 944

Gln Leu Asp Pro Ala Arg Asp Val Leu Cys Leu
1               5                   10

<210> SEQ ID NO 945
<211> LENGTH: 10
<212> TYPE: PRT
<213> ORGANISM: Orthohepadnaviridae hepatitis B virus

<400> SEQUENCE: 945

Gln Leu Leu Trp Phe His Ile Ser Cys Leu
1               5                   10

<210> SEQ ID NO 946

-continued

<211> LENGTH: 11
<212> TYPE: PRT
<213> ORGANISM: Orthohepadnaviridae hepatitis B virus

<400> SEQUENCE: 946

Gln Val Phe Ala Asp Ala Thr Pro Thr Gly Trp
1               5                   10

<210> SEQ ID NO 947
<211> LENGTH: 11
<212> TYPE: PRT
<213> ORGANISM: Orthohepadnaviridae hepatitis B virus

<400> SEQUENCE: 947

Gln Trp Phe Val Gly Leu Ser Pro Thr Val Trp
1               5                   10

<210> SEQ ID NO 948
<211> LENGTH: 8
<212> TYPE: PRT
<213> ORGANISM: Orthohepadnaviridae hepatitis B virus

<400> SEQUENCE: 948

Arg Phe Ile Ile Phe Leu Phe Ile
1               5

<210> SEQ ID NO 949
<211> LENGTH: 9
<212> TYPE: PRT
<213> ORGANISM: Orthohepadnaviridae hepatitis B virus

<400> SEQUENCE: 949

Arg Phe Ile Ile Phe Leu Phe Ile Leu
1               5

<210> SEQ ID NO 950
<211> LENGTH: 10
<212> TYPE: PRT
<213> ORGANISM: Orthohepadnaviridae hepatitis B virus

<400> SEQUENCE: 950

Arg Phe Ile Ile Phe Leu Phe Ile Leu Leu
1               5                   10

<210> SEQ ID NO 951
<211> LENGTH: 11
<212> TYPE: PRT
<213> ORGANISM: Orthohepadnaviridae hepatitis B virus

<400> SEQUENCE: 951

Arg Phe Ile Ile Phe Leu Phe Ile Leu Leu Leu
1               5                   10

<210> SEQ ID NO 952
<211> LENGTH: 8
<212> TYPE: PRT
<213> ORGANISM: Orthohepadnaviridae hepatitis B virus

<400> SEQUENCE: 952

Arg Phe Ser Trp Leu Ser Leu Leu
1               5

<210> SEQ ID NO 953
<211> LENGTH: 11
<212> TYPE: PRT

-continued

<213> ORGANISM: Orthohepadnaviridae hepatitis B virus

<400> SEQUENCE: 953

Arg Phe Ser Trp Leu Ser Leu Leu Val Pro Phe
1               5                   10

<210> SEQ ID NO 954
<211> LENGTH: 9
<212> TYPE: PRT
<213> ORGANISM: Orthohepadnaviridae hepatitis B virus

<400> SEQUENCE: 954

Arg Ile Leu Thr Ile Pro Gln Ser Leu
1               5

<210> SEQ ID NO 955
<211> LENGTH: 8
<212> TYPE: PRT
<213> ORGANISM: Orthohepadnaviridae hepatitis B virus

<400> SEQUENCE: 955

Arg Ile Val Gly Leu Leu Gly Phe
1               5

<210> SEQ ID NO 956
<211> LENGTH: 10
<212> TYPE: PRT
<213> ORGANISM: Orthohepadnaviridae hepatitis B virus

<400> SEQUENCE: 956

Arg Leu Lys Leu Ile Met Pro Ala Arg Phe
1               5                   10

<210> SEQ ID NO 957
<211> LENGTH: 11
<212> TYPE: PRT
<213> ORGANISM: Orthohepadnaviridae hepatitis B virus

<400> SEQUENCE: 957

Arg Leu Lys Leu Ile Met Pro Ala Arg Phe Tyr
1               5                   10

<210> SEQ ID NO 958
<211> LENGTH: 9
<212> TYPE: PRT
<213> ORGANISM: Orthohepadnaviridae hepatitis B virus

<400> SEQUENCE: 958

Arg Leu Val Val Asp Phe Ser Gln Phe
1               5

<210> SEQ ID NO 959
<211> LENGTH: 11
<212> TYPE: PRT
<213> ORGANISM: Orthohepadnaviridae hepatitis B virus

<400> SEQUENCE: 959

Arg Thr Pro Ala Arg Val Thr Gly Gly Val Phe
1               5                   10

<210> SEQ ID NO 960
<211> LENGTH: 8
<212> TYPE: PRT
<213> ORGANISM: Orthohepadnaviridae hepatitis B virus

```
<400> SEQUENCE: 960

Arg Val Ala Glu Asp Leu Asn Leu
1               5

<210> SEQ ID NO 961
<211> LENGTH: 11
<212> TYPE: PRT
<213> ORGANISM: Orthohepadnaviridae hepatitis B virus

<400> SEQUENCE: 961

Arg Val Ala Glu Asp Leu Asn Leu Gly Asn Leu
1               5                   10

<210> SEQ ID NO 962
<211> LENGTH: 8
<212> TYPE: PRT
<213> ORGANISM: Orthohepadnaviridae hepatitis B virus

<400> SEQUENCE: 962

Arg Val His Phe Ala Ser Pro Leu
1               5

<210> SEQ ID NO 963
<211> LENGTH: 8
<212> TYPE: PRT
<213> ORGANISM: Orthohepadnaviridae hepatitis B virus

<400> SEQUENCE: 963

Arg Val Thr Gly Gly Val Phe Leu
1               5

<210> SEQ ID NO 964
<211> LENGTH: 8
<212> TYPE: PRT
<213> ORGANISM: Orthohepadnaviridae hepatitis B virus

<400> SEQUENCE: 964

Arg Trp Gly Tyr Ser Leu Asn Phe
1               5

<210> SEQ ID NO 965
<211> LENGTH: 9
<212> TYPE: PRT
<213> ORGANISM: Orthohepadnaviridae hepatitis B virus

<400> SEQUENCE: 965

Arg Trp Gly Tyr Ser Leu Asn Phe Met
1               5

<210> SEQ ID NO 966
<211> LENGTH: 11
<212> TYPE: PRT
<213> ORGANISM: Orthohepadnaviridae hepatitis B virus

<400> SEQUENCE: 966

Arg Trp Gly Tyr Ser Leu Asn Phe Met Gly Tyr
1               5                   10

<210> SEQ ID NO 967
<211> LENGTH: 8
<212> TYPE: PRT
<213> ORGANISM: Orthohepadnaviridae hepatitis B virus

<400> SEQUENCE: 967
```

-continued

Arg Trp Met Cys Leu Arg Arg Phe
1               5

<210> SEQ ID NO 968
<211> LENGTH: 9
<212> TYPE: PRT
<213> ORGANISM: Orthohepadnaviridae hepatitis B virus

<400> SEQUENCE: 968

Arg Trp Met Cys Leu Arg Arg Phe Ile
1               5

<210> SEQ ID NO 969
<211> LENGTH: 10
<212> TYPE: PRT
<213> ORGANISM: Orthohepadnaviridae hepatitis B virus

<400> SEQUENCE: 969

Arg Trp Met Cys Leu Arg Arg Phe Ile Ile
1               5                   10

<210> SEQ ID NO 970
<211> LENGTH: 11
<212> TYPE: PRT
<213> ORGANISM: Orthohepadnaviridae hepatitis B virus

<400> SEQUENCE: 970

Arg Trp Met Cys Leu Arg Arg Phe Ile Ile Phe
1               5                   10

<210> SEQ ID NO 971
<211> LENGTH: 9
<212> TYPE: PRT
<213> ORGANISM: Orthohepadnaviridae hepatitis B virus

<400> SEQUENCE: 971

Ser Phe Cys Gly Ser Pro Tyr Ser Trp
1               5

<210> SEQ ID NO 972
<211> LENGTH: 8
<212> TYPE: PRT
<213> ORGANISM: Orthohepadnaviridae hepatitis B virus

<400> SEQUENCE: 972

Ser Phe Leu Pro Ser Asp Phe Phe
1               5

<210> SEQ ID NO 973
<211> LENGTH: 9
<212> TYPE: PRT
<213> ORGANISM: Orthohepadnaviridae hepatitis B virus

<400> SEQUENCE: 973

Ser Phe Val Tyr Val Pro Ser Ala Leu
1               5

<210> SEQ ID NO 974
<211> LENGTH: 11
<212> TYPE: PRT
<213> ORGANISM: Orthohepadnaviridae hepatitis B virus

<400> SEQUENCE: 974

Ser Ile Pro Trp Thr His Lys Val Gly Asn Phe
1               5                   10

-continued

<210> SEQ ID NO 975
<211> LENGTH: 9
<212> TYPE: PRT
<213> ORGANISM: Orthohepadnaviridae hepatitis B virus

<400> SEQUENCE: 975

Ser Leu Asp Ser Trp Trp Thr Ser Leu
1 5

<210> SEQ ID NO 976
<211> LENGTH: 11
<212> TYPE: PRT
<213> ORGANISM: Orthohepadnaviridae hepatitis B virus

<400> SEQUENCE: 976

Ser Leu Asp Ser Trp Trp Thr Ser Leu Asn Phe
1 5 10

<210> SEQ ID NO 977
<211> LENGTH: 8
<212> TYPE: PRT
<213> ORGANISM: Orthohepadnaviridae hepatitis B virus

<400> SEQUENCE: 977

Ser Leu Asp Val Ser Ala Ala Phe
1 5

<210> SEQ ID NO 978
<211> LENGTH: 9
<212> TYPE: PRT
<213> ORGANISM: Orthohepadnaviridae hepatitis B virus

<400> SEQUENCE: 978

Ser Leu Asp Val Ser Ala Ala Phe Tyr
1 5

<210> SEQ ID NO 979
<211> LENGTH: 9
<212> TYPE: PRT
<213> ORGANISM: Orthohepadnaviridae hepatitis B virus

<400> SEQUENCE: 979

Ser Leu Leu Val Pro Phe Val Gln Trp
1 5

<210> SEQ ID NO 980
<211> LENGTH: 10
<212> TYPE: PRT
<213> ORGANISM: Orthohepadnaviridae hepatitis B virus

<400> SEQUENCE: 980

Ser Leu Leu Val Pro Phe Val Gln Trp Phe
1 5 10

<210> SEQ ID NO 981
<211> LENGTH: 9
<212> TYPE: PRT
<213> ORGANISM: Orthohepadnaviridae hepatitis B virus

<400> SEQUENCE: 981

Ser Leu Asn Phe Met Gly Tyr Val Ile
1 5

```
<210> SEQ ID NO 982
<211> LENGTH: 10
<212> TYPE: PRT
<213> ORGANISM: Orthohepadnaviridae hepatitis B virus

<400> SEQUENCE: 982

Ser Leu Arg Gly Leu Pro Val Cys Ala Phe
1               5                   10

<210> SEQ ID NO 983
<211> LENGTH: 10
<212> TYPE: PRT
<213> ORGANISM: Orthohepadnaviridae hepatitis B virus

<400> SEQUENCE: 983

Ser Leu Thr Asn Leu Leu Ser Ser Asn Leu
1               5                   10

<210> SEQ ID NO 984
<211> LENGTH: 8
<212> TYPE: PRT
<213> ORGANISM: Orthohepadnaviridae hepatitis B virus

<400> SEQUENCE: 984

Ser Thr Thr Asp Leu Glu Ala Tyr
1               5

<210> SEQ ID NO 985
<211> LENGTH: 9
<212> TYPE: PRT
<213> ORGANISM: Orthohepadnaviridae hepatitis B virus

<400> SEQUENCE: 985

Ser Thr Thr Asp Leu Glu Ala Tyr Phe
1               5

<210> SEQ ID NO 986
<211> LENGTH: 8
<212> TYPE: PRT
<213> ORGANISM: Orthohepadnaviridae hepatitis B virus

<400> SEQUENCE: 986

Ser Val Pro Asn Pro Leu Gly Phe
1               5

<210> SEQ ID NO 987
<211> LENGTH: 8
<212> TYPE: PRT
<213> ORGANISM: Orthohepadnaviridae hepatitis B virus

<400> SEQUENCE: 987

Ser Val Gln His Leu Glu Ser Leu
1               5

<210> SEQ ID NO 988
<211> LENGTH: 9
<212> TYPE: PRT
<213> ORGANISM: Orthohepadnaviridae hepatitis B virus

<400> SEQUENCE: 988

Ser Val Arg Phe Ser Trp Leu Ser Leu
1               5

<210> SEQ ID NO 989
<211> LENGTH: 10
```

-continued

<212> TYPE: PRT
<213> ORGANISM: Orthohepadnaviridae hepatitis B virus

<400> SEQUENCE: 989

Ser Val Arg Phe Ser Trp Leu Ser Leu Leu
1 5 10

<210> SEQ ID NO 990
<211> LENGTH: 8
<212> TYPE: PRT
<213> ORGANISM: Orthohepadnaviridae hepatitis B virus

<400> SEQUENCE: 990

Ser Val Val Leu Ser Arg Lys Tyr
1 5

<210> SEQ ID NO 991
<211> LENGTH: 11
<212> TYPE: PRT
<213> ORGANISM: Orthohepadnaviridae hepatitis B virus

<400> SEQUENCE: 991

Ser Val Val Leu Ser Arg Lys Tyr Thr Ser Phe
1 5 10

<210> SEQ ID NO 992
<211> LENGTH: 11
<212> TYPE: PRT
<213> ORGANISM: Orthohepadnaviridae hepatitis B virus

<400> SEQUENCE: 992

Ser Val Val Arg Arg Ala Phe Pro His Cys Leu
1 5 10

<210> SEQ ID NO 993
<211> LENGTH: 11
<212> TYPE: PRT
<213> ORGANISM: Orthohepadnaviridae hepatitis B virus

<400> SEQUENCE: 993

Ser Trp Leu Ser Leu Asp Val Ser Ala Ala Phe
1 5 10

<210> SEQ ID NO 994
<211> LENGTH: 9
<212> TYPE: PRT
<213> ORGANISM: Orthohepadnaviridae hepatitis B virus

<400> SEQUENCE: 994

Ser Trp Leu Ser Leu Leu Val Pro Phe
1 5

<210> SEQ ID NO 995
<211> LENGTH: 10
<212> TYPE: PRT
<213> ORGANISM: Orthohepadnaviridae hepatitis B virus

<400> SEQUENCE: 995

Ser Trp Pro Lys Phe Ala Val Pro Asn Leu
1 5 10

<210> SEQ ID NO 996
<211> LENGTH: 8
<212> TYPE: PRT
<213> ORGANISM: Orthohepadnaviridae hepatitis B virus

```
<400> SEQUENCE: 996

Ser Trp Trp Thr Ser Leu Asn Phe
1               5

<210> SEQ ID NO 997
<211> LENGTH: 9
<212> TYPE: PRT
<213> ORGANISM: Orthohepadnaviridae hepatitis B virus

<400> SEQUENCE: 997

Ser Trp Trp Thr Ser Leu Asn Phe Leu
1               5

<210> SEQ ID NO 998
<211> LENGTH: 8
<212> TYPE: PRT
<213> ORGANISM: Orthohepadnaviridae hepatitis B virus

<400> SEQUENCE: 998

Ser Tyr Met Asp Asp Val Val Leu
1               5

<210> SEQ ID NO 999
<211> LENGTH: 8
<212> TYPE: PRT
<213> ORGANISM: Orthohepadnaviridae hepatitis B virus

<400> SEQUENCE: 999

Ser Tyr Gln His Phe Arg Lys Leu
1               5

<210> SEQ ID NO 1000
<211> LENGTH: 9
<212> TYPE: PRT
<213> ORGANISM: Orthohepadnaviridae hepatitis B virus

<400> SEQUENCE: 1000

Ser Tyr Gln His Phe Arg Lys Leu Leu
1               5

<210> SEQ ID NO 1001
<211> LENGTH: 10
<212> TYPE: PRT
<213> ORGANISM: Orthohepadnaviridae hepatitis B virus

<400> SEQUENCE: 1001

Ser Tyr Gln His Phe Arg Lys Leu Leu Leu
1               5                   10

<210> SEQ ID NO 1002
<211> LENGTH: 11
<212> TYPE: PRT
<213> ORGANISM: Orthohepadnaviridae hepatitis B virus

<400> SEQUENCE: 1002

Ser Tyr Gln His Phe Arg Lys Leu Leu Leu Leu
1               5                   10

<210> SEQ ID NO 1003
<211> LENGTH: 8
<212> TYPE: PRT
<213> ORGANISM: Orthohepadnaviridae hepatitis B virus

<400> SEQUENCE: 1003
```

<210> SEQ ID NO 1004
<211> LENGTH: 10
<212> TYPE: PRT
<213> ORGANISM: Orthohepadnaviridae hepatitis B virus

<400> SEQUENCE: 1004

Thr Phe Gly Arg Glu Thr Val Leu Glu Tyr
1               5                   10

<210> SEQ ID NO 1005
<211> LENGTH: 11
<212> TYPE: PRT
<213> ORGANISM: Orthohepadnaviridae hepatitis B virus

<400> SEQUENCE: 1005

Thr Phe Gly Arg Glu Thr Val Leu Glu Tyr Leu
1               5                   10

<210> SEQ ID NO 1006
<211> LENGTH: 9
<212> TYPE: PRT
<213> ORGANISM: Orthohepadnaviridae hepatitis B virus

<400> SEQUENCE: 1006

Thr Phe Ser Pro Thr Tyr Lys Ala Phe
1               5

<210> SEQ ID NO 1007
<211> LENGTH: 10
<212> TYPE: PRT
<213> ORGANISM: Orthohepadnaviridae hepatitis B virus

<400> SEQUENCE: 1007

Thr Phe Ser Pro Thr Tyr Lys Ala Phe Leu
1               5                   10

<210> SEQ ID NO 1008
<211> LENGTH: 9
<212> TYPE: PRT
<213> ORGANISM: Orthohepadnaviridae hepatitis B virus

<400> SEQUENCE: 1008

Thr Ile Pro Gln Ser Leu Asp Ser Trp
1               5

<210> SEQ ID NO 1009
<211> LENGTH: 10
<212> TYPE: PRT
<213> ORGANISM: Orthohepadnaviridae hepatitis B virus

<400> SEQUENCE: 1009

Thr Ile Pro Gln Ser Leu Asp Ser Trp Trp
1               5                   10

<210> SEQ ID NO 1010
<211> LENGTH: 8
<212> TYPE: PRT
<213> ORGANISM: Orthohepadnaviridae hepatitis B virus

<400> SEQUENCE: 1010

Thr Leu Trp Lys Ala Gly Ile Leu

-continued

```
<210> SEQ ID NO 1011
<211> LENGTH: 9
<212> TYPE: PRT
<213> ORGANISM: Orthohepadnaviridae hepatitis B virus

<400> SEQUENCE: 1011

Thr Leu Trp Lys Ala Gly Ile Leu Tyr
1               5

<210> SEQ ID NO 1012
<211> LENGTH: 8
<212> TYPE: PRT
<213> ORGANISM: Orthohepadnaviridae hepatitis B virus

<400> SEQUENCE: 1012

Thr Thr Asp Leu Glu Ala Tyr Phe
1               5

<210> SEQ ID NO 1013
<211> LENGTH: 8
<212> TYPE: PRT
<213> ORGANISM: Orthohepadnaviridae hepatitis B virus

<400> SEQUENCE: 1013

Thr Thr Gly Arg Thr Ser Leu Tyr
1               5

<210> SEQ ID NO 1014
<211> LENGTH: 8
<212> TYPE: PRT
<213> ORGANISM: Orthohepadnaviridae hepatitis B virus

<400> SEQUENCE: 1014

Thr Val Asn Glu Lys Arg Arg Leu
1               5

<210> SEQ ID NO 1015
<211> LENGTH: 9
<212> TYPE: PRT
<213> ORGANISM: Orthohepadnaviridae hepatitis B virus

<400> SEQUENCE: 1015

Thr Val Gln Ala Ser Lys Leu Cys Leu
1               5

<210> SEQ ID NO 1016
<211> LENGTH: 11
<212> TYPE: PRT
<213> ORGANISM: Orthohepadnaviridae hepatitis B virus

<400> SEQUENCE: 1016

Thr Val Gln Ala Ser Lys Leu Cys Leu Gly Trp
1               5                   10

<210> SEQ ID NO 1017
<211> LENGTH: 8
<212> TYPE: PRT
<213> ORGANISM: Orthohepadnaviridae hepatitis B virus

<400> SEQUENCE: 1017

Thr Val Trp Leu Ser Val Ile Trp
1               5
```

```
<210> SEQ ID NO 1018
<211> LENGTH: 9
<212> TYPE: PRT
<213> ORGANISM: Orthohepadnaviridae hepatitis B virus

<400> SEQUENCE: 1018

Thr Val Trp Leu Ser Val Ile Trp Met
1               5

<210> SEQ ID NO 1019
<211> LENGTH: 10
<212> TYPE: PRT
<213> ORGANISM: Orthohepadnaviridae hepatitis B virus

<400> SEQUENCE: 1019

Val Phe Ala Asp Ala Thr Pro Thr Gly Trp
1               5                   10

<210> SEQ ID NO 1020
<211> LENGTH: 11
<212> TYPE: PRT
<213> ORGANISM: Orthohepadnaviridae hepatitis B virus

<400> SEQUENCE: 1020

Val Phe Val Leu Gly Gly Cys Arg His Lys Leu
1               5                   10

<210> SEQ ID NO 1021
<211> LENGTH: 10
<212> TYPE: PRT
<213> ORGANISM: Orthohepadnaviridae hepatitis B virus

<400> SEQUENCE: 1021

Val Leu Gly Ala Lys Ser Val Gln His Leu
1               5                   10

<210> SEQ ID NO 1022
<211> LENGTH: 9
<212> TYPE: PRT
<213> ORGANISM: Orthohepadnaviridae hepatitis B virus

<400> SEQUENCE: 1022

Val Leu Gly Gly Cys Arg His Lys Leu
1               5

<210> SEQ ID NO 1023
<211> LENGTH: 9
<212> TYPE: PRT
<213> ORGANISM: Orthohepadnaviridae hepatitis B virus

<400> SEQUENCE: 1023

Val Leu His Lys Arg Thr Leu Gly Leu
1               5

<210> SEQ ID NO 1024
<211> LENGTH: 8
<212> TYPE: PRT
<213> ORGANISM: Orthohepadnaviridae hepatitis B virus

<400> SEQUENCE: 1024

Val Leu Leu Asp Tyr Gln Gly Met
1               5

<210> SEQ ID NO 1025
```

```
-continued

<211> LENGTH: 9
<212> TYPE: PRT
<213> ORGANISM: Orthohepadnaviridae hepatitis B virus

<400> SEQUENCE: 1025

Val Leu Leu Asp Tyr Gln Gly Met Leu
 1               5

<210> SEQ ID NO 1026
<211> LENGTH: 8
<212> TYPE: PRT
<213> ORGANISM: Orthohepadnaviridae hepatitis B virus

<400> SEQUENCE: 1026

Val Leu Gln Ala Gly Phe Phe Leu
 1               5

<210> SEQ ID NO 1027
<211> LENGTH: 9
<212> TYPE: PRT
<213> ORGANISM: Orthohepadnaviridae hepatitis B virus

<400> SEQUENCE: 1027

Val Leu Gln Ala Gly Phe Phe Leu Leu
 1               5

<210> SEQ ID NO 1028
<211> LENGTH: 9
<212> TYPE: PRT
<213> ORGANISM: Orthohepadnaviridae hepatitis B virus

<400> SEQUENCE: 1028

Val Leu Ser Arg Lys Tyr Thr Ser Phe
 1               5

<210> SEQ ID NO 1029
<211> LENGTH: 11
<212> TYPE: PRT
<213> ORGANISM: Orthohepadnaviridae hepatitis B virus

<400> SEQUENCE: 1029

Val Leu Ser Arg Lys Tyr Thr Ser Phe Pro Trp
 1               5                   10

<210> SEQ ID NO 1030
<211> LENGTH: 11
<212> TYPE: PRT
<213> ORGANISM: Orthohepadnaviridae hepatitis B virus

<400> SEQUENCE: 1030

Val Val Leu Gly Ala Lys Ser Val Gln His Leu
 1               5                   10

<210> SEQ ID NO 1031
<211> LENGTH: 10
<212> TYPE: PRT
<213> ORGANISM: Orthohepadnaviridae hepatitis B virus

<400> SEQUENCE: 1031

Val Val Leu Ser Arg Lys Tyr Thr Ser Phe
 1               5                   10

<210> SEQ ID NO 1032
<211> LENGTH: 10
<212> TYPE: PRT
```

<213> ORGANISM: Orthohepadnaviridae hepatitis B virus

<400> SEQUENCE: 1032

Val Val Arg Arg Ala Phe Pro His Cys Leu
1               5                   10

<210> SEQ ID NO 1033
<211> LENGTH: 9
<212> TYPE: PRT
<213> ORGANISM: Orthohepadnaviridae hepatitis B virus

<400> SEQUENCE: 1033

Val Trp Ile Arg Thr Pro Pro Ala Tyr
1               5

<210> SEQ ID NO 1034
<211> LENGTH: 8
<212> TYPE: PRT
<213> ORGANISM: Orthohepadnaviridae hepatitis B virus

<400> SEQUENCE: 1034

Val Trp Leu Ser Val Ile Trp Met
1               5

<210> SEQ ID NO 1035
<211> LENGTH: 9
<212> TYPE: PRT
<213> ORGANISM: Orthohepadnaviridae hepatitis B virus

<400> SEQUENCE: 1035

Trp Phe His Ile Ser Cys Leu Thr Phe
1               5

<210> SEQ ID NO 1036
<211> LENGTH: 10
<212> TYPE: PRT
<213> ORGANISM: Orthohepadnaviridae hepatitis B virus

<400> SEQUENCE: 1036

Trp Phe Val Gly Leu Ser Pro Thr Val Trp
1               5                   10

<210> SEQ ID NO 1037
<211> LENGTH: 11
<212> TYPE: PRT
<213> ORGANISM: Orthohepadnaviridae hepatitis B virus

<400> SEQUENCE: 1037

Trp Phe Val Gly Leu Ser Pro Thr Val Trp Leu
1               5                   10

<210> SEQ ID NO 1038
<211> LENGTH: 8
<212> TYPE: PRT
<213> ORGANISM: Orthohepadnaviridae hepatitis B virus

<400> SEQUENCE: 1038

Trp Ile Leu Arg Gly Thr Ser Phe
1               5

<210> SEQ ID NO 1039
<211> LENGTH: 10
<212> TYPE: PRT
<213> ORGANISM: Orthohepadnaviridae hepatitis B virus -continued

```
<400> SEQUENCE: 1039

Trp Ile Leu Arg Gly Thr Ser Phe Val Tyr
1               5                   10

<210> SEQ ID NO 1040
<211> LENGTH: 8
<212> TYPE: PRT
<213> ORGANISM: Orthohepadnaviridae hepatitis B virus

<400> SEQUENCE: 1040

Trp Ile Arg Thr Pro Pro Ala Tyr
1               5

<210> SEQ ID NO 1041
<211> LENGTH: 9
<212> TYPE: PRT
<213> ORGANISM: Orthohepadnaviridae hepatitis B virus

<400> SEQUENCE: 1041

Trp Leu Leu Gly Cys Ala Ala Asn Trp
1               5

<210> SEQ ID NO 1042
<211> LENGTH: 10
<212> TYPE: PRT
<213> ORGANISM: Orthohepadnaviridae hepatitis B virus

<400> SEQUENCE: 1042

Trp Leu Leu Gly Cys Ala Ala Asn Trp Ile
1               5                   10

<210> SEQ ID NO 1043
<211> LENGTH: 11
<212> TYPE: PRT
<213> ORGANISM: Orthohepadnaviridae hepatitis B virus

<400> SEQUENCE: 1043

Trp Leu Leu Gly Cys Ala Ala Asn Trp Ile Leu
1               5                   10

<210> SEQ ID NO 1044
<211> LENGTH: 10
<212> TYPE: PRT
<213> ORGANISM: Orthohepadnaviridae hepatitis B virus

<400> SEQUENCE: 1044

Trp Leu Ser Leu Asp Val Ser Ala Ala Phe
1               5                   10

<210> SEQ ID NO 1045
<211> LENGTH: 11
<212> TYPE: PRT
<213> ORGANISM: Orthohepadnaviridae hepatitis B virus

<400> SEQUENCE: 1045

Trp Leu Ser Leu Asp Val Ser Ala Ala Phe Tyr
1               5                   10

<210> SEQ ID NO 1046
<211> LENGTH: 8
<212> TYPE: PRT
<213> ORGANISM: Orthohepadnaviridae hepatitis B virus

<400> SEQUENCE: 1046
```

-continued

Trp Leu Ser Leu Leu Val Pro Phe
1               5

<210> SEQ ID NO 1047
<211> LENGTH: 11
<212> TYPE: PRT
<213> ORGANISM: Orthohepadnaviridae hepatitis B virus

<400> SEQUENCE: 1047

Trp Leu Ser Leu Leu Val Pro Phe Val Gln Trp
1               5                   10

<210> SEQ ID NO 1048
<211> LENGTH: 10
<212> TYPE: PRT
<213> ORGANISM: Orthohepadnaviridae hepatitis B virus

<400> SEQUENCE: 1048

Trp Leu Trp Gly Met Asp Ile Asp Pro Tyr
1               5                   10

<210> SEQ ID NO 1049
<211> LENGTH: 8
<212> TYPE: PRT
<213> ORGANISM: Orthohepadnaviridae hepatitis B virus

<400> SEQUENCE: 1049

Trp Met Cys Leu Arg Arg Phe Ile
1               5

<210> SEQ ID NO 1050
<211> LENGTH: 9
<212> TYPE: PRT
<213> ORGANISM: Orthohepadnaviridae hepatitis B virus

<400> SEQUENCE: 1050

Trp Met Cys Leu Arg Arg Phe Ile Ile
1               5

<210> SEQ ID NO 1051
<211> LENGTH: 10
<212> TYPE: PRT
<213> ORGANISM: Orthohepadnaviridae hepatitis B virus

<400> SEQUENCE: 1051

Trp Met Cys Leu Arg Arg Phe Ile Ile Phe
1               5                   10

<210> SEQ ID NO 1052
<211> LENGTH: 11
<212> TYPE: PRT
<213> ORGANISM: Orthohepadnaviridae hepatitis B virus

<400> SEQUENCE: 1052

Trp Met Cys Leu Arg Arg Phe Ile Ile Phe Leu
1               5                   10

<210> SEQ ID NO 1053
<211> LENGTH: 10
<212> TYPE: PRT
<213> ORGANISM: Orthohepadnaviridae hepatitis B virus

<400> SEQUENCE: 1053

Trp Met Met Trp Tyr Trp Gly Pro Ser Leu
1               5                   10

```
<210> SEQ ID NO 1054
<211> LENGTH: 11
<212> TYPE: PRT
<213> ORGANISM: Orthohepadnaviridae hepatitis B virus

<400> SEQUENCE: 1054

Trp Met Met Trp Tyr Trp Gly Pro Ser Leu Tyr
 1               5                  10

<210> SEQ ID NO 1055
<211> LENGTH: 8
<212> TYPE: PRT
<213> ORGANISM: Orthohepadnaviridae hepatitis B virus

<400> SEQUENCE: 1055

Trp Thr His Lys Val Gly Asn Phe
 1               5

<210> SEQ ID NO 1056
<211> LENGTH: 11
<212> TYPE: PRT
<213> ORGANISM: Orthohepadnaviridae hepatitis B virus

<400> SEQUENCE: 1056

Trp Thr His Lys Val Gly Asn Phe Thr Gly Leu
 1               5                  10

<210> SEQ ID NO 1057
<211> LENGTH: 8
<212> TYPE: PRT
<213> ORGANISM: Orthohepadnaviridae hepatitis B virus

<400> SEQUENCE: 1057

Trp Trp Thr Ser Leu Asn Phe Leu
 1               5

<210> SEQ ID NO 1058
<211> LENGTH: 8
<212> TYPE: PRT
<213> ORGANISM: Orthohepadnaviridae hepatitis B virus

<400> SEQUENCE: 1058

Trp Tyr Trp Gly Pro Ser Leu Tyr
 1               5

<210> SEQ ID NO 1059
<211> LENGTH: 10
<212> TYPE: PRT
<213> ORGANISM: Orthohepadnaviridae hepatitis B virus

<400> SEQUENCE: 1059

Tyr Leu His Thr Leu Trp Lys Ala Gly Ile
 1               5                  10

<210> SEQ ID NO 1060
<211> LENGTH: 11
<212> TYPE: PRT
<213> ORGANISM: Orthohepadnaviridae hepatitis B virus

<400> SEQUENCE: 1060

Tyr Leu His Thr Leu Trp Lys Ala Gly Ile Leu
 1               5                  10
```

```
<210> SEQ ID NO 1061
<211> LENGTH: 8
<212> TYPE: PRT
<213> ORGANISM: Orthohepadnaviridae hepatitis B virus

<400> SEQUENCE: 1061

Tyr Leu Pro Leu Asp Lys Gly Ile
1               5

<210> SEQ ID NO 1062
<211> LENGTH: 11
<212> TYPE: PRT
<213> ORGANISM: Orthohepadnaviridae hepatitis B virus

<400> SEQUENCE: 1062

Tyr Leu Pro Leu Asp Lys Gly Ile Lys Pro Tyr
1               5                   10

<210> SEQ ID NO 1063
<211> LENGTH: 8
<212> TYPE: PRT
<213> ORGANISM: Orthohepadnaviridae hepatitis B virus

<400> SEQUENCE: 1063

Tyr Leu Val Ser Phe Gly Val Trp
1               5

<210> SEQ ID NO 1064
<211> LENGTH: 9
<212> TYPE: PRT
<213> ORGANISM: Orthohepadnaviridae hepatitis B virus

<400> SEQUENCE: 1064

Tyr Leu Val Ser Phe Gly Val Trp Ile
1               5

<210> SEQ ID NO 1065
<211> LENGTH: 8
<212> TYPE: PRT
<213> ORGANISM: Orthohepadnaviridae hepatitis B virus

<400> SEQUENCE: 1065

Tyr Thr Ser Phe Pro Trp Leu Leu
1               5

<210> SEQ ID NO 1066
<211> LENGTH: 9
<212> TYPE: PRT
<213> ORGANISM: Orthohepadnaviridae hepatitis B virus

<400> SEQUENCE: 1066

Ala Pro Cys Asn Phe Phe Thr Ser Ala
1               5

<210> SEQ ID NO 1067
<211> LENGTH: 8
<212> TYPE: PRT
<213> ORGANISM: Orthohepadnaviridae hepatitis B virus

<400> SEQUENCE: 1067

Ala Pro Phe Thr Gln Cys Gly Tyr
1               5

<210> SEQ ID NO 1068
<211> LENGTH: 10
```

-continued

<212> TYPE: PRT
<213> ORGANISM: Orthohepadnaviridae hepatitis B virus

<400> SEQUENCE: 1068

Ala Pro Phe Thr Gln Cys Gly Tyr Pro Ala
1               5                   10

<210> SEQ ID NO 1069
<211> LENGTH: 11
<212> TYPE: PRT
<213> ORGANISM: Orthohepadnaviridae hepatitis B virus

<400> SEQUENCE: 1069

Ala Pro Phe Thr Gln Cys Gly Tyr Pro Ala Leu
1               5                   10

<210> SEQ ID NO 1070
<211> LENGTH: 9
<212> TYPE: PRT
<213> ORGANISM: Orthohepadnaviridae hepatitis B virus

<400> SEQUENCE: 1070

Cys Pro Gly Tyr Arg Trp Met Cys Leu
1               5

<210> SEQ ID NO 1071
<211> LENGTH: 9
<212> TYPE: PRT
<213> ORGANISM: Orthohepadnaviridae hepatitis B virus

<400> SEQUENCE: 1071

Cys Pro Thr Val Gln Ala Ser Lys Leu
1               5

<210> SEQ ID NO 1072
<211> LENGTH: 11
<212> TYPE: PRT
<213> ORGANISM: Orthohepadnaviridae hepatitis B virus

<400> SEQUENCE: 1072

Cys Pro Thr Val Gln Ala Ser Lys Leu Cys Leu
1               5                   10

<210> SEQ ID NO 1073
<211> LENGTH: 9
<212> TYPE: PRT
<213> ORGANISM: Orthohepadnaviridae hepatitis B virus

<400> SEQUENCE: 1073

Asp Pro Ala Arg Asp Val Leu Cys Leu
1               5

<210> SEQ ID NO 1074
<211> LENGTH: 8
<212> TYPE: PRT
<213> ORGANISM: Orthohepadnaviridae hepatitis B virus

<400> SEQUENCE: 1074

Asp Pro Arg Val Arg Gly Leu Tyr
1               5

<210> SEQ ID NO 1075
<211> LENGTH: 9
<212> TYPE: PRT
<213> ORGANISM: Orthohepadnaviridae hepatitis B virus

```
<400> SEQUENCE: 1075

Asp Pro Ser Arg Gly Arg Leu Gly Leu
1               5

<210> SEQ ID NO 1076
<211> LENGTH: 8
<212> TYPE: PRT
<213> ORGANISM: Orthohepadnaviridae hepatitis B virus

<400> SEQUENCE: 1076

Asp Pro Tyr Lys Glu Phe Gly Ala
1               5

<210> SEQ ID NO 1077
<211> LENGTH: 11
<212> TYPE: PRT
<213> ORGANISM: Orthohepadnaviridae hepatitis B virus

<400> SEQUENCE: 1077

Phe Pro Ala Gly Gly Ser Ser Ser Gly Thr Val
1               5                   10

<210> SEQ ID NO 1078
<211> LENGTH: 9
<212> TYPE: PRT
<213> ORGANISM: Orthohepadnaviridae hepatitis B virus

<400> SEQUENCE: 1078

Phe Pro Asp His Gln Leu Asp Pro Ala
1               5

<210> SEQ ID NO 1079
<211> LENGTH: 10
<212> TYPE: PRT
<213> ORGANISM: Orthohepadnaviridae hepatitis B virus

<400> SEQUENCE: 1079

Phe Pro Asp His Gln Leu Asp Pro Ala Phe
1               5                   10

<210> SEQ ID NO 1080
<211> LENGTH: 9
<212> TYPE: PRT
<213> ORGANISM: Orthohepadnaviridae hepatitis B virus

<400> SEQUENCE: 1080

Phe Pro His Cys Leu Ala Phe Ser Tyr
1               5

<210> SEQ ID NO 1081
<211> LENGTH: 10
<212> TYPE: PRT
<213> ORGANISM: Orthohepadnaviridae hepatitis B virus

<400> SEQUENCE: 1081

Phe Pro His Cys Leu Ala Phe Ser Tyr Met
1               5                   10

<210> SEQ ID NO 1082
<211> LENGTH: 8
<212> TYPE: PRT
<213> ORGANISM: Orthohepadnaviridae hepatitis B virus

<400> SEQUENCE: 1082
```

```
Phe Pro Trp Leu Leu Gly Cys Ala
 1               5

<210> SEQ ID NO 1083
<211> LENGTH: 9
<212> TYPE: PRT
<213> ORGANISM: Orthohepadnaviridae hepatitis B virus

<400> SEQUENCE: 1083

Phe Pro Trp Leu Leu Gly Cys Ala Ala
 1               5

<210> SEQ ID NO 1084
<211> LENGTH: 11
<212> TYPE: PRT
<213> ORGANISM: Orthohepadnaviridae hepatitis B virus

<400> SEQUENCE: 1084

Phe Pro Trp Leu Leu Gly Cys Ala Ala Asn Trp
 1               5                  10

<210> SEQ ID NO 1085
<211> LENGTH: 10
<212> TYPE: PRT
<213> ORGANISM: Orthohepadnaviridae hepatitis B virus

<400> SEQUENCE: 1085

Gly Pro Cys Ala Leu Arg Phe Thr Ser Ala
 1               5                  10

<210> SEQ ID NO 1086
<211> LENGTH: 10
<212> TYPE: PRT
<213> ORGANISM: Orthohepadnaviridae hepatitis B virus

<400> SEQUENCE: 1086

Gly Pro Leu Glu Glu Glu Leu Pro Arg Leu
 1               5                  10

<210> SEQ ID NO 1087
<211> LENGTH: 11
<212> TYPE: PRT
<213> ORGANISM: Orthohepadnaviridae hepatitis B virus

<400> SEQUENCE: 1087

Gly Pro Leu Glu Glu Glu Leu Pro Arg Leu Ala
 1               5                  10

<210> SEQ ID NO 1088
<211> LENGTH: 8
<212> TYPE: PRT
<213> ORGANISM: Orthohepadnaviridae hepatitis B virus

<400> SEQUENCE: 1088

Gly Pro Leu Leu Val Leu Gln Ala
 1               5

<210> SEQ ID NO 1089
<211> LENGTH: 10
<212> TYPE: PRT
<213> ORGANISM: Orthohepadnaviridae hepatitis B virus

<400> SEQUENCE: 1089

Gly Pro Leu Leu Val Leu Gln Ala Gly Phe
```

```
                        1               5               10

<210> SEQ ID NO 1090
<211> LENGTH: 11
<212> TYPE: PRT
<213> ORGANISM: Orthohepadnaviridae hepatitis B virus

<400> SEQUENCE: 1090

Gly Pro Leu Leu Val Leu Gln Ala Gly Phe Phe
 1               5                  10

<210> SEQ ID NO 1091
<211> LENGTH: 11
<212> TYPE: PRT
<213> ORGANISM: Orthohepadnaviridae hepatitis B virus

<400> SEQUENCE: 1091

Gly Pro Leu Thr Val Asn Glu Lys Arg Arg Leu
 1               5                  10

<210> SEQ ID NO 1092
<211> LENGTH: 8
<212> TYPE: PRT
<213> ORGANISM: Orthohepadnaviridae hepatitis B virus

<400> SEQUENCE: 1092

His Pro Ala Ala Met Pro His Leu
 1               5

<210> SEQ ID NO 1093
<211> LENGTH: 9
<212> TYPE: PRT
<213> ORGANISM: Orthohepadnaviridae hepatitis B virus

<400> SEQUENCE: 1093

His Pro Ala Ala Met Pro His Leu Leu
 1               5

<210> SEQ ID NO 1094
<211> LENGTH: 10
<212> TYPE: PRT
<213> ORGANISM: Orthohepadnaviridae hepatitis B virus

<400> SEQUENCE: 1094

His Pro Ala Ala Met Pro His Leu Leu Val
 1               5                  10

<210> SEQ ID NO 1095
<211> LENGTH: 10
<212> TYPE: PRT
<213> ORGANISM: Orthohepadnaviridae hepatitis B virus

<400> SEQUENCE: 1095

His Pro Ile Ile Leu Gly Phe Arg Lys Ile
 1               5                  10

<210> SEQ ID NO 1096
<211> LENGTH: 8
<212> TYPE: PRT
<213> ORGANISM: Orthohepadnaviridae hepatitis B virus

<400> SEQUENCE: 1096

Ile Pro Ile Pro Ser Ser Trp Ala
 1               5
```

<210> SEQ ID NO 1097
<211> LENGTH: 9
<212> TYPE: PRT
<213> ORGANISM: Orthohepadnaviridae hepatitis B virus

<400> SEQUENCE: 1097

Ile Pro Ile Pro Ser Ser Trp Ala Phe
1               5

<210> SEQ ID NO 1098
<211> LENGTH: 10
<212> TYPE: PRT
<213> ORGANISM: Orthohepadnaviridae hepatitis B virus

<400> SEQUENCE: 1098

Ile Pro Ile Pro Ser Ser Trp Ala Phe Ala
1               5                   10

<210> SEQ ID NO 1099
<211> LENGTH: 10
<212> TYPE: PRT
<213> ORGANISM: Orthohepadnaviridae hepatitis B virus

<400> SEQUENCE: 1099

Ile Pro Met Gly Val Gly Leu Ser Pro Phe
1               5                   10

<210> SEQ ID NO 1100
<211> LENGTH: 11
<212> TYPE: PRT
<213> ORGANISM: Orthohepadnaviridae hepatitis B virus

<400> SEQUENCE: 1100

Ile Pro Met Gly Val Gly Leu Ser Pro Phe Leu
1               5                   10

<210> SEQ ID NO 1101
<211> LENGTH: 8
<212> TYPE: PRT
<213> ORGANISM: Orthohepadnaviridae hepatitis B virus

<400> SEQUENCE: 1101

Ile Pro Gln Ser Leu Asp Ser Trp
1               5

<210> SEQ ID NO 1102
<211> LENGTH: 9
<212> TYPE: PRT
<213> ORGANISM: Orthohepadnaviridae hepatitis B virus

<400> SEQUENCE: 1102

Ile Pro Gln Ser Leu Asp Ser Trp Trp
1               5

<210> SEQ ID NO 1103
<211> LENGTH: 8
<212> TYPE: PRT
<213> ORGANISM: Orthohepadnaviridae hepatitis B virus

<400> SEQUENCE: 1103

Ile Pro Ser Ser Trp Ala Phe Ala
1               5

<210> SEQ ID NO 1104

```
<211> LENGTH: 10
<212> TYPE: PRT
<213> ORGANISM: Orthohepadnaviridae hepatitis B virus

<400> SEQUENCE: 1104

Ile Pro Trp Thr His Lys Val Gly Asn Phe
1               5                   10

<210> SEQ ID NO 1105
<211> LENGTH: 8
<212> TYPE: PRT
<213> ORGANISM: Orthohepadnaviridae hepatitis B virus

<400> SEQUENCE: 1105

Leu Pro Ile Phe Phe Cys Leu Trp
1               5

<210> SEQ ID NO 1106
<211> LENGTH: 9
<212> TYPE: PRT
<213> ORGANISM: Orthohepadnaviridae hepatitis B virus

<400> SEQUENCE: 1106

Leu Pro Ile Phe Phe Cys Leu Trp Val
1               5

<210> SEQ ID NO 1107
<211> LENGTH: 10
<212> TYPE: PRT
<213> ORGANISM: Orthohepadnaviridae hepatitis B virus

<400> SEQUENCE: 1107

Leu Pro Ile Phe Phe Cys Leu Trp Val Tyr
1               5                   10

<210> SEQ ID NO 1108
<211> LENGTH: 11
<212> TYPE: PRT
<213> ORGANISM: Orthohepadnaviridae hepatitis B virus

<400> SEQUENCE: 1108

Leu Pro Ile Phe Phe Cys Leu Trp Val Tyr Ile
1               5                   10

<210> SEQ ID NO 1109
<211> LENGTH: 8
<212> TYPE: PRT
<213> ORGANISM: Orthohepadnaviridae hepatitis B virus

<400> SEQUENCE: 1109

Leu Pro Ile His Thr Ala Glu Leu
1               5

<210> SEQ ID NO 1110
<211> LENGTH: 9
<212> TYPE: PRT
<213> ORGANISM: Orthohepadnaviridae hepatitis B virus

<400> SEQUENCE: 1110

Leu Pro Ile His Thr Ala Glu Leu Leu
1               5

<210> SEQ ID NO 1111
<211> LENGTH: 10
<212> TYPE: PRT
```

-continued

<213> ORGANISM: Orthohepadnaviridae hepatitis B virus

<400> SEQUENCE: 1111

Leu Pro Ile His Thr Ala Glu Leu Leu Ala
1               5                   10

<210> SEQ ID NO 1112
<211> LENGTH: 11
<212> TYPE: PRT
<213> ORGANISM: Orthohepadnaviridae hepatitis B virus

<400> SEQUENCE: 1112

Leu Pro Ile His Thr Ala Glu Leu Leu Ala Ala
1               5                   10

<210> SEQ ID NO 1113
<211> LENGTH: 10
<212> TYPE: PRT
<213> ORGANISM: Orthohepadnaviridae hepatitis B virus

<400> SEQUENCE: 1113

Leu Pro Lys Val Leu His Lys Arg Thr Leu
1               5                   10

<210> SEQ ID NO 1114
<211> LENGTH: 10
<212> TYPE: PRT
<213> ORGANISM: Orthohepadnaviridae hepatitis B virus

<400> SEQUENCE: 1114

Leu Pro Leu Asp Lys Gly Ile Lys Pro Tyr
1               5                   10

<210> SEQ ID NO 1115
<211> LENGTH: 11
<212> TYPE: PRT
<213> ORGANISM: Orthohepadnaviridae hepatitis B virus

<400> SEQUENCE: 1115

Leu Pro Leu Asp Lys Gly Ile Lys Pro Tyr Tyr
1               5                   10

<210> SEQ ID NO 1116
<211> LENGTH: 9
<212> TYPE: PRT
<213> ORGANISM: Orthohepadnaviridae hepatitis B virus

<400> SEQUENCE: 1116

Leu Pro Val Cys Ala Phe Ser Ser Ala
1               5

<210> SEQ ID NO 1117
<211> LENGTH: 9
<212> TYPE: PRT
<213> ORGANISM: Orthohepadnaviridae hepatitis B virus

<400> SEQUENCE: 1117

Leu Pro Val Asn Arg Pro Ile Asp Trp
1               5

<210> SEQ ID NO 1118
<211> LENGTH: 11
<212> TYPE: PRT
<213> ORGANISM: Orthohepadnaviridae hepatitis B virus

```
<400> SEQUENCE: 1118

Leu Pro Val Asn Arg Pro Ile Asp Trp Lys Val
1               5                   10

<210> SEQ ID NO 1119
<211> LENGTH: 11
<212> TYPE: PRT
<213> ORGANISM: Orthohepadnaviridae hepatitis B virus

<400> SEQUENCE: 1119

Met Pro His Leu Leu Val Gly Ser Ser Gly Leu
1               5                   10

<210> SEQ ID NO 1120
<211> LENGTH: 8
<212> TYPE: PRT
<213> ORGANISM: Orthohepadnaviridae hepatitis B virus

<400> SEQUENCE: 1120

Met Pro Leu Ser Tyr Gln His Phe
1               5

<210> SEQ ID NO 1121
<211> LENGTH: 11
<212> TYPE: PRT
<213> ORGANISM: Orthohepadnaviridae hepatitis B virus

<400> SEQUENCE: 1121

Met Pro Leu Ser Tyr Gln His Phe Arg Lys Leu
1               5                   10

<210> SEQ ID NO 1122
<211> LENGTH: 11
<212> TYPE: PRT
<213> ORGANISM: Orthohepadnaviridae hepatitis B virus

<400> SEQUENCE: 1122

Asn Pro Ala Asp Asp Pro Ser Arg Gly Arg Leu
1               5                   10

<210> SEQ ID NO 1123
<211> LENGTH: 11
<212> TYPE: PRT
<213> ORGANISM: Orthohepadnaviridae hepatitis B virus

<400> SEQUENCE: 1123

Asn Pro Leu Gly Phe Phe Pro Asp His Gln Leu
1               5                   10

<210> SEQ ID NO 1124
<211> LENGTH: 8
<212> TYPE: PRT
<213> ORGANISM: Orthohepadnaviridae hepatitis B virus

<400> SEQUENCE: 1124

Asn Pro Asn Lys Thr Lys Arg Trp
1               5

<210> SEQ ID NO 1125
<211> LENGTH: 10
<212> TYPE: PRT
<213> ORGANISM: Orthohepadnaviridae hepatitis B virus

<400> SEQUENCE: 1125
```

```
Asn Pro Asn Lys Thr Lys Arg Trp Gly Tyr
1               5                   10

<210> SEQ ID NO 1126
<211> LENGTH: 9
<212> TYPE: PRT
<213> ORGANISM: Orthohepadnaviridae hepatitis B virus

<400> SEQUENCE: 1126

Pro Pro Ala Tyr Arg Pro Pro Asn Ala
1               5

<210> SEQ ID NO 1127
<211> LENGTH: 11
<212> TYPE: PRT
<213> ORGANISM: Orthohepadnaviridae hepatitis B virus

<400> SEQUENCE: 1127

Pro Pro Ala Tyr Arg Pro Pro Asn Ala Pro Ile
1               5                   10

<210> SEQ ID NO 1128
<211> LENGTH: 9
<212> TYPE: PRT
<213> ORGANISM: Orthohepadnaviridae hepatitis B virus

<400> SEQUENCE: 1128

Pro Pro His Gly Gly Leu Leu Gly Trp
1               5

<210> SEQ ID NO 1129
<211> LENGTH: 10
<212> TYPE: PRT
<213> ORGANISM: Orthohepadnaviridae hepatitis B virus

<400> SEQUENCE: 1129

Pro Pro Asn Ala Pro Ile Leu Ser Thr Leu
1               5                   10

<210> SEQ ID NO 1130
<211> LENGTH: 11
<212> TYPE: PRT
<213> ORGANISM: Orthohepadnaviridae hepatitis B virus

<400> SEQUENCE: 1130

Arg Pro Ile Asp Trp Lys Val Cys Gln Arg Ile
1               5                   10

<210> SEQ ID NO 1131
<211> LENGTH: 8
<212> TYPE: PRT
<213> ORGANISM: Orthohepadnaviridae hepatitis B virus

<400> SEQUENCE: 1131

Arg Pro Pro Asn Ala Pro Ile Leu
1               5

<210> SEQ ID NO 1132
<211> LENGTH: 11
<212> TYPE: PRT
<213> ORGANISM: Orthohepadnaviridae hepatitis B virus

<400> SEQUENCE: 1132

Arg Pro Pro Asn Ala Pro Ile Leu Ser Thr Leu
1               5                   10
```

```
<210> SEQ ID NO 1133
<211> LENGTH: 11
<212> TYPE: PRT
<213> ORGANISM: Orthohepadnaviridae hepatitis B virus

<400> SEQUENCE: 1133

Ser Pro Glu His Cys Ser Pro His His Thr Ala
1               5                   10

<210> SEQ ID NO 1134
<211> LENGTH: 8
<212> TYPE: PRT
<213> ORGANISM: Orthohepadnaviridae hepatitis B virus

<400> SEQUENCE: 1134

Ser Pro Phe Leu Leu Ala Gln Phe
1               5

<210> SEQ ID NO 1135
<211> LENGTH: 11
<212> TYPE: PRT
<213> ORGANISM: Orthohepadnaviridae hepatitis B virus

<400> SEQUENCE: 1135

Ser Pro Phe Leu Leu Ala Gln Phe Thr Ser Ala
1               5                   10

<210> SEQ ID NO 1136
<211> LENGTH: 10
<212> TYPE: PRT
<213> ORGANISM: Orthohepadnaviridae hepatitis B virus

<400> SEQUENCE: 1136

Ser Pro His His Thr Ala Leu Arg Gln Ala
1               5                   10

<210> SEQ ID NO 1137
<211> LENGTH: 11
<212> TYPE: PRT
<213> ORGANISM: Orthohepadnaviridae hepatitis B virus

<400> SEQUENCE: 1137

Ser Pro His His Thr Ala Leu Arg Gln Ala Ile
1               5                   10

<210> SEQ ID NO 1138
<211> LENGTH: 8
<212> TYPE: PRT
<213> ORGANISM: Orthohepadnaviridae hepatitis B virus

<400> SEQUENCE: 1138

Ser Pro Gln Ala Gln Gly Ile Leu
1               5

<210> SEQ ID NO 1139
<211> LENGTH: 8
<212> TYPE: PRT
<213> ORGANISM: Orthohepadnaviridae hepatitis B virus

<400> SEQUENCE: 1139

Ser Pro Ser Val Pro Ser His Leu
1               5
```

<210> SEQ ID NO 1140
<211> LENGTH: 8
<212> TYPE: PRT
<213> ORGANISM: Orthohepadnaviridae hepatitis B virus

<400> SEQUENCE: 1140

Ser Pro Thr Val Trp Leu Ser Val
1               5

<210> SEQ ID NO 1141
<211> LENGTH: 9
<212> TYPE: PRT
<213> ORGANISM: Orthohepadnaviridae hepatitis B virus

<400> SEQUENCE: 1141

Ser Pro Thr Val Trp Leu Ser Val Ile
1               5

<210> SEQ ID NO 1142
<211> LENGTH: 10
<212> TYPE: PRT
<213> ORGANISM: Orthohepadnaviridae hepatitis B virus

<400> SEQUENCE: 1142

Ser Pro Thr Val Trp Leu Ser Val Ile Trp
1               5                   10

<210> SEQ ID NO 1143
<211> LENGTH: 11
<212> TYPE: PRT
<213> ORGANISM: Orthohepadnaviridae hepatitis B virus

<400> SEQUENCE: 1143

Ser Pro Thr Val Trp Leu Ser Val Ile Trp Met
1               5                   10

<210> SEQ ID NO 1144
<211> LENGTH: 8
<212> TYPE: PRT
<213> ORGANISM: Orthohepadnaviridae hepatitis B virus

<400> SEQUENCE: 1144

Ser Pro Thr Tyr Lys Ala Phe Leu
1               5

<210> SEQ ID NO 1145
<211> LENGTH: 9
<212> TYPE: PRT
<213> ORGANISM: Orthohepadnaviridae hepatitis B virus

<400> SEQUENCE: 1145

Thr Pro Ala Arg Val Thr Gly Gly Val
1               5

<210> SEQ ID NO 1146
<211> LENGTH: 10
<212> TYPE: PRT
<213> ORGANISM: Orthohepadnaviridae hepatitis B virus

<400> SEQUENCE: 1146

Thr Pro Ala Arg Val Thr Gly Gly Val Phe
1               5                   10

<210> SEQ ID NO 1147
<211> LENGTH: 11

<212> TYPE: PRT
<213> ORGANISM: Orthohepadnaviridae hepatitis B virus

<400> SEQUENCE: 1147

Thr Pro Ala Arg Val Thr Gly Gly Val Phe Leu
1 5 10

<210> SEQ ID NO 1148
<211> LENGTH: 10
<212> TYPE: PRT
<213> ORGANISM: Orthohepadnaviridae hepatitis B virus

<400> SEQUENCE: 1148

Thr Pro Pro Ala Tyr Arg Pro Pro Asn Ala
1 5 10

<210> SEQ ID NO 1149
<211> LENGTH: 8
<212> TYPE: PRT
<213> ORGANISM: Orthohepadnaviridae hepatitis B virus

<400> SEQUENCE: 1149

Thr Pro Pro His Gly Gly Leu Leu
1 5

<210> SEQ ID NO 1150
<211> LENGTH: 10
<212> TYPE: PRT
<213> ORGANISM: Orthohepadnaviridae hepatitis B virus

<400> SEQUENCE: 1150

Thr Pro Pro His Gly Gly Leu Leu Gly Trp
1 5 10

<210> SEQ ID NO 1151
<211> LENGTH: 8
<212> TYPE: PRT
<213> ORGANISM: Orthohepadnaviridae hepatitis B virus

<400> SEQUENCE: 1151

Thr Pro Thr Gly Trp Gly Leu Ala
1 5

<210> SEQ ID NO 1152
<211> LENGTH: 9
<212> TYPE: PRT
<213> ORGANISM: Orthohepadnaviridae hepatitis B virus

<400> SEQUENCE: 1152

Thr Pro Thr Gly Trp Gly Leu Ala Ile
1 5

<210> SEQ ID NO 1153
<211> LENGTH: 8
<212> TYPE: PRT
<213> ORGANISM: Orthohepadnaviridae hepatitis B virus

<400> SEQUENCE: 1153

Val Pro Phe Val Gln Trp Phe Val
1 5

<210> SEQ ID NO 1154
<211> LENGTH: 10
<212> TYPE: PRT
<213> ORGANISM: Orthohepadnaviridae hepatitis B virus -continued

```
<400> SEQUENCE: 1154

Val Pro Phe Val Gln Trp Phe Val Gly Leu
1               5                   10

<210> SEQ ID NO 1155
<211> LENGTH: 10
<212> TYPE: PRT
<213> ORGANISM: Orthohepadnaviridae hepatitis B virus

<400> SEQUENCE: 1155

Val Pro Asn Leu Gln Ser Leu Thr Asn Leu
1               5                   10

<210> SEQ ID NO 1156
<211> LENGTH: 11
<212> TYPE: PRT
<213> ORGANISM: Orthohepadnaviridae hepatitis B virus

<400> SEQUENCE: 1156

Val Pro Asn Leu Gln Ser Leu Thr Asn Leu Leu
1               5                   10

<210> SEQ ID NO 1157
<211> LENGTH: 8
<212> TYPE: PRT
<213> ORGANISM: Orthohepadnaviridae hepatitis B virus

<400> SEQUENCE: 1157

Val Pro Ser Ala Leu Asn Pro Ala
1               5

<210> SEQ ID NO 1158
<211> LENGTH: 9
<212> TYPE: PRT
<213> ORGANISM: Orthohepadnaviridae hepatitis B virus

<400> SEQUENCE: 1158

Trp Pro Lys Phe Ala Val Pro Asn Leu
1               5

<210> SEQ ID NO 1159
<211> LENGTH: 8
<212> TYPE: PRT
<213> ORGANISM: Orthohepadnaviridae hepatitis B virus

<400> SEQUENCE: 1159

Tyr Pro Ala Leu Met Pro Leu Tyr
1               5

<210> SEQ ID NO 1160
<211> LENGTH: 9
<212> TYPE: PRT
<213> ORGANISM: Orthohepadnaviridae hepatitis B virus

<400> SEQUENCE: 1160

Tyr Pro Ala Leu Met Pro Leu Tyr Ala
1               5

<210> SEQ ID NO 1161
<211> LENGTH: 11
<212> TYPE: PRT
<213> ORGANISM: Orthohepadnaviridae hepatitis B virus

<400> SEQUENCE: 1161
```

Tyr Pro Ala Leu Met Pro Leu Tyr Ala Cys Ile
1               5                   10

<210> SEQ ID NO 1162
<211> LENGTH: 8
<212> TYPE: PRT
<213> ORGANISM: Orthohepadnaviridae hepatitis B virus

<400> SEQUENCE: 1162

Ala His Leu Ser Leu Arg Gly Leu
1               5

<210> SEQ ID NO 1163
<211> LENGTH: 10
<212> TYPE: PRT
<213> ORGANISM: Orthohepadnaviridae hepatitis B virus

<400> SEQUENCE: 1163

Ala Lys Ser Val Gln His Leu Glu Ser Leu
1               5                   10

<210> SEQ ID NO 1164
<211> LENGTH: 8
<212> TYPE: PRT
<213> ORGANISM: Orthohepadnaviridae hepatitis B virus

<400> SEQUENCE: 1164

Ala Arg Val Thr Gly Gly Val Phe
1               5

<210> SEQ ID NO 1165
<211> LENGTH: 9
<212> TYPE: PRT
<213> ORGANISM: Orthohepadnaviridae hepatitis B virus

<400> SEQUENCE: 1165

Ala Arg Val Thr Gly Gly Val Phe Leu
1               5

<210> SEQ ID NO 1166
<211> LENGTH: 8
<212> TYPE: PRT
<213> ORGANISM: Orthohepadnaviridae hepatitis B virus

<400> SEQUENCE: 1166

Asp His Gly Ala His Leu Ser Leu
1               5

<210> SEQ ID NO 1167
<211> LENGTH: 11
<212> TYPE: PRT
<213> ORGANISM: Orthohepadnaviridae hepatitis B virus

<400> SEQUENCE: 1167

Asp His Gly Ala His Leu Ser Leu Arg Gly Leu
1               5                   10

<210> SEQ ID NO 1168
<211> LENGTH: 8
<212> TYPE: PRT
<213> ORGANISM: Orthohepadnaviridae hepatitis B virus

<400> SEQUENCE: 1168

Asp His Gln Leu Asp Pro Ala Phe

```
          1               5

<210> SEQ ID NO 1169
<211> LENGTH: 8
<212> TYPE: PRT
<213> ORGANISM: Orthohepadnaviridae hepatitis B virus

<400> SEQUENCE: 1169

Asp Lys Gly Ile Lys Pro Tyr Tyr
  1               5

<210> SEQ ID NO 1170
<211> LENGTH: 10
<212> TYPE: PRT
<213> ORGANISM: Orthohepadnaviridae hepatitis B virus

<400> SEQUENCE: 1170

Glu His Cys Ser Pro His His Thr Ala Leu
  1               5                  10

<210> SEQ ID NO 1171
<211> LENGTH: 8
<212> TYPE: PRT
<213> ORGANISM: Orthohepadnaviridae hepatitis B virus

<400> SEQUENCE: 1171

Phe His Ile Ser Cys Leu Thr Phe
  1               5

<210> SEQ ID NO 1172
<211> LENGTH: 10
<212> TYPE: PRT
<213> ORGANISM: Orthohepadnaviridae hepatitis B virus

<400> SEQUENCE: 1172

Phe Arg Lys Ile Pro Met Gly Val Gly Leu
  1               5                  10

<210> SEQ ID NO 1173
<211> LENGTH: 10
<212> TYPE: PRT
<213> ORGANISM: Orthohepadnaviridae hepatitis B virus

<400> SEQUENCE: 1173

Phe Arg Lys Leu Pro Val Asn Arg Pro Ile
  1               5                  10

<210> SEQ ID NO 1174
<211> LENGTH: 8
<212> TYPE: PRT
<213> ORGANISM: Orthohepadnaviridae hepatitis B virus

<400> SEQUENCE: 1174

Gly Arg Glu Thr Val Leu Glu Tyr
  1               5

<210> SEQ ID NO 1175
<211> LENGTH: 9
<212> TYPE: PRT
<213> ORGANISM: Orthohepadnaviridae hepatitis B virus

<400> SEQUENCE: 1175

Gly Arg Glu Thr Val Leu Glu Tyr Leu
  1               5
```

```
<210> SEQ ID NO 1176
<211> LENGTH: 9
<212> TYPE: PRT
<213> ORGANISM: Orthohepadnaviridae hepatitis B virus

<400> SEQUENCE: 1176

His His Thr Ala Leu Arg Gln Ala Ile
 1               5

<210> SEQ ID NO 1177
<211> LENGTH: 10
<212> TYPE: PRT
<213> ORGANISM: Orthohepadnaviridae hepatitis B virus

<400> SEQUENCE: 1177

His His Thr Ala Leu Arg Gln Ala Ile Leu
 1               5                  10

<210> SEQ ID NO 1178
<211> LENGTH: 9
<212> TYPE: PRT
<213> ORGANISM: Orthohepadnaviridae hepatitis B virus

<400> SEQUENCE: 1178

His Lys Val Gly Asn Phe Thr Gly Leu
 1               5

<210> SEQ ID NO 1179
<211> LENGTH: 10
<212> TYPE: PRT
<213> ORGANISM: Orthohepadnaviridae hepatitis B virus

<400> SEQUENCE: 1179

His Lys Val Gly Asn Phe Thr Gly Leu Tyr
 1               5                  10

<210> SEQ ID NO 1180
<211> LENGTH: 11
<212> TYPE: PRT
<213> ORGANISM: Orthohepadnaviridae hepatitis B virus

<400> SEQUENCE: 1180

Ile His Leu Asn Pro Asn Lys Thr Lys Arg Trp
 1               5                  10

<210> SEQ ID NO 1181
<211> LENGTH: 11
<212> TYPE: PRT
<213> ORGANISM: Orthohepadnaviridae hepatitis B virus

<400> SEQUENCE: 1181

Ile His Thr Ala Glu Leu Leu Ala Ala Cys Phe
 1               5                  10

<210> SEQ ID NO 1182
<211> LENGTH: 9
<212> TYPE: PRT
<213> ORGANISM: Orthohepadnaviridae hepatitis B virus

<400> SEQUENCE: 1182

Lys Arg Trp Gly Tyr Ser Leu Asn Phe
 1               5

<210> SEQ ID NO 1183
```

-continued

```
<211> LENGTH: 10
<212> TYPE: PRT
<213> ORGANISM: Orthohepadnaviridae hepatitis B virus

<400> SEQUENCE: 1183

Lys Arg Trp Gly Tyr Ser Leu Asn Phe Met
1               5                   10

<210> SEQ ID NO 1184
<211> LENGTH: 8
<212> TYPE: PRT
<213> ORGANISM: Orthohepadnaviridae hepatitis B virus

<400> SEQUENCE: 1184

Leu His Lys Arg Thr Leu Gly Leu
1               5

<210> SEQ ID NO 1185
<211> LENGTH: 8
<212> TYPE: PRT
<213> ORGANISM: Orthohepadnaviridae hepatitis B virus

<400> SEQUENCE: 1185

Leu His Leu Tyr Ser His Pro Ile
1               5

<210> SEQ ID NO 1186
<211> LENGTH: 9
<212> TYPE: PRT
<213> ORGANISM: Orthohepadnaviridae hepatitis B virus

<400> SEQUENCE: 1186

Leu His Leu Tyr Ser His Pro Ile Ile
1               5

<210> SEQ ID NO 1187
<211> LENGTH: 10
<212> TYPE: PRT
<213> ORGANISM: Orthohepadnaviridae hepatitis B virus

<400> SEQUENCE: 1187

Leu His Leu Tyr Ser His Pro Ile Ile Leu
1               5                   10

<210> SEQ ID NO 1188
<211> LENGTH: 9
<212> TYPE: PRT
<213> ORGANISM: Orthohepadnaviridae hepatitis B virus

<400> SEQUENCE: 1188

Leu His Pro Ala Ala Met Pro His Leu
1               5

<210> SEQ ID NO 1189
<211> LENGTH: 10
<212> TYPE: PRT
<213> ORGANISM: Orthohepadnaviridae hepatitis B virus

<400> SEQUENCE: 1189

Leu His Pro Ala Ala Met Pro His Leu Leu
1               5                   10

<210> SEQ ID NO 1190
<211> LENGTH: 9
<212> TYPE: PRT
```

<213> ORGANISM: Orthohepadnaviridae hepatitis B virus

<400> SEQUENCE: 1190

Leu His Thr Leu Trp Lys Ala Gly Ile
1               5

<210> SEQ ID NO 1191
<211> LENGTH: 10
<212> TYPE: PRT
<213> ORGANISM: Orthohepadnaviridae hepatitis B virus

<400> SEQUENCE: 1191

Leu His Thr Leu Trp Lys Ala Gly Ile Leu
1               5                   10

<210> SEQ ID NO 1192
<211> LENGTH: 11
<212> TYPE: PRT
<213> ORGANISM: Orthohepadnaviridae hepatitis B virus

<400> SEQUENCE: 1192

Leu His Thr Leu Trp Lys Ala Gly Ile Leu Tyr
1               5                   10

<210> SEQ ID NO 1193
<211> LENGTH: 9
<212> TYPE: PRT
<213> ORGANISM: Orthohepadnaviridae hepatitis B virus

<400> SEQUENCE: 1193

Leu Lys Leu Ile Met Pro Ala Arg Phe
1               5

<210> SEQ ID NO 1194
<211> LENGTH: 10
<212> TYPE: PRT
<213> ORGANISM: Orthohepadnaviridae hepatitis B virus

<400> SEQUENCE: 1194

Leu Lys Leu Ile Met Pro Ala Arg Phe Tyr
1               5                   10

<210> SEQ ID NO 1195
<211> LENGTH: 9
<212> TYPE: PRT
<213> ORGANISM: Orthohepadnaviridae hepatitis B virus

<400> SEQUENCE: 1195

Leu Arg Gly Leu Pro Val Cys Ala Phe
1               5

<210> SEQ ID NO 1196
<211> LENGTH: 8
<212> TYPE: PRT
<213> ORGANISM: Orthohepadnaviridae hepatitis B virus

<400> SEQUENCE: 1196

Leu Arg Gly Thr Ser Phe Val Tyr
1               5

<210> SEQ ID NO 1197
<211> LENGTH: 8
<212> TYPE: PRT
<213> ORGANISM: Orthohepadnaviridae hepatitis B virus

```
<400> SEQUENCE: 1197

Leu Arg Gln Ala Ile Leu Cys Trp
 1               5

<210> SEQ ID NO 1198
<211> LENGTH: 11
<212> TYPE: PRT
<213> ORGANISM: Orthohepadnaviridae hepatitis B virus

<400> SEQUENCE: 1198

Leu Arg Gln Ala Ile Leu Cys Trp Gly Glu Leu
 1               5                  10

<210> SEQ ID NO 1199
<211> LENGTH: 8
<212> TYPE: PRT
<213> ORGANISM: Orthohepadnaviridae hepatitis B virus

<400> SEQUENCE: 1199

Leu Arg Arg Phe Ile Ile Phe Leu
 1               5

<210> SEQ ID NO 1200
<211> LENGTH: 9
<212> TYPE: PRT
<213> ORGANISM: Orthohepadnaviridae hepatitis B virus

<400> SEQUENCE: 1200

Leu Arg Arg Phe Ile Ile Phe Leu Phe
 1               5

<210> SEQ ID NO 1201
<211> LENGTH: 10
<212> TYPE: PRT
<213> ORGANISM: Orthohepadnaviridae hepatitis B virus

<400> SEQUENCE: 1201

Leu Arg Arg Phe Ile Ile Phe Leu Phe Ile
 1               5                  10

<210> SEQ ID NO 1202
<211> LENGTH: 11
<212> TYPE: PRT
<213> ORGANISM: Orthohepadnaviridae hepatitis B virus

<400> SEQUENCE: 1202

Leu Arg Arg Phe Ile Ile Phe Leu Phe Ile Leu
 1               5                  10

<210> SEQ ID NO 1203
<211> LENGTH: 8
<212> TYPE: PRT
<213> ORGANISM: Orthohepadnaviridae hepatitis B virus

<400> SEQUENCE: 1203

Asn Lys Thr Lys Arg Trp Gly Tyr
 1               5

<210> SEQ ID NO 1204
<211> LENGTH: 10
<212> TYPE: PRT
<213> ORGANISM: Orthohepadnaviridae hepatitis B virus

<400> SEQUENCE: 1204
```

-continued

Asn Lys Thr Lys Arg Trp Gly Tyr Ser Leu
1               5                   10

<210> SEQ ID NO 1205
<211> LENGTH: 8
<212> TYPE: PRT
<213> ORGANISM: Orthohepadnaviridae hepatitis B virus

<400> SEQUENCE: 1205

Asn Arg Arg Val Ala Glu Asp Leu
1               5

<210> SEQ ID NO 1206
<211> LENGTH: 10
<212> TYPE: PRT
<213> ORGANISM: Orthohepadnaviridae hepatitis B virus

<400> SEQUENCE: 1206

Asn Arg Arg Val Ala Glu Asp Leu Asn Leu
1               5                   10

<210> SEQ ID NO 1207
<211> LENGTH: 8
<212> TYPE: PRT
<213> ORGANISM: Orthohepadnaviridae hepatitis B virus

<400> SEQUENCE: 1207

Pro His Cys Leu Ala Phe Ser Tyr
1               5

<210> SEQ ID NO 1208
<211> LENGTH: 9
<212> TYPE: PRT
<213> ORGANISM: Orthohepadnaviridae hepatitis B virus

<400> SEQUENCE: 1208

Pro His Cys Leu Ala Phe Ser Tyr Met
1               5

<210> SEQ ID NO 1209
<211> LENGTH: 8
<212> TYPE: PRT
<213> ORGANISM: Orthohepadnaviridae hepatitis B virus

<400> SEQUENCE: 1209

Pro His Gly Gly Leu Leu Gly Trp
1               5

<210> SEQ ID NO 1210
<211> LENGTH: 10
<212> TYPE: PRT
<213> ORGANISM: Orthohepadnaviridae hepatitis B virus

<400> SEQUENCE: 1210

Pro His His Thr Ala Leu Arg Gln Ala Ile
1               5                   10

<210> SEQ ID NO 1211
<211> LENGTH: 11
<212> TYPE: PRT
<213> ORGANISM: Orthohepadnaviridae hepatitis B virus

<400> SEQUENCE: 1211

Pro His His Thr Ala Leu Arg Gln Ala Ile Leu
1               5                   10

```
<210> SEQ ID NO 1212
<211> LENGTH: 10
<212> TYPE: PRT
<213> ORGANISM: Orthohepadnaviridae hepatitis B virus

<400> SEQUENCE: 1212

Pro His Leu Leu Val Gly Ser Ser Gly Leu
1               5                   10

<210> SEQ ID NO 1213
<211> LENGTH: 8
<212> TYPE: PRT
<213> ORGANISM: Orthohepadnaviridae hepatitis B virus

<400> SEQUENCE: 1213

Pro Lys Phe Ala Val Pro Asn Leu
1               5

<210> SEQ ID NO 1214
<211> LENGTH: 11
<212> TYPE: PRT
<213> ORGANISM: Orthohepadnaviridae hepatitis B virus

<400> SEQUENCE: 1214

Pro Lys Phe Ala Val Pro Asn Leu Gln Ser Leu
1               5                   10

<210> SEQ ID NO 1215
<211> LENGTH: 9
<212> TYPE: PRT
<213> ORGANISM: Orthohepadnaviridae hepatitis B virus

<400> SEQUENCE: 1215

Pro Lys Val Leu His Lys Arg Thr Leu
1               5

<210> SEQ ID NO 1216
<211> LENGTH: 11
<212> TYPE: PRT
<213> ORGANISM: Orthohepadnaviridae hepatitis B virus

<400> SEQUENCE: 1216

Pro Lys Val Leu His Lys Arg Thr Leu Gly Leu
1               5                   10

<210> SEQ ID NO 1217
<211> LENGTH: 8
<212> TYPE: PRT
<213> ORGANISM: Orthohepadnaviridae hepatitis B virus

<400> SEQUENCE: 1217

Gln His Phe Arg Lys Leu Leu Leu
1               5

<210> SEQ ID NO 1218
<211> LENGTH: 9
<212> TYPE: PRT
<213> ORGANISM: Orthohepadnaviridae hepatitis B virus

<400> SEQUENCE: 1218

Gln His Phe Arg Lys Leu Leu Leu Leu
1               5
```

<210> SEQ ID NO 1219
<211> LENGTH: 9
<212> TYPE: PRT
<213> ORGANISM: Orthohepadnaviridae hepatitis B virus

<400> SEQUENCE: 1219

Gln Arg Ile Val Gly Leu Leu Gly Phe
1               5

<210> SEQ ID NO 1220
<211> LENGTH: 8
<212> TYPE: PRT
<213> ORGANISM: Orthohepadnaviridae hepatitis B virus

<400> SEQUENCE: 1220

Arg His Tyr Leu His Thr Leu Trp
1               5

<210> SEQ ID NO 1221
<211> LENGTH: 9
<212> TYPE: PRT
<213> ORGANISM: Orthohepadnaviridae hepatitis B virus

<400> SEQUENCE: 1221

Arg Lys Ile Pro Met Gly Val Gly Leu
1               5

<210> SEQ ID NO 1222
<211> LENGTH: 9
<212> TYPE: PRT
<213> ORGANISM: Orthohepadnaviridae hepatitis B virus

<400> SEQUENCE: 1222

Arg Lys Leu Pro Val Asn Arg Pro Ile
1               5

<210> SEQ ID NO 1223
<211> LENGTH: 11
<212> TYPE: PRT
<213> ORGANISM: Orthohepadnaviridae hepatitis B virus

<400> SEQUENCE: 1223

Arg Lys Leu Pro Val Asn Arg Pro Ile Asp Trp
1               5                   10

<210> SEQ ID NO 1224
<211> LENGTH: 8
<212> TYPE: PRT
<213> ORGANISM: Orthohepadnaviridae hepatitis B virus

<400> SEQUENCE: 1224

Arg Lys Tyr Thr Ser Phe Pro Trp
1               5

<210> SEQ ID NO 1225
<211> LENGTH: 9
<212> TYPE: PRT
<213> ORGANISM: Orthohepadnaviridae hepatitis B virus

<400> SEQUENCE: 1225

Arg Lys Tyr Thr Ser Phe Pro Trp Leu
1               5

<210> SEQ ID NO 1226
<211> LENGTH: 10

```
<212> TYPE: PRT
<213> ORGANISM: Orthohepadnaviridae hepatitis B virus

<400> SEQUENCE: 1226

Arg Lys Tyr Thr Ser Phe Pro Trp Leu Leu
1               5                   10

<210> SEQ ID NO 1227
<211> LENGTH: 8
<212> TYPE: PRT
<213> ORGANISM: Orthohepadnaviridae hepatitis B virus

<400> SEQUENCE: 1227

Arg Arg Ala Phe Pro His Cys Leu
1               5

<210> SEQ ID NO 1228
<211> LENGTH: 10
<212> TYPE: PRT
<213> ORGANISM: Orthohepadnaviridae hepatitis B virus

<400> SEQUENCE: 1228

Arg Arg Ala Phe Pro His Cys Leu Ala Phe
1               5                   10

<210> SEQ ID NO 1229
<211> LENGTH: 8
<212> TYPE: PRT
<213> ORGANISM: Orthohepadnaviridae hepatitis B virus

<400> SEQUENCE: 1229

Arg Arg Phe Ile Ile Phe Leu Phe
1               5

<210> SEQ ID NO 1230
<211> LENGTH: 9
<212> TYPE: PRT
<213> ORGANISM: Orthohepadnaviridae hepatitis B virus

<400> SEQUENCE: 1230

Arg Arg Phe Ile Ile Phe Leu Phe Ile
1               5

<210> SEQ ID NO 1231
<211> LENGTH: 10
<212> TYPE: PRT
<213> ORGANISM: Orthohepadnaviridae hepatitis B virus

<400> SEQUENCE: 1231

Arg Arg Phe Ile Ile Phe Leu Phe Ile Leu
1               5                   10

<210> SEQ ID NO 1232
<211> LENGTH: 11
<212> TYPE: PRT
<213> ORGANISM: Orthohepadnaviridae hepatitis B virus

<400> SEQUENCE: 1232

Arg Arg Phe Ile Ile Phe Leu Phe Ile Leu Leu
1               5                   10

<210> SEQ ID NO 1233
<211> LENGTH: 11
<212> TYPE: PRT
<213> ORGANISM: Orthohepadnaviridae hepatitis B virus
```

```
<400> SEQUENCE: 1233

Arg Arg Leu Lys Leu Ile Met Pro Ala Arg Phe
 1               5                  10

<210> SEQ ID NO 1234
<211> LENGTH: 9
<212> TYPE: PRT
<213> ORGANISM: Orthohepadnaviridae hepatitis B virus

<400> SEQUENCE: 1234

Arg Arg Val Ala Glu Asp Leu Asn Leu
 1               5

<210> SEQ ID NO 1235
<211> LENGTH: 8
<212> TYPE: PRT
<213> ORGANISM: Orthohepadnaviridae hepatitis B virus

<400> SEQUENCE: 1235

Ser His Pro Ile Ile Leu Gly Phe
 1               5

<210> SEQ ID NO 1236
<211> LENGTH: 11
<212> TYPE: PRT
<213> ORGANISM: Orthohepadnaviridae hepatitis B virus

<400> SEQUENCE: 1236

Ser His Pro Ile Ile Leu Gly Phe Arg Lys Ile
 1               5                  10

<210> SEQ ID NO 1237
<211> LENGTH: 8
<212> TYPE: PRT
<213> ORGANISM: Orthohepadnaviridae hepatitis B virus

<400> SEQUENCE: 1237

Ser Lys Leu Cys Leu Gly Trp Leu
 1               5

<210> SEQ ID NO 1238
<211> LENGTH: 9
<212> TYPE: PRT
<213> ORGANISM: Orthohepadnaviridae hepatitis B virus

<400> SEQUENCE: 1238

Ser Lys Leu Cys Leu Gly Trp Leu Trp
 1               5

<210> SEQ ID NO 1239
<211> LENGTH: 11
<212> TYPE: PRT
<213> ORGANISM: Orthohepadnaviridae hepatitis B virus

<400> SEQUENCE: 1239

Ser Lys Leu Cys Leu Gly Trp Leu Trp Gly Met
 1               5                  10

<210> SEQ ID NO 1240
<211> LENGTH: 9
<212> TYPE: PRT
<213> ORGANISM: Orthohepadnaviridae hepatitis B virus

<400> SEQUENCE: 1240
```

```
Ser Arg Lys Tyr Thr Ser Phe Pro Trp
 1               5
```

<210> SEQ ID NO 1241
<211> LENGTH: 10
<212> TYPE: PRT
<213> ORGANISM: Orthohepadnaviridae hepatitis B virus

<400> SEQUENCE: 1241

```
Ser Arg Lys Tyr Thr Ser Phe Pro Trp Leu
 1               5                  10
```

<210> SEQ ID NO 1242
<211> LENGTH: 11
<212> TYPE: PRT
<213> ORGANISM: Orthohepadnaviridae hepatitis B virus

<400> SEQUENCE: 1242

```
Ser Arg Lys Tyr Thr Ser Phe Pro Trp Leu Leu
 1               5                  10
```

<210> SEQ ID NO 1243
<211> LENGTH: 10
<212> TYPE: PRT
<213> ORGANISM: Orthohepadnaviridae hepatitis B virus

<400> SEQUENCE: 1243

```
Ser Arg Leu Val Val Asp Phe Ser Gln Phe
 1               5                  10
```

<210> SEQ ID NO 1244
<211> LENGTH: 8
<212> TYPE: PRT
<213> ORGANISM: Orthohepadnaviridae hepatitis B virus

<400> SEQUENCE: 1244

```
Ser Arg Asn Leu Tyr Val Ser Leu
 1               5
```

<210> SEQ ID NO 1245
<211> LENGTH: 10
<212> TYPE: PRT
<213> ORGANISM: Orthohepadnaviridae hepatitis B virus

<400> SEQUENCE: 1245

```
Thr His Lys Val Gly Asn Phe Thr Gly Leu
 1               5                  10
```

<210> SEQ ID NO 1246
<211> LENGTH: 11
<212> TYPE: PRT
<213> ORGANISM: Orthohepadnaviridae hepatitis B virus

<400> SEQUENCE: 1246

```
Thr His Lys Val Gly Asn Phe Thr Gly Leu Tyr
 1               5                  10
```

<210> SEQ ID NO 1247
<211> LENGTH: 8
<212> TYPE: PRT
<213> ORGANISM: Orthohepadnaviridae hepatitis B virus

<400> SEQUENCE: 1247

```
Thr Lys Arg Trp Gly Tyr Ser Leu
```

```
<210> SEQ ID NO 1248
<211> LENGTH: 10
<212> TYPE: PRT
<213> ORGANISM: Orthohepadnaviridae hepatitis B virus

<400> SEQUENCE: 1248

Thr Lys Arg Trp Gly Tyr Ser Leu Asn Phe
1               5                   10

<210> SEQ ID NO 1249
<211> LENGTH: 11
<212> TYPE: PRT
<213> ORGANISM: Orthohepadnaviridae hepatitis B virus

<400> SEQUENCE: 1249

Thr Lys Arg Trp Gly Tyr Ser Leu Asn Phe Met
1               5                   10

<210> SEQ ID NO 1250
<211> LENGTH: 10
<212> TYPE: PRT
<213> ORGANISM: Orthohepadnaviridae hepatitis B virus

<400> SEQUENCE: 1250

Thr Lys Tyr Leu Pro Leu Asp Lys Gly Ile
1               5                   10

<210> SEQ ID NO 1251
<211> LENGTH: 8
<212> TYPE: PRT
<213> ORGANISM: Orthohepadnaviridae hepatitis B virus

<400> SEQUENCE: 1251

Thr Arg His Tyr Leu His Thr Leu
1               5

<210> SEQ ID NO 1252
<211> LENGTH: 9
<212> TYPE: PRT
<213> ORGANISM: Orthohepadnaviridae hepatitis B virus

<400> SEQUENCE: 1252

Thr Arg His Tyr Leu His Thr Leu Trp
1               5

<210> SEQ ID NO 1253
<211> LENGTH: 10
<212> TYPE: PRT
<213> ORGANISM: Orthohepadnaviridae hepatitis B virus

<400> SEQUENCE: 1253

Thr Arg Ile Leu Thr Ile Pro Gln Ser Leu
1               5                   10

<210> SEQ ID NO 1254
<211> LENGTH: 11
<212> TYPE: PRT
<213> ORGANISM: Orthohepadnaviridae hepatitis B virus

<400> SEQUENCE: 1254

Val His Phe Ala Ser Pro Leu His Val Ala Trp
1               5                   10
```

```
<210> SEQ ID NO 1255
<211> LENGTH: 8
<212> TYPE: PRT
<213> ORGANISM: Orthohepadnaviridae hepatitis B virus

<400> SEQUENCE: 1255

Val Arg Phe Ser Trp Leu Ser Leu
 1               5

<210> SEQ ID NO 1256
<211> LENGTH: 9
<212> TYPE: PRT
<213> ORGANISM: Orthohepadnaviridae hepatitis B virus

<400> SEQUENCE: 1256

Val Arg Phe Ser Trp Leu Ser Leu Leu
 1               5

<210> SEQ ID NO 1257
<211> LENGTH: 9
<212> TYPE: PRT
<213> ORGANISM: Orthohepadnaviridae hepatitis B virus

<400> SEQUENCE: 1257

Val Arg Arg Ala Phe Pro His Cys Leu
 1               5

<210> SEQ ID NO 1258
<211> LENGTH: 11
<212> TYPE: PRT
<213> ORGANISM: Orthohepadnaviridae hepatitis B virus

<400> SEQUENCE: 1258

Val Arg Arg Ala Phe Pro His Cys Leu Ala Phe
 1               5                  10

<210> SEQ ID NO 1259
<211> LENGTH: 10
<212> TYPE: PRT
<213> ORGANISM: Orthohepadnaviridae hepatitis B virus

<400> SEQUENCE: 1259

Trp Lys Val Cys Gln Arg Ile Val Gly Leu
 1               5                  10

<210> SEQ ID NO 1260
<211> LENGTH: 11
<212> TYPE: PRT
<213> ORGANISM: Orthohepadnaviridae hepatitis B virus

<400> SEQUENCE: 1260

Trp Lys Val Cys Gln Arg Ile Val Gly Leu Leu
 1               5                  10

<210> SEQ ID NO 1261
<211> LENGTH: 8
<212> TYPE: PRT
<213> ORGANISM: Orthohepadnaviridae hepatitis B virus

<400> SEQUENCE: 1261

Tyr Arg Pro Pro Asn Ala Pro Ile
 1               5

<210> SEQ ID NO 1262
```

-continued

<210> SEQ ID NO 1262
<211> LENGTH: 9
<212> TYPE: PRT
<213> ORGANISM: Orthohepadnaviridae hepatitis B virus

<400> SEQUENCE: 1262

Tyr Arg Pro Pro Asn Ala Pro Ile Leu
 1               5

<210> SEQ ID NO 1263
<211> LENGTH: 9
<212> TYPE: PRT
<213> ORGANISM: Orthohepadnaviridae hepatitis B virus

<400> SEQUENCE: 1263

Tyr Arg Trp Met Cys Leu Arg Arg Phe
 1               5

<210> SEQ ID NO 1264
<211> LENGTH: 10
<212> TYPE: PRT
<213> ORGANISM: Orthohepadnaviridae hepatitis B virus

<400> SEQUENCE: 1264

Tyr Arg Trp Met Cys Leu Arg Arg Phe Ile
 1               5                  10

<210> SEQ ID NO 1265
<211> LENGTH: 11
<212> TYPE: PRT
<213> ORGANISM: Orthohepadnaviridae hepatitis B virus

<400> SEQUENCE: 1265

Tyr Arg Trp Met Cys Leu Arg Arg Phe Ile Ile
 1               5                  10

<210> SEQ ID NO 1266
<211> LENGTH: 8
<212> TYPE: PRT
<213> ORGANISM: Orthohepadnaviridae hepatitis B virus

<400> SEQUENCE: 1266

Ala Asp Ala Thr Pro Thr Gly Trp
 1               5

<210> SEQ ID NO 1267
<211> LENGTH: 10
<212> TYPE: PRT
<213> ORGANISM: Orthohepadnaviridae hepatitis B virus

<400> SEQUENCE: 1267

Ala Asp Ala Thr Pro Thr Gly Trp Gly Leu
 1               5                  10

<210> SEQ ID NO 1268
<211> LENGTH: 11
<212> TYPE: PRT
<213> ORGANISM: Orthohepadnaviridae hepatitis B virus

<400> SEQUENCE: 1268

Ala Asp Ala Thr Pro Thr Gly Trp Gly Leu Ala
 1               5                  10

<210> SEQ ID NO 1269
<211> LENGTH: 9
<212> TYPE: PRT

-continued

<213> ORGANISM: Orthohepadnaviridae hepatitis B virus

<400> SEQUENCE: 1269

Ala Asp Asp Pro Ser Arg Gly Arg Leu
1               5

<210> SEQ ID NO 1270
<211> LENGTH: 11
<212> TYPE: PRT
<213> ORGANISM: Orthohepadnaviridae hepatitis B virus

<400> SEQUENCE: 1270

Ala Asp Asp Pro Ser Arg Gly Arg Leu Gly Leu
1               5                   10

<210> SEQ ID NO 1271
<211> LENGTH: 9
<212> TYPE: PRT
<213> ORGANISM: Orthohepadnaviridae hepatitis B virus

<400> SEQUENCE: 1271

Ala Glu Asp Leu Asn Leu Gly Asn Leu
1               5

<210> SEQ ID NO 1272
<211> LENGTH: 11
<212> TYPE: PRT
<213> ORGANISM: Orthohepadnaviridae hepatitis B virus

<400> SEQUENCE: 1272

Ala Glu Asp Leu Asn Leu Gly Asn Leu Asn Val
1               5                   10

<210> SEQ ID NO 1273
<211> LENGTH: 8
<212> TYPE: PRT
<213> ORGANISM: Orthohepadnaviridae hepatitis B virus

<400> SEQUENCE: 1273

Ala Glu Leu Leu Ala Ala Cys Phe
1               5

<210> SEQ ID NO 1274
<211> LENGTH: 9
<212> TYPE: PRT
<213> ORGANISM: Orthohepadnaviridae hepatitis B virus

<400> SEQUENCE: 1274

Ala Glu Leu Leu Ala Ala Cys Phe Ala
1               5

<210> SEQ ID NO 1275
<211> LENGTH: 8
<212> TYPE: PRT
<213> ORGANISM: Orthohepadnaviridae hepatitis B virus

<400> SEQUENCE: 1275

Asp Asp Pro Ser Arg Gly Arg Leu
1               5

<210> SEQ ID NO 1276
<211> LENGTH: 10
<212> TYPE: PRT
<213> ORGANISM: Orthohepadnaviridae hepatitis B virus

```
<400> SEQUENCE: 1276

Asp Asp Pro Ser Arg Gly Arg Leu Gly Leu
1               5                   10

<210> SEQ ID NO 1277
<211> LENGTH: 10
<212> TYPE: PRT
<213> ORGANISM: Orthohepadnaviridae hepatitis B virus

<400> SEQUENCE: 1277

Asp Asp Val Val Leu Gly Ala Lys Ser Val
1               5                   10

<210> SEQ ID NO 1278
<211> LENGTH: 10
<212> TYPE: PRT
<213> ORGANISM: Orthohepadnaviridae hepatitis B virus

<400> SEQUENCE: 1278

Asp Glu Ala Gly Pro Leu Glu Glu Glu Leu
1               5                   10

<210> SEQ ID NO 1279
<211> LENGTH: 8
<212> TYPE: PRT
<213> ORGANISM: Orthohepadnaviridae hepatitis B virus

<400> SEQUENCE: 1279

Glu Asp Leu Asn Leu Gly Asn Leu
1               5

<210> SEQ ID NO 1280
<211> LENGTH: 10
<212> TYPE: PRT
<213> ORGANISM: Orthohepadnaviridae hepatitis B virus

<400> SEQUENCE: 1280

Glu Asp Leu Asn Leu Gly Asn Leu Asn Val
1               5                   10

<210> SEQ ID NO 1281
<211> LENGTH: 8
<212> TYPE: PRT
<213> ORGANISM: Orthohepadnaviridae hepatitis B virus

<400> SEQUENCE: 1281

Glu Glu Glu Leu Pro Arg Leu Ala
1               5

<210> SEQ ID NO 1282
<211> LENGTH: 9
<212> TYPE: PRT
<213> ORGANISM: Orthohepadnaviridae hepatitis B virus

<400> SEQUENCE: 1282

Glu Glu Leu Gly Glu Glu Ile Arg Leu
1               5

<210> SEQ ID NO 1283
<211> LENGTH: 9
<212> TYPE: PRT
<213> ORGANISM: Orthohepadnaviridae hepatitis B virus

<400> SEQUENCE: 1283
```

Ile Asp Pro Tyr Lys Glu Phe Gly Ala
1               5

<210> SEQ ID NO 1284
<211> LENGTH: 9
<212> TYPE: PRT
<213> ORGANISM: Orthohepadnaviridae hepatitis B virus

<400> SEQUENCE: 1284

Ile Asp Trp Lys Val Cys Gln Arg Ile
1               5

<210> SEQ ID NO 1285
<211> LENGTH: 10
<212> TYPE: PRT
<213> ORGANISM: Orthohepadnaviridae hepatitis B virus

<400> SEQUENCE: 1285

Ile Asp Trp Lys Val Cys Gln Arg Ile Val
1               5                   10

<210> SEQ ID NO 1286
<211> LENGTH: 8
<212> TYPE: PRT
<213> ORGANISM: Orthohepadnaviridae hepatitis B virus

<400> SEQUENCE: 1286

Leu Asp Lys Gly Ile Lys Pro Tyr
1               5

<210> SEQ ID NO 1287
<211> LENGTH: 9
<212> TYPE: PRT
<213> ORGANISM: Orthohepadnaviridae hepatitis B virus

<400> SEQUENCE: 1287

Leu Asp Lys Gly Ile Lys Pro Tyr Tyr
1               5

<210> SEQ ID NO 1288
<211> LENGTH: 8
<212> TYPE: PRT
<213> ORGANISM: Orthohepadnaviridae hepatitis B virus

<400> SEQUENCE: 1288

Leu Asp Pro Ala Arg Asp Val Leu
1               5

<210> SEQ ID NO 1289
<211> LENGTH: 10
<212> TYPE: PRT
<213> ORGANISM: Orthohepadnaviridae hepatitis B virus

<400> SEQUENCE: 1289

Leu Asp Pro Ala Arg Asp Val Leu Cys Leu
1               5                   10

<210> SEQ ID NO 1290
<211> LENGTH: 8
<212> TYPE: PRT
<213> ORGANISM: Orthohepadnaviridae hepatitis B virus

<400> SEQUENCE: 1290

Leu Asp Ser Trp Trp Thr Ser Leu
1               5

<210> SEQ ID NO 1291
<211> LENGTH: 10
<212> TYPE: PRT
<213> ORGANISM: Orthohepadnaviridae hepatitis B virus

<400> SEQUENCE: 1291

Leu Asp Ser Trp Trp Thr Ser Leu Asn Phe
1               5                   10

<210> SEQ ID NO 1292
<211> LENGTH: 11
<212> TYPE: PRT
<213> ORGANISM: Orthohepadnaviridae hepatitis B virus

<400> SEQUENCE: 1292

Leu Asp Ser Trp Trp Thr Ser Leu Asn Phe Leu
1               5                   10

<210> SEQ ID NO 1293
<211> LENGTH: 8
<212> TYPE: PRT
<213> ORGANISM: Orthohepadnaviridae hepatitis B virus

<400> SEQUENCE: 1293

Leu Asp Thr Ala Ser Ala Leu Tyr
1               5

<210> SEQ ID NO 1294
<211> LENGTH: 11
<212> TYPE: PRT
<213> ORGANISM: Orthohepadnaviridae hepatitis B virus

<400> SEQUENCE: 1294

Leu Asp Thr Ala Ser Ala Leu Tyr Arg Glu Ala
1               5                   10

<210> SEQ ID NO 1295
<211> LENGTH: 8
<212> TYPE: PRT
<213> ORGANISM: Orthohepadnaviridae hepatitis B virus

<400> SEQUENCE: 1295

Leu Asp Val Ser Ala Ala Phe Tyr
1               5

<210> SEQ ID NO 1296
<211> LENGTH: 9
<212> TYPE: PRT
<213> ORGANISM: Orthohepadnaviridae hepatitis B virus

<400> SEQUENCE: 1296

Leu Asp Tyr Gln Gly Met Leu Pro Val
1               5

<210> SEQ ID NO 1297
<211> LENGTH: 8
<212> TYPE: PRT
<213> ORGANISM: Orthohepadnaviridae hepatitis B virus

<400> SEQUENCE: 1297

Leu Glu Glu Glu Leu Pro Arg Leu
1               5

<210> SEQ ID NO 1298
<211> LENGTH: 9
<212> TYPE: PRT
<213> ORGANISM: Orthohepadnaviridae hepatitis B virus

<400> SEQUENCE: 1298

Leu Glu Glu Glu Leu Pro Arg Leu Ala
1               5

<210> SEQ ID NO 1299
<211> LENGTH: 8
<212> TYPE: PRT
<213> ORGANISM: Orthohepadnaviridae hepatitis B virus

<400> SEQUENCE: 1299

Met Asp Asp Val Val Leu Gly Ala
1               5

<210> SEQ ID NO 1300
<211> LENGTH: 11
<212> TYPE: PRT
<213> ORGANISM: Orthohepadnaviridae hepatitis B virus

<400> SEQUENCE: 1300

Met Asp Asp Val Val Leu Gly Ala Lys Ser Val
1               5                   10

<210> SEQ ID NO 1301
<211> LENGTH: 9
<212> TYPE: PRT
<213> ORGANISM: Orthohepadnaviridae hepatitis B virus

<400> SEQUENCE: 1301

Met Asp Ile Asp Pro Tyr Lys Glu Phe
1               5

<210> SEQ ID NO 1302
<211> LENGTH: 11
<212> TYPE: PRT
<213> ORGANISM: Orthohepadnaviridae hepatitis B virus

<400> SEQUENCE: 1302

Met Asp Ile Asp Pro Tyr Lys Glu Phe Gly Ala
1               5                   10

<210> SEQ ID NO 1303
<211> LENGTH: 8
<212> TYPE: PRT
<213> ORGANISM: Orthohepadnaviridae hepatitis B virus

<400> SEQUENCE: 1303

Pro Asp His Gln Leu Asp Pro Ala
1               5

<210> SEQ ID NO 1304
<211> LENGTH: 9
<212> TYPE: PRT
<213> ORGANISM: Orthohepadnaviridae hepatitis B virus

<400> SEQUENCE: 1304

Pro Asp His Gln Leu Asp Pro Ala Phe
1               5

<210> SEQ ID NO 1305
<211> LENGTH: 10

```
<212> TYPE: PRT
<213> ORGANISM: Orthohepadnaviridae hepatitis B virus

<400> SEQUENCE: 1305

Pro Glu His Cys Ser Pro His His Thr Ala
1               5                   10

<210> SEQ ID NO 1306
<211> LENGTH: 11
<212> TYPE: PRT
<213> ORGANISM: Orthohepadnaviridae hepatitis B virus

<400> SEQUENCE: 1306

Pro Glu His Cys Ser Pro His His Thr Ala Leu
1               5                   10

<210> SEQ ID NO 1307
<211> LENGTH: 9
<212> TYPE: PRT
<213> ORGANISM: Orthohepadnaviridae hepatitis B virus

<400> SEQUENCE: 1307

Arg Asp Leu Leu Asp Thr Ala Ser Ala
1               5

<210> SEQ ID NO 1308
<211> LENGTH: 10
<212> TYPE: PRT
<213> ORGANISM: Orthohepadnaviridae hepatitis B virus

<400> SEQUENCE: 1308

Arg Asp Leu Leu Asp Thr Ala Ser Ala Leu
1               5                   10

<210> SEQ ID NO 1309
<211> LENGTH: 11
<212> TYPE: PRT
<213> ORGANISM: Orthohepadnaviridae hepatitis B virus

<400> SEQUENCE: 1309

Arg Asp Leu Leu Asp Thr Ala Ser Ala Leu Tyr
1               5                   10

<210> SEQ ID NO 1310
<211> LENGTH: 9
<212> TYPE: PRT
<213> ORGANISM: Orthohepadnaviridae hepatitis B virus

<400> SEQUENCE: 1310

Arg Asp Val Leu Cys Leu Arg Pro Val
1               5

<210> SEQ ID NO 1311
<211> LENGTH: 11
<212> TYPE: PRT
<213> ORGANISM: Orthohepadnaviridae hepatitis B virus

<400> SEQUENCE: 1311

Arg Asp Val Leu Cys Leu Arg Pro Val Gly Ala
1               5                   10

<210> SEQ ID NO 1312
<211> LENGTH: 8
<212> TYPE: PRT
<213> ORGANISM: Orthohepadnaviridae hepatitis B virus
```

```
<400> SEQUENCE: 1312

Arg Glu Thr Val Leu Glu Tyr Leu
 1               5

<210> SEQ ID NO 1313
<211> LENGTH: 9
<212> TYPE: PRT
<213> ORGANISM: Orthohepadnaviridae hepatitis B virus

<400> SEQUENCE: 1313

Arg Glu Thr Val Leu Glu Tyr Leu Val
 1               5

<210> SEQ ID NO 1314
<211> LENGTH: 11
<212> TYPE: PRT
<213> ORGANISM: Orthohepadnaviridae hepatitis B virus

<400> SEQUENCE: 1314

Thr Asp Asn Ser Val Val Leu Ser Arg Lys Tyr
 1               5                  10

<210> SEQ ID NO 1315
<211> LENGTH: 11
<212> TYPE: PRT
<213> ORGANISM: Orthohepadnaviridae hepatitis B virus

<400> SEQUENCE: 1315

Val Glu Leu Leu Ser Phe Leu Pro Ser Asp Phe
 1               5                  10

<210> SEQ ID NO 1316
<211> LENGTH: 8
<212> TYPE: PRT
<213> ORGANISM: Orthohepadnaviridae hepatitis B virus

<400> SEQUENCE: 1316

Trp Glu Glu Leu Gly Glu Glu Ile
 1               5

<210> SEQ ID NO 1317
<211> LENGTH: 10
<212> TYPE: PRT
<213> ORGANISM: Orthohepadnaviridae hepatitis B virus

<400> SEQUENCE: 1317

Trp Glu Glu Leu Gly Glu Glu Ile Arg Leu
 1               5                  10

<210> SEQ ID NO 1318
<211> LENGTH: 8
<212> TYPE: PRT
<213> ORGANISM: Orthohepadnaviridae hepatitis B virus

<400> SEQUENCE: 1318

Ala Ala Met Pro His Leu Leu Val
 1               5

<210> SEQ ID NO 1319
<211> LENGTH: 9
<212> TYPE: PRT
<213> ORGANISM: Orthohepadnaviridae hepatitis B virus

<400> SEQUENCE: 1319
```

```
Ala Ala Pro Phe Thr Gln Cys Gly Tyr
 1               5

<210> SEQ ID NO 1320
<211> LENGTH: 9
<212> TYPE: PRT
<213> ORGANISM: Orthohepadnaviridae hepatitis B virus

<400> SEQUENCE: 1320

Ala Ser Ala Leu Tyr Arg Glu Ala Leu
 1               5

<210> SEQ ID NO 1321
<211> LENGTH: 8
<212> TYPE: PRT
<213> ORGANISM: Orthohepadnaviridae hepatitis B virus

<400> SEQUENCE: 1321

Ala Ser Phe Cys Gly Ser Pro Tyr
 1               5

<210> SEQ ID NO 1322
<211> LENGTH: 10
<212> TYPE: PRT
<213> ORGANISM: Orthohepadnaviridae hepatitis B virus

<400> SEQUENCE: 1322

Ala Ser Phe Cys Gly Ser Pro Tyr Ser Trp
 1               5                   10

<210> SEQ ID NO 1323
<211> LENGTH: 8
<212> TYPE: PRT
<213> ORGANISM: Orthohepadnaviridae hepatitis B virus

<400> SEQUENCE: 1323

Ala Ser Lys Leu Cys Leu Gly Trp
 1               5

<210> SEQ ID NO 1324
<211> LENGTH: 9
<212> TYPE: PRT
<213> ORGANISM: Orthohepadnaviridae hepatitis B virus

<400> SEQUENCE: 1324

Ala Ser Lys Leu Cys Leu Gly Trp Leu
 1               5

<210> SEQ ID NO 1325
<211> LENGTH: 10
<212> TYPE: PRT
<213> ORGANISM: Orthohepadnaviridae hepatitis B virus

<400> SEQUENCE: 1325

Ala Ser Lys Leu Cys Leu Gly Trp Leu Trp
 1               5                   10

<210> SEQ ID NO 1326
<211> LENGTH: 8
<212> TYPE: PRT
<213> ORGANISM: Orthohepadnaviridae hepatitis B virus

<400> SEQUENCE: 1326

Ala Ser Pro Leu His Val Ala Trp
```

-continued

```
1               5

<210> SEQ ID NO 1327
<211> LENGTH: 8
<212> TYPE: PRT
<213> ORGANISM: Orthohepadnaviridae hepatitis B virus

<400> SEQUENCE: 1327

Ala Ser Val Arg Phe Ser Trp Leu
1               5

<210> SEQ ID NO 1328
<211> LENGTH: 10
<212> TYPE: PRT
<213> ORGANISM: Orthohepadnaviridae hepatitis B virus

<400> SEQUENCE: 1328

Ala Ser Val Arg Phe Ser Trp Leu Ser Leu
1               5                  10

<210> SEQ ID NO 1329
<211> LENGTH: 11
<212> TYPE: PRT
<213> ORGANISM: Orthohepadnaviridae hepatitis B virus

<400> SEQUENCE: 1329

Ala Ser Val Arg Phe Ser Trp Leu Ser Leu Leu
1               5                  10

<210> SEQ ID NO 1330
<211> LENGTH: 8
<212> TYPE: PRT
<213> ORGANISM: Orthohepadnaviridae hepatitis B virus

<400> SEQUENCE: 1330

Ala Thr Pro Thr Gly Trp Gly Leu
1               5

<210> SEQ ID NO 1331
<211> LENGTH: 10
<212> TYPE: PRT
<213> ORGANISM: Orthohepadnaviridae hepatitis B virus

<400> SEQUENCE: 1331

Ala Thr Pro Thr Gly Trp Gly Leu Ala Ile
1               5                  10

<210> SEQ ID NO 1332
<211> LENGTH: 11
<212> TYPE: PRT
<213> ORGANISM: Orthohepadnaviridae hepatitis B virus

<400> SEQUENCE: 1332

Cys Ala Phe Ser Ser Ala Gly Pro Cys Ala Leu
1               5                  10

<210> SEQ ID NO 1333
<211> LENGTH: 8
<212> TYPE: PRT
<213> ORGANISM: Orthohepadnaviridae hepatitis B virus

<400> SEQUENCE: 1333

Cys Ser Pro His His Thr Ala Leu
1               5
```

```
<210> SEQ ID NO 1334
<211> LENGTH: 9
<212> TYPE: PRT
<213> ORGANISM: Orthohepadnaviridae hepatitis B virus

<400> SEQUENCE: 1334

Cys Ser Arg Asn Leu Tyr Val Ser Leu
1               5

<210> SEQ ID NO 1335
<211> LENGTH: 8
<212> TYPE: PRT
<213> ORGANISM: Orthohepadnaviridae hepatitis B virus

<400> SEQUENCE: 1335

Cys Ser Val Val Arg Arg Ala Phe
1               5

<210> SEQ ID NO 1336
<211> LENGTH: 10
<212> TYPE: PRT
<213> ORGANISM: Orthohepadnaviridae hepatitis B virus

<400> SEQUENCE: 1336

Cys Thr Cys Ile Pro Ile Pro Ser Ser Trp
1               5                   10

<210> SEQ ID NO 1337
<211> LENGTH: 9
<212> TYPE: PRT
<213> ORGANISM: Orthohepadnaviridae hepatitis B virus

<400> SEQUENCE: 1337

Asp Ala Thr Pro Thr Gly Trp Gly Leu
1               5

<210> SEQ ID NO 1338
<211> LENGTH: 11
<212> TYPE: PRT
<213> ORGANISM: Orthohepadnaviridae hepatitis B virus

<400> SEQUENCE: 1338

Asp Ala Thr Pro Thr Gly Trp Gly Leu Ala Ile
1               5                   10

<210> SEQ ID NO 1339
<211> LENGTH: 9
<212> TYPE: PRT
<213> ORGANISM: Orthohepadnaviridae hepatitis B virus

<400> SEQUENCE: 1339

Asp Ser Trp Trp Thr Ser Leu Asn Phe
1               5

<210> SEQ ID NO 1340
<211> LENGTH: 10
<212> TYPE: PRT
<213> ORGANISM: Orthohepadnaviridae hepatitis B virus

<400> SEQUENCE: 1340

Asp Ser Trp Trp Thr Ser Leu Asn Phe Leu
1               5                   10

<210> SEQ ID NO 1341
```

```
<211> LENGTH: 10
<212> TYPE: PRT
<213> ORGANISM: Orthohepadnaviridae hepatitis B virus

<400> SEQUENCE: 1341

Asp Thr Ala Ser Ala Leu Tyr Arg Glu Ala
 1               5                  10

<210> SEQ ID NO 1342
<211> LENGTH: 11
<212> TYPE: PRT
<213> ORGANISM: Orthohepadnaviridae hepatitis B virus

<400> SEQUENCE: 1342

Asp Thr Ala Ser Ala Leu Tyr Arg Glu Ala Leu
 1               5                  10

<210> SEQ ID NO 1343
<211> LENGTH: 9
<212> TYPE: PRT
<213> ORGANISM: Orthohepadnaviridae hepatitis B virus

<400> SEQUENCE: 1343

Glu Ala Gly Pro Leu Glu Glu Glu Leu
 1               5

<210> SEQ ID NO 1344
<211> LENGTH: 8
<212> TYPE: PRT
<213> ORGANISM: Orthohepadnaviridae hepatitis B virus

<400> SEQUENCE: 1344

Glu Ser Arg Leu Val Val Asp Phe
 1               5

<210> SEQ ID NO 1345
<211> LENGTH: 11
<212> TYPE: PRT
<213> ORGANISM: Orthohepadnaviridae hepatitis B virus

<400> SEQUENCE: 1345

Glu Ser Arg Leu Val Val Asp Phe Ser Gln Phe
 1               5                  10

<210> SEQ ID NO 1346
<211> LENGTH: 8
<212> TYPE: PRT
<213> ORGANISM: Orthohepadnaviridae hepatitis B virus

<400> SEQUENCE: 1346

Glu Thr Val Leu Glu Tyr Leu Val
 1               5

<210> SEQ ID NO 1347
<211> LENGTH: 10
<212> TYPE: PRT
<213> ORGANISM: Orthohepadnaviridae hepatitis B virus

<400> SEQUENCE: 1347

Phe Ala Ala Pro Phe Thr Gln Cys Gly Tyr
 1               5                  10

<210> SEQ ID NO 1348
<211> LENGTH: 9
<212> TYPE: PRT
```

-continued

<213> ORGANISM: Orthohepadnaviridae hepatitis B virus

<400> SEQUENCE: 1348

Phe Ala Asp Ala Thr Pro Thr Gly Trp
1               5

<210> SEQ ID NO 1349
<211> LENGTH: 11
<212> TYPE: PRT
<213> ORGANISM: Orthohepadnaviridae hepatitis B virus

<400> SEQUENCE: 1349

Phe Ala Asp Ala Thr Pro Thr Gly Trp Gly Leu
1               5                   10

<210> SEQ ID NO 1350
<211> LENGTH: 9
<212> TYPE: PRT
<213> ORGANISM: Orthohepadnaviridae hepatitis B virus

<400> SEQUENCE: 1350

Phe Ala Ser Pro Leu His Val Ala Trp
1               5

<210> SEQ ID NO 1351
<211> LENGTH: 9
<212> TYPE: PRT
<213> ORGANISM: Orthohepadnaviridae hepatitis B virus

<400> SEQUENCE: 1351

Phe Ala Val Pro Asn Leu Gln Ser Leu
1               5

<210> SEQ ID NO 1352
<211> LENGTH: 8
<212> TYPE: PRT
<213> ORGANISM: Orthohepadnaviridae hepatitis B virus

<400> SEQUENCE: 1352

Phe Ser Pro Thr Tyr Lys Ala Phe
1               5

<210> SEQ ID NO 1353
<211> LENGTH: 9
<212> TYPE: PRT
<213> ORGANISM: Orthohepadnaviridae hepatitis B virus

<400> SEQUENCE: 1353

Phe Ser Pro Thr Tyr Lys Ala Phe Leu
1               5

<210> SEQ ID NO 1354
<211> LENGTH: 9
<212> TYPE: PRT
<213> ORGANISM: Orthohepadnaviridae hepatitis B virus

<400> SEQUENCE: 1354

Phe Ser Ser Ala Gly Pro Cys Ala Leu
1               5

<210> SEQ ID NO 1355
<211> LENGTH: 11
<212> TYPE: PRT
<213> ORGANISM: Orthohepadnaviridae hepatitis B virus

```
<400> SEQUENCE: 1355

Phe Ser Ser Ala Gly Pro Cys Ala Leu Arg Phe
1               5                   10

<210> SEQ ID NO 1356
<211> LENGTH: 8
<212> TYPE: PRT
<213> ORGANISM: Orthohepadnaviridae hepatitis B virus

<400> SEQUENCE: 1356

Phe Ser Trp Leu Ser Leu Leu Val
1               5

<210> SEQ ID NO 1357
<211> LENGTH: 10
<212> TYPE: PRT
<213> ORGANISM: Orthohepadnaviridae hepatitis B virus

<400> SEQUENCE: 1357

Phe Ser Trp Leu Ser Leu Leu Val Pro Phe
1               5                   10

<210> SEQ ID NO 1358
<211> LENGTH: 11
<212> TYPE: PRT
<213> ORGANISM: Orthohepadnaviridae hepatitis B virus

<400> SEQUENCE: 1358

Phe Ser Trp Leu Ser Leu Leu Val Pro Phe Val
1               5                   10

<210> SEQ ID NO 1359
<211> LENGTH: 8
<212> TYPE: PRT
<213> ORGANISM: Orthohepadnaviridae hepatitis B virus

<400> SEQUENCE: 1359

Phe Ser Tyr Met Asp Asp Val Val
1               5

<210> SEQ ID NO 1360
<211> LENGTH: 9
<212> TYPE: PRT
<213> ORGANISM: Orthohepadnaviridae hepatitis B virus

<400> SEQUENCE: 1360

Phe Ser Tyr Met Asp Asp Val Val Leu
1               5

<210> SEQ ID NO 1361
<211> LENGTH: 10
<212> TYPE: PRT
<213> ORGANISM: Orthohepadnaviridae hepatitis B virus

<400> SEQUENCE: 1361

Phe Thr Phe Ser Pro Thr Tyr Lys Ala Phe
1               5                   10

<210> SEQ ID NO 1362
<211> LENGTH: 11
<212> TYPE: PRT
<213> ORGANISM: Orthohepadnaviridae hepatitis B virus

<400> SEQUENCE: 1362
```

```
Phe Thr Phe Ser Pro Thr Tyr Lys Ala Phe Leu
1               5                   10

<210> SEQ ID NO 1363
<211> LENGTH: 9
<212> TYPE: PRT
<213> ORGANISM: Orthohepadnaviridae hepatitis B virus

<400> SEQUENCE: 1363

Phe Thr Gly Leu Tyr Ser Ser Thr Val
1               5

<210> SEQ ID NO 1364
<211> LENGTH: 9
<212> TYPE: PRT
<213> ORGANISM: Orthohepadnaviridae hepatitis B virus

<400> SEQUENCE: 1364

Phe Thr Gln Cys Gly Tyr Pro Ala Leu
1               5

<210> SEQ ID NO 1365
<211> LENGTH: 10
<212> TYPE: PRT
<213> ORGANISM: Orthohepadnaviridae hepatitis B virus

<400> SEQUENCE: 1365

Phe Thr Gln Cys Gly Tyr Pro Ala Leu Met
1               5                   10

<210> SEQ ID NO 1366
<211> LENGTH: 8
<212> TYPE: PRT
<213> ORGANISM: Orthohepadnaviridae hepatitis B virus

<400> SEQUENCE: 1366

Phe Thr Ser Ala Ile Cys Ser Val
1               5

<210> SEQ ID NO 1367
<211> LENGTH: 9
<212> TYPE: PRT
<213> ORGANISM: Orthohepadnaviridae hepatitis B virus

<400> SEQUENCE: 1367

Phe Thr Ser Ala Ile Cys Ser Val Val
1               5

<210> SEQ ID NO 1368
<211> LENGTH: 9
<212> TYPE: PRT
<213> ORGANISM: Orthohepadnaviridae hepatitis B virus

<400> SEQUENCE: 1368

Gly Ala His Leu Ser Leu Arg Gly Leu
1               5

<210> SEQ ID NO 1369
<211> LENGTH: 11
<212> TYPE: PRT
<213> ORGANISM: Orthohepadnaviridae hepatitis B virus

<400> SEQUENCE: 1369

Gly Ala His Leu Ser Leu Arg Gly Leu Pro Val
1               5                   10
```

<210> SEQ ID NO 1370
<211> LENGTH: 8
<212> TYPE: PRT
<213> ORGANISM: Orthohepadnaviridae hepatitis B virus

<400> SEQUENCE: 1370

Gly Ala Lys Ser Val Gln His Leu
1 5

<210> SEQ ID NO 1371
<211> LENGTH: 11
<212> TYPE: PRT
<213> ORGANISM: Orthohepadnaviridae hepatitis B virus

<400> SEQUENCE: 1371

Gly Ala Lys Ser Val Gln His Leu Glu Ser Leu
1 5 10

<210> SEQ ID NO 1372
<211> LENGTH: 10
<212> TYPE: PRT
<213> ORGANISM: Orthohepadnaviridae hepatitis B virus

<400> SEQUENCE: 1372

Gly Ser Ser Ser Gly Thr Val Asn Pro Val
1 5 10

<210> SEQ ID NO 1373
<211> LENGTH: 8
<212> TYPE: PRT
<213> ORGANISM: Orthohepadnaviridae hepatitis B virus

<400> SEQUENCE: 1373

Gly Thr Asp Asn Ser Val Val Leu
1 5

<210> SEQ ID NO 1374
<211> LENGTH: 10
<212> TYPE: PRT
<213> ORGANISM: Orthohepadnaviridae hepatitis B virus

<400> SEQUENCE: 1374

Gly Thr Asn Leu Ser Val Pro Asn Pro Leu
1 5 10

<210> SEQ ID NO 1375
<211> LENGTH: 11
<212> TYPE: PRT
<213> ORGANISM: Orthohepadnaviridae hepatitis B virus

<400> SEQUENCE: 1375

Gly Thr Ser Phe Val Tyr Val Pro Ser Ala Leu
1 5 10

<210> SEQ ID NO 1376
<211> LENGTH: 10
<212> TYPE: PRT
<213> ORGANISM: Orthohepadnaviridae hepatitis B virus

<400> SEQUENCE: 1376

His Thr Ala Glu Leu Leu Ala Ala Cys Phe
1 5 10

<210> SEQ ID NO 1377
<211> LENGTH: 8
<212> TYPE: PRT
<213> ORGANISM: Orthohepadnaviridae hepatitis B virus

<400> SEQUENCE: 1377

His Thr Ala Leu Arg Gln Ala Ile
1               5

<210> SEQ ID NO 1378
<211> LENGTH: 9
<212> TYPE: PRT
<213> ORGANISM: Orthohepadnaviridae hepatitis B virus

<400> SEQUENCE: 1378

His Thr Ala Leu Arg Gln Ala Ile Leu
1               5

<210> SEQ ID NO 1379
<211> LENGTH: 11
<212> TYPE: PRT
<213> ORGANISM: Orthohepadnaviridae hepatitis B virus

<400> SEQUENCE: 1379

His Thr Ala Leu Arg Gln Ala Ile Leu Cys Trp
1               5                   10

<210> SEQ ID NO 1380
<211> LENGTH: 8
<212> TYPE: PRT
<213> ORGANISM: Orthohepadnaviridae hepatitis B virus

<400> SEQUENCE: 1380

His Thr Leu Trp Lys Ala Gly Ile
1               5

<210> SEQ ID NO 1381
<211> LENGTH: 9
<212> TYPE: PRT
<213> ORGANISM: Orthohepadnaviridae hepatitis B virus

<400> SEQUENCE: 1381

His Thr Leu Trp Lys Ala Gly Ile Leu
1               5

<210> SEQ ID NO 1382
<211> LENGTH: 10
<212> TYPE: PRT
<213> ORGANISM: Orthohepadnaviridae hepatitis B virus

<400> SEQUENCE: 1382

His Thr Leu Trp Lys Ala Gly Ile Leu Tyr
1               5                   10

<210> SEQ ID NO 1383
<211> LENGTH: 11
<212> TYPE: PRT
<213> ORGANISM: Orthohepadnaviridae hepatitis B virus

<400> SEQUENCE: 1383

Ile Ser Cys Leu Thr Phe Gly Arg Glu Thr Val
1               5                   10

<210> SEQ ID NO 1384
<211> LENGTH: 9

-continued

<212> TYPE: PRT
<213> ORGANISM: Orthohepadnaviridae hepatitis B virus

<400> SEQUENCE: 1384

Lys Ser Val Gln His Leu Glu Ser Leu
1 5

<210> SEQ ID NO 1385
<211> LENGTH: 9
<212> TYPE: PRT
<213> ORGANISM: Orthohepadnaviridae hepatitis B virus

<400> SEQUENCE: 1385

Lys Thr Lys Arg Trp Gly Tyr Ser Leu
1 5

<210> SEQ ID NO 1386
<211> LENGTH: 11
<212> TYPE: PRT
<213> ORGANISM: Orthohepadnaviridae hepatitis B virus

<400> SEQUENCE: 1386

Lys Thr Lys Arg Trp Gly Tyr Ser Leu Asn Phe
1 5 10

<210> SEQ ID NO 1387
<211> LENGTH: 9
<212> TYPE: PRT
<213> ORGANISM: Orthohepadnaviridae hepatitis B virus

<400> SEQUENCE: 1387

Leu Ala Phe Ser Tyr Met Asp Asp Val
1 5

<210> SEQ ID NO 1388
<211> LENGTH: 10
<212> TYPE: PRT
<213> ORGANISM: Orthohepadnaviridae hepatitis B virus

<400> SEQUENCE: 1388

Leu Ala Phe Ser Tyr Met Asp Asp Val Val
1 5 10

<210> SEQ ID NO 1389
<211> LENGTH: 11
<212> TYPE: PRT
<213> ORGANISM: Orthohepadnaviridae hepatitis B virus

<400> SEQUENCE: 1389

Leu Ala Phe Ser Tyr Met Asp Asp Val Val Leu
1 5 10

<210> SEQ ID NO 1390
<211> LENGTH: 8
<212> TYPE: PRT
<213> ORGANISM: Orthohepadnaviridae hepatitis B virus

<400> SEQUENCE: 1390

Leu Ala Gln Phe Thr Ser Ala Ile
1 5

<210> SEQ ID NO 1391
<211> LENGTH: 11
<212> TYPE: PRT
<213> ORGANISM: Orthohepadnaviridae hepatitis B virus -continued

```
<400> SEQUENCE: 1391

Leu Ala Gln Phe Thr Ser Ala Ile Cys Ser Val
 1               5                  10

<210> SEQ ID NO 1392
<211> LENGTH: 8
<212> TYPE: PRT
<213> ORGANISM: Orthohepadnaviridae hepatitis B virus

<400> SEQUENCE: 1392

Leu Ser Phe Leu Pro Ser Asp Phe
 1               5

<210> SEQ ID NO 1393
<211> LENGTH: 9
<212> TYPE: PRT
<213> ORGANISM: Orthohepadnaviridae hepatitis B virus

<400> SEQUENCE: 1393

Leu Ser Phe Leu Pro Ser Asp Phe Phe
 1               5

<210> SEQ ID NO 1394
<211> LENGTH: 9
<212> TYPE: PRT
<213> ORGANISM: Orthohepadnaviridae hepatitis B virus

<400> SEQUENCE: 1394

Leu Ser Leu Asp Val Ser Ala Ala Phe
 1               5

<210> SEQ ID NO 1395
<211> LENGTH: 10
<212> TYPE: PRT
<213> ORGANISM: Orthohepadnaviridae hepatitis B virus

<400> SEQUENCE: 1395

Leu Ser Leu Asp Val Ser Ala Ala Phe Tyr
 1               5                  10

<210> SEQ ID NO 1396
<211> LENGTH: 8
<212> TYPE: PRT
<213> ORGANISM: Orthohepadnaviridae hepatitis B virus

<400> SEQUENCE: 1396

Leu Ser Leu Leu Val Pro Phe Val
 1               5

<210> SEQ ID NO 1397
<211> LENGTH: 10
<212> TYPE: PRT
<213> ORGANISM: Orthohepadnaviridae hepatitis B virus

<400> SEQUENCE: 1397

Leu Ser Leu Leu Val Pro Phe Val Gln Trp
 1               5                  10

<210> SEQ ID NO 1398
<211> LENGTH: 11
<212> TYPE: PRT
<213> ORGANISM: Orthohepadnaviridae hepatitis B virus

<400> SEQUENCE: 1398
```

Leu Ser Leu Leu Val Pro Phe Val Gln Trp Phe
1               5                   10

<210> SEQ ID NO 1399
<211> LENGTH: 8
<212> TYPE: PRT
<213> ORGANISM: Orthohepadnaviridae hepatitis B virus

<400> SEQUENCE: 1399

Leu Ser Leu Arg Gly Leu Pro Val
1               5

<210> SEQ ID NO 1400
<211> LENGTH: 11
<212> TYPE: PRT
<213> ORGANISM: Orthohepadnaviridae hepatitis B virus

<400> SEQUENCE: 1400

Leu Ser Leu Arg Gly Leu Pro Val Cys Ala Phe
1               5                   10

<210> SEQ ID NO 1401
<211> LENGTH: 9
<212> TYPE: PRT
<213> ORGANISM: Orthohepadnaviridae hepatitis B virus

<400> SEQUENCE: 1401

Leu Ser Pro Phe Leu Leu Ala Gln Phe
1               5

<210> SEQ ID NO 1402
<211> LENGTH: 9
<212> TYPE: PRT
<213> ORGANISM: Orthohepadnaviridae hepatitis B virus

<400> SEQUENCE: 1402

Leu Ser Pro Thr Val Trp Leu Ser Val
1               5

<210> SEQ ID NO 1403
<211> LENGTH: 10
<212> TYPE: PRT
<213> ORGANISM: Orthohepadnaviridae hepatitis B virus

<400> SEQUENCE: 1403

Leu Ser Pro Thr Val Trp Leu Ser Val Ile
1               5                   10

<210> SEQ ID NO 1404
<211> LENGTH: 11
<212> TYPE: PRT
<213> ORGANISM: Orthohepadnaviridae hepatitis B virus

<400> SEQUENCE: 1404

Leu Ser Pro Thr Val Trp Leu Ser Val Ile Trp
1               5                   10

<210> SEQ ID NO 1405
<211> LENGTH: 8
<212> TYPE: PRT
<213> ORGANISM: Orthohepadnaviridae hepatitis B virus

<400> SEQUENCE: 1405

Leu Ser Arg Lys Tyr Thr Ser Phe

```
<210> SEQ ID NO 1406
<211> LENGTH: 10
<212> TYPE: PRT
<213> ORGANISM: Orthohepadnaviridae hepatitis B virus

<400> SEQUENCE: 1406

Leu Ser Arg Lys Tyr Thr Ser Phe Pro Trp
1               5                   10

<210> SEQ ID NO 1407
<211> LENGTH: 11
<212> TYPE: PRT
<213> ORGANISM: Orthohepadnaviridae hepatitis B virus

<400> SEQUENCE: 1407

Leu Ser Arg Lys Tyr Thr Ser Phe Pro Trp Leu
1               5                   10

<210> SEQ ID NO 1408
<211> LENGTH: 8
<212> TYPE: PRT
<213> ORGANISM: Orthohepadnaviridae hepatitis B virus

<400> SEQUENCE: 1408

Leu Ser Ser Asn Leu Ser Trp Leu
1               5

<210> SEQ ID NO 1409
<211> LENGTH: 10
<212> TYPE: PRT
<213> ORGANISM: Orthohepadnaviridae hepatitis B virus

<400> SEQUENCE: 1409

Leu Ser Ser Asn Leu Ser Trp Leu Ser Leu
1               5                   10

<210> SEQ ID NO 1410
<211> LENGTH: 9
<212> TYPE: PRT
<213> ORGANISM: Orthohepadnaviridae hepatitis B virus

<400> SEQUENCE: 1410

Leu Ser Thr Leu Pro Glu Thr Thr Val
1               5

<210> SEQ ID NO 1411
<211> LENGTH: 10
<212> TYPE: PRT
<213> ORGANISM: Orthohepadnaviridae hepatitis B virus

<400> SEQUENCE: 1411

Leu Ser Thr Leu Pro Glu Thr Thr Val Val
1               5                   10

<210> SEQ ID NO 1412
<211> LENGTH: 9
<212> TYPE: PRT
<213> ORGANISM: Orthohepadnaviridae hepatitis B virus

<400> SEQUENCE: 1412

Leu Ser Val Pro Asn Pro Leu Gly Phe
1               5
```

<210> SEQ ID NO 1413
<211> LENGTH: 8
<212> TYPE: PRT
<213> ORGANISM: Orthohepadnaviridae hepatitis B virus

<400> SEQUENCE: 1413

Leu Ser Trp Leu Ser Leu Asp Val
1               5

<210> SEQ ID NO 1414
<211> LENGTH: 9
<212> TYPE: PRT
<213> ORGANISM: Orthohepadnaviridae hepatitis B virus

<400> SEQUENCE: 1414

Leu Ser Tyr Gln His Phe Arg Lys Leu
1               5

<210> SEQ ID NO 1415
<211> LENGTH: 10
<212> TYPE: PRT
<213> ORGANISM: Orthohepadnaviridae hepatitis B virus

<400> SEQUENCE: 1415

Leu Ser Tyr Gln His Phe Arg Lys Leu Leu
1               5                   10

<210> SEQ ID NO 1416
<211> LENGTH: 11
<212> TYPE: PRT
<213> ORGANISM: Orthohepadnaviridae hepatitis B virus

<400> SEQUENCE: 1416

Leu Ser Tyr Gln His Phe Arg Lys Leu Leu Leu
1               5                   10

<210> SEQ ID NO 1417
<211> LENGTH: 8
<212> TYPE: PRT
<213> ORGANISM: Orthohepadnaviridae hepatitis B virus

<400> SEQUENCE: 1417

Leu Thr Phe Gly Arg Glu Thr Val
1               5

<210> SEQ ID NO 1418
<211> LENGTH: 9
<212> TYPE: PRT
<213> ORGANISM: Orthohepadnaviridae hepatitis B virus

<400> SEQUENCE: 1418

Leu Thr Phe Gly Arg Glu Thr Val Leu
1               5

<210> SEQ ID NO 1419
<211> LENGTH: 11
<212> TYPE: PRT
<213> ORGANISM: Orthohepadnaviridae hepatitis B virus

<400> SEQUENCE: 1419

Leu Thr Phe Gly Arg Glu Thr Val Leu Glu Tyr
1               5                   10

<210> SEQ ID NO 1420

-continued

<211> LENGTH: 10
<212> TYPE: PRT
<213> ORGANISM: Orthohepadnaviridae hepatitis B virus

<400> SEQUENCE: 1420

Leu Thr Ile Pro Gln Ser Leu Asp Ser Trp
1 5 10

<210> SEQ ID NO 1421
<211> LENGTH: 11
<212> TYPE: PRT
<213> ORGANISM: Orthohepadnaviridae hepatitis B virus

<400> SEQUENCE: 1421

Leu Thr Ile Pro Gln Ser Leu Asp Ser Trp Trp
1 5 10

<210> SEQ ID NO 1422
<211> LENGTH: 9
<212> TYPE: PRT
<213> ORGANISM: Orthohepadnaviridae hepatitis B virus

<400> SEQUENCE: 1422

Leu Thr Asn Leu Leu Ser Ser Asn Leu
1 5

<210> SEQ ID NO 1423
<211> LENGTH: 11
<212> TYPE: PRT
<213> ORGANISM: Orthohepadnaviridae hepatitis B virus

<400> SEQUENCE: 1423

Leu Thr Asn Leu Leu Ser Ser Asn Leu Ser Trp
1 5 10

<210> SEQ ID NO 1424
<211> LENGTH: 11
<212> TYPE: PRT
<213> ORGANISM: Orthohepadnaviridae hepatitis B virus

<400> SEQUENCE: 1424

Leu Thr Arg Ile Leu Thr Ile Pro Gln Ser Leu
1 5 10

<210> SEQ ID NO 1425
<211> LENGTH: 9
<212> TYPE: PRT
<213> ORGANISM: Orthohepadnaviridae hepatitis B virus

<400> SEQUENCE: 1425

Leu Thr Val Asn Glu Lys Arg Arg Leu
1 5

<210> SEQ ID NO 1426
<211> LENGTH: 9
<212> TYPE: PRT
<213> ORGANISM: Orthohepadnaviridae hepatitis B virus

<400> SEQUENCE: 1426

Met Ser Thr Thr Asp Leu Glu Ala Tyr
1 5

<210> SEQ ID NO 1427
<211> LENGTH: 10
<212> TYPE: PRT

<213> ORGANISM: Orthohepadnaviridae hepatitis B virus

<400> SEQUENCE: 1427

Met Ser Thr Thr Asp Leu Glu Ala Tyr Phe
1               5                   10

<210> SEQ ID NO 1428
<211> LENGTH: 8
<212> TYPE: PRT
<213> ORGANISM: Orthohepadnaviridae hepatitis B virus

<400> SEQUENCE: 1428

Asn Ala Pro Ile Leu Ser Thr Leu
1               5

<210> SEQ ID NO 1429
<211> LENGTH: 9
<212> TYPE: PRT
<213> ORGANISM: Orthohepadnaviridae hepatitis B virus

<400> SEQUENCE: 1429

Asn Ser Val Val Leu Ser Arg Lys Tyr
1               5

<210> SEQ ID NO 1430
<211> LENGTH: 8
<212> TYPE: PRT
<213> ORGANISM: Orthohepadnaviridae hepatitis B virus

<400> SEQUENCE: 1430

Pro Ala Ala Met Pro His Leu Leu
1               5

<210> SEQ ID NO 1431
<211> LENGTH: 9
<212> TYPE: PRT
<213> ORGANISM: Orthohepadnaviridae hepatitis B virus

<400> SEQUENCE: 1431

Pro Ala Ala Met Pro His Leu Leu Val
1               5

<210> SEQ ID NO 1432
<211> LENGTH: 10
<212> TYPE: PRT
<213> ORGANISM: Orthohepadnaviridae hepatitis B virus

<400> SEQUENCE: 1432

Pro Ala Asp Asp Pro Ser Arg Gly Arg Leu
1               5                   10

<210> SEQ ID NO 1433
<211> LENGTH: 10
<212> TYPE: PRT
<213> ORGANISM: Orthohepadnaviridae hepatitis B virus

<400> SEQUENCE: 1433

Pro Ala Gly Gly Ser Ser Ser Gly Thr Val
1               5                   10

<210> SEQ ID NO 1434
<211> LENGTH: 10
<212> TYPE: PRT
<213> ORGANISM: Orthohepadnaviridae hepatitis B virus

```
<400> SEQUENCE: 1434

Pro Ala Leu Met Pro Leu Tyr Ala Cys Ile
1               5                   10

<210> SEQ ID NO 1435
<211

```
Pro Ala Tyr Arg Pro Pro Asn Ala Pro Ile
1               5                   10

<210> SEQ ID NO 1442
<211> LENGTH: 11
<212> TYPE: PRT
<213> ORGANISM: Orthohepadnaviridae hepatitis B virus

<400> SEQUENCE: 1442

Pro Ala Tyr Arg Pro Pro Asn Ala Pro Ile Leu
1               5                   10

<210> SEQ ID NO 1443
<211> LENGTH: 8
<212> TYPE: PRT
<213> ORGANISM: Orthohepadnaviridae hepatitis B virus

<400> SEQUENCE: 1443

Pro Ser Arg Gly Arg Leu Gly Leu
1               5

<210> SEQ ID NO 1444
<211> LENGTH: 8
<212> TYPE: PRT
<213> ORGANISM: Orthohepadnaviridae hepatitis B virus

<400> SEQUENCE: 1444

Pro Thr Gly Trp Gly Leu Ala Ile
1               5

<210> SEQ ID NO 1445
<211> LENGTH: 8
<212> TYPE: PRT
<213> ORGANISM: Orthohepadnaviridae hepatitis B virus

<400> SEQUENCE: 1445

Pro Thr Thr Gly Arg Thr Ser Leu
1               5

<210> SEQ ID NO 1446
<211> LENGTH: 9
<212> TYPE: PRT
<213> ORGANISM: Orthohepadnaviridae hepatitis B virus

<400> SEQUENCE: 1446

Pro Thr Thr Gly Arg Thr Ser Leu Tyr
1               5

<210> SEQ ID NO 1447
<211> LENGTH: 8
<212> TYPE: PRT
<213> ORGANISM: Orthohepadnaviridae hepatitis B virus

<400> SEQUENCE: 1447

Pro Thr Val Gln Ala Ser Lys Leu
1               5

<210> SEQ ID NO 1448
<211> LENGTH: 10
<212> TYPE: PRT
<213> ORGANISM: Orthohepadnaviridae hepatitis B virus

<400> SEQUENCE: 1448

Pro Thr Val Gln Ala Ser Lys Leu Cys Leu
1               5                   10
```

<210> SEQ ID NO 1449
<211> LENGTH: 8
<212> TYPE: PRT
<213> ORGANISM: Orthohepadnaviridae hepatitis B virus

<400> SEQUENCE: 1449

Pro Thr Val Trp Leu Ser Val Ile
 1               5

<210> SEQ ID NO 1450
<211> LENGTH: 9
<212> TYPE: PRT
<213> ORGANISM: Orthohepadnaviridae hepatitis B virus

<400> SEQUENCE: 1450

Pro Thr Val Trp Leu Ser Val Ile Trp
 1               5

<210> SEQ ID NO 1451
<211> LENGTH: 10
<212> TYPE: PRT
<213> ORGANISM: Orthohepadnaviridae hepatitis B virus

<400> SEQUENCE: 1451

Pro Thr Val Trp Leu Ser Val Ile Trp Met
 1               5                  10

<210> SEQ ID NO 1452
<211> LENGTH: 9
<212> TYPE: PRT
<213> ORGANISM: Orthohepadnaviridae hepatitis B virus

<400> SEQUENCE: 1452

Gln Ala Phe Thr Phe Ser Pro Thr Tyr
 1               5

<210> SEQ ID NO 1453
<211> LENGTH: 11
<212> TYPE: PRT
<213> ORGANISM: Orthohepadnaviridae hepatitis B virus

<400> SEQUENCE: 1453

Gln Ala Gly Phe Phe Leu Leu Thr Arg Ile Leu
 1               5                  10

<210> SEQ ID NO 1454
<211> LENGTH: 9
<212> TYPE: PRT
<213> ORGANISM: Orthohepadnaviridae hepatitis B virus

<400> SEQUENCE: 1454

Gln Ala Ile Leu Cys Trp Gly Glu Leu
 1               5

<210> SEQ ID NO 1455
<211> LENGTH: 10
<212> TYPE: PRT
<213> ORGANISM: Orthohepadnaviridae hepatitis B virus

<400> SEQUENCE: 1455

Gln Ala Ile Leu Cys Trp Gly Glu Leu Met
 1               5                  10

<210> SEQ ID NO 1456
<211> LENGTH: 10
<212> TYPE: PRT
<213> ORGANISM: Orthohepadnaviridae hepatitis B virus

<400> SEQUENCE: 1456

Gln Ala Met Gln Trp Asn Ser Thr Thr Phe
1               5                   10

<210> SEQ ID NO 1457
<211> LENGTH: 9
<212> TYPE: PRT
<213> ORGANISM: Orthohepadnaviridae hepatitis B virus

<400> SEQUENCE: 1457

Gln Ala Ser Lys Leu Cys Leu Gly Trp
1               5

<210> SEQ ID NO 1458
<211> LENGTH: 10
<212> TYPE: PRT
<213> ORGANISM: Orthohepadnaviridae hepatitis B virus

<400> SEQUENCE: 1458

Gln Ala Ser Lys Leu Cys Leu Gly Trp Leu
1               5                   10

<210> SEQ ID NO 1459
<211> LENGTH: 11
<212> TYPE: PRT
<213> ORGANISM: Orthohepadnaviridae hepatitis B virus

<400> SEQUENCE: 1459

Gln Ala Ser Lys Leu Cys Leu Gly Trp Leu Trp
1               5                   10

<210> SEQ ID NO 1460
<211> LENGTH: 10
<212> TYPE: PRT
<213> ORGANISM: Orthohepadnaviridae hepatitis B virus

<400> SEQUENCE: 1460

Gln Ser Leu Asp Ser Trp Trp Thr Ser Leu
1               5                   10

<210> SEQ ID NO 1461
<211> LENGTH: 11
<212> TYPE: PRT
<213> ORGANISM: Orthohepadnaviridae hepatitis B virus

<400> SEQUENCE: 1461

Gln Ser Leu Thr Asn Leu Leu Ser Ser Asn Leu
1               5                   10

<210> SEQ ID NO 1462
<211> LENGTH: 9
<212> TYPE: PRT
<213> ORGANISM: Orthohepadnaviridae hepatitis B virus

<400> SEQUENCE: 1462

Arg Ala Phe Pro His Cys Leu Ala Phe
1               5

<210> SEQ ID NO 1463
<211> LENGTH: 11

-continued

<212> TYPE: PRT
<213> ORGANISM: Orthohepadnaviridae hepatitis B virus

<400> SEQUENCE: 1463

Arg Ala Phe Pro His Cys Leu Ala Phe Ser Tyr
1               5                   10

<210> SEQ ID NO 1464
<211> LENGTH: 10
<212> TYPE: PRT
<213> ORGANISM: Orthohepadnaviridae hepatitis B virus

<400> SEQUENCE: 1464

Arg Thr Pro Ala Arg Val Thr Gly Gly Val
1               5                   10

<210> SEQ ID NO 1465
<211> LENGTH: 11
<212> TYPE: PRT
<213> ORGANISM: Orthohepadnaviridae hepatitis B virus

<400> SEQUENCE: 1465

Arg Thr Pro Ala Arg Val Thr Gly Gly Val Phe
1               5                   10

<210> SEQ ID NO 1466
<211> LENGTH: 9
<212> TYPE: PRT
<213> ORGANISM: Orthohepadnaviridae hepatitis B virus

<400> SEQUENCE: 1466

Ser Ala Gly Pro Cys Ala Leu Arg Phe
1               5

<210> SEQ ID NO 1467
<211> LENGTH: 11
<212> TYPE: PRT
<213> ORGANISM: Orthohepadnaviridae hepatitis B virus

<400> SEQUENCE: 1467

Ser Ala Ile Cys Ser Val Val Arg Arg Ala Phe
1               5                   10

<210> SEQ ID NO 1468
<211> LENGTH: 8
<212> TYPE: PRT
<213> ORGANISM: Orthohepadnaviridae hepatitis B virus

<400> SEQUENCE: 1468

Ser Ala Leu Tyr Arg Glu Ala Leu
1               5

<210> SEQ ID NO 1469
<211> LENGTH: 9
<212> TYPE: PRT
<213> ORGANISM: Orthohepadnaviridae hepatitis B virus

<400> SEQUENCE: 1469

Ser Ala Ser Phe Cys Gly Ser Pro Tyr
1               5

<210> SEQ ID NO 1470
<211> LENGTH: 11
<212> TYPE: PRT
<213> ORGANISM: Orthohepadnaviridae hepatitis B virus

```
<400> SEQUENCE: 1470

Ser Ala Ser Phe Cys Gly Ser Pro Tyr Ser Trp
1               5                   10

<210> SEQ ID NO 1471
<211> LENGTH: 8
<212> TYPE: PRT
<213> ORGANISM: Orthohepadnaviridae hepatitis B virus

<400> SEQUENCE: 1471

Ser Ser Ala Gly Pro Cys Ala Leu
1               5

<210> SEQ ID NO 1472
<211> LENGTH: 10
<212> TYPE: PRT
<213> ORGANISM: Orthohepadnaviridae hepatitis B virus

<400> SEQUENCE: 1472

Ser Ser Ala Gly Pro Cys Ala Leu Arg Phe
1               5                   10

<210> SEQ ID NO 1473
<211> LENGTH: 8
<212> TYPE: PRT
<213> ORGANISM: Orthohepadnaviridae hepatitis B virus

<400> SEQUENCE: 1473

Ser Ser Gly Thr Val Asn Pro Val
1               5

<210> SEQ ID NO 1474
<211> LENGTH: 9
<212> TYPE: PRT
<213> ORGANISM: Orthohepadnaviridae hepatitis B virus

<400> SEQUENCE: 1474

Ser Ser Asn Leu Ser Trp Leu Ser Leu
1               5

<210> SEQ ID NO 1475
<211> LENGTH: 11
<212> TYPE: PRT
<213> ORGANISM: Orthohepadnaviridae hepatitis B virus

<400> SEQUENCE: 1475

Ser Ser Asn Leu Ser Trp Leu Ser Leu Asp Val
1               5                   10

<210> SEQ ID NO 1476
<211> LENGTH: 9
<212> TYPE: PRT
<213> ORGANISM: Orthohepadnaviridae hepatitis B virus

<400> SEQUENCE: 1476

Ser Ser Ser Gly Thr Val Asn Pro Val
1               5

<210> SEQ ID NO 1477
<211> LENGTH: 8
<212> TYPE: PRT
<213> ORGANISM: Orthohepadnaviridae hepatitis B virus

<400> SEQUENCE: 1477
```

```
Ser Thr Leu Pro Glu Thr Thr Val
1               5

<210> SEQ ID NO 1478
<211> LENGTH: 9
<212> TYPE: PRT
<213> ORGANISM: Orthohepadnaviridae hepatitis B virus

<400> SEQUENCE: 1478

Ser Thr Leu Pro Glu Thr Thr Val Val
1               5

<210> SEQ ID NO 1479
<211> LENGTH: 8
<212> TYPE: PRT
<213> ORGANISM: Orthohepadnaviridae hepatitis B virus

<400> SEQUENCE: 1479

Ser Thr Thr Asp Leu Glu Ala Tyr
1               5

<210> SEQ ID NO 1480
<211> LENGTH: 9
<212> TYPE: PRT
<213> ORGANISM: Orthohepadnaviridae hepatitis B virus

<400> SEQUENCE: 1480

Ser Thr Thr Asp Leu Glu Ala Tyr Phe
1               5

<210> SEQ ID NO 1481
<211> LENGTH: 9
<212> TYPE: PRT
<213> ORGANISM: Orthohepadnaviridae hepatitis B virus

<400> SEQUENCE: 1481

Thr Ala Glu Leu Leu Ala Ala Cys Phe
1               5

<210> SEQ ID NO 1482
<211> LENGTH: 8
<212> TYPE: PRT
<213> ORGANISM: Orthohepadnaviridae hepatitis B virus

<400> SEQUENCE: 1482

Thr Ala Leu Arg Gln Ala Ile Leu
1               5

<210> SEQ ID NO 1483
<211> LENGTH: 10
<212> TYPE: PRT
<213> ORGANISM: Orthohepadnaviridae hepatitis B virus

<400> SEQUENCE: 1483

Thr Ala Leu Arg Gln Ala Ile Leu Cys Trp
1               5                   10

<210> SEQ ID NO 1484
<211> LENGTH: 10
<212> TYPE: PRT
<213> ORGANISM: Orthohepadnaviridae hepatitis B virus

<400> SEQUENCE: 1484

Thr Ala Ser Ala Leu Tyr Arg Glu Ala Leu
```

<210> SEQ ID NO 1485
<211> LENGTH: 8
<212> TYPE: PRT
<213> ORGANISM: Orthohepadnaviridae hepatitis B virus

<400> SEQUENCE: 1485

Thr Ser Ala Ile Cys Ser Val Val
1               5

<210> SEQ ID NO 1486
<211> LENGTH: 10
<212> TYPE: PRT
<213> ORGANISM: Orthohepadnaviridae hepatitis B virus

<400> SEQUENCE: 1486

Thr Ser Phe Val Tyr Val Pro Ser Ala Leu
1               5                   10

<210> SEQ ID NO 1487
<211> LENGTH: 8
<212> TYPE: PRT
<213> ORGANISM: Orthohepadnaviridae hepatitis B virus

<400> SEQUENCE: 1487

Thr Ser Gly Phe Leu Gly Pro Leu
1               5

<210> SEQ ID NO 1488
<211> LENGTH: 9
<212> TYPE: PRT
<213> ORGANISM: Orthohepadnaviridae hepatitis B virus

<400> SEQUENCE: 1488

Thr Ser Gly Phe Leu Gly Pro Leu Leu
1               5

<210> SEQ ID NO 1489
<211> LENGTH: 10
<212> TYPE: PRT
<213> ORGANISM: Orthohepadnaviridae hepatitis B virus

<400> SEQUENCE: 1489

Thr Ser Gly Phe Leu Gly Pro Leu Leu Val
1               5                   10

<210> SEQ ID NO 1490
<211> LENGTH: 11
<212> TYPE: PRT
<213> ORGANISM: Orthohepadnaviridae hepatitis B virus

<400> SEQUENCE: 1490

Thr Ser Gly Phe Leu Gly Pro Leu Leu Val Leu
1               5                   10

<210> SEQ ID NO 1491
<211> LENGTH: 8
<212> TYPE: PRT
<213> ORGANISM: Orthohepadnaviridae hepatitis B virus

<400> SEQUENCE: 1491

Thr Thr Asp Leu Glu Ala Tyr Phe
1               5

```
<210> SEQ ID NO 1492
<211> LENGTH: 8
<212> TYPE: PRT
<213> ORGANISM: Orthohepadnaviridae hepatitis B virus

<400> SEQUENCE: 1492

Thr Thr Gly Arg Thr Ser Leu Tyr
1               5

<210> SEQ ID NO 1493
<211> LENGTH: 10
<212> TYPE: PRT
<213> ORGANISM: Orthohepadnaviridae hepatitis B virus

<400> SEQUENCE: 1493

Val Ala Glu Asp Leu Asn Leu Gly Asn Leu
1               5                   10

<210> SEQ ID NO 1494
<211> LENGTH: 9
<212> TYPE: PRT
<213> ORGANISM: Orthohepadnaviridae hepatitis B virus

<400> SEQUENCE: 1494

Val Ser Ile Pro Trp Thr His Lys Val
1               5

<210> SEQ ID NO 1495
<211> LENGTH: 8
<212> TYPE: PRT
<213> ORGANISM: Orthohepadnaviridae hepatitis B virus

<400> SEQUENCE: 1495

Val Ser Trp Pro Lys Phe Ala Val
1               5

<210> SEQ ID NO 1496
<211> LENGTH: 11
<212> TYPE: PRT
<213> ORGANISM: Orthohepadnaviridae hepatitis B virus

<400> SEQUENCE: 1496

Val Ser Trp Pro Lys Phe Ala Val Pro Asn Leu
1               5                   10

<210> SEQ ID NO 1497
<211> LENGTH: 8
<212> TYPE: PRT
<213> ORGANISM: Orthohepadnaviridae hepatitis B virus

<400> SEQUENCE: 1497

Val Thr Gly Gly Val Phe Leu Val
1               5

<210> SEQ ID NO 1498
<211> LENGTH: 8
<212> TYPE: PRT
<213> ORGANISM: Orthohepadnaviridae hepatitis B virus

<400> SEQUENCE: 1498

Trp Ser Pro Gln Ala Gln Gly Ile
1               5

<210> SEQ ID NO 1499
```

```
<211> LENGTH: 9
<212> TYPE: PRT
<213> ORGANISM: Orthohepadnaviridae hepatitis B virus

<400> SEQUENCE: 1499

Trp Ser Pro Gln Ala Gln Gly Ile Leu
1               5

<210> SEQ ID NO 1500
<211> LENGTH: 8
<212> TYPE: PRT
<213> ORGANISM: Orthohepadnaviridae hepatitis B virus

<400> SEQUENCE: 1500

Trp Thr His Lys Val Gly Asn Phe
1               5

<210> SEQ ID NO 1501
<211> LENGTH: 11
<212> TYPE: PRT
<213> ORGANISM: Orthohepadnaviridae hepatitis B virus

<400> SEQUENCE: 1501

Trp Thr His Lys Val Gly Asn Phe Thr Gly Leu
1               5                   10

<210> SEQ ID NO 1502
<211> LENGTH: 9
<212> TYPE: PRT
<213> ORGANISM: Orthohepadnaviridae hepatitis B virus

<400> SEQUENCE: 1502

Tyr Ser His Pro Ile Ile Leu Gly Phe
1               5

<210> SEQ ID NO 1503
<211> LENGTH: 8
<212> TYPE: PRT
<213> ORGANISM: Orthohepadnaviridae hepatitis B virus

<400> SEQUENCE: 1503

Tyr Ser Leu Asn Phe Met Gly Tyr
1               5

<210> SEQ ID NO 1504
<211> LENGTH: 9
<212> TYPE: PRT
<213> ORGANISM: Orthohepadnaviridae hepatitis B virus

<400> SEQUENCE: 1504

Tyr Ser Leu Asn Phe Met Gly Tyr Val
1               5

<210> SEQ ID NO 1505
<211> LENGTH: 10
<212> TYPE: PRT
<213> ORGANISM: Orthohepadnaviridae hepatitis B virus

<400> SEQUENCE: 1505

Tyr Ser Leu Asn Phe Met Gly Tyr Val Ile
1               5                   10

<210> SEQ ID NO 1506
<211> LENGTH: 8
<212> TYPE: PRT
```

<213> ORGANISM: Orthohepadnaviridae hepatitis B virus

<400> SEQUENCE: 1506

Tyr Thr Ser Phe Pro Trp Leu Leu
1               5

<210> SEQ ID NO 1507
<211> LENGTH: 10
<212> TYPE: PRT
<213> ORGANISM: Orthohepadnaviridae hepatitis B virus

<400> SEQUENCE: 1507

Ala Ile Cys Ser Val Val Arg Arg Ala Phe
1               5                   10

<210> SEQ ID NO 1508
<211> LENGTH: 9
<212> TYPE: PRT
<213> ORGANISM: Orthohepadnaviridae hepatitis B virus

<400> SEQUENCE: 1508

Ala Ile Leu Cys Trp Gly Glu Leu Met
1               5

<210> SEQ ID NO 1509
<211> LENGTH: 9
<212> TYPE: PRT
<213> ORGANISM: Orthohepadnaviridae hepatitis B virus

<400> SEQUENCE: 1509

Ala Leu Met Pro Leu Tyr Ala Cys Ile
1               5

<210> SEQ ID NO 1510
<211> LENGTH: 9
<212> TYPE: PRT
<213> ORGANISM: Orthohepadnaviridae hepatitis B virus

<400> SEQUENCE: 1510

Ala Leu Arg Gln Ala Ile Leu Cys Trp
1               5

<210> SEQ ID NO 1511
<211> LENGTH: 9
<212> TYPE: PRT
<213> ORGANISM: Orthohepadnaviridae hepatitis B virus

<400> SEQUENCE: 1511

Ala Met Gln Trp Asn Ser Thr Thr Phe
1               5

<210> SEQ ID NO 1512
<211> LENGTH: 8
<212> TYPE: PRT
<213> ORGANISM: Orthohepadnaviridae hepatitis B virus

<400> SEQUENCE: 1512

Ala Pro Phe Thr Gln Cys Gly Tyr
1               5

<210> SEQ ID NO 1513
<211> LENGTH: 10
<212> TYPE: PRT
<213> ORGANISM: Orthohepadnaviridae hepatitis B virus -continued

```
<400> SEQUENCE: 1513

Ala Gln Phe Thr Ser Ala Ile Cys Ser Val
1               5                   10

<210> SEQ ID NO 1514
<211> LENGTH: 11
<212> TYPE: PRT
<213> ORGANISM: Orthohepadnaviridae hepatitis B virus

<400> SEQUENCE: 1514

Ala Gln Phe Thr Ser Ala Ile Cys Ser Val Val
1               5                   10

<210> SEQ ID NO 1515
<211> LENGTH: 8
<212> TYPE: PRT
<213> ORGANISM: Orthohepadnaviridae hepatitis B virus

<400> SEQUENCE: 1515

Cys Ile Pro Ile Pro Ser Ser Trp
1               5

<210> SEQ ID NO 1516
<211> LENGTH: 10
<212> TYPE: PRT
<213> ORGANISM: Orthohepadnaviridae hepatitis B virus

<400> SEQUENCE: 1516

Cys Ile Pro Ile Pro Ser Ser Trp Ala Phe
1               5                   10

<210> SEQ ID NO 1517
<211> LENGTH: 10
<212> TYPE: PRT
<213> ORGANISM: Orthohepadnaviridae hepatitis B virus

<400> SEQUENCE: 1517

Cys Leu Ala Phe Ser Tyr Met Asp Asp Val
1               5                   10

<210> SEQ ID NO 1518
<211> LENGTH: 11
<212> TYPE: PRT
<213> ORGANISM: Orthohepadnaviridae hepatitis B virus

<400> SEQUENCE: 1518

Cys Leu Ala Phe Ser Tyr Met Asp Asp Val Val
1               5                   10

<210> SEQ ID NO 1519
<211> LENGTH: 8
<212> TYPE: PRT
<213> ORGANISM: Orthohepadnaviridae hepatitis B virus

<400> SEQUENCE: 1519

Cys Leu Gly Trp Leu Trp Gly Met
1               5

<210> SEQ ID NO 1520
<211> LENGTH: 10
<212> TYPE: PRT
<213> ORGANISM: Orthohepadnaviridae hepatitis B virus

<400> SEQUENCE: 1520
```

Cys Leu Gly Trp Leu Trp Gly Met Asp Ile
1               5                   10

<210> SEQ ID NO 1521
<211> LENGTH: 11
<212> TYPE: PRT
<213> ORGANISM: Orthohepadnaviridae hepatitis B virus

<400> SEQUENCE: 1521

Cys Leu Ile Phe Leu Leu Val Leu Leu Asp Tyr
1               5                   10

<210> SEQ ID NO 1522
<211> LENGTH: 8
<212> TYPE: PRT
<213> ORGANISM: Orthohepadnaviridae hepatitis B virus

<400> SEQUENCE: 1522

Cys Leu Arg Arg Phe Ile Ile Phe
1               5

<210> SEQ ID NO 1523
<211> LENGTH: 10
<212> TYPE: PRT
<213> ORGANISM: Orthohepadnaviridae hepatitis B virus

<400> SEQUENCE: 1523

Cys Leu Arg Arg Phe Ile Ile Phe Leu Phe
1               5                   10

<210> SEQ ID NO 1524
<211> LENGTH: 11
<212> TYPE: PRT
<213> ORGANISM: Orthohepadnaviridae hepatitis B virus

<400> SEQUENCE: 1524

Cys Leu Arg Arg Phe Ile Ile Phe Leu Phe Ile
1               5                   10

<210> SEQ ID NO 1525
<211> LENGTH: 9
<212> TYPE: PRT
<213> ORGANISM: Orthohepadnaviridae hepatitis B virus

<400> SEQUENCE: 1525

Cys Leu Thr Phe Gly Arg Glu Thr Val
1               5

<210> SEQ ID NO 1526
<211> LENGTH: 9
<212> TYPE: PRT
<213> ORGANISM: Orthohepadnaviridae hepatitis B virus

<400> SEQUENCE: 1526

Cys Gln Leu Asp Pro Ala Arg Asp Val
1               5

<210> SEQ ID NO 1527
<211> LENGTH: 10
<212> TYPE: PRT
<213> ORGANISM: Orthohepadnaviridae hepatitis B virus

<400> SEQUENCE: 1527

Cys Gln Arg Ile Val Gly Leu Leu Gly Phe
1               5                   10

<210> SEQ ID NO 1528
<211> LENGTH: 8
<212> TYPE: PRT
<213> ORGANISM: Orthohepadnaviridae hepatitis B virus

<400> SEQUENCE: 1528

Asp Ile Asp Pro Tyr Lys Glu Phe
1               5

<210> SEQ ID NO 1529
<211> LENGTH: 10
<212> TYPE: PRT
<213> ORGANISM: Orthohepadnaviridae hepatitis B virus

<400> SEQUENCE: 1529

Asp Leu Leu Asp Thr Ala Ser Ala Leu Tyr
1               5                   10

<210> SEQ ID NO 1530
<211> LENGTH: 9
<212> TYPE: PRT
<213> ORGANISM: Orthohepadnaviridae hepatitis B virus

<400> SEQUENCE: 1530

Asp Leu Asn Leu Gly Asn Leu Asn Val
1               5

<210> SEQ ID NO 1531
<211> LENGTH: 11
<212> TYPE: PRT
<213> ORGANISM: Orthohepadnaviridae hepatitis B virus

<400> SEQUENCE: 1531

Asp Leu Asn Leu Gly Asn Leu Asn Val Ser Ile
1               5                   10

<210> SEQ ID NO 1532
<211> LENGTH: 8
<212> TYPE: PRT
<213> ORGANISM: Orthohepadnaviridae hepatitis B virus

<400> SEQUENCE: 1532

Asp Pro Arg Val Arg Gly Leu Tyr
1               5

<210> SEQ ID NO 1533
<211> LENGTH: 8
<212> TYPE: PRT
<213> ORGANISM: Orthohepadnaviridae hepatitis B virus

<400> SEQUENCE: 1533

Asp Val Leu Cys Leu Arg Pro Val
1               5

<210> SEQ ID NO 1534
<211> LENGTH: 9
<212> TYPE: PRT
<213> ORGANISM: Orthohepadnaviridae hepatitis B virus

<400> SEQUENCE: 1534

Asp Val Val Leu Gly Ala Lys Ser Val
1               5

<210> SEQ ID NO 1535
<211> LENGTH: 10
<212> TYPE: PRT
<213> ORGANISM: Orthohepadnaviridae hepatitis B virus

<400> SEQUENCE: 1535

Glu Leu Leu Ser Phe Leu Pro Ser Asp Phe
1               5                   10

<210> SEQ ID NO 1536
<211> LENGTH: 11
<212> TYPE: PRT
<213> ORGANISM: Orthohepadnaviridae hepatitis B virus

<400> SEQUENCE: 1536

Glu Leu Leu Ser Phe Leu Pro Ser Asp Phe Phe
1               5                   10

<210> SEQ ID NO 1537
<211> LENGTH: 8
<212> TYPE: PRT
<213> ORGANISM: Orthohepadnaviridae hepatitis B virus

<400> SEQUENCE: 1537

Phe Ile Leu Leu Leu Cys Leu Ile
1               5

<210> SEQ ID NO 1538
<211> LENGTH: 9
<212> TYPE: PRT
<213> ORGANISM: Orthohepadnaviridae hepatitis B virus

<400> SEQUENCE: 1538

Phe Ile Leu Leu Leu Cys Leu Ile Phe
1               5

<210> SEQ ID NO 1539
<211> LENGTH: 10
<212> TYPE: PRT
<213> ORGANISM: Orthohepadnaviridae hepatitis B virus

<400> SEQUENCE: 1539

Phe Leu Phe Ile Leu Leu Leu Cys Leu Ile
1               5                   10

<210> SEQ ID NO 1540
<211> LENGTH: 11
<212> TYPE: PRT
<213> ORGANISM: Orthohepadnaviridae hepatitis B virus

<400> SEQUENCE: 1540

Phe Leu Phe Ile Leu Leu Leu Cys Leu Ile Phe
1               5                   10

<210> SEQ ID NO 1541
<211> LENGTH: 10
<212> TYPE: PRT
<213> ORGANISM: Orthohepadnaviridae hepatitis B virus

<400> SEQUENCE: 1541

Phe Leu Leu Ala Gln Phe Thr Ser Ala Ile
1               5                   10

<210> SEQ ID NO 1542
<211> LENGTH: 9

```
<212> TYPE: PRT
<213> ORGANISM: Orthohepadnaviridae hepatitis B virus

<400> SEQUENCE: 1542

Phe Leu Leu Thr Arg Ile Leu Thr Ile
1               5

<210> SEQ ID NO 1543
<211> LENGTH: 8
<212> TYPE: PRT
<213> ORGANISM: Orthohepadnaviridae hepatitis B virus

<400> SEQUENCE: 1543

Phe Leu Leu Val Leu Leu Asp Tyr
1               5

<210> SEQ ID NO 1544
<211> LENGTH: 11
<212> TYPE: PRT
<213> ORGANISM: Orthohepadnaviridae hepatitis B virus

<400> SEQUENCE: 1544

Phe Leu Leu Val Leu Leu Asp Tyr Gln Gly Met
1               5                   10

<210> SEQ ID NO 1545
<211> LENGTH: 11
<212> TYPE: PRT
<213> ORGANISM: Orthohepadnaviridae hepatitis B virus

<400> SEQUENCE: 1545

Phe Pro Ala Gly Gly Ser Ser Ser Gly Thr Val
1               5                   10

<210> SEQ ID NO 1546
<211> LENGTH: 10
<212> TYPE: PRT
<213> ORGANISM: Orthohepadnaviridae hepatitis B virus

<400> SEQUENCE: 1546

Phe Pro Asp His Gln Leu Asp Pro Ala Phe
1               5                   10

<210> SEQ ID NO 1547
<211> LENGTH: 9
<212> TYPE: PRT
<213> ORGANISM: Orthohepadnaviridae hepatitis B virus

<400> SEQUENCE: 1547

Phe Pro His Cys Leu Ala Phe Ser Tyr
1               5

<210> SEQ ID NO 1548
<211> LENGTH: 10
<212> TYPE: PRT
<213> ORGANISM: Orthohepadnaviridae hepatitis B virus

<400> SEQUENCE: 1548

Phe Pro His Cys Leu Ala Phe Ser Tyr Met
1               5                   10

<210> SEQ ID NO 1549
<211> LENGTH: 11
<212> TYPE: PRT
<213> ORGANISM: Orthohepadnaviridae hepatitis B virus
```

-continued

<400> SEQUENCE: 1549

Phe Pro Trp Leu Leu Gly Cys Ala Ala Asn Trp
1               5                   10

<210> SEQ ID NO 1550
<211> LENGTH: 8
<212> TYPE: PRT
<213> ORGANISM: Orthohepadnaviridae hepatitis B virus

<400> SEQUENCE: 1550

Phe Val Gly Leu Ser Pro Thr Val
1               5

<210> SEQ ID NO 1551
<211> LENGTH: 9
<212> TYPE: PRT
<213> ORGANISM: Orthohepadnaviridae hepatitis B virus

<400> SEQUENCE: 1551

Phe Val Gly Leu Ser Pro Thr Val Trp
1               5

<210> SEQ ID NO 1552
<211> LENGTH: 11
<212> TYPE: PRT
<213> ORGANISM: Orthohepadnaviridae hepatitis B virus

<400> SEQUENCE: 1552

Phe Val Leu Gly Gly Cys Arg His Lys Leu Val
1               5                   10

<210> SEQ ID NO 1553
<211> LENGTH: 9
<212> TYPE: PRT
<213> ORGANISM: Orthohepadnaviridae hepatitis B virus

<400> SEQUENCE: 1553

Gly Leu Leu Gly Phe Ala Ala Pro Phe
1               5

<210> SEQ ID NO 1554
<211> LENGTH: 10
<212> TYPE: PRT
<213> ORGANISM: Orthohepadnaviridae hepatitis B virus

<400> SEQUENCE: 1554

Gly Leu Ser Pro Phe Leu Leu Ala Gln Phe
1               5                   10

<210> SEQ ID NO 1555
<211> LENGTH: 10
<212> TYPE: PRT
<213> ORGANISM: Orthohepadnaviridae hepatitis B virus

<400> SEQUENCE: 1555

Gly Leu Ser Pro Thr Val Trp Leu Ser Val
1               5                   10

<210> SEQ ID NO 1556
<211> LENGTH: 11
<212> TYPE: PRT
<213> ORGANISM: Orthohepadnaviridae hepatitis B virus

<400> SEQUENCE: 1556

```
Gly Leu Ser Pro Thr Val Trp Leu Ser Val Ile
1               5                   10

<210> SEQ ID NO 1557
<211> LENGTH: 10
<212> TYPE: PRT
<213> ORGANISM: Orthohepadnaviridae hepatitis B virus

<400> SEQUENCE: 1557

Gly Met Asp Ile Asp Pro Tyr Lys Glu Phe
1               5                   10

<210> SEQ ID NO 1558
<211> LENGTH: 10
<212> TYPE: PRT
<213> ORGANISM: Orthohepadnaviridae hepatitis B virus

<400> SEQUENCE: 1558

Gly Pro Leu Leu Val Leu Gln Ala Gly Phe
1               5                   10

<210> SEQ ID NO 1559
<211> LENGTH: 11
<212> TYPE: PRT
<213> ORGANISM: Orthohepadnaviridae hepatitis B virus

<400> SEQUENCE: 1559

Gly Pro Leu Leu Val Leu Gln Ala Gly Phe Phe
1               5                   10

<210> SEQ ID NO 1560
<211> LENGTH: 10
<212> TYPE: PRT
<213> ORGANISM: Orthohepadnaviridae hepatitis B virus

<400> SEQUENCE: 1560

Gly Val Trp Ile Arg Thr Pro Pro Ala Tyr
1               5                   10

<210> SEQ ID NO 1561
<211> LENGTH: 10
<212> TYPE: PRT
<213> ORGANISM: Orthohepadnaviridae hepatitis B virus

<400> SEQUENCE: 1561

His Leu Asn Pro Asn Lys Thr Lys Arg Trp
1               5                   10

<210> SEQ ID NO 1562
<211> LENGTH: 9
<212> TYPE: PRT
<213> ORGANISM: Orthohepadnaviridae hepatitis B virus

<400> SEQUENCE: 1562

His Leu Ser Leu Arg Gly Leu Pro Val
1               5

<210> SEQ ID NO 1563
<211> LENGTH: 8
<212> TYPE: PRT
<213> ORGANISM: Orthohepadnaviridae hepatitis B virus

<400> SEQUENCE: 1563

His Leu Tyr Ser His Pro Ile Ile
```

```
<210> SEQ ID NO 1564
<211> LENGTH: 11
<212> TYPE: PRT
<213> ORGANISM: Orthohepadnaviridae hepatitis B virus

<400> SEQUENCE: 1564

His Leu Tyr Ser His Pro Ile Ile Leu Gly Phe
 1               5                   10

<210> SEQ ID NO 1565
<211> LENGTH: 10
<212> TYPE: PRT
<213> ORGANISM: Orthohepadnaviridae hepatitis B virus

<400> SEQUENCE: 1565

His Pro Ala Ala Met Pro His Leu Leu Val
 1               5                   10

<210> SEQ ID NO 1566
<211> LENGTH: 10
<212> TYPE: PRT
<213> ORGANISM: Orthohepadnaviridae hepatitis B virus

<400> SEQUENCE: 1566

His Pro Ile Ile Leu Gly Phe Arg Lys Ile
 1               5                   10

<210> SEQ ID NO 1567
<211> LENGTH: 8
<212> TYPE: PRT
<213> ORGANISM: Orthohepadnaviridae hepatitis B virus

<400> SEQUENCE: 1567

Ile Ile Leu Gly Phe Arg Lys Ile
 1               5

<210> SEQ ID NO 1568
<211> LENGTH: 10
<212> TYPE: PRT
<213> ORGANISM: Orthohepadnaviridae hepatitis B virus

<400> SEQUENCE: 1568

Ile Ile Leu Gly Phe Arg Lys Ile Pro Met
 1               5                   10

<210> SEQ ID NO 1569
<211> LENGTH: 8
<212> TYPE: PRT
<213> ORGANISM: Orthohepadnaviridae hepatitis B virus

<400> SEQUENCE: 1569

Ile Leu Cys Trp Gly Glu Leu Met
 1               5

<210> SEQ ID NO 1570
<211> LENGTH: 9
<212> TYPE: PRT
<213> ORGANISM: Orthohepadnaviridae hepatitis B virus

<400> SEQUENCE: 1570

Ile Leu Gly Phe Arg Lys Ile Pro Met
 1               5
```

```
<210> SEQ ID NO 1571
<211> LENGTH: 8
<212> TYPE: PRT
<213> ORGANISM: Orthohepadnaviridae hepatitis B virus

<400> SEQUENCE: 1571

Ile Leu Leu Leu Cys Leu Ile Phe
1               5

<210> SEQ ID NO 1572
<211> LENGTH: 11
<212> TYPE: PRT
<213> ORGANISM: Orthohepadnaviridae hepatitis B virus

<400> SEQUENCE: 1572

Ile Leu Leu Leu Cys Leu Ile Phe Leu Leu Val
1               5                   10

<210> SEQ ID NO 1573
<211> LENGTH: 8
<212> TYPE: PRT
<213> ORGANISM: Orthohepadnaviridae hepatitis B virus

<400> SEQUENCE: 1573

Ile Leu Arg Gly Thr Ser Phe Val
1               5

<210> SEQ ID NO 1574
<211> LENGTH: 9
<212> TYPE: PRT
<213> ORGANISM: Orthohepadnaviridae hepatitis B virus

<400> SEQUENCE: 1574

Ile Leu Arg Gly Thr Ser Phe Val Tyr
1               5

<210> SEQ ID NO 1575
<211> LENGTH: 10
<212> TYPE: PRT
<213> ORGANISM: Orthohepadnaviridae hepatitis B virus

<400> SEQUENCE: 1575

Ile Leu Arg Gly Thr Ser Phe Val Tyr Val
1               5                   10

<210> SEQ ID NO 1576
<211> LENGTH: 10
<212> TYPE: PRT
<213> ORGANISM: Orthohepadnaviridae hepatitis B virus

<400> SEQUENCE: 1576

Ile Leu Ser Thr Leu Pro Glu Thr Thr Val
1               5                   10

<210> SEQ ID NO 1577
<211> LENGTH: 11
<212> TYPE: PRT
<213> ORGANISM: Orthohepadnaviridae hepatitis B virus

<400> SEQUENCE: 1577

Ile Leu Ser Thr Leu Pro Glu Thr Thr Val Val
1               5                   10

<210> SEQ ID NO 1578
```

```
<211> LENGTH: 11
<212> TYPE: PRT
<213> ORGANISM: Orthohepadnaviridae hepatitis B virus

<400> SEQUENCE: 1578

Ile Leu Thr Ile Pro Gln Ser Leu Asp Ser Trp
 1               5                  10

<210> SEQ ID NO 1579
<211> LENGTH: 9
<212> TYPE: PRT
<213> ORGANISM: Orthohepadnaviridae hepatitis B virus

<400> SEQUENCE: 1579

Ile Pro Ile Pro Ser Ser Trp Ala Phe
 1               5

<210> SEQ ID NO 1580
<211> LENGTH: 10
<212> TYPE: PRT
<213> ORGANISM: Orthohepadnaviridae hepatitis B virus

<400> SEQUENCE: 1580

Ile Pro Met Gly Val Gly Leu Ser Pro Phe
 1               5                  10

<210> SEQ ID NO 1581
<211> LENGTH: 8
<212> TYPE: PRT
<213> ORGANISM: Orthohepadnaviridae hepatitis B virus

<400> SEQUENCE: 1581

Ile Pro Gln Ser Leu Asp Ser Trp
 1               5

<210> SEQ ID NO 1582
<211> LENGTH: 9
<212> TYPE: PRT
<213> ORGANISM: Orthohepadnaviridae hepatitis B virus

<400> SEQUENCE: 1582

Ile Pro Gln Ser Leu Asp Ser Trp Trp
 1               5

<210> SEQ ID NO 1583
<211> LENGTH: 10
<212> TYPE: PRT
<213> ORGANISM: Orthohepadnaviridae hepatitis B virus

<400> SEQUENCE: 1583

Ile Pro Trp Thr His Lys Val Gly Asn Phe
 1               5                  10

<210> SEQ ID NO 1584
<211> LENGTH: 11
<212> TYPE: PRT
<213> ORGANISM: Orthohepadnaviridae hepatitis B virus

<400> SEQUENCE: 1584

Ile Val Gly Leu Leu Gly Phe Ala Ala Pro Phe
 1               5                  10

<210> SEQ ID NO 1585
<211> LENGTH: 11
<212> TYPE: PRT
```

<213> ORGANISM: Orthohepadnaviridae hepatitis B virus

<400> SEQUENCE: 1585

Lys Ile Pro Met Gly Val Gly Leu Ser Pro Phe
1               5                   10

<210> SEQ ID NO 1586
<211> LENGTH: 8
<212> TYPE: PRT
<213> ORGANISM: Orthohepadnaviridae hepatitis B virus

<400> SEQUENCE: 1586

Lys Leu Cys Leu Gly Trp Leu Trp
1               5

<210> SEQ ID NO 1587
<211> LENGTH: 10
<212> TYPE: PRT
<213> ORGANISM: Orthohepadnaviridae hepatitis B virus

<400> SEQUENCE: 1587

Lys Leu Cys Leu Gly Trp Leu Trp Gly Met
1               5                   10

<210> SEQ ID NO 1588
<211> LENGTH: 9
<212> TYPE: PRT
<213> ORGANISM: Orthohepadnaviridae hepatitis B virus

<400> SEQUENCE: 1588

Lys Leu His Leu Tyr Ser His Pro Ile
1               5

<210> SEQ ID NO 1589
<211> LENGTH: 10
<212> TYPE: PRT
<213> ORGANISM: Orthohepadnaviridae hepatitis B virus

<400> SEQUENCE: 1589

Lys Leu His Leu Tyr Ser His Pro Ile Ile
1               5                   10

<210> SEQ ID NO 1590
<211> LENGTH: 8
<212> TYPE: PRT
<213> ORGANISM: Orthohepadnaviridae hepatitis B virus

<400> SEQUENCE: 1590

Lys Leu Ile Met Pro Ala Arg Phe
1               5

<210> SEQ ID NO 1591
<211> LENGTH: 9
<212> TYPE: PRT
<213> ORGANISM: Orthohepadnaviridae hepatitis B virus

<400> SEQUENCE: 1591

Lys Leu Ile Met Pro Ala Arg Phe Tyr
1               5

<210> SEQ ID NO 1592
<211> LENGTH: 8
<212> TYPE: PRT
<213> ORGANISM: Orthohepadnaviridae hepatitis B virus

```
<400> SEQUENCE: 1592

Lys Leu Pro Val Asn Arg Pro Ile
 1               5

<210> SEQ ID NO 1593
<211> LENGTH: 10
<212> TYPE: PRT
<213> ORGANISM: Orthohepadnaviridae hepatitis B virus

<400> SEQUENCE: 1593

Lys Leu Pro Val Asn Arg Pro Ile Asp Trp
 1               5                  10

<210> SEQ ID NO 1594
<211> LENGTH: 10
<212> TYPE: PRT
<213> ORGANISM: Orthohepadnaviridae hepatitis B virus

<400> SEQUENCE: 1594

Lys Gln Ala Phe Thr Phe Ser Pro Thr Tyr
 1               5                  10

<210> SEQ ID NO 1595
<211> LENGTH: 9
<212> TYPE: PRT
<213> ORGANISM: Orthohepadnaviridae hepatitis B virus

<400> SEQUENCE: 1595

Lys Val Gly Asn Phe Thr Gly Leu Tyr
 1               5

<210> SEQ ID NO 1596
<211> LENGTH: 10
<212> TYPE: PRT
<213> ORGANISM: Orthohepadnaviridae hepatitis B virus

<400> SEQUENCE: 1596

Leu Ile Phe Leu Leu Val Leu Leu Asp Tyr
 1               5                  10

<210> SEQ ID NO 1597
<211> LENGTH: 8
<212> TYPE: PRT
<213> ORGANISM: Orthohepadnaviridae hepatitis B virus

<400> SEQUENCE: 1597

Leu Ile Met Pro Ala Arg Phe Tyr
 1               5

<210> SEQ ID NO 1598
<211> LENGTH: 9
<212> TYPE: PRT
<213> ORGANISM: Orthohepadnaviridae hepatitis B virus

<400> SEQUENCE: 1598

Leu Leu Ala Gln Phe Thr Ser Ala Ile
 1               5

<210> SEQ ID NO 1599
<211> LENGTH: 9
<212> TYPE: PRT
<213> ORGANISM: Orthohepadnaviridae hepatitis B virus

<400> SEQUENCE: 1599
```

```
Leu Leu Cys Leu Ile Phe Leu Leu Val
1               5

<210> SEQ ID NO 1600
<211> LENGTH: 9
<212> TYPE: PRT
<213> ORGANISM: Orthohepadnaviridae hepatitis B virus

<400> SEQUENCE: 1600

Leu Leu Asp Thr Ala Ser Ala Leu Tyr
1               5

<210> SEQ ID NO 1601
<211> LENGTH: 10
<212> TYPE: PRT
<213> ORGANISM: Orthohepadnaviridae hepatitis B virus

<400> SEQUENCE: 1601

Leu Leu Asp Tyr Gln Gly Met Leu Pro Val
1               5                   10

<210> SEQ ID NO 1602
<211> LENGTH: 8
<212> TYPE: PRT
<213> ORGANISM: Orthohepadnaviridae hepatitis B virus

<400> SEQUENCE: 1602

Leu Leu Gly Cys Ala Ala Asn Trp
1               5

<210> SEQ ID NO 1603
<211> LENGTH: 9
<212> TYPE: PRT
<213> ORGANISM: Orthohepadnaviridae hepatitis B virus

<400> SEQUENCE: 1603

Leu Leu Gly Cys Ala Ala Asn Trp Ile
1               5

<210> SEQ ID NO 1604
<211> LENGTH: 8
<212> TYPE: PRT
<213> ORGANISM: Orthohepadnaviridae hepatitis B virus

<400> SEQUENCE: 1604

Leu Leu Gly Phe Ala Ala Pro Phe
1               5

<210> SEQ ID NO 1605
<211> LENGTH: 11
<212> TYPE: PRT
<213> ORGANISM: Orthohepadnaviridae hepatitis B virus

<400> SEQUENCE: 1605

Leu Leu Gly Trp Ser Pro Gln Ala Gln Gly Ile
1               5                   10

<210> SEQ ID NO 1606
<211> LENGTH: 10
<212> TYPE: PRT
<213> ORGANISM: Orthohepadnaviridae hepatitis B virus

<400> SEQUENCE: 1606

Leu Leu Leu Cys Leu Ile Phe Leu Leu Val
1               5                   10
```

```
<210> SEQ ID NO 1607
<211> LENGTH: 9
<212> TYPE: PRT
<213> ORGANISM: Orthohepadnaviridae hepatitis B virus

<400> SEQUENCE: 1607

Leu Leu Pro Ile Phe Phe Cys Leu Trp
 1               5

<210> SEQ ID NO 1608
<211> LENGTH: 10
<212> TYPE: PRT
<213> ORGANISM: Orthohepadnaviridae hepatitis B virus

<400> SEQUENCE: 1608

Leu Leu Pro Ile Phe Phe Cys Leu Trp Val
 1               5                  10

<210> SEQ ID NO 1609
<211> LENGTH: 11
<212> TYPE: PRT
<213> ORGANISM: Orthohepadnaviridae hepatitis B virus

<400> SEQUENCE: 1609

Leu Leu Pro Ile Phe Phe Cys Leu Trp Val Tyr
 1               5                  10

<210> SEQ ID NO 1610
<211> LENGTH: 9
<212> TYPE: PRT
<213> ORGANISM: Orthohepadnaviridae hepatitis B virus

<400> SEQUENCE: 1610

Leu Leu Ser Phe Leu Pro Ser Asp Phe
 1               5

<210> SEQ ID NO 1611
<211> LENGTH: 10
<212> TYPE: PRT
<213> ORGANISM: Orthohepadnaviridae hepatitis B virus

<400> SEQUENCE: 1611

Leu Leu Ser Phe Leu Pro Ser Asp Phe Phe
 1               5                  10

<210> SEQ ID NO 1612
<211> LENGTH: 8
<212> TYPE: PRT
<213> ORGANISM: Orthohepadnaviridae hepatitis B virus

<400> SEQUENCE: 1612

Leu Leu Ser Ser Asn Leu Ser Trp
 1               5

<210> SEQ ID NO 1613
<211> LENGTH: 8
<212> TYPE: PRT
<213> ORGANISM: Orthohepadnaviridae hepatitis B virus

<400> SEQUENCE: 1613

Leu Leu Thr Arg Ile Leu Thr Ile
 1               5
```

<210> SEQ ID NO 1614
<211> LENGTH: 8
<212> TYPE: PRT
<213> ORGANISM: Orthohepadnaviridae hepatitis B virus

<400> SEQUENCE: 1614

Leu Leu Val Gly Ser Ser Gly Leu
1               5

<210> SEQ ID NO 1615
<211> LENGTH: 10
<212> TYPE: PRT
<213> ORGANISM: Orthohepadnaviridae hepatitis B virus

<400> SEQUENCE: 1615

Leu Leu Val Leu Leu Asp Tyr Gln Gly Met
1               5                   10

<210> SEQ ID NO 1616
<211> LENGTH: 8
<212> TYPE: PRT
<213> ORGANISM: Orthohepadnaviridae hepatitis B virus

<400> SEQUENCE: 1616

Leu Leu Val Leu Gln Ala Gly Phe
1               5

<210> SEQ ID NO 1617
<211> LENGTH: 9
<212> TYPE: PRT
<213> ORGANISM: Orthohepadnaviridae hepatitis B virus

<400> SEQUENCE: 1617

Leu Leu Val Leu Gln Ala Gly Phe Phe
1               5

<210> SEQ ID NO 1618
<211> LENGTH: 8
<212> TYPE: PRT
<213> ORGANISM: Orthohepadnaviridae hepatitis B virus

<400> SEQUENCE: 1618

Leu Leu Val Pro Phe Val Gln Trp
1               5

<210> SEQ ID NO 1619
<211> LENGTH: 9
<212> TYPE: PRT
<213> ORGANISM: Orthohepadnaviridae hepatitis B virus

<400> SEQUENCE: 1619

Leu Leu Val Pro Phe Val Gln Trp Phe
1               5

<210> SEQ ID NO 1620
<211> LENGTH: 10
<212> TYPE: PRT
<213> ORGANISM: Orthohepadnaviridae hepatitis B virus

<400> SEQUENCE: 1620

Leu Leu Val Pro Phe Val Gln Trp Phe Val
1               5                   10

<210> SEQ ID NO 1621
<211> LENGTH: 11

```
<212> TYPE: PRT
<213> ORGANISM: Orthohepadnaviridae hepatitis B virus

<400> SEQUENCE: 1621

Leu Leu Trp Phe His Ile Ser Cys Leu Thr Phe
1               5                   10

<210> SEQ ID NO 1622
<211> LENGTH: 8
<212> TYPE: PRT
<213> ORGANISM: Orthohepadnaviridae hepatitis B virus

<400> SEQUENCE: 1622

Leu Met Pro Leu Tyr Ala Cys Ile
1               5

<210> SEQ ID NO 1623
<211> LENGTH: 8
<212> TYPE: PRT
<213> ORGANISM: Orthohepadnaviridae hepatitis B virus

<400> SEQUENCE: 1623

Leu Pro Ile Phe Phe Cys Leu Trp
1               5

<210> SEQ ID NO 1624
<211> LENGTH: 9
<212> TYPE: PRT
<213> ORGANISM: Orthohepadnaviridae hepatitis B virus

<400> SEQUENCE: 1624

Leu Pro Ile Phe Phe Cys Leu Trp Val
1               5

<210> SEQ ID NO 1625
<211> LENGTH: 10
<212> TYPE: PRT
<213> ORGANISM: Orthohepadnaviridae hepatitis B virus

<400> SEQUENCE: 1625

Leu Pro Ile Phe Phe Cys Leu Trp Val Tyr
1               5                   10

<210> SEQ ID NO 1626
<211> LENGTH: 11
<212> TYPE: PRT
<213> ORGANISM: Orthohepadnaviridae hepatitis B virus

<400> SEQUENCE: 1626

Leu Pro Ile Phe Phe Cys Leu Trp Val Tyr Ile
1               5                   10

<210> SEQ ID NO 1627
<211> LENGTH: 10
<212> TYPE: PRT
<213> ORGANISM: Orthohepadnaviridae hepatitis B virus

<400> SEQUENCE: 1627

Leu Pro Leu Asp Lys Gly Ile Lys Pro Tyr
1               5                   10

<210> SEQ ID NO 1628
<211> LENGTH: 11
<212> TYPE: PRT
<213> ORGANISM: Orthohepadnaviridae hepatitis B virus
```

```
<400> SEQUENCE: 1628

Leu Pro Leu Asp Lys Gly Ile Lys Pro Tyr Tyr
1               5                   10

<210> SEQ ID NO 1629
<211> LENGTH: 9
<212> TYPE: PRT
<213> ORGANISM: Orthohepadnaviridae hepatitis B virus

<400> SEQUENCE: 1629

Leu Pro Val Asn Arg Pro Ile Asp Trp
1               5

<210> SEQ ID NO 1630
<211> LENGTH: 11
<212> TYPE: PRT
<213> ORGANISM: Orthohepadnaviridae hepatitis B virus

<400> SEQUENCE: 1630

Leu Pro Val Asn Arg Pro Ile Asp Trp Lys Val
1               5                   10

<210> SEQ ID NO 1631
<211> LENGTH: 11
<212> TYPE: PRT
<213> ORGANISM: Orthohepadnaviridae hepatitis B virus

<400> SEQUENCE: 1631

Leu Gln Ala Gly Phe Phe Leu Leu Thr Arg Ile
1               5                   10

<210> SEQ ID NO 1632
<211> LENGTH: 9
<212> TYPE: PRT
<213> ORGANISM: Orthohepadnaviridae hepatitis B virus

<400> SEQUENCE: 1632

Leu Val Leu Leu Asp Tyr Gln Gly Met
1               5

<210> SEQ ID NO 1633
<211> LENGTH: 8
<212> TYPE: PRT
<213> ORGANISM: Orthohepadnaviridae hepatitis B virus

<400> SEQUENCE: 1633

Leu Val Leu Gln Ala Gly Phe Phe
1               5

<210> SEQ ID NO 1634
<211> LENGTH: 8
<212> TYPE: PRT
<213> ORGANISM: Orthohepadnaviridae hepatitis B virus

<400> SEQUENCE: 1634

Leu Val Pro Phe Val Gln Trp Phe
1               5

<210> SEQ ID NO 1635
<211> LENGTH: 9
<212> TYPE: PRT
<213> ORGANISM: Orthohepadnaviridae hepatitis B virus

<400> SEQUENCE: 1635
```

Leu Val Pro Phe Val Gln Trp Phe Val
1               5

<210> SEQ ID NO 1636
<211> LENGTH: 8
<212> TYPE: PRT
<213> ORGANISM: Orthohepadnaviridae hepatitis B virus

<400> SEQUENCE: 1636

Leu Val Ser Phe Gly Val Trp Ile
1               5

<210> SEQ ID NO 1637
<211> LENGTH: 8
<212> TYPE: PRT
<213> ORGANISM: Orthohepadnaviridae hepatitis B virus

<400> SEQUENCE: 1637

Leu Val Val Asp Phe Ser Gln Phe
1               5

<210> SEQ ID NO 1638
<211> LENGTH: 10
<212> TYPE: PRT
<213> ORGANISM: Orthohepadnaviridae hepatitis B virus

<400> SEQUENCE: 1638

Met Met Trp Tyr Trp Gly Pro Ser Leu Tyr
1               5                   10

<210> SEQ ID NO 1639
<211> LENGTH: 8
<212> TYPE: PRT
<213> ORGANISM: Orthohepadnaviridae hepatitis B virus

<400> SEQUENCE: 1639

Met Pro Leu Ser Tyr Gln His Phe
1               5

<210> SEQ ID NO 1640
<211> LENGTH: 8
<212> TYPE: PRT
<213> ORGANISM: Orthohepadnaviridae hepatitis B virus

<400> SEQUENCE: 1640

Met Gln Trp Asn Ser Thr Thr Phe
1               5

<210> SEQ ID NO 1641
<211> LENGTH: 9
<212> TYPE: PRT
<213> ORGANISM: Orthohepadnaviridae hepatitis B virus

<400> SEQUENCE: 1641

Asn Leu Gly Asn Leu Asn Val Ser Ile
1               5

<210> SEQ ID NO 1642
<211> LENGTH: 11
<212> TYPE: PRT
<213> ORGANISM: Orthohepadnaviridae hepatitis B virus

<400> SEQUENCE: 1642

Asn Leu Gly Asn Leu Asn Val Ser Ile Pro Trp

```
1               5              10
```

<210> SEQ ID NO 1643
<211> LENGTH: 9
<212> TYPE: PRT
<213> ORGANISM: Orthohepadnaviridae hepatitis B virus

<400> SEQUENCE: 1643

```
Asn Leu Leu Ser Ser Asn Leu Ser Trp
1               5
```

<210> SEQ ID NO 1644
<211> LENGTH: 8
<212> TYPE: PRT
<213> ORGANISM: Orthohepadnaviridae hepatitis B virus

<400> SEQUENCE: 1644

```
Asn Leu Asn Val Ser Ile Pro Trp
1               5
```

<210> SEQ ID NO 1645
<211> LENGTH: 10
<212> TYPE: PRT
<213> ORGANISM: Orthohepadnaviridae hepatitis B virus

<400> SEQUENCE: 1645

```
Asn Leu Ser Val Pro Asn Pro Leu Gly Phe
1               5              10
```

<210> SEQ ID NO 1646
<211> LENGTH: 9
<212> TYPE: PRT
<213> ORGANISM: Orthohepadnaviridae hepatitis B virus

<400> SEQUENCE: 1646

```
Asn Leu Ser Trp Leu Ser Leu Asp Val
1               5
```

<210> SEQ ID NO 1647
<211> LENGTH: 8
<212> TYPE: PRT
<213> ORGANISM: Orthohepadnaviridae hepatitis B virus

<400> SEQUENCE: 1647

```
Asn Pro Asn Lys Thr Lys Arg Trp
1               5
```

<210> SEQ ID NO 1648
<211> LENGTH: 10
<212> TYPE: PRT
<213> ORGANISM: Orthohepadnaviridae hepatitis B virus

<400> SEQUENCE: 1648

```
Asn Pro Asn Lys Thr Lys Arg Trp Gly Tyr
1               5              10
```

<210> SEQ ID NO 1649
<211> LENGTH: 10
<212> TYPE: PRT
<213> ORGANISM: Orthohepadnaviridae hepatitis B virus

<400> SEQUENCE: 1649

```
Asn Val Ser Ile Pro Trp Thr His Lys Val
1               5              10
```

```
<210> SEQ ID NO 1650
<211> LENGTH: 10
<212> TYPE: PRT
<213> ORGANISM: Orthohepadnaviridae hepatitis B virus

<400> SEQUENCE: 1650

Pro Ile Asp Trp Lys Val Cys Gln Arg Ile
1               5                   10

<210> SEQ ID NO 1651
<211> LENGTH: 11
<212> TYPE: PRT
<213> ORGANISM: Orthohepadnaviridae hepatitis B virus

<400> SEQUENCE: 1651

Pro Ile Asp Trp Lys Val Cys Gln Arg Ile Val
1               5                   10

<210> SEQ ID NO 1652
<211> LENGTH: 8
<212> TYPE: PRT
<213> ORGANISM: Orthohepadnaviridae hepatitis B virus

<400> SEQUENCE: 1652

Pro Ile Phe Phe Cys Leu Trp Val
1               5

<210> SEQ ID NO 1653
<211> LENGTH: 9
<212> TYPE: PRT
<213> ORGANISM: Orthohepadnaviridae hepatitis B virus

<400> SEQUENCE: 1653

Pro Ile Phe Phe Cys Leu Trp Val Tyr
1               5

<210> SEQ ID NO 1654
<211> LENGTH: 10
<212> TYPE: PRT
<213> ORGANISM: Orthohepadnaviridae hepatitis B virus

<400> SEQUENCE: 1654

Pro Ile Phe Phe Cys Leu Trp Val Tyr Ile
1               5                   10

<210> SEQ ID NO 1655
<211> LENGTH: 9
<212> TYPE: PRT
<213> ORGANISM: Orthohepadnaviridae hepatitis B virus

<400> SEQUENCE: 1655

Pro Ile Ile Leu Gly Phe Arg Lys Ile
1               5

<210> SEQ ID NO 1656
<211> LENGTH: 11
<212> TYPE: PRT
<213> ORGANISM: Orthohepadnaviridae hepatitis B virus

<400> SEQUENCE: 1656

Pro Ile Ile Leu Gly Phe Arg Lys Ile Pro Met
1               5                   10

<210> SEQ ID NO 1657
```

-continued

<211> LENGTH: 11
<212> TYPE: PRT
<213> ORGANISM: Orthohepadnaviridae hepatitis B virus

<400> SEQUENCE: 1657

Pro Ile Leu Ser Thr Leu Pro Glu Thr Thr Val
1               5                   10

<210> SEQ ID NO 1658
<211> LENGTH: 8
<212> TYPE: PRT
<213> ORGANISM: Orthohepadnaviridae hepatitis B virus

<400> SEQUENCE: 1658

Pro Ile Pro Ser Ser Trp Ala Phe
1               5

<210> SEQ ID NO 1659
<211> LENGTH: 9
<212> TYPE: PRT
<213> ORGANISM: Orthohepadnaviridae hepatitis B virus

<400> SEQUENCE: 1659

Pro Leu Asp Lys Gly Ile Lys Pro Tyr
1               5

<210> SEQ ID NO 1660
<211> LENGTH: 10
<212> TYPE: PRT
<213> ORGANISM: Orthohepadnaviridae hepatitis B virus

<400> SEQUENCE: 1660

Pro Leu Asp Lys Gly Ile Lys Pro Tyr Tyr
1               5                   10

<210> SEQ ID NO 1661
<211> LENGTH: 10
<212> TYPE: PRT
<213> ORGANISM: Orthohepadnaviridae hepatitis B virus

<400> SEQUENCE: 1661

Pro Leu Leu Pro Ile Phe Phe Cys Leu Trp
1               5                   10

<210> SEQ ID NO 1662
<211> LENGTH: 11
<212> TYPE: PRT
<213> ORGANISM: Orthohepadnaviridae hepatitis B virus

<400> SEQUENCE: 1662

Pro Leu Leu Pro Ile Phe Phe Cys Leu Trp Val
1               5                   10

<210> SEQ ID NO 1663
<211> LENGTH: 9
<212> TYPE: PRT
<213> ORGANISM: Orthohepadnaviridae hepatitis B virus

<400> SEQUENCE: 1663

Pro Leu Leu Val Leu Gln Ala Gly Phe
1               5

<210> SEQ ID NO 1664
<211> LENGTH: 10
<212> TYPE: PRT

-continued

<213> ORGANISM: Orthohepadnaviridae hepatitis B virus

<400> SEQUENCE: 1664

Pro Leu Leu Val Leu Gln Ala Gly Phe Phe
1               5                   10

<210> SEQ ID NO 1665
<211> LENGTH: 9
<212> TYPE: PRT
<213> ORGANISM: Orthohepadnaviridae hepatitis B virus

<400> SEQUENCE: 1665

Pro Met Gly Val Gly Leu Ser Pro Phe
1               5

<210> SEQ ID NO 1666
<211> LENGTH: 11
<212> TYPE: PRT
<213> ORGANISM: Orthohepadnaviridae hepatitis B virus

<400> SEQUENCE: 1666

Pro Pro Ala Tyr Arg Pro Pro Asn Ala Pro Ile
1               5                   10

<210> SEQ ID NO 1667
<211> LENGTH: 9
<212> TYPE: PRT
<213> ORGANISM: Orthohepadnaviridae hepatitis B virus

<400> SEQUENCE: 1667

Pro Pro His Gly Gly Leu Leu Gly Trp
1               5

<210> SEQ ID NO 1668
<211> LENGTH: 11
<212> TYPE: PRT
<213> ORGANISM: Orthohepadnaviridae hepatitis B virus

<400> SEQUENCE: 1668

Pro Gln Ala Met Gln Trp Asn Ser Thr Thr Phe
1               5                   10

<210> SEQ ID NO 1669
<211> LENGTH: 8
<212> TYPE: PRT
<213> ORGANISM: Orthohepadnaviridae hepatitis B virus

<400> SEQUENCE: 1669

Pro Gln Ser Leu Asp Ser Trp Trp
1               5

<210> SEQ ID NO 1670
<211> LENGTH: 8
<212> TYPE: PRT
<213> ORGANISM: Orthohepadnaviridae hepatitis B virus

<400> SEQUENCE: 1670

Pro Val Asn Arg Pro Ile Asp Trp
1               5

<210> SEQ ID NO 1671
<211> LENGTH: 10
<212> TYPE: PRT
<213> ORGANISM: Orthohepadnaviridae hepatitis B virus

```
<400> SEQUENCE: 1671

Pro Val Asn Arg Pro Ile Asp Trp Lys Val
1               5                   10

<210> SEQ ID NO 1672
<211> LENGTH: 8
<212> TYPE: PRT
<213> ORGANISM: Orthohepadnaviridae hepatitis B virus

<400> SEQUENCE: 1672

Gln Leu Asp Pro Ala Arg Asp Val
1               5

<210> SEQ ID NO 1673
<211> LENGTH: 11
<212> TYPE: PRT
<213> ORGANISM: Orthohepadnaviridae hepatitis B virus

<400> SEQUENCE: 1673

Gln Val Phe Ala Asp Ala Thr Pro Thr Gly Trp
1               5                   10

<210> SEQ ID NO 1674
<211> LENGTH: 8
<212> TYPE: PRT
<213> ORGANISM: Orthohepadnaviridae hepatitis B virus

<400> SEQUENCE: 1674

Arg Ile Val Gly Leu Leu Gly Phe
1               5

<210> SEQ ID NO 1675
<211> LENGTH: 10
<212> TYPE: PRT
<213> ORGANISM: Orthohepadnaviridae hepatitis B virus

<400> SEQUENCE: 1675

Arg Leu Lys Leu Ile Met Pro Ala Arg Phe
1               5                   10

<210> SEQ ID NO 1676
<211> LENGTH: 11
<212> TYPE: PRT
<213> ORGANISM: Orthohepadnaviridae hepatitis B virus

<400> SEQUENCE: 1676

Arg Leu Lys Leu Ile Met Pro Ala Arg Phe Tyr
1               5                   10

<210> SEQ ID NO 1677
<211> LENGTH: 9
<212> TYPE: PRT
<213> ORGANISM: Orthohepadnaviridae hepatitis B virus

<400> SEQUENCE: 1677

Arg Leu Val Val Asp Phe Ser Gln Phe
1               5

<210> SEQ ID NO 1678
<211> LENGTH: 11
<212> TYPE: PRT
<213> ORGANISM: Orthohepadnaviridae hepatitis B virus

<400> SEQUENCE: 1678
```

-continued

Arg Pro Ile Asp Trp Lys Val Cys Gln Arg Ile
1               5                   10

<210> SEQ ID NO 1679
<211> LENGTH: 11
<212> TYPE: PRT
<213> ORGANISM: Orthohepadnaviridae hepatitis B virus

<400> SEQUENCE: 1679

Arg Gln Ala Ile Leu Cys Trp Gly Glu Leu Met
1               5                   10

<210> SEQ ID NO 1680
<211> LENGTH: 8
<212> TYPE: PRT
<213> ORGANISM: Orthohepadnaviridae hepatitis B virus

<400> SEQUENCE: 1680

Arg Gln Leu Leu Trp Phe His Ile
1               5

<210> SEQ ID NO 1681
<211> LENGTH: 10
<212> TYPE: PRT
<213> ORGANISM: Orthohepadnaviridae hepatitis B virus

<400> SEQUENCE: 1681

Arg Val His Phe Ala Ser Pro Leu His Val
1               5                   10

<210> SEQ ID NO 1682
<211> LENGTH: 9
<212> TYPE: PRT
<213> ORGANISM: Orthohepadnaviridae hepatitis B virus

<400> SEQUENCE: 1682

Arg Val Thr Gly Gly Val Phe Leu Val
1               5

<210> SEQ ID NO 1683
<211> LENGTH: 8
<212> TYPE: PRT
<213> ORGANISM: Orthohepadnaviridae hepatitis B virus

<400> SEQUENCE: 1683

Ser Ile Pro Trp Thr His Lys Val
1               5

<210> SEQ ID NO 1684
<211> LENGTH: 11
<212> TYPE: PRT
<213> ORGANISM: Orthohepadnaviridae hepatitis B virus

<400> SEQUENCE: 1684

Ser Ile Pro Trp Thr His Lys Val Gly Asn Phe
1               5                   10

<210> SEQ ID NO 1685
<211> LENGTH: 11
<212> TYPE: PRT
<213> ORGANISM: Orthohepadnaviridae hepatitis B virus

<400> SEQUENCE: 1685

Ser Leu Asp Ser Trp Trp Thr Ser Leu Asn Phe
1               5                   10

<210> SEQ ID NO 1686
<211> LENGTH: 8
<212> TYPE: PRT
<213> ORGANISM: Orthohepadnaviridae hepatitis B virus

<400> SEQUENCE: 1686

Ser Leu Asp Val Ser Ala Ala Phe
1               5

<210> SEQ ID NO 1687
<211> LENGTH: 9
<212> TYPE: PRT
<213> ORGANISM: Orthohepadnaviridae hepatitis B virus

<400> SEQUENCE: 1687

Ser Leu Asp Val Ser Ala Ala Phe Tyr
1               5

<210> SEQ ID NO 1688
<211> LENGTH: 9
<212> TYPE: PRT
<213> ORGANISM: Orthohepadnaviridae hepatitis B virus

<400> SEQUENCE: 1688

Ser Leu Leu Val Pro Phe Val Gln Trp
1               5

<210> SEQ ID NO 1689
<211> LENGTH: 10
<212> TYPE: PRT
<213> ORGANISM: Orthohepadnaviridae hepatitis B virus

<400> SEQUENCE: 1689

Ser Leu Leu Val Pro Phe Val Gln Trp Phe
1               5                   10

<210> SEQ ID NO 1690
<211> LENGTH: 11
<212> TYPE: PRT
<213> ORGANISM: Orthohepadnaviridae hepatitis B virus

<400> SEQUENCE: 1690

Ser Leu Leu Val Pro Phe Val Gln Trp Phe Val
1               5                   10

<210> SEQ ID NO 1691
<211> LENGTH: 8
<212> TYPE: PRT
<213> ORGANISM: Orthohepadnaviridae hepatitis B virus

<400> SEQUENCE: 1691

Ser Leu Asn Phe Met Gly Tyr Val
1               5

<210> SEQ ID NO 1692
<211> LENGTH: 9
<212> TYPE: PRT
<213> ORGANISM: Orthohepadnaviridae hepatitis B virus

<400> SEQUENCE: 1692

Ser Leu Asn Phe Met Gly Tyr Val Ile
1               5

```
<210> SEQ ID NO 1693
<211> LENGTH: 10
<212> TYPE: PRT
<213> ORGANISM: Orthohepadnaviridae hepatitis B virus

<400> SEQUENCE: 1693

Ser Leu Arg Gly Leu Pro Val Cys Ala Phe
1               5                   10

<210> SEQ ID NO 1694
<211> LENGTH: 8
<212> TYPE: PRT
<213> ORGANISM: Orthohepadnaviridae hepatitis B virus

<400> SEQUENCE: 1694

Ser Pro Phe Leu Leu Ala Gln Phe
1               5

<210> SEQ ID NO 1695
<211> LENGTH: 11
<212> TYPE: PRT
<213> ORGANISM: Orthohepadnaviridae hepatitis B virus

<400> SEQUENCE: 1695

Ser Pro His His Thr Ala Leu Arg Gln Ala Ile
1               5                   10

<210> SEQ ID NO 1696
<211> LENGTH: 8
<212> TYPE: PRT
<213> ORGANISM: Orthohepadnaviridae hepatitis B virus

<400> SEQUENCE: 1696

Ser Pro Thr Val Trp Leu Ser Val
1               5

<210> SEQ ID NO 1697
<211> LENGTH: 9
<212> TYPE: PRT
<213> ORGANISM: Orthohepadnaviridae hepatitis B virus

<400> SEQUENCE: 1697

Ser Pro Thr Val Trp Leu Ser Val Ile
1               5

<210> SEQ ID NO 1698
<211> LENGTH: 10
<212> TYPE: PRT
<213> ORGANISM: Orthohepadnaviridae hepatitis B virus

<400> SEQUENCE: 1698

Ser Pro Thr Val Trp Leu Ser Val Ile Trp
1               5                   10

<210> SEQ ID NO 1699
<211> LENGTH: 11
<212> TYPE: PRT
<213> ORGANISM: Orthohepadnaviridae hepatitis B virus

<400> SEQUENCE: 1699

Ser Pro Thr Val Trp Leu Ser Val Ile Trp Met
1               5                   10

<210> SEQ ID NO 1700
<211> LENGTH: 8
```

-continued

```
<212> TYPE: PRT
<213> ORGANISM: Orthohepadnaviridae hepatitis B virus

<400> SEQUENCE: 1700

Ser Val Pro Asn Pro Leu Gly Phe
1               5

<210> SEQ ID NO 1701
<211> LENGTH: 11
<212> TYPE: PRT
<213> ORGANISM: Orthohepadnaviridae hepatitis B virus

<400> SEQUENCE: 1701

Ser Val Arg Phe Ser Trp Leu Ser Leu Leu Val
1               5                   10

<210> SEQ ID NO 1702
<211> LENGTH: 8
<212> TYPE: PRT
<213> ORGANISM: Orthohepadnaviridae hepatitis B virus

<400> SEQUENCE: 1702

Ser Val Val Leu Ser Arg Lys Tyr
1               5

<210> SEQ ID NO 1703
<211> LENGTH: 11
<212> TYPE: PRT
<213> ORGANISM: Orthohepadnaviridae hepatitis B virus

<400> SEQUENCE: 1703

Ser Val Val Leu Ser Arg Lys Tyr Thr Ser Phe
1               5                   10

<210> SEQ ID NO 1704
<211> LENGTH: 9
<212> TYPE: PRT
<213> ORGANISM: Orthohepadnaviridae hepatitis B virus

<400> SEQUENCE: 1704

Thr Ile Pro Gln Ser Leu Asp Ser Trp
1               5

<210> SEQ ID NO 1705
<211> LENGTH: 10
<212> TYPE: PRT
<213> ORGANISM: Orthohepadnaviridae hepatitis B virus

<400> SEQUENCE: 1705

Thr Ile Pro Gln Ser Leu Asp Ser Trp Trp
1               5                   10

<210> SEQ ID NO 1706
<211> LENGTH: 8
<212> TYPE: PRT
<213> ORGANISM: Orthohepadnaviridae hepatitis B virus

<400> SEQUENCE: 1706

Thr Leu Pro Glu Thr Thr Val Val
1               5

<210> SEQ ID NO 1707
<211> LENGTH: 9
<212> TYPE: PRT
<213> ORGANISM: Orthohepadnaviridae hepatitis B virus
```

<400> SEQUENCE: 1707

Thr Leu Trp Lys Ala Gly Ile Leu Tyr
1               5

<210> SEQ ID NO 1708
<211> LENGTH: 9
<212> TYPE: PRT
<213> ORGANISM: Orthohepadnaviridae hepatitis B virus

<400> SEQUENCE: 1708

Thr Pro Ala Arg Val Thr Gly Gly Val
1               5

<210> SEQ ID NO 1709
<211> LENGTH: 10
<212> TYPE: PRT
<213> ORGANISM: Orthohepadnaviridae hepatitis B virus

<400> SEQUENCE: 1709

Thr Pro Ala Arg Val Thr Gly Gly Val Phe
1               5                   10

<210> SEQ ID NO 1710
<211> LENGTH: 10
<212> TYPE: PRT
<213> ORGANISM: Orthohepadnaviridae hepatitis B virus

<400> SEQUENCE: 1710

Thr Pro Pro His Gly Gly Leu Leu Gly Trp
1               5                   10

<210> SEQ ID NO 1711
<211> LENGTH: 9
<212> TYPE: PRT
<213> ORGANISM: Orthohepadnaviridae hepatitis B virus

<400> SEQUENCE: 1711

Thr Pro Thr Gly Trp Gly Leu Ala Ile
1               5

<210> SEQ ID NO 1712
<211> LENGTH: 9
<212> TYPE: PRT
<213> ORGANISM: Orthohepadnaviridae hepatitis B virus

<400> SEQUENCE: 1712

Thr Gln Cys Gly Tyr Pro Ala Leu Met
1               5

<210> SEQ ID NO 1713
<211> LENGTH: 11
<212> TYPE: PRT
<213> ORGANISM: Orthohepadnaviridae hepatitis B virus

<400> SEQUENCE: 1713

Thr Val Gln Ala Ser Lys Leu Cys Leu Gly Trp
1               5                   10

<210> SEQ ID NO 1714
<211> LENGTH: 8
<212> TYPE: PRT
<213> ORGANISM: Orthohepadnaviridae hepatitis B virus

<400> SEQUENCE: 1714

```
Thr Val Trp Leu Ser Val Ile Trp
 1               5
```

<210> SEQ ID NO 1715
<211> LENGTH: 9
<212> TYPE: PRT
<213> ORGANISM: Orthohepadnaviridae hepatitis B virus

<400> SEQUENCE: 1715

```
Thr Val Trp Leu Ser Val Ile Trp Met
 1               5
```

<210> SEQ ID NO 1716
<211> LENGTH: 10
<212> TYPE: PRT
<213> ORGANISM: Orthohepadnaviridae hepatitis B virus

<400> SEQUENCE: 1716

```
Val Leu Gly Gly Cys Arg His Lys Leu Val
 1               5                   10
```

<210> SEQ ID NO 1717
<211> LENGTH: 8
<212> TYPE: PRT
<213> ORGANISM: Orthohepadnaviridae hepatitis B virus

<400> SEQUENCE: 1717

```
Val Leu Leu Asp Tyr Gln Gly Met
 1               5
```

<210> SEQ ID NO 1718
<211> LENGTH: 11
<212> TYPE: PRT
<213> ORGANISM: Orthohepadnaviridae hepatitis B virus

<400> SEQUENCE: 1718

```
Val Leu Leu Asp Tyr Gln Gly Met Leu Pro Val
 1               5                   10
```

<210> SEQ ID NO 1719
<211> LENGTH: 9
<212> TYPE: PRT
<213> ORGANISM: Orthohepadnaviridae hepatitis B virus

<400> SEQUENCE: 1719

```
Val Leu Ser Arg Lys Tyr Thr Ser Phe
 1               5
```

<210> SEQ ID NO 1720
<211> LENGTH: 11
<212> TYPE: PRT
<213> ORGANISM: Orthohepadnaviridae hepatitis B virus

<400> SEQUENCE: 1720

```
Val Leu Ser Arg Lys Tyr Thr Ser Phe Pro Trp
 1               5                   10
```

<210> SEQ ID NO 1721
<211> LENGTH: 8
<212> TYPE: PRT
<213> ORGANISM: Orthohepadnaviridae hepatitis B virus

<400> SEQUENCE: 1721

```
Val Pro Phe Val Gln Trp Phe Val
```

```
                               1               5

<210> SEQ ID NO 1722
<211> LENGTH: 10
<212> TYPE: PRT
<213> ORGANISM: Orthohepadnaviridae hepatitis B virus

<400> SEQUENCE: 1722

Val Gln Ala Ser Lys Leu Cys Leu Gly Trp
 1               5                  10

<210> SEQ ID NO 1723
<211> LENGTH: 11
<212> TYPE: PRT
<213> ORGANISM: Orthohepadnaviridae hepatitis B virus

<400> SEQUENCE: 1723

Val Gln Trp Phe Val Gly Leu Ser Pro Thr Val
 1               5                  10

<210> SEQ ID NO 1724
<211> LENGTH: 8
<212> TYPE: PRT
<213> ORGANISM: Orthohepadnaviridae hepatitis B virus

<400> SEQUENCE: 1724

Val Val Leu Gly Ala Lys Ser Val
 1               5

<210> SEQ ID NO 1725
<211> LENGTH: 8
<212> TYPE: PRT
<213> ORGANISM: Orthohepadnaviridae hepatitis B virus

<400> SEQUENCE: 1725

Trp Ile Leu Arg Gly Thr Ser Phe
 1               5

<210> SEQ ID NO 1726
<211> LENGTH: 9
<212> TYPE: PRT
<213> ORGANISM: Orthohepadnaviridae hepatitis B virus

<400> SEQUENCE: 1726

Trp Ile Leu Arg Gly Thr Ser Phe Val
 1               5

<210> SEQ ID NO 1727
<211> LENGTH: 10
<212> TYPE: PRT
<213> ORGANISM: Orthohepadnaviridae hepatitis B virus

<400> SEQUENCE: 1727

Trp Ile Leu Arg Gly Thr Ser Phe Val Tyr
 1               5                  10

<210> SEQ ID NO 1728
<211> LENGTH: 11
<212> TYPE: PRT
<213> ORGANISM: Orthohepadnaviridae hepatitis B virus

<400> SEQUENCE: 1728

Trp Ile Leu Arg Gly Thr Ser Phe Val Tyr Val
 1               5                  10
```

```
<210> SEQ ID NO 1729
<211> LENGTH: 8
<212> TYPE: PRT
<213> ORGANISM: Orthohepadnaviridae hepatitis B virus

<400> SEQUENCE: 1729

Trp Ile Arg Thr Pro Pro Ala Tyr
 1               5

<210> SEQ ID NO 1730
<211> LENGTH: 9
<212> TYPE: PRT
<213> ORGANISM: Orthohepadnaviridae hepatitis B virus

<400> SEQUENCE: 1730

Trp Leu Leu Gly Cys Ala Ala Asn Trp
 1               5

<210> SEQ ID NO 1731
<211> LENGTH: 10
<212> TYPE: PRT
<213> ORGANISM: Orthohepadnaviridae hepatitis B virus

<400> SEQUENCE: 1731

Trp Leu Leu Gly Cys Ala Ala Asn Trp Ile
 1               5                  10

<210> SEQ ID NO 1732
<211> LENGTH: 10
<212> TYPE: PRT
<213> ORGANISM: Orthohepadnaviridae hepatitis B virus

<400> SEQUENCE: 1732

Trp Leu Ser Leu Asp Val Ser Ala Ala Phe
 1               5                  10

<210> SEQ ID NO 1733
<211> LENGTH: 11
<212> TYPE: PRT
<213> ORGANISM: Orthohepadnaviridae hepatitis B virus

<400> SEQUENCE: 1733

Trp Leu Ser Leu Asp Val Ser Ala Ala Phe Tyr
 1               5                  10

<210> SEQ ID NO 1734
<211> LENGTH: 8
<212> TYPE: PRT
<213> ORGANISM: Orthohepadnaviridae hepatitis B virus

<400> SEQUENCE: 1734

Trp Leu Ser Leu Leu Val Pro Phe
 1               5

<210> SEQ ID NO 1735
<211> LENGTH: 9
<212> TYPE: PRT
<213> ORGANISM: Orthohepadnaviridae hepatitis B virus

<400> SEQUENCE: 1735

Trp Leu Ser Leu Leu Val Pro Phe Val
 1               5

<210> SEQ ID NO 1736
```

```
<211> LENGTH: 11
<212> TYPE: PRT
<213> ORGANISM: Orthohepadnaviridae hepatitis B virus

<400> SEQUENCE: 1736

Trp Leu Ser Leu Leu Val Pro Phe Val Gln Trp
1               5                   10

<210> SEQ ID NO 1737
<211> LENGTH: 10
<212> TYPE: PRT
<213> ORGANISM: Orthohepadnaviridae hepatitis B virus

<400> SEQUENCE: 1737

Trp Leu Trp Gly Met Asp Ile Asp Pro Tyr
1               5                   10

<210> SEQ ID NO 1738
<211> LENGTH: 8
<212> TYPE: PRT
<213> ORGANISM: Orthohepadnaviridae hepatitis B virus

<400> SEQUENCE: 1738

Trp Met Cys Leu Arg Arg Phe Ile
1               5

<210> SEQ ID NO 1739
<211> LENGTH: 9
<212> TYPE: PRT
<213> ORGANISM: Orthohepadnaviridae hepatitis B virus

<400> SEQUENCE: 1739

Trp Met Cys Leu Arg Arg Phe Ile Ile
1               5

<210> SEQ ID NO 1740
<211> LENGTH: 10
<212> TYPE: PRT
<213> ORGANISM: Orthohepadnaviridae hepatitis B virus

<400> SEQUENCE: 1740

Trp Met Cys Leu Arg Arg Phe Ile Ile Phe
1               5                   10

<210> SEQ ID NO 1741
<211> LENGTH: 10
<212> TYPE: PRT
<213> ORGANISM: Orthohepadnaviridae hepatitis B virus

<400> SEQUENCE: 1741

Trp Met Met Trp Tyr Trp Gly Pro Ser Leu
1               5                   10

<210> SEQ ID NO 1742
<211> LENGTH: 10
<212> TYPE: PRT
<213> ORGANISM: Orthohepadnaviridae hepatitis B virus

<400> SEQUENCE: 1742

Tyr Leu His Thr Leu Trp Lys Ala Gly Ile
1               5                   10

<210> SEQ ID NO 1743
<211> LENGTH: 8
<212> TYPE: PRT
```

-continued

<213> ORGANISM: Orthohepadnaviridae hepatitis B virus

<400> SEQUENCE: 1743

Tyr Leu Pro Leu Asp Lys Gly Ile
 1               5

<210> SEQ ID NO 1744
<211> LENGTH: 11
<212> TYPE: PRT
<213> ORGANISM: Orthohepadnaviridae hepatitis B virus

<400> SEQUENCE: 1744

Tyr Leu Pro Leu Asp Lys Gly Ile Lys Pro Tyr
 1               5                  10

<210> SEQ ID NO 1745
<211> LENGTH: 8
<212> TYPE: PRT
<213> ORGANISM: Orthohepadnaviridae hepatitis B virus

<400> SEQUENCE: 1745

Tyr Leu Val Ser Phe Gly Val Trp
 1               5

<210> SEQ ID NO 1746
<211> LENGTH: 9
<212> TYPE: PRT
<213> ORGANISM: Orthohepadnaviridae hepatitis B virus

<400> SEQUENCE: 1746

Tyr Leu Val Ser Phe Gly Val Trp Ile
 1               5

<210> SEQ ID NO 1747
<211> LENGTH: 8
<212> TYPE: PRT
<213> ORGANISM: Orthohepadnaviridae hepatitis B virus

<400> SEQUENCE: 1747

Tyr Pro Ala Leu Met Pro Leu Tyr
 1               5

<210> SEQ ID NO 1748
<211> LENGTH: 11
<212> TYPE: PRT
<213> ORGANISM: Orthohepadnaviridae hepatitis B virus

<400> SEQUENCE: 1748

Tyr Pro Ala Leu Met Pro Leu Tyr Ala Cys Ile
 1               5                  10

<210> SEQ ID NO 1749
<211> LENGTH: 9
<212> TYPE: PRT
<213> ORGANISM: Orthohepadnaviridae hepatitis B virus

<400> SEQUENCE: 1749

Ala Met Gln Trp Asn Ser Thr Thr Phe
 1               5

<210> SEQ ID NO 1750
<211> LENGTH: 10
<212> TYPE: PRT
<213> ORGANISM: Orthohepadnaviridae hepatitis B virus

```
<400> SEQUENCE: 1750

Asp Asn Ser Val Val Leu Ser Arg Lys Tyr
1               5                   10

<210> SEQ ID NO 1751
<211> LENGTH: 10
<212> TYPE: PRT
<213> ORGANISM: Orthohepadnaviridae hepatitis B virus

<400> SEQUENCE: 1751

Phe Ala Ala Pro Phe Thr Gln Cys Gly Tyr
1               5                   10

<210> SEQ ID NO 1752
<211> LENGTH: 9
<212> TYPE: PRT
<213> ORGANISM: Orthohepadnaviridae hepatitis B virus

<400> SEQUENCE: 1752

Gly Tyr Ser Leu Asn Phe Met Gly Tyr
1               5

<210> SEQ ID NO 1753
<211> LENGTH: 10
<212> TYPE: PRT
<213> ORGANISM: Orthohepadnaviridae hepatitis B virus

<400> SEQUENCE: 1753

His Thr Leu Trp Lys Ala Gly Ile Leu Tyr
1               5                   10

<210> SEQ ID NO 1754
<211> LENGTH: 10
<212> TYPE: PRT
<213> ORGANISM: Orthohepadnaviridae hepatitis B virus

<400> SEQUENCE: 1754

Lys Gln Ala Phe Thr Phe Ser Pro Thr Tyr
1               5                   10

<210> SEQ ID NO 1755
<211> LENGTH: 9
<212> TYPE: PRT
<213> ORGANISM: Orthohepadnaviridae hepatitis B virus

<400> SEQUENCE: 1755

Leu Leu Asp Thr Ala Ser Ala Leu Tyr
1               5

<210> SEQ ID NO 1756
<211> LENGTH: 10
<212> TYPE: PRT
<213> ORGANISM: Orthohepadnaviridae hepatitis B virus

<400> SEQUENCE: 1756

Leu Ser Leu Asp Val Ser Ala Ala Phe Tyr
1               5                   10

<210> SEQ ID NO 1757
<211> LENGTH: 10
<212> TYPE: PRT
<213> ORGANISM: Orthohepadnaviridae hepatitis B virus

<400> SEQUENCE: 1757
```

```
Met Met Trp Tyr Trp Gly Pro Ser Leu Tyr
1               5                   10
```

<210> SEQ ID NO 1758
<211> LENGTH: 9
<212> TYPE: PRT
<213> ORGANISM: Orthohepadnaviridae hepatitis B virus

<400> SEQUENCE: 1758

```
Met Ser Thr Thr Asp Leu Glu Ala Tyr
1               5
```

<210> SEQ ID NO 1759
<211> LENGTH: 9
<212> TYPE: PRT
<213> ORGANISM: Orthohepadnaviridae hepatitis B virus

<400> SEQUENCE: 1759

```
Asn Ser Val Val Leu Ser Arg Lys Tyr
1               5
```

<210> SEQ ID NO 1760
<211> LENGTH: 9
<212> TYPE: PRT
<213> ORGANISM: Orthohepadnaviridae hepatitis B virus

<400> SEQUENCE: 1760

```
Pro Leu Asp Lys Gly Ile Lys Pro Tyr
1               5
```

<210> SEQ ID NO 1761
<211> LENGTH: 10
<212> TYPE: PRT
<213> ORGANISM: Orthohepadnaviridae hepatitis B virus

<400> SEQUENCE: 1761

```
Pro Leu Asp Lys Gly Ile Lys Pro Tyr Tyr
1               5                   10
```

<210> SEQ ID NO 1762
<211> LENGTH: 9
<212> TYPE: PRT
<213> ORGANISM: Orthohepadnaviridae hepatitis B virus

<400> SEQUENCE: 1762

```
Pro Thr Thr Gly Arg Thr Ser Leu Tyr
1               5
```

<210> SEQ ID NO 1763
<211> LENGTH: 9
<212> TYPE: PRT
<213> ORGANISM: Orthohepadnaviridae hepatitis B virus

<400> SEQUENCE: 1763

```
Ser Ala Ser Phe Cys Gly Ser Pro Tyr
1               5
```

<210> SEQ ID NO 1764
<211> LENGTH: 9
<212> TYPE: PRT
<213> ORGANISM: Orthohepadnaviridae hepatitis B virus

<400> SEQUENCE: 1764

```
Ser Leu Asp Val Ser Ala Ala Phe Tyr
1               5
```

```
<210> SEQ ID NO 1765
<211> LENGTH: 8
<212> TYPE: PRT
<213> ORGANISM: Orthohepadnaviridae hepatitis B virus

<400> SEQUENCE: 1765

Ala Ala Cys Phe Ala Arg Ser Arg
1               5

<210> SEQ ID NO 1766
<211> LENGTH: 9
<212> TYPE: PRT
<213> ORGANISM: Orthohepadnaviridae hepatitis B virus

<400> SEQUENCE: 1766

Ala Ala Pro Phe Thr Gln Cys Gly Tyr
1               5

<210> SEQ ID NO 1767
<211> LENGTH: 10
<212> TYPE: PRT
<213> ORGANISM: Orthohepadnaviridae hepatitis B virus

<400> SEQUENCE: 1767

Ala Phe Pro His Cys Leu Ala Phe Ser Tyr
1               5                   10

<210> SEQ ID NO 1768
<211> LENGTH: 9
<212> TYPE: PRT
<213> ORGANISM: Orthohepadnaviridae hepatitis B virus

<400> SEQUENCE: 1768

Ala Phe Ser Ser Ala Gly Pro Cys Ala
1               5

<210> SEQ ID NO 1769
<211> LENGTH: 9
<212> TYPE: PRT
<213> ORGANISM: Orthohepadnaviridae hepatitis B virus

<400> SEQUENCE: 1769

Ala Phe Thr Phe Ser Pro Thr Tyr Lys
1               5

<210> SEQ ID NO 1770
<211> LENGTH: 10
<212> TYPE: PRT
<213> ORGANISM: Orthohepadnaviridae hepatitis B virus

<400> SEQUENCE: 1770

Ala Phe Thr Phe Ser Pro Thr Tyr Lys Ala
1               5                   10

<210> SEQ ID NO 1771
<211> LENGTH: 10
<212> TYPE: PRT
<213> ORGANISM: Orthohepadnaviridae hepatitis B virus

<400> SEQUENCE: 1771

Ala Gly Pro Leu Glu Glu Glu Leu Pro Arg
1               5                   10
```

```
<210> SEQ ID NO 1772
<211> LENGTH: 8
<212> TYPE: PRT
<213> ORGANISM: Orthohepadnaviridae hepatitis B virus

<400> SEQUENCE: 1772

Ala Ile Cys Ser Val Val Arg Arg
1               5

<210> SEQ ID NO 1773
<211> LENGTH: 10
<212> TYPE: PRT
<213> ORGANISM: Orthohepadnaviridae hepatitis B virus

<400> SEQUENCE: 1773

Ala Ile Cys Ser Val Val Arg Arg Ala Phe
1               5                   10

<210> SEQ ID NO 1774
<211> LENGTH: 10
<212> TYPE: PRT
<213> ORGANISM: Orthohepadnaviridae hepatitis B virus

<400> SEQUENCE: 1774

Ala Leu Asn Pro Ala Asp Asp Pro Ser Arg
1               5                   10

<210> SEQ ID NO 1775
<211> LENGTH: 8
<212> TYPE: PRT
<213> ORGANISM: Orthohepadnaviridae hepatitis B virus

<400> SEQUENCE: 1775

Ala Leu Arg Phe Thr Ser Ala Arg
1               5

<210> SEQ ID NO 1776
<211> LENGTH: 9
<212> TYPE: PRT
<213> ORGANISM: Orthohepadnaviridae hepatitis B virus

<400> SEQUENCE: 1776

Ala Met Gln Trp Asn Ser Thr Thr Phe
1               5

<210> SEQ ID NO 1777
<211> LENGTH: 9
<212> TYPE: PRT
<213> ORGANISM: Orthohepadnaviridae hepatitis B virus

<400> SEQUENCE: 1777

Ala Met Gln Trp Asn Ser Thr Thr Phe
1               5

<210> SEQ ID NO 1778
<211> LENGTH: 10
<212> TYPE: PRT
<213> ORGANISM: Orthohepadnaviridae hepatitis B virus

<400> SEQUENCE: 1778

Ala Met Gln Trp Asn Ser Thr Thr Phe His
1               5                   10

<210> SEQ ID NO 1779
<211> LENGTH: 9
```

```
<212> TYPE: PRT
<213> ORGANISM: Orthohepadnaviridae hepatitis B virus

<400> SEQUENCE: 1779

Ala Ser Pro Leu His Val Ala Trp Arg
 1               5

<210> SEQ ID NO 1780
<211> LENGTH: 9
<212> TYPE: PRT
<213> ORGANISM: Orthohepadnaviridae hepatitis B virus

<400> SEQUENCE: 1780

Ala Ser Thr Asn Arg Gln Ser Gly Arg
 1               5

<210> SEQ ID NO 1781
<211> LENGTH: 8
<212> TYPE: PRT
<213> ORGANISM: Orthohepadnaviridae hepatitis B virus

<400> SEQUENCE: 1781

Cys Ala Ala Asn Trp Ile Leu Arg
 1               5

<210> SEQ ID NO 1782
<211> LENGTH: 9
<212> TYPE: PRT
<213> ORGANISM: Orthohepadnaviridae hepatitis B virus

<400> SEQUENCE: 1782

Cys Ala Leu Arg Phe Thr Ser Ala Arg
 1               5

<210> SEQ ID NO 1783
<211> LENGTH: 9
<212> TYPE: PRT
<213> ORGANISM: Orthohepadnaviridae hepatitis B virus

<400> SEQUENCE: 1783

Cys Phe Ala Arg Ser Arg Ser Gly Ala
 1               5

<210> SEQ ID NO 1784
<211> LENGTH: 9
<212> TYPE: PRT
<213> ORGANISM: Orthohepadnaviridae hepatitis B virus

<400> SEQUENCE: 1784

Cys Phe Arg Lys Leu Pro Val Asn Arg
 1               5

<210> SEQ ID NO 1785
<211> LENGTH: 10
<212> TYPE: PRT
<213> ORGANISM: Orthohepadnaviridae hepatitis B virus

<400> SEQUENCE: 1785

Cys Gly Tyr Pro Ala Leu Met Pro Leu Tyr
 1               5                  10

<210> SEQ ID NO 1786
<211> LENGTH: 10
<212> TYPE: PRT
<213> ORGANISM: Orthohepadnaviridae hepatitis B virus
```

```
<400> SEQUENCE: 1786

Cys Ile Pro Ile Pro Ser Ser Trp Ala Phe
 1               5                  10

<210> SEQ ID NO 1787
<211> LENGTH: 10
<212> TYPE: PRT
<213> ORGANISM: Orthohepadnaviridae hepatitis B virus

<400> SEQUENCE: 1787

Cys Leu Arg Pro Val Gly Ala Glu Ser Arg
 1               5                  10

<210> SEQ ID NO 1788
<211> LENGTH: 10
<212> TYPE: PRT
<213> ORGANISM: Orthohepadnaviridae hepatitis B virus

<400> SEQUENCE: 1788

Cys Leu Arg Arg Phe Ile Ile Phe Leu Phe
 1               5                  10

<210> SEQ ID NO 1789
<211> LENGTH: 9
<212> TYPE: PRT
<213> ORGANISM: Orthohepadnaviridae hepatitis B virus

<400> SEQUENCE: 1789

Cys Ser Pro His His Thr Ala Leu Arg
 1               5

<210> SEQ ID NO 1790
<211> LENGTH: 10
<212> TYPE: PRT
<213> ORGANISM: Orthohepadnaviridae hepatitis B virus

<400> SEQUENCE: 1790

Cys Ser Val Val Arg Arg Ala Phe Pro His
 1               5                  10

<210> SEQ ID NO 1791
<211> LENGTH: 10
<212> TYPE: PRT
<213> ORGANISM: Orthohepadnaviridae hepatitis B virus

<400> SEQUENCE: 1791

Asp Leu Leu Asp Thr Ala Ser Ala Leu Tyr
 1               5                  10

<210> SEQ ID NO 1792
<211> LENGTH: 11
<212> TYPE: PRT
<213> ORGANISM: Orthohepadnaviridae hepatitis B virus

<400> SEQUENCE: 1792

Asp Leu Leu Asp Thr Ala Ser Ala Leu Tyr Arg
 1               5                  10

<210> SEQ ID NO 1793
<211> LENGTH: 9
<212> TYPE: PRT
<213> ORGANISM: Orthohepadnaviridae hepatitis B virus

<400> SEQUENCE: 1793
```

```
Asp Ser Trp Trp Thr Ser Leu Asn Phe
1               5
```

<210> SEQ ID NO 1794
<211> LENGTH: 8
<212> TYPE: PRT
<213> ORGANISM: Orthohepadnaviridae hepatitis B virus

<400> SEQUENCE: 1794

```
Asp Thr Ala Ser Ala Leu Tyr Arg
1               5
```

<210> SEQ ID NO 1795
<211> LENGTH: 11
<212> TYPE: PRT
<213> ORGANISM: Orthohepadnaviridae hepatitis B virus

<400> SEQUENCE: 1795

```
Glu Ala Gly Pro Leu Glu Glu Glu Leu Pro Arg
1               5                   10
```

<210> SEQ ID NO 1796
<211> LENGTH: 9
<212> TYPE: PRT
<213> ORGANISM: Orthohepadnaviridae hepatitis B virus

<400> SEQUENCE: 1796

```
Glu Leu Leu Ala Ala Cys Phe Ala Arg
1               5
```

<210> SEQ ID NO 1797
<211> LENGTH: 11
<212> TYPE: PRT
<213> ORGANISM: Orthohepadnaviridae hepatitis B virus

<400> SEQUENCE: 1797

```
Glu Leu Leu Ala Ala Cys Phe Ala Arg Ser Arg
1               5                   10
```

<210> SEQ ID NO 1798
<211> LENGTH: 10
<212> TYPE: PRT
<213> ORGANISM: Orthohepadnaviridae hepatitis B virus

<400> SEQUENCE: 1798

```
Glu Leu Leu Ser Phe Leu Pro Ser Asp Phe
1               5                   10
```

<210> SEQ ID NO 1799
<211> LENGTH: 9
<212> TYPE: PRT
<213> ORGANISM: Orthohepadnaviridae hepatitis B virus

<400> SEQUENCE: 1799

```
Glu Ser Pro Glu His Cys Ser Pro His
1               5
```

<210> SEQ ID NO 1800
<211> LENGTH: 10
<212> TYPE: PRT
<213> ORGANISM: Orthohepadnaviridae hepatitis B virus

<400> SEQUENCE: 1800

```
Glu Ser Pro Glu His Cys Ser Pro His His
```

-continued

<210> SEQ ID NO 1801
<211> LENGTH: 8
<212> TYPE: PRT
<213> ORGANISM: Orthohepadnaviridae hepatitis B virus

<400> SEQUENCE: 1801

Glu Thr Thr Val Val Arg Arg Arg
1               5

<210> SEQ ID NO 1802
<211> LENGTH: 10
<212> TYPE: PRT
<213> ORGANISM: Orthohepadnaviridae hepatitis B virus

<400> SEQUENCE: 1802

Glu Thr Thr Val Val Arg Arg Arg Gly Arg
1               5                   10

<210> SEQ ID NO 1803
<211> LENGTH: 10
<212> TYPE: PRT
<213> ORGANISM: Orthohepadnaviridae hepatitis B virus

<400> SEQUENCE: 1803

Phe Ala Ala Pro Phe Thr Gln Cys Gly Tyr
1               5                   10

<210> SEQ ID NO 1804
<211> LENGTH: 10
<212> TYPE: PRT
<213> ORGANISM: Orthohepadnaviridae hepatitis B virus

<400> SEQUENCE: 1804

Phe Ala Ser Pro Leu His Val Ala Trp Arg
1               5                   10

<210> SEQ ID NO 1805
<211> LENGTH: 10
<212> TYPE: PRT
<213> ORGANISM: Orthohepadnaviridae hepatitis B virus

<400> SEQUENCE: 1805

Phe Phe Pro Asp His Gln Leu Asp Pro Ala
1               5                   10

<210> SEQ ID NO 1806
<211> LENGTH: 9
<212> TYPE: PRT
<213> ORGANISM: Orthohepadnaviridae hepatitis B virus

<400> SEQUENCE: 1806

Phe Gly Arg Glu Thr Val Leu Glu Tyr
1               5

<210> SEQ ID NO 1807
<211> LENGTH: 10
<212> TYPE: PRT
<213> ORGANISM: Orthohepadnaviridae hepatitis B virus

<400> SEQUENCE: 1807

Phe Gly Val Glu Pro Ser Gly Ser Gly His
1               5                   10

```
<210> SEQ ID NO 1808
<211> LENGTH: 9
<212> TYPE: PRT
<213> ORGANISM: Orthohepadnaviridae hepatitis B virus

<400> SEQUENCE: 1808

Phe Ile Leu Leu Leu Cys Leu Ile Phe
 1               5

<210> SEQ ID NO 1809
<211> LENGTH: 10
<212> TYPE: PRT
<213> ORGANISM: Orthohepadnaviridae hepatitis B virus

<400> SEQUENCE: 1809

Phe Ser Ser Ala Gly Pro Cys Ala Leu Arg
 1               5                  10

<210> SEQ ID NO 1810
<211> LENGTH: 10
<212> TYPE: PRT
<213> ORGANISM: Orthohepadnaviridae hepatitis B virus

<400> SEQUENCE: 1810

Phe Ser Trp Leu Ser Leu Leu Val Pro Phe
 1               5                  10

<210> SEQ ID NO 1811
<211> LENGTH: 8
<212> TYPE: PRT
<213> ORGANISM: Orthohepadnaviridae hepatitis B virus

<400> SEQUENCE: 1811

Phe Thr Phe Ser Pro Thr Tyr Lys
 1               5

<210> SEQ ID NO 1812
<211> LENGTH: 10
<212> TYPE: PRT
<213> ORGANISM: Orthohepadnaviridae hepatitis B virus

<400> SEQUENCE: 1812

Phe Thr Phe Ser Pro Thr Tyr Lys Ala Phe
 1               5                  10

<210> SEQ ID NO 1813
<211> LENGTH: 10
<212> TYPE: PRT
<213> ORGANISM: Orthohepadnaviridae hepatitis B virus

<400> SEQUENCE: 1813

Phe Thr Ser Ala Ile Cys Ser Val Val Arg
 1               5                  10

<210> SEQ ID NO 1814
<211> LENGTH: 11
<212> TYPE: PRT
<213> ORGANISM: Orthohepadnaviridae hepatitis B virus

<400> SEQUENCE: 1814

Phe Thr Ser Ala Ile Cys Ser Val Val Arg Arg
 1               5                  10

<210> SEQ ID NO 1815
```

```
<211> LENGTH: 9
<212> TYPE: PRT
<213> ORGANISM: Orthohepadnaviridae hepatitis B virus

<400> SEQUENCE: 1815

Phe Val Leu Gly Gly Cys Arg His Lys
 1               5

<210> SEQ ID NO 1816
<211> LENGTH: 9
<212> TYPE: PRT
<213> ORGANISM: Orthohepadnaviridae hepatitis B virus

<400> SEQUENCE: 1816

Gly Cys Ala Ala Asn Trp Ile Leu Arg
 1               5

<210> SEQ ID NO 1817
<211> LENGTH: 8
<212> TYPE: PRT
<213> ORGANISM: Orthohepadnaviridae hepatitis B virus

<400> SEQUENCE: 1817

Gly Ile His Leu Asn Pro Asn Lys
 1               5

<210> SEQ ID NO 1818
<211> LENGTH: 10
<212> TYPE: PRT
<213> ORGANISM: Orthohepadnaviridae hepatitis B virus

<400> SEQUENCE: 1818

Gly Ile His Leu Asn Pro Asn Lys Thr Lys
 1               5                  10

<210> SEQ ID NO 1819
<211> LENGTH: 11
<212> TYPE: PRT
<213> ORGANISM: Orthohepadnaviridae hepatitis B virus

<400> SEQUENCE: 1819

Gly Ile His Leu Asn Pro Asn Lys Thr Lys Arg
 1               5                  10

<210> SEQ ID NO 1820
<211> LENGTH: 9
<212> TYPE: PRT
<213> ORGANISM: Orthohepadnaviridae hepatitis B virus

<400> SEQUENCE: 1820

Gly Leu Leu Gly Phe Ala Ala Pro Phe
 1               5

<210> SEQ ID NO 1821
<211> LENGTH: 10
<212> TYPE: PRT
<213> ORGANISM: Orthohepadnaviridae hepatitis B virus

<400> SEQUENCE: 1821

Gly Leu Ser Pro Phe Leu Leu Ala Gln Phe
 1               5                  10

<210> SEQ ID NO 1822
<211> LENGTH: 8
<212> TYPE: PRT
```

<213> ORGANISM: Orthohepadnaviridae hepatitis B virus

<400> SEQUENCE: 1822

Gly Met Asp Ile Asp Pro Tyr Lys
 1               5

<210> SEQ ID NO 1823
<211> LENGTH: 10
<212> TYPE: PRT
<213> ORGANISM: Orthohepadnaviridae hepatitis B virus

<400> SEQUENCE: 1823

Gly Met Asp Ile Asp Pro Tyr Lys Glu Phe
 1               5                  10

<210> SEQ ID NO 1824
<211> LENGTH: 10
<212> TYPE: PRT
<213> ORGANISM: Orthohepadnaviridae hepatitis B virus

<400> SEQUENCE: 1824

Gly Thr Asp Asn Ser Val Val Leu Ser Arg
 1               5                  10

<210> SEQ ID NO 1825
<211> LENGTH: 11
<212> TYPE: PRT
<213> ORGANISM: Orthohepadnaviridae hepatitis B virus

<400> SEQUENCE: 1825

Gly Thr Asp Asn Ser Val Val Leu Ser Arg Lys
 1               5                  10

<210> SEQ ID NO 1826
<211> LENGTH: 9
<212> TYPE: PRT
<213> ORGANISM: Orthohepadnaviridae hepatitis B virus

<400> SEQUENCE: 1826

Gly Val Glu Pro Ser Gly Ser Gly His
 1               5

<210> SEQ ID NO 1827
<211> LENGTH: 10
<212> TYPE: PRT
<213> ORGANISM: Orthohepadnaviridae hepatitis B virus

<400> SEQUENCE: 1827

Gly Val Phe Leu Val Asp Lys Asn Pro His
 1               5                  10

<210> SEQ ID NO 1828
<211> LENGTH: 10
<212> TYPE: PRT
<213> ORGANISM: Orthohepadnaviridae hepatitis B virus

<400> SEQUENCE: 1828

Gly Val Trp Ile Arg Thr Pro Pro Ala Tyr
 1               5                  10

<210> SEQ ID NO 1829
<211> LENGTH: 11
<212> TYPE: PRT
<213> ORGANISM: Orthohepadnaviridae hepatitis B virus

```
<400> SEQUENCE: 1829

Gly Val Trp Ile Arg Thr Pro Pro Ala Tyr Arg
 1               5                  10

<210> SEQ ID NO 1830
<211> LENGTH: 10
<212> TYPE: PRT
<213> ORGANISM: Orthohepadnaviridae hepatitis B virus

<400> SEQUENCE: 1830

His Cys Ser Pro His His Thr Ala Leu Arg
 1               5                  10

<210> SEQ ID NO 1831
<211> LENGTH: 9
<212> TYPE: PRT
<213> ORGANISM: Orthohepadnaviridae hepatitis B virus

<400> SEQUENCE: 1831

His Phe Ala Ser Pro Leu His Val Ala
 1               5

<210> SEQ ID NO 1832
<211> LENGTH: 9
<212> TYPE: PRT
<213> ORGANISM: Orthohepadnaviridae hepatitis B virus

<400> SEQUENCE: 1832

His Ile Ser Cys Leu Thr Phe Gly Arg
 1               5

<210> SEQ ID NO 1833
<211> LENGTH: 8
<212> TYPE: PRT
<213> ORGANISM: Orthohepadnaviridae hepatitis B virus

<400> SEQUENCE: 1833

His Leu Asn Pro Asn Lys Thr Lys
 1               5

<210> SEQ ID NO 1834
<211> LENGTH: 9
<212> TYPE: PRT
<213> ORGANISM: Orthohepadnaviridae hepatitis B virus

<400> SEQUENCE: 1834

His Leu Asn Pro Asn Lys Thr Lys Arg
 1               5

<210> SEQ ID NO 1835
<211> LENGTH: 10
<212> TYPE: PRT
<213> ORGANISM: Orthohepadnaviridae hepatitis B virus

<400> SEQUENCE: 1835

His Thr Ala Glu Leu Leu Ala Ala Cys Phe
 1               5                  10

<210> SEQ ID NO 1836
<211> LENGTH: 11
<212> TYPE: PRT
<213> ORGANISM: Orthohepadnaviridae hepatitis B virus

<400> SEQUENCE: 1836
```

His Thr Leu Trp Lys Ala Gly Ile Leu Tyr Lys
1               5                   10

<210> SEQ ID NO 1837
<211> LENGTH: 9
<212> TYPE: PRT
<213> ORGANISM: Orthohepadnaviridae hepatitis B virus

<400> SEQUENCE: 1837

Ile Cys Ser Val Val Arg Arg Ala Phe
1               5

<210> SEQ ID NO 1838
<211> LENGTH: 9
<212> TYPE: PRT
<213> ORGANISM: Orthohepadnaviridae hepatitis B virus

<400> SEQUENCE: 1838

Ile Phe Leu Leu Val Leu Leu Asp Tyr
1               5

<210> SEQ ID NO 1839
<211> LENGTH: 9
<212> TYPE: PRT
<213> ORGANISM: Orthohepadnaviridae hepatitis B virus

<400> SEQUENCE: 1839

Ile Leu Arg Gly Thr Ser Phe Val Tyr
1               5

<210> SEQ ID NO 1840
<211> LENGTH: 8
<212> TYPE: PRT
<213> ORGANISM: Orthohepadnaviridae hepatitis B virus

<400> SEQUENCE: 1840

Ile Ser Cys Leu Thr Phe Gly Arg
1               5

<210> SEQ ID NO 1841
<211> LENGTH: 8
<212> TYPE: PRT
<213> ORGANISM: Orthohepadnaviridae hepatitis B virus

<400> SEQUENCE: 1841

Lys Ala Gly Ile Leu Tyr Lys Arg
1               5

<210> SEQ ID NO 1842
<211> LENGTH: 9
<212> TYPE: PRT
<213> ORGANISM: Orthohepadnaviridae hepatitis B virus

<400> SEQUENCE: 1842

Lys Leu Ile Met Pro Ala Arg Phe Tyr
1               5

<210> SEQ ID NO 1843
<211> LENGTH: 11
<212> TYPE: PRT
<213> ORGANISM: Orthohepadnaviridae hepatitis B virus

<400> SEQUENCE: 1843

Lys Leu Pro Val Asn Arg Pro Ile Asp Trp Lys
1               5                   10

```
<210> SEQ ID NO 1844
<211> LENGTH: 9
<212> TYPE: PRT
<213> ORGANISM: Orthohepadnaviridae hepatitis B virus

<400> SEQUENCE: 1844

Lys Val Phe Val Leu Gly Gly Cys Arg
 1               5

<210> SEQ ID NO 1845
<211> LENGTH: 10
<212> TYPE: PRT
<213> ORGANISM: Orthohepadnaviridae hepatitis B virus

<400> SEQUENCE: 1845

Lys Val Phe Val Leu Gly Gly Cys Arg His
 1               5                  10

<210> SEQ ID NO 1846
<211> LENGTH: 9
<212> TYPE: PRT
<213> ORGANISM: Orthohepadnaviridae hepatitis B virus

<400> SEQUENCE: 1846

Lys Val Gly Asn Phe Thr Gly Leu Tyr
 1               5

<210> SEQ ID NO 1847
<211> LENGTH: 9
<212> TYPE: PRT
<213> ORGANISM: Orthohepadnaviridae hepatitis B virus

<400> SEQUENCE: 1847

Leu Ala Ala Cys Phe Ala Arg Ser Arg
 1               5

<210> SEQ ID NO 1848
<211> LENGTH: 9
<212> TYPE: PRT
<213> ORGANISM: Orthohepadnaviridae hepatitis B virus

<400> SEQUENCE: 1848

Leu Asp Lys Gly Ile Lys Pro Tyr Tyr
 1               5

<210> SEQ ID NO 1849
<211> LENGTH: 10
<212> TYPE: PRT
<213> ORGANISM: Orthohepadnaviridae hepatitis B virus

<400> SEQUENCE: 1849

Leu Asp Ser Trp Trp Thr Ser Leu Asn Phe
 1               5                  10

<210> SEQ ID NO 1850
<211> LENGTH: 9
<212> TYPE: PRT
<213> ORGANISM: Orthohepadnaviridae hepatitis B virus

<400> SEQUENCE: 1850

Leu Asp Thr Ala Ser Ala Leu Tyr Arg
 1               5
```

-continued

<210> SEQ ID NO 1851
<211> LENGTH: 9
<212> TYPE: PRT
<213> ORGANISM: Orthohepadnaviridae hepatitis B virus

<400> SEQUENCE: 1851

Leu Asp Val Ser Ala Ala Phe Tyr His
1 5

<210> SEQ ID NO 1852
<211> LENGTH: 10
<212> TYPE: PRT
<213> ORGANISM: Orthohepadnaviridae hepatitis B virus

<400> SEQUENCE: 1852

Leu Phe Ile Leu Leu Leu Cys Leu Ile Phe
1 5 10

<210> SEQ ID NO 1853
<211> LENGTH: 10
<212> TYPE: PRT
<213> ORGANISM: Orthohepadnaviridae hepatitis B virus

<400> SEQUENCE: 1853

Leu Phe Ile Leu Leu Leu Cys Leu Ile Phe
1 5 10

<210> SEQ ID NO 1854
<211> LENGTH: 10
<212> TYPE: PRT
<213> ORGANISM: Orthohepadnaviridae hepatitis B virus

<400> SEQUENCE: 1854

Leu Gly Cys Ala Ala Asn Trp Ile Leu Arg
1 5 10

<210> SEQ ID NO 1855
<211> LENGTH: 9
<212> TYPE: PRT
<213> ORGANISM: Orthohepadnaviridae hepatitis B virus

<400> SEQUENCE: 1855

Leu Gly Ile His Leu Asn Pro Asn Lys
1 5

<210> SEQ ID NO 1856
<211> LENGTH: 10
<212> TYPE: PRT
<213> ORGANISM: Orthohepadnaviridae hepatitis B virus

<400> SEQUENCE: 1856

Leu Ile Phe Leu Leu Val Leu Leu Asp Tyr
1 5 10

<210> SEQ ID NO 1857
<211> LENGTH: 8
<212> TYPE: PRT
<213> ORGANISM: Orthohepadnaviridae hepatitis B virus

<400> SEQUENCE: 1857

Leu Leu Ala Ala Cys Phe Ala Arg
1 5

<210> SEQ ID NO 1858
<211> LENGTH: 10

-continued

```
<212> TYPE: PRT
<213> ORGANISM: Orthohepadnaviridae hepatitis B virus

<400> SEQUENCE: 1858

Leu Leu Ala Ala Cys Phe Ala Arg Ser Arg
 1               5                  10

<210> SEQ ID NO 1859
<211> LENGTH: 10
<212> TYPE: PRT
<213> ORGANISM: Orthohepadnaviridae hepatitis B virus

<400> SEQUENCE: 1859

Leu Leu Asp Thr Ala Ser Ala Leu Tyr Arg
 1               5                  10

<210> SEQ ID NO 1860
<211> LENGTH: 11
<212> TYPE: PRT
<213> ORGANISM: Orthohepadnaviridae hepatitis B virus

<400> SEQUENCE: 1860

Leu Leu Gly Cys Ala Ala Asn Trp Ile Leu Arg
 1               5                      10

<210> SEQ ID NO 1861
<211> LENGTH: 9
<212> TYPE: PRT
<213> ORGANISM: Orthohepadnaviridae hepatitis B virus

<400> SEQUENCE: 1861

Leu Leu Ser Phe Leu Pro Ser Asp Phe
 1               5

<210> SEQ ID NO 1862
<211> LENGTH: 10
<212> TYPE: PRT
<213> ORGANISM: Orthohepadnaviridae hepatitis B virus

<400> SEQUENCE: 1862

Leu Leu Ser Phe Leu Pro Ser Asp Phe Phe
 1               5                  10

<210> SEQ ID NO 1863
<211> LENGTH: 9
<212> TYPE: PRT
<213> ORGANISM: Orthohepadnaviridae hepatitis B virus

<400> SEQUENCE: 1863

Leu Leu Val Leu Gln Ala Gly Phe Phe
 1               5

<210> SEQ ID NO 1864
<211> LENGTH: 9
<212> TYPE: PRT
<213> ORGANISM: Orthohepadnaviridae hepatitis B virus

<400> SEQUENCE: 1864

Leu Leu Val Pro Phe Val Gln Trp Phe
 1               5

<210> SEQ ID NO 1865
<211> LENGTH: 9
<212> TYPE: PRT
<213> ORGANISM: Orthohepadnaviridae hepatitis B virus
```

-continued

```
<400> SEQUENCE: 1865

Leu Ser Phe Leu Pro Ser Asp Phe Phe
 1               5

<210> SEQ ID NO 1866
<211> LENGTH: 9
<212> TYPE: PRT
<213> ORGANISM: Orthohepadnaviridae hepatitis B virus

<400> SEQUENCE: 1866

Leu Ser Leu Asp Val Ser Ala Ala Phe
 1               5

<210> SEQ ID NO 1867
<211> LENGTH: 11
<212> TYPE: PRT
<213> ORGANISM: Orthohepadnaviridae hepatitis B virus

<400> SEQUENCE: 1867

Leu Ser Leu Gly Ile His Leu Asn Pro Asn Lys
 1               5                  10

<210> SEQ ID NO 1868
<211> LENGTH: 10
<212> TYPE: PRT
<213> ORGANISM: Orthohepadnaviridae hepatitis B virus

<400> SEQUENCE: 1868

Leu Ser Leu Arg Gly Leu Pro Val Cys Ala
 1               5                  10

<210> SEQ ID NO 1869
<211> LENGTH: 9
<212> TYPE: PRT
<213> ORGANISM: Orthohepadnaviridae hepatitis B virus

<400> SEQUENCE: 1869

Leu Ser Pro Phe Leu Leu Ala Gln Phe
 1               5

<210> SEQ ID NO 1870
<211> LENGTH: 11
<212> TYPE: PRT
<213> ORGANISM: Orthohepadnaviridae hepatitis B virus

<400> SEQUENCE: 1870

Leu Ser Thr Leu Pro Glu Thr Thr Val Val Arg
 1               5                  10

<210> SEQ ID NO 1871
<211> LENGTH: 9
<212> TYPE: PRT
<213> ORGANISM: Orthohepadnaviridae hepatitis B virus

<400> SEQUENCE: 1871

Leu Ser Val Pro Asn Pro Leu Gly Phe
 1               5

<210> SEQ ID NO 1872
<211> LENGTH: 10
<212> TYPE: PRT
<213> ORGANISM: Orthohepadnaviridae hepatitis B virus

<400> SEQUENCE: 1872
```

Leu Ser Trp Leu Ser Leu Asp Val Ser Ala
 1               5                  10

<210> SEQ ID NO 1873
<211> LENGTH: 8
<212> TYPE: PRT
<213> ORGANISM: Orthohepadnaviridae hepatitis B virus

<400> SEQUENCE: 1873

Leu Ser Tyr Gln His Phe Arg Lys
 1               5

<210> SEQ ID NO 1874
<211> LENGTH: 8
<212> TYPE: PRT
<213> ORGANISM: Orthohepadnaviridae hepatitis B virus

<400> SEQUENCE: 1874

Leu Thr Val Asn Glu Lys Arg Arg
 1               5

<210> SEQ ID NO 1875
<211> LENGTH: 9
<212> TYPE: PRT
<213> ORGANISM: Orthohepadnaviridae hepatitis B virus

<400> SEQUENCE: 1875

Leu Val Ser Phe Gly Val Trp Ile Arg
 1               5

<210> SEQ ID NO 1876
<211> LENGTH: 10
<212> TYPE: PRT
<213> ORGANISM: Orthohepadnaviridae hepatitis B virus

<400> SEQUENCE: 1876

Leu Val Val Asp Phe Ser Gln Phe Ser Arg
 1               5                  10

<210> SEQ ID NO 1877
<211> LENGTH: 9
<212> TYPE: PRT
<213> ORGANISM: Orthohepadnaviridae hepatitis B virus

<400> SEQUENCE: 1877

Met Cys Leu Arg Arg Phe Ile Ile Phe
 1               5

<210> SEQ ID NO 1878
<211> LENGTH: 9
<212> TYPE: PRT
<213> ORGANISM: Orthohepadnaviridae hepatitis B virus

<400> SEQUENCE: 1878

Met Asp Asp Val Val Leu Gly Ala Lys
 1               5

<210> SEQ ID NO 1879
<211> LENGTH: 9
<212> TYPE: PRT
<213> ORGANISM: Orthohepadnaviridae hepatitis B virus

<400> SEQUENCE: 1879

Met Asp Ile Asp Pro Tyr Lys Glu Phe

<210> SEQ ID NO 1880
<211> LENGTH: 10
<212> TYPE: PRT
<213> ORGANISM: Orthohepadnaviridae hepatitis B virus

<400> SEQUENCE: 1880

Met Met Trp Tyr Trp Gly Pro Ser Leu Tyr
 1               5                  10

<210> SEQ ID NO 1881
<211> LENGTH: 10
<212> TYPE: PRT
<213> ORGANISM: Orthohepadnaviridae hepatitis B virus

<400> SEQUENCE: 1881

Met Ser Thr Thr Asp Leu Glu Ala Tyr Phe
 1               5                  10

<210> SEQ ID NO 1882
<211> LENGTH: 11
<212> TYPE: PRT
<213> ORGANISM: Orthohepadnaviridae hepatitis B virus

<400> SEQUENCE: 1882

Met Ser Thr Thr Asp Leu Glu Ala Tyr Phe Lys
 1               5                  10

<210> SEQ ID NO 1883
<211> LENGTH: 9
<212> TYPE: PRT
<213> ORGANISM: Orthohepadnaviridae hepatitis B virus

<400> SEQUENCE: 1883

Asn Phe Leu Leu Ser Leu Gly Ile His
 1               5

<210> SEQ ID NO 1884
<211> LENGTH: 8
<212> TYPE: PRT
<213> ORGANISM: Orthohepadnaviridae hepatitis B virus

<400> SEQUENCE: 1884

Asn Leu Glu Asp Pro Ala Ser Arg
 1               5

<210> SEQ ID NO 1885
<211> LENGTH: 10
<212> TYPE: PRT
<213> ORGANISM: Orthohepadnaviridae hepatitis B virus

<400> SEQUENCE: 1885

Asn Leu Asn Val Ser Ile Pro Trp Thr His
 1               5                  10

<210> SEQ ID NO 1886
<211> LENGTH: 11
<212> TYPE: PRT
<213> ORGANISM: Orthohepadnaviridae hepatitis B virus

<400> SEQUENCE: 1886

Asn Leu Asn Val Ser Ile Pro Trp Thr His Lys
 1               5                  10

```
<210> SEQ ID NO 1887
<211> LENGTH: 10
<212> TYPE: PRT
<213> ORGANISM: Orthohepadnaviridae hepatitis B virus

<400> SEQUENCE: 1887

Asn Leu Ser Val Pro Asn Pro Leu Gly Phe
1               5                   10

<210> SEQ ID NO 1888
<211> LENGTH: 9
<212> TYPE: PRT
<213> ORGANISM: Orthohepadnaviridae hepatitis B virus

<400> SEQUENCE: 1888

Asn Ser Gln Ser Pro Thr Ser Asn His
1               5

<210> SEQ ID NO 1889
<211> LENGTH: 8
<212> TYPE: PRT
<213> ORGANISM: Orthohepadnaviridae hepatitis B virus

<400> SEQUENCE: 1889

Asn Ser Val Val Leu Ser Arg Lys
1               5

<210> SEQ ID NO 1890
<211> LENGTH: 9
<212> TYPE: PRT
<213> ORGANISM: Orthohepadnaviridae hepatitis B virus

<400> SEQUENCE: 1890

Asn Val Ser Ile Pro Trp Thr His Lys
1               5

<210> SEQ ID NO 1891
<211> LENGTH: 9
<212> TYPE: PRT
<213> ORGANISM: Orthohepadnaviridae hepatitis B virus

<400> SEQUENCE: 1891

Pro Ala Asp Asp Pro Ser Arg Gly Arg
1               5

<210> SEQ ID NO 1892
<211> LENGTH: 9
<212> TYPE: PRT
<213> ORGANISM: Orthohepadnaviridae hepatitis B virus

<400> SEQUENCE: 1892

Pro Ala Arg Asp Val Leu Cys Leu Arg
1               5

<210> SEQ ID NO 1893
<211> LENGTH: 9
<212> TYPE: PRT
<213> ORGANISM: Orthohepadnaviridae hepatitis B virus

<400> SEQUENCE: 1893

Pro Ala Arg Val Thr Gly Gly Val Phe
1               5

<210> SEQ ID NO 1894
```

```
<211> LENGTH: 10
<212> TYPE: PRT
<213> ORGANISM: Orthohepadnaviridae hepatitis B virus

<400> SEQUENCE: 1894

Pro Ala Ser Thr Asn Arg Gln Ser Gly Arg
 1               5                  10

<210> SEQ ID NO 1895
<211> LENGTH: 10
<212> TYPE: PRT
<213> ORGANISM: Orthohepadnaviridae hepatitis B virus

<400> SEQUENCE: 1895

Pro Cys Ala Leu Arg Phe Thr Ser Ala Arg
 1               5                  10

<210> SEQ ID NO 1896
<211> LENGTH: 9
<212> TYPE: PRT
<213> ORGANISM: Orthohepadnaviridae hepatitis B virus

<400> SEQUENCE: 1896

Pro Asp His Gln Leu Asp Pro Ala Phe
 1               5

<210> SEQ ID NO 1897
<211> LENGTH: 10
<212> TYPE: PRT
<213> ORGANISM: Orthohepadnaviridae hepatitis B virus

<400> SEQUENCE: 1897

Pro Phe Leu Leu Ala Gln Phe Thr Ser Ala
 1               5                  10

<210> SEQ ID NO 1898
<211> LENGTH: 9
<212> TYPE: PRT
<213> ORGANISM: Orthohepadnaviridae hepatitis B virus

<400> SEQUENCE: 1898

Pro Phe Thr Gln Cys Gly Tyr Pro Ala
 1               5

<210> SEQ ID NO 1899
<211> LENGTH: 9
<212> TYPE: PRT
<213> ORGANISM: Orthohepadnaviridae hepatitis B virus

<400> SEQUENCE: 1899

Pro Gly Tyr Arg Trp Met Cys Leu Arg
 1               5

<210> SEQ ID NO 1900
<211> LENGTH: 10
<212> TYPE: PRT
<213> ORGANISM: Orthohepadnaviridae hepatitis B virus

<400> SEQUENCE: 1900

Pro Gly Tyr Arg Trp Met Cys Leu Arg Arg
 1               5                  10

<210> SEQ ID NO 1901
<211> LENGTH: 9
<212> TYPE: PRT
```

-continued

<213> ORGANISM: Orthohepadnaviridae hepatitis B virus

<400> SEQUENCE: 1901

Pro Ile Asp Trp Lys Val Cys Gln Arg
1 5

<210> SEQ ID NO 1902
<211> LENGTH: 9
<212> TYPE: PRT
<213> ORGANISM: Orthohepadnaviridae hepatitis B virus

<400> SEQUENCE: 1902

Pro Ile Phe Phe Cys Leu Trp Val Tyr
1 5

<210> SEQ ID NO 1903
<211> LENGTH: 8
<212> TYPE: PRT
<213> ORGANISM: Orthohepadnaviridae hepatitis B virus

<400> SEQUENCE: 1903

Pro Ile Ile Leu Gly Phe Arg Lys
1 5

<210> SEQ ID NO 1904
<211> LENGTH: 8
<212> TYPE: PRT
<213> ORGANISM: Orthohepadnaviridae hepatitis B virus

<400> SEQUENCE: 1904

Pro Leu Glu Glu Glu Leu Pro Arg
1 5

<210> SEQ ID NO 1905
<211> LENGTH: 9
<212> TYPE: PRT
<213> ORGANISM: Orthohepadnaviridae hepatitis B virus

<400> SEQUENCE: 1905

Pro Leu His Pro Ala Ala Met Pro His
1 5

<210> SEQ ID NO 1906
<211> LENGTH: 9
<212> TYPE: PRT
<213> ORGANISM: Orthohepadnaviridae hepatitis B virus

<400> SEQUENCE: 1906

Pro Leu Leu Val Leu Gln Ala Gly Phe
1 5

<210> SEQ ID NO 1907
<211> LENGTH: 10
<212> TYPE: PRT
<213> ORGANISM: Orthohepadnaviridae hepatitis B virus

<400> SEQUENCE: 1907

Pro Leu Leu Val Leu Gln Ala Gly Phe Phe
1 5 10

<210> SEQ ID NO 1908
<211> LENGTH: 8
<212> TYPE: PRT
<213> ORGANISM: Orthohepadnaviridae hepatitis B virus -continued

```
<400> SEQUENCE: 1908

Pro Leu Ser Tyr Gln His Phe Arg
1               5

<210> SEQ ID NO 1909
<211> LENGTH: 9
<212> TYPE: PRT
<213> ORGANISM: Orthohepadnaviridae hepatitis B virus

<400> SEQUENCE: 1909

Pro Leu Ser Tyr Gln His Phe Arg Lys
1               5

<210> SEQ ID NO 1910
<211> LENGTH: 8
<212> TYPE: PRT
<213> ORGANISM: Orthohepadnaviridae hepatitis B virus

<400> SEQUENCE: 1910

Pro Leu Thr Val Asn Glu Lys Arg
1               5

<210> SEQ ID NO 1911
<211> LENGTH: 9
<212> TYPE: PRT
<213> ORGANISM: Orthohepadnaviridae hepatitis B virus

<400> SEQUENCE: 1911

Pro Leu Thr Val Asn Glu Lys Arg Arg
1               5

<210> SEQ ID NO 1912
<211> LENGTH: 9
<212> TYPE: PRT
<213> ORGANISM: Orthohepadnaviridae hepatitis B virus

<400> SEQUENCE: 1912

Pro Met Gly Val Gly Leu Ser Pro Phe
1               5

<210> SEQ ID NO 1913
<211> LENGTH: 9
<212> TYPE: PRT
<213> ORGANISM: Orthohepadnaviridae hepatitis B virus

<400> SEQUENCE: 1913

Pro Met Gly Val Gly Leu Ser Pro Phe
1               5

<210> SEQ ID NO 1914
<211> LENGTH: 9
<212> TYPE: PRT
<213> ORGANISM: Orthohepadnaviridae hepatitis B virus

<400> SEQUENCE: 1914

Pro Val Gly Ala Glu Ser Arg Gly Arg
1               5

<210> SEQ ID NO 1915
<211> LENGTH: 9
<212> TYPE: PRT
<213> ORGANISM: Orthohepadnaviridae hepatitis B virus

<400> SEQUENCE: 1915
```

-continued

Pro Val Asn Arg Pro Ile Asp Trp Lys
1               5

<210> SEQ ID NO 1916
<211> LENGTH: 9
<212> TYPE: PRT
<213> ORGANISM: Orthohepadnaviridae hepatitis B virus

<400> SEQUENCE: 1916

Gln Ala Phe Thr Phe Ser Pro Thr Tyr
1               5

<210> SEQ ID NO 1917
<211> LENGTH: 10
<212> TYPE: PRT
<213> ORGANISM: Orthohepadnaviridae hepatitis B virus

<400> SEQUENCE: 1917

Gln Ala Phe Thr Phe Ser Pro Thr Tyr Lys
1               5                   10

<210> SEQ ID NO 1918
<211> LENGTH: 9
<212> TYPE: PRT
<213> ORGANISM: Orthohepadnaviridae hepatitis B virus

<400> SEQUENCE: 1918

Gln Ala Gly Phe Phe Leu Leu Thr Arg
1               5

<210> SEQ ID NO 1919
<211> LENGTH: 10
<212> TYPE: PRT
<213> ORGANISM: Orthohepadnaviridae hepatitis B virus

<400> SEQUENCE: 1919

Gln Ala Met Gln Trp Asn Ser Thr Thr Phe
1               5                   10

<210> SEQ ID NO 1920
<211> LENGTH: 11
<212> TYPE: PRT
<213> ORGANISM: Orthohepadnaviridae hepatitis B virus

<400> SEQUENCE: 1920

Gln Ser Pro Arg Arg Arg Arg Ser Gln Ser Arg
1               5                   10

<210> SEQ ID NO 1921
<211> LENGTH: 8
<212> TYPE: PRT
<213> ORGANISM: Orthohepadnaviridae hepatitis B virus

<400> SEQUENCE: 1921

Gln Ser Ser Gly Ile Leu Ser Arg
1               5

<210> SEQ ID NO 1922
<211> LENGTH: 9
<212> TYPE: PRT
<213> ORGANISM: Orthohepadnaviridae hepatitis B virus

<400> SEQUENCE: 1922

Arg Ala Phe Pro His Cys Leu Ala Phe
1               5

<210> SEQ ID NO 1923
<211> LENGTH: 9
<212> TYPE: PRT
<213> ORGANISM: Orthohepadnaviridae hepatitis B virus

<400> SEQUENCE: 1923

Arg Leu Lys Leu Ile Met Pro Ala Arg
1               5

<210> SEQ ID NO 1924
<211> LENGTH: 10
<212> TYPE: PRT
<213> ORGANISM: Orthohepadnaviridae hepatitis B virus

<400> SEQUENCE: 1924

Arg Leu Lys Leu Ile Met Pro Ala Arg Phe
1               5                   10

<210> SEQ ID NO 1925
<211> LENGTH: 11
<212> TYPE: PRT
<213> ORGANISM: Orthohepadnaviridae hepatitis B virus

<400> SEQUENCE: 1925

Arg Leu Lys Val Phe Val Leu Gly Gly Cys Arg
1               5                   10

<210> SEQ ID NO 1926
<211> LENGTH: 9
<212> TYPE: PRT
<213> ORGANISM: Orthohepadnaviridae hepatitis B virus

<400> SEQUENCE: 1926

Arg Leu Val Val Asp Phe Ser Gln Phe
1               5

<210> SEQ ID NO 1927
<211> LENGTH: 11
<212> TYPE: PRT
<213> ORGANISM: Orthohepadnaviridae hepatitis B virus

<400> SEQUENCE: 1927

Arg Leu Val Val Asp Phe Ser Gln Phe Ser Arg
1               5                   10

<210> SEQ ID NO 1928
<211> LENGTH: 11
<212> TYPE: PRT
<213> ORGANISM: Orthohepadnaviridae hepatitis B virus

<400> SEQUENCE: 1928

Arg Ser Pro Arg Arg Thr Pro Ser Pro Arg
1               5                   10

<210> SEQ ID NO 1929
<211> LENGTH: 8
<212> TYPE: PRT
<213> ORGANISM: Orthohepadnaviridae hepatitis B virus

<400> SEQUENCE: 1929

Arg Ser Gln Ser Pro Arg Arg Arg
1               5

```
<210> SEQ ID NO 1930
<211> LENGTH: 9
<212> TYPE: PRT
<213> ORGANISM: Orthohepadnaviridae hepatitis B virus

<400> SEQUENCE: 1930

Arg Ser Gln Ser Pro Arg Arg Arg Arg
 1               5

<210> SEQ ID NO 1931
<211> LENGTH: 8
<212> TYPE: PRT
<213> ORGANISM: Orthohepadnaviridae hepatitis B virus

<400> SEQUENCE: 1931

Arg Thr Pro Ser Pro Arg Arg Arg
 1               5

<210> SEQ ID NO 1932
<211> LENGTH: 9
<212> TYPE: PRT
<213> ORGANISM: Orthohepadnaviridae hepatitis B virus

<400> SEQUENCE: 1932

Arg Thr Pro Ser Pro Arg Arg Arg Arg
 1               5

<210> SEQ ID NO 1933
<211> LENGTH: 9
<212> TYPE: PRT
<213> ORGANISM: Orthohepadnaviridae hepatitis B virus

<400> SEQUENCE: 1933

Arg Val His Phe Ala Ser Pro Leu His
 1               5

<210> SEQ ID NO 1934
<211> LENGTH: 11
<212> TYPE: PRT
<213> ORGANISM: Orthohepadnaviridae hepatitis B virus

<400> SEQUENCE: 1934

Arg Val Thr Gly Gly Val Phe Leu Val Asp Lys
 1               5                  10

<210> SEQ ID NO 1935
<211> LENGTH: 8
<212> TYPE: PRT
<213> ORGANISM: Orthohepadnaviridae hepatitis B virus

<400> SEQUENCE: 1935

Ser Ala Gly Pro Cys Ala Leu Arg
 1               5

<210> SEQ ID NO 1936
<211> LENGTH: 9
<212> TYPE: PRT
<213> ORGANISM: Orthohepadnaviridae hepatitis B virus

<400> SEQUENCE: 1936

Ser Ala Gly Pro Cys Ala Leu Arg Phe
 1               5

<210> SEQ ID NO 1937
<211> LENGTH: 8
```

-continued

<212> TYPE: PRT
<213> ORGANISM: Orthohepadnaviridae hepatitis B virus

<400> SEQUENCE: 1937

Ser Ala Ile Cys Ser Val Val Arg
1               5

<210> SEQ ID NO 1938
<211> LENGTH: 9
<212> TYPE: PRT
<213> ORGANISM: Orthohepadnaviridae hepatitis B virus

<400> SEQUENCE: 1938

Ser Ala Ile Cys Ser Val Val Arg Arg
1               5

<210> SEQ ID NO 1939
<211> LENGTH: 11
<212> TYPE: PRT
<213> ORGANISM: Orthohepadnaviridae hepatitis B virus

<400> SEQUENCE: 1939

Ser Ala Leu Asn Pro Ala Asp Asp Pro Ser Arg
1               5                   10

<210> SEQ ID NO 1940
<211> LENGTH: 9
<212> TYPE: PRT
<213> ORGANISM: Orthohepadnaviridae hepatitis B virus

<400> SEQUENCE: 1940

Ser Ala Ser Phe Cys Gly Ser Pro Tyr
1               5

<210> SEQ ID NO 1941
<211> LENGTH: 9
<212> TYPE: PRT
<213> ORGANISM: Orthohepadnaviridae hepatitis B virus

<400> SEQUENCE: 1941

Ser Phe Pro Trp Leu Leu Gly Cys Ala
1               5

<210> SEQ ID NO 1942
<211> LENGTH: 10
<212> TYPE: PRT
<213> ORGANISM: Orthohepadnaviridae hepatitis B virus

<400> SEQUENCE: 1942

Ser Phe Pro Trp Leu Leu Gly Cys Ala Ala
1               5                   10

<210> SEQ ID NO 1943
<211> LENGTH: 10
<212> TYPE: PRT
<213> ORGANISM: Orthohepadnaviridae hepatitis B virus

<400> SEQUENCE: 1943

Ser Leu Asp Val Ser Ala Ala Phe Tyr His
1               5                   10

<210> SEQ ID NO 1944
<211> LENGTH: 10
<212> TYPE: PRT
<213> ORGANISM: Orthohepadnaviridae hepatitis B virus

<400> SEQUENCE: 1944

Ser Leu Gly Ile His Leu Asn Pro Asn Lys
1               5                   10

<210> SEQ ID NO 1945
<211> LENGTH: 10
<212> TYPE: PRT
<213> ORGANISM: Orthohepadnaviridae hepatitis B virus

<400> SEQUENCE: 1945

Ser Leu Leu Val Pro Phe Val Gln Trp Phe
1               5                   10

<210> SEQ ID NO 1946
<211> LENGTH: 10
<212> TYPE: PRT
<213> ORGANISM: Orthohepadnaviridae hepatitis B virus

<400> SEQUENCE: 1946

Ser Leu Arg Gly Leu Pro Val Cys Ala Phe
1               5                   10

<210> SEQ ID NO 1947
<211> LENGTH: 9
<212> TYPE: PRT
<213> ORGANISM: Orthohepadnaviridae hepatitis B virus

<400> SEQUENCE: 1947

Ser Ser Ala Gly Pro Cys Ala Leu Arg
1               5

<210> SEQ ID NO 1948
<211> LENGTH: 10
<212> TYPE: PRT
<213> ORGANISM: Orthohepadnaviridae hepatitis B virus

<400> SEQUENCE: 1948

Ser Ser Ala Gly Pro Cys Ala Leu Arg Phe
1               5                   10

<210> SEQ ID NO 1949
<211> LENGTH: 10
<212> TYPE: PRT
<213> ORGANISM: Orthohepadnaviridae hepatitis B virus

<400> SEQUENCE: 1949

Ser Thr Leu Pro Glu Thr Thr Val Val Arg
1               5                   10

<210> SEQ ID NO 1950
<211> LENGTH: 11
<212> TYPE: PRT
<213> ORGANISM: Orthohepadnaviridae hepatitis B virus

<400> SEQUENCE: 1950

Ser Thr Leu Pro Glu Thr Thr Val Val Arg Arg
1               5                   10

<210> SEQ ID NO 1951
<211> LENGTH: 8
<212> TYPE: PRT
<213> ORGANISM: Orthohepadnaviridae hepatitis B virus

<400> SEQUENCE: 1951

```
Ser Thr Asn Arg Gln Ser Gly Arg
1               5

<210> SEQ ID NO 1952
<211> LENGTH: 9
<212> TYPE: PRT
<213> ORGANISM: Orthohepadnaviridae hepatitis B virus

<400> SEQUENCE: 1952

Ser Thr Thr Asp Leu Glu Ala Tyr Phe
1               5

<210> SEQ ID NO 1953
<211> LENGTH: 10
<212> TYPE: PRT
<213> ORGANISM: Orthohepadnaviridae hepatitis B virus

<400> SEQUENCE: 1953

Ser Thr Thr Asp Leu Glu Ala Tyr Phe Lys
1               5                   10

<210> SEQ ID NO 1954
<211> LENGTH: 9
<212> TYPE: PRT
<213> ORGANISM: Orthohepadnaviridae hepatitis B virus

<400> SEQUENCE: 1954

Ser Val Val Arg Arg Ala Phe Pro His
1               5

<210> SEQ ID NO 1955
<211> LENGTH: 9
<212> TYPE: PRT
<213> ORGANISM: Orthohepadnaviridae hepatitis B virus

<400> SEQUENCE: 1955

Thr Ala Glu Leu Leu Ala Ala Cys Phe
1               5

<210> SEQ ID NO 1956
<211> LENGTH: 11
<212> TYPE: PRT
<213> ORGANISM: Orthohepadnaviridae hepatitis B virus

<400> SEQUENCE: 1956

Thr Ala Glu Leu Leu Ala Ala Cys Phe Ala Arg
1               5                   10

<210> SEQ ID NO 1957
<211> LENGTH: 9
<212> TYPE: PRT
<213> ORGANISM: Orthohepadnaviridae hepatitis B virus

<400> SEQUENCE: 1957

Thr Asp Asn Ser Val Val Leu Ser Arg
1               5

<210> SEQ ID NO 1958
<211> LENGTH: 10
<212> TYPE: PRT
<213> ORGANISM: Orthohepadnaviridae hepatitis B virus

<400> SEQUENCE: 1958

Thr Asp Asn Ser Val Val Leu Ser Arg Lys
```

-continued

```
<210> SEQ ID NO 1959
<211> LENGTH: 10
<212> TYPE: PRT
<213> ORGANISM: Orthohepadnaviridae hepatitis B virus

<400> SEQUENCE: 1959

Thr Phe Gly Arg Glu Thr Val Leu Glu Tyr
1               5                   10

<210> SEQ ID NO 1960
<211> LENGTH: 9
<212> TYPE: PRT
<213> ORGANISM: Orthohepadnaviridae hepatitis B virus

<400> SEQUENCE: 1960

Thr Phe Ser Pro Thr Tyr Lys Ala Phe
1               5

<210> SEQ ID NO 1961
<211> LENGTH: 9
<212> TYPE: PRT
<213> ORGANISM: Orthohepadnaviridae hepatitis B virus

<400> SEQUENCE: 1961

Thr Gly Gly Val Phe Leu Val Asp Lys
1               5

<210> SEQ ID NO 1962
<211> LENGTH: 9
<212> TYPE: PRT
<213> ORGANISM: Orthohepadnaviridae hepatitis B virus

<400> SEQUENCE: 1962

Thr Leu Pro Glu Thr Thr Val Val Arg
1               5

<210> SEQ ID NO 1963
<211> LENGTH: 10
<212> TYPE: PRT
<213> ORGANISM: Orthohepadnaviridae hepatitis B virus

<400> SEQUENCE: 1963

Thr Leu Pro Glu Thr Thr Val Val Arg Arg
1               5                   10

<210> SEQ ID NO 1964
<211> LENGTH: 11
<212> TYPE: PRT
<213> ORGANISM: Orthohepadnaviridae hepatitis B virus

<400> SEQUENCE: 1964

Thr Leu Pro Glu Thr Thr Val Val Arg Arg Arg
1               5                   10

<210> SEQ ID NO 1965
<211> LENGTH: 9
<212> TYPE: PRT
<213> ORGANISM: Orthohepadnaviridae hepatitis B virus

<400> SEQUENCE: 1965

Thr Leu Trp Lys Ala Gly Ile Leu Tyr
1               5
```

<210> SEQ ID NO 1966
<211> LENGTH: 10
<212> TYPE: PRT
<213> ORGANISM: Orthohepadnaviridae hepatitis B virus

<400> SEQUENCE: 1966

Thr Leu Trp Lys Ala Gly Ile Leu Tyr Lys
1               5                   10

<210> SEQ ID NO 1967
<211> LENGTH: 11
<212> TYPE: PRT
<213> ORGANISM: Orthohepadnaviridae hepatitis B virus

<400> SEQUENCE: 1967

Thr Leu Trp Lys Ala Gly Ile Leu Tyr Lys Arg
1               5                   10

<210> SEQ ID NO 1968
<211> LENGTH: 9
<212> TYPE: PRT
<213> ORGANISM: Orthohepadnaviridae hepatitis B virus

<400> SEQUENCE: 1968

Thr Ser Ala Ile Cys Ser Val Val Arg
1               5

<210> SEQ ID NO 1969
<211> LENGTH: 10
<212> TYPE: PRT
<213> ORGANISM: Orthohepadnaviridae hepatitis B virus

<400> SEQUENCE: 1969

Thr Ser Ala Ile Cys Ser Val Val Arg Arg
1               5                   10

<210> SEQ ID NO 1970
<211> LENGTH: 10
<212> TYPE: PRT
<213> ORGANISM: Orthohepadnaviridae hepatitis B virus

<400> SEQUENCE: 1970

Thr Ser Phe Pro Trp Leu Leu Gly Cys Ala
1               5                   10

<210> SEQ ID NO 1971
<211> LENGTH: 9
<212> TYPE: PRT
<213> ORGANISM: Orthohepadnaviridae hepatitis B virus

<400> SEQUENCE: 1971

Thr Ser Phe Val Tyr Val Pro Ser Ala
1               5

<210> SEQ ID NO 1972
<211> LENGTH: 9
<212> TYPE: PRT
<213> ORGANISM: Orthohepadnaviridae hepatitis B virus

<400> SEQUENCE: 1972

Thr Thr Asp Leu Glu Ala Tyr Phe Lys
1               5

<210> SEQ ID NO 1973

-continued

```
<211> LENGTH: 8
<212> TYPE: PRT
<213> ORGANISM: Orthohepadnaviridae hepatitis B virus

<400> SEQUENCE: 1973

Thr Thr Ser Thr Gly Pro Cys Lys
1               5

<210> SEQ ID NO 1974
<211> LENGTH: 9
<212> TYPE: PRT
<213> ORGANISM: Orthohepadnaviridae hepatitis B virus

<400> SEQUENCE: 1974

Thr Thr Val Val Arg Arg Arg Gly Arg
1               5

<210> SEQ ID NO 1975
<211> LENGTH: 8
<212> TYPE: PRT
<213> ORGANISM: Orthohepadnaviridae hepatitis B virus

<400> SEQUENCE: 1975

Thr Val Val Arg Arg Arg Gly Arg
1               5

<210> SEQ ID NO 1976
<211> LENGTH: 11
<212> TYPE: PRT
<213> ORGANISM: Orthohepadnaviridae hepatitis B virus

<400> SEQUENCE: 1976

Thr Val Val Arg Arg Arg Gly Arg Ser Pro Arg
1               5                   10

<210> SEQ ID NO 1977
<211> LENGTH: 9
<212> TYPE: PRT
<213> ORGANISM: Orthohepadnaviridae hepatitis B virus

<400> SEQUENCE: 1977

Val Phe Leu Val Asp Lys Asn Pro His
1               5

<210> SEQ ID NO 1978
<211> LENGTH: 9
<212> TYPE: PRT
<213> ORGANISM: Orthohepadnaviridae hepatitis B virus

<400> SEQUENCE: 1978

Val Phe Val Leu Gly Gly Cys Arg His
1               5

<210> SEQ ID NO 1979
<211> LENGTH: 10
<212> TYPE: PRT
<213> ORGANISM: Orthohepadnaviridae hepatitis B virus

<400> SEQUENCE: 1979

Val Phe Val Leu Gly Gly Cys Arg His Lys
1               5                   10

<210> SEQ ID NO 1980
<211> LENGTH: 10
<212> TYPE: PRT
```

<213> ORGANISM: Orthohepadnaviridae hepatitis B virus

<400> SEQUENCE: 1980

Val Gly Leu Leu Gly Phe Ala Ala Pro Phe
1               5                   10

<210> SEQ ID NO 1981
<211> LENGTH: 9
<212> TYPE: PRT
<213> ORGANISM: Orthohepadnaviridae hepatitis B virus

<400> SEQUENCE: 1981

Val Gly Pro Leu Thr Val Asn Glu Lys
1               5

<210> SEQ ID NO 1982
<211> LENGTH: 10
<212> TYPE: PRT
<213> ORGANISM: Orthohepadnaviridae hepatitis B virus

<400> SEQUENCE: 1982

Val Gly Pro Leu Thr Val Asn Glu Lys Arg
1               5                   10

<210> SEQ ID NO 1983
<211> LENGTH: 9
<212> TYPE: PRT
<213> ORGANISM: Orthohepadnaviridae hepatitis B virus

<400> SEQUENCE: 1983

Val Leu Gly Ala Lys Ser Val Gln His
1               5

<210> SEQ ID NO 1984
<211> LENGTH: 8
<212> TYPE: PRT
<213> ORGANISM: Orthohepadnaviridae hepatitis B virus

<400> SEQUENCE: 1984

Val Leu Gly Gly Cys Arg His Lys
1               5

<210> SEQ ID NO 1985
<211> LENGTH: 11
<212> TYPE: PRT
<213> ORGANISM: Orthohepadnaviridae hepatitis B virus

<400> SEQUENCE: 1985

Val Leu Gln Ala Gly Phe Phe Leu Leu Thr Arg
1               5                   10

<210> SEQ ID NO 1986
<211> LENGTH: 9
<212> TYPE: PRT
<213> ORGANISM: Orthohepadnaviridae hepatitis B virus

<400> SEQUENCE: 1986

Val Leu Ser Arg Lys Tyr Thr Ser Phe
1               5

<210> SEQ ID NO 1987
<211> LENGTH: 8
<212> TYPE: PRT
<213> ORGANISM: Orthohepadnaviridae hepatitis B virus

```
<400> SEQUENCE: 1987

Val Ser Phe Gly Val Trp Ile Arg
1               5

<210> SEQ ID NO 1988
<211> LENGTH: 8
<212> TYPE: PRT
<213> ORGANISM: Orthohepadnaviridae hepatitis B virus

<400> SEQUENCE: 1988

Val Ser Ile Pro Trp Thr His Lys
1               5

<210> SEQ ID NO 1989
<211> LENGTH: 10
<212> TYPE: PRT
<213> ORGANISM: Orthohepadnaviridae hepatitis B virus

<400> SEQUENCE: 1989

Val Thr Gly Gly Val Phe Leu Val Asp Lys
1               5                   10

<210> SEQ ID NO 1990
<211> LENGTH: 9
<212> TYPE: PRT
<213> ORGANISM: Orthohepadnaviridae hepatitis B virus

<400> SEQUENCE: 1990

Val Val Asp Phe Ser Gln Phe Ser Arg
1               5

<210> SEQ ID NO 1991
<211> LENGTH: 10
<212> TYPE: PRT
<213> ORGANISM: Orthohepadnaviridae hepatitis B virus

<400> SEQUENCE: 1991

Val Val Leu Gly Ala Lys Ser Val Gln His
1               5                   10

<210> SEQ ID NO 1992
<211> LENGTH: 10
<212> TYPE: PRT
<213> ORGANISM: Orthohepadnaviridae hepatitis B virus

<400> SEQUENCE: 1992

Val Val Leu Ser Arg Lys Tyr Thr Ser Phe
1               5                   10

<210> SEQ ID NO 1993
<211> LENGTH: 10
<212> TYPE: PRT
<213> ORGANISM: Orthohepadnaviridae hepatitis B virus

<400> SEQUENCE: 1993

Val Val Arg Arg Arg Gly Arg Ser Pro Arg
1               5                   10

<210> SEQ ID NO 1994
<211> LENGTH: 11
<212> TYPE: PRT
<213> ORGANISM: Orthohepadnaviridae hepatitis B virus

<400> SEQUENCE: 1994
```

```
Val Val Arg Arg Arg Gly Arg Ser Pro Arg Arg
1               5                   10

<210> SEQ ID NO 1995
<211> LENGTH: 9
<212> TYPE: PRT
<213> ORGANISM: Orthohepadnaviridae hepatitis B virus

<400> SEQUENCE: 1995

Trp Phe His Ile Ser Cys Leu Thr Phe
1               5

<210> SEQ ID NO 1996
<211> LENGTH: 9
<212> TYPE: PRT
<213> ORGANISM: Orthohepadnaviridae hepatitis B virus

<400> SEQUENCE: 1996

Trp Phe His Ile Ser Cys Leu Thr Phe
1               5

<210> SEQ ID NO 1997
<211> LENGTH: 9
<212> TYPE: PRT
<213> ORGANISM: Orthohepadnaviridae hepatitis B virus

<400> SEQUENCE: 1997

Trp Gly Met Asp Ile Asp Pro Tyr Lys
1               5

<210> SEQ ID NO 1998
<211> LENGTH: 10
<212> TYPE: PRT
<213> ORGANISM: Orthohepadnaviridae hepatitis B virus

<400> SEQUENCE: 1998

Trp Gly Tyr Ser Leu Asn Phe Met Gly Tyr
1               5                   10

<210> SEQ ID NO 1999
<211> LENGTH: 10
<212> TYPE: PRT
<213> ORGANISM: Orthohepadnaviridae hepatitis B virus

<400> SEQUENCE: 1999

Trp Ile Leu Arg Gly Thr Ser Phe Val Tyr
1               5                   10

<210> SEQ ID NO 2000
<211> LENGTH: 9
<212> TYPE: PRT
<213> ORGANISM: Orthohepadnaviridae hepatitis B virus

<400> SEQUENCE: 2000

Trp Ile Arg Thr Pro Pro Ala Tyr Arg
1               5

<210> SEQ ID NO 2001
<211> LENGTH: 8
<212> TYPE: PRT
<213> ORGANISM: Orthohepadnaviridae hepatitis B virus

<400> SEQUENCE: 2001

Trp Leu Gln Phe Arg Asn Ser Lys
1               5
```

```
<210> SEQ ID NO 2002
<211> LENGTH: 10
<212> TYPE: PRT
<213> ORGANISM: Orthohepadnaviridae hepatitis B virus

<400> SEQUENCE: 2002

Trp Leu Ser Leu Asp Val Ser Ala Ala Phe
 1               5                  10

<210> SEQ ID NO 2003
<211> LENGTH: 10
<212> TYPE: PRT
<213> ORGANISM: Orthohepadnaviridae hepatitis B virus

<400> SEQUENCE: 2003

Trp Leu Trp Gly Met Asp Ile Asp Pro Tyr
 1               5                  10

<210> SEQ ID NO 2004
<211> LENGTH: 11
<212> TYPE: PRT
<213> ORGANISM: Orthohepadnaviridae hepatitis B virus

<400> SEQUENCE: 2004

Trp Leu Trp Gly Met Asp Ile Asp Pro Tyr Lys
 1               5                  10

<210> SEQ ID NO 2005
<211> LENGTH: 10
<212> TYPE: PRT
<213> ORGANISM: Orthohepadnaviridae hepatitis B virus

<400> SEQUENCE: 2005

Trp Met Cys Leu Arg Arg Phe Ile Ile Phe
 1               5                  10

<210> SEQ ID NO 2006
<211> LENGTH: 10
<212> TYPE: PRT
<213> ORGANISM: Orthohepadnaviridae hepatitis B virus

<400> SEQUENCE: 2006

Trp Met Cys Leu Arg Arg Phe Ile Ile Phe
 1               5                  10

<210> SEQ ID NO 2007
<211> LENGTH: 9
<212> TYPE: PRT
<213> ORGANISM: Orthohepadnaviridae hepatitis B virus

<400> SEQUENCE: 2007

Tyr Leu Pro Leu Asp Lys Gly Ile Lys
 1               5

<210> SEQ ID NO 2008
<211> LENGTH: 10
<212> TYPE: PRT
<213> ORGANISM: Orthohepadnaviridae hepatitis B virus

<400> SEQUENCE: 2008

Tyr Leu Val Ser Phe Gly Val Trp Ile Arg
 1               5                  10
```

```
<210> SEQ ID NO 2009
<211> LENGTH: 10
<212> TYPE: PRT
<213> ORGANISM: Orthohepadnaviridae hepatitis B virus

<400> SEQUENCE: 2009

Tyr Met Asp Asp Val Val Leu Gly Ala Lys
1               5                   10

<210> SEQ ID NO 2010
<211> LENGTH: 9
<212> TYPE: PRT
<213> ORGANISM: Orthohepadnaviridae hepatitis B virus

<400> SEQUENCE: 2010

Tyr Ser His Pro Ile Ile Leu Gly Phe
1               5

<210> SEQ ID NO 2011
<211> LENGTH: 10
<212> TYPE: PRT
<213> ORGANISM: Orthohepadnaviridae hepatitis B virus

<400> SEQUENCE: 2011

Tyr Ser His Pro Ile Ile Leu Gly Phe Arg
1               5                   10

<210> SEQ ID NO 2012
<211> LENGTH: 11
<212> TYPE: PRT
<213> ORGANISM: Orthohepadnaviridae hepatitis B virus

<400> SEQUENCE: 2012

Tyr Ser His Pro Ile Ile Leu Gly Phe Arg Lys
1               5                   10

<210> SEQ ID NO 2013
<211> LENGTH: 10
<212> TYPE: PRT
<213> ORGANISM: Orthohepadnaviridae hepatitis B virus

<400> SEQUENCE: 2013

Ala Phe Ser Ser Ala Gly Pro Cys Ala Leu
1               5                   10

<210> SEQ ID NO 2014
<211> LENGTH: 10
<212> TYPE: PRT
<213> ORGANISM: Orthohepadnaviridae hepatitis B virus

<400> SEQUENCE: 2014

Ala Phe Ser Tyr Met Asp Asp Val Val Leu
1               5                   10

<210> SEQ ID NO 2015
<211> LENGTH: 9
<212> TYPE: PRT
<213> ORGANISM: Orthohepadnaviridae hepatitis B virus

<400> SEQUENCE: 2015

Ala Met Gln Trp Asn Ser Thr Thr Phe
1               5

<210> SEQ ID NO 2016
<211> LENGTH: 9
```

```
<212> TYPE: PRT
<213> ORGANISM: Orthohepadnaviridae hepatitis B virus

<400> SEQUENCE: 2016

Ala Tyr Arg Pro Pro Asn Ala Pro Ile
 1               5

<210> SEQ ID NO 2017
<211> LENGTH: 10
<212> TYPE: PRT
<213> ORGANISM: Orthohepadnaviridae hepatitis B virus

<400> SEQUENCE: 2017

Ala Tyr Arg Pro Pro Asn Ala Pro Ile Leu
 1               5                  10

<210> SEQ ID NO 2018
<211> LENGTH: 9
<212> TYPE: PRT
<213> ORGANISM: Orthohepadnaviridae hepatitis B virus

<400> SEQUENCE: 2018

Glu Tyr Leu Val Ser Phe Gly Val Trp
 1               5

<210> SEQ ID NO 2019
<211> LENGTH: 10
<212> TYPE: PRT
<213> ORGANISM: Orthohepadnaviridae hepatitis B virus

<400> SEQUENCE: 2019

Glu Tyr Leu Val Ser Phe Gly Val Trp Ile
 1               5                  10

<210> SEQ ID NO 2020
<211> LENGTH: 10
<212> TYPE: PRT
<213> ORGANISM: Orthohepadnaviridae hepatitis B virus

<400> SEQUENCE: 2020

Phe Phe Leu Leu Thr Arg Ile Leu Thr Ile
 1               5                  10

<210> SEQ ID NO 2021
<211> LENGTH: 9
<212> TYPE: PRT
<213> ORGANISM: Orthohepadnaviridae hepatitis B virus

<400> SEQUENCE: 2021

Gly Phe Phe Leu Leu Thr Arg Ile Leu
 1               5

<210> SEQ ID NO 2022
<211> LENGTH: 9
<212> TYPE: PRT
<213> ORGANISM: Orthohepadnaviridae hepatitis B virus

<400> SEQUENCE: 2022

Gly Phe Leu Gly Pro Leu Leu Val Leu
 1               5

<210> SEQ ID NO 2023
<211> LENGTH: 10
<212> TYPE: PRT
<213> ORGANISM: Orthohepadnaviridae hepatitis B virus
```

-continued

<400> SEQUENCE: 2023

Gly Met Asp Ile Asp Pro Tyr Lys Glu Phe
1               5                   10

<210> SEQ ID NO 2024
<211> LENGTH: 9
<212> TYPE: PRT
<213> ORGANISM: Orthohepadnaviridae hepatitis B virus

<400> SEQUENCE: 2024

Gly Trp Ser Pro Gln Ala Gln Gly Ile
1               5

<210> SEQ ID NO 2025
<211> LENGTH: 10
<212> TYPE: PRT
<213> ORGANISM: Orthohepadnaviridae hepatitis B virus

<400> SEQUENCE: 2025

Gly Trp Ser Pro Gln Ala Gln Gly Ile Leu
1               5                   10

<210> SEQ ID NO 2026
<211> LENGTH: 10
<212> TYPE: PRT
<213> ORGANISM: Orthohepadnaviridae hepatitis B virus

<400> SEQUENCE: 2026

Gly Tyr Arg Trp Met Cys Leu Arg Arg Phe
1               5                   10

<210> SEQ ID NO 2027
<211> LENGTH: 10
<212> TYPE: PRT
<213> ORGANISM: Orthohepadnaviridae hepatitis B virus

<400> SEQUENCE: 2027

His Phe Ala Ser Pro Leu His Val Ala Trp
1               5                   10

<210> SEQ ID NO 2028
<211> LENGTH: 9
<212> TYPE: PRT
<213> ORGANISM: Orthohepadnaviridae hepatitis B virus

<400> SEQUENCE: 2028

Ile Phe Phe Cys Leu Trp Val Tyr Ile
1               5

<210> SEQ ID NO 2029
<211> LENGTH: 10
<212> TYPE: PRT
<213> ORGANISM: Orthohepadnaviridae hepatitis B virus

<400> SEQUENCE: 2029

Ile Phe Leu Phe Ile Leu Leu Leu Cys Leu
1               5                   10

<210> SEQ ID NO 2030
<211> LENGTH: 10
<212> TYPE: PRT
<213> ORGANISM: Orthohepadnaviridae hepatitis B virus

<400> SEQUENCE: 2030

```
Lys Phe Ala Val Pro Asn Leu Gln Ser Leu
1               5                   10

<210> SEQ ID NO 2031
<211> LENGTH: 9
<212> TYPE: PRT
<213> ORGANISM: Orthohepadnaviridae hepatitis B virus

<400> SEQUENCE: 2031

Lys Tyr Leu Pro Leu Asp Lys Gly Ile
1               5

<210> SEQ ID NO 2032
<211> LENGTH: 9
<212> TYPE: PRT
<213> ORGANISM: Orthohepadnaviridae hepatitis B virus

<400> SEQUENCE: 2032

Lys Tyr Thr Ser Phe Pro Trp Leu Leu
1               5

<210> SEQ ID NO 2033
<211> LENGTH: 9
<212> TYPE: PRT
<213> ORGANISM: Orthohepadnaviridae hepatitis B virus

<400> SEQUENCE: 2033

Leu Phe Ile Leu Leu Leu Cys Leu Ile
1               5

<210> SEQ ID NO 2034
<211> LENGTH: 10
<212> TYPE: PRT
<213> ORGANISM: Orthohepadnaviridae hepatitis B virus

<400> SEQUENCE: 2034

Leu Phe Ile Leu Leu Leu Cys Leu Ile Phe
1               5                   10

<210> SEQ ID NO 2035
<211> LENGTH: 10
<212> TYPE: PRT
<213> ORGANISM: Orthohepadnaviridae hepatitis B virus

<400> SEQUENCE: 2035

Leu Trp Phe His Ile Ser Cys Leu Thr Phe
1               5                   10

<210> SEQ ID NO 2036
<211> LENGTH: 10
<212> TYPE: PRT
<213> ORGANISM: Orthohepadnaviridae hepatitis B virus

<400> SEQUENCE: 2036

Leu Tyr Ser His Pro Ile Ile Leu Gly Phe
1               5                   10

<210> SEQ ID NO 2037
<211> LENGTH: 10
<212> TYPE: PRT
<213> ORGANISM: Orthohepadnaviridae hepatitis B virus

<400> SEQUENCE: 2037

Asn Phe Leu Leu Ser Leu Gly Ile His Leu
```

-continued

```
                1               5              10
```

<210> SEQ ID NO 2038
<211> LENGTH: 9
<212> TYPE: PRT
<213> ORGANISM: Orthohepadnaviridae hepatitis B virus

<400> SEQUENCE: 2038

Asn Trp Ile Leu Arg Gly Thr Ser Phe
 1               5

<210> SEQ ID NO 2039
<211> LENGTH: 10
<212> TYPE: PRT
<213> ORGANISM: Orthohepadnaviridae hepatitis B virus

<400> SEQUENCE: 2039

Pro Phe Thr Gln Cys Gly Tyr Pro Ala Leu
 1               5              10

<210> SEQ ID NO 2040
<211> LENGTH: 9
<212> TYPE: PRT
<213> ORGANISM: Orthohepadnaviridae hepatitis B virus

<400> SEQUENCE: 2040

Pro Phe Val Gln Trp Phe Val Gly Leu
 1               5

<210> SEQ ID NO 2041
<211> LENGTH: 9
<212> TYPE: PRT
<213> ORGANISM: Orthohepadnaviridae hepatitis B virus

<400> SEQUENCE: 2041

Pro Met Gly Val Gly Leu Ser Pro Phe
 1               5

<210> SEQ ID NO 2042
<211> LENGTH: 10
<212> TYPE: PRT
<213> ORGANISM: Orthohepadnaviridae hepatitis B virus

<400> SEQUENCE: 2042

Pro Trp Leu Leu Gly Cys Ala Ala Asn Trp
 1               5              10

<210> SEQ ID NO 2043
<211> LENGTH: 9
<212> TYPE: PRT
<213> ORGANISM: Orthohepadnaviridae hepatitis B virus

<400> SEQUENCE: 2043

Pro Trp Thr His Lys Val Gly Asn Phe
 1               5

<210> SEQ ID NO 2044
<211> LENGTH: 9
<212> TYPE: PRT
<213> ORGANISM: Orthohepadnaviridae hepatitis B virus

<400> SEQUENCE: 2044

Arg Phe Ile Ile Phe Leu Phe Ile Leu
 1               5

```
<210> SEQ ID NO 2045
<211> LENGTH: 10
<212> TYPE: PRT
<213> ORGANISM: Orthohepadnaviridae hepatitis B virus

<400> SEQUENCE: 2045

Arg Phe Ile Ile Phe Leu Phe Ile Leu Leu
1               5                   10

<210> SEQ ID NO 2046
<211> LENGTH: 9
<212> TYPE: PRT
<213> ORGANISM: Orthohepadnaviridae hepatitis B virus

<400> SEQUENCE: 2046

Arg Trp Met Cys Leu Arg Arg Phe Ile
1               5

<210> SEQ ID NO 2047
<211> LENGTH: 10
<212> TYPE: PRT
<213> ORGANISM: Orthohepadnaviridae hepatitis B virus

<400> SEQUENCE: 2047

Arg Trp Met Cys Leu Arg Arg Phe Ile Ile
1               5                   10

<210> SEQ ID NO 2048
<211> LENGTH: 9
<212> TYPE: PRT
<213> ORGANISM: Orthohepadnaviridae hepatitis B virus

<400> SEQUENCE: 2048

Ser Phe Cys Gly Ser Pro Tyr Ser Trp
1               5

<210> SEQ ID NO 2049
<211> LENGTH: 9
<212> TYPE: PRT
<213> ORGANISM: Orthohepadnaviridae hepatitis B virus

<400> SEQUENCE: 2049

Ser Phe Val Tyr Val Pro Ser Ala Leu
1               5

<210> SEQ ID NO 2050
<211> LENGTH: 9
<212> TYPE: PRT
<213> ORGANISM: Orthohepadnaviridae hepatitis B virus

<400> SEQUENCE: 2050

Ser Trp Leu Ser Leu Leu Val Pro Phe
1               5

<210> SEQ ID NO 2051
<211> LENGTH: 10
<212> TYPE: PRT
<213> ORGANISM: Orthohepadnaviridae hepatitis B virus

<400> SEQUENCE: 2051

Ser Trp Pro Lys Phe Ala Val Pro Asn Leu
1               5                   10

<210> SEQ ID NO 2052
```

-continued

```
<211> LENGTH: 9
<212> TYPE: PRT
<213> ORGANISM: Orthohepadnaviridae hepatitis B virus

<400> SEQUENCE: 2052

Ser Trp Trp Thr Ser Leu Asn Phe Leu
1               5

<210> SEQ ID NO 2053
<211> LENGTH: 9
<212> TYPE: PRT
<213> ORGANISM: Orthohepadnaviridae hepatitis B virus

<400> SEQUENCE: 2053

Ser Tyr Gln His Phe Arg Lys Leu Leu
1               5

<210> SEQ ID NO 2054
<211> LENGTH: 10
<212> TYPE: PRT
<213> ORGANISM: Orthohepadnaviridae hepatitis B virus

<400> SEQUENCE: 2054

Ser Tyr Gln His Phe Arg Lys Leu Leu Leu
1               5                   10

<210> SEQ ID NO 2055
<211> LENGTH: 9
<212> TYPE: PRT
<213> ORGANISM: Orthohepadnaviridae hepatitis B virus

<400> SEQUENCE: 2055

Thr Phe Ser Pro Thr Tyr Lys Ala Phe
1               5

<210> SEQ ID NO 2056
<211> LENGTH: 10
<212> TYPE: PRT
<213> ORGANISM: Orthohepadnaviridae hepatitis B virus

<400> SEQUENCE: 2056

Thr Phe Ser Pro Thr Tyr Lys Ala Phe Leu
1               5                   10

<210> SEQ ID NO 2057
<211> LENGTH: 10
<212> TYPE: PRT
<213> ORGANISM: Orthohepadnaviridae hepatitis B virus

<400> SEQUENCE: 2057

Val Phe Ala Asp Ala Thr Pro Thr Gly Trp
1               5                   10

<210> SEQ ID NO 2058
<211> LENGTH: 9
<212> TYPE: PRT
<213> ORGANISM: Orthohepadnaviridae hepatitis B virus

<400> SEQUENCE: 2058

Trp Phe His Ile Ser Cys Leu Thr Phe
1               5

<210> SEQ ID NO 2059
<211> LENGTH: 10
<212> TYPE: PRT
```

-continued

<213> ORGANISM: Orthohepadnaviridae hepatitis B virus

<400> SEQUENCE: 2059

Trp Phe Val Gly Leu Ser Pro Thr Val Trp
1               5                   10

<210> SEQ ID NO 2060
<211> LENGTH: 10
<212> TYPE: PRT
<213> ORGANISM: Orthohepadnaviridae hepatitis B virus

<400> SEQUENCE: 2060

Trp Met Cys Leu Arg Arg Phe Ile Ile Phe
1               5                   10

<210> SEQ ID NO 2061
<211> LENGTH: 15
<212> TYPE: PRT
<213> ORGANISM: Orthohepadnaviridae hepatitis B virus

<400> SEQUENCE: 2061

Ala Ala Asn Trp Ile Leu Arg Gly Thr Ser Phe Val Tyr Val Pro
1               5                   10                  15

<210> SEQ ID NO 2062
<211> LENGTH: 15
<212> TYPE: PRT
<213> ORGANISM: Orthohepadnaviridae hepatitis B virus

<400> SEQUENCE: 2062

Ala Glu Asp Leu Asn Leu Gly Asn Leu Asn Val Ser Ile Pro Trp
1               5                   10                  15

<210> SEQ ID NO 2063
<211> LENGTH: 15
<212> TYPE: PRT
<213> ORGANISM: Orthohepadnaviridae hepatitis B virus

<400> SEQUENCE: 2063

Ala Glu Leu Leu Ala Ala Cys Phe Ala Arg Ser Arg Ser Gly Ala
1               5                   10                  15

<210> SEQ ID NO 2064
<211> LENGTH: 15
<212> TYPE: PRT
<213> ORGANISM: Orthohepadnaviridae hepatitis B virus

<400> SEQUENCE: 2064

Ala Phe Ser Tyr Met Asp Asp Val Val Leu Gly Ala Lys Ser Val
1               5                   10                  15

<210> SEQ ID NO 2065
<211> LENGTH: 15
<212> TYPE: PRT
<213> ORGANISM: Orthohepadnaviridae hepatitis B virus

<400> SEQUENCE: 2065

Ala Gly Phe Phe Leu Leu Thr Arg Ile Leu Thr Ile Pro Gln Ser
1               5                   10                  15

<210> SEQ ID NO 2066
<211> LENGTH: 15
<212> TYPE: PRT
<213> ORGANISM: Orthohepadnaviridae hepatitis B virus

```
<400> SEQUENCE: 2066

Ala Gly Pro Leu Glu Glu Glu Leu Pro Arg Leu Ala Asp Glu Gly
1               5                   10                  15

<210> SEQ ID NO 2067
<211> LENGTH: 15
<212> TYPE: PRT
<213> ORGANISM: Orthohepadnaviridae hepatitis B virus

<400> SEQUENCE: 2067

Ala Lys Leu Ile Gly Thr Asp Asn Ser Val Val Leu Ser Arg Lys
1               5                   10                  15

<210> SEQ ID NO 2068
<211> LENGTH: 15
<212> TYPE: PRT
<213> ORGANISM: Orthohepadnaviridae hepatitis B virus

<400> SEQUENCE: 2068

Ala Asn Trp Ile Leu Arg Gly Thr Ser Phe Val Tyr Val Pro Ser
1               5                   10                  15

<210> SEQ ID NO 2069
<211> LENGTH: 15
<212> TYPE: PRT
<213> ORGANISM: Orthohepadnaviridae hepatitis B virus

<400> SEQUENCE: 2069

Ala Arg Asp Val Leu Cys Leu Arg Pro Val Gly Ala Glu Ser Arg
1               5                   10                  15

<210> SEQ ID NO 2070
<211> LENGTH: 15
<212> TYPE: PRT
<213> ORGANISM: Orthohepadnaviridae hepatitis B virus

<400> SEQUENCE: 2070

Ala Ser Ala Leu Tyr Arg Glu Ala Leu Glu Ser Pro Glu His Cys
1               5                   10                  15

<210> SEQ ID NO 2071
<211> LENGTH: 15
<212> TYPE: PRT
<213> ORGANISM: Orthohepadnaviridae hepatitis B virus

<400> SEQUENCE: 2071

Ala Ser Lys Leu Cys Leu Gly Trp Leu Trp Gly Met Asp Ile Asp
1               5                   10                  15

<210> SEQ ID NO 2072
<211> LENGTH: 15
<212> TYPE: PRT
<213> ORGANISM: Orthohepadnaviridae hepatitis B virus

<400> SEQUENCE: 2072

Cys Leu Ile Phe Leu Leu Val Leu Leu Asp Tyr Gln Gly Met Leu
1               5                   10                  15

<210> SEQ ID NO 2073
<211> LENGTH: 15
<212> TYPE: PRT
<213> ORGANISM: Orthohepadnaviridae hepatitis B virus

<400> SEQUENCE: 2073
```

```
Cys Leu Thr Phe Gly Arg Glu Thr Val Leu Glu Tyr Leu Val Ser
1               5                   10                  15
```

<210> SEQ ID NO 2074
<211> LENGTH: 15
<212> TYPE: PRT
<213> ORGANISM: Orthohepadnaviridae hepatitis B virus

<400> SEQUENCE: 2074

```
Cys Pro Gly Tyr Arg Trp Met Cys Leu Arg Arg Phe Ile Ile Phe
1               5                   10                  15
```

<210> SEQ ID NO 2075
<211> LENGTH: 15
<212> TYPE: PRT
<213> ORGANISM: Orthohepadnaviridae hepatitis B virus

<400> SEQUENCE: 2075

```
Cys Pro Thr Val Gln Ala Ser Lys Leu Cys Leu Gly Trp Leu Trp
1               5                   10                  15
```

<210> SEQ ID NO 2076
<211> LENGTH: 15
<212> TYPE: PRT
<213> ORGANISM: Orthohepadnaviridae hepatitis B virus

<400> SEQUENCE: 2076

```
Cys Gln Val Phe Ala Asp Ala Thr Pro Thr Gly Trp Gly Leu Ala
1               5                   10                  15
```

<210> SEQ ID NO 2077
<211> LENGTH: 15
<212> TYPE: PRT
<213> ORGANISM: Orthohepadnaviridae hepatitis B virus

<400> SEQUENCE: 2077

```
Cys Ser Val Val Arg Arg Ala Phe Pro His Cys Leu Ala Phe Ser
1               5                   10                  15
```

<210> SEQ ID NO 2078
<211> LENGTH: 15
<212> TYPE: PRT
<213> ORGANISM: Orthohepadnaviridae hepatitis B virus

<400> SEQUENCE: 2078

```
Cys Thr Cys Ile Pro Ile Pro Ser Ser Trp Ala Phe Ala Arg Phe
1               5                   10                  15
```

<210> SEQ ID NO 2079
<211> LENGTH: 15
<212> TYPE: PRT
<213> ORGANISM: Orthohepadnaviridae hepatitis B virus

<400> SEQUENCE: 2079

```
Cys Trp Trp Leu Gln Phe Arg Asn Ser Lys Pro Cys Ser Asp Tyr
1               5                   10                  15
```

<210> SEQ ID NO 2080
<211> LENGTH: 15
<212> TYPE: PRT
<213> ORGANISM: Orthohepadnaviridae hepatitis B virus

<400> SEQUENCE: 2080

```
Asp Asp Val Val Leu Gly Ala Lys Ser Val Gln His Leu Glu Ser
1               5                   10                  15
```

<210> SEQ ID NO 2081
<211> LENGTH: 15
<212> TYPE: PRT
<213> ORGANISM: Orthohepadnaviridae hepatitis B virus

<400> SEQUENCE: 2081

Asp Glu Gly Leu Asn Arg Arg Val Ala Glu Asp Leu Asn Leu Gly
 1               5                  10                  15

<210> SEQ ID NO 2082
<211> LENGTH: 15
<212> TYPE: PRT
<213> ORGANISM: Orthohepadnaviridae hepatitis B virus

<400> SEQUENCE: 2082

Asp Leu Asn Leu Gly Asn Leu Asn Val Ser Ile Pro Trp Thr His
 1               5                  10                  15

<210> SEQ ID NO 2083
<211> LENGTH: 15
<212> TYPE: PRT
<213> ORGANISM: Orthohepadnaviridae hepatitis B virus

<400> SEQUENCE: 2083

Asp Val Val Leu Gly Ala Lys Ser Val Gln His Leu Glu Ser Leu
 1               5                  10                  15

<210> SEQ ID NO 2084
<211> LENGTH: 15
<212> TYPE: PRT
<213> ORGANISM: Orthohepadnaviridae hepatitis B virus

<400> SEQUENCE: 2084

Asp Trp Lys Val Cys Gln Arg Ile Val Gly Leu Leu Gly Phe Ala
 1               5                  10                  15

<210> SEQ ID NO 2085
<211> LENGTH: 15
<212> TYPE: PRT
<213> ORGANISM: Orthohepadnaviridae hepatitis B virus

<400> SEQUENCE: 2085

Glu Ile Arg Leu Lys Val Phe Val Leu Gly Gly Cys Arg His Lys
 1               5                  10                  15

<210> SEQ ID NO 2086
<211> LENGTH: 15
<212> TYPE: PRT
<213> ORGANISM: Orthohepadnaviridae hepatitis B virus

<400> SEQUENCE: 2086

Glu Ser Arg Leu Val Val Asp Phe Ser Gln Phe Ser Arg Gly Asn
 1               5                  10                  15

<210> SEQ ID NO 2087
<211> LENGTH: 15
<212> TYPE: PRT
<213> ORGANISM: Orthohepadnaviridae hepatitis B virus

<400> SEQUENCE: 2087

Phe Phe Leu Leu Thr Arg Ile Leu Thr Ile Pro Gln Ser Leu Asp
 1               5                  10                  15

<210> SEQ ID NO 2088
<211> LENGTH: 15
<212> TYPE: PRT
<213> ORGANISM: Orthohepadnaviridae hepatitis B virus

<400> SEQUENCE: 2088

Phe Gly Val Trp Ile Arg Thr Pro Pro Ala Tyr Arg Pro Pro Asn
1               5                   10                  15

<210> SEQ ID NO 2089
<211> LENGTH: 15
<212> TYPE: PRT
<213> ORGANISM: Orthohepadnaviridae hepatitis B virus

<400> SEQUENCE: 2089

Phe Ile Ile Phe Leu Phe Ile Leu Leu Leu Cys Leu Ile Phe Leu
1 5 10 15

<210> SEQ ID NO 2090
<211> LENGTH: 15
<212> TYPE: PRT
<213> ORGANISM: Orthohepadnaviridae hepatitis B virus

<400> SEQUENCE: 2090

Phe Leu Phe Ile Leu Leu Leu Cys Leu Ile Phe Leu Leu Val Leu
1 5 10 15

<210> SEQ ID NO 2091
<211> LENGTH: 15
<212> TYPE: PRT
<213> ORGANISM: Orthohepadnaviridae hepatitis B virus

<400> SEQUENCE: 2091

Phe Pro Trp Leu Leu Gly Cys Ala Ala Asn Trp Ile Leu Arg Gly
1 5 10 15

<210> SEQ ID NO 2092
<211> LENGTH: 15
<212> TYPE: PRT
<213> ORGANISM: Orthohepadnaviridae hepatitis B virus

<400> SEQUENCE: 2092

Phe Arg Lys Leu Pro Val Asn Arg Pro Ile Asp Trp Lys Val Cys
1 5 10 15

<210> SEQ ID NO 2093
<211> LENGTH: 15
<212> TYPE: PRT
<213> ORGANISM: Orthohepadnaviridae hepatitis B virus

<400> SEQUENCE: 2093

Phe Ser Trp Leu Ser Leu Leu Val Pro Phe Val Gln Trp Phe Val
1 5 10 15

<210> SEQ ID NO 2094
<211> LENGTH: 15
<212> TYPE: PRT
<213> ORGANISM: Orthohepadnaviridae hepatitis B virus

<400> SEQUENCE: 2094

Phe Ser Tyr Met Asp Asp Val Val Leu Gly Ala Lys Ser Val Gln
1 5 10 15

<210> SEQ ID NO 2095
<211> LENGTH: 15

```
<212> TYPE: PRT
<213> ORGANISM: Orthohepadnaviridae hepatitis B virus

<400> SEQUENCE: 2095

Phe Val Gln Trp Phe Val Gly Leu Ser Pro Thr Val Trp Leu Ser
1               5                   10                  15

<210> SEQ ID NO 2096
<211> LENGTH: 15
<212> TYPE: PRT
<213> ORGANISM: Orthohepadnaviridae hepatitis B virus

<400> SEQUENCE: 2096

Gly Ala His Leu Ser Leu Arg Gly Leu Pro Val Cys Ala Phe Ser
1               5                   10                  15

<210> SEQ ID NO 2097
<211> LENGTH: 15
<212> TYPE: PRT
<213> ORGANISM: Orthohepadnaviridae hepatitis B virus

<400> SEQUENCE: 2097

Gly Phe Phe Leu Leu Thr Arg Ile Leu Thr Ile Pro Gln Ser Leu
1               5                   10                  15

<210> SEQ ID NO 2098
<211> LENGTH: 15
<212> TYPE: PRT
<213> ORGANISM: Orthohepadnaviridae hepatitis B virus

<400> SEQUENCE: 2098

Gly Ile His Leu Asn Pro Asn Lys Thr Lys Arg Trp Gly Tyr Ser
1               5                   10                  15

<210> SEQ ID NO 2099
<211> LENGTH: 15
<212> TYPE: PRT
<213> ORGANISM: Orthohepadnaviridae hepatitis B virus

<400> SEQUENCE: 2099

Gly Leu Pro Val Cys Ala Phe Ser Ser Ala Gly Pro Cys Ala Leu
1               5                   10                  15

<210> SEQ ID NO 2100
<211> LENGTH: 15
<212> TYPE: PRT
<213> ORGANISM: Orthohepadnaviridae hepatitis B virus

<400> SEQUENCE: 2100

Gly Leu Tyr Phe Pro Ala Gly Gly Ser Ser Ser Gly Thr Val Asn
1               5                   10                  15

<210> SEQ ID NO 2101
<211> LENGTH: 15
<212> TYPE: PRT
<213> ORGANISM: Orthohepadnaviridae hepatitis B virus

<400> SEQUENCE: 2101

Gly Thr Asn Leu Ser Val Pro Asn Pro Leu Gly Phe Phe Pro Asp
1               5                   10                  15

<210> SEQ ID NO 2102
<211> LENGTH: 15
<212> TYPE: PRT
<213> ORGANISM: Orthohepadnaviridae hepatitis B virus
```

```
<400> SEQUENCE: 2102

Gly Thr Ser Phe Val Tyr Val Pro Ser Ala Leu Asn Pro Ala Asp
 1               5                  10                  15

<210> SEQ ID NO 2103
<211> LENGTH: 15
<212> TYPE: PRT
<213> ORGANISM: Orthohepadnaviridae hepatitis B virus

<400> SEQUENCE: 2103

Gly Val Phe Leu Val Asp Lys Asn Pro His Asn Thr Thr Glu Ser
 1               5                  10                  15

<210> SEQ ID NO 2104
<211> LENGTH: 15
<212> TYPE: PRT
<213> ORGANISM: Orthohepadnaviridae hepatitis B virus

<400> SEQUENCE: 2104

Gly Val Gly Leu Ser Pro Phe Leu Leu Ala Gln Phe Thr Ser Ala
 1               5                  10                  15

<210> SEQ ID NO 2105
<211> LENGTH: 15
<212> TYPE: PRT
<213> ORGANISM: Orthohepadnaviridae hepatitis B virus

<400> SEQUENCE: 2105

Gly Val Trp Ile Arg Thr Pro Pro Ala Tyr Arg Pro Pro Asn Ala
 1               5                  10                  15

<210> SEQ ID NO 2106
<211> LENGTH: 15
<212> TYPE: PRT
<213> ORGANISM: Orthohepadnaviridae hepatitis B virus

<400> SEQUENCE: 2106

His Gly Gly Leu Leu Gly Trp Ser Pro Gln Ala Gln Gly Ile Leu
 1               5                  10                  15

<210> SEQ ID NO 2107
<211> LENGTH: 15
<212> TYPE: PRT
<213> ORGANISM: Orthohepadnaviridae hepatitis B virus

<400> SEQUENCE: 2107

His Leu Pro Leu His Pro Ala Ala Met Pro His Leu Leu Val Gly
 1               5                  10                  15

<210> SEQ ID NO 2108
<211> LENGTH: 15
<212> TYPE: PRT
<213> ORGANISM: Orthohepadnaviridae hepatitis B virus

<400> SEQUENCE: 2108

His Leu Ser Leu Arg Gly Leu Pro Val Cys Ala Phe Ser Ser Ala
 1               5                  10                  15

<210> SEQ ID NO 2109
<211> LENGTH: 15
<212> TYPE: PRT
<213> ORGANISM: Orthohepadnaviridae hepatitis B virus

<400> SEQUENCE: 2109
```

-continued

His Thr Ala Leu Arg Gln Ala Ile Leu Cys Trp Gly Glu Leu Met
1               5                   10                  15

<210> SEQ ID NO 2110
<211> LENGTH: 15
<212> TYPE: PRT
<213> ORGANISM: Orthohepadnaviridae hepatitis B virus

<400> SEQUENCE: 2110

His Thr Leu Trp Lys Ala Gly Ile Leu Tyr Lys Arg Glu Thr Thr
1               5                   10                  15

<210> SEQ ID NO 2111
<211> LENGTH: 15
<212> TYPE: PRT
<213> ORGANISM: Orthohepadnaviridae hepatitis B virus

<400> SEQUENCE: 2111

Ile Phe Leu Phe Ile Leu Leu Leu Cys Leu Ile Phe Leu Leu Val
1               5                   10                  15

<210> SEQ ID NO 2112
<211> LENGTH: 15
<212> TYPE: PRT
<213> ORGANISM: Orthohepadnaviridae hepatitis B virus

<400> SEQUENCE: 2112

Ile Ile Phe Leu Phe Ile Leu Leu Leu Cys Leu Ile Phe Leu Leu
1               5                   10                  15

<210> SEQ ID NO 2113
<211> LENGTH: 15
<212> TYPE: PRT
<213> ORGANISM: Orthohepadnaviridae hepatitis B virus

<400> SEQUENCE: 2113

Ile Leu Gly Phe Arg Lys Ile Pro Met Gly Val Gly Leu Ser Pro
1               5                   10                  15

<210> SEQ ID NO 2114
<211> LENGTH: 15
<212> TYPE: PRT
<213> ORGANISM: Orthohepadnaviridae hepatitis B virus

<400> SEQUENCE: 2114

Ile Leu Leu Leu Cys Leu Ile Phe Leu Leu Val Leu Leu Asp Tyr
1               5                   10                  15

<210> SEQ ID NO 2115
<211> LENGTH: 15
<212> TYPE: PRT
<213> ORGANISM: Orthohepadnaviridae hepatitis B virus

<400> SEQUENCE: 2115

Ile Arg Asp Leu Leu Asp Thr Ala Ser Ala Leu Tyr Arg Glu Ala
1               5                   10                  15

<210> SEQ ID NO 2116
<211> LENGTH: 15
<212> TYPE: PRT
<213> ORGANISM: Orthohepadnaviridae hepatitis B virus

<400> SEQUENCE: 2116

Ile Arg Gln Leu Leu Trp Phe His Ile Ser Cys Leu Thr Phe Gly

```
1               5                  10                  15
```

<210> SEQ ID NO 2117
<211> LENGTH: 15
<212> TYPE: PRT
<213> ORGANISM: Orthohepadnaviridae hepatitis B virus

<400> SEQUENCE: 2117

```
Ile Val Gly Leu Leu Gly Phe Ala Ala Pro Phe Thr Gln Cys Gly
1               5                   10                  15
```

<210> SEQ ID NO 2118
<211> LENGTH: 15
<212> TYPE: PRT
<213> ORGANISM: Orthohepadnaviridae hepatitis B virus

<400> SEQUENCE: 2118

```
Ile Trp Met Met Trp Tyr Trp Gly Pro Ser Leu Tyr Asn Ile Leu
1               5                   10                  15
```

<210> SEQ ID NO 2119
<211> LENGTH: 15
<212> TYPE: PRT
<213> ORGANISM: Orthohepadnaviridae hepatitis B virus

<400> SEQUENCE: 2119

```
Lys Phe Ala Val Pro Asn Leu Gln Ser Leu Thr Asn Leu Leu Ser
1               5                   10                  15
```

<210> SEQ ID NO 2120
<211> LENGTH: 15
<212> TYPE: PRT
<213> ORGANISM: Orthohepadnaviridae hepatitis B virus

<400> SEQUENCE: 2120

```
Lys Ile Pro Met Gly Val Gly Leu Ser Pro Phe Leu Leu Ala Gln
1               5                   10                  15
```

<210> SEQ ID NO 2121
<211> LENGTH: 15
<212> TYPE: PRT
<213> ORGANISM: Orthohepadnaviridae hepatitis B virus

<400> SEQUENCE: 2121

```
Lys Leu His Leu Tyr Ser His Pro Ile Ile Leu Gly Phe Arg Lys
1               5                   10                  15
```

<210> SEQ ID NO 2122
<211> LENGTH: 15
<212> TYPE: PRT
<213> ORGANISM: Orthohepadnaviridae hepatitis B virus

<400> SEQUENCE: 2122

```
Lys Gln Ala Phe Thr Phe Ser Pro Thr Tyr Lys Ala Phe Leu Cys
1               5                   10                  15
```

<210> SEQ ID NO 2123
<211> LENGTH: 15
<212> TYPE: PRT
<213> ORGANISM: Orthohepadnaviridae hepatitis B virus

<400> SEQUENCE: 2123

```
Lys Gln Cys Phe Arg Lys Leu Pro Val Asn Arg Pro Ile Asp Trp
1               5                   10                  15
```

<210> SEQ ID NO 2124
<211> LENGTH: 15
<212> TYPE: PRT
<213> ORGANISM: Orthohepadnaviridae hepatitis B virus

<400> SEQUENCE: 2124

Lys Arg Arg Leu Lys Leu Ile Met Pro Ala Arg Phe Tyr Pro Asn
1 5 10 15

<210> SEQ ID NO 2125
<211> LENGTH: 15
<212> TYPE: PRT
<213> ORGANISM: Orthohepadnaviridae hepatitis B virus

<400> SEQUENCE: 2125

Leu Ala Gln Phe Thr Ser Ala Ile Cys Ser Val Val Arg Arg Ala
1 5 10 15

<210> SEQ ID NO 2126
<211> LENGTH: 15
<212> TYPE: PRT
<213> ORGANISM: Orthohepadnaviridae hepatitis B virus

<400> SEQUENCE: 2126

Leu Cys Leu Ile Phe Leu Leu Val Leu Leu Asp Tyr Gln Gly Met
1 5 10 15

<210> SEQ ID NO 2127
<211> LENGTH: 15
<212> TYPE: PRT
<213> ORGANISM: Orthohepadnaviridae hepatitis B virus

<400> SEQUENCE: 2127

Leu Cys Gln Val Phe Ala Asp Ala Thr Pro Thr Gly Trp Gly Leu
1 5 10 15

<210> SEQ ID NO 2128
<211> LENGTH: 15
<212> TYPE: PRT
<213> ORGANISM: Orthohepadnaviridae hepatitis B virus

<400> SEQUENCE: 2128

Leu Glu Tyr Leu Val Ser Phe Gly Val Trp Ile Arg Thr Pro Pro
1 5 10 15

<210> SEQ ID NO 2129
<211> LENGTH: 15
<212> TYPE: PRT
<213> ORGANISM: Orthohepadnaviridae hepatitis B virus

<400> SEQUENCE: 2129

Leu Phe Ile Leu Leu Leu Cys Leu Ile Phe Leu Leu Val Leu Leu
1 5 10 15

<210> SEQ ID NO 2130
<211> LENGTH: 15
<212> TYPE: PRT
<213> ORGANISM: Orthohepadnaviridae hepatitis B virus

<400> SEQUENCE: 2130

Leu Gly Phe Phe Pro Asp His Gln Leu Asp Pro Ala Phe Gly Ala
1 5 10 15

<210> SEQ ID NO 2131

-continued

<211> LENGTH: 15
<212> TYPE: PRT
<213> ORGANISM: Orthohepadnaviridae hepatitis B virus

<400> SEQUENCE: 2131

Leu Gly Asn Leu Asn Val Ser Ile Pro Trp Thr His Lys Val Gly
1 5 10 15

<210> SEQ ID NO 2132
<211> LENGTH: 15
<212> TYPE: PRT
<213> ORGANISM: Orthohepadnaviridae hepatitis B virus

<400> SEQUENCE: 2132

Leu Gly Pro Leu Leu Val Leu Gln Ala Gly Phe Phe Leu Leu Thr
1 5 10 15

<210> SEQ ID NO 2133
<211> LENGTH: 15
<212> TYPE: PRT
<213> ORGANISM: Orthohepadnaviridae hepatitis B virus

<400> SEQUENCE: 2133

Leu Gly Trp Leu Trp Gly Met Asp Ile Asp Pro Tyr Lys Glu Phe
1 5 10 15

<210> SEQ ID NO 2134
<211> LENGTH: 15
<212> TYPE: PRT
<213> ORGANISM: Orthohepadnaviridae hepatitis B virus

<400> SEQUENCE: 2134

Leu His Leu Tyr Ser His Pro Ile Ile Leu Gly Phe Arg Lys Ile
1 5 10 15

<210> SEQ ID NO 2135
<211> LENGTH: 15
<212> TYPE: PRT
<213> ORGANISM: Orthohepadnaviridae hepatitis B virus

<400> SEQUENCE: 2135

Leu His Thr Leu Trp Lys Ala Gly Ile Leu Tyr Lys Arg Glu Thr
1 5 10 15

<210> SEQ ID NO 2136
<211> LENGTH: 15
<212> TYPE: PRT
<213> ORGANISM: Orthohepadnaviridae hepatitis B virus

<400> SEQUENCE: 2136

Leu Lys Val Phe Val Leu Gly Gly Cys Arg His Lys Leu Val Cys
1 5 10 15

<210> SEQ ID NO 2137
<211> LENGTH: 15
<212> TYPE: PRT
<213> ORGANISM: Orthohepadnaviridae hepatitis B virus

<400> SEQUENCE: 2137

Leu Leu Cys Leu Ile Phe Leu Leu Val Leu Leu Asp Tyr Gln Gly
1 5 10 15

<210> SEQ ID NO 2138
<211> LENGTH: 15
<212> TYPE: PRT

```
<213> ORGANISM: Orthohepadnaviridae hepatitis B virus

<400> SEQUENCE: 2138

Leu Leu Asp Tyr Gln Gly Met Leu Pro Val Cys Pro Leu Ile Pro
 1               5                  10                  15

<210> SEQ ID NO 2139
<211> LENGTH: 15
<212> TYPE: PRT
<213> ORGANISM: Orthohepadnaviridae hepatitis B virus

<400> SEQUENCE: 2139

Leu Leu Gly Phe Ala Ala Pro Phe Thr Gln Cys Gly Tyr Pro Ala
 1               5                  10                  15

<210> SEQ ID NO 2140
<211> LENGTH: 15
<212> TYPE: PRT
<213> ORGANISM: Orthohepadnaviridae hepatitis B virus

<400> SEQUENCE: 2140

Leu Leu Trp Phe His Ile Ser Cys Leu Thr Phe Gly Arg Glu Thr
 1               5                  10                  15

<210> SEQ ID NO 2141
<211> LENGTH: 15
<212> TYPE: PRT
<213> ORGANISM: Orthohepadnaviridae hepatitis B virus

<400> SEQUENCE: 2141

Leu Pro Lys Val Leu His Lys Arg Thr Leu Gly Leu Ser Ala Met
 1               5                  10                  15

<210> SEQ ID NO 2142
<211> LENGTH: 15
<212> TYPE: PRT
<213> ORGANISM: Orthohepadnaviridae hepatitis B virus

<400> SEQUENCE: 2142

Leu Pro Leu Leu Pro Ile Phe Phe Cys Leu Trp Val Tyr Ile Glx
 1               5                  10                  15

<210> SEQ ID NO 2143
<211> LENGTH: 15
<212> TYPE: PRT
<213> ORGANISM: Orthohepadnaviridae hepatitis B virus

<400> SEQUENCE: 2143

Leu Gln Ser Leu Thr Asn Leu Leu Ser Ser Asn Leu Ser Trp Leu
 1               5                  10                  15

<210> SEQ ID NO 2144
<211> LENGTH: 15
<212> TYPE: PRT
<213> ORGANISM: Orthohepadnaviridae hepatitis B virus

<400> SEQUENCE: 2144

Leu Ser Ala Met Ser Thr Thr Asp Leu Glu Ala Tyr Phe Lys Asp
 1               5                  10                  15

<210> SEQ ID NO 2145
<211> LENGTH: 15
<212> TYPE: PRT
<213> ORGANISM: Orthohepadnaviridae hepatitis B virus
```

<400> SEQUENCE: 2145

Leu Ser Thr Leu Pro Glu Thr Thr Val Val Arg Arg Arg Gly Arg
 1               5                  10                  15

<210> SEQ ID NO 2146
<211> LENGTH: 15
<212> TYPE: PRT
<213> ORGANISM: Orthohepadnaviridae hepatitis B virus

<400> SEQUENCE: 2146

Leu Ser Trp Leu Ser Leu Asp Val Ser Ala Ala Phe Tyr His Ile
 1               5                  10                  15

<210> SEQ ID NO 2147
<211> LENGTH: 15
<212> TYPE: PRT
<213> ORGANISM: Orthohepadnaviridae hepatitis B virus

<400> SEQUENCE: 2147

Leu Thr Asn Leu Leu Ser Ser Asn Leu Ser Trp Leu Ser Leu Asp
 1               5                  10                  15

<210> SEQ ID NO 2148
<211> LENGTH: 15
<212> TYPE: PRT
<213> ORGANISM: Orthohepadnaviridae hepatitis B virus

<400> SEQUENCE: 2148

Leu Val Leu Leu Asp Tyr Gln Gly Met Leu Pro Val Cys Pro Leu
 1               5                  10                  15

<210> SEQ ID NO 2149
<211> LENGTH: 15
<212> TYPE: PRT
<213> ORGANISM: Orthohepadnaviridae hepatitis B virus

<400> SEQUENCE: 2149

Leu Val Pro Phe Val Gln Trp Phe Val Gly Leu Ser Pro Thr Val
 1               5                  10                  15

<210> SEQ ID NO 2150
<211> LENGTH: 15
<212> TYPE: PRT
<213> ORGANISM: Orthohepadnaviridae hepatitis B virus

<400> SEQUENCE: 2150

Met Gln Leu Phe His Leu Cys Leu Ile Ile Ser Cys Ser Cys Pro
 1               5                  10                  15

<210> SEQ ID NO 2151
<211> LENGTH: 15
<212> TYPE: PRT
<213> ORGANISM: Orthohepadnaviridae hepatitis B virus

<400> SEQUENCE: 2151

Asn Ala Pro Ile Leu Ser Thr Leu Pro Glu Thr Thr Val Val Arg
 1               5                  10                  15

<210> SEQ ID NO 2152
<211> LENGTH: 15
<212> TYPE: PRT
<213> ORGANISM: Orthohepadnaviridae hepatitis B virus

<400> SEQUENCE: 2152

Asn Leu Asn Val Ser Ile Pro Trp Thr His Lys Val Gly Asn Phe
 1               5                  10                  15

<210> SEQ ID NO 2153
<211> LENGTH: 15
<212> TYPE: PRT
<213> ORGANISM: Orthohepadnaviridae hepatitis B virus

<400> SEQUENCE: 2153

Asn Leu Ser Trp Leu Ser Leu Asp Val Ser Ala Ala Phe Tyr His
 1               5                  10                  15

<210> SEQ ID NO 2154
<211> LENGTH: 15
<212> TYPE: PRT
<213> ORGANISM: Orthohepadnaviridae hepatitis B virus

<400> SEQUENCE: 2154

Asn Arg Pro Ile Asp Trp Lys Val Cys Gln Arg Ile Val Gly Leu
 1               5                  10                  15

<210> SEQ ID NO 2155
<211> LENGTH: 15
<212> TYPE: PRT
<213> ORGANISM: Orthohepadnaviridae hepatitis B virus

<400> SEQUENCE: 2155

Pro Ala Ala Met Pro His Leu Leu Val Gly Ser Ser Gly Leu Ser
 1               5                  10                  15

<210> SEQ ID NO 2156
<211> LENGTH: 15
<212> TYPE: PRT
<213> ORGANISM: Orthohepadnaviridae hepatitis B virus

<400> SEQUENCE: 2156

Pro Asp Arg Val His Phe Ala Ser Pro Leu His Val Ala Trp Arg
 1               5                  10                  15

<210> SEQ ID NO 2157
<211> LENGTH: 15
<212> TYPE: PRT
<213> ORGANISM: Orthohepadnaviridae hepatitis B virus

<400> SEQUENCE: 2157

Pro Phe Leu Leu Ala Gln Phe Thr Ser Ala Ile Cys Ser Val Val
 1               5                  10                  15

<210> SEQ ID NO 2158
<211> LENGTH: 15
<212> TYPE: PRT
<213> ORGANISM: Orthohepadnaviridae hepatitis B virus

<400> SEQUENCE: 2158

Pro His Cys Leu Ala Phe Ser Tyr Met Asp Asp Val Val Leu Gly
 1               5                  10                  15

<210> SEQ ID NO 2159
<211> LENGTH: 15
<212> TYPE: PRT
<213> ORGANISM: Orthohepadnaviridae hepatitis B virus

<400> SEQUENCE: 2159

Pro Ile Ile Leu Gly Phe Arg Lys Ile Pro Met Gly Val Gly Leu
 1               5                  10                  15

<210> SEQ ID NO 2160
<211> LENGTH: 15
<212> TYPE: PRT
<213> ORGANISM: Orthohepadnaviridae hepatitis B virus

<400> SEQUENCE: 2160

Pro Leu Pro Ile His Thr Ala Glu Leu Leu Ala Ala Cys Phe Ala
1               5                   10                  15

<210> SEQ ID NO 2161
<211> LENGTH: 15
<212> TYPE: PRT
<213> ORGANISM: Orthohepadnaviridae hepatitis B virus

<400> SEQUENCE: 2161

Pro Pro Ala Tyr Arg Pro Pro Asn Ala Pro Ile Leu Ser Thr Leu
1               5                   10                  15

<210> SEQ ID NO 2162
<211> LENGTH: 15
<212> TYPE: PRT
<213> ORGANISM: Orthohepadnaviridae hepatitis B virus

<400> SEQUENCE: 2162

Pro Gln Ala Met Gln Trp Asn Ser Thr Thr Phe His Gln Thr Leu
1               5                   10                  15

<210> SEQ ID NO 2163
<211> LENGTH: 15
<212> TYPE: PRT
<213> ORGANISM: Orthohepadnaviridae hepatitis B virus

<400> SEQUENCE: 2163

Pro Gln Ser Leu Asp Ser Trp Trp Thr Ser Leu Asn Phe Leu Gly
1               5                   10                  15

<210> SEQ ID NO 2164
<211> LENGTH: 15
<212> TYPE: PRT
<213> ORGANISM: Orthohepadnaviridae hepatitis B virus

<400> SEQUENCE: 2164

Gln Cys Gly Tyr Pro Ala Leu Met Pro Leu Tyr Ala Cys Ile Gln
1               5                   10                  15

<210> SEQ ID NO 2165
<211> LENGTH: 15
<212> TYPE: PRT
<213> ORGANISM: Orthohepadnaviridae hepatitis B virus

<400> SEQUENCE: 2165

Gln Leu Leu Trp Phe His Ile Ser Cys Leu Thr Phe Gly Arg Glu
1               5                   10                  15

<210> SEQ ID NO 2166
<211> LENGTH: 15
<212> TYPE: PRT
<213> ORGANISM: Orthohepadnaviridae hepatitis B virus

<400> SEQUENCE: 2166

Gln Gln Tyr Val Gly Pro Leu Thr Val Asn Glu Lys Arg Arg Leu
1               5                   10                  15

<210> SEQ ID NO 2167
<211> LENGTH: 15
<212> TYPE: PRT
<213> ORGANISM: Orthohepadnaviridae hepatitis B virus

<400> SEQUENCE: 2167

Gln Trp Phe Val Gly Leu Ser Pro Thr Val Trp Leu Ser Val Ile
1               5                   10                  15

<210> SEQ ID NO 2168
<211> LENGTH: 15
<212> TYPE: PRT
<213> ORGANISM: Orthohepadnaviridae hepatitis B virus

<400> SEQUENCE: 2168

Arg Asp Leu Leu Asp Thr Ala Ser Ala Leu Tyr Arg Glu Ala Leu
1               5                   10                  15

<210> SEQ ID NO 2169
<211> LENGTH: 15
<212> TYPE: PRT
<213> ORGANISM: Orthohepadnaviridae hepatitis B virus

<400> SEQUENCE: 2169

Arg Asp Val Leu Cys Leu Arg Pro Val Gly Ala Glu Ser Arg Gly
1               5                   10                  15

<210> SEQ ID NO 2170
<211> LENGTH: 15
<212> TYPE: PRT
<213> ORGANISM: Orthohepadnaviridae hepatitis B virus

<400> SEQUENCE: 2170

Arg Phe Ile Ile Phe Leu Phe Ile Leu Leu Leu Cys Leu Ile Phe
1               5                   10                  15

<210> SEQ ID NO 2171
<211> LENGTH: 15
<212> TYPE: PRT
<213> ORGANISM: Orthohepadnaviridae hepatitis B virus

<400> SEQUENCE: 2171

Arg Phe Ser Trp Leu Ser Leu Leu Val Pro Phe Val Gln Trp Phe
1               5                   10                  15

<210> SEQ ID NO 2172
<211> LENGTH: 15
<212> TYPE: PRT
<213> ORGANISM: Orthohepadnaviridae hepatitis B virus

<400> SEQUENCE: 2172

Arg Pro Gly Leu Cys Gln Val Phe Ala Asp Ala Thr Pro Thr Gly
1               5                   10                  15

<210> SEQ ID NO 2173
<211> LENGTH: 15
<212> TYPE: PRT
<213> ORGANISM: Orthohepadnaviridae hepatitis B virus

<400> SEQUENCE: 2173

Arg Gln Leu Leu Trp Phe His Ile Ser Cys Leu Thr Phe Gly Arg
1               5                   10                  15

<210> SEQ ID NO 2174
<211> LENGTH: 15

```
<212> TYPE: PRT
<213> ORGANISM: Orthohepadnaviridae hepatitis B virus

<400> SEQUENCE: 2174

Arg Arg Ala Phe Pro His Cys Leu Ala Phe Ser Tyr Met Asp Asp
 1               5                  10                  15

<210> SEQ ID NO 2175
<211> LENGTH: 15
<212> TYPE: PRT
<213> ORGANISM: Orthohepadnaviridae hepatitis B virus

<400> SEQUENCE: 2175

Arg Arg Phe Ile Ile Phe Leu Phe Ile Leu Leu Leu Cys Leu Ile
 1               5                  10                  15

<210> SEQ ID NO 2176
<211> LENGTH: 15
<212> TYPE: PRT
<213> ORGANISM: Orthohepadnaviridae hepatitis B virus

<400> SEQUENCE: 2176

Arg Arg Ser Phe Gly Val Glu Pro Ser Gly Ser Gly His Ile Asp
 1               5                  10                  15

<210> SEQ ID NO 2177
<211> LENGTH: 15
<212> TYPE: PRT
<213> ORGANISM: Orthohepadnaviridae hepatitis B virus

<400> SEQUENCE: 2177

Arg Val Ser Trp Pro Lys Phe Ala Val Pro Asn Leu Gln Ser Leu
 1               5                  10                  15

<210> SEQ ID NO 2178
<211> LENGTH: 15
<212> TYPE: PRT
<213> ORGANISM: Orthohepadnaviridae hepatitis B virus

<400> SEQUENCE: 2178

Arg Trp Gly Tyr Ser Leu Asn Phe Met Gly Tyr Val Ile Gly Ser
 1               5                  10                  15

<210> SEQ ID NO 2179
<211> LENGTH: 15
<212> TYPE: PRT
<213> ORGANISM: Orthohepadnaviridae hepatitis B virus

<400> SEQUENCE: 2179

Ser Phe Gly Val Trp Ile Arg Thr Pro Pro Ala Tyr Arg Pro Pro
 1               5                  10                  15

<210> SEQ ID NO 2180
<211> LENGTH: 15
<212> TYPE: PRT
<213> ORGANISM: Orthohepadnaviridae hepatitis B virus

<400> SEQUENCE: 2180

Ser Phe Pro Trp Leu Leu Gly Cys Ala Ala Asn Trp Ile Leu Arg
 1               5                  10                  15

<210> SEQ ID NO 2181
<211> LENGTH: 15
<212> TYPE: PRT
<213> ORGANISM: Orthohepadnaviridae hepatitis B virus
```

```
<400> SEQUENCE: 2181

Ser Phe Val Tyr Val Pro Ser Ala Leu Asn Pro Ala Asp Asp Pro
1               5                   10                  15

<210> SEQ ID NO 2182
<211> LENGTH: 15
<212> TYPE: PRT
<213> ORGANISM: Orthohepadnaviridae hepatitis B virus

<400> SEQUENCE: 2182

Ser Gly Phe Leu Gly Pro Leu Leu Val Leu Gln Ala Gly Phe Phe
1               5                   10                  15

<210> SEQ ID NO 2183
<211> LENGTH: 15
<212> TYPE: PRT
<213> ORGANISM: Orthohepadnaviridae hepatitis B virus

<400> SEQUENCE: 2183

Ser Pro Phe Leu Leu Ala Gln Phe Thr Ser Ala Ile Cys Ser Val
1               5                   10                  15

<210> SEQ ID NO 2184
<211> LENGTH: 15
<212> TYPE: PRT
<213> ORGANISM: Orthohepadnaviridae hepatitis B virus

<400> SEQUENCE: 2184

Ser Ser Asn Leu Ser Trp Leu Ser Leu Asp Val Ser Ala Ala Phe
1               5                   10                  15

<210> SEQ ID NO 2185
<211> LENGTH: 15
<212> TYPE: PRT
<213> ORGANISM: Orthohepadnaviridae hepatitis B virus

<400> SEQUENCE: 2185

Ser Val Glu Leu Leu Ser Phe Leu Pro Ser Asp Phe Phe Pro Ser
1               5                   10                  15

<210> SEQ ID NO 2186
<211> LENGTH: 15
<212> TYPE: PRT
<213> ORGANISM: Orthohepadnaviridae hepatitis B virus

<400> SEQUENCE: 2186

Ser Val Arg Phe Ser Trp Leu Ser Leu Leu Val Pro Phe Val Gln
1               5                   10                  15

<210> SEQ ID NO 2187
<211> LENGTH: 15
<212> TYPE: PRT
<213> ORGANISM: Orthohepadnaviridae hepatitis B virus

<400> SEQUENCE: 2187

Ser Val Val Leu Ser Arg Lys Tyr Thr Ser Phe Pro Trp Leu Leu
1               5                   10                  15

<210> SEQ ID NO 2188
<211> LENGTH: 15
<212> TYPE: PRT
<213> ORGANISM: Orthohepadnaviridae hepatitis B virus

<400> SEQUENCE: 2188
```

-continued

Thr Asn Phe Leu Leu Ser Leu Gly Ile His Leu Asn Pro Asn Lys
1               5                   10                  15

<210> SEQ ID NO 2189
<211> LENGTH: 15
<212> TYPE: PRT
<213> ORGANISM: Orthohepadnaviridae hepatitis B virus

<400> SEQUENCE: 2189

Thr Asn Leu Leu Ser Ser Asn Leu Ser Trp Leu Ser Leu Asp Val
1               5                   10                  15

<210> SEQ ID NO 2190
<211> LENGTH: 15
<212> TYPE: PRT
<213> ORGANISM: Orthohepadnaviridae hepatitis B virus

<400> SEQUENCE: 2190

Thr Arg Ile Leu Thr Ile Pro Gln Ser Leu Asp Ser Trp Trp Thr
1               5                   10                  15

<210> SEQ ID NO 2191
<211> LENGTH: 15
<212> TYPE: PRT
<213> ORGANISM: Orthohepadnaviridae hepatitis B virus

<400> SEQUENCE: 2191

Thr Ser Phe Val Tyr Val Pro Ser Ala Leu Asn Pro Ala Asp Asp
1               5                   10                  15

<210> SEQ ID NO 2192
<211> LENGTH: 15
<212> TYPE: PRT
<213> ORGANISM: Orthohepadnaviridae hepatitis B virus

<400> SEQUENCE: 2192

Thr Ser Gly Phe Leu Gly Pro Leu Leu Val Leu Gln Ala Gly Phe
1               5                   10                  15

<210> SEQ ID NO 2193
<211> LENGTH: 15
<212> TYPE: PRT
<213> ORGANISM: Orthohepadnaviridae hepatitis B virus

<400> SEQUENCE: 2193

Val Ala Pro Leu Pro Ile His Thr Ala Glu Leu Leu Ala Ala Cys
1               5                   10                  15

<210> SEQ ID NO 2194
<211> LENGTH: 15
<212> TYPE: PRT
<213> ORGANISM: Orthohepadnaviridae hepatitis B virus

<400> SEQUENCE: 2194

Val Cys Ala Phe Ser Ser Ala Gly Pro Cys Ala Leu Arg Phe Thr
1               5                   10                  15

<210> SEQ ID NO 2195
<211> LENGTH: 15
<212> TYPE: PRT
<213> ORGANISM: Orthohepadnaviridae hepatitis B virus

<400> SEQUENCE: 2195

Val Glu Leu Leu Ser Phe Leu Pro Ser Asp Phe Phe Pro Ser Ile

```
                1               5                  10                 15
```

<210> SEQ ID NO 2196
<211> LENGTH: 15
<212> TYPE: PRT
<213> ORGANISM: Orthohepadnaviridae hepatitis B virus

<400> SEQUENCE: 2196

```
Val Gly Leu Leu Gly Phe Ala Ala Pro Phe Thr Gln Cys Gly Tyr
 1               5                  10                 15
```

<210> SEQ ID NO 2197
<211> LENGTH: 15
<212> TYPE: PRT
<213> ORGANISM: Orthohepadnaviridae hepatitis B virus

<400> SEQUENCE: 2197

```
Val Gly Asn Phe Thr Gly Leu Tyr Ser Ser Thr Val Pro Val Phe
 1               5                  10                 15
```

<210> SEQ ID NO 2198
<211> LENGTH: 15
<212> TYPE: PRT
<213> ORGANISM: Orthohepadnaviridae hepatitis B virus

<400> SEQUENCE: 2198

```
Val Leu Cys Leu Arg Pro Val Gly Ala Glu Ser Arg Gly Arg Pro
 1               5                  10                 15
```

<210> SEQ ID NO 2199
<211> LENGTH: 15
<212> TYPE: PRT
<213> ORGANISM: Orthohepadnaviridae hepatitis B virus

<400> SEQUENCE: 2199

```
Val Gln Trp Phe Val Gly Leu Ser Pro Thr Val Trp Leu Ser Val
 1               5                  10                 15
```

<210> SEQ ID NO 2200
<211> LENGTH: 15
<212> TYPE: PRT
<213> ORGANISM: Orthohepadnaviridae hepatitis B virus

<400> SEQUENCE: 2200

```
Trp Ala Ser Val Arg Phe Ser Trp Leu Ser Leu Leu Val Pro Phe
 1               5                  10                 15
```

<210> SEQ ID NO 2201
<211> LENGTH: 15
<212> TYPE: PRT
<213> ORGANISM: Orthohepadnaviridae hepatitis B virus

<400> SEQUENCE: 2201

```
Trp Leu Ser Leu Asp Val Ser Ala Ala Phe Tyr His Ile Pro Leu
 1               5                  10                 15
```

<210> SEQ ID NO 2202
<211> LENGTH: 15
<212> TYPE: PRT
<213> ORGANISM: Orthohepadnaviridae hepatitis B virus

<400> SEQUENCE: 2202

```
Trp Leu Ser Leu Leu Val Pro Phe Val Gln Trp Phe Val Gly Leu
 1               5                  10                 15
```

-continued

```
<210> SEQ ID NO 2203
<211> LENGTH: 15
<212> TYPE: PRT
<213> ORGANISM: Orthohepadnaviridae hepatitis B virus

<400> SEQUENCE: 2203

Trp Met Cys Leu Arg Arg Phe Ile Ile Phe Leu Phe Ile Leu Leu
1               5                   10                  15

<210> SEQ ID NO 2204
<211> LENGTH: 15
<212> TYPE: PRT
<213> ORGANISM: Orthohepadnaviridae hepatitis B virus

<400> SEQUENCE: 2204

Trp Pro Lys Phe Ala Val Pro Asn Leu Gln Ser Leu Thr Asn Leu
1               5                   10                  15

<210> SEQ ID NO 2205
<211> LENGTH: 15
<212> TYPE: PRT
<213> ORGANISM: Orthohepadnaviridae hepatitis B virus

<400> SEQUENCE: 2205

Tyr Pro Ala Leu Met Pro Leu Tyr Ala Cys Ile Gln Ser Lys Gln
1               5                   10                  15

<210> SEQ ID NO 2206
<211> LENGTH: 15
<212> TYPE: PRT
<213> ORGANISM: Orthohepadnaviridae hepatitis B virus

<400> SEQUENCE: 2206

Ala Phe Ser Tyr Met Asp Asp Val Val Leu Gly Ala Lys Ser Val
1               5                   10                  15

<210> SEQ ID NO 2207
<211> LENGTH: 15
<212> TYPE: PRT
<213> ORGANISM: Orthohepadnaviridae hepatitis B virus

<400> SEQUENCE: 2207

Ala Phe Thr Phe Ser Pro Thr Tyr Lys Ala Phe Leu Cys Lys Gln
1               5                   10                  15

<210> SEQ ID NO 2208
<211> LENGTH: 15
<212> TYPE: PRT
<213> ORGANISM: Orthohepadnaviridae hepatitis B virus

<400> SEQUENCE: 2208

Ala Gly Pro Leu Glu Glu Glu Leu Pro Arg Leu Ala Asp Glu Gly
1               5                   10                  15

<210> SEQ ID NO 2209
<211> LENGTH: 15
<212> TYPE: PRT
<213> ORGANISM: Orthohepadnaviridae hepatitis B virus

<400> SEQUENCE: 2209

Ala Lys Leu Ile Gly Thr Asp Asn Ser Val Val Leu Ser Arg Lys
1               5                   10                  15

<210> SEQ ID NO 2210
```

-continued

<211> LENGTH: 15
<212> TYPE: PRT
<213> ORGANISM: Orthohepadnaviridae hepatitis B virus

<400> SEQUENCE: 2210

Ala Ser Ala Leu Tyr Arg Glu Ala Leu Glu Ser Pro Glu His Cys
1 5 10 15

<210> SEQ ID NO 2211
<211> LENGTH: 15
<212> TYPE: PRT
<213> ORGANISM: Orthohepadnaviridae hepatitis B virus

<400> SEQUENCE: 2211

Cys Leu Thr Phe Gly Arg Glu Thr Val Leu Glu Tyr Leu Val Ser
1 5 10 15

<210> SEQ ID NO 2212
<211> LENGTH: 15
<212> TYPE: PRT
<213> ORGANISM: Orthohepadnaviridae hepatitis B virus

<400> SEQUENCE: 2212

Asp His Gly Ala His Leu Ser Leu Arg Gly Leu Pro Val Cys Ala
1 5 10 15

<210> SEQ ID NO 2213
<211> LENGTH: 15
<212> TYPE: PRT
<213> ORGANISM: Orthohepadnaviridae hepatitis B virus

<400> SEQUENCE: 2213

Asp Asn Ser Val Val Leu Ser Arg Lys Tyr Thr Ser Phe Pro Trp
1 5 10 15

<210> SEQ ID NO 2214
<211> LENGTH: 15
<212> TYPE: PRT
<213> ORGANISM: Orthohepadnaviridae hepatitis B virus

<400> SEQUENCE: 2214

Glu Ser Arg Leu Val Val Asp Phe Ser Gln Phe Ser Arg Gly Asn
1 5 10 15

<210> SEQ ID NO 2215
<211> LENGTH: 15
<212> TYPE: PRT
<213> ORGANISM: Orthohepadnaviridae hepatitis B virus

<400> SEQUENCE: 2215

Phe His Gln Ala Val Leu Asp Pro Arg Val Arg Gly Leu Tyr Leu
1 5 10 15

<210> SEQ ID NO 2216
<211> LENGTH: 15
<212> TYPE: PRT
<213> ORGANISM: Orthohepadnaviridae hepatitis B virus

<400> SEQUENCE: 2216

Phe Leu Leu Val Leu Leu Asp Tyr Gln Gly Met Leu Pro Val Cys
1 5 10 15

<210> SEQ ID NO 2217
<211> LENGTH: 15
<212> TYPE: PRT

<213> ORGANISM: Orthohepadnaviridae hepatitis B virus

<400> SEQUENCE: 2217

Gly Gly Val Phe Leu Val Asp Lys Asn Pro His Asn Thr Thr Glu
1               5                   10                  15

<210> SEQ ID NO 2218
<211> LENGTH: 15
<212> TYPE: PRT
<213> ORGANISM: Orthohepadnaviridae hepatitis B virus

<400> SEQUENCE: 2218

Leu Cys Gln Val Phe Ala Asp Ala Thr Pro Thr Gly Trp Gly Leu
1               5                   10                  15

<210> SEQ ID NO 2219
<211> LENGTH: 15
<212> TYPE: PRT
<213> ORGANISM: Orthohepadnaviridae hepatitis B virus

<400> SEQUENCE: 2219

Leu Arg Pro Val Gly Ala Glu Ser Arg Gly Arg Pro Val Ser Gly
1               5                   10                  15

<210> SEQ ID NO 2220
<211> LENGTH: 15
<212> TYPE: PRT
<213> ORGANISM: Orthohepadnaviridae hepatitis B virus

<400> SEQUENCE: 2220

Leu Ser Trp Leu Ser Leu Asp Val Ser Ala Ala Phe Tyr His Ile
1               5                   10                  15

<210> SEQ ID NO 2221
<211> LENGTH: 15
<212> TYPE: PRT
<213> ORGANISM: Orthohepadnaviridae hepatitis B virus

<400> SEQUENCE: 2221

Leu Trp Gly Met Asp Ile Asp Pro Tyr Lys Glu Phe Gly Ala Ser
1               5                   10                  15

<210> SEQ ID NO 2222
<211> LENGTH: 15
<212> TYPE: PRT
<213> ORGANISM: Orthohepadnaviridae hepatitis B virus

<400> SEQUENCE: 2222

Asn Arg Arg Val Ala Glu Asp Leu Asn Leu Gly Asn Leu Asn Val
1               5                   10                  15

<210> SEQ ID NO 2223
<211> LENGTH: 15
<212> TYPE: PRT
<213> ORGANISM: Orthohepadnaviridae hepatitis B virus

<400> SEQUENCE: 2223

Asn Val Ser Ile Pro Trp Thr His Lys Val Gly Asn Phe Thr Gly
1               5                   10                  15

<210> SEQ ID NO 2224
<211> LENGTH: 15
<212> TYPE: PRT
<213> ORGANISM: Orthohepadnaviridae hepatitis B virus -continued
<210> SEQ ID NO 2224 (implicit continuation)

<400> SEQUENCE: 2224

Pro Leu Gly Phe Phe Pro Asp His Gln Leu Asp Pro Ala Phe Gly
1               5                   10                  15

<210> SEQ ID NO 2225
<211> LENGTH: 15
<212> TYPE: PRT
<213> ORGANISM: Orthohepadnaviridae hepatitis B virus

<400> SEQUENCE: 2225

Arg Arg Ser Phe Gly Val Glu Pro Ser Gly Ser Gly His Ile Asp
1               5                   10                  15

<210> SEQ ID NO 2226
<211> LENGTH: 15
<212> TYPE: PRT
<213> ORGANISM: Orthohepadnaviridae hepatitis B virus

<400> SEQUENCE: 2226

Thr Lys Tyr Leu Pro Leu Asp Lys Gly Ile Lys Pro Tyr Tyr Pro
1               5                   10                  15

<210> SEQ ID NO 2227
<211> LENGTH: 15
<212> TYPE: PRT
<213> ORGANISM: Orthohepadnaviridae hepatitis B virus

<400> SEQUENCE: 2227

Val Gly Pro Leu Thr Val Asn Glu Lys Arg Arg Leu Lys Leu Ile
1               5                   10                  15

<210> SEQ ID NO 2228
<211> LENGTH: 9
<212> TYPE: PRT
<213> ORGANISM: Orthohepadnaviridae hepatitis B virus

<400> SEQUENCE: 2228

Tyr Met Asp Asp Val Val Leu Gly Ala
1               5

<210> SEQ ID NO 2229
<211> LENGTH: 9
<212> TYPE: PRT
<213> ORGANISM: Orthohepadnaviridae hepatitis B virus

<400> SEQUENCE: 2229

Phe Ser Pro Thr Tyr Lys Ala Phe Leu
1               5

<210> SEQ ID NO 2230
<211> LENGTH: 9
<212> TYPE: PRT
<213> ORGANISM: Orthohepadnaviridae hepatitis B virus

<400> SEQUENCE: 2230

Leu Glu Glu Glu Leu Pro Arg Leu Ala
1               5

<210> SEQ ID NO 2231
<211> LENGTH: 9
<212> TYPE: PRT
<213> ORGANISM: Orthohepadnaviridae hepatitis B virus

<400> SEQUENCE: 2231

Ile Gly Thr Asp Asn Ser Val Val Leu
1               5

<210> SEQ ID NO 2232
<211> LENGTH: 9
<212> TYPE: PRT
<213> ORGANISM: Orthohepadnaviridae hepatitis B virus

<400> SEQUENCE: 2232

Leu Tyr Arg Glu Ala Leu Glu Ser Pro
1               5

<210> SEQ ID NO 2233
<211> LENGTH: 9
<212> TYPE: PRT
<213> ORGANISM: Orthohepadnaviridae hepatitis B virus

<400> SEQUENCE: 2233

Phe Gly Arg Glu Thr Val Leu Glu Tyr
1               5

<210> SEQ ID NO 2234
<211> LENGTH: 9
<212> TYPE: PRT
<213> ORGANISM: Orthohepadnaviridae hepatitis B virus

<400> SEQUENCE: 2234

Ala His Leu Ser Leu Arg Gly Leu Pro
1               5

<210> SEQ ID NO 2235
<211> LENGTH: 9
<212> TYPE: PRT
<213> ORGANISM: Orthohepadnaviridae hepatitis B virus

<400> SEQUENCE: 2235

Val Val Leu Ser Arg Lys Tyr Thr Ser
1               5

<210> SEQ ID NO 2236
<211> LENGTH: 9
<212> TYPE: PRT
<213> ORGANISM: Orthohepadnaviridae hepatitis B virus

<400> SEQUENCE: 2236

Leu Val Val Asp Phe Ser Gln Phe Ser
1               5

<210> SEQ ID NO 2237
<211> LENGTH: 9
<212> TYPE: PRT
<213> ORGANISM: Orthohepadnaviridae hepatitis B virus

<400> SEQUENCE: 2237

Ala Val Leu Asp Pro Arg Val Arg Gly
1               5

<210> SEQ ID NO 2238
<211> LENGTH: 9
<212> TYPE: PRT
<213> ORGANISM: Orthohepadnaviridae hepatitis B virus

<400> SEQUENCE: 2238

Val Leu Leu Asp Tyr Gln Gly Met Leu
1               5

<210> SEQ ID NO 2239
<211> LENGTH: 9
<212> TYPE: PRT
<213> ORGANISM: Orthohepadnaviridae hepatitis B virus

<400> SEQUENCE: 2239

Phe Leu Val Asp Lys Asn Pro His Asn
 1               5

<210> SEQ ID NO 2240
<211> LENGTH: 9
<212> TYPE: PRT
<213> ORGANISM: Orthohepadnaviridae hepatitis B virus

<400> SEQUENCE: 2240

Val Phe Ala Asp Ala Thr Pro Thr Gly
 1               5

<210> SEQ ID NO 2241
<211> LENGTH: 9
<212> TYPE: PRT
<213> ORGANISM: Orthohepadnaviridae hepatitis B virus

<400> SEQUENCE: 2241

Val Gly Ala Glu Ser Arg Gly Arg Pro
 1               5

<210> SEQ ID NO 2242
<211> LENGTH: 9
<212> TYPE: PRT
<213> ORGANISM: Orthohepadnaviridae hepatitis B virus

<400> SEQUENCE: 2242

Leu Ser Leu Asp Val Ser Ala Ala Phe
 1               5

<210> SEQ ID NO 2243
<211> LENGTH: 9
<212> TYPE: PRT
<213> ORGANISM: Orthohepadnaviridae hepatitis B virus

<400> SEQUENCE: 2243

Met Asp Ile Asp Pro Tyr Lys Glu Phe
 1               5

<210> SEQ ID NO 2244
<211> LENGTH: 9
<212> TYPE: PRT
<213> ORGANISM: Orthohepadnaviridae hepatitis B virus

<400> SEQUENCE: 2244

Val Ala Glu Asp Leu Asn Leu Gly Asn
 1               5

<210> SEQ ID NO 2245
<211> LENGTH: 9
<212> TYPE: PRT
<213> ORGANISM: Orthohepadnaviridae hepatitis B virus

<400> SEQUENCE: 2245

Ile Pro Trp Thr His Lys Val Gly Asn
 1               5

```
<210> SEQ ID NO 2246
<211> LENGTH: 9
<212> TYPE: PRT
<213> ORGANISM: Orthohepadnaviridae hepatitis B virus

<400> SEQUENCE: 2246

Phe Phe Pro Asp His Gln Leu Asp Pro
1               5

<210> SEQ ID NO 2247
<211> LENGTH: 9
<212> TYPE: PRT
<213> ORGANISM: Orthohepadnaviridae hepatitis B virus

<400> SEQUENCE: 2247

Phe Gly Val Glu Pro Ser Gly Ser Gly
1               5

<210> SEQ ID NO 2248
<211> LENGTH: 9
<212> TYPE: PRT
<213> ORGANISM: Orthohepadnaviridae hepatitis B virus

<400> SEQUENCE: 2248

Leu Pro Leu Asp Lys Gly Ile Lys Pro
1               5

<210> SEQ ID NO 2249
<211> LENGTH: 9
<212> TYPE: PRT
<213> ORGANISM: Orthohepadnaviridae hepatitis B virus

<400> SEQUENCE: 2249

Leu Thr Val Asn Glu Lys Arg Arg Leu
1               5

<210> SEQ ID NO 2250
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2250

Ala Leu Phe Lys Asp Trp Glu Glu Leu
1               5

<210> SEQ ID NO 2251
<211> LENGTH: 9
<212> TYPE: PRT
<213> ORGANISM: Artificial Sequence
<220> FEATURE:
<223> OTHER INFORMATION: HBV analog peptide L2.IV9

<400> SEQUENCE: 2251

Ala Leu Met Pro Leu Tyr Ala Cys Val
1               5

<210> SEQ ID NO 2252
<211> LENGTH: 9
<212> TYPE: PRT
<213> ORGANISM: Orthohepadnaviridae hepatitis B virus

<400> SEQUENCE: 2252

Ala Leu Met Pro Leu Tyr Ala Ser Ile
1               5
```

```
<210> SEQ ID NO 2253
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 8
<223> OTHER INFORMATION: Xaa=Any amino acid

<400> SEQUENCE: 2253

Ala Leu Met Pro Leu Tyr Ala Xaa Ile
1               5

<210> SEQ ID NO 2254
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2254

Ala Leu Pro Ser Asp Phe Phe Pro Ser Val
1               5                   10

<210> SEQ ID NO 2255
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 10
<223> OTHER INFORMATION: Xaa=V-NH-2

<400> SEQUENCE: 2255

Ala Leu Pro Ser Asp Phe Phe Pro Ser Xaa
1               5                   10

<210> SEQ ID NO 2256
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2256

Ala Leu Ser Leu Ile Val Asn Leu Leu
1               5

<210> SEQ ID NO 2257
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2257

Ala Met Thr Phe Ser Pro Thr Tyr Lys
1               5

<210> SEQ ID NO 2258
<211> LENGTH: 17
<212> TYPE: PRT
<213> ORGANISM: Artificial Sequence
```

-continued

<220> FEATURE:
<223> OTHER INFORMATION: HBV analog peptide
<220> FEATURE:
<221> NAME/KEY: MOD_RES
<222> LOCATION: 17
<223> OTHER INFORMATION: Xaa=V-NH-2

<400> SEQUENCE: 2258

Ala Thr Val Glu Leu Leu Ser Phe Leu Pro Ser Asp Phe Phe Pro Ser
1 5 10 15
Xaa

<210> SEQ ID NO 2259
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2259

Cys Ile Leu Leu Leu Cys Leu Ile Phe Leu
1 5 10

<210> SEQ ID NO 2260
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2260

Cys Ile Leu Leu Leu Cys Leu Ile Phe Leu Leu
1 5 10

<210> SEQ ID NO 2261
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2261

Asp Pro Phe Arg Gly Arg Leu Gly Leu
1 5

<210> SEQ ID NO 2262
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2262

Asp Pro Ser Arg Gly Arg Leu Gly Ile
1 5

<210> SEQ ID NO 2263
<211> LENGTH: 14
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 14
<223> OTHER INFORMATION: Xaa=V-NH-2

<400> SEQUENCE: 2263

```
Glu Leu Leu Ser Phe Leu Pro Ser Asp Phe Phe Pro Ser Xaa
1               5                   10
```

<210> SEQ ID NO 2264
<211> LENGTH: 10
<212> TYPE: PRT
<213> ORGANISM: Artificial Sequence
<220> FEATURE:
<223> OTHER INFORMATION: HBV analog peptide LA2.V10

<400> SEQUENCE: 2264

```
Phe Ala Pro Ser Asp Phe Phe Pro Ser Val
1               5                   10
```

<210> SEQ ID NO 2265
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 6
<223> OTHER INFORMATION: Xaa=Any amino acid

<400> SEQUENCE: 2265

```
Phe Ile Leu Leu Leu Xaa Leu Ile Phe Leu
1               5                   10
```

<210> SEQ ID NO 2266
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2266

```
Phe Leu Ala Ser Asp Phe Phe Pro Ser Val
1               5                   10
```

<210> SEQ ID NO 2267
<211> LENGTH: 10
<212> TYPE: PRT
<213> ORGANISM: Artificial Sequence
<220> FEATURE:
<223> OTHER INFORMATION: HBV analog peptide VL2.LV1

<400> SEQUENCE: 2267

```
Phe Leu Gly Leu Ser Pro Thr Val Trp Val
1               5                   10
```

<210> SEQ ID NO 2268
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2268

```
Phe Leu Lys Ser Asp Phe Phe Pro Ser Val
1               5                   10
```

<210> SEQ ID NO 2269
<211> LENGTH: 10
<212> TYPE: PRT
<213> ORGANISM: Artificial Sequence
<220> FEATURE:
<223> OTHER INFORMATION: HBV analog peptide L2.IV10

```
<400> SEQUENCE: 2269

Phe Leu Leu Ala Gln Phe Thr Ser Ala Val
1               5                   10

<210> SEQ ID NO 2270
<211> LENGTH: 9
<212> TYPE: PRT
<213> ORGANISM: Artificial Sequence
<220> FEATURE:
<223> OTHER INFORMATION: HBV analog peptide L2.AV9

<400> SEQUENCE: 2270

Phe Leu Leu Ala Gln Phe Thr Ser Val
1               5

<210> SEQ ID NO 2271
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2271

Phe Leu Leu Pro Ile Phe Phe Cys Leu
1               5

<210> SEQ ID NO 2272
<211> LENGTH: 9
<212> TYPE: PRT
<213> ORGANISM: Artificial Sequence
<220> FEATURE:
<223> OTHER INFORMATION: HBV analog peptide L2.LV9

<400> SEQUENCE: 2272

Phe Leu Leu Ser Leu Gly Ile His Val
1               5

<210> SEQ ID NO 2273
<211> LENGTH: 9
<212> TYPE: PRT
<213> ORGANISM: Artificial Sequence
<220> FEATURE:
<223> OTHER INFORMATION: HBV analog peptide L2.IV9

<400> SEQUENCE: 2273

Phe Leu Leu Thr Arg Ile Leu Thr Val
1               5

<210> SEQ ID NO 2274
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2274

Phe Leu Leu Thr Arg Ile Leu Tyr Ile
1               5

<210> SEQ ID NO 2275
<211> LENGTH: 9
<212> TYPE: PRT
<213> ORGANISM: Artificial Sequence
<220> FEATURE:
<223> OTHER INFORMATION: HBV analog peptide
```

```
<400> SEQUENCE: 2275

Phe Leu Leu Thr Tyr Ile Leu Thr Ile
1               5

<210> SEQ ID NO 2276
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2276

Phe Leu Met Ser Asp Tyr Phe Pro Ser Val
1               5                   10

<210> SEQ ID NO 2277
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2277

Phe Leu Met Ser Tyr Phe Pro Ser Val
1               5

<210> SEQ ID NO 2278
<211> LENGTH: 10
<212> TYPE: PRT
<213> ORGANISM: Artificial Sequence
<220> FEATURE:
<223> OTHER INFORMATION: HBV analog peptide L2.SA4

<400> SEQUENCE: 2278

Phe Leu Pro Ala Asp Phe Phe Pro Ser Ile
1               5                   10

<210> SEQ ID NO 2279
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2279

Phe Leu Pro Ala Asp Phe Phe Pro Ser Val
1               5                   10

<210> SEQ ID NO 2280
<211> LENGTH: 10
<212> TYPE: PRT
<213> ORGANISM: Artificial Sequence
<220> FEATURE:
<223> OTHER INFORMATION: HBV analog peptide L2.SD4

<400> SEQUENCE: 2280

Phe Leu Pro Asp Asp Phe Phe Pro Ser Ala
1               5                   10

<210> SEQ ID NO 2281
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2281
```

Phe Leu Pro Asp Asp Phe Phe Pro Ser Val
1               5                   10

<210> SEQ ID NO 2282
<211> LENGTH: 10
<212> TYPE: PRT
<213> ORGANISM: Artificial Sequence
<220> FEATURE:
<223> OTHER INFORMATION: HBV analog peptide L2.SN4

<400> SEQUENCE: 2282

Phe Leu Pro Asn Asp Phe Phe Pro Ser Ala
1               5                   10

<210> SEQ ID NO 2283
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2283

Phe Leu Pro Asn Asp Phe Phe Pro Ser Val
1               5                   10

<210> SEQ ID NO 2284
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 5
<223> OTHER INFORMATION: Xaa=Any amino acid

<400> SEQUENCE: 2284

Phe Leu Pro Ser Xaa Tyr Phe Pro Ser Val
1 5 10

<210> SEQ ID NO 2285
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2285

Phe Leu Pro Ser Ala Phe Phe Pro Ser Val
1 5 10

<210> SEQ ID NO 2286
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 6
<223> OTHER INFORMATION: Xaa=Any amino acid

<400> SEQUENCE: 2286

Phe Leu Pro Ser Asp Xaa Phe Pro Ser Val
1 5 10

<210> SEQ ID NO 2287

```
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2287

Phe Leu Pro Ser Asp Ala Phe Pro Ser Val
1               5                   10

<210> SEQ ID NO 2288
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2288

Phe Leu Pro Ser Asp Phe Ala Pro Ser Val
1               5                   10

<210> SEQ ID NO 2289
<211> LENGTH: 7
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 7
<223> OTHER INFORMATION: Xaa=F-NH-2

<400> SEQUENCE: 2289

Phe Leu Pro Ser Asp Phe Xaa
1               5

<210> SEQ ID NO 2290
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2290

Phe Leu Pro Ser Asp Phe Phe Ala Ser Val
1               5                   10

<210> SEQ ID NO 2291
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2291

Phe Leu Pro Ser Asp Phe Phe Lys Ser Val
1               5                   10

<210> SEQ ID NO 2292
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2292

Phe Leu Pro Ser Asp Phe Phe Pro
1               5
```

```
<210> SEQ ID NO 2293
<211> LENGTH: 8
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 8
<223> OTHER INFORMATION: Xaa=P-NH-2

<400> SEQUENCE: 2293

Phe Leu Pro Ser Asp Phe Phe Xaa
 1               5

<210> SEQ ID NO 2294
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2294

Phe Leu Pro Ser Asp Phe Phe Pro Ala Val
 1               5                  10

<210> SEQ ID NO 2295
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2295

Phe Leu Pro Ser Asp Phe Phe Pro Lys Val
 1               5                  10

<210> SEQ ID NO 2296
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2296

Phe Leu Pro Ser Asp Phe Phe Pro Ser
 1               5

<210> SEQ ID NO 2297
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 9
<223> OTHER INFORMATION: Xaa=S-NH2

<400> SEQUENCE: 2297

Phe Leu Pro Ser Asp Phe Phe Pro Xaa
 1               5

<210> SEQ ID NO 2298
<211> LENGTH: 10
<212> TYPE: PRT
<213> ORGANISM: Artificial Sequence
```

-continued

```
<220> FEATURE:
<223> OTHER INFORMATION: HBV analog peptide L2.VA10

<400> SEQUENCE: 2298

Phe Leu Pro Ser Asp Phe Phe Pro Ser Ala
1               5                   10

<210> SEQ ID NO 2299
<211> LENGTH: 10
<212> TYPE: PRT
<213> ORGANISM: Artificial Sequence
<220> FEATURE:
<223> OTHER INFORMATION: HBV analog peptide L2.VI10

<400> SEQUENCE: 2299

Phe Leu Pro Ser Asp Phe Phe Pro Ser Ile
1               5                   10

<210> SEQ ID NO 2300
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 10
<223> OTHER INFORMATION: Xaa=V(CONH2)

<400> SEQUENCE: 2300

Phe Leu Pro Ser Asp Phe Phe Pro Ser Xaa
1               5                   10

<210> SEQ ID NO 2301
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 10
<223> OTHER INFORMATION: Xaa=V-NH-2

<400> SEQUENCE: 2301

Phe Leu Pro Ser Asp Phe Phe Pro Ser Xaa
1               5                   10

<210> SEQ ID NO 2302
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2302

Phe Leu Pro Ser Asp Phe Phe Pro Ser Val Arg
1               5                   10

<210> SEQ ID NO 2303
<211> LENGTH: 11
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 11
<223> OTHER INFORMATION: Xaa=R-NH-2
```

```
<400> SEQUENCE: 2303

Phe Leu Pro Ser Asp Phe Phe Pro Ser Val Xaa
1               5                   10

<210> SEQ ID NO 2304
<211> LENGTH: 12
<212> TYPE: PRT
<213> ORGANISM: Artificial Sequence
<220> FEATURE:
<223> OTHER INFORMATION: HBV analog peptide

<400> SEQUENCE: 2304

Phe Leu Pro Ser Asp Phe Phe Pro Ser Val Arg Asp
1               5                   10

<210> SEQ ID NO 2305
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2305

Phe Leu Pro Ser Asp Phe Tyr Pro Ser Val
1               5                   10

<210> SEQ ID NO 2306
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2306

Phe Leu Pro Ser Asp Leu Leu Pro Ser Val Arg
1               5                   10

<210> SEQ ID NO 2307
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2307

Phe Leu Pro Ser Asp Tyr Phe Pro Ser Val
1               5                   10

<210> SEQ ID NO 2308
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2308

Phe Leu Pro Ser Glu Phe Phe Pro Ser Val
1               5                   10

<210> SEQ ID NO 2309
<211> LENGTH: 9
<212> TYPE: PRT
<213> ORGANISM: Artificial Sequence
<220> FEATURE:
<223> OTHER INFORMATION: HBV analog peptide L2.FY5
```

-continued

```
<400> SEQUENCE: 2309

Phe Leu Pro Ser Tyr Phe Pro Ser Ala
1               5

<210> SEQ ID NO 2310
<211> LENGTH: 9
<212> TYPE: PRT
<213> ORGANISM: Artificial Sequence
<220> FEATURE:
<223> OTHER INFORMATION: HBV analog peptide L2.FY5

<400> SEQUENCE: 2310

Phe Leu Pro Ser Tyr Phe Pro Ser Val
1               5

<210> SEQ ID NO 2311
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2311

Phe Leu Pro Ser Glx Phe Phe Pro Ser Val
1               5                   10

<210> SEQ ID NO 2312
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2312

Phe Leu Pro Ser Glx Phe Phe Pro Ser Val
1               5                   10

<210> SEQ ID NO 2313
<211> LENGTH: 10
<212> TYPE: PRT
<213> ORGANISM: Artificial Sequence
<220> FEATURE:
<223> OTHER INFORMATION: HBV analog peptide L2.5V4

<400> SEQUENCE: 2313

Phe Leu Pro Val Asp Phe Phe Pro Ser Ile
1               5                   10

<210> SEQ ID NO 2314
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2314

Phe Leu Pro Val Asp Phe Phe Pro Ser Val
1               5                   10

<210> SEQ ID NO 2315
<211> LENGTH: 9
<212> TYPE: PRT
<213> ORGANISM: Orthohepadnaviridae hepatitis B virus

<400> SEQUENCE: 2315

Phe Leu Ser Lys Gln Tyr Leu Asn Leu
```

```
<210> SEQ ID NO 2316
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2316

Phe Leu Tyr Thr Arg Ile Leu Thr Ile
1               5

<210> SEQ ID NO 2317
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2317

Phe Met Phe Ser Pro Thr Tyr Lys
1               5

<210> SEQ ID NO 2318
<211> LENGTH: 10
<212> TYPE: PRT
<213> ORGANISM: Artificial Sequence
<220> FEATURE:
<223> OTHER INFORMATION: HBV analog peptide IM2.L10

<400> SEQUENCE: 2318

Phe Met Leu Leu Leu Cys Leu Ile Phe Leu
1               5                   10

<210> SEQ ID NO 2319
<211> LENGTH: 10
<212> TYPE: PRT
<213> ORGANISM: Artificial Sequence
<220> FEATURE:
<223> OTHER INFORMATION: HBV analog peptide LM2.V1

<400> SEQUENCE: 2319

Phe Met Pro Ser Asp Phe Phe Pro Ser Val
1               5                   10

<210> SEQ ID NO 2320
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2320

Phe Pro Ala Ala Met Pro His Leu
1               5

<210> SEQ ID NO 2321
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2321

Phe Pro Ala Ala Met Pro His Leu Leu
1               5
```

<210> SEQ ID NO 2322
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2322

Phe Pro Ala Ala Met Pro His Leu Leu Val
1               5                   10

<210> SEQ ID NO 2323
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2323

Phe Pro Ala Leu Met Pro Leu Tyr Ala
1               5

<210> SEQ ID NO 2324
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2324

Phe Pro Ala Arg Val Thr Gly Gly Val Phe
1               5                   10

<210> SEQ ID NO 2325
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2325

Phe Pro Cys Ala Leu Arg Phe Thr Ser Ala
1               5                   10

<210> SEQ ID NO 2326
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2326

Phe Pro Phe Cys Leu Ala Phe Ser Tyr
1               5

<210> SEQ ID NO 2327
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2327

Phe Pro Phe Cys Leu Ala Phe Ser Tyr Met
1               5                   10

```
<210> SEQ ID NO 2328
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2328

Phe Pro His Cys Leu Ala Phe Ala Leu
 1               5

<210> SEQ ID NO 2329
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2329

Phe Pro His Cys Leu Ala Phe Ala Tyr
 1               5

<210> SEQ ID NO 2330
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2330

Phe Pro His Cys Leu Ala Phe Ser Ala
 1               5

<210> SEQ ID NO 2331
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2331

Phe Pro His Cys Leu Ala Phe Ser Ile
 1               5

<210> SEQ ID NO 2332
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2332

Phe Pro His Cys Leu Ala Phe Ser Leu
 1               5

<210> SEQ ID NO 2333
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2333

Phe Pro His Cys Leu Ala Phe Ser Tyr Ile
 1               5                  10
```

```
<210> SEQ ID NO 2334
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 4
<223> OTHER INFORMATION: Xaa=Any amino acid

<400> SEQUENCE: 2334

Phe Pro His Xaa Leu Ala Phe Ser Tyr Met
 1               5                  10

<210> SEQ ID NO 2335
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2335

Phe Pro Ile Pro Ser Ser Trp Ala Phe
 1               5

<210> SEQ ID NO 2336
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2336

Phe Pro Ser Arg Gly Arg Leu Gly Leu
 1               5

<210> SEQ ID NO 2337
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2337

Phe Pro Val Cys Ala Phe Ser Ser Ala
 1               5

<210> SEQ ID NO 2338
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2338

Phe Pro Val Cys Leu Ala Phe Ser Tyr
 1               5

<210> SEQ ID NO 2339
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2339

Phe Gln Pro Ser Asp Tyr Phe Pro Ser Val
```

```
1               5                   10

<210> SEQ ID NO 2340
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2340

Phe Val Phe Ser Pro Thr Tyr Lys
1               5

<210> SEQ ID NO 2341
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 6
<223> OTHER INFORMATION: Xaa=Any amino acid

<400> SEQUENCE: 2341

Phe Val Leu Gly Gly Xaa Arg His Lys
1               5

<210> SEQ ID NO 2342
<211> LENGTH: 9
<212> TYPE: PRT
<213> ORGANISM: Artificial Sequence
<220> FEATURE:
<223> OTHER INFORMATION: HBV analog peptide L2.AV9

<400> SEQUENCE: 2342

Gly Leu Cys Gln Val Phe Ala Asp Val
1               5

<210> SEQ ID NO 2343
<211> LENGTH: 9
<212> TYPE: PRT
<213> ORGANISM: Artificial Sequence
<220> FEATURE:
<223> OTHER INFORMATION: HBV analog peptide L2.AV9

<400> SEQUENCE: 2343

Gly Leu Leu Gly Trp Ser Pro Gln Val
1               5

<210> SEQ ID NO 2344
<211> LENGTH: 9
<212> TYPE: PRT
<213> ORGANISM: Artificial Sequence
<220> FEATURE:
<223> OTHER INFORMATION: HBV analog peptide VL2.AV9

<400> SEQUENCE: 2344

Gly Leu Trp Ile Arg Thr Pro Pro Val
1               5

<210> SEQ ID NO 2345
<211> LENGTH: 9
<212> TYPE: PRT
<213> ORGANISM: Artificial Sequence
<220> FEATURE:
<223> OTHER INFORMATION: HBV analog peptide
<220> FEATURE:
```

```
<221> NAME/KEY: MOD_RES
<222> LOCATION: 3
<223> OTHER INFORMATION: Xaa=Any amino acid

<400> SEQUENCE: 2345

Gly Leu Xaa Gln Val Phe Ala Asp Ala
1               5

<210> SEQ ID NO 2346
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2346

Gly Met Asp Asn Ser Val Val Leu Ser Arg
1               5                   10

<210> SEQ ID NO 2347
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2347

Gly Met Asp Asn Ser Val Val Leu Ser Arg Lys
1               5                   10

<210> SEQ ID NO 2348
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2348

Gly Pro Cys Ala Leu Arg Phe Thr Ser Ile
1               5                   10

<210> SEQ ID NO 2349
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2349

Gly Pro Phe Ala Leu Arg Phe Thr Ser Ala
1               5                   10

<210> SEQ ID NO 2350
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 3
<223> OTHER INFORMATION: Xaa=Any amino acid

<400> SEQUENCE: 2350

Gly Pro Xaa Ala Leu Arg Phe Thr Ser Ala
1               5                   10
```

```
<210> SEQ ID NO 2351
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2351

Gly Thr Phe Asn Ser Val Val Leu Ser Arg
1               5                   10

<210> SEQ ID NO 2352
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2352

Gly Thr Phe Asn Ser Val Val Leu Ser Arg Lys
1               5                   10

<210> SEQ ID NO 2353
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2353

Gly Val Asp Asn Ser Val Val Leu Ser Arg
1               5                   10

<210> SEQ ID NO 2354
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2354

Gly Val Asp Asn Ser Val Val Leu Ser Arg Lys
1               5                   10

<210> SEQ ID NO 2355
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 6
<223> OTHER INFORMATION: Xaa=Any amino acid

<400> SEQUENCE: 2355

Gly Tyr Arg Trp Met Xaa Leu Arg Arg Phe
1               5                   10

<210> SEQ ID NO 2356
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 4
<223> OTHER INFORMATION: Xaa=Any amino acid
```

```
<400> SEQUENCE: 2356

His Ile Ser Xaa Leu Thr Phe Gly Arg
1               5

<210> SEQ ID NO 2357
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2357

His Met Leu Trp Lys Ala Gly Ile Leu Tyr
1               5                   10

<210> SEQ ID NO 2358
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2358

His Met Leu Trp Lys Ala Gly Ile Leu Tyr Lys
1               5                   10

<210> SEQ ID NO 2359
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2359

His Pro Ala Ala Met Pro His Ile
1               5

<210> SEQ ID NO 2360
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2360

His Pro Ala Ala Met Pro His Leu Ile
1               5

<210> SEQ ID NO 2361
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2361

His Pro Ala Ala Met Pro His Leu Leu Ile
1               5                   10

<210> SEQ ID NO 2362
<211> LENGTH: 8
<212> TYPE: PRT
<213> ORGANISM: Artificial Sequence
<220> FEATURE:
<223> OTHER INFORMATION: HBV analog peptide
```

-continued

```
<400> SEQUENCE: 2362

His Pro Phe Ala Met Pro His Leu
 1               5

<210> SEQ ID NO 2363
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2363

His Pro Phe Ala Met Pro His Leu Leu
 1               5

<210> SEQ ID NO 2364
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2364

His Pro Phe Ala Met Pro His Leu Leu Val
 1               5                   10

<210> SEQ ID NO 2365
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2365

His Thr Leu Trp Lys Ala Gly Ile Leu Lys
 1               5                   10

<210> SEQ ID NO 2366
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2366

His Thr Leu Trp Lys Ala Gly Ile Leu Arg
 1               5                   10

<210> SEQ ID NO 2367
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2367

His Val Leu Trp Lys Ala Gly Ile Leu Tyr
 1               5                   10

<210> SEQ ID NO 2368
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2368
```

```
His Val Leu Trp Lys Ala Gly Ile Leu Tyr Lys
1               5                   10

<210> SEQ ID NO 2369
<211> LENGTH: 9
<212> TYPE: PRT
<213> ORGANISM: Artificial Sequence
<220> FEATURE:
<223> OTHER INFORMATION: Orthohepadnaviridae hepatitis B virus

<400> SEQUENCE: 2369

Ile Ile Lys Lys Ser Glu Gln Phe Val
1               5

<210> SEQ ID NO 2370
<211> LENGTH: 9
<212> TYPE: PRT
<213> ORGANISM: Artificial Sequence
<220> FEATURE:
<223> OTHER INFORMATION: HBV analog peptide VL2.AV9

<400> SEQUENCE: 2370

Ile Leu Gly Leu Leu Gly Phe Ala Val
1               5

<210> SEQ ID NO 2371
<211> LENGTH: 10
<212> TYPE: PRT
<213> ORGANISM: Artificial Sequence
<220> FEATURE:
<223> OTHER INFORMATION: HBV analog peptide L2.LV10

<400> SEQUENCE: 2371

Ile Leu Leu Leu Cys Leu Ile Phe Leu Val
1               5                   10

<210> SEQ ID NO 2372
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 5
<223> OTHER INFORMATION: Xaa=Any amino acid

<400> SEQUENCE: 2372

Ile Leu Leu Leu Xaa Leu Ile Phe Leu
1               5

<210> SEQ ID NO 2373
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 5
<223> OTHER INFORMATION: Xaa=Any amino acid

<400> SEQUENCE: 2373

Ile Leu Leu Leu Xaa Leu Ile Phe Leu Leu
1               5                   10

<210> SEQ ID NO 2374
```

```
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2374

Ile Pro Phe Pro Ser Ser Trp Ala Phe
1               5

<210> SEQ ID NO 2375
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2375

Ile Pro Ile Leu Ser Ser Trp Ala Phe
1               5

<210> SEQ ID NO 2376
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2376

Ile Pro Ile Pro Met Ser Trp Ala Phe
1               5

<210> SEQ ID NO 2377
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2377

Ile Pro Ile Pro Ser Ser Trp Ala Ile
1               5

<210> SEQ ID NO 2378
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2378

Ile Pro Ile Thr Ser Ser Trp Ala Phe
1               5

<210> SEQ ID NO 2379
<211> LENGTH: 9
<212> TYPE: PRT
<213> ORGANISM: Orthohepadnaviridae hepatitis B virus

<400> SEQUENCE: 2379

Lys Ile Lys Glu Ser Phe Arg Lys Leu
1               5

<210> SEQ ID NO 2380
<211> LENGTH: 9
<212> TYPE: PRT
<213> ORGANISM: Artificial Sequence
```

```
<220> FEATURE:
<223> OTHER INFORMATION: HBV analog peptide

<400> SEQUENCE: 2380

Lys Leu Phe Leu Tyr Ser His Pro Ile
 1               5

<210> SEQ ID NO 2381
<211> LENGTH: 9
<212> TYPE: PRT
<213> ORGANISM: Artificial Sequence
<220> FEATURE:
<223> OTHER INFORMATION: HBV analog peptide L2.IV9

<400> SEQUENCE: 2381

Lys Leu His Leu Tyr Ser His Pro Val
 1               5

<210> SEQ ID NO 2382
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2382

Lys Val Gly Asn Phe Thr Gly Leu Lys
 1               5

<210> SEQ ID NO 2383
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2383

Lys Val Gly Asn Phe Thr Gly Leu Arg
 1               5

<210> SEQ ID NO 2384
<211> LENGTH: 9
<212> TYPE: PRT
<213> ORGANISM: Artificial Sequence
<220> FEATURE:
<223> OTHER INFORMATION: HBV analog peptide L2.IV9

<400> SEQUENCE: 2384

Leu Leu Ala Gln Phe Thr Ser Ala Val
 1               5

<210> SEQ ID NO 2385
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2385

Leu Leu Phe Tyr Gln Gly Met Leu Pro Val
 1               5                   10

<210> SEQ ID NO 2386
<211> LENGTH: 9
<212> TYPE: PRT
<213> ORGANISM: Orthohepadnaviridae hepatitis B virus
```

-continued

<400> SEQUENCE: 2386

Leu Leu Gly Ser Ala Ala Asn Trp Ile
1               5

<210> SEQ ID NO 2387
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 4
<223> OTHER INFORMATION: Xaa=Any amino acid

<400> SEQUENCE: 2387

Leu Leu Gly Xaa Ala Ala Asn Trp Ile Leu
1               5                   10

<210> SEQ ID NO 2388
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 4
<223> OTHER INFORMATION: Xaa=Any amino acid

<400> SEQUENCE: 2388

Leu Leu Leu Xaa Leu Ile Phe Leu Leu
1               5

<210> SEQ ID NO 2389
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 4
<223> OTHER INFORMATION: Xaa=Any amino acid

<400> SEQUENCE: 2389

Leu Leu Leu Xaa Leu Ile Phe Leu Leu Val
1               5                   10

<210> SEQ ID NO 2390
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2390

Leu Leu Leu Tyr Gln Gly Met Leu Pro Val
1               5                   10

<210> SEQ ID NO 2391
<211> LENGTH: 9
<212> TYPE: PRT
<213> ORGANISM: Artificial Sequence
<220> FEATURE:
<223> OTHER INFORMATION: HBV analog peptide VL2.V9

<400> SEQUENCE: 2391

```
Leu Leu Pro Phe Val Gln Trp Phe Val
1               5

<210> SEQ ID NO 2392
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 7
<223> OTHER INFORMATION: Xaa=Any amino acid

<400> SEQUENCE: 2392

Leu Leu Pro Ile Phe Phe Xaa Leu Trp Val
1               5                   10

<210> SEQ ID NO 2393
<211> LENGTH: 13
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 13
<223> OTHER INFORMATION: Xaa=V-NH-2

<400> SEQUENCE: 2393

Leu Leu Ser Phe Leu Pro Ser Asp Phe Phe Pro Ser Xaa
1               5                   10

<210> SEQ ID NO 2394
<211> LENGTH: 9
<212> TYPE: PRT
<213> ORGANISM: Artificial Sequence
<220> FEATURE:
<223> OTHER INFORMATION: HBV analog peptide L2.LV9

<400> SEQUENCE: 2394

Leu Leu Ser Ser Asn Leu Ser Trp Val
1               5

<210> SEQ ID NO 2395
<211> LENGTH: 10
<212> TYPE: PRT
<213> ORGANISM: Artificial Sequence
<220> FEATURE:
<223> OTHER INFORMATION: HBV analog peptide L2.LV10

<400> SEQUENCE: 2395

Leu Leu Val Leu Gln Ala Gly Phe Phe Val
1               5                   10

<210> SEQ ID NO 2396
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 3
<223> OTHER INFORMATION: Xaa=Any amino acid

<400> SEQUENCE: 2396

Leu Leu Xaa Leu Ile Phe Leu Leu Val
1               5
```

<210> SEQ ID NO 2397
<211> LENGTH: 10
<212> TYPE: PRT
<213> ORGANISM: Artificial Sequence
<220> FEATURE:
<223> OTHER INFORMATION: HBV analog peptide VM2.LV

<400> SEQUENCE: 2397

Leu Met Leu Leu Asp Tyr Gln Gly Met Val
1               5                   10

<210> SEQ ID NO 2398
<211> LENGTH: 10
<212> TYPE: PRT
<213> ORGANISM: Artificial Sequence
<220> FEATURE:
<223> OTHER INFORMATION: HBV analog peptide VM2.LV

<400> SEQUENCE: 2398

Leu Met Leu Gln Ala Gly Phe Phe Leu Val
1 5 10

<210> SEQ ID NO 2399
<211> LENGTH: 9
<212> TYPE: PRT
<213> ORGANISM: Artificial Sequence
<220> FEATURE:
<223> OTHER INFORMATION: HBV analog peptide VM2.V9

<400> SEQUENCE: 2399

Leu Met Pro Phe Val Gln Trp Phe Val
1 5

<210> SEQ ID NO 2400
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2400

Leu Pro Phe Cys Ala Phe Ser Ser Ala
1 5

<210> SEQ ID NO 2401
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2401

Leu Pro Ile Phe Phe Cys Leu Ile
1 5

<210> SEQ ID NO 2402
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2402

Leu Pro Ile Phe Phe Cys Leu Trp Ile
1 5

```
<210> SEQ ID NO 2403
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2403

Leu Pro Ile His Thr Ala Glu Leu Ile
 1               5

<210> SEQ ID NO 2404
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2404

Leu Pro Ile His Thr Ala Glu Leu Leu Ala Ile
 1               5                  10

<210> SEQ ID NO 2405
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 9
<223> OTHER INFORMATION: Xaa=V-NH-2

<400> SEQUENCE: 2405

Leu Pro Ser Asp Phe Phe Pro Ser Xaa
 1               5

<210> SEQ ID NO 2406
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2406

Leu Pro Val Cys Ala Phe Ser Ser Ile
 1               5

<210> SEQ ID NO 2407
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 4
<223> OTHER INFORMATION: Xaa=Any amino acid

<400> SEQUENCE: 2407

Leu Pro Val Xaa Ala Phe Ser Ser Ala
 1               5

<210> SEQ ID NO 2408
<211> LENGTH: 12
<212> TYPE: PRT
<213> ORGANISM: Artificial Sequence
<220> FEATURE:
```

<223> OTHER INFORMATION: HBV analog peptide

<400> SEQUENCE: 2408

Leu Ser Phe Leu Pro Ser Asp Phe Phe Pro Ser Val
1               5                   10

<210> SEQ ID NO 2409
<211> LENGTH: 12
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 12
<223> OTHER INFORMATION: Xaa=V-NH-2

<400> SEQUENCE: 2409

Leu Ser Phe Leu Pro Ser Asp Phe Phe Pro Ser Xaa
1               5                   10

<210> SEQ ID NO 2410
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2410

Met Met Trp Tyr Trp Gly Pro Ser Leu Lys
1               5                   10

<210> SEQ ID NO 2411
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2411

Met Met Trp Tyr Trp Gly Pro Ser Leu Arg
1               5                   10

<210> SEQ ID NO 2412
<211> LENGTH: 9
<212> TYPE: PRT
<213> ORGANISM: Artificial Sequence
<220> FEATURE:
<223> OTHER INFORMATION: HBV analog peptide M2.LV9

<400> SEQUENCE: 2412

Met Met Trp Tyr Trp Gly Pro Ser Val
1               5

<210> SEQ ID NO 2413
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2413

Met Pro Leu Ser Tyr Gln His Ile
1               5

<210> SEQ ID NO 2414
<211> LENGTH: 9

```
<212> TYPE: PRT
<213> ORGANISM: Artificial Sequence
<220> FEATURE:
<223> OTHER INFORMATION: HBV analog peptide L2.IV9

<400> SEQUENCE: 2414

Asn Leu Gly Asn Leu Asn Val Ser Val
 1               5

<210> SEQ ID NO 2415
<211> LENGTH: 9
<212> TYPE: PRT
<213> ORGANISM: Orthohepadnaviridae hepatitis B virus

<400> SEQUENCE: 2415

Asn Leu Asn Asn Leu Asn Val Ser Ile
 1               5

<210> SEQ ID NO 2416
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2416

Asn Met Gly Leu Lys Tyr Arg Gln Leu
 1               5

<210> SEQ ID NO 2417
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2417

Asn Pro Leu Gly Phe Phe Pro Asp His Gln Ile
 1               5                   10

<210> SEQ ID NO 2418
<211> LENGTH: 9
<212> TYPE: PRT
<213> ORGANISM: Artificial Sequence
<220> FEATURE:
<223> OTHER INFORMATION: HBV analog peptide L2.LV9

<400> SEQUENCE: 2418

Pro Leu Leu Pro Ile Phe Phe Cys Val
 1               5

<210> SEQ ID NO 2419
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 8
<223> OTHER INFORMATION: Xaa=Any amino acid

<400> SEQUENCE: 2419

Pro Leu Leu Pro Ile Phe Phe Xaa Leu
 1               5

<210> SEQ ID NO 2420
```

```
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2420

Pro Ser Asp Phe Phe Pro Ser Val
 1               5

<210> SEQ ID NO 2421
<211> LENGTH: 8
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 8
<223> OTHER INFORMATION: Xaa=V-NH-2

<400> SEQUENCE: 2421

Pro Ser Asp Phe Phe Pro Ser Xaa
 1               5

<210> SEQ ID NO 2422
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 9
<223> OTHER INFORMATION: Xaa=Any amino acid

<400> SEQUENCE: 2422

Gln Leu Leu Trp Phe His Ile Ser Xaa Leu
 1               5                  10

<210> SEQ ID NO 2423
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2423

Gln Met Phe Thr Phe Ser Pro Thr Tyr Lys
 1               5                  10

<210> SEQ ID NO 2424
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2424

Gln Val Phe Thr Phe Ser Pro Thr Tyr Lys
 1               5                  10

<210> SEQ ID NO 2425
<211> LENGTH: 9
<212> TYPE: PRT
<213> ORGANISM: Orthohepadnaviridae hepatitis B virus

<400> SEQUENCE: 2425
```

Arg Ile Pro Arg Thr Pro Arg Ser Val
1               5

<210> SEQ ID NO 2426
<211> LENGTH: 9
<212> TYPE: PRT
<213> ORGANISM: Artificial Sequence
<220> FEATURE:
<223> OTHER INFORMATION: HBV analog peptide VL2.V9

<400> SEQUENCE: 2426

Arg Leu Ser Trp Pro Lys Phe Ala Val
1               5

<210> SEQ ID NO 2427
<211> LENGTH: 9
<212> TYPE: PRT
<213> ORGANISM: Artificial Sequence
<220> FEATURE:
<223> OTHER INFORMATION: HBV analog peptide VL2.V9

<400> SEQUENCE: 2427

Arg Leu Thr Gly Gly Val Phe Leu Val
1               5

<210> SEQ ID NO 2428
<211> LENGTH: 9
<212> TYPE: PRT
<213> ORGANISM: Artificial Sequence
<220> FEATURE:
<223> OTHER INFORMATION: HBV analog peptide IM2.LV9

<400> SEQUENCE: 2428

Arg Met Leu Thr Ile Pro Gln Ser Val
1               5

<210> SEQ ID NO 2429
<211> LENGTH: 9
<212> TYPE: PRT
<213> ORGANISM: Artificial Sequence
<220> FEATURE:
<223> OTHER INFORMATION: HBV analog peptide VM2.V9

<400> SEQUENCE: 2429

Arg Met Thr Gly Gly Val Phe Leu Val
1               5

<210> SEQ ID NO 2430
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2430

Arg Met Tyr Leu His Thr Leu Trp Lys
1               5

<210> SEQ ID NO 2431
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2431

Arg Val Tyr Leu His Thr Leu Trp Lys

-continued

```
<210> SEQ ID NO 2432
<211> LENGTH: 9
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 4
<223> OTHER INFORMATION: Xaa=Any amino acid

<400> SEQUENCE: 2432

Ser Ala Ile Xaa Ser Val Val Arg Arg
1               5

<210> SEQ ID NO 2433
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2433

Ser Phe Leu Pro Ser Asp Phe Phe Pro Ser Val
1               5                   10

<210> SEQ ID NO 2434
<211> LENGTH: 11
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 11
<223> OTHER INFORMATION: Xaa=V-NH-2

<400> SEQUENCE: 2434

Ser Phe Leu Pro Ser Asp Phe Phe Pro Ser Xaa
1               5                   10

<210> SEQ ID NO 2435
<211> LENGTH: 9
<212> TYPE: PRT
<213> ORGANISM: Artificial Sequence
<220> FEATURE:
<223> OTHER INFORMATION: HBV analog peptide L2.LV9

<400> SEQUENCE: 2435

Ser Leu Asp Ser Trp Trp Thr Ser Val
1               5

<210> SEQ ID NO 2436
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 10
<223> OTHER INFORMATION: Xaa=V-NH-2

<400> SEQUENCE: 2436

Ser Leu Asn Phe Leu Gly Gly Thr Thr Xaa
1               5                   10
```

```
<210> SEQ ID NO 2437
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2437

Ser Met Ile Cys Ser Val Val Arg Arg
 1               5

<210> SEQ ID NO 2438
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2438

Ser Met Leu Pro Glu Thr Thr Val Val Arg
 1               5                  10

<210> SEQ ID NO 2439
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2439

Ser Met Leu Pro Glu Thr Thr Val Val Arg Arg
 1               5                  10

<210> SEQ ID NO 2440
<211> LENGTH: 10
<212> TYPE: PRT
<213> ORGANISM: Artificial Sequence
<220> FEATURE:
<223> OTHER INFORMATION: HBV analog peptide IM2.LV1

<400> SEQUENCE: 2440

Ser Met Leu Ser Pro Phe Leu Pro Leu Val
 1               5                  10

<210> SEQ ID NO 2441
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2441

Ser Pro Phe Leu Leu Ala Gln Ile
 1               5

<210> SEQ ID NO 2442
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2442

Ser Thr Leu Pro Glu Thr Tyr Val Val Arg Arg
 1               5                  10
```

```
<210> SEQ ID NO 2443
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2443

Ser Val Ile Cys Ser Val Val Arg Arg
 1               5

<210> SEQ ID NO 2444
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2444

Ser Val Leu Pro Glu Thr Thr Val Val Arg
 1               5                  10

<210> SEQ ID NO 2445
<211> LENGTH: 11
<212> TYPE: PRT
<213> ORGANISM: Artificial Sequence
<220> FEATURE:
<223> OTHER INFORMATION: HBV analog peptide

<400> SEQUENCE: 2445

Ser Val Leu Pro Glu Thr Thr Val Val Arg Arg
 1               5                  10

<210> SEQ ID NO 2446
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2446

Ser Val Asn Arg Pro Ile Asp Trp Lys
 1               5

<210> SEQ ID NO 2447
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2447

Ser Val Val Arg Arg Ala Phe Pro Lys
 1               5

<210> SEQ ID NO 2448
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2448

Ser Val Val Arg Arg Ala Phe Pro Arg
 1               5

<210> SEQ ID NO 2449
```

```
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2449

Thr Leu Trp Lys Ala Gly Ile Leu Lys
1               5

<210> SEQ ID NO 2450
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2450

Thr Leu Trp Lys Ala Gly Ile Leu Arg
1               5

<210> SEQ ID NO 2451
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2451

Thr Met Pro Glu Thr Thr Val Val Arg Arg
1               5                   10

<210> SEQ ID NO 2452
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2452

Thr Met Trp Lys Ala Gly Ile Leu Tyr
1               5

<210> SEQ ID NO 2453
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2453

Thr Met Trp Lys Ala Gly Ile Leu Tyr Lys
1               5                   10

<210> SEQ ID NO 2454
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2454

Thr Pro Ala Arg Val Thr Gly Gly Val Ile
1               5                   10

<210> SEQ ID NO 2455
<211> LENGTH: 10
```

```
<212> TYPE: PRT
<213> ORGANISM: Artificial Sequence
<220> FEATURE:
<223> OTHER INFORMATION: HBV analog peptide

<400> SEQUENCE: 2455

Thr Pro Phe Arg Val Thr Gly Gly Val Phe
1               5                   10

<210> SEQ ID NO 2456
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 5
<223> OTHER INFORMATION: Xaa=Any amino acid

<400> SEQUENCE: 2456

Thr Ser Ala Ile Xaa Ser Val Val Arg Arg
1               5                   10

<210> SEQ ID NO 2457
<211> LENGTH: 16
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 16
<223> OTHER INFORMATION: Xaa=V-NH-2

<400> SEQUENCE: 2457

Thr Val Glu Leu Leu Ser Phe Leu Pro Ser Asp Phe Phe Pro Ser Xaa
1               5                   10                  15

<210> SEQ ID NO 2458
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2458

Thr Val Pro Glu Thr Thr Val Val Arg Arg
1               5                   10

<210> SEQ ID NO 2459
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2459

Thr Val Trp Lys Ala Gly Ile Leu Tyr
1               5

<210> SEQ ID NO 2460
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2460
```

```
Thr Val Trp Lys Ala Gly Ile Leu Tyr Lys
 1               5                  10

<210> SEQ ID NO 2461
<211> LENGTH: 15
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 15
<223> OTHER INFORMATION: Xaa=V-NH-2

<400> SEQUENCE: 2461

Val Glu Leu Leu Ser Phe Leu Pro Ser Asp Phe Phe Pro Ser Xaa
 1               5                  10                  15

<210> SEQ ID NO 2462
<211> LENGTH: 10
<212> TYPE: PRT
<213> ORGANISM: Artificial Sequence
<220> FEATURE:
<223> OTHER INFORMATION: HBV analog peptide
<220> FEATURE:
<221> NAME/KEY: MOD_RES
<222> LOCATION: 10
<223> OTHER INFORMATION: Xaa=V-NH-2

<400> SEQUENCE: 2462

Val Leu Glu Tyr Leu Val Ser Phe Gly Xaa
 1               5                  10

<210> SEQ ID NO 2463
<211> LENGTH: 9
<212> TYPE: PRT
<213> ORGANISM: Orthohepadnaviridae hepatitis B virus

<400> SEQUENCE: 2463

Val Leu Gly Gly Ser Arg His Lys Leu
 1               5

<210> SEQ ID NO 2464
<211> LENGTH: 9
<212> TYPE: PRT
<213> ORGANISM: Artificial Sequence
<220> FEATURE:
<223> OTHER INFORMATION: HBV analog peptide L2.LV9

<400> SEQUENCE: 2464

Val Leu Leu Asp Tyr Gln Gly Met Val
 1               5

<210> SEQ ID NO 2465
<211> LENGTH: 9
<212> TYPE: PRT
<213> ORGANISM: Artificial Sequence
<220> FEATURE:
<223> OTHER INFORMATION: HBV analog peptide L2.LV9

<400> SEQUENCE: 2465

Val Leu Gln Ala Gly Phe Phe Leu Val
 1               5

<210> SEQ ID NO 2466
<211> LENGTH: 10
<212> TYPE: PRT
```

```
-continued

<213> ORGANISM: Artificial Sequence
<220> FEATURE:
<223> OTHER INFORMATION: HBV analog peptide

<400> SEQUENCE: 2466

Val Met Gly Gly Val Phe Leu Val Asp Lys
 1               5                  10

<210> SEQ ID NO 2467
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2467

Val Pro Phe Val Gln Trp Phe Val Gly Ile
 1               5                  10

<210> SEQ ID NO 2468
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2468

Val Pro Ser Ala Leu Asn Pro Ile
 1               5

<210> SEQ ID NO 2469
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2469

Val Val Phe Phe Ser Gln Phe Ser Arg
 1               5

<210> SEQ ID NO 2470
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2470

Val Val Gly Gly Val Phe Leu Val Asp Lys
 1               5                  10

<210> SEQ ID NO 2471
<211> LENGTH: 9
<212> TYPE: PRT
<213> ORGANISM: Artificial Sequence
<220> FEATURE:
<223> OTHER INFORMATION: HBV analog peptide IL2.V9

<400> SEQUENCE: 2471

Trp Leu Leu Arg Gly Thr Ser Phe Val
 1               5

<210> SEQ ID NO 2472
<211> LENGTH: 10
<212> TYPE: PRT
<213> ORGANISM: Artificial Sequence
```

-continued

<220> FEATURE:
<223> OTHER INFORMATION: clostridium tetani

<400> SEQUENCE: 2472

Tyr Leu Phe Thr Leu Trp Lys Ala Gly Ile
1 5 10

<210> SEQ ID NO 2473
<211> LENGTH: 10
<212> TYPE: PRT
<213> ORGANISM: Artificial Sequence
<220> FEATURE:
<223> OTHER INFORMATION: HBV analog peptide L2.IV10

<400> SEQUENCE: 2473

Tyr Leu His Thr Leu Trp Lys Ala Gly Val
1 5 10

<210> SEQ ID NO 2474
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2474

Tyr Leu Leu Thr Leu Trp Lys Ala Gly Ile
1 5 10

<210> SEQ ID NO 2475
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2475

Tyr Leu Leu Thr Arg Ile Leu Thr Ile
1 5

<210> SEQ ID NO 2476
<211> LENGTH: 9
<212> TYPE: PRT
<213> ORGANISM: Artificial Sequence
<220> FEATURE:
<223> OTHER INFORMATION: HBV analog peptide VL2.AV9

<400> SEQUENCE: 2476

Tyr Leu Pro Ser Ala Leu Asn Pro Val
1 5

<210> SEQ ID NO 2477
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2477

Tyr Leu Pro Ser Asp Phe Phe Pro Ser Val
1 5 10

<210> SEQ ID NO 2478
<211> LENGTH: 9
<212> TYPE: PRT
<213> ORGANISM: Artificial Sequence
<220> FEATURE:

<223> OTHER INFORMATION: HBV analog peptide M2.AV9

<400> SEQUENCE: 2478

Tyr Met Asp Asp Val Val Leu Gly Val
1 5

<210> SEQ ID NO 2479
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2479

Tyr Met Phe Asp Val Val Leu Gly Ala
1 5

<210> SEQ ID NO 2480
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2480

Tyr Met Phe Asp Val Val Leu Gly Ala Lys
1 5 10

<210> SEQ ID NO 2481
<211> LENGTH: 10
<212> TYPE: PRT
<213> ORGANISM: Artificial Sequence
<220> FEATURE:
<223> OTHER INFORMATION: HBV analog peptide

<400> SEQUENCE: 2481

Tyr Asn Met Gly Leu Lys Phe Arg Gln Leu
1 5 10

<210> SEQ ID NO 2482
<211> LENGTH: 8
<212> TYPE: PRT
<213> ORGANISM: Artificial Sequence
<220> FEATURE:
<223> OTHER INFORMATION: HBV analog peptide

<400> SEQUENCE: 2482

Tyr Pro Ala Leu Met Pro Leu Ile
1 5

<210> SEQ ID NO 2483
<211> LENGTH: 9
<212> TYPE: PRT
<213> ORGANISM: Artificial Sequence
<220> FEATURE:
<223> OTHER INFORMATION: HBV analog peptide

<400> SEQUENCE: 2483

Tyr Pro Ala Leu Met Pro Leu Tyr Ile
1 5

<210> SEQ ID NO 2484
<211> LENGTH: 9
<212> TYPE: PRT
<213> ORGANISM: Artificial Sequence
<220> FEATURE:
<223> OTHER INFORMATION: HBV analog peptide

```
<400> SEQUENCE: 2484

Tyr Pro Phe Leu Met Pro Leu Tyr Ala
1               5

<210> SEQ ID NO 2485
<211> LENGTH: 12
<212> TYPE: PRT
<213> ORGANISM: Artificial Sequence
<220> FEATURE:
<223> OTHER INFORMATION: HBV analog peptide

<400> SEQUENCE: 2485

Tyr Ser Phe Leu Pro Ser Asp Phe Phe Pro Ser Val
1               5                   10

<210> SEQ ID NO 2486
<211> LENGTH: 9
<212> TYPE: PRT
<213> ORGANISM: Artificial Sequence
<220> FEATURE:
<223> OTHER INFORMATION: Standard peptide that binds to HLA A*0101

<400> SEQUENCE: 2486

Tyr Leu Glu Pro Ala Ile Ala Lys Tyr
1               5

<210> SEQ ID NO 2487
<211> LENGTH: 10
<212> TYPE: PRT
<213> ORGANISM: Artificial Sequence
<220> FEATURE:
<223> OTHER INFORMATION: Standard peptide that binds to HLA A*0201, HLA
      A*0202, HLA A*0203, HLAA*0206, HLA A*0207

<400> SEQUENCE: 2487

Phe Leu Pro Ser Asp Tyr Phe Pro Ser Val
1               5                   10

<210> SEQ ID NO 2488
<211> LENGTH: 9
<212> TYPE: PRT
<213> ORGANISM: Artificial Sequence
<220> FEATURE:
<223> OTHER INFORMATION: Standard peptide that binds to HLA A*6802

<400> SEQUENCE: 2488

Phe Thr Gln Ala Gly Tyr Pro Ala Leu
1               5

<210> SEQ ID NO 2489
<211> LENGTH: 10
<212> TYPE: PRT
<213> ORGANISM: Artificial Sequence
<220> FEATURE:
<223> OTHER INFORMATION: Standard peptide that binds to HLA A*0301,
      A*6801

<400> SEQUENCE: 2489

Lys Val Phe Pro Tyr Ala Leu Ile Asn Lys
1               5                   10

<210> SEQ ID NO 2490
<211> LENGTH: 9
<212> TYPE: PRT
<213> ORGANISM: Artificial Sequence
<220> FEATURE:
```

-continued

```
<223> OTHER INFORMATION: Standard peptide that binds to HLA A*1101

<400> SEQUENCE: 2490

Ala Val Asp Leu Tyr His Phe Leu Lys
1               5

<210> SEQ ID NO 2491
<211> LENGTH: 11
<212> TYPE: PRT
<213> ORGANISM: Artificial Sequence
<220> FEATURE:
<223> OTHER INFORMATION: Standard peptide that binds to HLA A*3301

<400> SEQUENCE: 2491

Ser Thr Leu Pro Glu Thr Tyr Val Val Arg Arg
1               5                   10

<210> SEQ ID NO 2492
<211> LENGTH: 9
<212> TYPE: PRT
<213> ORGANISM: Artificial Sequence
<220> FEATURE:
<223> OTHER INFORMATION: Standard peptide that binds to HLA A*2401

<400> SEQUENCE: 2492

Ala Tyr Ile Asp Asn Tyr Asn Lys Phe
1               5

<210> SEQ ID NO 2493
<211> LENGTH: 9
<212> TYPE: PRT
<213> ORGANISM: Artificial Sequence
<220> FEATURE:
<223> OTHER INFORMATION: Standard peptide that binds to HLA B*0702

<400> SEQUENCE: 2493

Ala Pro Arg Thr Leu Val Tyr Leu Leu
1               5

<210> SEQ ID NO 2494
<211> LENGTH: 9
<212> TYPE: PRT
<213> ORGANISM: Artificial Sequence
<220> FEATURE:
<223> OTHER INFORMATION: Standard peptide that binds to HLA B*3501, B51,
      B*5301, B*5401

<400> SEQUENCE: 2494

Phe Pro Phe Lys Tyr Ala Ala Ala Phe
1               5

<210> SEQ ID NO 2495
<211> LENGTH: 13
<212> TYPE: PRT
<213> ORGANISM: Artificial Sequence
<220> FEATURE:
<223> OTHER INFORMATION: Standard peptide that binds to HLA DRB1*0101,
      DRB1*0401

<400> SEQUENCE: 2495

Pro Lys Tyr Val Lys Gln Asn Thr Leu Lys Leu Ala Thr
1               5                   10

<210> SEQ ID NO 2496
<211> LENGTH: 12
<212> TYPE: PRT
<213> ORGANISM: Artificial Sequence
```

```
<220> FEATURE:
<223> OTHER INFORMATION: Standard peptide that binds to HLA DRB1*0301

<400> SEQUENCE: 2496

Tyr Lys Thr Ile Ala Phe Asp Glu Glu Ala Arg Arg
1               5                   10

<210> SEQ ID NO 2497
<211> LENGTH: 14
<212> TYPE: PRT
<213> ORGANISM: Artificial Sequence
<220> FEATURE:
<223> OTHER INFORMATION: Standard peptide that binds to HLA DRB1*0404,
      DRB1*0405

<400> SEQUENCE: 2497

Tyr Ala Arg Phe Gln Ser Gln Thr Thr Leu Lys Gln Lys Thr
1               5                   10

<210> SEQ ID NO 2498
<211> LENGTH: 14
<212> TYPE: PRT
<213> ORGANISM: Artificial Sequence
<220> FEATURE:
<223> OTHER INFORMATION: Standard peptide that binds to HLA DRB1*0701,
      DRB1*0802, DRB1*0803, DRB1*0901, DRB1*1101

<400> SEQUENCE: 2498

Gln Tyr Ile Lys Ala Asn Ser Lys Phe Ile Gly Ile Thr Glu
1               5                   10

<210> SEQ ID NO 2499
<211> LENGTH: 15
<212> TYPE: PRT
<213> ORGANISM: Artificial Sequence
<220> FEATURE:
<223> OTHER INFORMATION: Standard peptide that binds to HLA DRB1*1201

<400> SEQUENCE: 2499

Glu Ala Leu Ile His Gln Leu Lys Ile Asn Pro Tyr Val Leu Ser
1               5                   10                  15

<210> SEQ ID NO 2500
<211> LENGTH: 14
<212> TYPE: PRT
<213> ORGANISM: Artificial Sequence
<220> FEATURE:
<223> OTHER INFORMATION: Standard peptide that binds to HLA DRB1*1302

<400> SEQUENCE: 2500

Gln Tyr Ile Lys Ala Asn Ala Lys Phe Ile Gly Ile Thr Glu
1               5                   10

<210> SEQ ID NO 2501
<211> LENGTH: 24
<212> TYPE: PRT
<213> ORGANISM: Artificial Sequence
<220> FEATURE:
<223> OTHER INFORMATION: Standard peptide that binds to HLA DRB1*1501

<400> SEQUENCE: 2501

Gly Arg Thr Gln Asp Glu Asn Pro Val Val His Phe Phe Lys Asn Ile
1               5                   10                  15

Val Thr Pro Arg Thr Pro Pro Pro
            20
```

<210> SEQ ID NO 2502
<211> LENGTH: 13
<212> TYPE: PRT
<213> ORGANISM: Artificial Sequence
<220> FEATURE:
<223> OTHER INFORMATION: Standard peptide that binds to HLA DRB3*0101

<400> SEQUENCE: 2502

Asn Gly Gln Ile Gly Asn Asp Pro Asn Arg Asp Ile Leu
1               5                   10

<210> SEQ ID NO 2503
<211> LENGTH: 14
<212> TYPE: PRT
<213> ORGANISM: Artificial Sequence
<220> FEATURE:
<223> OTHER INFORMATION: Standard peptide that binds to HLA DRB4*0101

<400> SEQUENCE: 2503

Tyr Ala Arg Phe Gln Ser Gln Thr Thr Leu Lys Gln Lys Thr
1               5                   10

<210> SEQ ID NO 2504
<211> LENGTH: 14
<212> TYPE: PRT
<213> ORGANISM: Artificial Sequence
<220> FEATURE:
<223> OTHER INFORMATION: Standard peptide that binds to HLA DRB5*0101

<400> SEQUENCE: 2504

Gln Tyr Ile Lys Ala Asn Ser Lys Phe Ile Gly Ile Thr Glu
1               5                   10

<210> SEQ ID NO 2505
<211> LENGTH: 9
<212> TYPE: PRT
<213> ORGANISM: Orthohepadnaviridae hepatitis B virus

<400> SEQUENCE: 2505

Ile Pro Ile Pro Ser Ser Trp Ala Phe
1               5

<210> SEQ ID NO 2506
<211> LENGTH: 9
<212> TYPE: PRT
<213> ORGANISM: Artificial Sequence
<220> FEATURE:
<223> OTHER INFORMATION: HBV ENV 313 substitution peptide

<400> SEQUENCE: 2506

Phe Pro Ile Pro Ser Ser Trp Ala Phe
1               5

<210> SEQ ID NO 2507
<211> LENGTH: 9
<212> TYPE: PRT
<213> ORGANISM: Artificial Sequence
<220> FEATURE:
<223> OTHER INFORMATION: HBV ENV 313 substitution peptide

<400> SEQUENCE: 2507

Ile Pro Ile Pro Ser Ser Trp Ala Ile
1               5

<210> SEQ ID NO 2508
<211> LENGTH: 9
<212> TYPE: PRT

<213> ORGANISM: Orthohepadnaviridae hepatitis B virus

<400> SEQUENCE: 2508

Phe Pro His Cys Leu Ala Phe Ser Tyr
1               5

<210> SEQ ID NO 2509
<211> LENGTH: 9
<212> TYPE: PRT
<213> ORGANISM: Artificial Sequence
<220> FEATURE:
<223> OTHER INFORMATION: HBV POL 541 substitution peptide

<400> SEQUENCE: 2509

Phe Pro His Cys Leu Ala Phe Ala Leu
1               5

<210> SEQ ID NO 2510
<211> LENGTH: 9
<212> TYPE: PRT
<213> ORGANISM: Artificial Sequence
<220> FEATURE:
<223> OTHER INFORMATION: HBV POL 541 substitution peptide

<400> SEQUENCE: 2510

Phe Pro His Cys Leu Ala Phe Ser Leu
1               5

<210> SEQ ID NO 2511
<211> LENGTH: 9
<212> TYPE: PRT
<213> ORGANISM: Artificial Sequence
<220> FEATURE:
<223> OTHER INFORMATION: HBV POL 541 substitution peptide

<400> SEQUENCE: 2511

Phe Pro Phe Cys Leu Ala Phe Ser Tyr
1               5

<210> SEQ ID NO 2512
<211> LENGTH: 9
<212> TYPE: PRT
<213> ORGANISM: Artificial Sequence
<220> FEATURE:
<223> OTHER INFORMATION: HBV POL 541 substitution peptide

<400> SEQUENCE: 2512

Phe Pro His Cys Leu Ala Phe Ser Ile
1               5

<210> SEQ ID NO 2513
<211> LENGTH: 9
<212> TYPE: PRT
<213> ORGANISM: Artificial Sequence
<220> FEATURE:
<223> OTHER INFORMATION: HBV POL 541 substitution peptide

<400> SEQUENCE: 2513

Phe Pro His Cys Leu Ala Phe Ser Ala
1               5

<210> SEQ ID NO 2514
<211> LENGTH: 9
<212> TYPE: PRT
<213> ORGANISM: Orthohepadnaviridae hepatitis C virus

<400> SEQUENCE: 2514

```
Leu Pro Gly Cys Ser Phe Ser Ile Phe
 1               5
```

```
<210> SEQ ID NO 2515
<211> LENGTH: 9
<212> TYPE: PRT
<213> ORGANISM: Artificial Sequence
<220> FEATURE:
<223> OTHER INFORMATION: HCV Core 168 substitution peptide

<400> SEQUENCE: 2515

Phe Pro Gly Cys Ser Phe Ser Ile Phe
 1               5
```

```
<210> SEQ ID NO 2516
<211> LENGTH: 9
<212> TYPE: PRT
<213> ORGANISM: Homo sapiens

<400> SEQUENCE: 2516

Val Pro Ile Ser His Leu Tyr Ile Leu
 1               5
```

```
<210> SEQ ID NO 2517
<211> LENGTH: 9
<212> TYPE: PRT
<213> ORGANISM: Artificial Sequence
<220> FEATURE:
<223> OTHER INFORMATION: MAGE2 170 substitution peptide

<400> SEQUENCE: 2517

Phe Pro Ile Ser His Leu Tyr Ile Leu
 1               5
```

```
<210> SEQ ID NO 2518
<211> LENGTH: 9
<212> TYPE: PRT
<213> ORGANISM: Homo sapiens

<400> SEQUENCE: 2518

Met Pro Lys Ala Gly Leu Leu Ile Ile
 1               5
```

```
<210> SEQ ID NO 2519
<211> LENGTH: 9
<212> TYPE: PRT
<213> ORGANISM: Artificial Sequence
<220> FEATURE:
<223> OTHER INFORMATION: MAGE3 196 substitution peptide

<400> SEQUENCE: 2519

Phe Pro Lys Ala Gly Leu Leu Ile Ile
 1               5
```

```
<210> SEQ ID NO 2520
<211> LENGTH: 9
<212> TYPE: PRT
<213> ORGANISM: Artificial Sequence
<220> FEATURE:
<223> OTHER INFORMATION: MAGE3 196 substitution peptide

<400> SEQUENCE: 2520

Met Pro Phe Ala Gly Leu Leu Ile Ile
 1               5
```

```
<210> SEQ ID NO 2521
<211> LENGTH: 10
<212> TYPE: PRT
<213> ORGANISM: Orthohepadnaviridae hepatitis B virus

<400> SEQUENCE: 2521

Phe Leu Pro Ser Asp Phe Phe Pro Ser Val
1               5                   10

<210> SEQ ID NO 2522
<211> LENGTH: 9
<212> TYPE: PRT
<213> ORGANISM: Orthohepadnaviridae hepatitis B virus

<400> SEQUENCE: 2522

Phe Leu Leu Thr Arg Ile Leu Thr Ile
1               5

<210> SEQ ID NO 2523
<211> LENGTH: 9
<212> TYPE: PRT
<213> ORGANISM: Orthohepadnaviridae hepatitis B virus

<400> SEQUENCE: 2523

Ala Leu Met Pro Leu Tyr Ala Cys Ile
1               5

<210> SEQ ID NO 2524
<211> LENGTH: 9
<212> TYPE: PRT
<213> ORGANISM: Orthohepadnaviridae hepatitis B virus

<400> SEQUENCE: 2524

Trp Leu Ser Leu Leu Val Pro Phe Val
1               5

<210> SEQ ID NO 2525
<211> LENGTH: 9
<212> TYPE: PRT
<213> ORGANISM: Orthohepadnaviridae hepatitis B virus

<400> SEQUENCE: 2525

Tyr Met Asp Asp Val Val Leu Gly Ala
1               5

<210> SEQ ID NO 2526
<211> LENGTH: 9
<212> TYPE: PRT
<213> ORGANISM: Orthohepadnaviridae hepatitis B virus

<400> SEQUENCE: 2526

Gly Leu Ser Arg Tyr Val Ala Arg Leu
1               5

<210> SEQ ID NO 2527
<211> LENGTH: 9
<212> TYPE: PRT
<213> ORGANISM: Orthohepadnaviridae hepatitis B virus

<400> SEQUENCE: 2527

Phe Leu Leu Ser Leu Gly Ile His Leu
1               5

<210> SEQ ID NO 2528
<211> LENGTH: 10
```

```
<212> TYPE: PRT
<213> ORGANISM: Orthohepadnaviridae hepatitis B virus

<400> SEQUENCE: 2528

Leu Leu Pro Ile Phe Phe Cys Leu Trp Val
1               5                   10

<210> SEQ ID NO 2529
<211> LENGTH: 10
<212> TYPE: PRT
<213> ORGANISM: Orthohepadnaviridae hepatitis B virus

<400> SEQUENCE: 2529

Leu Leu Val Pro Phe Val Gln Trp Phe Val
1               5                   10

<210> SEQ ID NO 2530
<211> LENGTH: 11
<212> TYPE: PRT
<213> ORGANISM: Orthohepadnaviridae hepatitis B virus

<400> SEQUENCE: 2530

His Thr Leu Trp Lys Ala Gly Ile Leu Tyr Lys
1               5                   10

<210> SEQ ID NO 2531
<211> LENGTH: 11
<212> TYPE: PRT
<213> ORGANISM: Orthohepadnaviridae hepatitis B virus

<400> SEQUENCE: 2531

Ser Thr Leu Pro Glu Thr Thr Val Val Arg Arg
1               5                   10

<210> SEQ ID NO 2532
<211> LENGTH: 9
<212> TYPE: PRT
<213> ORGANISM: Orthohepadnaviridae hepatitis B virus

<400> SEQUENCE: 2532

Asn Val Ser Ile Pro Trp Thr His Lys
1               5

<210> SEQ ID NO 2533
<211> LENGTH: 10
<212> TYPE: PRT
<213> ORGANISM: Orthohepadnaviridae hepatitis B virus

<400> SEQUENCE: 2533

Leu Val Val Asp Phe Ser Gln Phe Ser Arg
1               5                   10

<210> SEQ ID NO 2534
<211> LENGTH: 10
<212> TYPE: PRT
<213> ORGANISM: Orthohepadnaviridae hepatitis B virus

<400> SEQUENCE: 2534

Gln Ala Phe Thr Phe Ser Pro Thr Tyr Lys
1               5                   10

<210> SEQ ID NO 2535
<211> LENGTH: 9
<212> TYPE: PRT
<213> ORGANISM: Orthohepadnaviridae hepatitis B virus
```

```
<400> SEQUENCE: 2535

Ser Ala Ile Cys Ser Val Val Arg Arg
1               5

<210> SEQ ID NO 2536
<211> LENGTH: 9
<212> TYPE: PRT
<213> ORGANISM: Orthohepadnaviridae hepatitis B virus

<400> SEQUENCE: 2536

Lys Val Gly Asn Phe Thr Gly Leu Tyr
1               5

<210> SEQ ID NO 2537
<211> LENGTH: 10
<212> TYPE: PRT
<213> ORGANISM: Orthohepadnaviridae hepatitis B virus

<400> SEQUENCE: 2537

Phe Pro His Cys Leu Ala Phe Ser Tyr Met
1               5                   10

<210> SEQ ID NO 2538
<211> LENGTH: 9
<212> TYPE: PRT
<213> ORGANISM: Orthohepadnaviridae hepatitis B virus

<400> SEQUENCE: 2538

Leu Pro Ser Asp Phe Phe Pro Ser Val
1               5

<210> SEQ ID NO 2539
<211> LENGTH: 9
<212> TYPE: PRT
<213> ORGANISM: Orthohepadnaviridae hepatitis B virus

<400> SEQUENCE: 2539

Ile Pro Ile Pro Ser Ser Trp Ala Phe
1               5

<210> SEQ ID NO 2540
<211> LENGTH: 9
<212> TYPE: PRT
<213> ORGANISM: Orthohepadnaviridae hepatitis B virus

<400> SEQUENCE: 2540

His Pro Ala Ala Met Pro His Leu Leu
1               5

<210> SEQ ID NO 2541
<211> LENGTH: 11
<212> TYPE: PRT
<213> ORGANISM: Orthohepadnaviridae hepatitis B virus

<400> SEQUENCE: 2541

Tyr Pro Ala Leu Met Pro Leu Tyr Ala Cys Ile
1               5                   10

<210> SEQ ID NO 2542
<211> LENGTH: 10
<212> TYPE: PRT
<213> ORGANISM: Orthohepadnaviridae hepatitis B virus

<400> SEQUENCE: 2542
```

Thr Pro Ala Arg Val Thr Gly Gly Val Phe
1               5                   10

<210> SEQ ID NO 2543
<211> LENGTH: 10
<212> TYPE: PRT
<213> ORGANISM: Orthohepadnaviridae hepatitis B virus

<400> SEQUENCE: 2543

Asp Leu Leu Asp Thr Ala Ser Ala Leu Tyr
1               5                   10

<210> SEQ ID NO 2544
<211> LENGTH: 10
<212> TYPE: PRT
<213> ORGANISM: Orthohepadnaviridae hepatitis B virus

<400> SEQUENCE: 2544

Leu Ser Leu Asp Val Ser Ala Ala Phe Tyr
1               5                   10

<210> SEQ ID NO 2545
<211> LENGTH: 11
<212> TYPE: PRT
<213> ORGANISM: Orthohepadnaviridae hepatitis B virus

<400> SEQUENCE: 2545

Trp Met Met Trp Tyr Trp Gly Pro Ser Leu Tyr
1               5                   10

<210> SEQ ID NO 2546
<211> LENGTH: 10
<212> TYPE: PRT
<213> ORGANISM: Orthohepadnaviridae hepatitis B virus

<400> SEQUENCE: 2546

Arg Trp Met Cys Leu Arg Arg Phe Ile Ile
1               5                   10

<210> SEQ ID NO 2547
<211> LENGTH: 9
<212> TYPE: PRT
<213> ORGANISM: Orthohepadnaviridae hepatitis B virus

<400> SEQUENCE: 2547

Ser Trp Leu Ser Leu Leu Val Pro Phe
1               5

<210> SEQ ID NO 2548
<211> LENGTH: 9
<212> TYPE: PRT
<213> ORGANISM: Orthohepadnaviridae hepatitis B virus

<400> SEQUENCE: 2548

Ser Trp Trp Thr Ser Leu Asn Phe Leu
1               5

<210> SEQ ID NO 2549
<211> LENGTH: 10
<212> TYPE: PRT
<213> ORGANISM: Orthohepadnaviridae hepatitis B virus

<400> SEQUENCE: 2549

Glu Tyr Leu Val Ser Phe Gly Val Trp Ile

-continued

```
                1               5                  10

<210> SEQ ID NO 2550
<211> LENGTH: 9
<212> TYPE: PRT
<213> ORGANISM: Orthohepadnaviridae hepatitis B virus

<400> SEQUENCE: 2550

Ala Tyr Arg Pro Pro Asn Ala Pro Ile
1               5

<210> SEQ ID NO 2551
<211> LENGTH: 9
<212> TYPE: PRT
<213> ORGANISM: Orthohepadnaviridae hepatitis B virus

<400> SEQUENCE: 2551

Trp Phe His Ile Ser Cys Leu Thr Phe
1               5

<210> SEQ ID NO 2552
<211> LENGTH: 10
<212> TYPE: PRT
<213> ORGANISM: Orthohepadnaviridae hepatitis B virus

<400> SEQUENCE: 2552

Ser Trp Pro Lys Phe Ala Val Pro Asn Leu
1               5                  10

<210> SEQ ID NO 2553
<211> LENGTH: 9
<212> TYPE: PRT
<213> ORGANISM: Orthohepadnaviridae hepatitis B virus

<400> SEQUENCE: 2553

Lys Tyr Thr Ser Phe Pro Trp Leu Leu
1               5

<210> SEQ ID NO 2554
<211> LENGTH: 10
<212> TYPE: PRT
<213> ORGANISM: Orthohepadnaviridae hepatitis B virus

<400> SEQUENCE: 2554

Leu Tyr Ser His Pro Ile Ile Leu Gly Phe
1               5                  10

<210> SEQ ID NO 2555
<211> LENGTH: 15
<212> TYPE: PRT
<213> ORGANISM: Orthohepadnaviridae hepatitis B virus

<400> SEQUENCE: 2555

Leu Gln Ser Leu Thr Asn Leu Leu Ser Ser Asn Leu Ser Trp Leu
1               5                  10                  15

<210> SEQ ID NO 2556
<211> LENGTH: 15
<212> TYPE: PRT
<213> ORGANISM: Orthohepadnaviridae hepatitis B virus

<400> SEQUENCE: 2556

Lys Gln Ala Phe Thr Phe Ser Pro Thr Tyr Lys Ala Phe Leu Cys
1               5                  10                  15
```

```
<210> SEQ ID NO 2557
<211> LENGTH: 15
<212> TYPE: PRT
<213> ORGANISM: Orthohepadnaviridae hepatitis B virus

<400> SEQUENCE: 2557

Ala Gly Phe Phe Leu Leu Thr Arg Ile Leu Thr Ile Pro Gln Ser
1               5                   10                  15

<210> SEQ ID NO 2558
<211> LENGTH: 15
<212> TYPE: PRT
<213> ORGANISM: Orthohepadnaviridae hepatitis B virus

<400> SEQUENCE: 2558

Gly Thr Ser Phe Val Tyr Val Pro Ser Ala Leu Asn Pro Ala Asp
1               5                   10                  15

<210> SEQ ID NO 2559
<211> LENGTH: 20
<212> TYPE: PRT
<213> ORGANISM: Orthohepadnaviridae hepatitis B virus

<400> SEQUENCE: 2559

Val Ser Phe Gly Val Trp Ile Arg Thr Pro Pro Ala Tyr Arg Pro Pro
1               5                   10                  15

Asn Ala Pro Ile
            20

<210> SEQ ID NO 2560
<211> LENGTH: 15
<212> TYPE: PRT
<213> ORGANISM: Orthohepadnaviridae hepatitis B virus

<400> SEQUENCE: 2560

Arg His Tyr Leu His Thr Leu Trp Lys Ala Gly Ile Leu Tyr Lys
1               5                   10                  15

<210> SEQ ID NO 2561
<211> LENGTH: 15
<212> TYPE: PRT
<213> ORGANISM: Orthohepadnaviridae hepatitis B virus

<400> SEQUENCE: 2561

Leu Val Pro Phe Val Gln Trp Phe Val Gly Leu Ser Pro Thr Val
1               5                   10                  15

<210> SEQ ID NO 2562
<211> LENGTH: 15
<212> TYPE: PRT
<213> ORGANISM: Orthohepadnaviridae hepatitis B virus

<400> SEQUENCE: 2562

Leu His Leu Tyr Ser His Pro Ile Ile Leu Gly Phe Arg Lys Ile
1               5                   10                  15

<210> SEQ ID NO 2563
<211> LENGTH: 15
<212> TYPE: PRT
<213> ORGANISM: Orthohepadnaviridae hepatitis B virus

<400> SEQUENCE: 2563

Pro Phe Leu Leu Ala Gln Phe Thr Ser Ala Ile Cys Ser Val Val
1               5                   10                  15
```

<210> SEQ ID NO 2564
<211> LENGTH: 15
<212> TYPE: PRT
<213> ORGANISM: Orthohepadnaviridae hepatitis B virus

<400> SEQUENCE: 2564

Lys Gln Cys Phe Arg Lys Leu Pro Val Asn Arg Pro Ile Asp Trp
1               5                   10                  15

<210> SEQ ID NO 2565
<211> LENGTH: 15
<212> TYPE: PRT
<213> ORGANISM: Orthohepadnaviridae hepatitis B virus

<400> SEQUENCE: 2565

Ala Ala Asn Trp Ile Leu Arg Gly Thr Ser Phe Val Tyr Val Pro
1               5                   10                  15

<210> SEQ ID NO 2566
<211> LENGTH: 20
<212> TYPE: PRT
<213> ORGANISM: Orthohepadnaviridae hepatitis B virus

<400> SEQUENCE: 2566

Pro His His Thr Ala Leu Arg Gln Ala Ile Leu Cys Trp Gly Glu Leu
1               5                   10                  15

Met Thr Leu Ala
            20

<210> SEQ ID NO 2567
<211> LENGTH: 15
<212> TYPE: PRT
<213> ORGANISM: Orthohepadnaviridae hepatitis B virus

<400> SEQUENCE: 2567

Leu Cys Gln Val Phe Ala Asp Ala Thr Pro Thr Gly Trp Gly Leu
1               5                   10                  15

<210> SEQ ID NO 2568
<211> LENGTH: 15
<212> TYPE: PRT
<213> ORGANISM: Orthohepadnaviridae hepatitis B virus

<400> SEQUENCE: 2568

Glu Ser Arg Leu Val Val Asp Phe Ser Gln Phe Ser Arg Gly Asn
1               5                   10                  15

<210> SEQ ID NO 2569
<211> LENGTH: 15
<212> TYPE: PRT
<213> ORGANISM: Orthohepadnaviridae hepatitis B virus

<400> SEQUENCE: 2569

Val Gly Pro Leu Thr Val Asn Glu Lys Arg Arg Leu Lys Leu Ile
1               5                   10                  15

<210> SEQ ID NO 2570
<211> LENGTH: 15
<212> TYPE: PRT
<213> ORGANISM: Orthohepadnaviridae hepatitis B virus

<400> SEQUENCE: 2570

Ser Ser Asn Leu Ser Trp Leu Ser Leu Asp Val Ser Ala Ala Phe

```
1               5                  10                  15
```

<210> SEQ ID NO 2571
<211> LENGTH: 15
<212> TYPE: PRT
<213> ORGANISM: Orthohepadnaviridae hepatitis B virus

<400> SEQUENCE: 2571

```
Asn Leu Ser Trp Leu Ser Leu Asp Val Ser Ala Ala Phe Tyr His
 1               5                  10                  15
```

<210> SEQ ID NO 2572
<211> LENGTH: 14
<212> TYPE: PRT
<213> ORGANISM: Clostridium tetani
<220> FEATURE:
<221> NAME/KEY: PEPTIDE
<222> LOCATION: (1)...(14)
<223> OTHER INFORMATION: tetanus toxoid positions 830-843

<400> SEQUENCE: 2572

```
Gln Tyr Ile Lys Ala Asn Ser Lys Phe Ile Gly Ile Thr Glu
 1               5                  10
```

<210> SEQ ID NO 2573
<211> LENGTH: 21
<212> TYPE: PRT
<213> ORGANISM: Plasmodium falciparum
<220> FEATURE:
<221> NAME/KEY: PEPTIDE
<222> LOCATION: (1)...(21)
<223> OTHER INFORMATION: CS protein positions 378-398

<400> SEQUENCE: 2573

```
Asp Ile Glu Lys Lys Ile Ala Lys Met Glu Lys Ala Ser Ser Val Phe
 1               5                  10                  15

Asn Val Val Asn Ser
                20
```

<210> SEQ ID NO 2574
<211> LENGTH: 16
<212> TYPE: PRT
<213> ORGANISM: Streptococcus sp.
<220> FEATURE:
<221> NAME/KEY: PEPTIDE
<222> LOCATION: (1)...(16)
<223> OTHER INFORMATION: 18kd protein position 116

<400> SEQUENCE: 2574

```
Gly Ala Val Asp Ser Ile Leu Gly Gly Val Ala Thr Tyr Gly Ala Ala
 1               5                  10                  15
```

<210> SEQ ID NO 2575
<211> LENGTH: 13
<212> TYPE: PRT
<213> ORGANISM: Artificial Sequence
<220> FEATURE:
<223> OTHER INFORMATION: pan-DR binding epitope peptide
<220> FEATURE:
<221> NAME/KEY: MOD_RES
<222> LOCATION: 3
<223> OTHER INFORMATION: Xaa=cyclohexylalanine, phenylalanine, or
      tyrosine

<400> SEQUENCE: 2575

```
Ala Lys Xaa Val Trp Ala Asn Thr Leu Lys Ala Ala Ala
 1               5                  10
```

```
<210> SEQ ID NO 2576
<211> LENGTH: 10
<212> TYPE: PRT
<213> ORGANISM: A3CON1 peptide

<400> SEQUENCE: 2576

Lys Val Phe Pro Tyr Ala Leu Ile Asn Lys
 1               5                  10

<210> SEQ ID NO 2577
<211> LENGTH: 11
<212> TYPE: PRT
<213> ORGANISM: Artificial Sequence
<220> FEATURE:
<223> OTHER INFORMATION: T7Y analogue of HBVc 141-151

<400> SEQUENCE: 2577

Ser Thr Leu Pro Glu Thr Tyr Val Val Arg Arg
 1               5                  10

<210> SEQ ID NO 2578
<211> LENGTH: 9
<212> TYPE: PRT
<213> ORGANISM: Artificial Sequence
<220> FEATURE:
<223> OTHER INFORMATION: DR7 preferred motif
<220> FEATURE:
<221> NAME/KEY: MISC_FEATURE
<222> LOCATION: 1
<223> OTHER INFORMATION: Xaa=Met, Phe, Leu, Ile, Val, Trp or Tyr
<220> FEATURE:
<221> NAME/KEY: MISC_FEATURE
<222> LOCATION: 5
<223> OTHER INFORMATION: Xaa=Any amino acid
<220> FEATURE:
<221> NAME/KEY: MISC_FEATURE
<222> LOCATION: 6
<223> OTHER INFORMATION: Xaa=Ile, Val, Met, Ser, Ala, Cys, Thr, Pro, Leu
<220> FEATURE:
<221> NAME/KEY: MISC_FEATURE
<222> LOCATION: 8
<223> OTHER INFORMATION: Xaa=Any amino acid
<220> FEATURE:
<221> NAME/KEY: MISC_FEATURE
<222> LOCATION: 9
<223> OTHER INFORMATION: Xaa=Ile or Val

<400> SEQUENCE: 2578

Xaa Met Trp Ala Xaa Xaa Met Xaa Xaa
 1               5

<210> SEQ ID NO 2579
<211> LENGTH: 9
<212> TYPE: PRT
<213> ORGANISM: Artificial Sequence
<220> FEATURE:
<223> OTHER INFORMATION: DR7 deleterious motif
<220> FEATURE:
<221> NAME/KEY: MISC_FEATURE
<222> LOCATION: 1
<223> OTHER INFORMATION: Xaa=Any amino acid
<220> FEATURE:
<221> NAME/KEY: MISC_FEATURE
<222> LOCATION: 3
<223> OTHER INFORMATION: Xaa=Any amino acid
<220> FEATURE:
<221> NAME/KEY: MISC_FEATURE
<222> LOCATION: 5
<223> OTHER INFORMATION: Xaa=Any amino acid
<220> FEATURE:
<221> NAME/KEY: MISC_FEATURE
<222> LOCATION: 6
```

```
<223> OTHER INFORMATION: Xaa=Any amino acid
<220> FEATURE:
<221> NAME/KEY: MISC_FEATURE
<222> LOCATION: 7
<223> OTHER INFORMATION: Xaa=Gly, Arg or Asp

<400> SEQUENCE: 2579

Xaa Cys Xaa Gly Xaa Xaa Xaa Asn Gly
 1               5
```

INDUCING CELLULAR IMMUNE RESPONSES TO HEPATITIS B VIRUS USING PEPTIDE COMPOSITIONS

CROSS-REFERENCES TO RELATED APPLICATIONS

This application is divisional of U.S. application Ser. No. 09/239,043, now U.S. Pat. No. 6,689,363 filed Jan. 27, 1999, which is herein incorporated by reference. This application is related to U.S. Ser. No. 08/820,360 filed Mar. 12, 1997 and now abandoned, which claims the benefit of U.S. Provisional Application No. 60/013,363 filed Mar. 13, 1996 and now abandoned. The present application is also related to U.S. Ser. No. 09/189,702 filed Nov. 10, 1998, which is a CIP of U.S. Ser. No. 08/205,713 filed Mar. 4, 1994 and now abandoned, which is a CIP of Ser. No. 08/159,184 filed Nov. 29, 1993 and now abandoned, which is a CIP of 08/073,205 filed Jun. 4, 1993 and now abandoned, which is a CIP of Ser. No. 08/027,146 filed Mar. 5, 1993 and now abandoned. The present application is also related to U.S. Ser. No. 08/197,484, now U.S. Pat. No. 6,419,931, abandoned U.S. Ser. No. 08/464,234, U.S. Ser. No. 08/464,496, now U.S. Pat. No. 6,322,789, abandoned U.S. Ser. No. 08/464,031, abandoned U.S. Ser. No. 08/464,433, and abandoned U.S. Ser. No. 08/461,603, which is a continuation of abandoned U.S. Ser. No. 07/935,811, which is a CIP of abandoned U.S. Ser. No. 07/874,491, which is a CIP of abandoned U.S. Ser. No. 07/827,682, which is a CIP of abandoned 07/749,568. The present application is also related to U.S. patent application Ser. No. entitled "Peptides and Methods for Creating Synthetic Peptides with Modulated Binding Affinity for HLA Molecules", filed Jan. 6, 1999, which is a CIP of abandoned U.S. Ser. No. 08/815,396, which is a CIP of abandoned U.S. Ser. No. 60/013,113. Furthermore, the present application is related to abandoned U.S. Ser. No. 09/017,735, which is a CIP of abandoned U.S. Ser. No. 08/589,108; abandoned U.S. Ser. No. 08/753,622, abandoned U.S. Ser. No. 08/822,382, abandoned U.S. Ser. No. 60/013,980, abandoned U.S. Ser. No. 08/454,033, abandoned U.S. Ser. No. 09/116,424, abandoned U.S. Ser. No. 08/205,713, and abandoned U.S. Ser. No. 08/349,177, which is a CIP of abandoned U.S. Ser. No. 08/159,184, which is a CIP of abandoned U.S. Ser. No. 08/073,205, which is a CIP of abandoned U.S. Ser. No. 08/027,146. The present application is also related to abandoned U.S. Ser. No. 09/017,524, abandoned U.S. Ser. No. 08/821,739, abandoned U.S. Ser. No. 60/013,833, abandoned U.S. Ser. No. 08/758,409, abandoned U.S. Ser. No. 08/589,107, abandoned U.S. Ser. No. 08/451,913, U.S. Ser. No. 08/186,266, now U.S. Pat. No. 5,662,907, abandoned U.S. Ser. No. 09/116,061, and abandoned U.S. Ser. No. 08/347,610, which is a CIP of U.S. Ser. No. 08/159,339, now U.S. Pat. No. 6,037,135, which is a CIP of abandoned U.S. Ser. No. 08/103,396, which is a CIP of abandoned U.S. Ser. No. 08/027,746, which is a CIP of abandoned U.S. Ser. No. 07/926,666. The present application is also related to abandoned U.S. Ser. No. 09/017,743, abandoned U.S. Ser. No. 08/753,615; U.S. Ser. No. abandoned 08/590,298, abandoned U.S. Ser. No. 09/115,400, and abandoned U.S. Ser. No. 08/452,843, which is a CIP of abandoned U.S. Ser. No. 08/344,824, which is a CIP of abandoned U.S. Ser. No. 08/278,634. The present application is also related to provisional U.S. Ser. No. 60/087,192 and U.S. Ser. No. 09/009,953, now U.S. Pat. No. 6,413,517, which is a CIP of abandoned U.S. Ser. No. 60/036,713 and abandoned U.S. Ser. No. 60/037,432. In addition, the present application is related to abandoned U.S. Ser. No. 09/098,584 and to Provisional U.S. patent application entitled "Identification of Broadly Reactive HLA Restricted T Cell Epitopes", filed of even date herewith. All of the above applications are incorporated herein by reference.

FEDERALLY SPONSORED RESEARCH AND DEVELOPMENT

This invention was funded, in part, by the United States government under grants with the National Institutes of Health. The U.S. government has certain rights in this invention.

INDEX

I. Background of the Invention
II. Summary of the Invention
III. Brief Description of the Figures
IV. Detailed Description of the Invention
   A. Definitions
   B. Stimulation of CTL and HTL responses against HBV
   C. Immune Response Stimulating Peptides
      1. Binding Affinity of the Peptides for HLA Molecules
      2. Peptide Binding Motifs and Supermotifs
         a) HLA-A1 supermotif
         b) HLA-A2 supermotif
         c) HLA-A3 supermotif
         d) HLA-A24 supermotif
         e) HLA-B7 supermotif
         f) HLA-B27 supermotif
         g) HLA-B44 supermotif
         h) HLA-B58 supermotif
         i) HLA-B62 supermotif
         j) HLA-A1 motif
         k) HLA-A3 motif
         l) HLA-A11 motif
         m) HLA-A24 motif
         n) HLA-A2.1 motif
         o) HLA-DR-1-4-7 supermotif
         p) HLA-DR3 motifs
      3. Enhancing Population Coverage of the Vaccine
   D. Immune Response Stimulating Peptide Analogs
   E. Computer Screening of Protein Sequences from Disease-Related Antigens for Supermotif or Motif Containing Peptides
   F. Assays to Detect T-Cell Responses
   G. Preparation of Peptides
   H. Use of Peptide Epitopes for Evaluating Immune Responses
   I. Vaccine Compositions
      1. Minigene Vaccines
      2. Combinations with Helper Peptides
   J. Administration of Vaccines for Therapeutic or Prophylactic Purposes
   K. Kits
V. Examples

I. BACKGROUND OF THE INVENTION

Chronic infection by hepatitis B virus (HBV) affects at least 5% of the world's population and is a major cause of cirrhosis and hepatocellular carcinoma (Hoofnagle, J., *N. Engl. J. Med.* 323:337, 1990; Fields, B. and Knipe, D., In: *Fields Virology* 2:2137, 1990). The World Health Organization lists hepatitis B as a leading cause of death worldwide, close behind chronic pulmonary disease, and more prevalent than AIDS. Chronic HBV infection can range from an asymptomatic carrier state to continuous hepatocellular necrosis and inflammation, and can lead to hepatocellular carcinoma.

The immune response to HBV is believed to play an important role in controlling hepatitis B infection. A variety of humoral and cellular responses to different regions of the HBV nucleocapsid core and surface antigens have been identified. T cell mediated immunity, particularly involving class I human leukocyte antigen-restricted cytotoxic T lymphocytes (CTL), is believed to be crucial in combatting established HBV infection.

Class I human leukocyte antigen (HLA) molecules are expressed on the surface of almost all nucleated cells. CTL recognize peptide fragments, derived from intracellular processing of various antigens, in the form of a complex with class I HLA molecules. This recognition event then results in the destruction of the cell bearing the HLA-peptide complex directly or the activation of non-destructive mechanisms e.g., the production of interferon, that inhibit viral replication.

Several studies have emphasized the association between self-limiting acute hepatitis and multispecific CTL responses (Penna, A. et al., *J. Exp. Med.* 174:1565, 1991; Nayersina, R. et al., *J. Immunol.* 150:4659, 1993). Spontaneous and interferon-related clearance of chronic HBV infection is also associated with the resurgence of a vigorous CTL response (Guidotti, L. G. et al., *Proc. Natl. Acad. Sci. USA* 91:3764, 1994). In all such cases the CTL responses are polyclonal, and specific for multiple viral proteins including the HBV envelope, core and polymerase antigens. By contrast, in patients with chronic hepatitis, the CTL activity is usually absent or weak, and antigenically restricted.

The crucial role of CTL in resolution of HBV infection has been further underscored by studies using HBV transgenic mice. Adoptive transfer of HBV-specific CTL into mice transgenic for the HBV genome resulted in suppression of virus replication. This effect was primarily mediated by a non-lytic, lymphokine-based mechanism (Guidotti, L. G. et al., *Proc. Natl. Acad. Sci. USA* 91:3764, 1994; Guidotti, L. G., Guilhot, S., and Chisari, F. V. *J. Virol.* 68:1265, 1994; Guidotti, L. G. et al., *J. Virol.* 69:6158, 1995; Gilles, P. N., Fey, G., and Chisari, F. V., *J. Virol.* 66:3955, 1992).

As is the case for HLA class I restricted responses, HLA class II restricted T cell responses are usually detected in patients with acute hepatitis, and are absent or weak in patients with chronic infection (Chisari, F. V. and Ferrari, C., *Annu. Rev. Immunol.* 1':29, 1995). HLA Class II responses are tied to activation of helper T cells (IT Ls) Helper T lymphocytes, which recognize Class II HLA molecules, may directly contribute to the clearance of HBV infection through the secretion of cytokines which suppress viral replication (Franco, A. et al., *J. Immunol.* 159:2001, 1997). However, their primary role in disease resolution is believed to be mediated by inducing activation and expansion of virus-specific CTL and B cells.

In view of the heterogeneous immune response observed with HBV infection, induction of a multi-specific cellular immune response directed simultaneously against multiple epitopes appears to be important for the development of an efficacious vaccine against HBV. There is a need to establish vaccine embodiments that elicit immune responses that correspond to responses seen in patients that clear HBV infection. Epitope-based vaccines appear useful.

Upon development of appropriate technology, the use of epitope-based vaccines has several advantages over current vaccines. The epitopes for inclusion in such a vaccine are to be selected from conserved regions of viral or tumor-associated antigens, in order to reduce the likelihood of escape mutants. The advantage of an epitope-based approach over the use of whole antigens is that there is evidence that the immune response to whole antigens is directed largely toward variable regions of the antigen, allowing for immune escape due to mutations. Furthermore, immunosuppressive epitopes that may be present in whole antigens can be avoided with the use of epitope-based vaccines.

Additionally, with an epitope-based vaccine approach, there is an ability to combine selected epitopes (CTL and HTL) and additionally to modify the composition of the epitopes, achieving, for example, enhanced immunogenicity. Accordingly, the immune response can be modulated, as appropriate, for the target disease. Similar engineering of the response is not possible with traditional approaches.

Another major benefit of epitope-based immune-stimulating vaccines is their safety. The possible pathological side effects caused by infectious agents or whole protein antigens, which might have their own intrinsic biological activity, is eliminated.

An epitope-based vaccine also provides the ability to direct and focus an immune response to multiple selected antigens from the same pathogen. Thus, patient-by-patient variability in the immune response to a particular pathogen may be alleviated by inclusion of epitopes from multiple antigens from that pathogen in a vaccine composition. A "pathogen" may be an infectious agent or a tumor associated molecule.

However, one of the most formidable obstacles to the development of broadly efficacious epitope-based immunotherapeutics has been the extreme polymorphism of HLA molecules. To date, effective non-genetically biased coverage of a population has been a task of considerable complexity; such coverage has required that epitopes be used specific for HLA molecules corresponding to each individual HLA allele, therefore, impractically large numbers of epitopes would have to be used in order to cover ethnically diverse populations. There has existed a need to develop peptide epitopes that are bound by multiple HLA antigen molecules for use in epitope-based vaccines. The greater the number of HLA antigen molecules bound, the greater the breadth of population coverage by the vaccine.

Furthermore, as described herein in greater detail, a need has existed to modulate peptide binding properties, for example so that peptides that are able to bind to multiple HLA antigens do so with an affinity that will stimulate an immune response. Identification of epitopes restricted by more than one HLA allele at an affinity that correlates with immunogenicity is important to provide thorough population coverage, and to allow the elicitation of responses of sufficient vigor whereby the natural immune responses noted in self-limiting acute hepatitis, or of spontaneous clearance of chronic HBV infection is induced in a diverse segment of the population. Such a response can also target a broad array of epitopes. The technology disclosed herein provides for such favored immune responses.

The information provided in this section is intended to disclose the presently understood state of the art as of the filing date of the present application. Information is included in this section which was generated subsequent to the priority date of this application. Accordingly, background in this section is not intended, in any way, to delineate the priority date for the invention.

II. SUMMARY OF THE INVENTION

This invention applies our knowledge of the mechanisms by which antigen is recognized by T cells, for example, to develop epitope-based vaccines directed towards HBV. More specifically, this application communicates our discovery of specific epitope pharmaceutical compositions and methods of use in the prevention and treatment of HBV infection.

An embodiment of the present invention includes a peptide composition of less than 100 amino acid residues comprising a peptide epitope useful for inducing an immune response against hepatitis B virus (HBV) said epitope (a) having an amino acid sequence of about 8 to about 13 amino acid residues that have at least 65% identity with a native amino acid sequence for HBV, and, (b) binding to at least one MHC class I HLA allele with a dissociation constant of less than about 500 nM. Further, the peptide composition may comprise an amino acid sequence of at least 77% identity, or at least 100% identity with a native HBV amino acid sequence. In a preferred embodiment, the peptide is one of the peptides designated as being from the envelope, polymerase, protein X, or nucleocapsid core regions of HBV. Preferred peptides are described in Tables VI through XVII or XXI.

An additional embodiment of the present invention comprises a composition of less than 100 amino acid residues comprising a peptide epitope useful for inducing an immune response against hepatitis B virus (HBV) said peptide (a) having an amino acid sequence of about 8 to about 13 amino acid residues and (b) bearing one of the HLA supernotifs or motifs set out in Tables I and II. Furthermore, the composition may comprise a peptide wherein the peptide is one of those described in Tables VI through XVII or Table XXI which bear an HLA A1, A2, A3, A24, B7, B27, B44, B58, or B62 supermotif; or an HLA A1, A3, A11, A24, or A2.1 motif or an HLA A*3301, A*3101, A*6801, B*0702, B*3501, B51, B*5301, B*5401 motif.

In one embodiment of a peptide comprising an HLA A2.1 motif, the peptide does not bear an L or M at position 2 and V at the C-terminal position 9 of a 9 amino acid peptide.

An alternative embodiment of the invention comprises an analog of an HBV peptide of less than 100 amino acid residues in length that bears an HLA binding motif, the analog bearing the same HLA binding motif as the peptide but comprising at least one anchor residue that is different from that of the peptide. In a preferred embodiment, said peptide is an analog of a peptide described in Table VI through Table XVII bearing an HLA A1, A2, A3, A24, B7, B27, B44, B58, or B62 supermotif; or an HLA A1, A3, A11, A24, or A2.1 motif or A3301, A3101, A6801, B0702, B3501, B51, B5301, B5401 motif.

Embodiments of the invention further include a composition of less than 100 amino acid residues comprising a peptide epitope useful for inducing an immune response against hepatitis B virus (HBV) said peptide (a) having an amino acid sequence of about 9 to about 25 amino acid residues that have at least 65% identity with a native amino acid sequence for HBV and (b) binding to at least one MHC class II HLA allele with a dissociation constant of less than about 1000 nM. In a preferred embodiment, the composition comprises a peptide that has at least 77%, or, 100% identity with a native HBV amino acid sequence. Further, the composition may comprise a peptide wherein said peptide is one of those peptides described in Table XVIII or Table XIX.

The invention also includes a peptide composition of less than 100 amino acid residues, said composition comprising an epitope useful for inducing an immune response against hepatitis B virus (HBV) said epitope (a) having an amino acid sequence of about 10 to about 20 amino acids and (b) bearing one of the class II HLA motifs set out in Table III. In a preferred embodiment, said peptide is one of those peptides described in Table XVIII or XIX.

Additional embodiments of the invention include a composition that comprises an isolated nucleic acid sequence that encodes one of the peptides set out in Tables VI through XIX or XXI or XXIII.

Alternatively, an embodiment of the invention comprises a composition that comprises at least two peptides, at least one of said at least two peptides selected from Tables VI-XIX or XXI or XXIII. In a preferred embodiment, two or more of the at least two peptides are depicted in Tables VI-XIX or XXI or XXIII. The composition may further comprise at least one nucleic acid sequence. In a preferred embodiment each of said at least two peptides are encoded by a nucleic acid sequence, wherein each of the nucleic acid sequences are located on a single vector.

Embodiments of the invention additionally include a peptide composition of less than 100 amino acid residues, said composition comprising an epitope useful for inducing an immune response against HBV, said epitope having at least one of the amino acid sequences set out in Table XXIII.

An alternative modality for defining the peptides in accordance with the invention is to recite the physical properties, such as length; primary, secondary and/or tertiary structure; or charge, which are correlated with binding to a particular allele-specific HLA molecule or group of allele-specific HLA molecules. A further modality for defining peptides is to recite the physical properties of an HLA binding pocket, or properties shared by several allele-specific HLA binding pockets (e.g. pocket configuration and charge distribution) and reciting that the peptide fits and binds to said pocket or pockets.

An additional embodiment of the invention comprises a method for inducing a cytotoxic T cell response to HBV in a mammal comprising administering to said mammal at least one peptide from Tables VI to XIX or Table XXI.

Further embodiments of the invention include a vaccine for treating HBV infection that induces a protective immune response, wherein said vaccine comprises at least one peptide selected from Tables VI to Table XIX or Table XXI in a pharmaceutically acceptable carrier.

Also included as an embodiment of the invention is a vaccine for preventing HBV infection that induces a protective immune response, wherein said vaccine comprises at least one peptide selected from Tables VI to XIX or Table XXI in a pharmaceutically acceptable carrier.

The invention further includes an embodiment comprising a method for inducing a cytotoxic T cell response to HBV in a mammal, comprising administering to said mammal a nucleic acid sequence encoding a peptide selected from Tables VI to XIX or Table XXI.

A further embodiment of the invention comprises a kit for a vaccine for treating or preventing HBV infection, wherein the vaccine induces a protective immune response, said vaccine comprising at least one peptide selected from Tables VI to XIX or Table XXI in a pharmaceutically acceptable carrier and instructions for administration to a patient.

Lastly, the invention includes an embodiment comprising a method for monitoring immunogenic activity of a vaccine for HBV in a patient having a known HLA-type, the method comprising incubating a T lymphocyte sample from the patient with a peptide selected from Tables VI to XIX or Table XXI which binds the product of at least one HLA allele present in said patient, and detecting for the presence of a T lymphocyte that binds to the peptide. In a preferred embodiment, the peptide comprises a tetrameric complex.

As will be apparent from the discussion below, other methods and embodiments are also contemplated. Further, novel synthetic peptides produced by any of the methods described herein are also part of the invention.

III. BRIEF DESCRIPTION OF THE FIGURES

FIG. 1: FIG. 1 Illustrates the Position of Peptide Epitopes in Experimental Model Minigene Constructs

IV. DETAILED DESCRIPTION OF THE INVENTION

The peptides and corresponding nucleic acid compositions of the present invention are useful for stimulating an immune response to HBV either by stimulating the production of CTL or HTL responses. The peptides, which are derived directly or indirectly from native HBV amino acid sequences, are able to bind to HLA molecules and stimulate an immune response to HBV. The complete polyprotein sequence from HBV and its variants can be obtained from Genbank. Peptides can also be readily determined from sequence information that may subsequently be discovered for heretofore unknown variants of HBV as will be clear from the disclosure provided below.

The peptides of the invention have been identified in a number of ways, as will be discussed below. Further, analog peptides have been derived and the binding activity for HLA molecules modulated by modifying specific amino acid residues to create peptide analogs exhibiting altered immunogenicity. Further, the present invention provides compositions and combinations of compositions that enable epitope-based vaccines that are capable of interacting with multiple HLA antigens to provide broader population coverage than prior vaccines.

The invention can be better understood with reference to the following definitions:

IV.A. Definitions

"Cross-reactive binding" indicates that a peptide is bound by more than one HLA molecule; a synonym is degenerate binding.

A "cryptic epitope" elicits a response by immunization with an isolated peptide, but the response is not cross-reactive in vitro when intact whole protein which comprises the epitope is used as an antigen.

A "dominant epitope" is an epitope that induces an immune response upon immunization with a whole native antigen. (See, e.g., Sercarz, et al., *Annu. Rev. Immunol.* 11:729766 (1993)) Such a response is cross-reactive in vitro with an isolated peptide epitope.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vivo or in vitro, an epitope is the collective features of a molecule, such as primary, secondary and tertiary peptide structure, and charge, that together form a site recognized by an immunoglobulin, T cell receptor or HLA molecule.

As used herein, "high affinity" with respect to HLA class I molecules is defined as binding with an $IC_{50}$ (or $K_D$) of less than 50 nM. "Intermediate affinity" is binding with an $IC_{50}$ (or $K_D$) of between about 50 and about 500 nM. "High affinity" with respect to binding to HLA class II molecules is defined as binding with an $K_D$ of less than 100 nM. "Intermediate affinity" is binding with a $K_D$ of between about 100 and about 1000 nM. Assays for determining binding are described in detail in PCT publications WO 94/20127 and WO 94/03205. Alternatively, binding is expressed relative to a reference peptide. As a particular assay becomes more, or less, sensitive, the $IC_{50}$'s of the peptides tested may change somewhat. However, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide.

"Human Leukocyte Antigen" or "HLA" is a human class I or class II Major Histocompatibility Complex (MHC) protein (see, Stites, et al., IMMUNOLOGY, $8^{TH}$ ED., Lange Publishing, Los Altos, Calif. (1994).

An "HLA supertype or family", as used herein, describes sets of HLA molecules grouped on the basis of shared peptide-binding specificities. HLA class I molecules that share somewhat similar binding affinity for peptides bearing certain amino acid motifs We grouped into HLA supertypes. The terms HLA superfamily, HLA supertype family, and HLA xx-like supertype molecules (where xx denotes a particular HLA type) are synonyms.

Throughout this disclosure, results are expressed in terms of "$IC_{50}$'s." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithms or by manual alignment and visual inspection.

An "immunogenic peptide" or "peptide epitope" is a peptide which comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment.

"Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, Paul, FUNDAMENTAL IMMUNOLOGY, $3^{RD}$ ED., Raven Press, N.Y., 1993.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "negative binding residue" is an amino acid which if present at certain positions (typically not primary anchor positions) of peptide epitope results in decreased binding affinity of the peptide for the peptide's corresponding HLA molecule.

The term "peptide" is used interchangeably with "oligopeptide" in the present specification to designate a series of residues, typically L-amino acids, connected one to the other, typically by peptide bonds between the a-amino and carboxyl groups of adjacent amino acids. The preferred CTL-inducing oligopeptides of the invention are fewer than 25 residues in length, or less than 15 residues in length or 13 residues or less in length and usually consist of between about 8 and about 11 residues, preferably 9 or 10 residues. The preferred HTL-inducing oligopeptides are less than about 50 residues in length and usually consist of between about 6 and about 30 residues, more usually between about 12 and 25, and often between about 15 and 20 residues.

"Pharmaceutically acceptable" refers to a non-toxic, inert, and physiologically compatible composition.

A "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding grooves of an HLA molecule, with their side chains buried in specific pockets of the binding grooves themselves. In one embodiment, the primary anchor residues are located at position 2 (from the amino terminal position) and at the carboxyl terminal position of a 9 residue peptide in accordance with the invention. The primary anchor positions for each motif and supermotif are set forth in Table I. For example, analog peptides can be created by altering the presence or absence of particular residues in these primary anchor positions. Such analogs are used to finely modulate the binding affinity of a peptide comprising a particular motif or supermotif.

"Promiscuous binding" is where a distinct peptide is recognized by the same T cell clone in the context of various HLA molecules.

A "protective immune response" refers to a CTL and/or an HTL response to an antigen from an infectious agent or a tumor antigen from which an immunogenic peptide is derived, and thereby preventing or at least partially arresting disease symptoms or progression. The immune response may also include an antibody response which has been facilitated by the stimulation of helper T cells.

The term "residue" refers to an amino acid or amino acid mimetic incorporated into an oligopeptide by an amide bond or amide bond mimetic.

A "secondary anchor residue" is an amino acid at a position other than a primary anchor position in a peptide which may influence peptide binding. A secondary anchor residue occurs at a significantly higher frequency amongst bound peptides than would be expected by random distribution of amino acids at one position. The secondary anchor residues are said to occur at "secondary anchor positions." A secondary anchor residue can be identified as a residue which is present at a higher frequency among high affinity binding peptides, or a residue otherwise associated with high affinity binding. For example, analog peptides can be created by altering the presence or absence of particular residues in these secondary anchor positions. Such analogs are used to finely modulate the binding affinity of a peptide comprising a particular motif or supermotif.

A "subdominant epitope" is an epitope which evokes little or no response upon immunization with whole antigens which comprise the epitope, but for which a response can be obtained by immunization with an isolated peptide, and this response (unlike the case of cryptic epitopes) is detected when whole protein is used to recall the response in vitro or in vivo.

A "supermotif" is a peptide binding specificity shared by HLA molecules encoded by two or more HLA alleles. Thus, a preferably is recognized with high or intermediate affinity (as defined herein) by two or more HLA antigens.

"Synthetic peptide" refers to a peptide that is not naturally occurring, but is man-made using such methods as chemical synthesis or recombinant DNA technology.

The nomenclature used to describe peptide compounds follows the conventional practice wherein the amino group is presented to the left (the N-terminus) and the carboxyl group to the right (the C-terminus) of each amino acid residue. When amino acid residue positions are referred to in a peptide epitope they are numbered in an amino to carboxyl direction with position one being the position closest to the amino terminal. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G. Symbols for the amino acids are shown below.

| Single Letter Symbol | Three Letter Symbol | Amino Acids |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

IV.B. Stimulation of CTL and HTL Responses Against HBV

The mechanism by which T cells recognize antigens has been delineated during the past ten years. Based on our new understanding of the immune system we have generated efficacious peptide epitope vaccine compositions that can induce a therapeutic or prophylactic immune response to HBV infection in a broad population. For an understanding of the value and efficacy of the claimed compositions, a brief review of the technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317:359, 1985; Townsend, A., and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are described here and set forth in Tables I, II, and III (see also, e.g., Sette, A. and Grey, H. M, *Curr. Opin. Immunol.* 4:79, 1992; Sinigaglia, F. and Hammer, J., *Curr. Biol.* 6:52, 1994; Engelhard, V. H., *Curr. Opin. Immunol.* 6:13, 1994). Furthermore, x-ray crystallographic analysis of HLA-peptide complexes has revealed pockets within the peptide binding cleft of HLA molecules which accommodate allele-specific residues borne by peptide ligands; these residues in turn determine the HLA binding capacity of the peptides in which they are present (Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991).

Accordingly, the definition of class I and class II allele-specific HLA binding motifs or class I supermotifs allows identification of regions within a protein that have the potential of binding particular HLA antigens (see also e.g., Sette, A. and Grey, H. M., *Curr. Opin. Immunol.* 4:79, 1992; Sinigaglia, F. and Hammer, J., *Curr. Biol.* 6:52, 1994; Engelhard, V. H., *Curr. Opin. Immunol.* 6:13, 1994Kast, W. M. et al., *J. Immunol.*, 152:3904, 1994).

Furthermore, a variety of assays to detect and quantify the affinity of interaction between peptide and HLA have also been established (Sette, A. and Grey, H. M., *Curr. Opin. Immunol.* 4:79, 1992; Sinigaglia, F. and Hammer, J., *Curr. Biol.* 6:52, 1994; Engelhard, V. H., *Curr. Opin. Immunol.* 6:13, 1994).

We have found that the correlation of binding affinity with immunogenicity is an important factor to be considered when evaluating candidate peptides. Thus, by a combination of motif searches and HLA-peptide binding assays, candidates for epitope-based vaccines have been identified. After determining their binding affinity, additional confirmatory work can be performed to select, amongst these vaccine candidates, epitopes with desired characteristics in terms of antigenicity and immunogenicity. Various strategies can be utilized to evaluate immunogenicity, including:

1) Primary T cell cultures from normal individuals (Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998); This procedure involves the stimulation of PBL from normal subjects with a test peptide in the presence of antigen presenting cells in vitro over a period of several weeks. T cells specific for the peptide become activated during this time and are detected using a $^{51}$Cr-release assay involving peptide sensitized target cells.

2) Immunization of HLA transgenic mice (Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997); In this method, peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using a $^{51}$Cr-release assay involving peptide sensitized target cells and target cells expressing endogenously generated antigen.

3) Demonstration of recall T cell responses from immune individuals who have recovered from infection, and/or from chronically infected patients (Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). In applying this strategy, recall responses were detected by culturing PBL from subjects that had been naturally exposed to the antigen, for instance through infection, and thus had generated an immune response "naturally". PBL from subjects were cultured in vitro for 1-2 weeks in the presence of test peptide plus antigen presenting cells (APC) to allow activation of "memory" T cells, as compared to "naive" Tcells. At the end of the culture period, T cell activity is detected using assays for T cell activity including $^{51}$Cr release involving peptide-sensitized targets, T cell proliferation or lymphokine release.

The following describes the peptide epitopes and corresponding nucleic acids of the invention.

IV.C. Immune Response Stimulating Peptides

As indicated herein, the large degree of HLA polymorphism is an important factor to be taken into account with the epitope-based approach to vaccine development. To address this factor, epitope selection encompassing identification of peptides capable of binding at high or intermediate affinity to multiple HLA molecules is preferably utilized, most preferably these epitopes bind at high or intermediate affinity to two or more allele specific HLA molecules.

IV.C.1. Binding Affinity of the Peptides for HLA Molecules

CTL-inducing peptides of interest for vaccine compositions preferably include those that have a binding affinity for class I HLA molecules of less than 500 nM. HTL-inducing peptides preferably include those that have a binding affinity for class II HLA molecules of less than 1000 nM. For example, peptide binding is assessed by testing the capacity of a candidate peptide to bind to a purified HLA molecule in vitro. Peptides exhibiting high or intermediate affinity are then considered for further analysis. Selected peptides are tested on other members of the supertype family. In preferred embodiments, peptides that exhibit cross-reactive binding preferably are then used in cellular screening analyses. A peptide is considered to be an epitope if it possesses the molecular features that form the binding site for a particular immunoglobulin or T cell receptor protein.

As disclosed herein, high HLA binding affinity is correlated with greater immunogenicity. Greater immunogenicity can be manifested in several different ways. Immunogenicity corresponds to whether an immune response is elicited at all, and to the vigor of any particular response. For example, a peptide might elicit an immune response in a diverse array of the population, yet in no instance produce a vigorous response. In accordance with these principles, close to 90% of high binding peptides have been found to be immunogenic, as contrasted with about 50% of the peptides which bind with intermediate affinity. Moreover, higher binding affinity peptides leads to more vigorous immunogenic responses. As a result, less peptide is required to elicit a similar biological effect if a high affinity binding peptide is used. Thus, in preferred embodiments of the invention, high binding epitopes are particularly desired.

The relationship between binding affinity for HLA class I molecules and immunogenicity of discrete peptide epitopes on bound antigens has been determined for the first time in the art by the present inventors. The correlation between binding affinity and immunogenicity was analyzed in two different experimental approaches (Sette, et al., *J. Immunol.* 153:5586-5592, 1994). In the first approach, the immunogenicity of potential epitopes ranging in HLA binding affinity over a 10,000-fold range was analyzed in HLA-A*0201 transgenic mice. In the second approach, the antigenicity of approximately 100 different hepatitis B virus (HBV)-derived potential epitopes, all carrying A*0201 binding motifs, was assessed by using PBL (peripheral blood lymphocytes) of acute hepatitis patients. Pursuant to these approaches, it was determined that an affinity threshold of approximately 500 nM (preferably 500 nM or less) determines the capacity of a peptide epitope to elicit a CTL response. These data are true for class I binding affinity measurements for naturally processed peptides and for synthesized T cell epitopes. These data also indicate the important role of determinant selection in the shaping of T cell responses.

An affinity threshold associated with immunogenicity in the context of HLA class II DR molecules has also been delineated (Southwood et al. *J. Immunology* 160:3363-3373, 1998, and U.S. Ser. No. 60/087,192 filed May 29, 1998). In order to define a biologically significant threshold of DR binding affinity, a database of the binding affinities of 32 DR-restricted epitopes for their restricting element was compiled. In approximately half of the cases (15 of 32 epitopes), DR restriction was associated with high binding affinities, i.e. binding affinities of less than 100 nM. In the other half of the cases (16 of 32), DR restriction was associated with intermediate affinity (binding affinities in the 100-1000 nM range). In only one of 32 cases was DR restriction associated with an $IC_{50}$ of 1000 nM or greater. Thus, 1000 nM can be defined as an affinity threshold associated with immunogenicity in the context of DR molecules.

The binding affinity of peptides for HLA molecules can be determined as described in Example 1, below.

IV.C.2. Peptide Binding Motifs and Supermotifs

In the past few years evidence has accumulated to demonstrate that a large fraction of HLA class I, and possibly class II molecules can be classified into a relatively few supertypes characterized by largely overlapping peptide binding repertoires, and consensus structures of the main peptide binding pockets. Through the study of single amino acid substituted antigen analogs and the sequencing of endogenously bound, naturally processed peptides, critical residues required for allele-specific binding to HLA molecules have been identified. These motifs are relevant since they indicate peptides that have binding affinity for HLA molecules.

For HLA molecule pocket analyses, the residues comprising the B and F pockets of HLA class I molecules as described in crystallographic studies (Guo, H. C. et al., *Nature* 360:364, 1992; Saper, M. A., Bjorkman, P. J. and Wiley, D. C., *J. Mol. Biol.* 219:277, 1991; Madden, D. R., Garboczi, D. N. and Wiley, D. C., *Cell* 75:693, 1993), have been compiled from the database of Parham, et al. (Parham, P., Adams, E. J., and Arnett, K. L., *Immunol. Rev.* 143:141, 1995). In these analyses, residues 9, 45, 63, 66, 67, 70, and 99 were considered to make up the B pocket, and to determine the specificity for the residue in the second position of peptide ligands. Similarly, residues 77, 80, 81, and 116 were considered to determine the specificity of the F pocket, and to determine the specificity for the C-terminal residue of a peptide ligand bound by the HLA molecule.

Peptides of the present invention may also include epitopes that bind to MHC class II DR molecules. A significant difference between class I and class II HLA molecules is that, although a stringent size restriction exists for peptide binding to class I molecules, a greater degree of heterogeneity in both sizes and binding frame positions of the motif, relative to the N and C termini of the peptide, can be demonstrated for class II peptide ligands. This increased heterogeneity is due to the structure of the class II-binding groove which, unlike its class I counterpart, is open at both ends. Crystallographic analysis of DRB*0101-peptide complexes (see, e.g., Madden, D. R. *Ann. Rev. Immunol.* 13:587 (1995)) showed that the residues occupying position 1 and position 6 of peptides complexed with DRB*0101 engage two complementary pockets on the DRBa*0101 molecules, with the P1 position corresponding to the most crucial anchor residue and the deepest hydrophobic pocket. Other studies have also pointed to the P6 position as a crucial anchor residue for binding to various other DR molecules.

Thus, peptides of the present invention are identified by any one of several HLA-specific amino acid motifs. If the presence of the motif corresponds to the ability to bind several allele-specific LLA antigens it is referred to as a supermotif. The allele-specific HLA molecules that bind to peptides that possess a particular amino acid supermotif are collectively referred to as an HLA "supertype."

The peptide motifs and supermotifs described below provide guidance for the identification and use of peptides in accordance with the invention. Examples of peptide epitopes bearing the respective supermotif or motif are included in Tables as designated in the description of each motif or supermotif. The Tables include a binding affinity ratio listing for some of the peptide epitopes. The ratio may be converted to $IC_{50}$ by using the following formula: $IC_{50}$ of the standard peptide/ratio=$IC_{50}$ of the test peptide (i.e. the peptide epitope). The $IC_{50}$ values of standard peptides used to determine binding affinities for Class I peptides are shown in Table IV. The $IC_{50}$ values of standard peptides used to determine binding affinities for Class II peptides are shown in Table V. The peptides used as standards for the binding assay are examples of standards; alternative standard peptides can also be used when performing such an analysis.

To obtain the peptide epitope sequences listed in each Table, protein sequence data from twenty HBV strains (HPBADR, HPBADR1CG, HPBADRA, HPBADRC, HPBADRCG, HPBCGADR, HPBVADRM, HPBADW, HPBADW1, HPBADW2, HPBADW3, HPBADWZ, HPBHEPB, HPBVADW2, HPBAYR, HPBV, HPBVAYWC, HPBVAYWCI, NAD HPBVAYWE) were evaluated for the presence of the designated supermotif or motif. Peptide epitopes were also selected on the basis of their conservancy. A criterion for conservancy requires that the entire sequence of a peptide be totally conserved in 75% of the sequences available for a specific protein. The percent conservancy of the selected peptide epitopes is indicated on the Tables. The frequency, i.e. the number of strains of the 20 strains in which the peptide sequence was identified, is also shown. The "1st position" column in the Tables designates the amino acid position of the HBV polyprotein that corresponds to the first amino acid residue of the epitope. Preferred peptides are designated by an asterisk.

HLA Class I Motifs Indicative of CTL Inducing Peptide Epitopes:

IV.C.2.a) HLA-A1 Supermotif

The HLA-A1 supermotif is characterized by peptides having a general motif of small (T or S) and hydrophobic (L, I, V, M, or F) primary anchor residues in position 2, and aromatic (Y, F, or W) primary anchor residues at the C-terminal position The corresponding family of HLA molecules that bind to the A1 supermotif (the HLA-A1 supertype) includes A*0101, A*2601, A*2602, A*2501, and A*3201. (DiBrino, M. et al., *J. Immunol.* 151:5930, 1993; DiBrino, M. et al., *J. Immunol.* 152:620, 1994; Kondo, A. et al., *Immunogenetics* 45:249, 1997; Dumrese et al., submitted). Peptides binding to each of the individual HLA proteins can be modulated by substitutions at primary anchor positions.

Representative peptide epitopes that contain the A1 supermotif are set forth on the attached Table VI.

IV.C.2.b) HLA-A2 Supermotif

The HLA-A2 supermotif is characterized by the presence in peptide ligands of small or aliphatic amino acids (L, I, V, M, A, T, or Q) at position 2 and L, I, V, M, A, or T at the C-terminal position. These positions ate referred to as primary anchors. The corresponding family of HLA molecules (the HLA-A2 supertype that binds these peptides) is comprised of at least nine HLA-A proteins: A*0201, A*0202, A*0203, A*0204, A*0205, A*0206, A*0207, A*6802, and A*6901. As explained in detail below, binding to each of the individual allele-specific HLA molecules can be modulated by substitutions at the primary anchor and/or secondary anchor positions.

Representative peptide epitopes that contain the A2 supermotif are set forth on the attached Table VII.

IV.C.2.c) HLA-A3 Supermotif

The HLA-A3 supermotif is characterized by peptide ligands having primary anchor residues: A, L, I, V, M, S, or, T at position 2, and positively charged residues, such as R or K at the C-terminal position (in position 9 of 9-mers). Exemplary members of the corresponding HLA family of HLA molecules (the HLA-A3 superfamily) that bind the A3 supermotif include: A3 (A*0301), A11 (A*1101), A31 (A*3101), A*3301, and A*6801. Other allele-encoded HLA molecules predicted to be members of the A3 superfamily include A34, A66, and A*7401. As explained in detail below, peptide binding to each of the individual allele-specific HLA proteins can be modulated by substitutions of amino acids at the primary and/or secondary anchor positions of the peptide.

Representative peptide epitopes that contain the A3 supermotif are set forth on the attached Table VIII.

IV.C.2.d) HLA-A24 Supermotif

The HLA-A24 supermotif is characterized by the presence in peptide ligands of an aromatic (F, W, or Y) residue as a primary anchor in position 2 and a hydrophobic (Y, F, L, I, V, or M) residue as primary anchor at the C-terminal position. The corresponding family of HLA molecules that bind to the A24 supermotif (the A24 supertype) includes A*2402, A*3001, and A*2301. Peptide binding to each of the allele-specific HLA molecules can be modulated by substitutions at primary anchor positions.

Representative peptide epitopes that contain the A24 supermotif are set forth on the attached Table IX.

IV.C.2.e) HLA-B7 Supermotif

The HLA-B7 supermotif is characterized by peptides bearing proline in position 2 as a primary anchor and hydrophobic or aliphatic amino acids (L, I, V, M, A, F, W, or Y) as the primary anchor at the C-terminal position. The corresponding family of HLA molecules that bind the B7 supermotif (the HLA-B7 supertype) is comprised of at least a dozen HLA-B proteins including B7, B*3501-1, B*3502-2, B*3501-3, B51, B*5301, B*5401, B*5501, B*5401, B*5501, B*5502, B*5601, B*6701, and B*7801 (See, e.g., Sidney, et al., *J. Immunol.* 154:247 (1995); Barber, et al., *Curr. Biol.* 5:179 (1995); Hill, et al., *Nature* 360:434 (1992); Rammensee, et al., *Immunogenetics* 41:178 (1995)). As explained in detail below, peptide binding to each of the individual allele-specific HLA proteins can be modulated by substitutions at the primary and/or secondary anchor positions of the peptide.

Representative peptide epitopes that contain the B7 supermotif are set forth on the attached Table X.

IV.C.2.f) HLA-B27 Supermotif

The HLA-B27 supermnotif is characterized by the presence in peptide ligands of positively charged (R, H, or K) residues as primary anchors at position 2 and hydrophobic (A, L, I, V, M, Y, F, or W) residues as primary anchors at the C-terminal. Exemplary members of the corresponding HLA molecules that bind to the B27 supermotif (the B27 supertype) include B*14, B*1509, B*38, B*3901, B*3902, B*73, and various B27 subtypes. Peptide binding to each of the allele-specific HLA molecules can be modulated by substitutions at primary anchor positions.

Representative peptide epitopes that contain the B27 supermotif are set forth on the attached Table XI.

IV.C.2.g) HLA-B44 Supermotif

The HLA-B44 supermotif is characterized by the presence in peptide ligands of negatively charged (D or E) residues as a primary anchor in position 2, and hydrophobic residues (F, W, Y, L, I, M V, or A) as a primary anchor at the C-terminal. Exemplary members of the corresponding family of HLA molecules that bind to the B44 supermnotif (the B44 supertype) include B*3701, B*4402, B*4403, B60, and B61. Peptide binding to each of the allele-specific HLA molecules can be modulated by substitutions at primary anchor positions.

Representative peptide epitopes that contain the B44 supermotif are set forth on the attached Table XII.

IV.C.2.h) HLA-B58 Supermotif

The HLA-B58 supermotif is characterized by the presence in peptide ligands of small aliphatic residues (A, S, or T) as primary anchor residues at position 2 and aromatic or hydrophobic residues (F, W, Y, L, I, or V) as primary anchor residues at the C-terminal. Exemplary members of the corresponding HLA molecules that bind to the B58 supermotif (the B58 supertype) include B*1516, B*1517, B*5701, B*5702, and B*58. Peptide binding to each of the allele-specific HLA molecules can be modulated by substitutions at primary anchor positions.

Representative peptide epitopes that contain the B58 supermotif are set forth on the attached Table XIII.

IV.C.2.i) HLA-B62 Supermotif

The HLA-B62 supermotif is characterized by the presence in peptide ligands of the polar aliphatic residue Q or the hydrophobic aliphatic residues (L, V, M, or I) as a primary anchor in position 2 and hydrophobic residues (F, W, Y, M, I, or V) as a primary anchor at the C-terminal position. Exemplary members of the corresponding HLA molecules that a bind to the B62 supermotif (the B62 supertype) include B46, B52, B62, B75, and B77. Peptide binding to each of the allele-specific HLA molecules can be modulated by substitutions at primary anchor positions.

Representative peptide epitopes that contain the B62 supermotif are set forth on the attached Table XIV.

IV.C.2.j) HLA-A1 Motif

The allele-specific HLA-A1 motif is characterized by the presence in peptide ligands of T, S, or M as a primary anchor residue at position 2 and the presence of Y as a primary anchor residue at the C-terminal position. Alternatively, a primary anchor residue may be present at position 3 rather than position 2. This motif is characterized by the presence of D, E, A, or S as a primary anchor residue in position 3 and a Y as a primary anchor residue at the C-terminus. Peptide binding to HLA A1 can be modulated by substitutions at primary and/or secondary anchor positions.

Representative peptide epitopes that contain the A1 motif are set forth on the attached Table XV.

IV.C.2.k) HLA-A3 Motif

The allele-specific HLA-A3 motif is characterized by the presence in peptide ligands of L, M, V, I, S, A, T, F, C, G, or D as a primary anchor residue at position 2 and the presence of K, Y, R, H, F, or A as the primary anchor residue at the C-terminal position. Peptide binding to HLA-A3 can be modulated by substitutions at primary and/or secondary anchor positions.

Representative peptide epitopes that contain the A3 motif are set forth on the attached Table XVI.

IV.C.2.1) HLA-A11 Motif

The allele-specific HLA-A11 motif is characterized by the presence in peptide ligands of V, T, M, L, I, S, A, G, N, C, D, or F as a primary anchor residue in position 2 and K, R, Y, or H as a primary anchor residue at the C-terminal position. Peptide binding to HLA-A 11 can be modulated by substitutions at primary and/or secondary anchor positions.

Representative peptide epitopes that contain the A11 motif are set forth on the attached Table XVI; peptides bearing the A3 allele-specific motif are also present in Table XVII. The A11 and A3 motifs have a number of anchor residues in common, separate tables would provide a number of redundant entries.

IV.C.2.m) HLA-A24 Motif

The allele-specific HLA-A24 motif is characterized by the presence in peptide ligands of Y, F, W, or M as a primary anchor residue in position 2 and F, L, I, or W as a primary anchor residue at the C-terminal position. Peptide binding to HLA-A24 molecules can be modulated by substitutions at primary and/or secondary anchor positions.

Representative peptide epitopes that contain the A24 motif are set forth on the attached Table XVII.

IV.C.2.n) HLA-A2.1 Motif

The allele-specific HLA-A2.1 motif was first determined to be characterized by the presence in peptide ligands of L, M, V, I, A or T as a primary anchor residue in position 2 and, L, V, I, A, or T as a primary anchor residue at the C-terminal position. The preferred and tolerated residues that characterize the primary anchor positions of the HLA-A2.1 motif are identical to the preferred residue of the A2 supermotif. Secondary anchor residues that characterize the A2.1 motif have additionally been defined as disclosed herein. These are disclosed in Table II. Peptide binding to HLA-A2.1 molecules can be modulated by substitutions at primary and/or secondary anchor positions.

Representative peptide epitopes that contain the A2.1 motif are set forth on the attached Table VII. These peptides, which bear the HLA-A2 supermotif, also contain secondary anchor residues that are characteristic of the HLA-A2.1 motif. In one embodiment, the peptide epitope does not bear an L or M at position 2 and V at the C-terminal position 9 of a 9-amino acid peptide.

The primary anchor residues of the HLA class I peptide epitope supermotifs and motifs delineated above are summarized in Table I. Primary and secondary anchor positions are summarized in Table II.

Motifs Indicative of Class II HTL Inducing Peptide Epitopes

IV.C.2.o) HLA DR-1-4-7 Supermotif

Motifs have also been identified for peptides that bind to three common HLA class II types, HLA DRB1*0401, DRB1*0101, and DRB1*0701. Peptides binding to these DR molecules carry a motif characterized by a large aromatic or hydrophobic residue in position 1 (Y, F, W, L, I, V, or M) and a small, non-charged residue in position 6 (S, T, C, AP, V, I, L, or M). Allele specific secondary effects and secondary anchors for each of these HLA types have also been identified. These are set forth in Table III. Peptide binding to HLA-DR4, DR1, and DR7 can be modulated by substitutions at primary and/or secondary anchor positions.

Representative peptides are set forth in Table XVIII.

IV.C.2.p) HLA DR3 Motifs

Two alternative motifs characterize peptides that bind to HLA-DR3 molecules. In the first motif, a large, hydrophobic residue (I, L, V, M, Y, or F) is present in anchor position 1 and D is present as an anchor at position 4, which is defined as being 3 positions from anchor position 1 towards the carboxyl terminus regardless of the location of anchor position 1 in the peptide. Lack of either the large, hydrophobic residue at anchor position 1, or of the negatively charged or amide-like anchor residue at position 4 may be compensated for by the presence of a positive charge at position 6 (which is defined as being 5 positions from anchor position 1 towards the carboxyl terminus). Thus for the second, alternative motif I, L, V, M, Y, F, or A is present at anchor position 1; D, N, Q, E, S, or T is present at anchor position 4; and K, R, or H is present at anchor position 6. Peptide binding to HLA-DR3 can be modulated by substitutions at primary and/or secondary anchor positions.

Representative peptides are set forth in Table IXX.

IV.C.3. Enhancing Population Coverage of the Vaccine

Vaccines that have broad population coverage are preferred because they are more commercially viable and generally applicable to the most people. Broad population coverage can be obtained using the peptides of the invention (and nucleic acid compositions that encode such peptides) through selecting peptide epitopes that bind to HLA alleles which, when considered in total, are present in most of the population. Table XX lists the overall frequencies of the A2-, A3-, and B7-supertypes in various ethnicities. Coverage in excess of 80% is achieved with these motifs. These results suggest that effective and non-ethnically biased population coverage is achieved upon use of a limited number of cross-reactive peptides. Although the population coverage reached with these three main peptide specificities is high, coverage can be expanded to reach 95% population coverage and above, and more easily achieve truly multispecific responses upon use of additional supermotif or allele-specific motif bearing peptides.

Table XX summarizes the HLA supertypes that have been identified, and indicates an estimate of their combined prevalence in major ethnic groups. The B44-, A1-, and A24-supertypes are present, on average, in over 25% of the world's major ethnic populations. While less prevalent overall, the B27-, B58-, and B62 supertypes are each present with a frequency >25% in at least one major ethnic group. The Table indicates the population coverage achieved by the A2-, A3-, and B7-supertypes, and the incremental coverage obtained by the addition of A1-, A24-, and B44-supertypes, or all of the supertypes described herein. As shown, by including epitopes from the six most frequent supertypes, an average population coverage of 99% is obtained for five major ethnic groups.

The data presented herein, together with the previous definition of the A2-, A3-, and B7-supertypes, indicates that all antigens, with the possible exception of A29, B8, and B46, can be classified into a total of nine HLA supertypes. Focusing on the six most common supertypes affords population coverage greater than 98% for all major ethnic populations.

IV.D. Immune Response Stimulating Peptide Analogs

Although peptides with suitable cross-reactivity among all alleles of a superfamily are identified by the screening procedures described above, cross-reactivity is not always complete and in such cases procedures to further increase cross-reactivity of peptides can be useful; such procedures can also be used to modify other properties of the peptides. Having established the general rules that govern cross-reactivity of peptides for HLA alleles within a given motif or supermotif, modification (i.e., analoging) of the structure of peptides of particular interest in order to achieve broader (or otherwise modified) HLA binding capacity can be performed. More specifically, peptides which exhibit the broadest cross-reactivity patterns, (both amongst the known T cell epitopes, as well as the more extended set of peptides that contain the appropriate supermotifs), can be produced in accordance with the teachings herein.

The strategy employed utilizes the motifs or supermotifs which correlate with binding to certain HLA molecules. The motifs or supermotifs are defined by having primary anchors, though secondary anchors can also be modified. Analog peptides can be created by substituting amino acids residues at primary anchor, secondary anchor, or at primary and secondary anchor positions. Generally, analogs are made for peptides that already bear a motif or supermotif. Preferred secondary anchor residues of supermotifs and motifs that have been defined for HLA class I and class II binding peptides are shown in Tables II and III, respectively.

For a number of the motifs or supermotifs in accordance with the invention, residues are defined which are deleterious to binding to allele-specific HLA molecules or members of HLA supertypes that bind to the respective motif or supermotif (Tables II and III). Accordingly, removal of residues that are detrimental to binding can be performed in accordance with the present invention. For example, in the case of the A3 supertype, when all peptides that have such deleterious residues are removed from the population of analyzed peptides, the incidence of cross-reactivity increases from 22% to 37% (see, e.g., Sidney, J. et al., *Hu. Immunol.* 45:79, 1996). Thus, one strategy to improve the cross-reactivity of peptides within a given supermotif is simply to delete one or more of the deleterious residues present within a peptide and substitute a small "neutral" residue such as Ala (that may not influence T cell recognition of the peptide). An enhanced likelihood of cross-reactivity is expected if, together with elimination of detrimental residues within a peptide, residues associated with high affinity binding to multiple alleles within a superfamily are inserted.

To ensure that changes in the native or original epitope recognized by T cells do not lead to a failure of killing antigen presenting cells presenting the unaltered "wild type" peptide (or, in the case of class II epitopes, a failure to elicit helper T cells that cross-react with the wild type peptides), the variant peptide may be used to immunize T cells in vitro from individuals of the appropriate HLA allele, and the cells' capacity to induce lysis of wild type peptide sensitized target cells is evaluated. In both class I and class II systems it will be desirable to use as targets, cells that have been either infected or transfected with the appropriate genes to establish whether endogenously produced antigen is also recognized by the relevant T cells.

Another embodiment of the invention to ensure adequate numbers of cross-reactive cellular binders is to create analogs of weak binding peptides. Class I peptides exhibiting binding affinities of 500-50000 nM, and carrying an acceptable but suboptimal primary anchor residue at one or both positions can be "fixed" by substituting preferred anchor residues in accordance with the respective supertype. The analog peptides can then be tested for crossbinding activity.

Another embodiment for generating effective peptide analogs involves the substitution of residues that have an adverse impact on peptide stability or solubility in a liquid environment. This substitution may occur at any position of the peptide epitope. For example, a cysteine (C) can be substituted out in favor of α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances (Review: A. Sette et al, In: Persistent Viral Infections, Eds. R. Ahmed and I. Chen, John Wiley & Sons, England, in press, 1998). Substitution of cysteine with α-amino butyric acid may occur at any residue of a peptide epitope, i.e. at either anchor or non-anchor positions.

In general, CTL and HTL responses are not directed against all possible epitopes. Rather, they are restricted to a few immunodominant determinants (Zinkemagel, et al., *Adv. Immunol.* 27:5159, 1979; Bennink, et al., *J. Exp. Med.* 168: 19351939, 1988; Rawle, et al., *J. Immunol.* 146:3977-3984, 1991). It has been recognized that immunodominance (Benacerraf, et al., *Science* 175:273-279, 1972) could be explained by either the ability of a given epitope to selectively bind a particular HLA protein (determinant selection theory) (Vitiello, et al., *J. Immunol.* 131:1635, 1983); Rosenthal, et al., *Nature* 267:156-158, 1977), or being selectively recognized by the existing TCR (T cell receptor) specificity (repertoire theory) (Klein, J., IMMUNOLOGY, THE SCIENCE OF SELFNONSELF DISCRIMINATION, John Wiley & Sons, N.Y., pp. 270-310, 1982). It has been demonstrated that additional factors, mostly linked to processing events, can also play a key role in dictating, beyond strict immunogenicity, which of the many potential determinants will be presented as immunodominant (Sercarz, et al., *Annu. Rev. Immunol.* 11:729-766, 1993).

The concept of dominance and subdominance is relevant to immunotherapy of both infectious diseases and cancer. For example, in the course of chronic viral disease, recruitment of subdominant epitopes can be important for successful clearance of the infection, especially if dominant CTL or HTL specificities have been inactivated by functional tolerance, suppression, mutation of viruses and other mechanisms (Franco, et al., *Curr. Opin. Immunol.* 7:524-531, (1995)). In the case of cancer and tumor antigens, CTLs recognizing at least some of the highest binding affinity peptides might be functionally inactivated. Lower binding affinity peptides are preferentially recognized at these times.

In particular, it has been noted that a significant number of epitopes derived from known non-viral tumor associated antigens (TAA) bind HLA class I with intermediate affinity ($IC_{50}$ in the 50-500 nM range). For example, it has been found that 8 of 15 known TAA peptides recognized by tumor infiltrating lymphocytes (TIL) or CTL bound in the 50-500 nM range. (These data are in contrast with estimates that 90% of known viral antigens that were recognized as peptides bound HLA with $IC_{50}$ of 50 nM or less, while only approximately 10% bound in the 50-500 nM range (Sette, et al., *J. Immunol.*, 153:558-5592 (1994)). In the cancer setting this phenomenon is probably due to elimination, or functional inhibition of the CTL recognizing several of the highest binding peptides, presumably because of T cell tolerization events.

Without intending to be bound by theory, it is believed that because T cells to dominant epitopes may have been clonally deleted, selecting subdominant epitopes may allow extant T cells to be recruited, which will then lead to a therapeutic response. However, the binding of HLA molecules to subdominant epitopes is often less vigorous than to dominant ones. Accordingly, there is a need to be able to modulate the binding affinity of particular immunogenic epitopes for one or more BLA molecules, and thereby to modulate the immune response elicited by the peptide. Thus a need exists to prepare analog peptides which elicit a more vigorous response. This ability would greatly enhance the usefulness of peptide-based vaccines and therapeutic agents.

Representative analog peptides are set forth in Table XXI. The Table indicates the length and sequence of the analog peptide as well as the motif or supermotif, if appropriate. The information in the "Fixed Nomenclature" column indicates the residues substituted at the indicated position numbers for the respective analog.

IV.E. Computer Screening of Protein Sequences from Disease-Related Antigens for Supermotif or Motif Containing Peptides Computer programs that allow the rapid screening of protein sequences for the occurrence of the subject supermotifs or motifs are encompassed by the present invention; as are programs that permit the generation of analog peptides. These programs are implemented to analyze any identified amino acid sequence or operate on an unknown sequence and simultaneously determine the sequence and identify motif-bearing epitopes thereof; analogs can be simultaneously determined as well. Generally, the identified sequences will be from a pathogenic organism or a tumor-associated peptide. For example, the target molecules considered herein include all of the HBV proteins (e.g. surface, core, polymerase, and X).

In cases where the sequence of multiple variants of the same target protein are available, peptides are also selected on the basis of their conservancy. A presently preferred criterion for conservancy defines that the entire sequence of a peptide be totally conserved in 75% of the sequences evaluated for a specific protein; this definition of conservancy has been employed herein.

It is important that the selection criteria utilized for prediction of peptide binding are as accurate as possible, to correlate most efficiently with actual binding. Prediction of peptides that bind, for example, to HLA-A*0201, on the basis of the presence of the appropriate primary anchors, is positive at about a 30% rate (Ruppert, J. et al. *Cell* 74:929, 1993). However, by analyzing an extensive peptide-HLA binding database, the present inventors have developed a number of allele specific polynomial algorithms that dramatically increase the predictive value over identification on the basis of the presence of primary anchor residues alone. These algorithms take into account not only the presence or absence of the correct primary anchors, but also consider the positive or deleterious presence of secondary anchor residues (to account for the impact of different amino acids at different positions). The algorithms are essentially based on the premise that the overall affinity (or ΔG) of peptide-HLA interactions can be approximated as a linear polynomial function of the type:

$$\Delta G = a_{1i} \times a_{2i} \times a_{3i} \ldots \times a_{ni}$$

where $a_{ij}$ is a coefficient that represents the effect of the presence of a given amino acid (j) at a given position (i) along the sequence of a peptide of n amino acids. An important assumption of this method is that the effects at each position are essentially independent of each other. This assumption is justified by studies that demonstrated that peptides are bound to HLA molecules and recognized by T cells in essentially an extended conformation. Derivation of specific algorithm coefficients has been described in Gulukota et al. (Gulukota, K. et al., *J. Mol. Biol.* 267:1258, 1997).

Additional methods to identify preferred peptide sequences, which also make use of specific motifs, include the use of neural networks and molecular modeling programs (Gulukota, K. et al., *J. Mol. Biol.* 267:1258, 1997; Milik et al., *Nature Biotechnology* 16:753, 1998; Altuvia et al., *Hum. Immunol.* 58:1, 1997; Altuvia et al, *J. Mol. Biol.* 249:244, 1995).

For example, it has been shown that in sets of A*0201 motif peptides, 69% of the peptides containing at least one preferred secondary anchor residue while avoiding the presence of any deleterious secondary anchor residues, will bind A*0201 with an $IC_{50}$ less than 500 nM (Ruppert, J. et al. *Cell* 74:929, 1993). These algorithms are also flexible in that cut-off scores may be adjusted to select sets of peptides with greater or lower predicted binding properties, as desired.

In utilizing computer screening to identify peptide epitopes, all protein sequence or translated sequence may be analyzed using software developed to search for motifs, for example the "FINDPATTERNS" program (Devereux, et al. *Nucl. Acids Res.* 12:387-395, 1984) or MotifSearch 1.4 software program (D. Brown, San Diego, Calif.) to identify potential peptide sequences containing appropriate HLA binding motifs. As appreciated by one of ordinary skill in the art a large array of software and hardware options are available which can be employed to implement the motifs of the invention relative to known or unknown peptide sequences. The identified peptides will then be scored using customized polynomial algorithms to predict their capacity to bind specific HLA class I or class II alleles.

In accordance with the procedures described above, HBV peptides and analogs thereof that are able to bind HLA supertype groups or allele-specific BLA molecules have been identified (Tables VI-XIX; Table XI).

IV.F. Assays to Detect T-Cell Responses

Once HLA binding peptides are identified, they can be tested for the ability to elicit a T-cell response. The preparation and evaluation of motif-bearing peptides are described in PCT publications WO 94/20127 and WO 94/03205. Briefly, peptides comprising epitopes from a particular antigen are synthesized and tested for their ability to bind to the appropriate HLA proteins in assays using, for example, purified HLA class I molecules and radioiodonated peptides and/or cells expressing empty class I molecules (which lack peptide in their receptor) by, for instance, immunofluorescent staining and flow microfluorimetry, peptide-dependent class I assembly assays, and inhibition of CTL recognition by peptide competition. Those peptides that bind to the class I molecule are further evaluated for their ability to serve as targets for CTLs derived from infected or immunized individuals, as well as for their capacity to induce primary in vitro or in vivo CTL responses that can give rise to CTL populations capable of reacting with selected target cells associated with a disease. Corresponding assays are used for evaluation of HLA class II binding peptides.

Conventional assays utilized to detect CTL responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations. Antigen-presenting cells can be normal cells such as peripheral blood mononuclear cells or dendritic cells. Alternatively, mutant mammalian cell lines that are deficient in their ability to load class I molecules with internally processed peptides and that have been transfected with the appropriate human class I gene may be used to test for the capacity of the peptide to induce in vitro primary CTL responses.

Peripheral blood lymphocytes may be used as the responder cell source of CTL precursors. The appropriate antigen-presenting cells are incubated with peptide and the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the HBV antigen from which the peptide sequence was derived.

More recently, a method has also been devised which allows direct quantification of antigen-specific T cells by staining with Fluorescein-labelled HLA tetrameric complexes (Altman, J. D. et al., *Proc. Natl. Acad. Sci. USA* 90:10330, 1993; Altman, J. D. et al., *Science* 274:94, 1996). Other relatively recent technical developments include staining for intracellular lymphokines, and interferon release assays or ELISPOT assays. Tetramer staining, intracellular lymphokine staining and ELISPOT assays all appear to be at least 10-fold more sensitive than more conventional assays (Lalvani, A. et al., *J. Exp. Med.* 186:859, 1997; Dunbar, P. R. et al., *Curr. Biol.* 8:413, 1998; Murali-Krishna, K. et al., *Immunity* 8:177, 1998).

HTL activation may also be assessed using such techniques as T cell proliferation and secretion of lymphokines, e.g. IL-2.

Alternatively, immunization of HLA transgenic mice can be used to determine immunogenicity of peptide epitopes. Several transgenic mouse models including mice with human A2.1, A11, and B7 alleles have been characterized and others (e.g., transgenic mice for HLA-A1 and A24) are being developed. HLA-DR1 and HLA-DR3 mouse models have also been developed. Additional transgenic mouse models with other HLA alleles may be generated as necessary. Mice may be immunized with peptides emulsified in Incomplete Freund's Adjuvant and the resulting T cells tested for their capacity to recognize peptide-pulsed target cells and target cells transfected with appropriate genes. CTL responses may be analyzed using cytotoxicity assays described above. Similarly, HTL responses may be analyzed using such assays as T cell proliferation or secretion of lymphokines.

IV.G. Preparation of Peptides

Peptides in accordance with the invention can be prepared synthetically, by recombinant DNA technology, or from natural sources such as native tumors or pathogenic organisms. Peptide epitopes may be synthesized individually or as polyepitopic peptides. Although the peptide will preferably be substantially free of other naturally occurring host cell proteins and fragments thereof, in some embodiments the peptides may be synthetically conjugated to native fragments or particles.

The peptides in accordance with the invention can be a variety of lengths, and either in their neutral (uncharged) forms or in forms which are salts. Peptides may be synthesized The peptides in accordance with the invention are either free of modifications such as glycosylation, side chain oxidation, or phosphorylation; or they contain these modifications, subject to the condition that modifications do not destroy the biological activity of the peptides as described herein.

Desirably, the peptide will be as small as possible while still maintaining substantially all of the biological activity of the large peptide. When possible, it may be desirable to optimize HLA class I binding peptides of the invention to a length of about 8 to about 13 amino acid residues, preferably 9 to 10. HLA class II binding peptides may be optimized to a length of about 6 to about 25 amino acids in length, preferably to between about 13 and about 20 residues. Preferably, the peptides are commensurate in size with endogenously processed pathogen-derived peptides or tumor cell peptides that are bound to the relevant HLA molecules. Moreover, the identification and preparation of peptides of other lengths can be carried out using the techniques described herein (e.g., the disclosures regarding primary and secondary anchor positions). However, it is also preferred to identify a larger region of a native peptide that encompasses one and preferably two or more epitopes in accordance with the invention. This sequence is selected on the basis that it contains the greatest number of epitopes per amino acid length. It is to be appreciated that epitopes can be present in a frame-shifted manner, e.g. a 10 amino acid long peptide could contain two 9 amino acid long epitopes and one 10 amino acid long epitope; each epitope can be exposed and bound by an HLA molecule upon administration of a plurality of such peptides. This larger, preferably multi-epitopic, peptide can then be generated synthetically, recombinantly, or via cleavage from the native source.

The peptides of the invention can be prepared in a wide variety of ways. For the preferred relatively short size, the peptides can be synthesized in solution or on a solid support in accordance with conventional techniques. Various automatic synthesizers are commercially available and can be used in accordance with known protocols. See, for example, Stewart & Young, SOLID PHASE PEPTIDE SYNTHESIS, 2D. ED., Pierce Chemical Co. (1984). Further, individual peptides may be joined using chemical ligation to produce larger peptides.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., MOLECULAR CLONING, A LABORATORY MANUAL, Cold Spring Harbor Press, Cold Spring Harbor, N.Y. (1989). Thus, recombinant polypeptides which comprise one or more peptide sequences of the invention can be used to present the appropriate T cell epitope.

As the nucleotide coding sequence for peptides of the preferred lengths contemplated herein can be synthesized by chemical techniques, for example, the phosphotriester method of Matteucci, et al., *J. Am. Chem. Soc.* 103:3185 (1981) modification can be made simply by substituting the appropriate and desired nucleic acid base(s) for those that encode the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast, insect or mammalian cell hosts may also be used, employing suitable vectors and control sequences.

IV.H. Peptide Epitope Reagents to Evaluate Immune Responses.

HLA class I and class II binding peptides as described herein can be used, in one embodiment of the invention, as reagents to evaluate an immune response. The immune response to be evaluated may be induced by using as an immunogen any agent that would potentially result in the production of antigen-specific CTLs or HTLs to the peptide epitope(s) to be employed as the reagent. The peptide reagent is not used as the immunogen.

For example, a peptide of the invention may be used in a tetramer staining assay to assess peripheral blood mononuclear cells for the presence of antigen-specific CTLs following exposure to a pathogen or immunogen. The HLA-tetrameric complex is used to directly visualize antigen-specific CTLs (see, e.g., Ogg et al. Science 279:2103-2106, 1998; and Altman et al. Science 174:94-96, 1996) and determine the frequency of the antigen-specific CTL population in a sample of peripheral blood mononuclear cells. A tetramer reagent using a peptide of the invention may be generated as follows: A peptide that binds to an allele-specific HLA molecules, or supertype molecules, is refolded in the presence of the corresponding HLA heavy chain and $\beta_2$-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells may then be identified, for example, by flow cytometry. Such an analysis may be used for diagnostic or prognostic purposes.

Peptides of the invention may also be used as reagents to evaluate immune recall responses. (see, e.g., Bertoni et al. *J. Clin. Invest.* 100:503-513, 1997 and Penna et al. *J. Exp. Med.* 174:1565-1570, 1991.) For example, patient PBC samples from individuals with acute hepatitis B or who have recently recovered from acute hepatitis B may be analyzed for the presence of HBV antigen-specific CTLs using HBV-specific peptides. A blood sample containing mononuclear cells may be evaluated by cultivating the PBCs and stimulating the cells with a peptide of the invention. After an appropriate cultivation period, the expanded cell population may be analyzed for cytotoxic activity.

The peptides may also be used as reagents to evaluate the efficacy of a vaccine. PBMCs obtained from a patient vaccinated with an immunogen may be analyzed using, for example, either of the methods described above. A patient is HLA typed, and appropriate peptide reagents that recognize allele-specific molecules present in that patient may be selected for the analysis. The immunogenicity of the vaccine will be indicated by the presence of HBV epitope-specific CTLs in the PBMC sample.

IV.I. Vaccine Compositions

Vaccines that contain as an active ingredient an immunogenically effective amount of one or more peptides as described herein are a further embodiment of the invention.

Once appropriately immunogenic epitopes have been defined, they can be sorted and delivered by various means, herein referred to as "vaccine" compositions. Such vaccine compositions can include, for example, lipopeptides (Vitiello, A. et al., *J. Clin. Invest.* 95:341, 1995), peptides compositions encapsulated in poly(DL-lactide-co-glycolide) (PLG) microspheres (see, e.g., Eldridge, et al. *Molec. Immunol.* 28:287-294, 1991: Alonso et al. *Vaccine* 12:299-306, 1994; Jones et al. *Vaccine* 13:675-681, 1995), peptide compositions encapsulated in immune stimulating complexes (ISCOMS) (see, e.g., Takahashi et al. *Nature* 344:873-875, 1990; Hu et al. Clin Exp Immunol. 113:235-243, 1998), multiple antigen peptide systems (MAPs) (see e.g., Tam, J. P., Proc. Natl. Acad. Sci. U.S.A. 85:5409-5413, 1988; Tam, J. P., J. Immunol. Methods 196:17-32, 1996), viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M. -P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted, also know as receptor mediated targeting, delivery technologies also may be used such as those of Avant Immunotherapeutics, Inc. (Needham, Mass.).

Furthermore, vaccines in accordance with the invention encompass compositions of one or more of the claimed peptide(s) that can be introduced into a host, including humans, linked to its own carrier, or as a homopolymer or heteropolymer of active peptide units., Such a polymer has the advantage of increased immunological reaction and, where different peptides are used to make up the polymer, the additional ability to induce antibodies and/or CTLs that react with different antigenic determinants of the pathogenic organism or tumor-related peptide targetted for an immune response.

Furthermore, useful carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, hepatitis B virus recombinant vaccine and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinly-seryl-serine P$_3$CSS).

As disclosed in greater detail herein, upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs specific for the desired antigen, and the host becomes at least partially immune to later infection, or at least partially resistant to developing an ongoing chronic infection.

In some instances it may be desirable to combine the class I peptide vaccines of the invention with vaccines which induce or facilitate neutralizing antibody responses to the target antigen of interest, particularly to viral envelope antigens. A preferred embodiment of such a composition comprises class I and class II epitopes in accordance with the invention. An alternative embodiment of such a composition comprises a class I and/or class II epitope in accordance with the invention, along with a PADRE®(Epimmune, San Diego, Calif.) molecule (described in the related U.S. Ser. No. 08/485,218, which is a CIP of U.S. Ser. No. 08/305,871, now U.S. Pat. No. 5,736,142, which is a CIP of abandoned application U.S. Ser. No. 08/121,101.) Furthermore, any of these embodiments can be administered as a nucleic acid mediated modality.

For therapeutic or immunization purposes, the peptides of the invention can also be expressed by viral or bacterial vectors. Examples of expression vectors include attenuated viral hosts, such as vaccinia or fowlpox. This approach involves the use of vaccinia virus as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848. Another vector is BCG (Bacille Calmette Guerin). BCG vectors are described in Stover, et al. *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Antigenic peptides are used to elicit a CTL and/or HTL response ex vivo, as well. The resulting CTL or HTL cells, can be used to treat chronic infections, or tumors in patients that do not respond to other conventional forms of therapy, or will not respond to a therapeutic vaccine peptide or nucleic acid in accordance with the invention. Ex vivo CTL or HTL responses to a particular pathogen (infectious agent or tumor antigen) are induced by incubating in tissue culture the patient's CTL or HTL precursor cells together with a source of antigen-presenting cells (APC), such as dendritic cells, and the appropriate immunogenic peptide. After an appropriate incubation time (typically about 14 weeks), in which the precursor cells are activated, mature and expand into effector cells, the cells are infused back into the patient, where they will destroy (CTL) or facilitate destruction (HTL) of their specific target cell (an infected cell or a tumor cell).

Transfected dendritic cells may also be used as antigen presenting cells. Alternatively, dendritic cells are transfected, e.g., with a minigene construct in accordance with the invention, in order to elicit immune responses. Minigenes will be discussed in greater detail in a following section.

DNA or RNA encoding one or more of the peptides of the invention can also be administered to a patient. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720; and in more detail below. Examples of DNA-based delivery technologies include "naked DNA", facilitated (bupivicaine, polymers, peptide-mediated) delivery, cationic lipid complexes, and particle-mediated ("gene gun") delivery.

Preferably, the following principles are utilized when selecting an array of epitopes for inclusion in a polyepitopic composition, or for selecting epitopes to be included in a vaccine composition and/or to be encoded by a minigene. It is preferred that each of the following principles are balanced in order to make the selection.

1.) Epitopes are selected which, upon administration, mimic immune responses that have been observed to be correlated with HBV clearance. For HLA Class I this includes 3-4 epitopes that come from at least one antigen of HBV. In other words, it has been observed that in patients who spontaneously clear HBV, that they had generated an immune response to at least 3 epitopes on at least one HBV antigen. For HLA Class II a similar rationale is employed; again 3-4 epitopes are selected from at least one HBV antigen (see e.g., Rosenberg et al. *Science* 278:1447-1450).

2.) Epitopes are selected that have the requisite binding affinity established to be correlated with immunogenicity: for HLA Class I an $IC_{50}$ of 500 nM or less, or for Class II an $IC_{50}$ of 1000 nM or less.

3.) Sufficient supermotif bearing peptides, or a sufficient array of allele-specific motif bearing peptides, are selected to give broad population coverage. For example, it is preferable to have at least 80% population coverage. A Monte Carlo analysis, a statistical evaluation known in the art, can be employed to assess population coverage.

4.) When selecting epitopes from cancer-related antigens it is often preferred to select analogs. When selecting epitopes for infectious disease-related antigens it is often preferable to select native epitopes. Therefore, of particular relevance for infectious disease vaccines (but for cancer-related vaccines as well), are epitopes referred to as "nested epitopes." Nested epitopes occur where at least two epitopes overlap in a given peptide sequence. A peptide comprising "transcendent nested epitopes" is a peptide that has both HLA class I and HLA class II epitopes in it.

When providing nested epitopes, it is preferable to provide a sequence that has the greatest number of epitopes per provided sequence. A limitation on this principle is to avoid providing a peptide that is any longer than the amino terminus of the amino terminal epitope and the carboxyl terminus of the carboxyl terminal epitope in the peptide. When providing a longer peptide sequence, such as a sequence comprising nested epitopes, it is important to screen the sequence in order to insure that it does not have pathological or other deleterious biological properties.

5.) When creating a minigene, as disclosed in greater detail in the following section, an objective is to generate the smallest peptide possible that encompasses the epitopes of interest. The principles employed are similar, if not the same as those employed when selecting a peptide comprising nested epitopes. Thus, upon determination of the nucleic acid sequence to be provided as a minigene, the peptide encoded thereby is analyzed to determine whether any "junctional epitopes" have been created. A junctional epitope is an actual binding epitope, as predicted, e.g., by motif analysis. Junctional epitopes are to be avoided because the recipient may generate an immune response to that epitope. Of particular concern is a junctional epitope that is a "dominant epitope." A dominant epitope may lead to such a zealous response that immune responses to other epitopes are diminished or suppressed.

IV.I.1. Minigene Vaccines

A growing body of experimental evidence demonstrates that a number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines above. A preferred means of administering nucleic acids encoding the peptides of the invention uses minigene constructs encoding one or multiple epitopes of the invention. The use of multi-epitope minigenes is described below and in, e.g. An, L. and Whitton, J. L., .1 *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding nine dominant HLA-A*0201- and A11-restricted epitopes derived from the polymerase, envelope, and core proteins of HBV and HIV, the PADRE® universal helper T cell (HTL) epitope, and an ER-translocating signal sequence was engineered. Immunization of HLA transgenic mice with this plasmid construct resulted in strong CTL induction responses against the nine epitopes tested, similar to those observed with a lipopeptide of known immunogenicity in humans, and significantly greater than immunization in oil-based adjuvants. Moreover, the immunogenicity of DNA-encoded epitopes in vivo correlated with the in vitro responses of specific CTL lines against target cells transfected with the DNA plasmid.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that could be reverse translated and included in the minigene sequence include: HLA class I epitopes, HLA class II epitopes, a ubiquitination signal sequence, a leader sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF) or costimulatory molecules. Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving CTL induction. In contrast to HTL or CTL induction, specifically decreasing the immune response by co-expression of immunosuppressive molecules (e.g. TGF-$\beta$) may be beneficial in certain diseases).

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes, respectively. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates production of HLA presentation of minigene-encoded CTL epitopes.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, IP for lipid-complexed DNA). Twenty-one days after immunization, splenocytes are harvested and restimulated for 1 week in the presence of peptides encoding each epitope being tested. For CTL effector cells, assays are conducted for cytolysis of peptide-loaded, chromium-51 labeled target cells using standard techniques. Lysis of target cells sensitized by HLA loading of peptides corresponding to minigene-encoded epitopes demonstrates DNA vaccine function for in vivo induction of CTLs.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

IV.I.2. Combinations with Helper Pepides

The peptides of the present invention, or analogs thereof, which have immunostimulatory activity may be modified to provide desired attributes, such as improved serum half life, or to enhance immunogenicity.

For instance, the ability of the peptides to induce CTL activity can be enhanced by linking the peptide to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer.

The immunogenic peptide may be linked to the T helper peptide either directly or via a spacer either at the amino or carboxy terminus of the CTL peptide. The amino terminus of either the immunogenic peptide or the T helper peptide may be acylated. The T helper peptides used in the invention can be modified in the same manner as CTL peptides. For instance, they may be modified to include D-amino acids or be conjugated to other molecules such as lipids, proteins, sugars and the like. Exemplary T helper peptides include tetanus toxoid 830-843, influenza 307-319, and malarial circumsporozoite 382-398 and 378-389.

In certain embodiments, the T helper peptide is one that is recognized by T helper cells present in the majority of the population. This can be accomplished by selecting amino acid sequences that bind to many, most, or all of the HLA class II molecules. These are known as "loosely HLA-restricted" or "promiscuous" T helper sequences. Examples of amino acid sequences that are promiscuous include sequences from antigens such as tetanus toxoid at positions 830-843 (QYIKANSKFIGITE; SEQ ID NO:2572), *Plasmodium falciparum* CS protein at positions 378-398 (DIEKKIAKMEKASSVFNVVNS; SEQ ID NO: 2573), and *Streptococcus* 18kD protein at positions 116 (GAVDSILGGVATYGAA; SEQ ID NO:2574). Other examples include peptides bearing a DR 1-4-7 supermotif.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE® Epimmune, Inc., San Diego, Calif.) are designed on the basis of their binding activity to most HLA-DR (human HLA class II) molecules. For instance, a pan-DR-binding epitope peptide having the formula: aKXVWANTL-KAAa, where "X" is either cyclohexylalanine, phenylalanine, or tyrosine, and a is either D-alanine or L-alanine (SEQ ID NO:2575), has been found to bind to most HLA-DR alleles, and to stimulate the response of T helper lymphocytes from most individuals, regardless of their HLA type.

T helper epitopes can also be modified to alter their biological properties. For example, peptides presenting T helper epitopes can contain D-amino acids to increase their resistance to proteases and thus extend their serum half-life. Also, the epitope peptides of the invention can be conjugated to other molecules such as lipids, proteins or sugars, or any other synthetic compounds, to increase their biological activity. Specifically, the T helper peptide can be conjugated to one or more palmitic acid chains at either the amino or carboxyl termini.

In some embodiments it may be desirable to include in the pharmaceutical compositions of the invention at least one component which primes cytotoxic T lymphocytes. Lipids have been identified as agents capable of priming CTL in vivo against viral antigens. For example, palmitic acid residues can be attached to the ε-and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinly-seryl-serine ($P_3CSS$) can be used to prime virus specific CTL when covalently attached to an appropriate peptide. See, Deres, et al., *Nature* 342:561 (1989). Peptides of the invention can be coupled to $P_3CSS$, for example, and the lipopeptide administered to an individual to specifically prime a CTL response to the target antigen. Moreover, because the induction of neutralizing antibodies can also be primed with $P_3CSS$-conjugated epitopes, two such compositions can be combined to more effectively elicit both humoral and cell-mediated responses to infection.

In addition, additional amino acids can be added to the termini of a peptide to provide for ease of linking peptides one to another, for coupling to a carrier support, or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide, particularly class I peptides. However, it is to be noted that modification at the carboxyl terminus may, in some cases, alter binding characteristics of the peptide. In addition, the peptide or oligopeptide sequences can differ from the natural sequence by being modified by terminal-$NH_2$ acylation, e.g., by alkanoyl ($C_1$-$C_{20}$) or thioglycolyl acetylation, terminal-carboxylamidation, e.g., ammonia, methylamine, etc. In some instances these modifications may provide sites for linking to a support or other molecule.

IV.J. Administration of Vaccines for Therapeutic or Prophylactic Purposes

The peptides of the present invention and pharmaceutical and vaccine compositions of the invention are useful for administration to mammals, particularly humans, to treat and/or prevent HBV infection. Vaccine compositions containing the peptides of the invention are administered to a patient susceptible to or otherwise at risk for HBV infection to elicit an immune response against HBV antigens and thus enhance the patient's own immune response capabilities. In therapeutic applications, compositions are administered to a patient in an amount sufficient to elicit an effective CTL response to the virus or tumor antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician. Generally the dosage range for an initial immunization (i.e., therapeutic or prophylactic administration) is between about 1.0 µg to about 5000 µg of peptide, typically between about 10 µg to about 1000 µg, for a 70 kg patient, followed by boosting dosages of between about 1.0 µg to about 5000 µg of peptide pursuant to a boosting regimen over weeks to months depending upon the patient's response and condition as determined by measuring specific CTL activity in the patient's blood. The peptides and compositions of the present invention may be employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

As noted above, the "CTL" peptides of the invention induce immune responses when contacted with a CTL specific to an epitope comprised by the peptide. The manner in which the peptide is contacted with the CTL is not critical to the invention. For instance, the peptide can be contacted with the CTL either in vivo or in vitro. If the contacting occurs in vivo, the peptide itself can be administered to the patient, or other vehicles, e.g., DNA vectors encoding one or more peptides, vital vectors encoding the peptide(s), liposomes and the like, can be used, as described herein.

For pharmaceutical compositions, the immunogenic peptides, or DNA encoding them, are generally administered to an individual already infected with HBV. The peptides or DNA encoding them can be administered individually or as fusions of one or more peptide sequences. Those in the incubation phase or the acute phase of infection can be treated with the immunogenic peptides separately or in conjunction with other treatments, as appropriate.

For therapeutic use, administration should generally begin at the first diagnosis of HBV infection. This is followed by boosting doses until at least symptoms are substantially abated and for a period thereafter. In chronic infection, loading doses followed by boosting doses may be required.

Treatment of an infected individual with the compositions of the invention may hasten resolution of the infection in acutely infected individuals. For those individuals susceptible (or predisposed) to developing chronic infection, the compositions are particularly useful in methods for preventing the evolution from acute to chronic infection. Where susceptible individuals are identified prior to or during infection, the composition can be targeted to them, minimizing need for administration to a larger population.

The peptide or other compositions as used for the treatment of chronic HBV infection and to stimulate the immune system to eliminate pathogen-infected cells in, e.g., persons who have not manifested symptoms of disease but who act as a disease vector. In this context, it is generally important to provide an amount of immuno-potentiating peptide in a formulation and mode of administration sufficient to effectively stimulate a cytotoxic T cell response; compositions which stimulate helper T cell responses can also be given in accordance with this embodiment of the invention. Thus, for treatment of chronic infection, a representative dose is in the range of about 1.0 µg to about 5000 µg, preferably about 10 µg to 1000 µg, per 70 kg patient weight per dose. Immunizing doses followed by boosting doses at established intervals, e.g., from four weeks to six months, may be required, possibly for a prolonged period of time to effectively immunize an individual. In the case of chronic infection, administration should continue until at least clinical symptoms or laboratory tests indicate that the viral infection has been eliminated or substantially abated and for a period thereafter. The dosages, routes of administration, and dose schedules are adjusted in accordance with methodologies known in the art.

The pharmaceutical compositions for therapeutic treatment are intended for parenteral, topical, oral, intrathecal, or local administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, ie., from less than about 0.1%, usually at or at least about 2% to as much as 20% to 50% or more by weight, and will be selected primarily by fluid volumes, viscosities, etc., in accordance with the particular mode of administration selected.

The peptides of the invention may also be administered via liposomes, which serve to target the peptides to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

The vaccine compositions of the invention may also be used purely as prophylactic agents. Vaccine compositions containing the peptide epitopes of the invention are administered to a patient susceptible to, or otherwise at risk for, HBV infection to elicit an immune response against HBV antigens and thus enhance the patient's own immune response capabilities following exposure to HBV. Generally the dosage range for an initial prophylactic immunization is between about 1.0 μg to about 5000 μg of peptide, typically between about 10 μg to about 1000 μg, for a 70 kg patient. This is followed by boosting dosages of between about 1.0 μg to about 5000 μg of peptide administered at defined intervals from about four weeks to six months after the initial administration of vaccine. The immunogenicity of the vaccine may be assessed by measuring specific CTL activity in the patient's blood.

IV.K. Kits

The peptide and nucleic acid compositions of this invention can be provided in kit form together with instructions for vaccine administration. Typically the kit would include desired peptide compositions in a container, preferably in unit dosage form and instructions for administration. An alternative kit would include a minigene construct with desired nucleic acids of the invention in a container, preferably in unit dosage form together with instruction for administration. Lymphokines such as IL-2 or IL-12 may also be included in the kit. Other kit components that may also be desirable include, for example, a sterile syringe, booster dosages, and other desired excipients.

The invention will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments in accordance with the invention.

V. EXAMPLES

Example 1

HLA Class I Binding Assays

The following example of peptide binding to HLA-A3 supertype molecules demonstrates quantification of binding affinities of HLA class I peptides. Analogous binding assays can be performed for other peptides that bind class I or class II HLA molecules. Furthermore, binding assays can be performed with peptides that are not motif-bearing.

For example, the affinity of peptides bearing an HLA-A3 supermotif was determined as follows. Epstein-Barr virus (EBV)-transformed homozygous cell lines were used as sources of class I molecules. Cell lines include, e.g., GM3107 (A3, B7; Human Genetic Mutant Repository); BVR (A11, B35.3, Cw4; Human Genetic Mutant Repository); SPACH (A31, B62, Cw1/3; ASHI Repository Collection); LWAGS (A*3301, B14, and Cw8; ASHI Repository Collection) (Bodmer, et al., *Hum. Immunol.* 43:149, 1995), and a C1R transfectant characterized by Dr. Walter Storkus (University of Pittsburgh) for the isolation of A*6801. Cell lines were maintained as previously described (Sidney, et al., *J. Immunol.* 154:247 (1995); Sette, et al., *Mol. Immunol.* 31:813 (1994)).

Cell lysates were prepared and HLA class I molecules purified in accordance with disclosed protocols (Sidney, et al., *J. Immunol.* 154:247 (1995); Sette, et al., *Mol. Immunol.* 31:813 (1994)). Briefly, cells were lysed at a concentration of $10^8$ cells/ml in 50 mM Tris-HCl, pH 8.5, containing 1% Nonidet P-40 (Fluka Biochemika, Buchs, Switzerland), 150 mM NaCl, 5 mM EDTA, and 2 mM PMSF. The lysates were passed through 0.45 μM filters and cleared of nuclei and debris by centrifugation at 10,000 g for 20 minutes. HILA proteins were then purified by affinity chromatography. Columns of inactivated Sepharose CL 4B and Protein A Sepharose were used as precolumns. The cell lysate was depleted of HLA-B and HLA-C proteins by repeated passage over Protein A Sepharose beads conjugated with the anti-HLA(B,C) antibody B1.23.2 (Rebai, et al., *Tissue Antigens* 22:107 (1983)). Typically two to four passages were required for effective depletion. Subsequently, the anti HLA(A,B,C) antibody W6/32 (Barnstable, et al., *Cell* 14:9 (1978)) was used to capture HLA-A molecules. Protein purity, concentration, and effectiveness of depletion steps were monitored by sodium dodecyl sulfate-polyacrylamide gel electrophoresis (SDS-PAGE).

Binding Assays

Quantitative assays for the binding of peptides to soluble class I molecules on the basis of the inhibition of binding of a radiolabeled standard probe peptide to detergent solubilized HLA molecules were performed as described in the literature (Kubo, et al., *J. Immunol.* 152:3913 (1994); Kast, et al., *J. Immunol.* 152:3904 (1994); Sidney, et al., *J. Immunol.* 154: 247 (1995); Sette, et al., *Mol. Immunol.* 31:813 (1994); Ruppert, et al., *Cell* 74:929 (1993)). Briefly, 1-10 nM of radiolabeled probe peptide, iodinated by the Chloramine-T method (Greenwood, et al., *Biochem. J.* 89:114 (1963)), was co-incubated at room temperature with various amounts of HLA in the presence of 1 μM human $\beta_2$-microglobulin (Scripps Laboratories, San Diego, Calif., USA) and a cocktail of protease inhibitors. At the end of a two day incubation period, the percent of HLA-bound radioactivity was determined by size exclusion gel filtration chromatography on a TSK 2000 column.

The A3CON1 peptide (sequence KVFPYALINK; SEQ ID NO:2576) (Kubo, et al., *J. Immunol.* 152:3913 (1994)) was used as the radiolabeled probe for the A3, A11, A31, and A*6801 assays. A T7Y analogue of HBVc $_{141-151}$ (sequence STLPETYVVRRL; SEQ ID No:2577) (Missale, et al., *J. Exp. Med.* 177:751 (1993)) was used as the radiolabeled probe for the A*3301 assay. In the case of competitive assays, the concentration of peptide yielding 50% inhibition of the binding of the radiolabeled probe peptide ($IC_{50}$) was calculated. Peptides were usually tested at one or two high doses, and the $IC_{50}$ of peptides yielding positive inhibition were determined in subsequent experiments, in which two to six further dilutions were tested, as necessary. To achieve a suitable signal, HLA concentrations yielding approximately 15% binding of the radiolabled probe peptide were used for all competitive inhibition assays. Under these conditions the concentration of the labeled peptide is less than the concentration of the HLA molecule and the $IC_{50}$ is less than the concentration of the HLA molecule, therefore the measured $IC_{50}$s are reasonable approximations of the true $K_D$ values. Each competitor peptide was tested in two to four completely independent experiments. As a positive control, in each experiment, the unlabeled version of the relevant radiolabeled probe was tested and its $IC_{50}$ measured. The average $IC_{50}$ of A3CON1 for the A3, A11, A31, and A*6801 assays were 11, 6, 18, and 8 nM, respectively. The average $IC_{50}$ of the $HBV_c$ 141-151 peptide in the A*3301 assay was 29 nM.

Example 2

Implementation of the Extended Supermotif to Improve the Binding Capacity of Native Peptides by Creating Analogs HLA motifs and supermotifs (comprising primary and/or secondary residues) are useful in preparing highly cross-reactive native peptides, as demonstrated herein. Moreover, the definition of HLA motifs and supermotifs also allows one to engineer highly cross-reactive epitopes by identifying residues within a native peptide sequence which can be analoged, or "fixed", to confer upon a peptide certain characteristics, e.g., greater cross-reactivity within the group of HLA molecules that make-up the supertype, and/or greater binding affinity for some or all of those HLA molecules Examples of analog peptides that exhibit modulated binding affinity are provided.

Analogs representing primary anchor single amino acid residues substituted with I residues at the C-terminus of two different B7-like peptides (HBV env 313 and HBV pol 541) were synthesized and tested for their B7-supertype binding capacity. It was found that the I substitution had an overall positive effect on binding affinity and/or cross-reactivity in both cases. In the case of HBV env 313 the 19 (I at C-terminal position 9) replacement was effective in increasing cross-reactivity from 4 to 5 alleles bound by virtue of an almost 400-fold increase B*5401 binding affinity. In the case of HBV pol 541, increased cross-reactivity was similarly achieved by a substantial increase in B*5401 binding. Also, significant gains in binding affinity for B*0702, B51, and B*5301 were observed with the HBV pol 541 I9 analog.

Moreover, HLA supermotifs are of value in engineering highly cross-reactive peptides by identifying particular residues at secondary anchor positions that are associated with such cross-reactive properties. Demonstrating this, the capacity of a second set of peptides representing discreet single amino acid substitutions at positions one and three of five different B7-supertype binding peptides were synthesized and tested for their B-7 supertype binding capacity. In 4/4 cases the effect of replacing the native residue at position 1 with the aromatic residue F (an "F1" substitution) resulted in an increase in cross-reactivity, compared to the parent peptide, and, in most instances, binding affinity was increased three-fold or better (Table XXII). More specifically, for HBV env 313, MAGE2 170, and HCV core 168 complete supertype cross-reactivity was achieved with the F1 substitution analogs. These gains were achieved by dramatically increasing B*5401 binding affinity. Also, gains in affinity were noted for other alleles in the cases of HCV core 168((B*3501 and B*5301) and MAGE2 170((B*3501, B51 and B*5301). Finally, in the case of MAGE3 196, the F1 replacement was effective in increasing cross-reactivity because of gains in B*0702 binding. An almost 70-fold increase in B51 binding capacity was also noted.

Two analogs were also made using the supermotif positive F substitution at position three (an "F3" substitution). In both instances increases in binding affinity and cross-reactivity were achieved. Specifically, in the case of HBV pol 541, the F3 substitution was effective in increasing cross-reactivity by virtue of its effect on B*5401 binding. In the case of MAGE3 196, complete supertype cross-reactivity was achieved by increasing B*0702 and B*3501 binding capacity. Also, in the case of MAGE3 196, it is notable that increases in binding capacity between 40- and 5000-fold were obtained for B*3501, B51, B*5301, and B*5401.

In conclusion, these data demonstrate that by the use of even single amino acid substitutions, it is possible to increase the binding affinity and/or cross-reactivity of peptide ligands for HLA supertype molecules.

Example 3

Induction Of HLA-Restricted CTL By Subcutaneous Priming With HBV Peptide In Incomplete Freund's Adjuvant (IFA)

The immunogenicity of HLA class I binding peptides can be assessed in vivo as described in, e.g., Sette et al. *J. Immunol.* 153:5586-5592 (1994). This example illustrates such a procedure, whereby subcutaneous injection of HBV peptide in Incomplete Freund's Adjuvant (IFA) can be used to induce HBV-specific CTL in mice that are transgenic for a human HLA allele such as the human HLA-A11 allele.

Priming and In Vitro Restimulation: Mice that are transgenic for HLA-A11, (e.g. HLA-A11/Kb strain) are injected with 100 microliters of an emulsion of purified HBV peptide in IFA. The purified peptide comprises an A11 motif, and is selected from the preferred peptides listed in Table XVI or, alternatively, may be an analog peptide. The peptide epitope (50 μg/mouse) and equimolar amounts of the helper epitope HBV core 128-140 (140 μg/mouse) are dissolved in PBS/5% DMSO, emulsified in IFA, and injected subcutaneously at the base of the tail of the transgenic mice. Eleven days after priming, splenocytes ($5\times10^6$ cells/well in a 24-well plate) obtained from these animals are restimulated with syngeneic irradiated LPS blasts ($2\times10^6$/well) coated with peptide.

LPS blasts from unprimed HLA-A11 transgenic mice are prepared 72 hours before use by suspending splenocytes in medium containing LPS (25 μg/ml) and dextran sulfate (7 μg/ml). Coating is achieved by incubating 50 μg of peptide with $1.2\times10^6$ LPS blasts in a volume of 0.4 ml of RPMI medium supplemented with 10% FCS for 1 hour at 37° C. The cells are washed once and then co-cultured with splenocytes. After six days, effector cells are assayed, as outlined for example in Example 5, for cytotoxicity against $^{51}$Cr-labeled 3A4-721.221-A11$K^b$ target cells in the presence of the peptide.

The effector cells ($2\times10^6$ cells/well) are re-stimulated at weekly intervals. For the first re-stimulation, peptide-coated LPS blasts are used, followed by peptide-coated A11/$K^b$ cells. Six days after re-stimulation, effector cells are assayed for cytotoxicity as above.

Example 4

Recognition of Generation of Endogenous Processed Antigens After Priming

This example determines that CTL induced by in vivo priming with peptide (as disclosed in Example 3) recognize endogenously synthesized antigens.

Effector cells from the procedure disclosed in Example 3 are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled 3A4-721.221-A11/$K^b$ target cells, in the absence or presence of peptide, and also tested on $^{51}$Cr labeled target cells bearing the endogenously synthesized antigen.

The result will demonstrate that CTL lines obtained from animals primed with peptide epitope recognize endogenously synthesized HBV antigen.

Example 5

Activity of CTL-HTL Conjugated Epitopes in Transgenic Mice

This example illustrates the induction of CTLs in transgenic mice by use of an HBV CTL/HTL peptide conjugate. An analagous study may be found in Oseroff et al. *Vaccine* 16:823-833 (1998). The peptide composition can comprise multiple CTL and/o HTL epitopes. Such a peptide composition can comprise a lipidated HTL epitope conjugated to a preferred CTL epitope containing, for example, an A11 motif or an analog of that epitope.

Lipopeptides are prepared by coupling the appropriate fatty acid to the amino terminus of the resin bound peptide. A typical procedure is as follows: A dichloromethane solution of a four-fold excess of a pre-formed symmetrical anhydride of the appropriate fatty acid is added to the resin and the mixture is allowed to react for two hours. The resin is washed with dichloromethane and dried. The resin is then treated with trifluoroacetic acid in the presence of appropriate scavengers [e.g. 5% (v/v) water] for 60 minutes at 20° C. After evaporation of excess trifluoroacetic acid, the crude peptide is washed with diethyl ether, dissolved in methanol and precipitated by the addition of water. The peptide is collected by filtration and dried.

Preparation of peptides for immunization: Peptide compositions are typically resuspended in DMSO at a concentration of 20 mg/ml. Before use, peptides are prepared at the required concentration by dilution in saline or the appropriate medium.

Immunization procedures: A11/$K^b$ mice, which are transgenic for the human HLA A11 allele, are primed subcutaneously (base of the tail) with 0.1 ml of peptide conjugate formulated in saline, or DMSO/saline. Seven days after priming, splenocytes obtained from these animals are restimulated with syngeneic irradiated LPS-activated lymphoblasts coated with peptide.

Media:
a. RPMI-1640 supplemented with 10% fetal calf serum (FCS) 2 mM Glutamine, 50 μg/ml Gentamicin and $5\times10^{-5}$ M 2-mercaptoethanol serves as culture medium
b. RPMI-1640 containing 25 mM HEPES buffer and supplemented with 2% (FCS) is used as cell washing medium.

Cell lines: The 3A4-721.221-A11/$K^b$ cell line is used as target cells. This cell line is an EBV transformed cell line that was mutagenized and selected to be Class I negative which was transfected with an HLA-A11/$K^b$ gene.

LPS-activated lymphoblasts: Splenocytes obtained from transgenic mice are resuspended at a concentration of 1-1.5$\times 10^6$/ml in culture medium supplemented with 25 μg/ml LPS and 7 μg/ml dextran sulfate in 75 cm tissue culture flasks. After 72 hours at 37° C., the lymphoblasts are collected for use by centrifugation.

Peptide coating of lymphoblasts: Peptide coating of the LPS activated lymphoblasts is achieved by incubating $30\times10^6$ irradiated (3000 rads) lymphoblasts with 100 μg of peptide in 1 ml of R10 medium for 1 hr at 37° C. Cells are then washed once and resuspended in culture medium at the desired concentration.

In vitro CTL activation: One week after priming, spleen cells ($30\times10^6$ cells/flask) are co-cultured at 37° C. with syngeneic, irradiated (3000 rads), peptide coated lymphoblasts ($10\times10^6$ cells/flask) in 10 ml of culture medium/T25 flask. After six days, the effector cells are harvested and assayed for cytotoxic activity.

Assay for cytotoxic activity: Target cells (1.0-1.5$\times10^6$) are incubated at 37° C. in the presence of 200 μl of sodium $^{51}$Cr chromate. After 60 minutes, cells are washed three times and resuspended in R10 medium. Peptide is added where required at a concentration of 1 μg/ml. For the assay, 10$^4$ $^{51}$Cr-labeled target cells are added to different concentrations of effector cells (final volume of 200 μl) in U-bottom 96-well plates. After a 6 hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a 6 hour SiCr release assay. To obtain specific lytic units/$10^6$, the lytic units/$10^6$ obtained in the absence of peptide is subtracted from the lytic units/$10^6$ obtained in the presence of peptide. For example, if 30% $^{51}$Cr release is obtained at the E:T of 50:1 (i.e., $5\times10^5$ effector cells for 10,000 targets) in the absence of peptide and 5:1 (i.e., $5\times10^4$ effector cells for 10,000 targets) in the presence of peptide, the specific lytic units would be: $(1\times10^6(5\times10^4)-(1\times10^6(5\times10^5)=18$ LU/$10^6$.

The results are analyzed to assess the magnitude of the CTL responses of animals injected with the immunogenic CTL/HTL conjugate vaccine preparation. Analyses similar to this may be performed to evaluate the immunogenicity of peptide conjugates containing multiple CTL epitopes and/or multiple HTL epitopes. In accordance with these procedures it is found that CTL and HTL responses are induced.

Example 7

Induction Of Specific CTL Response In Humans

A human clinical trial for an immunogenic composition comprising CTL and HTL epitopes is set up as an IND Phase I, dose escalation study (5, 50 and 500 μg) and carried out as a randomized, double-blind, placebo-controlled trial. Such a trial is designed, for example, as follows:

A total of about 27 subjects are enrolled and divided into 3 groups:

Group I: 3 subjects are injected with placebo and 6 subjects are injected with 5 μg of peptide composition;

Group II: 3 subjects are injected with placebo and 6 subjects are injected with 50 μg peptide composition;

Group III: 3 subjects are injected with placebo and 6 subjects are injected with 500 μg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

Thus, the vaccine is found to be both safe and efficacious.

Example 8

Phase II Trials in Patients Infected with HBV

Phase II trials are performed to study the effect of administering the CTL-HTL peptide compositions to patients (male and female) having chronic HBV infection. A main objective of the trials is to determine an effective dose and regimen for inducing CTLs in chronically infected HBV patients, to establish the safety of inducing a CTL response in these patients, and to see to what extent activation of CTLs improves the clinical picture of chronically infected CTL patients, as manifested by a transient flare in alanine aminotransferase (ALT), normalization of ALT, and reduction in HBV DNA. Such a study is designed, for example, as follows:

The studies are performed in multiple centers in the U.S. and Canada. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects are recorded.

There are three patient groupings. The first group is injected with 50 micrograms of the peptide composition and the second and third groups with 500 and 5,000 micrograms of peptide composition, respectively. The patients within each group range in age from 21-65 and include both males and females. The patients represent diverse ethnic backgrounds. All of them are infected with HBV for over five years and are HIV, HCV and HDV negative, but have positive levels of HBe antigen and HBs antigen.

The magnitude and incidence of ALT flares and the levels of HBV DNA in the blood are monitored to assess the effects of administering the peptide compositions. The levels of HBV DNA in the blood are an indirect indication of the progress of treatment. The vaccine composition is found to be both safe and efficacious in the treatment of chronic HBV infection.

Example 9

Selection of CTL and HTL Epitopes for Inclusion in an HBV-specific Vaccine

This example illustrates the procedure for the selection of peptide epitopes for vaccine compositions of the invention.

The following principles are utilized when selecting an array of epitopes for inclusion in a polyepitopic composition, or for selecting epitopes to be included in a vaccine composition and/or to be encoded by a minigene. Each of the following principles are balanced in order to make the selection.

1.) Epitopes are selected which, upon administration, mimic immune responses that have been observed to be correlated with HBV clearance. For HLA Class I this includes 3-4 epitopes that come from at least one antigen of HBV. In other words, it has been observed that in patients who spontaneously clear HBV, that they had generated an immune response to at least 3 epitopes on at least one HBV antigen. For HLA Class II a similar rationale is employed; again 3-4 epitopes are selected from at least one HBV antigen.

2.) Epitopes are selected that have the requisite binding affinity established to be correlated with immunogenicity: for HLA Class I an $IC_{50}$ of 500 nM or less, or for Class II an $IC_{50}$ of 1000 nM or less.

3.) Sufficient supermotif bearing peptides, or a sufficient array of allele-specific motif bearing peptides, are selected to give broad population coverage. For example, epitopes are selected to provide at least 80% population coverage. A Monte Carlo analysis, a statistical evaluation known in the art, is employed to assess population coverage.

4.) When selecting epitopes for HBV antigens it is often preferable to select native epitopes. Therefore, of particular relevance for infectious disease vaccines, are epitopes referred to as "nested epitopes." Nested epitopes occur where at least two epitopes overlap in a given peptide sequence. A peptide comprising "transcendent nested epitopes" is a peptide that has both HLA class I and HLA class II epitopes in it.

When providing nested epitopes, a sequence that has the greatest number of epitopes per provided sequence is provided. A limitation on this principle is to avoid providing a peptide that is any longer than the amino terminus of the amino terminal epitope and the carboxyl terminus of the carboxyl terminal epitope in the peptide. When providing a longer peptide sequence, such as a sequence comprising nested epitopes, the sequence is screened in order to insure that it does not have pathological or other deleterious biological properties.

5.) When creating a minigene, as disclosed in greater detail in the Example 10, an objective is to generate the smallest peptide possible that encompasses the epitopes of interest. The principles employed are similar, if not the same as those employed when selecting a peptide comprising nested epitopes. Thus, upon determination of the nucleic acid sequence to be provided as a minigene, the peptide encoded thereby is analyzed to determine whether any "junctional epitopes" have been created. A junctional epitope is an actual binding epitope, as predicted, e.g., by motif analysis. Junctional epitopes are to be avoided because the recipient may generate an immune response to that epitope. Of particular concern is a junctional epitope that is a "dominant epitope." A dominant epitope may lead to such a zealous response that immune responses to other epitopes are diminished or suppressed.

Peptide epitopes for inclusion in vaccine compositions are, for example, selected from those lsited in Table XXIII. A vaccine composition comprised of selected peptides, when administered, is safe, efficacious, and elicits an immune response similar in magnitude of an immune response that clears an acute HBV infection.

Example 10

Construction of Minigene Multi-Epitope DNA Pslasmids

Expression plasmids have been constructed and evaluated as described, for example, in U.S. Ser. No. 60/085,751 filed May 15, 1998 and U.S. Ser. No. 09/078,904 filed May 13, 1998. The binding peptide epitopes and their positions for some of the plasmids described therein are shown in FIG. 1 as example of the orientation of peptide epitopes in minigene constructs. Such a plasmid may, for example, also include multiple CTL and HTL peptide epitopes. In the present example, HLA-A11 motif-bearing peptides are used in conjunction with DR supermotif-bearing peptides. Preferred A11 epitopes are identified, for example, in Table XVI or Table XXI and peptide epitopes recognized by HLA DR molecules (Tables XVIII and XIX). Four class I A11 motif-bearing peptide epitopes or analogs of those peptide epitopes derived from the same HBV antigen, e.g. the envelope protein, are selected as CTL epitopes. Four class II motif-bearing peptide epitopes derived from the same antigen, e.g., the envelope protein, are selected as HTL epitopes. These epitopes are then incorporated into a minigene for expression in an expression vector.

This example illustrates the methods to be used for construction of such a minigene-bearing expression plasmid. Other expression vectors that may be used for minigene compositions are available and known to those of skill in the art.

A pMin minigene DNA plasmid is constructed from an early generation DNA plasmid designated as pMin.0. This plasmid contains a consensus Kozak sequence and a consensus murine kappa Ig-light chain signal sequence followed by a string of CTL and HTL epitopes selected in accordance with principles disclosed herein. The pMIN sequence encodes an open reading frame fused to the Myc and His antibody epitope tag coded for by the pcDNA 3.1 Myc-His vector.

Overlapping oligonucleotides, for example eight oligonucleotides, averaging approximately 70 nucleotides in length with 15 nucleotide overlaps, are synthesized and HPLC-purified. The oligonucleotides encode the selected peptide epitopes as well as appropriate linker nucleotides. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For the first PCR reaction, 5 µg of each of two oligonucleotides are annealed and extended: Oligonucleotides 1+2, 3+4, 5+6, and 7+8 are combined in 100 µl reactions containing Pfu polymerase buffer (1×=10 mM KCL, 10 mM $(NH_4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product for 25 additional cycles. The full-length product is gel-purified and cloned into pCR-blunt (Invitrogen) and individual clones are screened by sequencing.

Example 11

The Plasmid Construct and the Degree to which it Induces Immunogenicity

The degree to which the plasmid construct prepared using the methodology outlined in Example 10 is able to induce immunogenicity is evaluated through in vivo injections into mice and in vitro CTL culture and cytotoxicity assays as detailed e.g., in U.S. Ser. No. 60/085,751 filed May 15, 1998. To assess the capacity of the pMin minigene construct to induce CTLs in vivo, HLA-A11/$K^b$ transgenic mice are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide.

Splenocytes from immunized animals are stimulated twice with each of the peptide epitopes encoded in the minigene, then assayed for peptide-specific cytotoxic activity in a $^{51}Cr$ release assay. The results indicate the magnitude of the CTL response directed against each of its A11-restricted epitopes, thus indicating the in vivo immunogenicity of the minigene vaccine. It is, therefore, found that the minigene elicits immune responses directed toward A11-restricted epitopes.

Example 12

Peptide Composition for Prophylactic Uses

Vaccine compositions of the present invention are used to prevent HBV infection in persons who are at risk. For example, a polyepitopic peptide epitope composition containing multiple CTL and HTL epitopes such as those selected in Examples 9 and/or 10, which are also selected to target greater than 80% of the population, is administered to individuals at risk for HBV infection. The composition is provided as a single lipidated polypeptide that encompasses multiple epitopes. The vaccine is administered in an aqueous carrier comprised of Freunds Incomplete Adjuvant. The dose of peptide for the initial immunization is from about 1 to about 5,000 µg for a 70 kg patient. The initial administration of vaccine is followed by booster dosages at 4 weeks followed by evaluation of the magnitude of the immune response in the patient by techniques that determine the presence of epitope-specific CTL populations in a PBMC sample. Additional booster doses are administered as required. The composition is found to be both safe and efficacious as a prophylaxis against HBV infection.

Alternatively, the polyepitopic peptide composition can be administered as a nucleic acid in accordance with methodologies known in the art and disclosed herein.

Example 13

Polyepitopic Vaccine Compositions Derived from Native HBV Sequences

A native HBV polyprotein sequence is screened, preferably using computer algorithms defined for each class I and/or class II supermotif or motif, to identify "relatively short" regions of the polyprotein that comprise multiple epitopes. This relatively short sequence that contains multiple distinct, even overlapping, epitopes is selected and used to generate a minigene construct. The construct is engineered to express the peptide, which corresponds to the native protein sequence. The "relatively short" peptide is less than 100 amino acids in length, preferably less than 75 amino acids in length, and more preferably less than 50 amino acids in length. The protein sequence of the vaccine composition is selected because it has maximal number of epitopes contained within the sequence. As noted herein, epitope motifs may be overlapping (i.e., frame shifted relative to one another) with frame shifted overlapping epitopes, e.g. two 9-mer epitopes can be present in a 10 amino acid peptide. Such a vaccine composition is administered for therapeutic or prophylactic purposes.

The vaccine composition will preferably include, for example, three CTL epitopes and at least one HTL epitope from the source antigen. Junctional sequences will be analyzed to avoid sequences containing a potentially immunodominant epitope. This polyepitopic native sequence is administered either as a peptide or as a nucleic acid sequence which encodes the peptide. Alternatively, an analog can be made of this native sequence.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment directs the immune response to sequences that are present in native HBV antigens. Lastly, the embodiment provides an economy of scale when producing nucleic acid vaccine compositions.

Related to this embodiment, computer programs can be derived which identify, in a target sequence, the greatest number of epitopes per sequence length.

Example 14

Polyepitotpic Vaccine Compositions Directed to Multiple Diseases

The HBV peptide epitopes of the present invention are used in conjunction with peptide epitopes from target antigens related to one or more other diseases, to create a vaccine composition that is useful for the prevention or treatment of HBV as well as another disease. Examples of other diseases include, but are not limited to, HIV, HCV, and HPV.

For example, a polyepitopic peptide composition comprising multiple CTL and HTL epitopes that target greater than 98% of the population may be created for administration to individuals at risk for both HBV and HIV infection. The composition can be provided as a single polypeptide that incorporates the multiple epitopes from the various disease-associated sources.

Example 15

Use of Peptides to Evaluate an Immune Response

Peptides of the invention may be used to analyze an immune response for the presence of specific CTL populations corresponding to HBV. Such an analysis may be performed as described by Ogg et al., *Science* 279:2103-2106, 1998. In the following example, peptides in accordance with the invention are used as a reagent for diagnostic or prognostic purposes, not as an immunogen.

In this example highly sensitive human leukocyte antigen tetrameric complexes ("tetramers") may be used for a cross-sectional analysis of, for example, HBV Env-specific CTL frequencies from untreated HLA A*0201-positive indiviuals at different stages of infection using an HBV Env peptide containing an A2.1 extended motif. Tetrameric complexes are synethesized as described (Musey et al., *N. Engl. J. Med.* 337:1267, 1997). Briefly, purified HLA heavy chain (A2.1 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5'triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

Approximately one million PBMCs are centrifuged at 300 g for 5 minutes and resuspended in 50 ul of cold phosphate-buffered saline. Tri-color analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixaation. Gates are applied to contain >99.98% of control samples. Controls for the tetramers include both A*0201-negative individuals and A*0201-positive uninfected donors. The percentage of cells stained with the tetramer is then determined by flow cytometry. The results indicate the number of cells in the PBMC sample that contain epitope-restricted CTLs, thereby readily indicating the stage of infection with HBV or the status of exposure to HBV or to a vaccine that elicits a protective response.

Example 16

Use of Peptide Epitopes to Evaluate Recall Responses

The peptide epitopes of the invention are used as reagents to evaluate T cell responses such as acute or recall responses, in patients. Such an analysis may be performed on patients who have recovered from infection or who are chronically infected with HBV or who have been vaccinated with an HBV vaccine.

For example, the class I restricted CTL response of persons at risk for HBV infection who have been vaccinated may be analyzed. The vaccine may be any HBV vaccine. PBMC are collected from vaccinated individuals and HLA typed. Appropriate peptide reagents that, are highly conserved and, optimally, bear supermotifs to provide cross-reactivity with multiple HLA supertype family members are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 μg/ml), and Hepes (10 mM) containing 10% heat-inactivated human AB serum (complete RPMI) and plated using microculture formats. Synthetic peptide is added at 10 μg/ml to each well and recombinant HBc Ag is added at 1 μg/ml to each well as a source of T cell help during the first week of stimulation.

In the microculture format, 4×10$^5$ PBMC are stimulated with peptide in 8 replicate cultures in 96-well round bottom plate in 100 μl/well of complete RPMI. On days 3 and 10, 100 ml of complete RPMI and 20 U/ml final concentration of rIL-2 are added to each well. On day 7 the cultures are transferred into a 96-well flat-bottom plate and restimualted with peptide, rIL-2 and 10$^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with uninfected control subjects as previously described (Rehermann, et al., *Nature Med.* 2:1104,1108, 1996; Rehermann et al., *J. Clin. Invest.* 97:1655-1665, 1996; and Rehermann et al., *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2678, 1992).

Cytotoxicity assays are performed in the following manner. Target cells consist of either allogeneic HLA-matched or autologous EBV-transformed B lymphoblastoid cell line that are incubated overnight with synthetic peptide at 10 μM and labeled with 100 μCi of $^{51}$Cr (Amersham Corp., Arlington Heights, Ill.) for 1 hour after which they are washed four times with HBSS. Cytolytic activity is determined in a standard 4-h, split well $^{51}$Cr release assay using U-bottomed 96 well plates containing 3,000 targets/well. Stimulated PBMC are tested at E/T ratios of 20-50:1 on day 14. Percent cytotoxicity is determined from the formula: 100 x [(experimental release-spontaneous release)/maximum release-spontaneous release)]. Maximum release is determined by lysis of targets by detergent (2% Triton X-100® Sigma Chemical Co., St. Louis, Mo.). Spontaneous release is <25% of maximum release for all experiments.

The results of such an analysis will indicate to what extent HLA-restricted CTL populations have been stimulated with the vaccine. Of course, this protocol can also be used to monitor prior HBV exposure.

The above examples are provided to illustrate the invention but not to limit its scope. For example, the human terminology for the Major Histocompatibility Complex, namely HLA, is used throughout this document. It is to be appreciated that these principles can be extended to other species as well. Moreover, peptide epitopes have been disclosed in the related application U.S. Ser. No. 08/820,360, which was previously incorporated by reference. Thus, other variants of the invention will be readily apparent to one of ordinary skill in the art and are encompassed by the appended claims. All publications, patents, and patent application cited herein are hereby incorporated by reference for all purposes.

TABLE I

| | POSITION 2 (Primary Anchor) | POSITION 3 (Primary Anchor) | POSITION C Terminus (Primary Anchor) |
|---|---|---|---|
| SUPERMOTIF | | | |
| A1 | T,I,*L,V,M,S* | | F,W,Y |
| A2 | L,I,V,M,*A,T,Q* | | I,V,*M,A,T,L* |
| A3 | V,S,M,A,*T,L,I* | | R,K |
| A24 | Y,F,*W,I,V,L,M,T* | | F,I,*Y,W,L,M* |
| B7 | | P | V,I,L,F,*M,W,Y,A* |
| B27 | | R,H,K | F,Y,L,*W,M,I* |
| B44 | | E,D | F,W,Y,L,I,M,V,A |
| B58 | | A,T,S | F,W,Y,*L,I,V* |
| B62 | | Q,L,*I,V,M,P* | F,W,Y,*M,I,V* |
| MOTIF | | | |
| A1 | T,S,M | | Y |
| A1 | | D,E,*A,S* | Y |
| A2.1 | L,M,*V,O,I,A,T* | | V,*L,I,M,A,T* |
| A3 | | L,M,V,I,S,A,T,F,C,G,D | K,Y,R,*H,F,A* |
| A11 | | V,T,M,L,I,S,A,G,N,C,D,F | K,*R,Y,H* |
| A24 | | Y,F,W,*M* | F,L,I,W |
| A*3101 | | M,V,T,*A,L,I,S* | R,*K* |
| A*3301 | | M,V,A,L,F,*I,S,T* | R,K |
| A*6801 | | A,V,T,*M,S,L,I* | R,K |
| B*0702 | | P | L,M,F,*W,Y,A,I,V* |
| B*3501 | | P | L,M,F,W,Y,*I,V,A* |
| B51 | | P | L,I,V,F,*W,Y,A,M* |
| B*5301 | | P | I,M,F,W,Y,*A,L,V* |
| B*5401 | | P | A,T,I,V,*L,M,F,W,Y* |

Bold residues are preferred, italicized residues are less preferred. A peptide is considered motif-bearing if it has primary anchors at each primary anchor position for a motif or supermotif as specified in the above table.

TABLE II

| SUPER-MOTIFS | | 1 | 2 | 3 | 4 | 5 | 6 | 7 | 8 | C-terminus |
|---|---|---|---|---|---|---|---|---|---|---|
| A1 | | | | 1° Anchor T, I, L, V, M, S | | | | | | 1° Anchor F, W, Y |
| A2 | preferred | | | 1° Anchor L, I, V, M, A, T, Q | Y,F,W (4/5) | | Y,F,W (3/5) | Y,F,W (4/5) | P (4/5) | 1° Anchor L, I, V, M, A, T |
| A3 | preferred | | F,W,Y (5/5); L,I,V,M (3/5) | 1° Anchor V, S, M, A, T, L, I | | | | | | 1° Anchor R, K |
| | deleterious | | D,E (3/5); P (5/5); G (4/5); A (3/5); Q,N (3/5) | | D,E (4/5) | | | | | |
| A24 | | | | 1° Anchor Y, F, W, I, V, L, M, T | | | | | | 1° Anchor F, I, Y, W, L, M |
| B7 | preferred | | F,W,Y (5/5); L,I,V,M (3/5) | 1° Anchor P | F,W,Y (4/5) | | | | F,W,Y (3/5) | 1° Anchor V, I, L, F, M, W, Y, A |
| | deleterious | | D,E (3/5); P (5/5); G (4/5); A (3/5); Q,N (3/5) | | | D,E (3/5) | G (4/5) | Q,N (4/5) | D,E (4/5) | |
| B27 | | | | 1° Anchor R, H, K | | | | | | 1° Anchor F, Y, L, W, M, I |
| B44 | | | | 1° Anchor E, D | | | | | | 1° Anchor F, W, Y, L, I, M, V, A |
| B58 | | | | 1° Anchor A, T, S | | | | | | 1° Anchor F, W, Y, L, I, V |
| B62 | | | | 1° Anchor Q, L, I, V, M, P | | | | | | 1° Anchor F, W, Y, M, I, V |

| MOTIFS | | 1 | 2 | 3 | 4 | 5 | 6 | 7 | 8 | C-terminus |
|---|---|---|---|---|---|---|---|---|---|---|
| A1 9-mer | preferred | | G,F,Y,W | 1° Anchor S, T, M | D,E,A | Y,F,W | | P | D,E,Q,N | 1° Anchor Y |
| | deleterious | | D,E | | R,H,K,L,I,V,M P | A | H | A | | Y,F,W |

TABLE II-continued

| | | | 1 | 2 | 3 | 4 | 5 | 6 | 7 | 8 | 9 |
|---|---|---|---|---|---|---|---|---|---|---|---|
| A1 9-mer | preferred | | G,R,H,K | A,S,T,C,I,V,M | 1° Anchor D,E,A,S | G,S,T,C | A,S,T,C | Y,F,W,Q,N | A,S,T,C | L,I,V,M | D,E | 1° Anchor Y |
| | deleterious | | A | R,H,K,D,E,P,Y,F,W | | D,E | P,Q,N | | R,H,K | P,G | G,P | |

POSITION

| | | 1 | 2 | 3 | 4 | 5 | 6 | 7 | 8 | 9 or C-terminus | C-terminus |
|---|---|---|---|---|---|---|---|---|---|---|---|
| A1 9-mer | preferred | Y,F,W | 1° Anchor S,T,M | D,E,A,Q,N | A | Y,F,W,Q,N | | P,A,S,T,C | G,D,E | P | |
| A1 10-mer | preferred | | G,P | R,H,K,G,L,I,V,M | D,E | R,H,K | | R,H,K, Y,F,W | R,H,K | A | |
| | deleterious | Y,F,W | S,T,C,L,I,V,M | 1° Anchor D,E,A,S | A | Y,F,W | | P,G | G | Y,F,W | |
| A2.1 9-mer | preferred | R,H,K | R,H,K,D,E,P,Y,F,W | | | P | G | P,R,H,K | Q,N | | |
| | deleterious | Y,F,W | 1° Anchor L,M,I,V,Q,A,T | Y,F,W | S,T,C | Y,F,W | | A | P | 1° Anchor V,L,I,M,A,T | |
| A2.1 10-mer | preferred | D,E,P | | D,E,R,K,H | | | | R,K,H | D,E,R,K,H | F,Y,W,L,V,I,M | |
| | deleterious | A,Y,F,W | 1° Anchor L,M,I,V,Q,A,T | L,V,I,M | G | R,K,H,A P | G | | R,K,H | D,E,R K,L,H | 1° Anchor V,L,I,M,A,T |
| A3 | preferred | D,E,P | | D,E | | | | | | | |
| | deleterious | R,H,K | 1° Anchor L,M,V,I,S, A,T,F,C,G,D | Y,F,W | P,R,H,K,K, Y,F,W | A | Y,F,W | | P | 1° Anchor K,Y,R,H,F,A | |
| A11 | preferred | D,E,P | | D,E | | | | | | | |
| | deleterious | A | 1° Anchor V,T,L,M,I,S, A,G,N,C,D,F | Y,F,W | Y,F,W | A | Y,F,W | Y,F,W | P | 1° Anchor K,R,Y,H | |
| | deleterious | D,E,P | | | | | | A | G | | |

TABLE II-continued

| | | 1 | 2 | 3 | 4 | 5 | 6 | 7 | 8 | C-terminus |
|---|---|---|---|---|---|---|---|---|---|---|
| A24 9-mer | preferred | Y,F,W,R,H,K | 1° Anchor Y,F,W,M | | S,T,C | | Y,F,W | Y,F,W | | 1° Anchor F,L,I,W |
| | deleterious | D,E,G | D,E | | G | Q,N,P | | | A,Q,N | |
| A24 10-mer | preferred | | 1° Anchor Y,F,W,M | | P | YFWP | D,E,R,H,K | | | 1° Anchor F,L,I,W |
| A3101 | preferred | R,H,K | 1° Anchor M,V,T,A,L,I,S | Y,F,W | Q,N | R,H,K | D,E | Y,F,W | Q,N | 1° Anchor R,K |
| | deleterious | | | | P | | Y,F,W | D,E | A,P | D,E,A |
| A3301 | preferred | D,E,P | 1° Anchor M,V,A,L,F,I,S,T | D,E | | A,D,E | | A,Y,F,W | | 1° Anchor R,K |
| | deleterious | | | | | | | | D,E | |
| A6801 | preferred | G,P Y,F,W,S,T,C | 1° Anchor A,V,T,M,S,L,I | D,E | Y,F,W,I,V,M | | Y,F,W | Y,F,W | P | 1° Anchor R,K |
| | deleterious | | | | | | | | | |
| B0702 | preferred | R,H,K,F,W,Y | 1° Anchor P | D,E,G R,H,K | R,H,K | R,H,K | R,H,K | R,H,K | A,P | 1° Anchor L,M,F,W,Y,I,V,A |
| | deleterious | G,P | | | | | | | | |
| B3501 | preferred | D,E,Q,N,P | 1° Anchor P | D,E,P | D,E | D,E | G,D,E | Q,N | D,E | 1° Anchor L,M,F,W,Y,I,V,A |
| | deleterious | F,W,Y,L,I,V,M | | | | | F,W,Y | | | |
| B51 | preferred | A,G,P | | | G | | | | | |
| | deleterious | L,I,V,M,F,W,Y | 1° Anchor P | F,W,Y | S,T,C | F,W,Y | | G | F,W,Y | 1° Anchor L,I,V,F,W,Y,A,M |
| | | A,G,P,D,E,R,H,K,S,T,C | | | | D,E | | D,E,Q,N | G,D,E | |
| B5301 | preferred | L,I,V,M,F,W,Y | 1° Anchor P | F,W,Y | S,T,C | F,W,Y | | L,I,V,M, F,W,Y | F,W,Y | 1° Anchor I,M,F,W,Y,A,L,V |
| | deleterious | A,G,P,Q,N | | | | | G | R,H,K,Q,N | D,E | |

TABLE II-continued

| | preferred | 1° Anchor P | F,W,Y | | L,I,V,M | A,L,I,V,M | F,W,Y,A,P | 1° Anchor A, T, I, V, L, *M, F, W, Y* |
|---|---|---|---|---|---|---|---|---|
| B5401 | | | F,W,Y,L, I,V,M | | L,I,V,M | A,L,I,V,M | F,W,Y,A,P | |
| | deleterious | G,P,Q,N,D,E | G,D,E,S, T,C | | R,H,K,D,E D,E | Q,N,D,G,E | D,E | |

Italicized residues indicate less preferred or "tolerated" residues.
The information in this Table II specific for 9-mers unless otherwise specified.

TABLE III

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | F,M,Y,*L,I,V,W* | M | T | | I | V,S,T,C,*P, A,L,I,M* | M,H | | M,H |
| | deleterious | | | | W | | | R | | W,D,E |
| DR1 | preferred | M,F,*L,I,V,W,Y* | | | P,A,M,Q | | V,M,A,T, *S,P,L,I,C* | M | | A,V,M |
| | deleterious | | C | C,H | F,D | C,W,D | | G,D,E | D | |
| DR7 | preferred | M,F,*L,I,V,W,Y* | M | W | A | | I,V,M,S,A, *C,T,P,L* | M | | I,V |
| | deleterious | | C | | G | | | G,R,D | N | G |
| DR | Supermotif | M,F,*L,I,V,W,Y* | | | | | V,M,S,T,A, *C,P,L,I* | | | |

| DR3 MOTIFS | 1° anchor 1 | 2 | 3 | 1° anchor 4 | 5 | 1° anchor 6 |
|---|---|---|---|---|---|---|
| motif a preferred | L,I,V,M,F,Y | | | D | | |
| motif b preferred | L,I,V,M,F,A,Y | | | D,N,Q,E,S,T | | K,R,H |

Italicized residues indicate less preferred or "tolerated" residues.

TABLE IV

HLA Class I Standard Peptide Binding Affinity.

| ALLELE | STANDARD PEPTIDE | SEQUENCE | STANDARD BINDING AFFINITY (nM) | SEQ ID NO: |
|---|---|---|---|---|
| A*0101 | 944.02 | YLEPAIAKY | 25 | 2486 |
| A*0201 | 941.01 | FLPSDYFPSV | 5.0 | 2487 |
| A*0202 | 941.01 | FLPSDYFPSV | 4.3 | 2487 |
| A*0203 | 941.01 | FLPSDYFPSV | 10 | 2487 |
| A*0206 | 941.01 | FLPSDYFPSV | 3.7 | 2487 |
| A*0207 | 941.01 | FLPSDYFPSV | 23 | 2487 |
| A*6802 | 1141.02 | FTQAGYPAL | 40 | 2488 |
| A*0301 | 941.12 | KVFPYALINK | 11 | 2489 |
| A*1101 | 940.06 | AVDLYHFLK | 6.0 | 2490 |
| A*3101 | 941.12 | KVFPYALINK | 18 | 2489 |
| A*3301 | 1083.02 | STLPETYVVRR | 29 | 2491 |
| A*6801 | 941.12 | KVFPYALINK | 8.0 | 2489 |
| A*2401 | 979.02 | AYIDNYNKF | 12 | 2492 |
| B*0702 | 1075.23 | APRTLVYLL | 5.5 | 2493 |
| B*3501 | 1021.05 | FPFKYAAAF | 7.2 | 2494 |
| B51 | 1021.05 | FPFKYAAAF | 5.5 | 2494 |
| B*5301 | 1021.05 | FPFKYAAAF | 9.3 | 2494 |
| B*5401 | 1021.05 | FPFKYAAAF | 10 | 2494 |

TABLE V

HLA Class II Standard Peptide Binding Affinity.

| Allele | Nomenclature | Standard Peptide | Sequence | Binding Affinity (nM) | SEQ ID NO: |
|---|---|---|---|---|---|
| DRB1*0101 | DR1 | 515.01 | PKYVKQNTLKLAT | 5.0 | 2495 |
| DRB1*0301 | DR3 | 829.02 | YKTIAFDEEARR | 300 | 2496 |
| DRB1*0401 | DR4w4 | 515.01 | PKYVKQNTLKLAT | 45 | 2495 |
| DRB1*0404 | DR4w14 | 717.01 | YARFQSQTTLKQKT | 50 | 2497 |
| DRB1*0405 | DR4w15 | 717.01 | YARFQSQTTLKQKT | 38 | 2497 |
| DRB1*0701 | DR7 | 553.01 | QYIKANSKFIGITE | 25 | 2498 |

TABLE V-continued

HLA Class II Standard Peptide Binding Affinity.

| Allele | Nomen-clature | Standard Peptide Sequence | Binding Affinity (nM) | SEQ ID NO: |
|---|---|---|---|---|
| DRB1*0802 | DR8w2 | 553.01 QYIKANSKFIGITE | 49 | 2498 |
| DRB1*0803 | DR8w3 | 553.01 QYIKANSKFIGITE | 1600 | 2498 |
| DRB1*0901 | DR9 | 553.01 QYIKANSKFIGITE | 75 | 2498 |
| DRB1*1101 | DR5w11 | 553.01 QYIKANSKFIGITE | 20 | 2498 |
| DRB1*1201 | DR5w12 | 1200.05 EALIHQLKINPYVLS | 298 | 2499 |
| DRB1*1302 | DR6w19 | 650.22 QYIKANAKFIGITE | 3.5 | 2500 |
| DRB1*1501 | DR2w2β1 | 507.02 GRTQDENPVVHFFK NIVTPRTPPP | 9.1 | 2501 |
| DRB3*0101 | DR52a | 511 NGQIGNDPNRDIL | 470 | 2502 |
| DRB4*0101 | DRw53 | 717.01 YARFQSQTTLKQKT | 58 | 2503 |
| DRB5*0101 | DR2w2β2 | 553.01 QYIKANSKFIGITE | 20 | 2504 |

The "Nomenclature" column lists the allelic designations used in Table XVIII.

TABLE VI

HBV A01 SUPER MOTIF (With binding information)

| Conservancy | Freq. | Protein | Position | Sequence | String | Peptide | Filed | A*0101 | SEQ ID NO: |
|---|---|---|---|---|---|---|---|---|---|
| 95 | 19 | POL | 521 | AICSVVRRAF | XIXXXXXXXF | | | | 1 |
| 95 | 19 | NUC | 54 | ALRQAILCW | XLXXXXXXW | | | | 2 |
| 80 | 16 | ENV | 108 | AMQWNSTTF | XMXXXXXXF | | | | 3 |
| 100 | 20 | POL | 166 | ASFCGSPY | XSXXXXXY | 26.0026 | * | | 4 |
| 100 | 20 | POL | 166 | ASFCGSPYSW | XSXXXXXXXW | | | | 5 |
| 90 | 18 | NUC | 19 | ASKLCLGW | XSXXXXXW | | | | 6 |
| 85 | 17 | NUC | 19 | ASKLCLGWLW | XSXXXXXXXW | | | | 7 |
| 80 | 16 | POL | 822 | ASPLHVAW | XSXXXXXW | | | | 8 |
| 100 | 20 | ENV | 312 | CIPIPSSW | XIXXXXXW | | | | 9 |
| 100 | 20 | ENV | 312 | CIPIPSSWAF | XIXXXXXXXF | | | | 10 |
| 95 | 19 | ENV | 253 | CLIFLLVLLDY | XLXXXXXXXXY | 26.0548 | | | 11 |
| 95 | 19 | ENV | 239 | CLRRFIIF | XLXXXXXF | | | | 12 |
| 75 | 15 | ENV | 239 | CLRRFIIFLF | XLXXXXXXXF | | | | 13 |
| 95 | 19 | POL | 523 | CSVVRRAF | XSXXXXXF | | | | 14 |
| 100 | 20 | ENV | 310 | CTCIPIPSSW | XTXXXXXXXW | | | | 15 |
| 90 | 18 | NUC | 31 | DIDPYKEF | XIXXXXXF | | | | 16 |
| 85 | 17 | NUC | 29 | DLLDTASALY | XLXXXXXXXY | 1.0519 | * | 11.1000 | 17 |
| 95 | 19 | ENV | 196 | DSWWTSLNF | XSXXXXXXF | 20.0120 | | | 18 |
| 95 | 19 | NUC | 43 | ELLSFLPSDF | XLXXXXXXXF | | | | 19 |

TABLE VI-continued

HBV A01 SUPER MOTIF (With binding information)

| Conservancy | Freq. | Protein | Position | Sequence | String | Peptide | Filed | A*0101 | SEQ ID NO: |
|---|---|---|---|---|---|---|---|---|---|
| 95 | 19 | NUC | 43 | ELLSFLPSDFF | XLXXXXXXXXF | | | | 20 |
| 95 | 19 | POL | 374 | ESRLVVDF | XSXXXXXF | | | | 21 |
| 95 | 19 | POL | 374 | ESRLVVDFSQF | XSXXXXXXXXF | | | | 22 |
| 80 | 16 | ENV | 248 | FILLLCLIF | XIXXXXXXF | | | | 23 |
| 80 | 16 | ENV | 246 | FLFILLLCLIF | XLXXXXXXXXF | | | | 24 |
| 95 | 19 | ENV | 256 | FLLVLLDY | XLXXXXXY | 26.0027 | | | 25 |
| 95 | 19 | POL | 658 | FSPTYKAF | XSXXXXXF | | | | 26 |
| 90 | 18 | X | 63 | FSSAGPCALRF | XSXXXXXXXXF | | | | 27 |
| 100 | 20 | ENV | 333 | FSWLSLLVPF | XSXXXXXXXF | 20.0263 | | | 28 |
| 95 | 19 | POL | 656 | FTFSPTYKAF | XTXXXXXXXF | 20.0262 | | | 29 |
| 95 | 19 | ENV | 346 | FVGLSPTVW | XVXXXXXXW | | | | 30 |
| 95 | 19 | POL | 627 | GLLGFAAPF | XLXXXXXXF | 20.0124 | | | 31 |
| 95 | 19 | POL | 509 | GLSPFLLAQF | XLXXXXXXXF | | | | 32 |
| 85 | 17 | NUC | 29 | GMDIDPYKEF | XMXXXXXXXF | 26.0372 | | | 33 |
| 95 | 19 | NUC | 123 | GVWIRTPPAY | XVXXXXXXXY | 1.0525 | | 0.0017 | 34 |
| 75 | 15 | POL | 569 | HLNPNKTKRW | XLXXXXXXXW | | | | 35 |
| 80 | 16 | POL | 491 | HLYSHPIILGF | XLXXXXXXXXF | | | | 36 |
| 85 | 17 | POL | 715 | HTAELLAACF | XTXXXXXXXF | | | | 37 |
| 95 | 19 | NUC | 52 | HTALRQAILCW | XTXXXXXXXXW | | | | 38 |
| 100 | 20 | POL | 149 | HTLWKAGILY | XTXXXXXXXY | 1.0542 | * | 0.0300 | 39 |
| 100 | 20 | ENV | 249 | ILLLCLIF | XLXXXXXF | | | | 40 |
| 80 | 16 | POL | 760 | ILRGTSFVY | XLXXXXXXY | 1.0205 | * | 0.0017 | 41 |
| 90 | 18 | ENV | 188 | ILTIPQSLDSW | XLXXXXXXXXW | | | | 42 |
| 90 | 18 | POL | 625 | IVGLLGFAAPF | XVXXXXXXXXF | | | | 43 |
| 80 | 16 | POL | 503 | KIPMGVGLSPF | XIXXXXXXXXF | | | | 44 |
| 85 | 17 | NUC | 21 | KLCLGWLW | XLXXXXXW | | | | 45 |
| 75 | 15 | POL | 108 | KLIMPARF | XLXXXXXF | | | | 46 |
| 75 | 15 | POL | 108 | KLIMPARFY | XLXXXXXXY | 1.0171 | | 0.0017 | 47 |
| 80 | 16 | POL | 610 | KLPVNRPIDW | XLXXXXXXXW | | | | 48 |
| 85 | 17 | POL | 574 | KTKRWGYSLNF | XTXXXXXXXXF | | | | 49 |
| 95 | 19 | POL | 55 | KVGNFTGLY | XVXXXXXXY | 1.0166 | * | 0.0680 | 50 |
| 95 | 19 | ENV | 254 | LIFLLVLLDY | XIXXXXXXXY | 1.0899 | * | 0.0084 | 51 |
| 100 | 20 | POL | 109 | LIMPARFY | XIXXXXXY | 26.0028 | | | 52 |
| 85 | 17 | NUC | 30 | LLDTASALY | XLXXXXXXY | 1.0155 | * | 25.0000 | 53 |
| 80 | 16 | POL | 752 | LLGCAANW | XLXXXXXW | | | | 54 |
| 95 | 19 | POL | 628 | LLGFAAPF | XLXXXXXF | | | | 55 |
| 100 | 20 | ENV | 378 | LLPIFFCLW | XLXXXXXXW | | | | 56 |

TABLE VI-continued

HBV A01 SUPER MOTIF (With binding information)

| Conservancy | Freq. | Protein | Position | Sequence | String | Peptide | Filed | A*0101 | SEQ ID NO: |
|---|---|---|---|---|---|---|---|---|---|
| 100 | 20 | ENV | 378 | LLPIFFCLWVY | XLXXXXXXXY | 26.0549 | * | | 57 |
| 95 | 19 | NUC | 44 | LLSFLPSDF | XLXXXXXXF | | | | 58 |
| 95 | 19 | NUC | 44 | LLSFLPSDFF | XLXXXXXXXF | | | | 59 |
| 90 | 18 | POL | 407 | LLSSNLSW | XLXXXXXW | | | | 60 |
| 95 | 19 | ENV | 175 | LLVLQAGF | XLXXXXXF | | | | 61 |
| 95 | 19 | ENV | 175 | LLVLQAGFF | XLXXXXXXF | 20.0121 | | | 62 |
| 100 | 20 | ENV | 338 | LLVPFVQW | XLXXXXXW | | | | 63 |
| 100 | 20 | ENV | 338 | LLVPFVQWF | XLXXXXXXF | | | | 64 |
| 85 | 17 | NUC | 100 | LLWFHISCLTF | XLXXXXXXXXF | | | | 65 |
| 95 | 19 | NUC | 45 | LSFLPSDF | XSXXXXXF | | | | 66 |
| 95 | 19 | NUC | 45 | LSFLPSDFF | XSXXXXXXF | 20.0123 | | | 67 |
| 95 | 19 | POL | 415 | LSLDVSAAF | XSXXXXXXF | | | | 68 |
| 95 | 19 | POL | 415 | LSLDVSAAFY | XSXXXXXXXY | 2.0239 | * | 4.2000 | 69 |
| 100 | 20 | ENV | 336 | LSLLVPFVQW | XSXXXXXXXW | | | | 70 |
| 100 | 20 | ENV | 336 | LSLLVPFVQWF | XSXXXXXXXXF | | | | 71 |
| 95 | 19 | X | 53 | LSLRGLPVCAF | XSXXXXXXXXF | | | | 72 |
| 95 | 19 | POL | 510 | LSPFLLAQF | XSXXXXXXF | | | | 73 |
| 75 | 15 | ENV | 349 | LSPTVWLSVIW | XSXXXXXXXXW | | | | 74 |
| 85 | 17 | POL | 742 | LSRKYTSF | XSXXXXXF | | | | 75 |
| 85 | 17 | POL | 742 | LSRKYTSFPW | XSXXXXXXXW | | | | 76 |
| 75 | 15 | ENV | 16 | LSVPNPLGF | XSXXXXXXF | | | | 77 |
| 75 | 15 | NUC | 137 | LTFGRETVLEY | XTXXXXXXXXY | | | | 78 |
| 90 | 18 | ENV | 189 | LTIPQSLDSW | XTXXXXXXXW | | | | 79 |
| 90 | 18 | ENV | 189 | LTIPQSLDSWW | XTXXXXXXXXW | | | | 80 |
| 90 | 18 | POL | 404 | LTNLLSSNLSW | XTXXXXXXXXW | | | | 81 |
| 95 | 19 | ENV | 176 | LVLQAGFF | XVXXXXXF | | | | 82 |
| 100 | 20 | ENV | 339 | LVPFVQWF | XVXXXXXF | | | | 83 |
| 100 | 20 | POL | 377 | LWDFSQF | XVXXXXF | | | | 84 |
| 85 | 17 | ENV | 360 | MMWYWGPSLY | XMXXXXXXXY | 1039.01 | * | 0.0810 | 85 |
| 75 | 15 | X | 103 | MSTTDLEAY | XSXXXXXY | 2.0126 | * | 0.8500 | 86 |
| 75 | 15 | X | 103 | MSTTDLEAYF | XSXXXXXXF | | | | 87 |
| 95 | 19 | POL | 42 | NLGNLNVSIPW | XLXXXXXXXXW | | | | 88 |
| 90 | 18 | POL | 406 | NLLSSNLSW | XLXXXXXXW | | | | 89 |
| 95 | 19 | POL | 45 | NLNVSIPW | XLXXXXXW | | | | 90 |
| 75 | 15 | ENV | 15 | NLSVPNPLGF | XLXXXXXXXF | | | | 91 |
| 90 | 18 | POL | 738 | NSVVLSRKY | XSXXXXXXY | 2.0123 | | 0.0005 | 92 |
| 100 | 20 | ENV | 380 | PIFFCLWVY | XIXXXXXXY | 1.0843 | | 0.0078 | 93 |

TABLE VI-continued

HBV A01 SUPER MOTIF (With binding information)

| Conservancy | Freq. | Protein | Position | Sequence | String | Peptide | Filed | A*0101 | SEQ ID NO: |
|---|---|---|---|---|---|---|---|---|---|
| 100 | 20 | ENV | 314 | PIPSSWAF | XIXXXXXF | | | | 94 |
| 100 | 20 | POL | 124 | PLDKGIKPY | XLXXXXXXY | 1.0174 | * | 0.0190 | 95 |
| 100 | 20 | POL | 124 | PLDKGIKPYY | XLXXXXXXXY | 1.0541 | * | 0.1600 | 96 |
| 100 | 20 | ENV | 377 | PLLPIFFCLW | XLXXXXXXXW | | | | 97 |
| 95 | 19 | ENV | 174 | PLLVLQAGF | XLXXXXXXF | | | | 98 |
| 95 | 19 | ENV | 174 | PLLVLQAGFF | XLXXXXXXXF | | | | 99 |
| 80 | 16 | POL | 505 | PMGVGLSPF | XMXXXXXXF | | | | 100 |
| 85 | 17 | POL | 797 | PTTGRTSLY | XTXXXXXXY | 1.0208 | * | 0.7700 | 101 |
| 75 | 15 | ENV | 351 | PTVWLSVIW | XTXXXXXXW | | | | 102 |
| 85 | 17 | POL | 612 | PVNRPIDW | XVXXXXXW | | | | 103 |
| 95 | 19 | POL | 685 | QVFADATPTG | XVXXXXXXXXW | | | | 104 |
| 90 | 18 | POL | 624 | RIVGLLGF | XIXXXXXF | | | | 105 |
| 75 | 15 | POL | 106 | RLKLIMPARF | XLXXXXXXXF | | | | 106 |
| 75 | 15 | POL | 106 | RLKLIMPARFY | XLXXXXXXXXY | | | | 107 |
| 95 | 19 | POL | 376 | RLVVDFSQF | XLXXXXXXF | 20.0122 | | | 108 |
| 90 | 18 | POL | 353 | RTPARVTGGVF | XTXXXXXXXXF | | | | 109 |
| 100 | 20 | POL | 49 | SIPWTHKVGNF | XIXXXXXXXXF | | | | 110 |
| 95 | 19 | ENV | 194 | SLDSWWTSLNF | XLXXXXXXXXF | | | | 111 |
| 95 | 19 | POL | 416 | SLDVSAAF | XLXXXXXF | | | | 112 |
| 95 | 19 | POL | 416 | SLDVSAAFY | XLXXXXXXY | 1.0186 | * | 17.2000 | 113 |
| 100 | 20 | ENV | 337 | SLLVPFVQW | XLXXXXXXW | | | | 114 |
| 100 | 20 | ENV | 337 | SLLVPFVQWF | XLXXXXXXXF | | | | 115 |
| 95 | 19 | X | 54 | SLRGLPVCAF | XLXXXXXXXF | 20.0259 | | | 116 |
| 90 | 18 | X | 64 | SSAGPCALRF | XSXXXXXXXF | 26.0374 | | | 117 |
| 75 | 15 | X | 104 | STTDLEAY | XTXXXXY | | | | 118 |
| 75 | 15 | X | 104 | STTDLEAYF | XTXXXXXF | | | | 119 |
| 75 | 15 | ENV | 17 | SVPNPLGF | XVXXXXXF | | | | 120 |
| 90 | 18 | POL | 739 | SVVLSRKY | XVXXXXXY | 26.0029 | | | 121 |
| 85 | 17 | POL | 739 | SVVLSRKYTSF | XVXXXXXXXXF | | | | 122 |
| 90 | 18 | ENV | 190 | TIPQSLDSW | XIXXXXXXW | | | | 123 |
| 90 | 18 | ENV | 190 | TIPQSLDSWW | XIXXXXXXXW | | | | 124 |
| 100 | 20 | POL | 150 | TLWKAGILY | XLXXXXXXY | 1.0177 | * | 0.0017 | 125 |
| 75 | 15 | X | 105 | TTDLEAYF | XTXXXXXF | | | | 126 |
| 85 | 17 | POL | 798 | TTGRTSLY | XTXXXXXY | 26.0030 | | | 127 |
| 80 | 16 | NUC | 16 | TVQASKLCLGW | XVXXXXXXXXW | | | | 128 |
| 75 | 15 | ENV | 352 | TVWLSVIW | XVXXXXXW | | | | 129 |
| 85 | 17 | POL | 741 | VLSRKYTSF | XLXXXXXXF | | | | 130 |

TABLE VI-continued

HBV A01 SUPER MOTIF (With binding information)

| Conservancy | Freq. | Protein | Position | Sequence | String | Peptide | Filed | A*0101 | SEQ ID NO: |
|---|---|---|---|---|---|---|---|---|---|
| 85 | 17 | POL | 741 | VLSRKYTSFPW | XLXXXXXXXXW | | | | 131 |
| 85 | 17 | POL | 740 | VVLSRKYTSF | XVXXXXXXXF | 20.0261 | | | 132 |
| 80 | 16 | POL | 759 | WILRGTSF | XIXXXXXF | | | | 133 |
| 80 | 16 | POL | 759 | WILRGTSFVY | XIXXXXXXXY | 1.0572 | | 0.0023 | 134 |
| 95 | 19 | NUC | 125 | WIRTPPAY | XIXXXXXY | 26.0031 | | | 135 |
| 80 | 16 | POL | 751 | WLLGCAANW | XLXXXXXXW | | | | 136 |
| 95 | 19 | POL | 414 | WLSLDVSAAF | XLXXXXXXXF | | | | 137 |
| 95 | 19 | POL | 414 | WLSLDVSAAFY | XLXXXXXXXXY | 26.0551 | | | 138 |
| 100 | 20 | ENV | 335 | WLSLLVPF | XLXXXXXF | | | | 139 |
| 100 | 20 | ENV | 335 | WLSLLVPFVQW | XLXXXXXXXXW | | | | 140 |
| 85 | 17 | NUC | 26 | WLWGMDIDPY | XLXXXXXXXY | 1.0774 | * | 0.0810 | 141 |
| 95 | 19 | ENV | 237 | WMCLRRFIIF | XMXXXXXXXF | 20.0266 | | | 142 |
| 85 | 17 | ENV | 359 | WMMWYWGPS | XMXXXXXXXXY | 26.0552 | * | | 143 |
| 100 | 20 | POL | 52 | WTHKVGNF | XTXXXXXF | | | | 144 |
| 100 | 20 | POL | 122 | YLPLDKGIKPY | XLXXXXXXXXY | 26.0553 | | | 145 |
| 90 | 18 | NUC | 118 | YLVSFGVW | XLXXXXXW | | | | 146 |
| 80 | 16 | POL | 493 | YSHPIILGF | XSXXXXXXF | | | | 147 |
| 85 | 17 | POL | 580 | YSLNFMGY | XSXXXXXY | 26.0032 | | | 148 |

TABLE VII

HBV A02 SUPER MOTIF (With binding information)

| Conser-vancy | Fre-quency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 85 | 17 | POL | 721 | AACFARSRSGA | A | A |  | 11 |  |  |  |  |  |  | 149 |
| 85 | 17 | POL | 431 | AAMPHLLV | A | V |  | 8 |  |  |  |  |  |  | 150 |
| 80 | 16 | POL | 756 | AANWILRGT | A | T |  | 9 |  |  |  |  |  |  | 151 |
| 95 | 19 | POL | 632 | AAPFTQCGYPA | A | A |  | 11 |  |  |  |  |  |  | 152 |
| 95 | 19 | POL | 521 | AICSVVRRA | I | A | 5.0025 | 9 |  |  |  |  |  |  | 153 |
| 90 | 18 | NUC | 58 | AILCWGEL | I | L |  | 8 |  | 0.0001 |  |  |  |  | 154 |
| 90 | 18 | NUC | 58 | AILCWGELM | I | M |  | 9 |  |  |  |  |  |  | 155 |
| 95 | 19 | POL | 642 | ALMPLYACI | L | I | 927.15 | 9 | * | 0.5000 | 0.0340 | 3.3000 | 0.2500 | 0.0470 | 156 |
| 80 | 16 | ENV | 108 | AMQWNSTT | M | T |  | 8 |  |  |  |  |  |  | 157 |
| 75 | 15 | X | 102 | AMSTTDLEA | M | A | 3.0051 | 9 |  | 0.0013 |  |  |  |  | 158 |
| 95 | 19 | POL | 690 | ATPTGWGL | T | L |  | 8 |  |  |  |  |  |  | 159 |
| 80 | 16 | POL | 690 | ATPTGWGLA | T | A |  | 9 |  |  |  |  |  |  | 160 |
| 75 | 15 | POL | 690 | ATPTGWGLAI | T | I |  | 10 |  |  |  |  |  |  | 161 |
| 95 | 19 | POL | 397 | AVPNLQSL | V | L |  | 8 |  |  |  |  |  |  | 162 |
| 95 | 19 | POL | 397 | AVPNLQSLT | V | T | 5.0026 | 9 |  | 0.0001 |  |  |  |  | 163 |
| 95 | 19 | POL | 397 | AVPNLQSLTNL | V | L |  | 11 |  |  |  |  |  |  | 164 |
| 80 | 16 | POL | 755 | CAANWILRGT | A | T |  | 10 |  |  |  |  |  |  | 165 |
| 95 | 19 | X | 61 | CAFSSAGPCA | A | A | 5.0090 | 10 |  | 0.0001 |  |  |  |  | 166 |
| 95 | 19 | X | 61 | CAFSSAGPCAL | A | L |  | 11 |  |  |  |  |  |  | 167 |
| 90 | 18 | X | 69 | CALRFTSA | A | A |  | 8 |  |  |  |  |  |  | 168 |
| 100 | 20 | ENV | 312 | CIPIPSSWA | I | A | 5.0007 | 9 |  | 0.0010 |  |  |  |  | 169 |
| 80 | 16 | ENV | 312 | CIPIPSSWAFA | I | A |  | 11 |  |  |  |  |  |  | 170 |
| 90 | 18 | POL | 533 | CLAFSYMDDV | L | V | 1.0559 | 10 |  | 0.0008 |  |  |  |  | 171 |

TABLE VII-continued

HBV A02 SUPER MOTIF (with binding information)

| Conservancy | Frequency | Protein | Position | Sequence | P2 | C-term | Peptide Filed | AA | A*0201 | A*0202 | A*0203 | A*0206 | A*6802 | SEQ ID NO: |
|---|---|---|---|---|---|---|---|---|---|---|---|---|---|---|
| 90 | 18 | POL | 533 | CLAFSYMDDW | L | V | | 11 | | | | | | 172 |
| 85 | 17 | NUC | 23 | CLGWLWGM | L | M | | 8 | | | | | | 173 |
| 85 | 17 | NUC | 23 | CLGWLWGMDI | L | I | 3.0210 | 10 | 0.0093 | | | | | 174 |
| 100 | 20 | ENV | 253 | CLIFLLVL | L | L | Chisari 4.011 | 8 | 0.0002 | | | | | 175 |
| 100 | 20 | ENV | 253 | CLIFLLVLL | L | L | 1.0836 | 9 | 0.0006 | | | | | 176 |
| 95 | 19 | ENV | 239 | CLRRFIIFL | L | L | 1.0829 | 9 | 0.0002 | | | | | 177 |
| 75 | 15 | ENV | 239 | CLRRFIIFLFI | L | I | Chisari 4.055 | 11 | 0.0004 | | | | | 178 |
| 90 | 18 | NUC | 107 | CLTFGRET | L | T | | 8 | | | | | | 179 |
| 90 | 18 | NUC | 107 | CLTFGRETV | L | V | 1.0160 | 9 | 0.0001 | | | | | 180 |
| 100 | 20 | ENV | 310 | CTCIPIPSSWA | T | A | | 11 | | | | | | 181 |
| 95 | 19 | POL | 689 | DATPTGWGL | A | L | 5.0027 | 9 | 0.0001 | | | | | 182 |
| 80 | 16 | POL | 689 | DATPTGWGLA | A | A | | 10 | | | | | | 183 |
| 75 | 15 | POL | 689 | DATPTGWGLAI | A | I | | 11 | | | | | | 184 |
| 90 | 18 | NUC | 31 | DIDPYKEFGA | I | A | | 10 | | | | | | 185 |
| 85 | 17 | NUC | 29 | DLLDTASA | L | A | | 8 | | | | | | 186 |
| 85 | 17 | NUC | 29 | DLLDTASAL | L | L | 1.0154 | 9 | 0.0001 | | | | | 187 |
| 95 | 19 | POL | 40 | DLNLGNLNV | L | V | 927.30 | 9 | 0.0004 | | | | | 188 |
| 95 | 19 | POL | 40 | DLNLGNLNVSI | L | I | | 11 | | | | | | 189 |
| 80 | 16 | NUC | 32 | DTASALYREA | T | A | | 10 | | | | | | 190 |
| 80 | 16 | NUC | 32 | DTASALYREAL | T | L | | 11 | | | | | | 191 |
| 95 | 19 | X | 14 | DVLCLRPV | V | V | | 8 | | | | | | 192 |
| 95 | 19 | X | 14 | DVLCLRPVGA | V | A | 5.0091 | 10 | 0.0001 | | | | | 193 |

TABLE VII-continued

HBV A02 SUPER MOTIF (With binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 90 | 18 | POL | 541 | DVVLGAKSV | V | V | 1.0190 | 9 |  | 0.0003 |  |  |  |  | 194 |
| 100 | 20 | POL | 17 | EAGPLEEEL | A | L | 5.0028 | 9 |  | 0.0001 |  |  |  |  | 195 |
| 80 | 16 | X | 122 | ELGEEFL | L | L |  | 8 |  |  |  |  |  |  | 196 |
| 90 | 18 | POL | 718 | ELLAACFA | L | A |  | 8 |  |  |  |  |  |  | 197 |
| 75 | 15 | NUC | 142 | ETVLEYLV | T | V |  | 8 |  |  |  |  |  |  | 198 |
| 95 | 19 | POL | 687 | FADATPTGWGL | A | L |  | 11 |  |  |  |  |  |  | 199 |
| 85 | 17 | POL | 724 | FARSRSGA | A | A |  | 8 |  |  |  |  |  |  | 200 |
| 80 | 16 | POL | 821 | FASPLHVA | A | A |  | 8 |  |  |  |  |  |  | 201 |
| 95 | 19 | POL | 396 | FAVPNLQSL | A | L |  | 9 |  |  |  |  |  |  | 202 |
| 95 | 19 | POL | 396 | FAVPNLQSLT | A | T | 5.0083 | 10 |  | 0.0003 |  |  |  |  | 203 |
| 80 | 16 | ENV | 243 | FIIFLFIL | I | L | Chisari 4.047 | 8 |  | 0.0006 |  |  |  |  | 204 |
| 80 | 16 | ENV | 243 | FIIFLFILL | I | L | 1.0830 | 9 |  | 0.0002 |  |  |  |  | 205 |
| 80 | 16 | ENV | 243 | FIIFLFILLL | I | L | 1.0894 | 10 |  | 0.0012 |  |  |  |  | 206 |
| 80 | 16 | ENV | 248 | FILLLCLI | I | I | Chisari 4.048 | 8 |  | 0.0003 |  |  |  |  | 207 |
| 80 | 16 | ENV | 248 | FILLLCLIFL | I | L | 1.0895 | 10 | * | 0.0280 |  |  |  |  | 208 |
| 80 | 16 | ENV | 248 | FILLLCLIFLL | I | L | Chisari 4.049 | 11 |  | 0.0010 |  |  |  |  | 209 |
| 80 | 16 | ENV | 246 | FLFILLLCL | L | L | 1.0832 | 9 |  | 0.0002 |  |  |  |  | 210 |
| 80 | 16 | ENV | 246 | FLFILLLCLI | L | I | 3.0206 | 10 |  | 0.0013 |  |  |  |  | 211 |
| 75 | 15 | ENV | 171 | FLGPLLVL | L | L |  | 8 |  |  |  |  |  |  | 212 |
| 75 | 15 | ENV | 171 | FLGPLLVLQA | L | A | 3.0205 | 10 | * | 0.0190 |  |  |  |  | 213 |
| 95 | 19 | POL | 513 | FLLAQFTSA | L | A | 1069.07 | 9 | * | 0.2400 |  |  |  |  | 214 |

TABLE VII-continued

HBV A02 SUPER MOTIF (With binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | POL | 513 | FLLAQFTSAI | L | I | 1147.13 | 10 | * | 0.2100 | 0.0320 | 7.0000 | 0.1100 | 0.0880 | 215 |
| 95 | 19 | POL | 562 | FLLSLGIHL | L | L | 927.11 | 9 | * | 0.6500 | 0.0010 | 0.0100 | 0.1100 | 0.0035 | 216 |
| 80 | 16 | ENV | 183 | FLLTRILT | L | T |  | 8 |  |  |  |  |  |  | 217 |
| 80 | 16 | ENV | 183 | FLLTRILTI | L | I | 777.03 | 9 | * | 0.5100 | 0.0430 | 8.0000 | 0.2000 | 0.0010 | 218 |
| 95 | 19 | ENV | 256 | FLLVLLDYQGM | L | M |  | 11 |  |  |  |  |  |  | 219 |
| 100 | 20 | POL | 363 | FLVDKNPHNT | L | T | 5.0084 | 10 |  |  |  |  |  |  | 220 |
| 95 | 19 | POL | 656 | FTFSPTYKA | T | A | 1147.15 | 9 | * | 0.0056 | 0.0150 | 0.0031 | 0.8000 | 7.3000 | 221 |
| 95 | 19 | POL | 656 | FTFSPTYKAFL | T | L |  | 11 |  |  |  |  |  |  | 222 |
| 95 | 19 | POL | 59 | FTGLYSST | T | T |  | 8 |  |  |  |  |  |  | 223 |
| 90 | 18 | POL | 59 | FTGLYSSTV | T | V | 20.0118 | 9 |  | 0.0005 |  |  |  |  | 224 |
| 95 | 19 | POL | 635 | FTQCGYPA | T | A |  | 8 |  |  |  |  |  |  | 225 |
| 95 | 19 | POL | 635 | FTQCGYPAL | T | L | 5.0031 | 9 |  | 0.0009 |  |  |  |  | 226 |
| 95 | 19 | POL | 635 | FTQCGYPALM | T | M | 5.0085 | 10 |  | 0.0024 |  |  |  |  | 227 |
| 95 | 19 | POL | 518 | FTSAICSV | T | V |  | 8 |  |  |  |  |  |  | 228 |
| 95 | 19 | POL | 518 | FTSAICSVV | T | V | 5.0032 | 9 |  | 0.0090 |  |  |  |  | 229 |
| 95 | 19 | ENV | 346 | FVGLSPTV | V | V |  | 8 |  |  |  |  |  |  | 230 |
| 95 | 19 | ENV | 346 | FVGLSPTVWL | V | L | 1.0931 | 10 |  | 0.0008 |  |  |  |  | 231 |
| 90 | 18 | X | 132 | FVLGGCRHKL | V | L | Chisari 4.114 | 10 |  | 0.0030 |  |  |  |  | 232 |
| 90 | 18 | X | 132 | FVLGGCRHKLV | V | V |  | 11 |  |  |  |  |  |  | 233 |
| 95 | 19 | ENV | 342 | FVQMFVGL | V | L |  | 8 |  |  |  |  |  |  | 234 |
| 95 | 19 | ENV | 342 | FVQMFVGLSPT | V | T |  | 11 |  |  |  |  |  |  | 235 |
| 90 | 18 | POL | 766 | FVVVPSAL | V | L |  | 8 |  |  |  |  |  |  | 236 |
| 90 | 18 | POL | 766 | FVVVPSALNPA | V | A |  | 11 |  |  |  |  |  |  | 237 |

TABLE VII-continued

HBV A02 SUPER MOTIF (With binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | X | 50 | GAHLSLRGL | A | L | 5.0040 | 9 | | 0.0001 | | | | | 238 |
| 90 | 18 | X | 50 | GAHLSLRGLPV | A | V | | 11 | | | | | | | 239 |
| 85 | 17 | POL | 545 | GAKSVQHL | A | L | | 8 | | | | | | | 240 |
| 85 | 17 | POL | 545 | GAKSVQHLESL | A | L | | 11 | | | | | | | 241 |
| 75 | 15 | POL | 567 | GIHLNPNKT | I | T | | 9 | | | | | | | 242 |
| 90 | 18 | POL | 155 | GILYKRET | I | T | | 8 | | | | | | | 243 |
| 90 | 18 | POL | 155 | GILYKRETT | I | T | | 9 | | | | | | | 244 |
| 85 | 17 | POL | 682 | GLCQVFADA | L | A | 1142.04 | 9 | * | 0.0024 | | | | | 245 |
| 85 | 17 | POL | 682 | GLCQVFADAT | L | T | | 10 | | | | | | | 246 |
| 95 | 19 | POL | 627 | GLLGFAAPFT | L | T | 5.0086 | 10 | | 0.0049 | | | | | 247 |
| 85 | 17 | ENV | 62 | GLLGWSPQA | L | A | 1142.07 | 9 | * | 0.4000 | 0.0003 | 0.0350 | 0.2800 | 0.0005 | 248 |
| 95 | 19 | X | 57 | GLPVCAFSSA | L | A | 5.0092 | 10 | | 0.0008 | | | | | 249 |
| 95 | 19 | POL | 509 | GLSPFLLA | L | A | | 8 | | | | | | | 250 |
| 95 | 19 | POL | 509 | GLSPFLLAQFT | L | T | | 11 | | | | | | | 251 |
| 100 | 20 | ENV | 348 | GLSPTVWL | L | L | Chisari 4.012 | 8 | * | 0.0036 | | | | | 252 |
| 75 | 15 | ENV | 348 | GLSPTVWLSV | L | V | 1.0518 | 10 | | 0.2800 | | | | | 253 |
| 75 | 15 | ENV | 348 | GLSPTVWLSVI | L | I | Chisari 4.031 | 11 | | 0.0036 | | | | | 254 |
| 90 | 18 | ENV | 265 | GMLPVCPL | M | L | | 8 | | | | | | | 255 |
| 90 | 18 | POL | 735 | GTDNSVVL | T | L | | 8 | | | | | | | 256 |
| 75 | 15 | ENV | 13 | GTNLSVPNPL | T | L | | 10 | | | | | | | 257 |
| 80 | 16 | POL | 763 | GTSFVYVPSA | T | A | | 10 | | | | | | | 258 |
| 80 | 16 | POL | 763 | GTSFVYVPSAL | T | L | | 11 | | | | | | | 259 |

TABLE VII-continued

HBV A02 SUPER MOTIF (With binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 80 | 16 | POL | 507 | GVGLSPFL | V | L | | 8 | | | | | | | 260 |
| 80 | 16 | POL | 507 | GVGLSPFLL | V | L | Chisari 4.082 | 9 | | 0.0002 | | | | | 261 |
| 80 | 16 | POL | 507 | GVGLSPFLLA | V | A | | 10 | | | | | | | 262 |
| 95 | 19 | NUC | 123 | GVWIRTPPA | V | A | 3.0040 | 9 | | 0.0030 | | | | | 263 |
| 90 | 18 | NUC | 104 | HISCLTFGRET | I | T | | 11 | | | | | | | 264 |
| 80 | 16 | POL | 435 | HLLVGSSGL | L | L | 927.43 | 9 | | 0.0031 | | | | | 265 |
| 90 | 18 | X | 52 | HLSLRGLPV | L | V | 927.02 | 9 | | 0.0014 | | | | | 266 |
| 90 | 18 | X | 52 | HLSLRGLPVCA | L | A | | 11 | | | | | | | 267 |
| 80 | 16 | POL | 491 | HLYSHPII | L | I | 17.0256 | 8 | | | | | | | 268 |
| 80 | 16 | POL | 491 | HLYSHPIIL | L | L | 927.47 | 9 | * | 0.2200 | 0.0003 | 0.9300 | 0.1700 | 0.0530 | 269 |
| 85 | 17 | POL | 715 | HTAELLAA | T | A | | 8 | | | | | | | 270 |
| 85 | 17 | POL | 715 | HTAELLAACFA | T | A | | 11 | | | | | | | 271 |
| 100 | 20 | NUC | 52 | HTALRQAI | T | I | | 8 | | | | | | | 272 |
| 95 | 19 | NUC | 52 | HTALRQAIL | T | L | 5.0021 | 9 | | 0.0001 | | | | | 273 |
| 100 | 20 | POL | 149 | HTLWKAGI | T | I | | 8 | | | | | | | 274 |
| 100 | 20 | POL | 149 | HTLWKAGIL | T | L | 5.0033 | 9 | | 0.0001 | | | | | 275 |
| 80 | 16 | ENV | 244 | IIFLFILL | I | L | Chisari 4.051 | 8 | | 0.0004 | | | | | 276 |
| 80 | 16 | ENV | 244 | IIFLFILLL | I | L | 1.0831 | 9 | | 0.0002 | | | | | 277 |
| 80 | 16 | ENV | 244 | IIFLFILLCL | I | L | Chisari 4.052 | 11 | | 0.0002 | | | | | 278 |
| 80 | 16 | POL | 497 | IILGFRKI | I | I | | 8 | | | | | | | 279 |
| 80 | 16 | POL | 497 | IILGFRKIPM | I | M | | 10 | | | | | | | 280 |

TABLE VII-continued

HBV A02 SUPER MOTIF (With binding information)

| Conser-vancy | Fre-quency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 90 | 18 | NUC | 59 | ILCWGELM | L | M | | 8 | | | | | | | 281 |
| 80 | 16 | POL | 498 | ILGFRKIPM | L | M | 3.0016 | 9 | | 0.0002 | | | | | 282 |
| 100 | 20 | ENV | 249 | ILLLCLIFL | L | L | 1137.04 | 9 | * | 0.0015 | | | | | 283 |
| 100 | 20 | ENV | 249 | ILLLCLIFLL | L | L | 1069.08 | 10 | * | 0.0190 | 0.0001 | 0.0002 | 0.1300 | 0.0015 | 284 |
| 100 | 20 | ENV | 249 | ILLLCLIFLLV | L | V | Chisari 4.013 | 11 | | 0.0056 | | | | | 285 |
| 80 | 16 | POL | 760 | ILRGTSFV | L | V | | 8 | | | | | | | 286 |
| 80 | 16 | POL | 760 | ILRGTSFVYV | L | V | 1.0573 | 10 | * | 0.0160 | | | | | 287 |
| 100 | 20 | NUC | 139 | ILSTLPET | L | T | | 8 | | | | | | | 288 |
| 100 | 20 | NUC | 139 | ILSTLPETT | L | T | 5.0022 | 9 | | 0.0001 | | | | | 289 |
| 100 | 20 | NUC | 139 | ILSTLPETTV | L | V | 1069.14 | 10 | * | 0.0210 | 0.0085 | 0.0770 | 0.3100 | 0.0067 | 290 |
| 100 | 20 | NUC | 139 | ILSTLPETTVV | L | V | | 11 | | | | | | | 291 |
| 95 | 19 | ENV | 188 | ILTIPQSL | L | L | | 8 | | | | | | | 292 |
| 90 | 18 | POL | 156 | ILYKRETT | L | T | | 8 | | | | | | | 293 |
| 90 | 18 | POL | 625 | IVGLLGFA | V | A | | 8 | | | | | | | 294 |
| 90 | 18 | POL | 625 | IVGLLGFAA | V | A | 3.0041 | 9 | | 0.0009 | | | | | 295 |
| 90 | 18 | POL | 153 | KAGILYKRET | A | T | | 10 | | | | | | | 296 |
| 90 | 18 | POL | 153 | KAGILYKRETT | A | T | | 11 | | | | | | | 297 |
| 80 | 16 | POL | 503 | KIPMGVGL | I | L | | 8 | | | | | | | 298 |
| 85 | 17 | NUC | 21 | KLCLGWLWGM | L | M | 1142.02 | 10 | * | 0.0001 | 0.0340 | 2.7000 | 0.5900 | | 299 |
| 95 | 19 | POL | 489 | KLHLYSHPI | L | I | 927.46 | 9 | * | 0.0690 | | | | 0.0015 | 300 |
| 80 | 16 | POL | 489 | KLHLYSHPII | L | I | | 10 | | | | | | | 301 |
| 80 | 16 | POL | 489 | KLHLYSHPIIL | L | L | | 11 | | | | | | | 302 |
| 80 | 16 | POL | 610 | KLPVNRPI | L | I | | 8 | | | | | | | 303 |

TABLE VII-continued

HBV A02 SUPER MOTIF (With binding information)

| Conser-vancy | Fre-quency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | POL | 574 | KTKRWGYSL | T | L | 5.0034 | 9 | | 0.0001 | | | | | 304 |
| 85 | 17 | POL | 620 | KVCQRIVGL | V | L | 1.0198 | 9 | | 0.0003 | | | | | 305 |
| 85 | 17 | POL | 620 | KVCQRIVGLL | V | L | 1.0567 | 10 | | 0.0001 | | | | | 306 |
| 95 | 19 | POL | 55 | KVGNFTGL | V | L | 17.0116 | 8 | | | | | | | 307 |
| 85 | 17 | X | 91 | KVLHKRTL | V | L | | 8 | | | | | | | 308 |
| 85 | 17 | X | 91 | KVLHKRTLGL | V | L | Chisari 4.115 | 10 | | 0.0004 | | | | | 309 |
| 90 | 18 | POL | 534 | LAFSYMDDV | A | V | 20.0119 | 9 | | 0.0002 | | | | | 310 |
| 90 | 18 | POL | 534 | LAFSYMDDVV | A | V | 20.0257 | 10 | | 0.0003 | | | | | 311 |
| 90 | 18 | POL | 534 | LAFSYMDDVVL | A | L | | 11 | | | | | | | 312 |
| 95 | 19 | POL | 515 | LAQFTSAI | A | I | | 8 | | | | | | | 313 |
| 95 | 19 | POL | 515 | LAQFTSAICSV | A | V | | 11 | | | | | | | 314 |
| 100 | 20 | ENV | 254 | LIFLLVLL | I | L | Chisari 4.014 | 8 | | 0.0025 | | | | | 315 |
| 95 | 19 | POL | 514 | LLAQFTSA | L | A | | 8 | | | | | | | 316 |
| 95 | 19 | POL | 514 | LLAQFTSAI | L | I | 1069.05 | 9 | * | 0.1000 | 0.2700 | 3.7000 | 0.2600 | 0.7900 | 317 |
| 100 | 20 | ENV | 251 | LLCLIFLL | L | L | Chisari 4.015 | 8 | | 0.0004 | | | | | 318 |
| 100 | 20 | ENV | 251 | LLCLIFLLV | L | V | 1137.03 | 9 | * | 0.0048 | | | | | 319 |
| 100 | 20 | ENV | 251 | LLCLIFLLVL | L | L | 1.0898 | 10 | | 0.0075 | | | | | 320 |
| 100 | 20 | ENV | 251 | LLCLIFLLVLL | L | L | Chisari 4.016 | 11 | | 0.0013 | | | | | 321 |
| 85 | 17 | NUC | 30 | LLDTASAL | L | L | | 8 | | | | | | | 322 |
| 95 | 19 | ENV | 260 | LLDYQGML | L | L | Chisari 4.021 | 8 | | 0.0004 | | | | | 323 |

TABLE VII-continued

HBV A02 SUPER MOTIF (with binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 90 | 18 | ENV | 260 | LLDYQGMLPV | L | V | 1137.02 | 10 | * | 0.0980 | 0.0001 | 0.0200 | 0.6700 | 0.0009 | 324 |
| 80 | 16 | POL | 752 | LLGCAANWI | L | I | 927.22 | 9 | | 0.0011 | | | | | 325 |
| 80 | 16 | POL | 752 | LLGCAANWIL | L | L | 1.0912 | 10 | * | 0.0140 | | | | | 326 |
| 95 | 19 | POL | 628 | LLGFAAPFT | L | T | 5.0035 | 9 | | 0.0008 | | | | | 327 |
| 85 | 17 | ENV | 63 | LLGWSPQA | L | A | | 8 | | | | | | | 328 |
| 75 | 15 | ENV | 63 | LLGWSPQAQGI | L | I | | 11 | | | | | | | 329 |
| 100 | 20 | ENV | 250 | LLLCLIFL | L | L | Chisari 4.017 | 8 | * | 0.0006 | | | | | 330 |
| 100 | 20 | ENV | 250 | LLLCLIFLL | L | L | 1090.05 | 9 | * | 0.0065 | | | | | 331 |
| 100 | 20 | ENV | 250 | LLLCLIFLLV | L | V | 1137.01 | 10 | * | 0.0036 | | | | | 332 |
| 100 | 20 | ENV | 250 | LLLCLIFLLVL | L | L | ChisaRi 4.018 | 11 | | 0.0005 | | | | | 333 |
| 100 | 20 | ENV | 378 | LLPIFFCL | L | L | Chisari 4.019 | 8 | | 0.0055 | | | | | 334 |
| 100 | 20 | ENV | 378 | LLPIFFCLWV | L | V | 1069.10 | 10 | * | 0.0320 | 0.0008 | 0.0150 | 0.8000 | 0.0005 | 335 |
| 95 | 19 | POL | 563 | LLSLGIHL | L | L | | 8 | | | | | | | 336 |
| 90 | 18 | POL | 407 | LLSSNLSWL | L | L | 927.41 | 9 | * | 0.0110 | 0.0780 | 3.9000 | 0.2700 | 0.0100 | 337 |
| 90 | 18 | POL | 407 | LLSSNLSWLSL | L | L | | 11 | | 0.0050 | | | | | 338 |
| 80 | 16 | ENV | 184 | LLTRILTI | L | I | Chisari 4.053 | 8 | * | 0.0026 | | | | | 339 |
| 80 | 16 | POL | 436 | LLVGSSGL | L | L | | 8 | | | | | | | 340 |
| 95 | 19 | ENV | 257 | LLVLLDYQGM | L | M | 3.0207 | 10 | | 0.0050 | | | | | 341 |
| 95 | 19 | ENV | 257 | LLVLLDYQGML | L | L | | 11 | | | | | | | 342 |
| 90 | 18 | ENV | 175 | LLVLQAGFFL | L | L | 1090.06 | 10 | * | 0.0310 | 0.0037 | 0.0045 | 0.1500 | 0.0110 | 343 |
| 90 | 18 | ENV | 175 | LLVLQAGFFLL | L | L | Chisari 4.028 | 11 | | 0.0074 | | | | | 344 |

TABLE VII-continued

HBV A02 SUPER MOTIF (With binding information)

| Conser-vancy | Fre-quency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | ENV | 338 | LLVPFVQWFV | L | V | 1069.06 | 10 | * | 0.6700 | 0.3800 | 1.7000 | 0.2900 | 0.1400 | 345 |
| 90 | 18 | NUC | 100 | LLMFHISCL | L | L | 1142.01 | 9 | * | 0.0130 | 0.0002 | 0.0420 | 0.3100 | 0.0098 | 346 |
| 85 | 17 | NUC | 100 | LLMFHISCLT | L | T |  | 10 |  |  |  |  |  |  | 347 |
| 95 | 19 | POL | 643 | LMPLYACI | M | I | 17.0130 | 8 |  |  |  |  |  |  | 348 |
| 95 | 19 | NUC | 108 | LTFGRETV | T | V |  | 8 |  |  |  |  |  |  | 349 |
| 75 | 15 | NUC | 137 | LTFGRETVL | T | L |  | 9 |  |  |  |  |  |  | 350 |
| 90 | 18 | POL | 404 | LTNLLSSNL | T | L |  | 9 |  |  |  |  |  |  | 351 |
| 80 | 16 | ENV | 185 | LTRILTIPQSL | T | L |  | 11 |  |  |  |  |  |  | 352 |
| 85 | 17 | POL | 99 | LTVNEKRRL | T | L |  | 9 |  |  |  |  |  |  | 353 |
| 100 | 20 | POL | 364 | LVDKNPHNT | V | T | 5.0036 | 9 |  |  |  |  |  |  | 354 |
| 95 | 19 | ENV | 258 | LVLLDYQGM | V | M | 3.0034 | 9 | | 0.0001 | | | | | 355 |
| 95 | 19 | ENV | 258 | LVLLDYQGML | V | L | 1.0515 | 10 | | 0.0001 | | | | | 356 |
| 90 | 18 | ENV | 176 | LVIQAGFFL | V | L | 1.0827 | 9 | | 0.0096 | | | | | 357 |
| 90 | 18 | ENV | 176 | LVIQAGFFLL | V | L | 1132.17 | 10 | * | 0.0022 | | | | | 358 |
| 90 | 18 | ENV | 176 | LVIQAGFFLLT | V | T |  | 11 |  |  |  |  |  |  | 359 |
| 95 | 19 | ENV | 339 | LVPFVQWFV | V | V | 1132.01 | 9 | * | 0.0420 | 0.0150 | 0.0048 | 0.7900 | 2.8000 | 360 |
| 95 | 19 | ENV | 339 | LVPFVQWFVGL | V | L |  | 11 |  | 0.0004 | | | | | 361 |
| 90 | 18 | NUC | 119 | LVSFGVWI | V | I | Chisari 4.078 | 8 |  |  |  |  |  |  | 362 |
| 90 | 18 | NUC | 119 | LVSFGVWIRT | V | T |  | 10 |  |  |  |  |  |  | 363 |
| 85 | 17 | ENV | 360 | MMWYWGPSL | M | L | 1039.03 | 9 | * | 0.6400 | | | | | 364 |
| 100 | 20 | NUC | 136 | NAPILSTL | A | L |  | 8 |  |  |  |  |  |  | 365 |
| 100 | 20 | NUC | 136 | NAPILSTLPET | A | T |  | 11 |  |  |  |  |  |  | 366 |

TABLE VII-continued

HBV A02 SUPER MOTIF (with binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | POL | 42 | NLGNLNVSI | L | I | 3.0008 | 9 | | 0.0047 | | | | | 367 |
| 90 | 18 | POL | 406 | NLLSSNLSWL | L | L | 1.0549 | 10 | | 0.0016 | | | | | 368 |
| 95 | 19 | POL | 45 | NLNVSIPWT | L | T | 5.0037 | 9 | | 0.0005 | | | | | 369 |
| 100 | 20 | POL | 400 | NLQSLTNL | L | L | | 8 | | | | | | | 370 |
| 100 | 20 | POL | 400 | NLQSLTNLL | L | L | 927.40 | 9 | | 0.0047 | | | | | 371 |
| 75 | 15 | ENV | 15 | NLSVPNPL | L | L | | 8 | | | | | | | 372 |
| 90 | 18 | POL | 411 | NLSWLSLDV | L | V | 927.42 | 9 | * | 0.0650 | 0.0051 | 0.6400 | 0.1600 | 0.0990 | 373 |
| 90 | 18 | POL | 411 | NLSWLSLDVSA | L | A | | 11 | | | | | | | 374 |
| 100 | 20 | POL | 47 | NVSIPWTHKV | V | V | 1.0532 | 10 | | 0.0001 | | | | | 375 |
| 100 | 20 | POL | 430 | PAAMPHLL | A | L | | 8 | | | | | | | 376 |
| 85 | 17 | POL | 430 | PAAMPHLLIV | A | V | | 9 | | | | | | | 377 |
| 90 | 18 | POL | 775 | PADDPSRGRL | A | L | | 10 | | | | | | | 378 |
| 90 | 18 | ENV | 131 | PAGGSSSGT | A | T | | 9 | | | | | | | 379 |
| 90 | 18 | ENV | 131 | PAGGSSSGTV | A | V | | 10 | | | | | | | 380 |
| 95 | 19 | POL | 641 | PALMPLYA | A | A | | 8 | | | | | | | 381 |
| 95 | 19 | POL | 641 | PALMPLYACI | A | I | 5.0087 | 10 | | 0.0001 | | | | | 382 |
| 75 | 15 | X | 145 | PAPCNFFT | A | T | | 8 | | | | | | | 383 |
| 75 | 15 | X | 145 | PAPCNFFTSA | A | A | | 10 | | | | | | | 384 |
| 80 | 16 | X | 11 | PARDVLCL | A | L | | 8 | | | | | | | 385 |
| 75 | 15 | X | 11 | PARDVLCLRPV | A | V | | 11 | | | | | | | 386 |
| 90 | 18 | POL | 355 | PARVTGGV | A | V | | 8 | | | | | | | 387 |
| 90 | 18 | POL | 355 | PARVTGGVFL | A | L | | 10 | | | | | | | 388 |
| 90 | 18 | POL | 355 | PARVTGGVFLV | A | V | | 11 | | | | | | | 389 |

TABLE VII-continued

HBV A02 SUPER MOTIF (With binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | NUC | 130 | PAYRPPNA | A | A | | 8 | | | | | | | 390 |
| 95 | 19 | NUC | 130 | PAYRPPNAPI | A | I | 5.0081 | 10 | | 0.0001 | | | | | 391 |
| 95 | 19 | NUC | 130 | PAYRPPNAPIL | A | L | | 11 | | | | | | | 392 |
| 85 | 17 | POL | 616 | PIDWKVCQRI | I | I | Chisari 4.091 | 10 | | 0.0001 | | | | | 393 |
| 85 | 17 | POL | 616 | PIDWKVCQRIV | I | V | | 11 | | | | | | | 394 |
| 100 | 20 | ENV | 380 | PIFFCLWV | I | V | | 8 | | | | | | | 395 |
| 100 | 20 | ENV | 380 | PIFFCLWVYI | I | I | Chisari 3.074 | 10 | | 0.0004 | | | | | 396 |
| 85 | 17 | POL | 713 | PIHTAELL | I | L | | 8 | | | | | | | 397 |
| 85 | 17 | POL | 713 | PIHTAELLA | I | A | | 9 | | | | | | | 398 |
| 85 | 17 | POL | 713 | PIHTAELLAA | I | A | | 10 | | | | | | | 399 |
| 80 | 16 | POL | 496 | PIILGFRKI | I | I | 927.48 | 9 | | 0.0001 | | | | | 400 |
| 80 | 16 | POL | 496 | PIILGFRKIPM | I | M | | 11 | | | | | | | 401 |
| 100 | 20 | NUC | 138 | PILSTLPET | I | T | 5.0023 | 9 | 0.0001 | | | | | 402 | |
| 100 | 20 | NUC | 138 | PILSTLPETT | I | T | 5.0082 | 10 | | 0.0001 | | | | | 403 |
| 100 | 20 | NUC | 138 | PILSTLPETTV | I | V | Chisari 5.125 | 11 | | 0.0001 | | | | | 404 |
| 80 | 16 | ENV | 314 | PIPSSWAFA | I | A | | 9 | | | | | | | 405 |
| 95 | 19 | POL | 20 | PLEEELPRL | L | L | 927.29 | 9 | | 0.0003 | | | | | 406 |
| 90 | 18 | POL | 20 | PLEEELPRLA | L | A | 3.0225 | 10 | | 0.0001 | | | | | 407 |
| 95 | 19 | ENV | 10 | PLGFFPDHQL | L | L | 1.0511 | 10 | | 0.0002 | | | | | 408 |
| 100 | 20 | POL | 427 | PLHPAAMPHL | L | L | 1.0550 | 10 | | 0.0001 | | | | | 409 |
| 100 | 20 | POL | 427 | PLHPAAMPHLL | L | L | | 11 | | | | | | | 410 |
| 100 | 20 | ENV | 377 | PLLPIFFCL | L | L | 1069.13 | 9 | * | 0.0650 | 0.0001 | 0.0018 | 0.1100 | 0.0047 | 411 |

TABLE VII-continued

HBV A02 SUPER MOTIF (With binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 100 | 20 | ENV | 377 | PLLPIFFCLWV | L | V | | 11 | | | | | | | 412 |
| 90 | 18 | ENV | 174 | PLLVLQAGFFL | L | L | Chisari 4.029 | 11 | | 0.0008 | | | | | 413 |
| 80 | 16 | POL | 711 | PLPIHTAEL | L | L | 927.19 | 9 | | 0.0004 | | | | | 414 |
| 80 | 16 | POL | 711 | PLPIHTAELL | L | L | 1.0569 | 10 | | 0.0001 | | | | | 415 |
| 80 | 16 | POL | 711 | PLPIHTAELLA | L | A | | 11 | | | | | | | 416 |
| 75 | 15 | POL | 2 | PLSYQHFRKL | L | L | 1.0527 | 10 | | 0.0001 | | | | | 417 |
| 75 | 15 | POL | 2 | PLSYQHFRKLL | L | L | | 11 | | | | | | | 418 |
| 85 | 17 | POL | 98 | PLTVNEKRL | L | L | 1.0536 | 10 | | 0.0001 | | | | | 419 |
| 80 | 16 | POL | 505 | PMGVGLSPFL | M | L | 1.0557 | 10 | | 0.0001 | | | | | 420 |
| 80 | 16 | POL | 505 | PMGVGLSPFLL | M | L | | 11 | | | | | | | 421 |
| 75 | 15 | POL | 692 | PTGWGLAI | T | I | | 8 | | | | | | | 422 |
| 80 | 16 | ENV | 219 | PTSNHSPT | T | T | | 8 | | | | | | | 423 |
| 85 | 17 | POL | 797 | PTTGRTSL | T | L | | 8 | | | | | | | 424 |
| 85 | 17 | POL | 797 | PTTGRTSLYA | T | A | | 10 | | | | | | | 425 |
| 80 | 16 | NUC | 15 | PTVQASKL | T | L | | 8 | | | | | | | 426 |
| 80 | 16 | NUC | 15 | PTVQASKLCL | T | L | | 10 | | | | | | | 427 |
| 85 | 17 | ENV | 351 | PTVWLSVI | T | I | | 8 | | | | | | | 428 |
| 75 | 15 | ENV | 351 | PTVWLSVIWM | T | M | | 10 | | | | | | | 429 |
| 95 | 19 | X | 59 | PVCAFSSA | V | A | | 8 | | | | | | | 430 |
| 85 | 17 | POL | 612 | PVNRPIDWKV | V | V | 1.0566 | 10 | | 0.0002 | | | | | 431 |
| 95 | 19 | POL | 654 | QAFTFSPT | A | T | | 8 | | | | | | | 432 |
| 95 | 19 | POL | 654 | QAFTFSPTYKA | A | A | | 11 | | | | | | | 433 |

TABLE VII-continued

HBV A02 SUPER MOTIF (With binding information)

| Conser-vancy | Fre-quency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | ENV | 179 | QAGFFLLT | A | T | | 8 | | | | | | | 434 |
| 80 | 16 | ENV | 179 | QAGFFLLTRI | A | I | | 10 | | | | | | | 435 |
| 80 | 16 | ENV | 179 | QAGFFLLTRIL | A | L | | 11 | | | | | | | 436 |
| 90 | 18 | NUC | 57 | QAILCWGEL | A | L | | 9 | | | | | | | 437 |
| 90 | 18 | NUC | 57 | QAILCWGELM | A | M | | 10 | | | | | | | 438 |
| 95 | 19 | ENV | 107 | QAMQWNST | A | T | | 8 | | | | | | | 439 |
| 80 | 16 | ENV | 107 | QAMQWNSTT | A | T | | 9 | | | | | | | 440 |
| 80 | 16 | NUC | 18 | QASKLCLGWL | A | L | | 10 | | | | | | | 441 |
| 80 | 16 | X | 8 | QLDPARDV | L | V | Chisari 4.116 | 8 | | 0.0001 | | | | | 442 |
| 80 | 16 | X | 8 | QLDPARDVL | L | L | 927.01 | 9 | | 0.0001 | | | | | 443 |
| 80 | 16 | X | 8 | QLDPARDVLCL | L | L | Chisari 4.073 | 11 | | 0.0001 | | | | | 444 |
| 90 | 18 | NUC | 99 | QLLWFHISCL | L | L | 1142.03 | 10 | * | 0.0060 | | | | | 445 |
| 85 | 17 | NUC | 99 | QLLWFHISCLT | L | T | | 11 | | | | | | | 446 |
| 95 | 19 | POL | 685 | QVFADATPT | V | T | 5.0038 | 9 | | 0.0001 | | | | | 447 |
| 95 | 19 | POL | 528 | RAFPHCLA | A | A | | 8 | | | | | | | 448 |
| 80 | 16 | ENV | 187 | RILTIPQSL | I | L | Chisari 4.054 | 9 | | 0.0010 | | | | | 449 |
| 90 | 16 | POL | 624 | RIVGLLGFA | I | A | | 9 | | | | | | | 450 |
| 90 | 18 | POL | 624 | RIVGLLGFAA | I | A | | 10 | | | | | | | 451 |
| 75 | 15 | POL | 106 | RLKLIMPA | L | A | | 8 | | | | | | | 452 |
| 90 | 18 | POL | 353 | RTPARVTGGV | T | V | | 10 | | | | | | | 453 |
| 95 | 19 | NUC | 127 | RTPPAYRPPNA | T | A | | 11 | | | | | | | 454 |
| 95 | 19 | POL | 36 | RVAEDLNL | V | L | | 8 | | | | | | | 455 |

TABLE VII-continued

HBV A02 SUPER MOTIF (With binding information)

| Conser-vancy | Fre-quency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 90 | 18 | POL | 36 | RVAEDLNLGNL | V | L | | 11 | | | | | | | 456 |
| 80 | 16 | POL | 818 | RVHFASPL | V | L | | 8 | | | | | | | 457 |
| 75 | 15 | POL | 818 | RVHFASPLHV | V | V | 1.0576 | 10 | | 0.0001 | | | | | 458 |
| 75 | 15 | POL | 818 | RVHFASPLHVA | V | A | | 11 | | | | | | | 459 |
| 100 | 20 | POL | 357 | RVTGGVFL | V | L | | 8 | | | | | | | 460 |
| 100 | 20 | POL | 357 | RVTGGVFLV | V | V | 1.0181 | 9 | | 0.0041 | | | | | 461 |
| 90 | 18 | X | 65 | SAGPCALRFT | A | T | | 10 | | | | | | | 462 |
| 95 | 19 | POL | 520 | SAICSVVRRA | A | A | 5.0088 | 10 | | 0.0001 | | | | | 463 |
| 90 | 18 | NUC | 35 | SALYREAL | A | L | | 8 | | | | | | | 464 |
| 100 | 20 | POL | 49 | SIPWTHKV | I | V | | 8 | | | | | | | 465 |
| 95 | 19 | ENV | 194 | SLDSWWTSL | L | L | F126.64 | 9 | | | | | | | 466 |
| 75 | 15 | POL | 565 | SLGIHLNPNKT | L | T | | 11 | | | | | | | 467 |
| 95 | 19 | ENV | 337 | SLLVPFVQWFV | L | V | | 11 | | | | | | | 468 |
| 75 | 15 | POL | 581 | SLNFMGYV | L | V | | 8 | | | | | | | 469 |
| 75 | 15 | POL | 581 | SLNFMGYVI | L | I | 927.12 | 9 | | 0.0038 | | | | | 470 |
| 95 | 19 | X | 54 | SLRGLPVCA | L | A | 3.0030 | 9 | | 0.0007 | | | | | 471 |
| 90 | 18 | POL | 403 | SLTNLLSSNL | L | L | 1.0548 | 10 | | 0.0014 | | | | | 472 |
| 75 | 15 | ENV | 280 | STGPCKTCT | T | T | | 9 | | | | | | | 473 |
| 100 | 20 | NUC | 141 | STLPETTV | T | V | | 8 | | | | | | | 474 |
| 100 | 20 | NUC | 141 | STLPETTVV | T | V | 5.0024 | 9 | | 0.0019 | | | | | 475 |
| 80 | 16 | ENV | 85 | STNRQSGRQPT | T | T | | 11 | | | | | | | 476 |
| 85 | 17 | POL | 548 | SVQHLESL | V | L | | 8 | | | | | | | 477 |

TABLE VII-continued

HBV A02 SUPER MOTIF (with binding information)

| Conser-vancy | Fre-quency | Protein | Position

TABLE VII-continued

HBV A02 SUPER MOTIF (With binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 90 | 18 | X | 133 | VLGGCRHKLIV | L | V | 1.0589 | 10 | | 0.0001 | | | | | 500 |
| 85 | 17 | X | 92 | VLHKRTLGL | L | L | 927.03 | 9 | | 0.0012 | | | | | 501 |
| 95 | 19 | ENV | 259 | VLLDYQGM | L | M | 17.0107 | 8 | | | | | | | 502 |
| 95 | 19 | ENV | 259 | VLLDYQGML | L | L | 1069.09 | 9 | * | 0.0440 | 0.0001 | 0.0210 | 0.9000 | 0.0002 | 503 |
| 90 | 18 | ENV | 259 | VLLDYQGMLPV | L | V | 1147.14 | 11 | * | 0.5800 | 0.2200 | 4.9000 | 0.3400 | 0.0170 | 504 |
| 95 | 19 | ENV | 177 | VLQAGFFL | L | L | Chisari 4.027 | 8 | | 0.0019 | | | | | 505 |
| 95 | 19 | ENV | 177 | VLQAGFFLL | L | L | 1013.14 | 9 | * | 0.0660 | | | | | 506 |
| 95 | 19 | ENV | 177 | VLQAGFFLLT | L | T | 5.0066 | 10 | | 0.0011 | | | | | 507 |
| 100 | 20 | POL | 358 | VTGGVFLV | T | V | | 8 | | | | | | | 508 |
| 90 | 18 | POL | 542 | VVLGAKSV | V | V | | 8 | | | | | | | 509 |
| 80 | 16 | POL | 542 | VVLGAKSVQHL | V | L | | 11 | | | | | | | 510 |
| 90 | 18 | POL | 740 | VVLSRKYT | V | T | | 8 | | | | | | | 511 |
| 95 | 19 | POL | 525 | VVRRAFPHCL | V | L | 2.0217 | 10 | | 0.0003 | | | | | 512 |
| 95 | 19 | POL | 525 | VVRRAFPHCLA | V | A | | 11 | | | | | | | 513 |
| 80 | 16 | POL | 759 | WILRGTSFV | I | V | 927.24 | 9 | * | 0.0270 | | | | | 514 |
| 80 | 16 | POL | 759 | WILRGTSFVYV | I | V | | 11 | | | | | | | 515 |
| 80 | 16 | POL | 751 | WLLGCAANWI | L | I | Chisari 4.101 | 10 | * | 0.0053 | | | | | 516 |
| 80 | 16 | POL | 751 | WLLGCAANWIL | L | L | | 11 | | | | | | | 517 |
| 100 | 20 | POL | 414 | WLSLDVSA | L | A | | 8 | | | | | | | 518 |
| 95 | 19 | POL | 414 | WLSLDVSAA | L | A | 3.0023 | 9 | | 0.0059 | | | | | 519 |
| 100 | 20 | ENV | 335 | WLSLLVPFV | L | V | 1013.0102 | 9 | * | 1.1000 | 0.0380 | 7.2000 | 0.3600 | 0.0310 | 520 |
| 95 | 19 | ENV | 237 | WMCLRRFI | M | I | | 8 | | | | | | | 521 |

TABLE VII-continued

HBV A02 SUPER MOTIF (With binding information)

| Conser-vancy | Fre-quency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | ENV | 237 | WMCLRRFII | M | I | 1147.10 | 9 | * | 0.0005 | | | | | 522 |
| 95 | 19 | ENV | 237 | WMCLRRFIIFL | M | L | Chisari 4.024 | 11 | | 0.0019 | | | | | 523 |
| 85 | 17 | ENV | 359 | WMMWYWGPSL | M | L | 1137.05 | 10 | * | 0.0009 | | | | | 524 |
| 100 | 20 | POL | 52 | WTHKVGNFT | T | T | 5.0039 | 9 | | 0.0001 | | | | | 525 |
| 95 | 19 | POL | 52 | WTHKVGNFTGL | T | L | | 11 | | | | | | | 526 |
| 100 | 20 | POL | 147 | YLHTLWKA | L | A | | 8 | | | | | | | 527 |
| 100 | 20 | POL | 147 | YLHTLWKAGI | L | I | 1069.11 | 10 | * | 0.0160 | 0.0005 | 0.5600 | 0.1000 | 0.0320 | 528 |
| 100 | 20 | POL | 147 | YLHTLWKAGIL | L | L | | 11 | | | | | | | 529 |
| 100 | 20 | POL | 122 | YLPLDKGI | L | I | | 8 | | | | | | | 530 |
| 90 | 18 | NUC | 118 | YLVSFGVWI | L | I | 1090.12 | 9 | * | 0.3800 | | | | | 531 |
| 90 | 18 | NUC | 118 | YLVSFGVWIRT | L | T | | 11 | | | | | | | 532 |
| 90 | 18 | POL | 538 | YMDDVVLGA | M | A | 1090.14 | 9 | * | 0.0250 | 0.0001 | 0.0024 | 0.1000 | 0.0002 | 533 |
| 85 | 17 | POL | 746 | YTSFPWLL | T | L | | 8 | | | | | | | 534 |
| 75 | 15 | POL | 746 | YTSFPWLLGCA | T | A | | 11 | | | | | | | 535 |
| 90 | 18 | POL | 768 | YVPSALNPA | V | A | 3.0042 | 9 | | 0.0039 | | | | | 536 |
| | | | | 388 | | | | | | | | | | | |

TABLE VIII

HBV A03 SUPER MOTIF (With binding information)

| Conservancy | Frequency | Protein | Position | Sequence | P2 | C-term | Peptide | AA | Filed | A*0301 | A*1101 | A*3101 | A*3301 | A*6801 | SEQ ID NO: |
|---|---|---|---|---|---|---|---|---|---|---|---|---|---|---|---|
| 85 | 17 | POL | 721 | AACFARSR | A | R | 26.0003 | 8 | | 0.0004 | 0.0003 | 0.0056 | 0.0035 | 0.0014 | 537 |
| 95 | 19 | POL | 521 | AICSVVRR | I | R | 26.0004 | 8 | | -0.0002 | 0.0003 | 0.0014 | -0.0009 | 0.0006 | 538 |
| 90 | 18 | POL | 772 | ALNPADDPSR | L | R | 1.1090 | 10 | | 0.0003 | 0.0001 | | | | 539 |
| 85 | 17 | X | 70 | ALRFTSAR | L | R | 26.0005 | 8 | | 0.0047 | 0.0009 | 0.0450 | 0.0230 | 0.0004 | 540 |
| 80 | 16 | POL | 822 | ASPLHVAWR | S | R | | 9 | | | | | | | 541 |
| 75 | 15 | ENV | 84 | ASTNRQSGR | S | R | 1150.60 | 9 | | 0.0009 | 0.0002 | 0.0088 | 0.0008 | 0.0001 | 542 |
| 80 | 16 | POL | 755 | CAANWILR | A | R | | 8 | | | | | | | 543 |
| 85 | 17 | X | 69 | CALRFTSAR | A | R | 26.0149 | 9 | * | 0.0034 | 0.0230 | 1.5000 | 8.0000 | 0.7300 | 544 |
| 90 | 16 | X | 17 | CLRPVGAESR | L | R | 1.1093 | 10 | | 0.0011 | 0.0001 | | | | 545 |
| 100 | 20 | NUC | 48 | CSPHHTALR | S | R | 5.0055 | 9 | * | 0.0029 | 0.0001 | 0.0520 | 0.0250 | 0.0440 | 546 |
| 85 | 17 | NUC | 29 | DLLDTASALYR | L | R | 26.0530 | 11 | | 0.0042 | -0.0003 | -0.0012 | 3.7000 | 0.0410 | 547 |
| 85 | 17 | NUC | 32 | DTASALYR | T | R | 26.0006 | 8 | | 0.0004 | -0.0002 | -0.0009 | 0.0018 | 0.0009 | 548 |
| 95 | 19 | POL | 17 | EAGPLEEELPR | A | R | 26.0531 | 11 | | -0.0009 | -0.0003 | -0.0012 | 0.0015 | 0.0110 | 549 |
| 90 | 18 | POL | 718 | ELLAACFAR | L | R | 1.0988 | 9 | | 0.0002 | 0.0004 | | | | 550 |
| 85 | 17 | POL | 718 | ELLAACFARSR | L | R | 26.0532 | 11 | | 0.0062 | 0.0016 | 0.0200 | 0.2000 | 0.1600 | 551 |
| 95 | 19 | NUC | 174 | ETTVVRRR | T | R | 26.0007 | 8 | | 0.0003 | -0.0002 | -0.0009 | 0.1400 | 0.0027 | 552 |
| 80 | 16 | NUC | 174 | ETTVVRRRGR | T | R | 1.1073 | 10 | | 0.0003 | 0.0001 | | | | 553 |
| 80 | 16 | POL | 821 | FASPLHVAWR | A | R | | 10 | | | | | | | 554 |
| 90 | 18 | X | 83 | FSSAGPCALR | S | R | | 10 | | | | | | | 555 |
| 95 | 19 | POL | 856 | FTFSPTYK | T | K | 1147.19 | 8 | * | 0.0100 | 0.0100 | 0.0023 | 0.2100 | 0.0590 | 556 |
| 95 | 19 | POL | 518 | FTSAICSVVR | T | R | 1.1085 | 10 | | 0.0003 | 0.0003 | | | | 557 |
| 95 | 19 | POL | 518 | FTSAICSVVRR | T | R | 26.0533 | 11 | | 0.0065 | 0.0092 | 0.0170 | 0.0350 | 1.5000 | 558 |
| 90 | 18 | X | 132 | FVLGGCRHK | V | K | 1090.03 | 9 | * | 0.0430 | 0.0090 | | | | 559 |

TABLE VIII-continued

HBV A03 SUPER MOTIF (with binding information)

| Conservancy | Frequency | Protein | Position | Sequence | P2 | C-term | Peptide | AA | Filed | A*0301 | A*1101 | A*3101 | A*3301 | A*6801 | SEQ ID NO: |
|---|---|---|---|---|---|---|---|---|---|---|---|---|---|---|---|
| 75 | 15 | POL | 567 | GIHLNPNK | I | K | | 8 | | | | | | | 560 |
| 75 | 15 | POL | 567 | GIHLNPNKTK | I | K | 1.0563 | 10 | | 0.0025 | 0.0011 | 0.0009 | 0.0009 | 0.0003 | 561 |
| 75 | 15 | POL | 567 | GIHLNPNKTKR | I | R | | 11 | | | | | | | 562 |
| 85 | 17 | NUC | 29 | GMDIDPYK | M | K | 26.0009 | 8 | | 0.0006 | 0.0004 | -0.0009 | -0.0009 | 0.0001 | 563 |
| 90 | 16 | POL | 735 | GTDNSVVLSR | T | R | 1090.04 | 10 | * | 0.0010 | 0.0420 | 0.0030 | 0.0019 | 0.0008 | 564 |
| 90 | 16 | POL | 735 | GTDNSVVLSRK | T | K | 1147.17 | 11 | * | 0.0140 | 0.5600 | -0.0002 | -0.0006 | 0.0001 | 565 |
| 95 | 19 | NUC | 123 | GVWIRTPPAYR | V | R | 26.0535 | 11 | * | 0.1900 | 0.1700 | 6.8000 | 0.7300 | 0.6600 | 566 |
| 90 | 18 | NUC | 104 | HISCLTFGR | I | R | 1069.16 | 9 | * | 0.0160 | 0.0065 | | | | 567 |
| 75 | 15 | POL | 569 | HLNPNKTK | L | K | | 8 | | | | | | | 568 |
| 75 | 15 | POL | 569 | HLNPNKTKR | L | R | 1.0983 | 9 | | 0.0025 | 0.0001 | | | | 569 |
| 100 | 20 | POL | 149 | HTLWKAGILYK | T | K | 1147.16 | 11 | * | 0.5400 | 0.4400 | 0.0370 | 0.0720 | 0.1900 | 570 |
| 90 | 18 | NUC | 105 | ISCLTFGR | S | R | 26.0010 | 8 | | 0.0004 | 0.0002 | 0.0017 | -0.0009 | 0.0017 | 571 |
| 100 | 20 | POL | 153 | KAGILYKR | A | R | 26.0011 | 8 | | 0.0002 | -0.0002 | 0.0015 | -0.0009 | 0.0001 | 572 |
| 80 | 16 | POL | 610 | KLPVNRPIDWK | L | K | | 11 | | | | | | | 573 |
| 75 | 15 | X | 130 | KVFVLGGCR | V | R | 1.0993 | 9 | * | 0.0420 | 0.0820 | 0.6000 | 0.0710 | 0.0030 | 574 |
| 85 | 17 | POL | 720 | LAACFARSR | A | R | 20.0129 | 9 | | 0.0058 | 0.0065 | | | | 575 |
| 90 | 18 | POL | 719 | LIAACFAR | L | R | 26.0012 | 8 | | 0.0024 | 0.0003 | 0.0015 | 0.0029 | 0.0064 | 576 |
| 85 | 17 | POL | 719 | LIAACFARSR | L | R | | 10 | | | | | | | 577 |
| 85 | 17 | NUC | 30 | LLDTASALYR | L | R | 1.1070 | 10 | | 0.0050 | 0.0002 | | | | 578 |
| 80 | 16 | POL | 752 | LLGCAANWILR | L | R | | 11 | | | | | | | 579 |
| 75 | 15 | POL | 564 | LSLGIHLNPNK | S | K | | 11 | | | | | | | 580 |
| 95 | 19 | NUC | 169 | LSTLPETTVVR | S | R | 26.0537 | 11 | | -0.0009 | 0.0008 | -0.0012 | -0.0023 | 0.0078 | 581 |
| 75 | 15 | POL | 3 | LSYQHFRK | S | K | | 8 | | | | | | | 582 |

TABLE VIII-continued

HBV A03 SUPER MOTIF (with binding information)

| Conservancy | Frequency | Protein | Protein Position | Sequence | P2 | C-term | Peptide | AA | Filed | A*0301 | A*1101 | A*3101 | A*3301 | A*6801 | SEQ ID NO: |
|---|---|---|---|---|---|---|---|---|---|---|---|---|---|---|---|
| 85 | 17 | POL | 99 | LITVNEKRR | T | R | 26.0013 | 8 | | -0.0002 | -0.0002 | -0.0009 | -0.0009 | 0.0001 | 583 |
| 90 | 18 | NUC | 119 | LVSFGVWIR | V | R | 1090.08 | 9 | * | 0.0028 | 0.0120 | | | | 584 |
| 100 | 20 | POL | 377 | LVVDFSQFSR | V | R | 1069.20 | 10 | * | 0.0016 | 0.3600 | 0.0260 | 0.2300 | 0.4900 | 585 |
| 75 | 15 | X | 103 | MSTTDLEAYFK | S | K | | 11 | | | | | | | 586 |
| 90 | 18 | NUC | 75 | NLEDPASR | L | R | 26.0014 | 8 | | -0.0002 | -0.0002 | -0.0009 | -0.0009 | 0.0001 | 587 |
| 95 | 19 | POL | 45 | NLNVSIPWTHK | L | K | 26.0538 | 11 | | -0.0009 | 0.0005 | -0.0012 | -0.0023 | 0.0019 | 588 |
| 90 | 18 | POL | 738 | NSVVLSRK | S | K | 26.0015 | 8 | | 0.0006 | 0.0010 | -0.0009 | -0.0009 | 0.0007 | 589 |
| 100 | 20 | POL | 47 | NVSIPWTHK | V | K | 1069.16 | 9 | * | 0.0620 | 0.0570 | 0.0002 | 0.0100 | 0.0320 | 590 |
| 90 | 18 | POL | 775 | PADDPSRGR | A | R | 1150.35 | 9 | | 0.0008 | 0.0002 | 0.0004 | 0.0015 | 0.0002 | 591 |
| 80 | 16 | X | 11 | PARDVLCLR | A | R | 1150.36 | 9 | | 0.0002 | 0.0002 | 0.0100 | 0.0180 | 0.0002 | 592 |
| 75 | 15 | ENV | 83 | PASTNRQSGR | A | R | | 10 | | 0.0002 | 0.0005 | | | | 593 |
| 90 | 18 | POL | 616 | PIDWKVCQR | I | R | 1.0985 | 9 | | | | | | | 594 |
| 80 | 16 | POL | 496 | PIILGFRK | I | K | | 8 | | | | | | | 595 |
| 95 | 19 | POL | 20 | PLEEELPR | L | R | 26.0016 | 8 | | -0.0002 | -0.0002 | -0.0009 | -0.0009 | 0.0001 | 596 |
| 100 | 20 | POL | 2 | PLSYQHFR | L | R | 26.0017 | 8 | | -0.0002 | -0.0002 | -0.0009 | -0.0009 | 0.0001 | 597 |
| 75 | 15 | POL | 2 | PLSYQHFRK | L | K | 1.0161 | 9 | | 0.0011 | 0.0031 | 0.0006 | 0.0008 | 0.0002 | 598 |
| 85 | 17 | POL | 98 | PLTVNEKR | L | R | 26.0018 | 8 | | -0.0002 | -0.0002 | -0.0009 | -0.0009 | 0.0001 | 599 |
| 85 | 17 | POL | 98 | PLTVNEKRR | L | R | 1.0974 | 9 | | 0.0008 | 0.0005 | 0.0004 | 0.0027 | 0.0002 | 600 |
| 90 | 18 | X | 20 | PVGAESRGR | V | R | 1.0990 | 9 | | 0.0002 | 0.0005 | 0.0004 | 0.0043 | 0.0002 | 601 |
| 85 | 17 | POL | 612 | PVNRPIDVVK | V | K | 1142.06 | 10 | * | 0.0310 | 0.1400 | 0.0002 | 0.0006 | 0.0009 | 602 |
| 95 | 19 | POL | 654 | QAFTFSPTYK | A | K | 1090.10 | 10 | * | 0.0450 | 0.5400 | 0.0010 | 0.0057 | 1.2000 | 603 |
| 80 | 16 | ENV | 179 | QAGFFLLTR | A | R | | 9 | | | | | | | 604 |
| 75 | 15 | NUC | 169 | QSPRRRSQSR | S | R | 28.0839 | 11 | | | | | | | 605 |

TABLE VIII-continued

HBV A03 SUPER MOTIF (With binding information)

| Conservancy | Frequency | Protein | Position | Sequence | P2 | C-term | Peptide | AA | Filed | A*0301 | A*1101 | A*3101 | A*3301 | A*6801 | SEQ ID NO: |
|---|---|---|---|---|---|---|---|---|---|---|---|---|---|---|---|
| 80 | 16 | POL | 189 | QSSGILSR | S | R | | 8 | | | | | | | 606 |
| 75 | 15 | POL | 106 | RLKLIMPAR | L | R | 1.0975 | 9 | * | 0.0950 | 0.0002 | 3.1000 | 0.0490 | 0.0002 | 607 |
| 75 | 15 | X | 128 | RLKVFVLGGCR | L | R | | 11 | | | | | | | 608 |
| 95 | 19 | POL | 376 | RLVVDFSQFSR | L | R | 26.0539 | 11 | * | 0.2800 | 3.8000 | 2.6000 | 1.2000 | 6.1000 | 609 |
| 95 | 19 | NUC | 183 | RSPRRRTPSPR | S | R | 26.0540 | 11 | | -0.0007 | -0.0003 | 0.0190 | -0.0023 | 0.0003 | 610 |
| 75 | 15 | NUC | 167 | RSQSPRRR | S | R | | 8 | | | | | | | 611 |
| 75 | 15 | NUC | 167 | RSQSPRRRR | S | R | | 9 | | | | | | | 612 |
| 95 | 19 | NUC | 188 | RTPSPRRR | T | R | 26.0019 | 8 | | -0.0002 | -0.0002 | 0.0033 | 0.0014 | 0.0002 | 613 |
| 95 | 19 | NUC | 188 | RTPSPRRRR | T | R | 1.0971 | 9 | * | 0.0054 | 0.0005 | 0.2000 | 0.0016 | 0.0003 | 614 |
| 100 | 20 | POL | 357 | RVTGGVFLVDK | V | K | 1147.18 | 11 | * | 0.0190 | 0.0290 | -0.0002 | -0.0003 | 0.0001 | 615 |
| 90 | 18 | X | 65 | SAGPCALR | A | R | 26.0020 | 8 | | -0.0002 | 0.0020 | 0.0029 | 0.0024 | 0.0360 | 616 |
| 95 | 19 | POL | 520 | SAICSVVR | A | R | 26.0021 | 8 | | -0.0002 | 0.0071 | 0.0280 | 0.0081 | 0.0690 | 617 |
| 95 | 19 | POL | 520 | SAICSVVRR | A | R | 1090.11 | 9 | * | 0.0058 | 0.2100 | 0.0150 | 0.0650 | 0.3800 | 618 |
| 90 | 18 | POL | 771 | SALNPADDPSR | A | R | 26.0542 | 11 | | -0.0004 | -0.0003 | -0.0012 | -0.0023 | 0.0003 | 619 |
| 75 | 15 | POL | 565 | SLGIHLNPNK | L | K | 28.0758 | 10 | * | | | | | | 620 |
| 90 | 18 | X | 64 | SSAGPCALR | S | R | 26.0153 | 9 | * | 0.0080 | 0.1400 | 0.3300 | 0.1600 | 0.7500 | 621 |
| 95 | 19 | NUC | 170 | STLPETTVVR | T | R | 1069.21 | 10 | * | 0.0007 | 0.0600 | 0.0080 | 0.0240 | 0.0250 | 622 |
| 95 | 19 | NUC | 170 | STLPETTVVRR | T | R | 1083.01 | 11 | | 0.0150 | 1.4000 | 0.1000 | 0.1600 | 0.3100 | 623 |
| 80 | 16 | ENV | 85 | STNRQSGR | T | R | | 8 | | | | | | | 624 |
| 75 | 15 | X | 104 | STTDLEAYFK | T | K | 1.0584 | 10 | * | 0.0066 | 2.7000 | | | | 625 |
| 85 | 17 | POL | 716 | TAELLAACFAR | A | R | 26.0544 | 11 | | 0.0006 | 0.0023 | 0.0066 | 0.1600 | 0.0590 | 626 |
| 95 | 19 | NUC | 171 | TLPETTVVR | L | R | 1.0969 | 9 | | 0.0008 | 0.0002 | 0.0009 | 0.0024 | 0.0180 | 627 |
| 95 | 19 | NUC | 171 | TLPETTVVRR | L | R | 1069.22 | 10 | * | 0.0007 | 0.0230 | 0.0006 | 0.0120 | 0.0440 | 628 |

TABLE VIII-continued

HBV A03 SUPER MOTIF (With binding information)

| Conservancy | Frequency | Protein | Position | Sequence | P2 | C-term | Peptide | AA | Filed | A*0301 | A*1101 | A*3101 | A*3301 | A*6801 | SEQ ID NO: |
|---|---|---|---|---|---|---|---|---|---|---|---|---|---|---|---|
| 95 | 19 | NUC | 171 | TLPETTVVRRR | L | R | 26.0545 | 11 |  | 0.0005 | 0.0160 | 0.0061 | 0.0710 | 0.6400 | 629 |
| 100 | 20 | POL | 150 | TLWKAGILYK | L | K | 1069.15 | 10 | * | 5.3000 | 0.3600 | 0.0051 | 0.0010 | 0.0130 | 630 |
| 100 | 20 | POL | 150 | TLWKAGILYKR | L | R | 26.0546 | 11 |  | 0.0082 | 0.0095 | 0.1000 | 0.1100 | 0.0640 | 631 |
| 95 | 19 | POL | 519 | TSAICSVVR | S | R | 5.0057 | 9 |  | 0.0005 | 0.0008 | 0.0600 | 0.0200 | 0.0820 | 632 |
| 95 | 19 | POL | 519 | TSAICSVVRR | S | R | 1142.08 | 10 | * | 0.0018 | 0.0006 | 0.0030 | 0.0066 | 0.0048 | 633 |
| 75 | 15 | X | 105 | TTDLEAYFK | T | K | 1.0215 | 9 | * | 0.0006 | 0.9200 | 0.0006 | 0.0012 | 0.0170 | 634 |
| 75 | 15 | ENV | 278 | TTSTGPCK | T | K |  | 8 |  |  |  |  |  |  | 635 |
| 80 | 16 | NUC | 175 | TTVVRRRGR | T | R | 1.0970 | 9 |  | 0.0008 | 0.0005 | 0.2500 | 0.1400 | 0.0095 | 636 |
| 80 | 16 | NUC | 176 | TVVRRRGR | V | R | 3.0324 | 8 |  | 0.0003 | 0.0001 |  |  |  | 637 |
| 80 | 18 | NUC | 176 | TVVRRRGRSPR | V | R | 28.0837 | 11 |  |  |  |  |  |  | 638 |
| 90 | 18 | X | 133 | VLGGCRHK | L | K | 26.0022 | 8 |  | 0.0150 | 0.0002 | -0.0005 | -0.0009 | 0.0001 | 639 |
| 80 | 16 | ENV | 177 | VLQAGFFLLTR | L | R |  | 11 |  |  |  |  |  |  | 640 |
| 90 | 18 | NUC | 120 | VSFGVWIR | S | R | 26.0023 | 8 | * | 0.0040 | 0.0290 | 0.0750 | 0.0270 | 0.0360 | 641 |
| 100 | 20 | POL | 48 | VSIPWTHK | S | K | 26.0024 | 8 | * | 0.0130 | 0.0170 | 0.0031 | 0.0013 | 0.0004 | 642 |
| 100 | 20 | POL | 358 | VTGGVFLVDK | T | K | 1069.17 | 10 | * | 0.0390 | 0.0920 | 0.0002 | 0.0006 | 0.0022 | 643 |
| 100 | 20 | POL | 378 | VVDFSQFSR | V | R | 1069.19 | 9 | * | 0.0015 | 0.0750 | 0.0013 | 0.0170 | 0.0330 | 644 |
| 80 | 16 | NUC | 177 | VVRRRGRSPR | V | R | 1.1074 | 10 |  | 0.0027 | 0.0001 | -0.0005 |  |  | 645 |
| 80 | 16 | NUC | 177 | VVRRRGRSPRR | V | R | 28.0838 | 11 |  |  |  |  |  |  | 646 |
| 95 | 19 | NUC | 125 | WIRTPPAYR | I | R | 1.0968 | 9 |  | 0.0008 | 0.0005 |  |  |  | 647 |
| 90 | 18 | POL | 314 | WLQFRNSK | L | K | 26.0025 | 8 | * | -0.0002 | 0.0005 | 0.0020 | 0.0052 | 0.0001 | 648 |
| 85 | 17 | NUC | 26 | WLWGMDIDPYK | L | K | 26.0547 | 11 |  | 0.0030 | 0.0013 | -0.0003 | 0.0039 | 0.0490 | 649 |
| 100 | 20 | POL | 122 | YLPLDKGIK | L | K | 1.0173 | 9 |  | 0.0001 | 0.0001 | 0.0006 | 0.0008 | 0.0002 | 650 |
| 90 | 18 | NUC | 118 | YLVSFGVWIR | L | R | 1090.13 | 10 | * | 0.0005 | 0.0002 |  |  |  | 651 |

TABLE VIII-continued

HBV A03 SUPER MOTIF (With binding information)

| Conservancy | Frequency | Protein | Position | Sequence | P2 | C-term | Peptide | AA | Filed | A*0301 | A*1101 | A*3101 | A*3301 | A*6801 | SEQ ID NO: |
|---|---|---|---|---|---|---|---|---|---|---|---|---|---|---|---|
| 90 | 18 | POL | 538 | YMDDVVLGAK | M | K | 1090.15 | 10 | * | 0.0330 | 0.0043 | 0.0002 | 0.0008 | 0.0001 | 652 |
| 80 | 16 | POL | 493 | YSHPIILGFR | S | R | | 10 | | | | | | | 653 |
| 80 | 16 | POL | 493 | YSHPIILGFRK 118 | S | K | | 11 | | | | | | | 654 |

TABLE IX

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 95 | 19 | POL | 529 | AFPHCLAF | XFXXXXXF | | | | 655 |
| 95 | 19 | POL | 529 | AFPHCLAFSY | XFXXXXXXXY | | | | 656 |
| 95 | 19 | POL | 529 | AFPHCLAFSYM | XFXXXXXXXXM | | | | 657 |
| 95 | 19 | X | 62 | AFSSAGPCAL | XFXXXXXXXL | 5.0118 | | 0.0012 | 658 |
| 90 | 18 | POL | 535 | AFSYMDDVVL | XFXXXXXXXL | 13.0130 | | 0.0009 | 659 |
| 95 | 19 | POL | 655 | AFTFSPTY | XFXXXXXY | | | | 660 |
| 95 | 19 | POL | 655 | AFTFSPTYKAF | XFXXXXXXXXF | | | | 661 |
| 95 | 19 | POL | 521 | AICSVVRRAF | XIXXXXXXXF | | | | 662 |
| 90 | 18 | NUC | 58 | AILCWGEL | XIXXXXXL | | | | 663 |
| 90 | 18 | NUC | 58 | AILCWGELM | XIXXXXXXM | | | | 664 |
| 95 | 19 | POL | 642 | ALMPLYACI | XLXXXXXXI | 3.0012 | * | | 665 |
| 95 | 19 | NUC | 54 | ALRQAILCW | XLXXXXXXW | | | | 666 |
| 80 | 16 | ENV | 108 | AMQWNSTTF | XMXXXXXXF | | | | 667 |
| 95 | 19 | POL | 690 | ATPTGWGL | XTXXXXXL | | | | 668 |
| 75 | 15 | POL | 690 | ATPTGWGLAI | XTXXXXXXXI | | | | 669 |
| 95 | 19 | POL | 397 | AVPNLQSL | XVXXXXXL | | | | 670 |
| 95 | 19 | POL | 397 | AVPNLQSLTNL | XVXXXXXXXXL | | | | 671 |
| 100 | 20 | NUC | 131 | AYRPPNAPI | XYXXXXXXI | 5.0062 | * | 0.0260 | 672 |
| 100 | 20 | NUC | 131 | AYRPPNAPIL | XYXXXXXXXL | 2.0172 | * | 0.0220 | 673 |
| 75 | 15 | POL | 607 | CFRKLPVNRPI | XFXXXXXXXXI | | | | 674 |
| 100 | 20 | ENV | 312 | CIPIPSSW | XIXXXXXW | | | | 675 |
| 100 | 20 | ENV | 312 | CIPIPSSWAF | XIXXXXXXXF | | | | 676 |
| 85 | 17 | NUC | 23 | CLGWLWGM | XLXXXXXM | | | | 677 |
| 85 | 17 | NUC | 23 | CLGWLWGMDI | XLXXXXXXXI | 2.0229 | | | 678 |
| 100 | 20 | ENV | 253 | CLIFLLVL | XLXXXXXL | 17.0248 | | | 679 |
| 100 | 20 | ENV | 253 | CLIFLLVLL | XLXXXXXXL | 1.0836 | | | 680 |
| 95 | 19 | ENV | 253 | CLIFLLVLLDY | XLXXXXXXXXY | 26.0548 | | | 681 |
| 95 | 19 | ENV | 239 | CLRRFIIF | XLXXXXXF | | | | 682 |
| 95 | 19 | ENV | 239 | CLRRFIIFL | XLXXXXXXL | 1.0829 | | | 683 |
| 75 | 15 | ENV | 239 | CLRRFIIFLF | XLXXXXXXXF | | | | 684 |
| 75 | 15 | ENV | 239 | CLRRFIIFLFI | XLXXXXXXXXI | Chisari 4.055 | | | 685 |
| 100 | 20 | ENV | 310 | CTCIPIPSSW | XTXXXXXXXW | | | | 686 |
| 90 | 18 | NUC | 31 | DIDPYKEF | XIXXXXXF | | | | 687 |
| 85 | 17 | NUC | 29 | DLLDTASAL | XLXXXXXXL | 1.0154 | | | 688 |
| 85 | 17 | NUC | 29 | DLLDTASALY | XLXXXXXXXY | 1.0519 | * | | 689 |
| 95 | 19 | POL | 40 | DLNLGNLNVSI | XLXXXXXXXXI | | | | 690 |
| 80 | 16 | NUC | 32 | DTASALYREAL | XTXXXXXXXXL | | | | 691 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 85 | 17 | POL | 618 | DWKVCQRI | XWXXXXXI | | | | 692 |
| 85 | 17 | POL | 618 | DWKVCQRIVGL | XWXXXXXXXL | | | | 693 |
| 90 | 18 | ENV | 262 | DYQGMLPVCPL | XYXXXXXXXL | 3.0441 | | 0.0002 | 694 |
| 80 | 16 | X | 122 | ELGEEIRL | XLXXXXXL | | | | 695 |
| 95 | 19 | NUC | 43 | ELLSFLPSDF | XLXXXXXXXF | | | | 696 |
| 95 | 19 | NUC | 43 | ELLSFLPSDFF | XLXXXXXXXXF | | | | 697 |
| 90 | 18 | NUC | 117 | EYLVSFGVW | XYXXXXXXW | 26.0150 | | | 698 |
| 90 | 18 | NUC | 117 | EYLVSFGVWI | XYXXXXXXXI | 13.0129 | * | 0.0340 | 699 |
| 100 | 20 | ENV | 382 | FFCLWVYI | XFXXXXXI | | | | 700 |
| 80 | 16 | ENV | 182 | FFLLTRIL | XFXXXXXL | | | | 701 |
| 80 | 16 | ENV | 182 | FFLLTRILTI | XFXXXXXXXI | | | | 702 |
| 85 | 17 | ENV | 13 | FFPDHQLDPAF | XFXXXXXXXXF | | | | 703 |
| 80 | 16 | ENV | 243 | FIIFLFIL | XIXXXXXL | 17.0246 | | | 704 |
| 80 | 16 | ENV | 243 | FIIFLFILL | XIXXXXXXL | 1.0830 | | | 705 |
| 80 | 16 | ENV | 243 | FIIFLFILLL | XIXXXXXXXL | 1.0894 | | | 706 |
| 80 | 16 | ENV | 248 | FILLLCLI | XIXXXXXI | Chisari 4.048 | | | 707 |
| 80 | 16 | ENV | 248 | FILLLCLIF | XIXXXXXXF | | | | 708 |
| 80 | 16 | ENV | 248 | FILLLCLIFL | XIXXXXXXXL | 1.0895 | | | 709 |
| 80 | 16 | ENV | 248 | FILLLCLIFLL | XIXXXXXXXXL | Chisari 4.049 | | | 710 |
| 80 | 16 | ENV | 246 | FLFILLLCL | XLXXXXXXL | 1.0832 | | | 711 |
| 80 | 16 | ENV | 246 | FLFILLLCLI | XLXXXXXXXI | 3.0206 | | | 712 |
| 80 | 16 | ENV | 246 | FLFILLLCLIF | XLXXXXXXXXF | | | | 713 |
| 75 | 15 | ENV | 171 | FLGPLLVL | XLXXXXXL | | | | 714 |
| 95 | 19 | POL | 513 | FLLAQFTSAI | XLXXXXXXXI | 1147.13 | * | | 715 |
| 95 | 19 | POL | 562 | FLLSLGIHL | XLXXXXXXL | 1.0851 | * | | 716 |
| 80 | 16 | ENV | 183 | FLLTRILTI | XLXXXXXXI | 3.0005 | * | | 717 |
| 95 | 19 | ENV | 256 | FLLVLLDY | XLXXXXXY | 26.0027 | | | 718 |
| 95 | 19 | ENV | 256 | FLLVLLDYQGM | XLXXXXXXXXM | | | | 719 |
| 95 | 19 | POL | 656 | FTFSPTYKAF | XTXXXXXXXF | 20.0262 | | | 720 |
| 95 | 19 | POL | 656 | FTFSPTYKAFL | XTXXXXXXXXL | | | | 721 |
| 95 | 19 | POL | 635 | FTQCGYPAL | XTXXXXXXL | 5.0031 | | | 722 |
| 95 | 19 | POL | 635 | FTQCGYPALM | XTXXXXXXXM | 5.0085 | | | 723 |
| 95 | 19 | ENV | 346 | FVGLSPTVW | XVXXXXXXXW | | | | 724 |
| 95 | 19 | ENV | 346 | FVGLSPTVWL | XVXXXXXXXL | 1.0931 | | | 725 |
| 90 | 18 | X | 132 | FVLGGCRHKL | XVXXXXXXXL | 1.0588 | | | 726 |
| 95 | 19 | ENV | 342 | FVQWFVGL | XVXXXXXL | 17.0109 | * | | 727 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 90 | 18 | POL | 766 | FVYVPSAL | XVXXXXXL | 17.0260 | * | | 728 |
| 95 | 19 | POL | 630 | GFAAPFTQCGY | XFXXXXXXXXY | | | | 729 |
| 80 | 16 | ENV | 181 | GFFLLTRI | XFXXXXXI | | | | 730 |
| 80 | 16 | ENV | 181 | GFFLLTRIL | XFXXXXXXL | | | | 731 |
| 80 | 16 | ENV | 181 | GFFLLTRILTI | XFXXXXXXXXI | | | | 732 |
| 95 | 19 | ENV | 12 | GFFPDHQL | XFXXXXXL | | | | 733 |
| 75 | 15 | ENV | 170 | GFLGPLLVL | XFXXXXXXL | | | | 734 |
| 80 | 16 | POL | 500 | GFRKIPMGVGL | XFXXXXXXXXL | | | | 735 |
| 95 | 19 | POL | 627 | GLLGFAAPF | XLXXXXXXF | 20.0124 | | | 736 |
| 95 | 19 | POL | 509 | GLSPFLLPAQF | XLXXXXXXXF | | | | 737 |
| 100 | 20 | ENV | 348 | GLSPTVWL | XLXXXXXL | Chisari 4.012 | | | 738 |
| 75 | 15 | ENV | 348 | GLSPTVWLSVI | XLXXXXXXXXI | Chisari 4.031 | | | 739 |
| 85 | 17 | NUC | 29 | GMDIDPYKEF | XMXXXXXXXF | 26.0372 | | | 740 |
| 90 | 18 | ENV | 265 | GMLPVCPL | XMXXXXXL | | | | 741 |
| 90 | 18 | POL | 735 | GTDNSVVL | XTXXXXXL | | | | 742 |
| 75 | 15 | ENV | 13 | GTNLSVPNPL | XTXXXXXXXL | | | | 743 |
| 80 | 16 | POL | 763 | GTSFVYVPSAL | XTXXXXXXXXL | | | | 744 |
| 80 | 16 | POL | 507 | GVGLSPFL | XVXXXXXL | | | | 745 |
| 80 | 16 | POL | 507 | GVGLSPFLL | XVXXXXXXL | 1.0850 | | | 746 |
| 95 | 19 | NUC | 123 | GVWIRTPPAY | XVXXXXXXXV | 1.0525 | | | 747 |
| 85 | 17 | NUC | 25 | GWLWGMDI | XWXXXXXI | | | | 748 |
| 85 | 17 | NUC | 25 | GWLWGMDIDPY | XWXXXXXXXXY | | | | 749 |
| 85 | 17 | ENV | 65 | GWSPQAQGI | XWXXXXXXI | 20.0134 | | 0.0024 | 750 |
| 85 | 17 | ENV | 65 | GWSPQAQGIL | XWXXXXXXXL | 20.0268 | | 0.0003 | 751 |
| 95 | 19 | POL | 639 | GYPALMPL | XYXXXXXL | | | | 752 |
| 95 | 19 | POL | 639 | GYPALMPLY | XYXXXXXXY | 2.0060 | * | 0.0490 | 753 |
| 95 | 19 | ENV | 234 | GYRWMCLRRF | XYXXXXXXXF | 2.0171 | * | 0.0110 | 754 |
| 95 | 19 | ENV | 234 | GYRWMCLRRFI | XYXXXXXXXXI | | | | 755 |
| 85 | 17 | POL | 579 | GYSLNFMGY | XYXXXXXXY | 2.0058 | | 0.0002 | 756 |
| 75 | 15 | POL | 579 | GYSLNFMGYVI | XYXXXXXXXXI | | | | 757 |
| 80 | 16 | POL | 820 | HFASPLHVAW | XFXXXXXXXW | | | | 758 |
| 75 | 15 | POL | 7 | HFRKLLLL | XFXXXXXL | | | | 759 |
| 80 | 16 | POL | 435 | HLLVGSSGL | XLXXXXXXL | 1.0187 | | | 760 |
| 75 | 15 | POL | 569 | HLNPNKTKRW | XLXXXXXXXW | | | | 761 |
| 80 | 16 | POL | 491 | HLYSHPII | XLXXXXXI | 17.0256 | | | 762 |
| 80 | 16 | POL | 491 | HLYSHPIIL | XLXXXXXXL | 1.0849 | * | | 763 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 80 | 16 | POL | 491 | HLYSHPIILGF | XLXXXXXXXXF | | | | 764 |
| 85 | 17 | POL | 715 | HTAELLAACF | XTXXXXXXXF | | | | 765 |
| 100 | 20 | NUC | 52 | HTALRQAI | XTXXXXXI | | | | 766 |
| 95 | 19 | NUC | 52 | HTALRQAIL | XTXXXXXXL | 5.0021 | | | 767 |
| 95 | 19 | NUC | 52 | HTALRQAILCW | XTXXXXXXXXW | | | | 768 |
| 100 | 20 | POL | 149 | HTLWKAGI | XTXXXXXI | | | | 769 |
| 100 | 20 | POL | 149 | HTLWKAGIL | XTXXXXXXL | 5.0033 | | | 770 |
| 100 | 20 | POL | 149 | HTLWKAGILY | XTXXXXXXXY | 1.0542 | * | | 771 |
| 100 | 20 | POL | 146 | HYLHTLWKAGI | XYXXXXXXXXI | | | | 772 |
| 100 | 20 | ENV | 381 | IFFCLWVY | XFXXXXXY | | | | 773 |
| 100 | 20 | ENV | 381 | IFFCLWVYI | XFXXXXXXI | 5.0058 | | 0.0087 | 774 |
| 80 | 16 | ENV | 245 | IFLFILLL | XFXXXXXL | | | | 775 |
| 80 | 16 | ENV | 245 | IFLFILLLCL | XFXXXXXXXL | | | | 776 |
| 80 | 16 | ENV | 245 | IFLFILLLCLI | XFXXXXXXXXI | | | | 777 |
| 95 | 19 | ENV | 255 | IFLLVLLDY | XFXXXXXXY | | | | 778 |
| 80 | 16 | ENV | 244 | IIFLFILL | XIXXXXXL | 17.0105 | | | 779 |
| 80 | 16 | ENV | 244 | IIFLFILLL | XIXXXXXXL | 1.0831 | | | 780 |
| 80 | 16 | ENV | 244 | IIFLFILLLCL | XIXXXXXXXXL | Chisari 4.052 | | | 781 |
| 80 | 16 | POL | 497 | IILGFRKI | XIXXXXXI | 17.0124 | * | | 782 |
| 80 | 16 | POL | 497 | IILGFRKIPM | XIXXXXXXXM | | | | 783 |
| 90 | 18 | NUC | 59 | ILCWGELM | XLXXXXXM | | | | 784 |
| 80 | 16 | POL | 498 | ILGFRKIPM | XLXXXXXXM | 3.0016 | | | 785 |
| 100 | 20 | ENV | 249 | ILLLCLIF | XLXXXXXF | | | | 786 |
| 100 | 20 | ENV | 249 | ILLLCLIFL | XLXXXXXXL | 1.0833 | * | | 787 |
| 100 | 20 | ENV | 249 | ILLLCLIFLL | XLXXXXXXXL | 1.0896 | * | | 788 |
| 80 | 16 | POL | 760 | ILRGTSFVY | XLXXXXXXY | 1.0205 | * | | 789 |
| 95 | 19 | ENV | 188 | ILTIPQSL | XLXXXXXL | | | | 790 |
| 90 | 18 | ENV | 188 | ILTIPQSLDSW | XLXXXXXXXXW | | | | 791 |
| 90 | 18 | POL | 625 | IVGLLGFAAPF | XVXXXXXXXXF | | | | 792 |
| 85 | 17 | ENV | 358 | IWMMWYWGPS | XWXXXXXXXXL | 1039.07 | | 0.0004 | 793 |
| 95 | 19 | POL | 395 | KFAVPNLQSL | XFXXXXXL | 5.0114 | | 0.0020 | 794 |
| 80 | 16 | POL | 503 | KIPMGVGL | XIXXXXXL | | | | 795 |
| 80 | 16 | POL | 503 | KIPMGVGLSPF | XIXXXXXXXXF | | | | 796 |
| 85 | 17 | NUC | 21 | KLCLGWLW | XLXXXXXW | | | | 797 |
| 85 | 17 | NUC | 21 | KLCLGWLWGM | XLXXXXXXXM | 3.0209 | * | | 798 |
| 95 | 19 | POL | 489 | KLHLYSHPI | XLXXXXXXI | 3.0009 | * | | 799 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 80 | 16 | POL | 489 | KLHLYSHPII | XLXXXXXXXI | | | | 800 |
| 80 | 16 | POL | 489 | KLHLYSHPIIL | XLXXXXXXXXL | | | | 801 |
| 75 | 15 | POL | 108 | KLIMPARF | XLXXXXXF | | | | 802 |
| 75 | 15 | POL | 108 | KLIMPARFY | XLXXXXXXY | 1.0171 | | | 803 |
| 80 | 16 | POL | 610 | KLPVNRPI | XLXXXXXI | | | | 804 |
| 80 | 16 | POL | 610 | KLPVNRPIDW | XLXXXXXXXW | | | | 805 |
| 95 | 19 | POL | 574 | KTKRWGYSL | XTXXXXXXL | 5.0034 | | | 806 |
| 85 | 17 | POL | 574 | KTKRWGYSLNF | XTXXXXXXXXF | | | | 807 |
| 85 | 17 | POL | 620 | KVCQRIVGL | XVXXXXXXL | 1.0198 | | | 808 |
| 85 | 17 | POL | 620 | KVCQRIVGLL | XVXXXXXXXL | 1.0567 | | | 809 |
| 95 | 19 | POL | 55 | KVGNFTGL | XVXXXXXL | 17.0116 | | | 810 |
| 95 | 19 | POL | 55 | KVGNFTGLY | XVXXXXXXY | 1.0166 | * | | 811 |
| 85 | 17 | X | 91 | KVLHKRTL | XVXXXXXL | | | | 812 |
| 85 | 17 | X | 91 | KVLHKRTLGL | XVXXXXXXXL | 1.0800 | | | 813 |
| 100 | 20 | POL | 121 | KYLPLDKGI | XYXXXXXXI | 5.0063 | * | 0.0028 | 814 |
| 85 | 17 | POL | 745 | KYTSFPWL | XYXXXXXL | 17.0132 | | | 815 |
| 85 | 17 | POL | 745 | KYTSFPWLL | XYXXXXXXL | 2.0061 | * | 3.6000 | 816 |
| 80 | 16 | ENV | 247 | LFILLLCL | XFXXXXXL | 17.0247 | | | 817 |
| 80 | 16 | ENV | 247 | LFILLLCLI | XFXXXXXXI | | | | 818 |
| 80 | 16 | ENV | 247 | LFILLLCLIF | XFXXXXXXXF | | | | 819 |
| 80 | 16 | ENV | 247 | LFILLLCLIFL | XFXXXXXXXXL | | | | 820 |
| 100 | 20 | ENV | 254 | LIFLLVLL | XIXXXXXL | Chisari 4.014 | | | 821 |
| 95 | 19 | ENV | 254 | LIFLLVLLDY | XIXXXXXXXY | 1.0899 | | | 822 |
| 100 | 20 | POL | 109 | LIMPARFY | XIXXXXXY | 26.0028 | | | 823 |
| 95 | 19 | POL | 514 | LLAQFTSAI | XLXXXXXXI | 3.0010 | * | | 824 |
| 100 | 20 | ENV | 251 | LLCLIFLL | XLXXXXXL | Chisari 4.015 | | | 825 |
| 100 | 20 | ENV | 251 | LLCLIFLLVL | XLXXXXXXXL | 1.0898 | | | 826 |
| 100 | 20 | ENV | 251 | LLCLIFLLVLL | XLXXXXXXXXL | Chisari 4.016 | | | 827 |
| 85 | 17 | NUC | 30 | LLDTASAL | XLXXXXXL | | | | 828 |
| 85 | 17 | NUC | 30 | LLDTASALY | XLXXXXXXY | 1.0155 | * | | 829 |
| 95 | 19 | ENV | 260 | LLDYQGML | XLXXXXXL | Chisari 4.021 | | | 830 |
| 80 | 16 | POL | 752 | LLGCAANW | XLXXXXXW | | | | 831 |
| 80 | 16 | POL | 752 | LLGCAANWI | XLXXXXXXI | 3.0013 | | | 832 |
| 80 | 16 | POL | 752 | LLGCAANWIL | XLXXXXXXXL | 1.0912 | * | | 833 |
| 95 | 19 | POL | 628 | LLGFAAPF | XLXXXXXF | | | | 834 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 75 | 15 | ENV | 63 | LLGWSPQAQGI | XLXXXXXXXXI | | | | 835 |
| 100 | 20 | ENV | 250 | LLLCLIFL | XLXXXXXL | Chisari 4.017 | | | 836 |
| 100 | 20 | ENV | 250 | LLLCLIFLL | XLXXXXXXL | 1.0834 | * | | 837 |
| 100 | 20 | ENV | 250 | LLLCLIFLLVL | XLXXXXXXXXL | Chisari 4.018 | | | 838 |
| 100 | 20 | ENV | 378 | LLPIFFCL | XLXXXXXL | 17.0112 | | | 839 |
| 100 | 20 | ENV | 378 | LLPIFFCLW | XLXXXXXXW | | | | 840 |
| 100 | 20 | ENV | 378 | LLPIFFCLWVY | XLXXXXXXXXY | 26.0549 | * | | 841 |
| 95 | 19 | NUC | 44 | LLSFLPSDF | XLXXXXXXF | | | | 842 |
| 95 | 19 | NUC | 44 | LLSFLPSDFF | XLXXXXXXXF | | | | 843 |
| 95 | 19 | POL | 563 | LLSLGIHL | XLXXXXXL | | | | 844 |
| 90 | 18 | POL | 407 | LLSSNLSW | XLXXXXXW | | | | 845 |
| 90 | 18 | POL | 407 | LLSSNLSWL | XLXXXXXXL | 1.0184 | * | | 846 |
| 90 | 18 | POL | 407 | LLSSNLSWLSL | XLXXXXXXXXL | | | | 847 |
| 80 | 16 | ENV | 184 | LLTRILTI | XLXXXXXI | Chisari 4.053 | | | 848 |
| 80 | 16 | POL | 436 | LLVGSSGL | XLXXXXXL | | | | 849 |
| 95 | 19 | ENV | 257 | LLVLLDYQGM | XLXXXXXXXM | 3.0207 | | | 850 |
| 95 | 19 | ENV | 257 | LLVLLDYQGML | XLXXXXXXXXL | | | | 851 |
| 95 | 19 | ENV | 175 | LLVLQAGF | XLXXXXXF | | | | 852 |
| 95 | 19 | ENV | 175 | LLVLQAGFF | XLXXXXXXF | 20.0121 | | | 853 |
| 90 | 18 | ENV | 175 | LLVLQAGFFL | XLXXXXXXXL | 1.0892 | * | | 854 |
| 90 | 18 | ENV | 175 | LLVLQAGFFLL | XLXXXXXXXXL | Chisari 4.028 | | | 855 |
| 100 | 20 | ENV | 338 | LLVPFVQW | XLXXXXXW | | | | 856 |
| 100 | 20 | ENV | 338 | LLVPFVQWF | XLXXXXXXF | | | | 857 |
| 90 | 18 | NUC | 100 | LLWFHISCL | XLXXXXXXL | 1.0844 | * | | 858 |
| 85 | 17 | NUC | 100 | LLWFHISCLTF | XLXXXXXXXXF | | | | 859 |
| 95 | 19 | POL | 643 | LMPLYACI | XMXXXXXI | 17.0130 | | | 860 |
| 75 | 15 | NUC | 137 | LTFGRETVL | XTXXXXXXL | | | | 861 |
| 75 | 15 | NUC | 137 | LTFGRETVLEY | XTXXXXXXXXY | | | | 862 |
| 90 | 18 | ENV | 189 | LTIPQSLDSW | XTXXXXXXXW | | | | 863 |
| 90 | 18 | ENV | 189 | LTIPQSLDSWW | XTXXXXXXXXW | | | | 864 |
| 90 | 18 | POL | 404 | LTNLLSSNL | XTXXXXXXL | | | | 865 |
| 90 | 18 | POL | 404 | LTNLLSSNLSW | XTXXXXXXXXW | | | | 866 |
| 80 | 16 | ENV | 185 | LTRILTIPQSL | XTXXXXXXXXL | | | | 867 |
| 85 | 17 | POL | 99 | LTVNEKRRL | XTXXXXXXL | | | | 868 |
| 95 | 19 | ENV | 258 | LVLLDYQGM | XVXXXXXXM | 3.0034 | | | 869 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 95 | 19 | ENV | 258 | LVLLDYQGML | XVXXXXXXXL | 1.0515 | | | 870 |
| 95 | 19 | ENV | 176 | LVLQAGFF | XVXXXXXF | | | | 871 |
| 90 | 16 | ENV | 176 | LVLQAGFFL | XVXXXXXXL | 1.0827 | | | 872 |
| 90 | 18 | ENV | 176 | LVLQAGFFLL | XVXXXXXXXL | 1.0893 | * | | 873 |
| 100 | 20 | ENV | 339 | LVPPVQWF | XVXXXXXF | | | | 874 |
| 95 | 19 | ENV | 339 | LVPFVQWFVGL | XVXXXXXXXXL | | | | 875 |
| 90 | 18 | NUC | 119 | LVSFGVWI | XVXXXXXI | Chisari 4.078 | | | 876 |
| 100 | 20 | POL | 377 | LVVDFSQF | XVXXXXXF | | | | 877 |
| 90 | 18 | NUC | 101 | LWFHISCL | XWXXXXXL | | | | 878 |
| 85 | 17 | NUC | 101 | LWFHISCLTF | XWXXXXXXXF | 26.0373 | | | 879 |
| 85 | 17 | NUC | 27 | LWGMDIDPY | XWXXXXXXY | | | | 880 |
| 100 | 20 | POL | 151 | LWKAGILY | XWXXXXXY | | | | 881 |
| 80 | 16 | POL | 492 | LYSHPIIL | XYXXXXXL | | | | 882 |
| 80 | 16 | POL | 492 | LYSHPIILGF | XYXXXXXXXF | 2.0161 | * | 1.1000 | 883 |
| 85 | 17 | ENV | 360 | MMWYWGPSL | XMXXXXXXL | 1.0839 | * | 0.0012 | 884 |
| 85 | 17 | ENV | 360 | MMWYWGPSLY | XMXXXXXXXY | 1039.01 | * | 0.0001 | 885 |
| 85 | 17 | ENV | 361 | MWYWGPSL | XWXXXXXL | 17.0249 | | | 886 |
| 85 | 17 | ENV | 361 | MWYWGPSLY | XWXXXXXXY | 1039.02 | | 0.0027 | 887 |
| 95 | 19 | POL | 561 | NFLLSLGI | XFXXXXXI | | | | 888 |
| 95 | 19 | POL | 561 | NFLLSLGIHL | XFXXXXXXXL | 5.0115 | | 0.0099 | 889 |
| 95 | 19 | POL | 42 | NLGNLNVSI | XLXXXXXXI | 3.0008 | | | 890 |
| 95 | 19 | POL | 42 | NLGNLNVSIPW | XLXXXXXXXXW | | | | 891 |
| 90 | 18 | POL | 406 | NLLSSNLSW | XLXXXXXXW | | | | 892 |
| 90 | 18 | POL | 406 | NLLSSNLSWL | XLXXXXXXXL | 1.0549 | | | 893 |
| 95 | 19 | POL | 45 | NLNVSIPW | XLXXXXXW | | | | 894 |
| 100 | 20 | POL | 400 | NLQSLTNL | XLXXXXXL | | | | 895 |
| 100 | 20 | POL | 400 | NLQSLTNLL | XLXXXXXXL | 1.0189 | | | 896 |
| 75 | 15 | ENV | 15 | NLSVPNPL | XLXXXXXL | | | | 897 |
| 75 | 15 | ENV | 15 | NLSVPNPLGF | XLXXXXXXXF | | | | 898 |
| 80 | 16 | POL | 758 | NWILRGTSF | XWXXXXXXF | | | | 899 |
| 80 | 16 | POL | 758 | NWILRGTSFVY | XWXXXXXXXXY | | | | 900 |
| 95 | 19 | POL | 512 | PFLLAQFTSAI | XFXXXXXXXXI | | | | 901 |
| 95 | 19 | POL | 634 | PFTQCGYPAL | XFXXXXXXXL | 5.0116 | | 0.0002 | 902 |
| 95 | 19 | POL | 634 | PFTQCGYPALM | XFXXXXXXXXM | | | | 903 |
| 95 | 19 | ENV | 341 | PFVQWFVGL | XFXXXXXXL | 5.0059 | | 0.0003 | 904 |
| 85 | 17 | POL | 616 | PIDWKVCQRI | XIXXXXXXXI | Chisari 4.091 | | | 905 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 100 | 20 | ENV | 380 | PIFFCLWVY | XIXXXXXXY | 1.0843 | | | 906 |
| 100 | 20 | ENV | 380 | PIFFCLWVYI | XIXXXXXXXI | 20.0258 | | | 907 |
| 85 | 17 | POL | 713 | PIHTAELL | XIXXXXXL | | | | 908 |
| 80 | 16 | POL | 496 | PIILGFRKI | XIXXXXXXI | 927.48 | | | 909 |
| 80 | 15 | POL | 496 | PIILGFRKlPM | XIXXXXXXXXM | | | | 910 |
| 100 | 20 | ENV | 314 | PIPSSWAF | XIXXXXXF | | | | 911 |
| 100 | 20 | POL | 124 | PLDKGIKPY | XLXXXXXXY | 1.0174 | * | | 912 |
| 100 | 20 | POL | 124 | PLDKGIKPYY | XLXXXXXXXY | 1.0541 | * | | 913 |
| 95 | 19 | POL | 20 | PLEEELPRL | XLXXXXXXL | 1.0163 | | | 914 |
| 95 | 19 | ENV | 10 | PLGFFPDHQL | XLXXXXXXXL | 1.0511 | | | 915 |
| 100 | 20 | POL | 427 | PLHPAAMPHL | XLXXXXXXXL | 1.0550 | | | 916 |
| 100 | 20 | POL | 427 | PLHPAAMPHLL | XLXXXXXXXXL | | | | 917 |
| 100 | 20 | ENV | 377 | PLLPIFFCL | XLXXXXXXL | 1.0842 | * | | 918 |
| 100 | 20 | ENV | 377 | PLLPIFFCLW | XLXXXXXXXW | | | | 919 |
| 95 | 19 | ENV | 174 | PLLVLQAGF | XLXXXXXXF | | | | 920 |
| 95 | 19 | ENV | 174 | PLLVLQAGFF | XLXXXXXXXF | | | | 921 |
| 90 | 18 | ENV | 174 | PLLVLQAGFFL | XLXXXXXXXXL | Chisari 4.029 | | | 922 |
| 80 | 16 | POL | 711 | PLPIHTAEL | XLXXXXXXL | 1.0201 | | | 923 |
| 80 | 18 | POL | 711 | PLPIHTAELL | XLXXXXXXXL | 1.0569 | | | 924 |
| 75 | 16 | POL | 2 | PLSYQHFRKL | XLXXXXXXXL | 1.0527 | | | 925 |
| 75 | 15 | POL | 2 | PLSYQHFRKLL | XLXXXXXXXXL | | | | 926 |
| 85 | 17 | POL | 98 | PLTVNEKRRL | XLXXXXXXXL | 1.0536 | | | 927 |
| 80 | 16 | POL | 505 | PMGVGLSPF | XMXXXXXXF | | | | 928 |
| 80 | 16 | POL | 505 | PMGVGLSPFL | XMXXXXXXXL | 1.0557 | | | 929 |
| 80 | 16 | POL | 505 | PMGVGLSPFLL | XMXXXXXXXXL | | | | 930 |
| 75 | 15 | POL | 692 | PTGWGLAI | XTXXXXXI | | | | 931 |
| 85 | 17 | POL | 797 | PTTGRTSL | XTXXXXXL | | | | 932 |
| 85 | 17 | POL | 797 | PTTGRTSLY | XTXXXXXXY | 1.0208 | * | | 933 |
| 80 | 16 | NUC | 15 | PTVQASKL | XTXXXXXL | | | | 934 |
| 80 | 16 | NUC | 15 | PTVQASKLCL | XTXXXXXXXL | | | | 935 |
| 75 | 15 | ENV | 361 | PTVWLSVI | XTXXXXXI | | | | 936 |
| 75 | 15 | ENV | 351 | PTVWLSVIW | XTXXXXXXW | | | | 937 |
| 75 | 15 | ENV | 351 | PTVWLSVIWM | XTXXXXXXXM | | | | 938 |
| 85 | 17 | POL | 612 | PVNRPIDW | XVXXXXXW | | | | 939 |
| 80 | 16 | POL | 750 | PWLLGCAANW | XWXXXXXXXW | | | | 940 |
| 80 | 15 | POL | 750 | PWLLGCAANWI | XWXXXXXXXXI | | | | 941 |
| 100 | 20 | POL | 51 | PWTHKVGNF | XWXXXXXXF | 20.0138 | * | 0.0280 | 942 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 80 | 16 | X | 8 | QLDPARDVL | XLXXXXXXL | 1.0210 | | | 943 |
| 80 | 16 | X | 8 | QLDPARDVLCL | XLXXXXXXXXL | Chisari 4.073 | | | 944 |
| 90 | 18 | NUC | 99 | QLLWFHISCL | XLXXXXXXL | 1.0908 | * | | 945 |
| 95 | 19 | POL | 665 | QVFADATPTGW | XVXXXXXXXXW | | | | 946 |
| 95 | 19 | ENV | 344 | QWFVGLSPTVW | XWXXXXXXXX | | | | 947 |
| 75 | 15 | ENV | 242 | RFIIFLFI | XFXXXXXI | 17.0151 | | | 948 |
| 75 | 15 | ENV | 242 | RFIIFLFIL | XFXXXXXXL | | | | 949 |
| 75 | 15 | ENV | 242 | RFIIFLFILL | XFXXXXXXXL | | | | 950 |
| 75 | 15 | ENV | 242 | RFIIFLFILLL | XFXXXXXXXXL | | | | 951 |
| 100 | 20 | ENV | 332 | RFSWLSLL | XFXXXXXL | | | | 952 |
| 100 | 20 | ENV | 332 | RFSWLSLLVPF | XFXXXXXXXXF | | | | 953 |
| 80 | 16 | ENV | 167 | RILTIPQSL | XIXXXXXXL | 1.0149 | | | 954 |
| 90 | 18 | POL | 524 | RIVGLLGF | XIXXXXXF | | | | 955 |
| 75 | 15 | POL | 106 | RLKLIMPARF | XLXXXXXXXF | | | | 956 |
| 75 | 15 | POL | 106 | RLKLIMPARFY | XLXXXXXXXXY | | | | 957 |
| 95 | 19 | POL | 376 | RLVVDFSQF | XLXXXXXXF | 20.0122 | | | 958 |
| 90 | 18 | POL | 355 | RTPARVTGGVF | XTXXXXXXXXF | | | | 959 |
| 95 | 19 | POL | 36 | RVAEDLNL | XVXXXXXL | | | | 960 |
| 90 | 18 | POL | 36 | RVAEDLNLGNL | XVXXXXXXXXL | | | | 961 |
| 80 | 16 | POL | 818 | RVHFASPL | XVXXXXXL | | | | 962 |
| 100 | 20 | POL | 357 | RVTGGVFL | XVXXXXXL | | | | 963 |
| 85 | 17 | POL | 577 | RWGYSLNF | XWXXXXXF | | | | 964 |
| 85 | 17 | POL | 577 | RWGYSLNFM | XWXXXXXXM | | | | 965 |
| 85 | 17 | POL | 577 | RWGYSLNRMGY | XWXXXXXXXXY | | | | 966 |
| 95 | 19 | ENV | 238 | RWMCLRRF | XWXXXXXF | | | | 967 |
| 95 | 19 | ENV | 236 | RWMCLRRFI | XWXXXXXXI | 20.0135 | * | 0.0710 | 968 |
| 95 | 19 | ENV | 236 | RWMCLRRFII | XWXXXXXXXI | 20.0269 | * | 1.1000 | 969 |
| 95 | 19 | ENV | 236 | RWMCLRRRIF | XWXXXXXXXF | | | | 970 |
| 100 | 20 | POL | 167 | SFCGSPYSW | XFXXXXXXW | 20.0139 | * | 0.0710 | 971 |
| 95 | 19 | NUC | 46 | SFLPSDFF | XFXXXXXF | | | | 972 |
| 80 | 16 | POL | 765 | SFVYVPSAL | XFXXXXXXL | | | | 973 |
| 100 | 20 | POL | 49 | SIPWTHKVGNF | XIXXXXXXXXF | | | | 974 |
| 95 | 19 | ENV | 194 | SLDSWWTSL | XLXXXXXXL | 1.0150 | | | 975 |
| 95 | 19 | ENV | 194 | SLDSWWTSLNF | XLXXXXXXXXF | | | | 976 |
| 95 | 19 | POL | 416 | SLDVSAAF | XLXXXXXF | | | | 977 |
| 95 | 19 | POL | 416 | SLDVSAAFY | XLXXXXXXY | 1.0186 | * | | 978 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 100 | 20 | ENV | 337 | SLLVPFVQW | XLXXXXXXW | | | | 979 |
| 100 | 20 | ENV | 337 | SLLVPFVQWF | XLXXXXXXXF | | | | 980 |
| 75 | 15 | POL | 581 | SLNFMGYVI | XLXXXXXXI | 3.0011 | | | 981 |
| 95 | 19 | X | 54 | SLRGLPVCAF | XLXXXXXXXF | 20.0259 | | | 982 |
| 90 | 18 | POL | 403 | SLTNLLSSNL | XLXXXKXXXL | 1.0548 | | | 983 |
| 75 | 15 | X | 104 | STTDLEAY | XTXXXXXY | | | | 984 |
| 75 | 15 | X | 104 | STTDLEAYF | XTXXXXXXF | | | | 985 |
| 75 | 15 | ENV | 17 | SVPNPLGF | XVXXXXXF | | | | 986 |
| 85 | 17 | POL | 548 | SVQHLESL | XVXXXXXL | | | | 987 |
| 80 | 16 | ENV | 330 | SVRFSWLSL | XVXXXXXXL | 1.0153 | | | 988 |
| 80 | 16 | ENV | 330 | SVRFSWLSLL | XVXXXXXXXL | 1.0517 | | | 989 |
| 90 | 18 | POL | 739 | SVVLSRKY | XVXXXXXY | 26.0029 | | | 990 |
| 85 | 17 | POL | 739 | SVVLSRKYTSF | XVXXXXXXXXF | | | | 991 |
| 95 | 19 | POL | 524 | SVVRRAFPHCL | XVXXXXXXXXL | | | | 992 |
| 95 | 19 | POL | 413 | SWLSLDVSAAF | XWXXXXXXXXF | | | | 993 |
| 100 | 20 | ENV | 334 | SWLSLLVPF | XWXXXXXXF | 20.0136 | * | 0.3900 | 994 |
| 95 | 19 | POL | 392 | SWPKFAVPNL | XWXXXXXXXL | 20.0271 | * | 5.6000 | 995 |
| 100 | 20 | ENV | 197 | SWWTSLNF | XWXXXXXF | | | | 996 |
| 95 | 19 | ENV | 197 | SWWTSLNFL | XWXXXXXXL | 20.0137 | * | 0.3800 | 997 |
| 90 | 18 | POL | 537 | SYMDDVVL | XYXXXXXL | | | | 998 |
| 75 | 15 | POL | 4 | SYQHFRKL | XYXXXXXL | | | | 999 |
| 75 | 15 | POL | 4 | SYQHFRKLL | XYXXXXXXL | 2.0042 | | 0.0051 | 1000 |
| 75 | 15 | POL | 4 | SVQHFRKLLL | XYXXXXXXXL | 2.0173 | * | 0.0660 | 1001 |
| 75 | 15 | POL | 4 | SYQHFRKLLLL | XYXXXXXXXXL | | | | 1002 |
| 75 | 15 | NUC | 138 | TFGRETVL | XFXXXXXL | | | | 1003 |
| 75 | 15 | NUC | 138 | TFGRETVLEY | XFXXXXXXXY | | | | 1004 |
| 75 | 15 | NUC | 138 | TFGRETVLEYL | XFXXXXXXXXL | | | | 1005 |
| 95 | 19 | POL | 657 | TFSPTYKAF | XFXXXXXXF | 5.0064 | | 0.0060 | 1006 |
| 95 | 19 | POL | 657 | TFSPTYKAFL | XFXXXXXXKL | 5.0117 | | 0.0043 | 1007 |
| 90 | 18 | ENV | 190 | TIPQSLDSW | XIXXXXXXW | | | | 1008 |
| 90 | 18 | ENV | 190 | TIPQSLDSWW | XIXXXXXXXW | | | | 1009 |
| 100 | 20 | POL | 150 | TLWKAGIL | XLXXXXXL | | | | 1010 |
| 100 | 20 | POL | 150 | TLWKAGILY | XLXXXXXXY | 1.0177 | * | | 1011 |
| 75 | 15 | X | 105 | TTDLEAYF | XTXXXXXF | | | | 1012 |
| 85 | 17 | POL | 798 | TTGRTSLY | XTXXXXXY | 26.0030 | | | 1013 |
| 85 | 17 | POL | 100 | TVNEKRRL | XVXXXXXL | | | | 1014 |
| 80 | 16 | NUC | 16 | TVQASKLCL | XVXXXXXXL | 1.0365 | | | 1015 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 80 | 16 | NUC | 16 | TVQASKLCLGW | XVXXXXXXXXW | | | | 1016 |
| 75 | 15 | ENV | 352 | TVWLSVIW | XVXXXXXW | | | | 1017 |
| 75 | 15 | ENV | 352 | TVWLSVIWM | XVXXXXXXM | 3.0035 | | | 1018 |
| 95 | 19 | POL | 686 | VFADATPTGW | XFXXXXXXXW | 20.0272 | * | 0.0180 | 1019 |
| 75 | 15 | X | 131 | VFVLGGCRHKL | XFXXXXXXXXL | | | | 1020 |
| 85 | 17 | POL | 543 | VLGAKSVQHL | XLXXXXXXXL | 1.0560 | | | 1021 |
| 90 | 18 | X | 133 | VLGGCRHKL | XLXXXXXXL | 1.0220 | | | 1022 |
| 85 | 17 | X | 92 | VLHKRTLGL | XLXXXXXXL | 1.0391 | | | 1023 |
| 95 | 19 | ENV | 259 | VLLDYQGM | XLXXXXXM | 17.0107 | | | 1024 |
| 95 | 19 | ENV | 259 | VLLDYQGML | XLXXXXXXL | 1.0151 | * | | 1025 |
| 95 | 19 | ENV | 177 | VLQAGFFL | XLXXXXXL | Chisari 4.027 | | | 1026 |
| 95 | 19 | ENV | 177 | VLQAGFFLL | XLXXXXXXL | 1.0828 | * | | 1027 |
| 85 | 17 | POL | 741 | VLSRKYTSF | XLXXXXXXF | | | | 1028 |
| 85 | 17 | POL | 741 | VLSRKYTSFPW | XLXXXXXXXXW | | | | 1029 |
| 80 | 16 | POL | 542 | VVLGAKSVQHL | XVXXXXXXXXL | | | | 1030 |
| 85 | 17 | POL | 740 | VVLSRKYTSF | XVXXXXXXXF | 20.0261 | | | 1031 |
| 95 | 19 | POL | 525 | VVRRAFPHCL | XVXXXXXXXL | 1.0558 | | | 1032 |
| 95 | 19 | NUC | 124 | VWIRTPPAY | XWXXXXXXY | | | | 1033 |
| 75 | 15 | ENV | 353 | VWLSVIWM | XWXXXXXM | | | | 1034 |
| 90 | 18 | NUC | 102 | WFHISCLTF | XFXXXXXXF | 13.0073 | * | 0.0300 | 1035 |
| 95 | 19 | ENV | 345 | WFVGLSPTVW | XFXXXXXXXW | 20.0270 | * | 0.0120 | 1036 |
| 95 | 19 | ENV | 345 | WFVGLSPTVWL | XFXXXXXXXXL | | | | 1037 |
| 80 | 16 | POL | 759 | WILRGTSF | XIXXXXXF | | | | 1038 |
| 80 | 16 | POL | 759 | WLRGTSFVY | XIXXXXXXXY | 1.0572 | | | 1039 |
| 95 | 19 | NUC | 125 | WIRTPPAY | XIXXXXXY | 26.0031 | | | 1040 |
| 80 | 16 | POL | 751 | WLLGCAANW | XLXXXXXXW | | | | 1041 |
| 80 | 16 | POL | 751 | WLLGCAANWI | XLXXXXXXXI | Chisari 4.104 | | | 1042 |
| 80 | 16 | POL | 751 | WLLGCAANWIL | XLXXXXXXXXL | | | | 1043 |
| 95 | 19 | POL | 414 | WLSLDVSAAF | XLXXXXXXXF | | | | 1044 |
| 95 | 19 | POL | 414 | WLSLDVSAAFY | XLXXXXXXXXY | 26.0551 | | | 1045 |
| 100 | 20 | ENV | 335 | WLSLLVPF | XLXXXXXF | | | | 1046 |
| 100 | 20 | ENV | 335 | WLSLLVPFVQW | XLXXXXXXXXW | | | | 1047 |
| 85 | 17 | NUC | 26 | WLWGMDIDPY | XLXXXXXXXY | 1.0774 | * | | 1048 |
| 95 | 19 | ENV | 237 | WMCLRRFI | XMXXXXXI | | | | 1049 |
| 95 | 19 | ENV | 237 | WMCLRRFII | XMXXXXXXI | 3.0031 | * | 0.0230 | 1050 |
| 95 | 19 | ENV | 237 | WMCLRRFIIF | XMXXXXXXXF | 20.0266 | | 0.0013 | 1051 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 95 | 19 | ENV | 237 | WMCLRRFIIFL | XMXXXXXXXXL | Chisari 4.024 | | | 1052 |
| 85 | 17 | ENV | 359 | WMMWYWGPSL | XMXXXXXXXL | 1.0901 | * | 0.0005 | 1053 |
| 85 | 17 | ENV | 359 | WMMWYWGPSL | XMXXXXXXXXY | 26.0552 | * | | 1054 |
| 100 | 20 | POL | 52 | WTHKVGNF | XTXXXXXF | | | | 1055 |
| 95 | 19 | POL | 52 | WTHKVGNFTGL | XTXXXXXXXXL | | | | 1056 |
| 95 | 19 | ENV | 198 | WWTSLNFL | XWXXXXXL | | | | 1057 |
| 95 | 17 | ENV | 362 | WYWGPSLY | XYXXXXXY | 3.0362 | | 0.0001 | 1058 |
| 100 | 20 | POL | 147 | YLHTLWKAGI | XLXXXXXXXI | 7.0066 | * | | 1059 |
| 100 | 20 | POL | 147 | YLHTLWKAGIL | XLXXXXXXXXL | | | | 1060 |
| 100 | 20 | POL | 122 | YLPLDKGI | XLXXXXXI | | | | 1061 |
| 100 | 20 | POL | 122 | YLPLDKGIKPY | XLXXXXXXXXY | 26.0553 | | | 1062 |
| 90 | 18 | NUC | 118 | YLVSFGVW | XLXXXXXW | | | | 1063 |
| 90 | 18 | NUC | 118 | YLVSFGVWI | XLXXXXXI | 3.0007 | * | | 1064 |
| 85 | 17 | POL | 746 | YTSFPWLL | XTXXXXXL | | | | 1065 |
| | | | | 411 | | | | | |

TABLE X

HBV B07 SUPER MOTIF (with binding information)

| Conservancy | Frequency | Protein | Position | Sequence | P2 | C-term | Peptide | A TABLE X-continued HBV B07 SUPER MOTIF (with binding information)

| Conservancy | Frequency | Protein | Position | Sequence | P2 | C-term | Peptide | AA | Filed | B*0702 | B*3501 | B*5101 | B*5301 | B*5401 | SEQ ID NO: |
|---|---|---|---|---|---|---|---|---|---|---|---|---|---|---|---|
| 95 | 19 | ENV | 173 | GPLLVLQAGF | P | A | 15.0212 | 10 |  | 0.0001 | 0.0001 | 0.0002 | 0.0001 | 0.0002 | 1089 |
| 95 | 19 | ENV | 173 | GPLLVLQAGFF | P | F | 26.0556 | 11 |  | 0.0011 | 0.0001 | 0.0001 | 0.0008 | 0.0009 | 1090 |
| 85 | 17 | POL | 97 | GPLTVNEKRRL | P | L | 26.0557 | 11 |  | 0.0031 | 0.0001 | 0.0001 | -0.0003 | 0.0001 | 1091 |
| 100 | 20 | POL | 429 | HPAAMPHL | P | L | 19.0011 | 8 | * | 0.0650 | 0.0004 | 0.3100 | 0.0037 | 0.0160 | 1092 |
| 100 | 20 | POL | 429 | HPAAMPHLL | P | L | 1147.02 | 9 | * | 0.0980 | 0.0270 | 0.0110 | 0.0500 | 0.0120 | 1093 |
| 85 | 17 | POL | 429 | HPAAMPHLLV | P | V | 20.0273 | 10 | * | 0.0160 | 0.0020 | 0.0078 | 0.0140 | 0.0170 | 1094 |
| 80 | 16 | POL | 495 | HPILGFRKI | P | I | | 10 |  | | | | | | 1095 |
| 100 | 20 | ENV | 313 | IPIPSSWA | P | A | 19.0005 | 8 | * | 0.0004 | 0.0004 | 0.0019 | 0.0002 | 0.0600 | 1096 |
| 100 | 20 | ENV | 313 | IPIPSSWAF | P | F | 1145.04 | 9 | * | 0.1300 | 2.7679 | 2.3500 | 0.7450 | 0.0034 | 1097 |
| 80 | 16 | ENV | 313 | IPIPSSWAFA | P | A | 16.0177 | 10 | * | 0.0013 | 0.0024 | | 0.0014 | 0.4500 | 1098 |
| 80 | 16 | POL | 504 | IPMGVGLSPF | P | F | | 10 |  | | | | | | 1099 |
| 80 | 16 | POL | 504 | IPMGVGLSPFL | P | L | | 11 |  | | | | | | 1100 |
| 90 | 18 | ENV | 191 | IPQSLDSW | P | W | F126.65 | 8 |  | | | | | | 1101 |
| 90 | 18 | ENV | 191 | IPQSLDSWW | P | W | F126.60 | 9 | * | | | | | | 1102 |
| 80 | 16 | ENV | 315 | IPSSWAFA | P | A | | 8 | * | | | | | | 1103 |
| 100 | 20 | POL | 50 | IPWTHKVGNF | P | F | 15.0209 | 10 |  | 0.0013 | 0.0001 | 0.0007 | 0.0001 | 0.0002 | 1104 |
| 100 | 20 | ENV | 379 | LPIFFCLW | P | W | 19.0007 | 8 | * | 0.0001 | 0.0001 | 0.0360 | 0.1400 | 0.0035 | 1105 |
| 100 | 20 | ENV | 379 | LPIFFCLWV | P | V | 1308.22 | 9 |  | | | | | | 1106 |
| 100 | 20 | ENV | 379 | LPIFFCLWVY | P | Y | 15.0215 | 10 |  | 0.0002 | 0.0079 | 0.0002 | 0.0006 | 0.0002 | 1107 |
| 100 | 20 | ENV | 379 | LPIFFCLWVYI | P | I | 26.0558 | 11 |  | 0.0002 | 0.0001 | 0.0043 | 0.0139 | 0.0021 | 1108 |
| 85 | 17 | POL | 712 | LPIHTAEL | P | L | 17.0259 | 8 |  | | | | | | 1109 |
| 85 | 17 | POL | 712 | LPIHTAELL | P | L | 20.0140 | 9 | * | 0.0040 | 0.0630 | 0.0052 | 0.3100 | 0.0005 | 1110 |
| 85 | 17 | POL | 712 | LPIHTAELLA | P | A | 16.0181 | 10 | * | 0.0018 | 0.0011 | | 0.0016 | 0.3300 | 1111 |

TABLE X-continued

HBV B07 SUPER MOTIF (With binding information)

| Conservancy | Frequency | Protein | Position | Sequence | P2 | C-term | Peptide | AA | Filed | B*0702 | B*3501 | B*5101 | B*5301 | B*5401 | SEQ ID NO: |
|---|---|---|---|---|---|---|---|---|---|---|---|---|---|---|---|
| 85 | 17 | POL | 712 | LPIHTAELLAA | P | A | 26.0559 | 11 |  | 0.0090 | 0.0027 | -0.0003 | 0.0120 | 2.7500 | 1112 |
| 80 | 16 | X | 89 | LPKVLHKRTL | P | L |  | 10 |  |  |  |  |  |  | 1113 |
| 100 | 20 | POL | 123 | LPLDKGIKPY | P | Y | 15.0210 | 10 | * | 0.0001 | 0.0290 | 0.0002 | 0.0003 | 0.0002 | 1114 |
| 100 | 20 | POL | 123 | LPLDKGIKPYY | P | Y | 26.0560 | 11 |  | -0.0002 | 0.0009 | 0.0001 | 0.0007 | 0.0001 | 1115 |
| 95 | 19 | X | 58 | LPVCAFSSA | P | A | 1147.06 | 9 | * | 0.0480 | 0.0710 | 0.0110 | 0.0009 | 19.0000 | 1116 |
| 80 | 16 | POL | 611 | LPVNRPIDW | P | W |  | 9 |  |  |  |  |  |  | 1117 |
| 80 | 16 | POL | 611 | LPVNRPIDWKV | P | V |  | 11 |  |  |  |  |  |  |  |
| 80 | 16 | POL | 433 | MPHLLVGSSGL | P | L |  | 11 |  |  |  |  |  |  |  |
| 100 | 20 | POL | 1 | MPLSYQHF | P | F | 19.0010 | 8 | * | 0.0001 | 0.0097 | 0.0120 | 0.0370 | 0.0190 |  |
| 75 | 15 | POL | 1 | MPLSYQHFRKL | P | L |  | 11 |  |  |  |  |  |  |  |
| 90 | 18 | POL | 774 | NPADDPSRGRL | P | L | 26.0561 | 11 | * | 0.0120 | 0.0001 | 0.0001 | -0.0003 | 0.0001 |  |
| 95 | 19 | ENV | 9 | NPLGFFPDHQL | P | L | 26.0562 | 11 |  | 0.0012 | 0.0021 | 0.0001 | 0.0028 | 0.0001 |  |
| 75 | 15 | POL | 571 | NPNKTKRW | P | W |  | 8 |  |  |  |  |  |  |  |
| 75 | 15 | POL | 571 | NPNKTKRWGY | P | Y |  | 10 |  |  |  |  |  |  |  |
| 95 | 19 | NUC | 129 | PPAYRPPNA | P | A | 16.0007 | 9 |  | 0.0001 | 0.0001 | 0.0001 | 0.0002 | 0.0003 |  |
| 95 | 19 | NUC | 129 | PPAYRPPNAPI | P | I | 26.0583 | 11 |  | 0.0003 | 0.0001 | 0.0001 | -0.0003 | 0.0001 |  |
| 85 | 17 | ENV | 58 | PPHGGLLGW | P | W | 20.0141 | 9 |  | 0.0001 | 0.0002 | 0.0001 | 0.0003 | 0.0002 |  |
| 100 | 20 | NUC | 134 | PPNAPILSTL | P | L | 15.0211 | 10 |  | 0.0001 | 0.0001 | 0.0035 | 0.0001 | 0.0002 |  |
| 80 | 16 | POL | 615 | RPIDWKVCQRI | P | I |  | 11 |  |  |  |  |  |  |  |
| 95 | 19 | NUC | 133 | RPPNAPIL | P | L | 19.0009 | 8 | * | 0.0076 | 0.0001 | 0.0280 | 0.0002 | 0.0002 |  |
| 100 | 20 | NUC | 133 | RPPNAPILSTL | P | L | 26.0564 | 11 | * | 0.1300 | 0.0001 | 0.0018 | -0.0003 | 0.0001 |  |
| 100 | 20 | NUC | 44 | SPEHCSPHHTA | P | A | 26.0565 | 11 |  | -0.0002 | 0.0001 | 0.0001 | -0.0003 | 0.0011 |  |
| 95 | 19 | POL | 511 | SPFLLAQF | P | F | 19.0012 | 8 | * | 0.5500 | 0.0009 | 0.0180 | 0.0009 | 0.0093 |  |

TABLE X-continued

HBV B07 SUPER MOTIF (With binding information)

| Conservancy | Frequency | Protein | Position | Sequence | P2 | C-term | Peptide | AA | Filed | B*0702 | B*3501 | B*5101 | B*5301 | B*5401 | SEQ ID NO: |
|---|---|---|---|---|---|---|---|---|---|---|---|---|---|---|---|
| 95 | 19 | POL | 511 | SPFLLAQFTSA | P | A | 26.0566 | 11 | * | 0.0820 | 0.0001 | 0.0001 | -0.0003 | 12.0500 | |
| 100 | 20 | NUC | 49 | SPHHTALRQA | P | A | 16.0178 | 10 | | 0.0012 | 0.0001 | | 0.0002 | 0.0035 | |
| 100 | 20 | NUC | 49 | SPHHTALRQAI | P | I | 26.0567 | 11 | * | 0.5800 | 0.0001 | 0.0004 | 0.0005 | 0.0002 | |
| 85 | 17 | ENV | 67 | SPQAQGIL | P | L | | 8 | | | | | | | |
| 85 | 17 | POL | 808 | SPSVPSHL | P | L | | 8 | | | | | | | |
| 75 | 15 | ENV | 350 | SPTVWLSV | P | V | | 8 | | | | | | | |
| 75 | 15 | ENV | 350 | SPTVWLSVI | P | I | 1308.16 | 9 | | | | | | | |
| 75 | 15 | ENV | 350 | SPTVWLSVIW | P | W | 1308.17 | 10 | | | | | | | |
| 75 | 15 | ENV | 350 | SPTVWLSVIWM | P | M | | 11 | | | | | | | |
| 95 | 19 | POL | 659 | SPTYKAFL | P | L | 19.0015 | 8 | * | 0.3900 | 0.0001 | 0.0019 | 0.0002 | 0.0002 | |
| 90 | 18 | POL | 354 | TPARVTGGV | P | V | 1147.07 | 9 | | 0.0078 | 0.0001 | 0.0013 | 0.0001 | 0.0015 | |
| 90 | 18 | POL | 354 | TPARVTGGVF | P | F | 1147.04 | 10 | | 0.3200 | 0.1000 | 0.0001 | 0.0099 | 0.0006 | |
| 90 | 18 | POL | 354 | TPARVTGGVFL | P | L | 26.0568 | 11 | * | 0.0950 | 0.0001 | 0.0001 | 0.0005 | 0.0005 | |
| 95 | 19 | NUC | 128 | TPPAYRPPNA | P | A | 16.0179 | 10 | * | 0.0001 | 0.0001 | | 0.0002 | 0.0100 | |
| 75 | 15 | ENV | 57 | TPPHGGLL | P | L | | 8 | | | | | | | |
| 75 | 15 | ENV | 57 | TPPHGGLLGW | P | W | 1308.04 | 10 | | | | | | | |
| 80 | 16 | POL | 691 | TPTGWGLA | P | A | | 8 | | | | | | | |
| 75 | 15 | POL | 691 | TPTGWGLAI | P | I | | 9 | | | | | | | |
| 95 | 19 | ENV | 340 | VPFVQWFV | P | V | 19.0008 | 8 | * | 0.0010 | 0.0001 | 19.0000 | 0.0002 | 0.1100 | |
| 95 | 19 | ENV | 340 | VPFVQWFVGL | P | L | 15.0213 | 10 | | 0.0011 | 0.0001 | 0.0100 | 0.0001 | 0.0025 | |
| 95 | 19 | POL | 398 | VPNLQSLTNL | P | L | 15.0216 | 10 | | 0.0006 | 0.0001 | 0.0004 | 0.0001 | 0.0002 | |
| 95 | 19 | POL | 398 | VPNLQSLTNLL | P | L | 26.0569 | 11 | | 0.0004 | 0.0001 | 0.0001 | -0.0003 | 0.0002 | |
| 90 | 18 | POL | 769 | VPSALNPA | P | A | 19.0016 | 8 | * | 0.0011 | 0.0001 | 0.0070 | 0.0002 | 1.0000 | |

TABLE X-continued

| HBV B07 SUPER MOTIF (with binding information) | | | | | | | | | | | | |
|---|---|---|---|---|---|---|---|---|---|---|---|---|
| Conservancy | Frequency | Protein | Position | Sequence | P2 | C-term | Peptide | AA | Filed | B*0702 | B*3501 | B*5101 | B*5301 | B*5401 | SEQ ID NO: |
| 95 | 19 | POL | 393 | WPKFAVPNL | P | L | 15.0035 | 9 | | 0.0054 | 0.0002 | 0.0016 | 0.0001 | 0.0015 | |
| 95 | 19 | POL | 640 | YPALMPLY | P | Y | 19.0014 | 8 | * | 0.0004 | 0.2600 | 0.4100 | 0.0450 | 0.0056 | |
| 95 | 19 | POL | 640 | YPALMPLYA | P | A | 1147.08 | 9 | * | 0.0180 | 0.0480 | 0.0340 | 0.0140 | 16.0000 | |
| 95 | 19 | POL | 640 | YPALMPLYACI | P | I | 26.0570 | 11 | | 0.0040 | 0.0001 | 0.0470 | 0.0320 | 0.0700 | 96 |

TABLE XI

HBV B27 SUPER MOTIF

| Source | Conservancy | Freq | Protein | Position | Sequence | String | Super-Motif | Peptide Filed | SEQ ID NO: |
|---|---|---|---|---|---|---|---|---|---|
| HBV | 95 | 19 | X | 51 | AHLSLRGL | XHXXXXXL | B27s | | 1162 |
| HBV | 85 | 17 | POL | 546 | AKSVQHLESL | XKXXXXXXXL | B27s | | 1163 |
| HBV | 90 | 18 | POL | 356 | ARVTGGVF | XRXXXXXF | B27s | | 1164 |
| HBV | 90 | 18 | POL | 356 | ARVTGGVFL | XRXXXXXXL | B27s | | 1165 |
| HBV | 95 | 19 | X | 48 | DHGAHLSL | XHXXXXXL | B27s | | 1166 |
| HBV | 95 | 19 | X | 48 | DHGAHLSLRGL | XHXXXXXXXXL | B27s | | 1167 |
| HBV | 90 | 18 | ENV | 16 | DHQLDPAF | XHXXXXXF | B27s | | 1168 |
| HBV | 100 | 20 | POL | 126 | DKGIKPYY | XKXXXXXY | B27s | | 1169 |
| HBV | 100 | 20 | NUC | 46 | EHCSPHHTAL | XHXXXXXXXL | B27s | | 1170 |
| HBV | 90 | 18 | NUC | 103 | FHISCLTF | XHXXXXXF | B27s | | 1171 |
| HBV | 80 | 16 | POL | 501 | FRKIPMGVGL | XRXXXXXXXL | B27s | | 1172 |
| HBV | 80 | 16 | POL | 608 | FRKLPVNRPI | XRXXXXXXXI | B27s | | 1173 |
| HBV | 75 | 15 | NUC | 140 | GRETVLEY | XRXXXXXY | B27s | | 1174 |
| HBV | 75 | 15 | NUC | 140 | GRETVLEYL | XRXXXXXXL | B27s | | 1175 |
| HBV | 100 | 20 | NUC | 51 | HHTALRQAI | XHXXXXXXI | B27s | | 1176 |
| HBV | 95 | 19 | NUC | 51 | HHTALRQAIL | XHXXXXXXXL | B27s | | 1177 |
| HBV | 95 | 19 | POL | 54 | HKVGNFTGL | XKXXXXXXL | B27s | 17.0358 | 1178 |
| HBV | 95 | 19 | POL | 54 | HKVGNFTGLY | XKXXXXXXXY | B27s | | 1179 |
| HBV | 75 | 15 | POL | 568 | IHLNPNKTKRW | XHXXXXXXXXW | B27s | | 1180 |
| HBV | 85 | 17 | POL | 714 | IHTAELLAACF | XHXXXXXXXXF | B27s | | 1181 |
| HBV | 85 | 17 | POL | 576 | KRWGYSLNF | XRXXXXXF | B27s | | 1182 |
| HBV | 85 | 17 | POL | 576 | KRWGYSLNFM | XRXXXXXXXM | B27s | | 1183 |
| HBV | 90 | 18 | X | 93 | LHKRTLGL | XHXXXXXL | B27s | | 1184 |
| HBV | 95 | 19 | POL | 490 | LHLYSHPI | XHXXXXXI | B27s | | 1185 |
| HBV | 80 | 16 | POL | 490 | LHLYSHPII | XHXXXXXXI | B27s | | 1186 |
| HBV | 80 | 16 | POL | 490 | LHLYSHPIIL | XHXXXXXXXL | B27s | | 1187 |
| HBV | 100 | 20 | POL | 428 | LHPAAMPHL | XHXXXXXXL | B27s | | 1188 |
| HBV | 100 | 20 | POL | 428 | LHPAAMPHLL | XHXXXXXXXL | B27s | | 1189 |
| HBV | 100 | 20 | POL | 148 | LHTLWKAGI | XHXXXXXXI | B27s | | 1190 |
| HBV | 100 | 20 | POL | 148 | LHTLWKAGIL | XHXXXXXXXL | B27s | | 1191 |
| HBV | 100 | 20 | POL | 148 | LHTLWKAGILY | XHXXXXXXXXY | B27s | | 1192 |
| HBV | 75 | 15 | POL | 107 | LKLIMPARF | XKXXXXXXF | B27s | | 1193 |
| HBV | 75 | 15 | POL | 107 | LKLIMPARFY | XKXXXXXXXY | B27s | | 1194 |
| HBV | 95 | 19 | X | 55 | LRGLPVCAF | XRXXXXXXF | B27s | | 1195 |
| HBV | 80 | 16 | POL | 761 | LRGTSFVY | XRXXXXXY | B27s | | 1196 |
| HBV | 95 | 19 | NUC | 55 | LRQAILCW | XRXXXXXW | B27s | | 1197 |
| HBV | 90 | 18 | NUC | 55 | LRQAILCWGEL | XRXXXXXXXXL | B27s | | 1198 |

TABLE XI-continued

HBV B27 SUPER MOTIF

| Source | Conservancy | Freq | Protein | Position | Sequence | String | Super-Motif | Peptide Filed | SEQ ID NO: |
|---|---|---|---|---|---|---|---|---|---|
| HBV | 95 | 19 | ENV | 240 | LRRFIIFL | XRXXXXXL | B27s | | 1199 |
| HBV | 75 | 15 | ENV | 240 | LRRFIIFLF | XRXXXXXXF | B27s | | 1200 |
| HBV | 75 | 15 | ENV | 240 | LRRFIIFLFI | XRXXXXXXXI | B27s | | 1201 |
| HBV | 75 | 15 | ENV | 240 | LRRFIIFLFIL | XRXXXXXXXXL | B27s | | 1202 |
| HBV | 75 | 15 | POL | 573 | NKTKRWGY | XKXXXXXY | B27s | | 1203 |
| HBV | 75 | 15 | POL | 573 | NKTKRWGYSL | XKXXXXXXXL | B27s | | 1204 |
| HBV | 85 | 17 | POL | 34 | NRRVAEDL | XRXXXXXL | B27s | | 1205 |
| HBV | 85 | 17 | POL | 34 | NRRVAEDLNL | XRXXXXXXXL | B27s | | 1206 |
| HBV | 95 | 19 | POL | 531 | PHCLAFSY | XHXXXXXY | B27s | | 1207 |
| HBV | 95 | 19 | POL | 531 | PHCLAFSYM | XHXXXXXXM | B27s | | 1208 |
| HBV | 85 | 17 | ENV | 59 | PHGGLLGW | XHXXXXXW | B27s | | 1209 |
| HBV | 100 | 20 | NUC | 50 | PHHTALRQAI | XHXXXXXXXI | B27s | | 1210 |
| HBV | 95 | 19 | NUC | 50 | PHHTALRQAIL | XHXXXXXXXXL | B27s | | 1211 |
| HBV | 80 | 16 | POL | 434 | PHLLVGSSGL | XHXXXXXXXL | B27s | | 1212 |
| HBV | 95 | 19 | POL | 394 | PKFAVPNL | XKXXXXXL | B27s | | 1213 |
| HBV | 95 | 19 | POL | 394 | PKFAVPNLQSL | XKXXXXXXXXL | B27s | | 1214 |
| HBV | 85 | 17 | X | 90 | PKVLHKRTL | XKXXXXXXL | B27s | | 1215 |
| HBV | 85 | 17 | X | 90 | PKVLHKRTLGL | XKXXXXXXXXL | B27s | | 1216 |
| HBV | 75 | 15 | POL | 6 | QHFRKLLL | XHXXXXXL | B27s | | 1217 |
| HBV | 75 | 15 | POL | 6 | QHFRKLLLL | XHXXXXXXL | B27s | | 1218 |
| HBV | 90 | 18 | POL | 623 | QRIVGLLGF | XRXXXXXXF | B27s | | 1219 |
| HBV | 100 | 20 | POL | 145 | RHYLHTLW | XHXXXXXW | B27s | | 1220 |
| HBV | 80 | 16 | POL | 502 | RKIPMGVGL | XKXXXXXXL | B27s | | 1221 |
| HBV | 80 | 16 | POL | 609 | RKLPVNRPI | XKXXXXXXI | B27s | | 1222 |
| HBV | 80 | 16 | POL | 609 | RKLPVNRPIDW | XKXXXXXXXXW | B27s | | 1223 |
| HBV | 85 | 17 | POL | 744 | RKYTSFPW | XKXXXXXW | B27s | | 1224 |
| HBV | 85 | 17 | POL | 744 | RKYTSFPWL | XKXXXXXXL | B27s | | 1225 |
| HBV | 85 | 17 | POL | 744 | RKYTSFPWLL | XKXXXXXXXL | B27s | | 1226 |
| HBV | 95 | 19 | POL | 527 | RRAFPHCL | XRXXXXXL | B27s | | 1227 |
| HBV | 95 | 19 | POL | 527 | RRAFPHCLAF | XRXXXXXXXF | B27s | | 1228 |
| HBV | 75 | 15 | ENV | 241 | RRFIIFLF | XRXXXXXF | B27s | | 1229 |
| HBV | 75 | 15 | ENV | 241 | RRFIIFLFI | XRXXXXXXI | B27s | | 1230 |
| HBV | 75 | 15 | ENV | 241 | RRFIIFLFIL | XRXXXXXXXL | B27s | | 1231 |
| HBV | 75 | 15 | ENV | 241 | RRFIIFLFILL | XRXXXXXXXXL | B27s | | 1232 |
| HBV | 75 | 15 | POL | 105 | RRLKLIMPARF | XRXXXXXXXXF | B27s | | 1233 |
| HBV | 90 | 16 | POL | 35 | RRVAEDLNL | XRXXXXXXL | B27s | | 1234 |

TABLE XI-continued

HBV B27 SUPER MOTIF

| Source | Conservancy | Freq | Protein | Position | Sequence | String | Super-Motif | Peptide Filed | SEQ ID NO: |
|---|---|---|---|---|---|---|---|---|---|
| HBV | 80 | 16 | POL | 494 | SHPIILGF | XHXXXXXF | B27s | | 1235 |
| HBV | 80 | 16 | POL | 494 | SHPIILGFRKI | XHXXXXXXXXI | B27s | | 1236 |
| HBV | 90 | 18 | NUC | 20 | SKLCLGWL | XKKXXXXL | B27s | | 1237 |
| HBV | 85 | 17 | NUC | 20 | SKLCLGWLW | XKXXXXXXW | B27s | | 1238 |
| HBV | 85 | 17 | NUC | 20 | SKLCLGWLWGM | XKXXXXXXXXM | B27s | | 1239 |
| HBV | 85 | 17 | POL | 743 | SRKYTSFPW | XRXXXXXXW | B27s | | 1240 |
| HBV | 85 | 17 | POL | 743 | SRKYTSFPWL | XRXXXXXXXL | B27s | | 1241 |
| HBV | 85 | 17 | POL | 743 | SRKYTSFPWLL | XRXXXXXXXXL | B27s | | 1242 |
| HBV | 95 | 19 | POL | 375 | SRLVVDFSQF | XRXXXXXXXF | B27s | | 1243 |
| HBV | 80 | 16 | POL | 472 | SRNLYVSL | XRXXXXXL | B27s | 17.0123 | 1244 |
| HBV | 95 | 19 | POL | 53 | THKVGNFTGL | XHXXXXXXXL | B27s | | 1245 |
| HBV | 95 | 19 | POL | 53 | THKVGNFTGLY | XHXXXXXXXXY | B27s | | 1246 |
| HBV | 95 | 19 | POL | 575 | TKRWGYSL | XKXXXXXL | B27s | | 1247 |
| HBV | 85 | 17 | POL | 575 | TKRWGYSLNF | XKXXXXXXXF | B27s | | 1248 |
| HBV | 85 | 17 | POL | 575 | TKRWGYSLNFM | XKXXXXXXXXM | B27s | | 1249 |
| HBV | 100 | 20 | POL | 120 | TKYLPLDKGI | XKXXXXXXXI | B27s | | 1250 |
| HBV | 100 | 20 | POL | 144 | TRHYLHTL | XRXXXXXL | B27s | | 1251 |
| HBV | 100 | 20 | POL | 144 | TRHYLHTLW | XRXXXXXXW | B27s | | 1252 |
| HBV | 80 | 16 | ENV | 186 | TRILTIPQSL | XRXXXXXXXL | B27s | | 1253 |
| HBV | 80 | 16 | POL | 819 | VHFASPLHVAW | XHXXXXXXXXW | B27s | | 1254 |
| HBV | 80 | 16 | ENV | 331 | VRFSWLSL | XRXXXXXL | B27s | | 1255 |
| HBV | 80 | 16 | ENV | 331 | VRFSWLSLL | XRXXXXXXL | B27s | | 1256 |
| HBV | 95 | 19 | POL | 526 | VRRAFPHCL | XRXKXXXXL | B27s | | 1257 |
| HBV | 95 | 19 | POL | 526 | VRRAFPHCLAF | XRXXXXXXXXF | B27s | | 1258 |
| HBV | 85 | 17 | POL | 619 | WKVCQRIVGL | XKXXXXXXXL | B27s | | 1259 |
| HBV | 85 | 17 | POL | 619 | WKVCQRIVGLL | XKXXXXXXXXL | B27s | | 1260 |
| HBV | 100 | 20 | NUC | 132 | YRPPNAPI | XRXXXXXI | B27s | | 1261 |
| HBV | 100 | 20 | NUC | 132 | YRPPNAPIL | XRXXXXXXL | B27s | 17.0356 | 1262 |
| HBV | 95 | 19 | ENV | 235 | YRWMCLRRF | XRXXXXXXF | B27s | | 1263 |
| HBV | 95 | 19 | ENV | 235 | YRWMCLRRFI | XRXXXXXXXI | B27s | | 1264 |
| HBV | 95 | 19 | ENV | 235 | YRWMCLRRFII | XRXXXXXXXXI | B27s | | 1265 |

TABLE XII

HBV B44 SUPER MOTIF

| Source | Conservancy | Freq | Protein | Position | Sequence | String | Supermotif | Peptide Filed | SEQ ID NO: |
|---|---|---|---|---|---|---|---|---|---|
| HBV | 95 | 19 | POL | 688 | ADATPTGW | XDXXXXXW | B44 | | 1266 |
| HBV | 95 | 19 | POL | 688 | ADATPTGWGL | XDXXXXXXXL | B44 | | 1267 |
| HBV | 80 | 16 | POL | 688 | ADATPTGWGL | XDXXXXXXXXA | B44 | | 1268 |
| HBV | 90 | 18 | POL | 776 | ADDPSRGRL | XDXXXXXXL | B44 | | 1269 |
| HBV | 90 | 18 | POL | 776 | ADDPSRGRLGL | XDXXXXXXXXL | B44 | | 1270 |
| HBV | 95 | 19 | POL | 38 | AEDLNLGNL | XEXXXXXXL | B44 | 17.0357 | 1271 |
| HBV | 95 | 19 | POL | 38 | AEDLNLGNLNV | XEXXXXXXXXV | B44 | | 1272 |
| HBV | 85 | 17 | POL | 717 | AELLAACF | XEXXXXXF | B44 | | 1273 |
| HBV | 85 | 17 | POL | 717 | AELLAACFA | XEXXXXXXA | B44 | | 1274 |
| HBV | 90 | 18 | POL | 777 | DDPSAGRL | XDXXXXXL | B44 | 17.0010 | 1275 |
| HBV | 90 | 18 | POL | 777 | DDPSRGRLGL | XDXXXXXXXL | B44 | 17.0418 | 1276 |
| HBV | 90 | 18 | POL | 540 | DDVVLGAKSV | XDXXXXXXXV | B44 | | 1277 |
| HBV | 75 | 15 | POL | 18 | DEAGPLEEEL | XEXXXXXXXL | B44 | | 1278 |
| HBV | 95 | 19 | POL | 39 | EDUNLGNL | XDXXXXXL | B44 | | 1279 |
| HBV | 95 | 19 | POL | 39 | EDUNLGNUNV | XDXXXXXXXV | B44 | | 1280 |
| HBV | 90 | 18 | POL | 22 | EEELPRLA | XEXXXXXA | B44 | | 1281 |
| HBV | 80 | 16 | X | 121 | EELGEEIRL | XEXXXXXXL | B44 | | 1282 |
| HBV | 90 | 18 | NUC | 32 | IDPYKEFGA | XDXXXXXXA | B44 | | 1283 |
| HBV | 85 | 17 | POL | 617 | IDWKVCORI | XDXXXXXXI | B44 | | 1284 |
| HBV | 85 | 17 | POL | 617 | IDWKVCORIV | XDXXXXXXXV | B44 | | 1285 |
| HBV | 100 | 20 | POL | 125 | LDKGIKPY | XDXXXXXY | B44 | | 1286 |
| HBV | 100 | 20 | POL | 125 | LDKGIKPYY | XDXXXXXXY | B44 | | 1287 |
| HBV | 80 | 16 | X | 9 | LDPARDVL | XDXXXXXL | B44 | 17.0012 | 1288 |
| HBV | 80 | 16 | X | 9 | LDPARDVLCL | XDXXXXXXXL | B44 | 17.0419 | 1289 |
| HBV | 95 | 19 | ENV | 195 | LDSWWTSL | XDXXXXXL | B44 | | 1290 |
| HBV | 95 | 19 | ENV | 195 | LDSWWTSLNF | XDXXXXXXXF | B44 | | 1291 |
| HBV | 90 | 18 | BW | 195 | LDSWWTSLNFL | XDXXXXXXXXL | B44 | | 1292 |
| HBV | 85 | 17 | NUC | 31 | LDTASALY | XDXXXXXY | B44 | | 1293 |
| HBV | 80 | 16 | NUC | 31 | LDTASALYREA | XDXXXXXXXXA | B44 | | 1294 |
| HBV | 95 | 19 | POL | 417 | LDVSAAFY | XDXXXXXY | B44 | | 1295 |
| HBV | 90 | 18 | ENV | 261 | LDYQGMLPV | XDXXXXXXV | B44 | | 1296 |
| HBV | 95 | 19 | POL | 21 | LEEELPRL | XEXXXXXL | B44 | | 1297 |
| HBV | 90 | 18 | POL | 21 | LEEELPRLA | XEXXXXXXA | B44 | | 1298 |
| HBV | 90 | 18 | POL | 539 | MDDVVLGA | XDXXXXXA | B44 | | 1299 |
| HBV | 90 | 18 | POL | 539 | MDDVVGAKSV | XDXXXXXXXV | B44 | | 1300 |
| HBV | 90 | 18 | NUC | 30 | MDIDPYKEF | XDXXXXXXF | B44 | | 1301 |
| HBV | 90 | 18 | NUC | 30 | MDIDPYKEFGA | XDXXXXXXXXA | B44 | | 1302 |
| HBV | 95 | 19 | ENV | 15 | PDHQLDPA | XDXXXXXA | B44 | | 1303 |

TABLE XII-continued

HBV B44 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 90 | 18 | ENV | 15 | PDHQLDPAF | XDXXXXXXF | B44 | | | 1304 |
| HBV | 100 | 20 | NUC | 45 | PEHCSPHHTA | XEXXXXXXXA | B44 | | | 1305 |
| HBV | 100 | 20 | NUC | 45 | PEHCSPHHTAL | XEXXXXXXXXL | B44 | | | 1306 |
| HBV | 85 | 17 | NUC | 28 | RDLLDTASA | XDXXXXXXA | B44 | | | 1307 |
| HBV | 85 | 17 | NUC | 28 | RDLLDTASAL | XDXXXXXXXL | B44 | | | 1308 |
| HBV | 85 | 17 | NUC | 28 | RDLLDTASALY | XDXXXXXXXXY | B44 | | | 1309 |
| HBV | 95 | 19 | X | 13 | RDVLCLRPV | XDXXXXXXV | B44 | | | 1310 |
| HBV | 95 | 19 | X | 13 | RDVLCLRPVGA | XDXXXXXXXXA | B44 | | | 1311 |
| HBV | 75 | 15 | NUC | 141 | RETVLEYL | XEXXXXXL | B44 | | | 1312 |
| HBV | 75 | 15 | NUC | 141 | RETVLEYLV | XEXXXXXXV | B44 | | | 1313 |
| HBV | 90 | 18 | POL | 736 | TDNSVVLSRKY | XDXXXXXXXXY | B44 | | | 1314 |
| HBV | 95 | 19 | NUC | 42 | VELLSFLPSDF | XEXXXXXXXXF | B44 | | | 1315 |
| HBV | 80 | 16 | X | 120 | WEELGEEEI | XEXXXXXI | B44 | | | 1316 |
| HBV | 80 | 16 | X | 120 | WEELGEEIRL | XEXXXXXXXL | B44 | | | 1317 |
| | | | | 52 | | | | | | |

TABLE XIII

HBV B58 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 85 | 17 | POL | 431 | AAMPHLLV | XAXXXXXV | B58 | | | 1318 |
| HBV | 95 | 19 | POL | 632 | AAPFTQCGY | XAXXXXXXY | B58 | | | 1319 |
| HBV | 85 | 17 | NUC | 34 | ASALYREAL | XSXXXXXXL | B58 | | | 1320 |
| HBV | 100 | 20 | POL | 166 | ASFCGSPY | XSXXXXXY | B58 | 26.0026 | * | 1321 |
| HBV | 100 | 20 | POL | 166 | ASFCGSPYSW | XSXXXXXXXW | B58 | | | 1322 |
| HBV | 90 | 18 | NUC | 19 | ASKLCLGW | XSXXXXXW | B58 | | | 1323 |
| HBV | 90 | 18 | NUC | 19 | ASKLCLGWL | XSXXXXXXL | B58 | | | 1324 |
| HBV | 85 | 17 | NUC | 19 | ASKLCLGWLW | XSXXXXXXXW | B58 | | | 1325 |
| HBV | 80 | 16 | POL | 822 | ASPLHVAW | XSXXXXXW | B58 | | | 1326 |
| HBV | 80 | 16 | ENV | 329 | ASVRFSWL | XSXXXXXL | B58 | | | 1327 |
| HBV | 80 | 16 | ENV | 329 | ASVRFSWLSL | XSXXXXXXXL | B58 | | | 1328 |
| HBV | 80 | 16 | ENV | 329 | ASVRFSWLSLL | XSXXXXXXXXL | B58 | | | 1329 |
| HBV | 95 | 19 | POL | 690 | ATPTGWGL | XTXXXXXL | B58 | | | 1330 |
| HBV | 75 | 15 | POL | 690 | ATPTGWGLAI | XTXXXXXXXI | B58 | | | 1331 |
| HBV | 95 | 19 | X | 61 | CAFSSAGPCAL | XAXXXXXXXXL | B58 | | | 1332 |
| HBV | 100 | 20 | NUC | 48 | CSPHHTAL | XSXXXXXL | B58 | | | 1333 |
| HBV | 80 | 16 | POL | 471 | CSRNLYVSL | XSXXXXXXL | B58 | | | 1334 |
| HBV | 95 | 19 | POL | 523 | CSVVRRAF | XSXXXXXF | B58 | | | 1335 |

TABLE XIII-continued

HBV B58 SUPER MOTIF

| Source | Convervancy | Freq | Protein | Position | Sequence | String | Supermotif | Peptide | Filed | SEQ ID NO: |
|---|---|---|---|---|---|---|---|---|---|---|
| HBV | 100 | 20 | ENV | 310 | CTCIPIPSSW | XTXXXXXXXW | B58 | | | 1336 |
| HBV | 95 | 19 | POL | 689 | DATPTGWGL | XAXXXXXXL | B58 | 5.0027 | | 1337 |
| HBV | 75 | 15 | POL | 689 | DATPTGWGLAI | XAXXXXXXXXI | B58 | | | 1338 |
| HBV | 95 | 19 | ENV | 196 | DSWWTSLNF | XSXXXXXXF | B58 | 20.0120 | | 1339 |
| HBV | 90 | 18 | ENV | 196 | DSWWTSLNFL | XSXXXXXXXL | B58 | | | 1340 |
| HBV | 80 | 16 | NUC | 32 | DTASALYREA | XTXXXXXXXXL | B58 | | | 1341 |
| HBV | 80 | 16 | NUC | 32 | DTASALYREAL | XTXXXXXXXXL | B58 | | | 1342 |
| HBV | 100 | 20 | POL | 17 | EAGPLEEEL | XAXXXXXXL | B58 | 5.0028 | | 1343 |
| HBV | 95 | 19 | POL | 374 | ESRLVVDF | XSXXXXXF | B58 | | | 1344 |
| HBV | 95 | 19 | POL | 374 | ESRLVVDFSQF | XSXXXXXXXXF | B58 | | | 1345 |
| HBV | 75 | 15 | NUC | 142 | ETVLEYLV | XTXXXXXV | B58 | | | 1346 |
| HBV | 95 | 19 | POL | 631 | FAAPFTQCGY | XAXXXXXXXV | B58 | 20.0254 | * | 1347 |
| HBV | 95 | 19 | POL | 687 | FADATPTGW | XAXXXXXXW | B58 | | | 1348 |
| HBV | 95 | 19 | POL | 687 | FADATPTGWGL | XAXXXXXXXXL | B58 | | | 1349 |
| HBV | 80 | 16 | POL | 821 | FASPLHVAW | XAXXXXXXW | B58 | | | 1350 |
| HBV | 95 | 19 | POL | 396 | FAVPNLQSL | XAXXXXXXL | B58 | 5.0029 | * | 1351 |
| HBV | 95 | 19 | POL | 658 | FSPTYKAF | XSXXXXXF | B58 | | | 1352 |
| HBV | 95 | 19 | POL | 658 | FSPTYKAFL | XSXXXXXXL | B58 | | | 1353 |
| HBV | 95 | 19 | X | 63 | FSSAGPCAL | XSXXXXXXL | B58 | | | 1354 |
| HBV | 90 | 18 | X | 63 | FSSAGPCALRF | XSXXXXXXXXF | B58 | | | 1355 |
| HBV | 100 | 20 | ENV | 333 | FSWLSLLV | XSXXXXXV | B58 | | | 1356 |
| HBV | 100 | 20 | ENV | 333 | FSWLSLLVPF | XSXXXXXXXF | B58 | 20.0263 | | 1357 |
| HBV | 100 | 20 | ENV | 333 | FSWLSLLVPFV | XSXXXXXXXXV | B58 | | | 1358 |
| HBV | 90 | 18 | POL | 536 | FSYMDDVV | XSXXXXXV | B58 | 17.0257 | | 1359 |
| HBV | 90 | 18 | POL | 536 | FSYMDDVVL | XSXXXXXXL | B58 | | | 1360 |
| HBV | 95 | 19 | POL | 656 | FTFSPTYKAF | XTXXXXXXXF | B58 | 20.0262 | | 1361 |
| HBV | 95 | 19 | POL | 656 | FTFSPTYKAFL | XTXXXXXXXXL | B58 | | | 1362 |
| HBV | 90 | 18 | POL | 59 | FTGLYSSTV | XTXXXXXXV | B58 | 20.0118 | | 1363 |
| HBV | 95 | 19 | POL | 635 | FTQCGYPAL | XTXXXXXXL | B58 | 5.0031 | | 1364 |
| HBV | 95 | 19 | POL | 635 | FTQCGYPALM | XTXXXXXXXM | B58 | 5.0085 | | 1365 |
| HBV | 95 | 19 | POL | 518 | FTSAICSV | XTXXXXXV | B58 | | | 1366 |
| HBV | 95 | 19 | POL | 518 | FTSAICSVV | XTXXXXXXV | B58 | 5.0032 | | 1367 |
| HBV | 95 | 19 | X | 50 | GAHLSLRGL | XAXXXXXXL | B58 | 5.0040 | | 1368 |
| HBV | 90 | 18 | X | 50 | GAHLSLRGLPV | XAXXXXXXXXV | B58 | | | 1369 |
| HBV | 85 | 17 | POL | 545 | GAKSVQHL | XAXXXXXL | B58 | | | 1370 |
| HBV | 85 | 17 | POL | 545 | GAKSVQHLESL | XAXXXXXXXXL | B58 | | | 1371 |
| HBV | 75 | 15 | ENV | 134 | GSSSGTVNPV | XSXXXXXXXV | B58 | | | 1372 |

TABLE XIII-continued

HBV B58 SUPER MOTIF

| Source | Convervancy | Freq | Protein | Position | Sequence | String | Supermotif | Peptide | Filed | SEQ ID NO: |
|---|---|---|---|---|---|---|---|---|---|---|
| HBV | 90 | 18 | POL | 735 | GTDNSVVL | XTXXXXXL | B58 | | | 1373 |
| HBV | 75 | 15 | ENV | 13 | GTNLSVPNPL | XTXXXXXXXL | B58 | | | 1374 |
| HBV | 80 | 16 | POL | 763 | GTSFVYVPSAL | XTXXXXXXXXL | B58 | | | 1375 |
| HBV | 85 | 17 | POL | 715 | HTAELLAACF | XTXXXXXXXF | B58 | | | 1376 |
| HBV | 100 | 20 | NUC | 52 | HTALRQAI | XTXXXXXI | B58 | | | 1377 |
| HBV | 95 | 19 | NUC | 52 | HTALRQAIL | XTXXXXXXL | B58 | 5.0021 | | 1378 |
| HBV | 95 | 19 | NUC | 52 | HTALRQAILCW | XTXXXXXXXXW | B58 | | | 1379 |
| HBV | 100 | 20 | POL | 149 | HTLWKAGI | XTXXXXXI | B58 | | | 1380 |
| HBV | 100 | 20 | POL | 149 | HTLWKAGIL | XTXXXXXXL | B58 | 5.0033 | | 1381 |
| HBV | 100 | 20 | POL | 149 | HTLWKAGILY | XTXXXXXXXY | B58 | 1.0542 | * | 1382 |
| HBV | 90 | 18 | NUC | 105 | ISCLTFGRETV | XSXXXXXXXXV | B58 | | | 1383 |
| HBV | 85 | 17 | POL | 547 | KSVQHLESL | XSXXXXXXL | B58 | | | 1384 |
| HBV | 95 | 19 | POL | 574 | KTKRWGYSL | XTXXXXXXL | B58 | 5.0034 | | 1385 |
| HBV | 85 | 17 | POL | 574 | KTKRWGYSLNF | XTXXXXXXXXF | B58 | | | 1386 |
| HBV | 90 | 18 | POL | 534 | LAFSYMDDV | XAXXXXXXV | B58 | 20.0118 | | 1387 |
| HBV | 90 | 18 | POL | 534 | LAFSYMDDVV | XAXXXXXXXV | B58 | 20.0257 | | 1388 |
| HBV | 90 | 18 | POL | 534 | LAFSYMDDVVL | XAXXXXXXXXL | B58 | | | 1389 |
| HBV | 95 | 19 | POL | 515 | LAQFTSAI | XAXXXXXI | B58 | | | 1390 |
| HBV | 95 | 19 | POL | 515 | LAQFTSAICSV | XAXXXXXXXXV | B58 | | | 1391 |
| HBV | 95 | 19 | NUC | 45 | LSFLPSDF | XSXXXXXF | B58 | | | 1392 |
| HBV | 95 | 19 | NUC | 45 | LSFLPSDFF | XSXXXXXXF | B58 | 20.0123 | | 1393 |
| HBV | 95 | 19 | POL | 415 | LSLDVSAAF | XSXXXXXXF | B58 | | | 1394 |
| HBV | 95 | 19 | POL | 415 | LSLDVSAAFY | XSXXXXXXXY | B58 | 2.0239 | * | 1395 |
| HBV | 100 | 20 | ENV | 336 | LSLLVPFV | XSXXXXXV | B58 | | | 1396 |
| HBV | 100 | 20 | ENV | 336 | LSLLVPFVQW | XSXXXXXXXW | B58 | | | 1397 |
| HBV | 100 | 20 | ENV | 336 | LSLLVPFVQWF | XSXXXXXXXXF | B58 | | | 1398 |
| HBV | 95 | 19 | X | 53 | LSLRGLPV | XSXXXXXV | B58 | | | 1399 |
| HBV | 95 | 19 | X | 53 | LSLRGLPVCAF | XSXXXXXXXXF | B58 | | | 1400 |
| HBV | 95 | 19 | POL | 510 | LSPFLLAQF | XSXXXXXXF | B58 | | | 1401 |
| HBV | 75 | 15 | ENV | 349 | LSPTVWLSV | XSXXXXXXV | B58 | | | 1402 |
| HBV | 75 | 15 | ENV | 349 | LSPTVWLSVI | XSXXXXXXXI | B58 | | | 1403 |
| HBV | 75 | 15 | ENV | 349 | LSPTVWLSVIW | XSXXXXXXXXW | B58 | | | 1404 |
| HBV | 85 | 17 | POL | 742 | LSRKYTSF | XSXXXXXF | B58 | | | 1405 |
| HBV | 85 | 17 | POL | 742 | LSRKYTSFPW | XSXXXXXXXW | B58 | | | 1406 |
| HBV | 85 | 17 | POL | 742 | LSRKYTSFPWL | XSXXXXXXXXL | B58 | | | 1407 |
| HBV | 90 | 18 | POL | 408 | LSSNLSWL | XSXXXXXL | B58 | | | 1408 |
| HBV | 90 | 18 | POL | 408 | LSSNLSWLSL | XSXXXXXXXL | B58 | | | 1409 |
| HBV | 100 | 20 | NUC | 140 | LSTLPETTV | XSXXXXXXV | B58 | | | 1410 |

TABLE XIII-continued

HBV B58 SUPER MOTIF

| Source | Convervancy | Freq | Protein | Position | Sequence | String | Supermotif | Peptide | Filed | SEQ ID NO: |
|---|---|---|---|---|---|---|---|---|---|---|
| HBV | 100 | 20 | NUC | 140 | LSTLPETTVV | XSXXXXXXXV | B58 | | | 1411 |
| HBV | 75 | 15 | ENV | 16 | LSVPNPLGF | XSXXXXXXF | B58 | | | 1412 |
| HBV | 100 | 20 | POL | 412 | LSWLSLDV | XSXXXXXV | B58 | | | 1413 |
| HBV | 75 | 15 | POL | 3 | LSYQHFRKL | XSXXXXXXL | B58 | | | 1414 |
| HBV | 75 | 15 | POL | 3 | LSYQHFFRKLL | XSXXXXXXXL | B58 | | | 1415 |
| HBV | 75 | 15 | POL | 3 | LSYQHFRKLLL | XSXXXXXXXXL | B58 | | | 1416 |
| HBV | 95 | 19 | NUC | 108 | LTFGRETV | XTXXXXXV | B58 | | | 1417 |
| HBV | 75 | 15 | NUC | 137 | LTFGRETVL | XTXXXXXXL | B58 | | | 1418 |
| HBV | 75 | 15 | NUC | 137 | LTFGRETVLEY | XTXXXXXXXXY | B58 | | | 1419 |
| HBV | 90 | 18 | ENV | 189 | LTIPQSLDSW | XTXXXXXXXW | B58 | | | 1420 |
| HBV | 90 | 18 | ENV | 189 | LTIPQSLDSWW | XTXXXXXXXXW | B58 | | | 1421 |
| HBV | 90 | 18 | POL | 404 | LTNLLSSNL | XTXXXXXXL | B58 | | | 1422 |
| HBV | 90 | 18 | POL | 404 | LTNLLSSNLSW | XTXXXXXXXXW | B58 | | | 1423 |
| HBV | 80 | 16 | ENV | 185 | LTRILTIPQSL | XTXXXXXXXXL | B58 | | | 1424 |
| HBV | 85 | 17 | POL | 99 | LTVNEKRRL | XTXXXXXXL | B58 | | | 1425 |
| HBV | 75 | 15 | X | 103 | MSTTDLEAY | XSXXXXXXY | B58 | 2.0126 | * | 1426 |
| HBV | 75 | 15 | X | 103 | MSTTDLEAYF | XSXXXXXXXF | B58 | | | 1427 |
| HBV | 100 | 20 | NUC | 136 | NAPILSTL | XAXXXXXL | B58 | | | 1428 |
| HBV | 90 | 18 | POL | 738 | NSVVLSRKY | XSXXXXXXY | B58 | 2.0123 | | 1429 |
| HBV | 100 | 20 | POL | 430 | PAAMPHLL | XAXXXXXL | B58 | | | 1430 |
| HBV | 85 | 17 | POL | 430 | PAAMPHLLV | XAXXXXXXV | B58 | | | 1431 |
| HBV | 90 | 18 | POL | 775 | PADDPSRGRL | XAXXXXXXXL | B58 | | | 1432 |
| HBV | 90 | 18 | ENV | 131 | PAGGSSSGTV | XAXXXXXXXV | B58 | | | 1433 |
| HBV | 95 | 19 | POL | 641 | PALMPLYACI | XAXXXXXXXI | B58 | 5.0087 | | 1434 |
| HBV | 80 | 16 | X | 11 | PARDVLCL | XAXXXXXL | B58 | | | 1435 |
| HBV | 75 | 15 | X | 11 | PARDVLCLRPV | XAXXXXXXXXV | B58 | | | 1436 |
| HBV | 90 | 18 | POL | 355 | PARVTGGV | XAXXXXXV | B58 | | | 1437 |
| HBV | 90 | 18 | POL | 355 | PARVTGGVF | XAXXXXXXF | B58 | | | 1438 |
| HBV | 90 | 18 | POL | 355 | PARVTGGVFL | XAXXXXXXXL | B58 | | | 1439 |
| HBV | 90 | 18 | POL | 355 | PARVTGGVFLV | XAXXXXXXXXV | B58 | | | 1440 |
| HBV | 95 | 19 | NUC | 130 | PAYRPPNAPI | XAXXXXXXXI | B58 | 5.0081 | | 1441 |
| HBV | 95 | 19 | NUC | 130 | PAYRPPNAPIL | XAXXXXXXXXL | B58 | | | 1442 |
| HBV | 90 | 18 | POL | 779 | PSRGRLGL | XSXXXXXL | B58 | | | 1443 |
| HBV | 75 | 15 | POL | 692 | PTGWGLAI | XTXXXXXI | B58 | | | 1444 |
| HBV | 85 | 17 | POL | 797 | PTTGRTSL | XTXXXXXL | B58 | | | 1445 |
| HBV | 85 | 17 | POL | 797 | PTTGRTSLY | XTXXXXXXY | B58 | 1.0208 | * | 1446 |
| HBV | 80 | 16 | NUC | 15 | PTVQASKL | XTXXXXXL | B58 | | | 1447 |

TABLE XIII-continued

HBV B58 SUPER MOTIF

| Source | Convervancy | Freq | Protein | Position | Sequence | String | Supermotif | Peptide | Filed | SEQ ID NO: |
|---|---|---|---|---|---|---|---|---|---|---|
| HBV | 80 | 16 | NUC | 15 | PTVQASKLCL | XTXXXXXXXL | B58 | | | 1448 |
| HBV | 75 | 15 | ENV | 351 | PTVWLSVI | XTXXXXXI | B58 | | | 1449 |
| HBV | 75 | 15 | ENV | 351 | PTVWLSVIW | XTXXXXXXW | B58 | | | 1450 |
| HBV | 150 | 30 | ENV | 351 | PTVWLSVIWM | XTXXXXXXXM | B58 | | | 1451 |
| HBV | 95 | 19 | POL | 654 | QAFTFSPTY | XAXXXXXXY | B58 | 20.0127 | | 1452 |
| HBV | 80 | 16 | ENV | 179 | QAGFFLLTRIL | XAXXXXXXXXL | B58 | | | 1453 |
| HBV | 90 | 18 | NUC | 57 | QAILCWGEL | XAXXXXXXL | B58 | | | 1454 |
| HBV | 180 | 36 | NUC | 57 | QAILCWGELM | XAXXXXXXXM | B58 | | | 1455 |
| HBV | 80 | 16 | ENV | 107 | QAMQWNSTTF | XAXXXXXXXF | B58 | | | 1456 |
| HBV | 80 | 16 | NUC | 18 | QASKLCLGW | XAXXXXXXW | B58 | | | 1457 |
| HBV | 80 | 16 | NUC | 18 | QASKLCLGWL | XAXXXXXXXL | B58 | | | 1458 |
| HBV | 75 | 15 | NUC | 18 | QASKLCLGWLW | XAXXXXXXXXW | B58 | | | 1459 |
| HBV | 90 | 18 | ENV | 193 | QSLDSWWTSL | XSXXXXXXXL | B58 | F126.63 | | 1460 |
| HBV | 90 | 18 | POL | 402 | QSLTNLLSSNL | XSXXXXXXXXL | B58 | | | 1461 |
| HBV | 95 | 19 | POL | 528 | RAFPHCLAF | XAXXXXXXF | B58 | 20.0125 | | 1462 |
| HBV | 95 | 19 | POL | 528 | RAFPHCLAFSY | XAXXXXXXXXY | B58 | 26.0550 | * | 1463 |
| HBV | 90 | 18 | POL | 353 | RTPARVTGGV | XTXXXXXXXV | B58 | | | 1464 |
| HBV | 90 | 18 | POL | 353 | RTPARVTGGVF | XTXXXXXXXXF | B58 | | | 1465 |
| HBV | 90 | 18 | X | 65 | SAGPCALRF | XAXXXXXXF | B58 | 26.0152 | | 1466 |
| HBV | 95 | 19 | POL | 520 | SAICSVVRRAF | XAXXXXXXXXF | B58 | | | 1467 |
| HBV | 90 | 18 | NUC | 35 | SALYREAL | XAXXXXXL | B58 | | | 1468 |
| HBV | 100 | 20 | POL | 165 | SASFCGSPY | XAXXXXXXY | B58 | 20.0117 | * | 1469 |
| HBV | 100 | 20 | POL | 165 | SASFCGSPYSW | XAXXXXXXXXW | B58 | | | 1470 |
| HBV | 95 | 19 | X | 64 | SSAGPCAL | XSXXXXXL | B58 | | | 1471 |
| HBV | 90 | 18 | X | 64 | SSAGPCALRF | XSXXXXXXXF | B58 | 26.0374 | | 1472 |
| HBV | 75 | 15 | ENV | 136 | SSGTVNPV | XSXXXXXV | B58 | | | 1473 |
| HBV | 90 | 18 | POL | 409 | SSNLSWLSL | XSXXXXXXL | B58 | | | 1474 |
| HBV | 90 | 18 | POL | 409 | SSNLSWSLDV | XSXXXXXXXXV | B58 | | | 1475 |
| HBV | 75 | 15 | ENV | 135 | SSSGTVNPV | XSXXXXXXV | B58 | | | 1476 |
| HBV | 100 | 20 | NUC | 141 | STLPETTV | XTXXXXXV | B58 | | | 1477 |
| HBV | 100 | 20 | NUC | 141 | STLPETTVV | XTXXXXXXV | B58 | 5.0024 | | 1478 |
| HBV | 75 | 15 | X | 104 | STTDLEAY | XTXXXXXY | B58 | | | 1479 |
| HBV | 75 | 15 | X | 104 | STTDLEAYF | XTXXXXXXF | B58 | | | 1480 |
| HBV | 85 | 17 | POL | 716 | TAELLAACF | XAXXXXXXF | B58 | | | 1481 |
| HBV | 95 | 19 | NUC | 53 | TALRQAIL | XAXXXXXL | B58 | | | 1482 |
| HBV | 95 | 19 | NUC | 53 | TALRQAILCW | XAXXXXXXXW | B58 | | | 1483 |
| HBV | 80 | 16 | NUC | 33 | TASALYREAL | XAXXXXXXXL | B58 | | | 1484 |
| HBV | 95 | 19 | POL | 519 | TSAICSVV | XSXXXXXV | B58 | | | 1485 |

TABLE XIII-continued

HBV B58 SUPER MOTIF

| Source | Conservancy | Freq | Protein | Position | Sequence | String | Supermotif | Peptide Filed | SEQ ID NO: |
|---|---|---|---|---|---|---|---|---|---|
| HBV | 80 | 16 | POL | 764 | TSFVYVPSAL | XSXXXXXXXL | B58 | | 1486 |
| HBV | 80 | 16 | ENV | 168 | TSGFLGPL | XSXXXXXL | B58 | | 1487 |
| HBV | 75 | 15 | ENV | 168 | TSGFLGPLL | XSXXXXXXL | B58 | | 1488 |
| HBV | 75 | 15 | ENV | 168 | TSGFLGPLLV | XSXXXXXXXV | B58 | | 1489 |
| HBV | 75 | 15 | ENV | 168 | TSGFLGPLLVL | XSXXXXXXXXL | B58 | | 1490 |
| HBV | 75 | 15 | X | 105 | TTDLEAYF | XTXXXXXF | B58 | | 1491 |
| HBV | 85 | 17 | POL | 798 | TTGRTSLY | XTXXXXXY | B58 | 26.0030 | 1492 |
| HBV | 95 | 19 | POL | 37 | VAEDLNLGNL | XAXXXXXXXL | B58 | 5.0089 | 1493 |
| HBV | 100 | 20 | POL | 48 | VSIPWTHKV | XSXXXXXXV | B58 | | 1494 |
| HBV | 95 | 19 | POL | 391 | VSWPKFAV | XSXXXXXV | B58 | | 1495 |
| HBV | 95 | 19 | POL | 391 | VSWPKFAVPNL | XSXXXXXXXXL | B58 | | 1496 |
| HBV | 100 | 20 | POL | 358 | VTGGVFLV | XTXXXXXV | B58 | | 1497 |
| HBV | 85 | 17 | ENV | 66 | WSPQAQGI | XSXXXXXI | B58 | | 1498 |
| HBV | 85 | 17 | ENV | 66 | WSPQAQGIL | XSXXXXXXL | B58 | | 1499 |
| HBV | 100 | 20 | POL | 52 | WTHKVGNF | XTXXXXXF | B58 | | 1500 |
| HBV | 95 | 19 | POL | 52 | WTHKVGNFTGL | XTXXXXXXXXL | B58 | | 1501 |
| HBV | 80 | 16 | POL | 493 | YSHPIILGF | XSXXXXXXF | B58 | | 1502 |
| HBV | 85 | 17 | POL | 580 | YSLNFMGY | XSXXXXXY | B58 | 26.0032 | 1503 |
| HBV | 75 | 15 | POL | 580 | YSLNFMGYV | XSXXXXXXV | B58 | | 1504 |
| HBV | 75 | 15 | POL | 580 | YSLNFMGYVI | XSXXXXXXXI | B58 | | 1505 |
| HBV | 85 | 17 | POL | 746 | YTSFPWLL | XTXXXXXL | B58 | | 1506 |

189

TABLE XIV

HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 95 | 19 | POL | 521 | AICSVVRRAF | XIXXXXXXXF | B62s | | | 1507 |
| HBV | 90 | 18 | NUC | 58 | ALLCWGELM | XIXXXXXXM | B62s | | | 1508 |
| HBV | 95 | 19 | POL | 642 | ALMPLYACI | XLXXXKXXI | B62s | 3.0012 | * | 1509 |
| HBV | 95 | 19 | NUC | 54 | ALRQAILCW | XLXXXXXXW | B62s | | | 1510 |
| HBV | 80 | 16 | ENV | 108 | AMQWNSTTF | XMXXXXXXF | B62s | | | 1511 |
| HBV | 95 | 19 | POL | 633 | APFTQCGY | XPXXXXXY | B62s | 19.0013 | | 1512 |
| HBV | 95 | 19 | POL | 516 | AQFTSAICSV | XQXXXXXXXV | B62s | | | 1513 |
| HBV | 95 | 19 | POL | 516 | AQFTSAICSVV | XQXXXXXXXXV | B62s | | | 1514 |
| HBV | 100 | 20 | ENV | 312 | CIPIPSSW | XIXXXXXW | B62s | | | 1515 |
| HBV | 100 | 20 | ENV | 312 | CIPIPSSWAF | XIXXXXXXXF | B62s | | | 1516 |
| HBV | 90 | 16 | POL | 533 | CLAFSYMDDV | XLXXXXXXXV | B62s | 1.0559 | | 1517 |

TABLE XIV-continued

HBV B62 SUPER MOTIF

| Source | Conservancy | Freq | Protein | Position | Sequence | String | Supermotif | Peptide | | Filed SEQ ID NO: |
|---|---|---|---|---|---|---|---|---|---|---|
| HBV | 90 | 18 | POL | 533 | CLAFSYMDDVV | XLXXXXXXXXV | B62s | | | 1518 |
| HBV | 85 | 17 | NUC | 23 | CLGWLWGM | XLXXXXXM | B62s | | | 1519 |
| HBV | 85 | 17 | NUC | 23 | CLGWLWGMDI | XLXXXXXXXI | B62s | 2.0229 | | 1520 |
| HBV | 95 | 19 | ENV | 253 | CLIFLLVLLDY | XLXXXXXXXXY | B62s | 26.0548 | | 1521 |
| HBV | 95 | 19 | ENV | 239 | CLRRFIIF | XLXXXXXF | B62s | | | 1522 |
| HBV | 75 | 15 | ENV | 239 | CLRRFIIFLF | XLXXXXXXXF | B62s | | | 1523 |
| HBV | 75 | 15 | ENV | 239 | CLRRFIIFLFI | XLXXXXXXXXI | B62s | Chisari | | 1524 |
| HBV | 90 | 15 | NUC | 107 | CLTFGRETV | XLXXXXXXV | B62s | 1.0160 | | 1525 |
| HBV | 80 | 16 | X | 7 | CQLDRADV | XQXXXXXV | B62s | | | 1526 |
| HBV | 85 | 17 | POL | 622 | CQRIVGLLGF | XQXXXXXXXF | B62s | | | 1527 |
| HBV | 90 | 18 | NUC | 31 | DIDPYKEF | XIXXXXXF | B62s | | | 1528 |
| HBV | 85 | 17 | NUC | 29 | DLLDTASALY | XLXXXXXXXY | B62s | 1.0519 | * | 1529 |
| HBV | 95 | 19 | POL | 40 | DLNLGNLNV | XLXXXXXXV | B62s | 1.0164 | | 1530 |
| HBV | 95 | 19 | POL | 40 | DLNLGNLNVSI | XLXXXXXXXXI | B62s | | | 1531 |
| HBV | 80 | 16 | ENV | 122 | DPRVRGLY | XPXXXXXY | B62s | | | 1532 |
| HBV | 95 | 19 | X | 14 | DVLCLRPV | XVXXXXXV | B62s | | | 1533 |
| HBV | 90 | 18 | POL | 541 | DVVLGAKSV | XVXXXXXXV | B62s | 1.0190 | | 1534 |
| HBV | 95 | 19 | NUC | 43 | ELLSFLPSDF | XLXXXXXXXF | B62s | | | 1535 |
| HBV | 95 | 19 | NUC | 43 | ELLSFLPSDFF | XLXXXXXXXXF | B62s | | | 1536 |
| HBV | 80 | 16 | ENV | 248 | FILLLCLI | XIXXXXXI | B62s | Chisari | | 1537 |
| HBV | 80 | 16 | ENV | 248 | FILLLCLIF | XIXXXXXXF | B62s | | | 1538 |
| HBV | 80 | 16 | ENV | 246 | FIFLLLLCLI | XLXXXXXXXI | B62s | 3.0206 | | 1539 |
| HBV | 80 | 16 | ENV | 246 | FLFILLLCLIF | XLXXXXXXXXF | B62s | | | 1540 |
| HBV | 95 | 19 | POL | 513 | FLLAQFTSAI | XLXXXXXXXI | B62s | 1147.13 | * | 1541 |
| HBV | 80 | 16 | ENV | 183 | FLLTRILTI | XLXXXXXXI | B62s | 3.0005 | * | 1542 |
| HBV | 95 | 19 | ENV | 256 | FLLVLLDY | XLXXXXXY | B62s | 26.0027 | | 1543 |
| HBV | 95 | 19 | ENV | 256 | FLLVLLDYQGM | XLXXXXXXXXM | B62s | | | 1544 |
| HBV | 75 | 15 | ENV | 130 | FPAGGSSSGTV | XPXXXXXXXXV | B62s | | | 1545 |
| HBV | 85 | 17 | ENV | 14 | FPDHQLDPAF | XPXXXXXXXF | B62s | 20.0274 | | 1546 |
| HBV | 95 | 19 | POL | 530 | FPHCLAFSY | XPXXXXXXY | B62s | 15.0037 | * | 1547 |
| HBV | 95 | 19 | POL | 530 | FPHCLAFSYM | XPXXXXXXXM | B62s | 15.0217 | * | 1548 |
| HBV | 75 | 15 | POL | 749 | FPWLLGCAANW | XPXXXXXXXXW | B62s | | | 1549 |
| HBV | 95 | 19 | ENV | 346 | FVGLSPTV | XVXXXXXV | B62s | | | 1550 |
| HBV | 95 | 19 | ENV | 346 | FVGLSPTVW | XVXXXXXXW | B62s | | | 1551 |
| HBV | 90 | 18 | X | 132 | FVLGGCRHKLV | XVXXXXXXXXV | B62s | | | 1552 |
| HBV | 95 | 19 | POL | 627 | GLLGFAAPF | XLXXXXXXF | B62s | 20.0124 | | 1553 |
| HBV | 95 | 19 | POL | 509 | GLSPFLLAQF | XLXXXXXXXF | B62s | | | 1554 |

TABLE XIV-continued

HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 75 | 15 | ENV | 348 | GLSPTVWLSV | XLXXXXXXXV | B62s | 1.0518 | * | 1555 |
| HBV | 75 | 15 | ENV | 348 | GLSPTVWLSVI | XLXXXXXXXXI | B62s | Chisari | | 1556 |
| HBV | 85 | 17 | NUC | 29 | GMDIDPYKEF | XMXXXXXXXF | B62s | 26.0372 | | 1557 |
| HBV | 95 | 19 | ENV | 173 | GPLLVLQAGF | XPXXXXXXXF | B62s | 15.0212 | | 1558 |
| HBV | 95 | 19 | ENV | 173 | GPLLVLQAGFF | XPXXXXXXXXF | B62s | 26.0556 | | 1559 |
| HBV | 95 | 19 | NUC | 123 | GVWIRTPPAY | XVXXXXXXXY | B62s | 1.0525 | | 1560 |
| HBV | 75 | 15 | POL | 569 | HLNPNKTKRW | XLXXXXXXXW | B62s | | | 1561 |
| HBV | 90 | 18 | X | 52 | HLSLRGLPV | XLXXXXXXV | B62s | 1.0212 | | 1562 |
| HBV | 80 | 16 | POL | 491 | HLYSHPII | XLXXXXXI | B62s | 17.0256 | | 1563 |
| HBV | 80 | 16 | POL | 491 | HLYSHPIILGF | XLXXXXXXXXF | B62s | | | 1564 |
| HBV | 85 | 17 | POL | 429 | HPAAMPHLLV | XPXXXXXXXV | B62s | 20.0273 | * | 1565 |
| HBV | 80 | 16 | POL | 495 | HPIILGFRKI | XPXXXXXXXI | B62s | | | 1566 |
| HBV | 80 | 16 | POL | 497 | IILGFRKI | XIXXXXXI | B62s | 17.0124 | * | 1567 |
| HBV | 80 | 16 | POL | 497 | IILGFRKIPM | XIXXXXXXXM | B62s | | | 1568 |
| HBV | 90 | 18 | NUC | 59 | ILCQGELM | XLXXXXXM | B62s | | | 1569 |
| HBV | 80 | 16 | POL | 498 | ILGFRKIPM | XLXXXXXXM | B62s | 3.0016 | | 1570 |
| HBV | 100 | 20 | ENV | 249 | ILLLCLIF | XLXXXXXF | B62s | | | 1571 |
| HBV | 100 | 20 | ENV | 249 | ILLLCLIFLLV | XLXXXXXXXXV | B62s | Chisari | | 1572 |
| HBV | 80 | 16 | POL | 760 | ILRGTSFV | XLXXXXXV | B62s | | | 1573 |
| HBV | 80 | 16 | POL | 760 | ILRGTSFVY | XLXXXXXXY | B62s | 1.0205 | * | 1574 |
| HBV | 80 | 16 | POL | 760 | ILRGTSFVYV | XLXXXXXXXV | B62s | 1.0573 | * | 1575 |
| HBV | 100 | 20 | NUC | 139 | ILSTLPETTV | XLXXXXXXXV | B62 | 1.0526 | | 1576 |
| HBV | 100 | 20 | NUC | 139 | ILSTLPETTVV | XLXXXXXXXXV | B62s | | * | 1577 |
| HBV | 90 | 18 | ENV | 188 | ILTIPQSLDSW | XLXXXXXXXXW | B62s | | | 1578 |
| HBV | 100 | 20 | ENV | 313 | IPIPSSWAF | XPXXXXXXF | B62s | 15.0032 | * | 1579 |
| HBV | 80 | 16 | POL | 504 | IPMGVGLSPF | XPXXXXXXXF | B62s | | | 1580 |
| HBV | 90 | 18 | ENV | 191 | IPQSLDSW | XPXXXXXW | B62s | 19.0004 | | 1581 |
| HBV | 90 | 18 | ENV | 191 | IPQSLDSWW | XPXXXXXXW | B62s | 15.0030 | * | 1582 |
| HBV | 100 | 20 | POL | 50 | IPWTHKVGNF | XPXXXXXXXF | B62s | 15.0209 | | 1583 |
| HBV | 90 | 18 | POL | 625 | IVGLLGFAAPF | XVXXXXXXXXF | B62s | | | 1584 |
| HBV | 80 | 16 | POL | 503 | KIPMGVGLSPF | XIXXXXXXXXF | B62s | | | 1585 |
| HBV | 85 | 17 | NUC | 21 | KLCLGWLW | XLXXXXXW | B62s | | | 1586 |
| HBV | 85 | 17 | NUC | 21 | KLCLGWLWGM | XLXXXXXXXM | B62s | 3.0209 | * | 1587 |
| HBV | 95 | 19 | POL | 489 | KLHLYSHPI | XLXXXXXXI | B62s | 3.0009 | * | 1588 |
| HBV | 80 | 16 | POL | 489 | KLHLYSHPII | XLXXXXXXXI | B62s | | | 1589 |
| HBV | 75 | 15 | POL | 108 | KLIMPARF | XLXXXXXF | B62s | | | 1590 |
| HBV | 75 | 15 | POL | 108 | KLIMPARFY | XLXXXXXXY | B62s | 1.0171 | | 1591 |
| HBV | 80 | 16 | POL | 610 | KLPVNRPI | XLXXXXXI | B62s | | | 1592 |

TABLE XIV-continued

HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 80 | 16 | POL | 610 | KLPVNRPIDW | XLXXXXXXXW | B62s | | | 1593 |
| HBV | 95 | 19 | POL | 653 | KQAFTFSPTY | XQXXXXXXXY | B62s | 20.0256 | | 1594 |
| HBV | 95 | 19 | POL | 55 | KVGNFTGLY | XVXXXXXXY | B62s | 1.0166 | * | 1595 |
| HBV | 95 | 19 | ENV | 254 | LIFLLVLLDY | XIXXXXXXXY | B62s | 1.0899 | | 1596 |
| HBV | 100 | 20 | POL | 109 | LIMPARFY | XIXXXXXY | B62s | 26.0028 | | 1597 |
| HBV | 95 | 19 | POL | 514 | LLAQFTSAI | XLXXXXXXI | B62s | 3.0010 | * | 1598 |
| HBV | 100 | 20 | ENV | 251 | LLCLIFLLV | XLXXXXXXV | B62s | 1.0835 | * | 1599 |
| HBV | 85 | 17 | NUC | 30 | LLDTASALY | XLXXXXXXY | B62s | 1.0155 | * | 1600 |
| HBV | 90 | 18 | ENV | 260 | LLDYQGMLPV | XLXXXXXXXV | B62s | 1.0516 | * | 1601 |
| HBV | 80 | 16 | POL | 752 | LLGCAANW | XLXXXXXW | B62s | | | 1602 |
| HBV | 80 | 16 | POL | 752 | LLGCAANWI | XLXXXXXXI | B62s | 3.0013 | | 1603 |
| HBV | 95 | 19 | POL | 628 | LLGFAAPF | XLXXXXXF | B62s | | | 1604 |
| HBV | 75 | 15 | ENV | 63 | LLGWSPQAQGI | XLXXXXXXXXI | B62s | | | 1605 |
| HBV | 100 | 20 | ENV | 250 | LLLCLIFLLV | XLXXXXXXXV | B62s | 1.0897 | * | 1606 |
| HBV | 100 | 20 | ENV | 378 | LLPIFFCLW | XLXXXXXXW | B62s | | * | 1607 |
| HBV | 100 | 20 | ENV | 378 | LLPIFFCLWV | XLXXXXXXXV | B62s | 1.0904 | * | 1608 |
| HBV | 100 | 20 | ENV | 378 | LLPIFFCLWVY | XLXXXXXXXXY | B62s | 26.0549 | | 1609 |
| HBV | 95 | 19 | NUC | 44 | LLSFLPSDF | XLXXXXXXF | B62s | | | 1610 |
| HBV | 95 | 19 | NUC | 44 | LLSFLPSDFF | XLXXXXXXXF | B62s | | | 1611 |
| HBV | 90 | 18 | POL | 407 | LLSSNLSW | XLXXXXXW | B62s | | | 1612 |
| HBV | 80 | 16 | ENV | 184 | LLTRILTI | XLXXXXXI | B62s | Chisari | | 1613 |
| HBV | 80 | 16 | POL | 436 | LLVGSSGL | XLXXXXXL | b62S | | | 1614 |
| HBV | 95 | 19 | ENV | 257 | LLVLLDYQGM | XLXXXXXXXM | B62s | 3.0207 | | 1615 |
| HBV | 95 | 19 | ENV | 175 | LLVLQAGF | XLXXXXXF | B62s | | | 1616 |
| HBV | 95 | 19 | ENV | 175 | LLVLQAGFF | XLXXXXXXF | B62s | 20.0121 | | 1617 |
| HBV | 100 | 20 | ENV | 338 | LLVPFVQW | XLXXXXXW | B62s | | | 1618 |
| HBV | 100 | 20 | ENV | 338 | LLVPFVQWF | XLXXXXXXF | B62s | | | 1619 |
| HBV | 95 | 19 | ENV | 338 | LLVPFVQWFV | XLXXXXXXXV | B62s | 1.0930 | * | 1620 |
| HBV | 85 | 17 | NUC | 100 | LLWFHISCLTF | XLXXXXXXXXF | B62s | | | 1621 |
| HBV | 95 | 19 | POL | 643 | LMPLYACI | XMXXXXXI | B62s | 17.0130 | | 1622 |
| HBV | 100 | 20 | ENV | 379 | LPIFFCLW | XPXXXXXW | B62s | 19.0007 | | 1623 |
| HBV | 100 | 20 | ENV | 379 | LPIFFCLWV | XPXXXXXXV | B62s | 15.0034 | | 1624 |
| HBV | 100 | 20 | ENV | 379 | LPIFFCLWVY | XPXXXXXXXY | B62s | 15.0215 | | 1625 |
| HBV | 100 | 20 | ENV | 379 | LPIFFCLWVYI | XPXXXXXXXXI | B62s | 26.0558 | | 1626 |
| HBV | 100 | 20 | POL | 123 | LPLDKGIKPY | XPXXXXXXXY | B62s | 15.0210 | * | 1627 |
| HBV | 100 | 20 | POL | 123 | LPLDKGIKPYY | XPXXXXXXXXY | B62s | 26.0560 | | 1628 |
| HBV | 80 | 16 | POL | 611 | LPVNRPIDW | XPXXXXXXW | B62s | | | 1629 |

TABLE XIV-continued

HBV B62 SUPER MOTIF

| Source | Conservancy | Freq | Protein | Position | Sequence | String | Supermotif | Peptide | | Filed SEQ ID NO: |
|---|---|---|---|---|---|---|---|---|---|---|
| HBV | 80 | 16 | POL | 611 | LPVNRPIDWKV | XPXXXXXXXXV | B62s | | | 1630 |
| HBV | 80 | 16 | ENV | 178 | LQAGFFLLTRI | XQXXXXXXXXI | B62s | | | 1631 |
| HBV | 95 | 19 | ENV | 258 | LVLLDYQGM | XVXXXXXXM | B62s | 3.0034 | | 1632 |
| HBV | 95 | 19 | ENV | 176 | LVLQAGFF | XVXXXXXF | B62s | | | 1633 |
| HBV | 100 | 20 | ENV | 339 | LVPFVQWF | XVXXXXXF | B62s | | | 1634 |
| HBV | 95 | 19 | ENV | 339 | LVPFVQWFV | XVXXXXXXV | B62s | 1.0877 | * | 1635 |
| HBV | 90 | 18 | NUC | 119 | LVSFGVWI | XVXXXXXI | B62s | Chisari | | 1636 |
| HBV | 100 | 20 | POL | 377 | LWDFSQF | XVXXXXF | B62s | | | 1637 |
| HBV | 85 | 17 | ENV | 360 | MMWYWGPSLY | XMXXXXXXXY | B62s | 1039.01 | * | 1638 |
| HBV | 100 | 20 | POL | 1 | MPLSYQHF | XPXXXXXF | B62s | 19.0010 | * | 1639 |
| HBV | 60 | 16 | ENV | 109 | MQWNSTTF | XQXXXXXF | B62s | | | 1640 |
| HBV | 95 | 19 | POL | 42 | NLGNLNVSI | XLXXXXXXI | B62s | 3.0008 | | 1641 |
| HBV | 95 | 19 | POL | 42 | NLGNLNVSIPW | XLXXXXXXXXW | B62s | | | 1642 |
| HBV | 90 | 18 | POL | 406 | NLLSSNLSW | XLXXXXXXW | B62s | | | 1643 |
| HBV | 95 | 19 | POL | 45 | NLNVSIPW | XLXXXXXW | B62s | | | 1644 |
| HBV | 75 | 15 | ENV | 15 | NLSVPNPLGF | XLXXXXXXXF | B62s | | | 1645 |
| HBV | 90 | 18 | POL | 411 | NLSWLSLDV | XLXXXXXXV | B62s | 1.0185 | * | 1646 |
| HBV | 75 | 15 | POL | 571 | NPNKTKRW | XPXXXXXW | B62s | | | 1647 |
| HBV | 75 | 15 | POL | 571 | NPNKTKRWGY | XPXXXXXXXY | B62s | | | 1648 |
| HBV | 100 | 20 | POL | 47 | NVSIPWTHKV | XVXXXXXXXV | B62s | 1.0532 | | 1649 |
| HBV | 85 | 17 | POL | 616 | PIDWKVCQRI | XIXXXXXXXI | B62s | Chisari | | 1650 |
| HBV | 85 | 17 | POL | 616 | PIDWKVCQRIV | XIXXXXXXXXV | B62s | | | 1651 |
| HBV | 100 | 20 | ENV | 380 | PIFFCLWV | XIXXXXXV | B62s | | | 1652 |
| HBV | 100 | 20 | ENV | 380 | PIFFCLWVY | XIXXXXXXY | B62s | 1.0843 | | 1653 |
| HBV | 100 | 20 | ENV | 380 | PIFFCLWVYI | XIXXXXXXXI | B62s | 20.0258 | | 1654 |
| HBV | 80 | 16 | POL | 496 | PIILGFRKI | XIXXXXXXI | B62s | 927.48 | | 1655 |
| HBV | 80 | 16 | POL | 496 | PIILGFRKIPM | XIXXXXXXXXM | B62s | | | 1656 |
| HBV | 100 | 20 | NUC | 138 | PILSTLPETTV | XIXXXXXXXXV | B62s | Chisari | | 1657 |
| HBV | 100 | 20 | ENV | 314 | PIPSSWAF | XIXXXXXF | B62s | | | 1658 |
| HBV | 100 | 20 | POL | 124 | PLDKGIKPY | XLXXXXXXY | B62s | 1.0174 | * | 1659 |
| HBV | 100 | 20 | POL | 124 | PLDKGIKPYY | XLXXXXXXXY | B62s | 1.0541 | * | 1660 |
| HBV | 100 | 20 | ENV | 377 | PLLPIFFCLW | XLXXXXXXXW | B62s | | | 1661 |
| HBV | 100 | 20 | ENV | 377 | PLLPIFFCLWV | XLXXXXXXXXV | B62s | | | 1662 |
| HBV | 95 | 19 | ENV | 174 | PLLVLQAGF | XLXXXXXXF | B62s | | | 1663 |
| HBV | 95 | 19 | ENV | 174 | PLLVLQAGFF | XLXXXXXXXF | B62s | | | 1664 |
| HBV | 80 | 16 | POL | 505 | PMGVGLSPF | XMXXXXXXF | B62s | | | 1665 |
| HBV | 95 | 19 | NUC | 129 | PPAYRPPNAPI | XPXXXXXXXXI | B62s | 26.0563 | | 1666 |
| HBV | 85 | 17 | ENV | 58 | PPHGGLLGW | XPXXXXXXW | B62s | 20.0141 | | 1667 |

TABLE XIV-continued

HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 80 | 16 | ENV | 106 | PQAMQWNSTT | XQXXXXXXXXF | B62s | | | 1668 |
| HBV | 90 | 18 | ENV | 192 | PQSLDSWW | XQXXXXXW | B62s | | | 1669 |
| HBV | 85 | 17 | POL | 612 | PVNRPIDW | XVXXXXXW | B62s | | | 1670 |
| HBV | 85 | 17 | POL | 612 | PVNRPIDWKV | XVXXXXXXXV | B62s | 1.0566 | | 1671 |
| HBV | 80 | 16 | X | 8 | QLDPARDV | XLXXXXXV | B62s | Chisari | | 1672 |
| HBV | 95 | 19 | POL | 685 | QVFADATPTGW | XVXXXXXXXXW | B62s | | | 1673 |
| HBV | 90 | 18 | POL | 624 | RIVGLLGF | XIXXXXXF | B62s | | | 1674 |
| HBV | 75 | 15 | POL | 106 | RLKLIMPARF | XLXXXXXXXF | B62s | | | 1675 |
| HBV | 75 | 15 | POL | 106 | RLKLIMPARFY | XLXXXXXXXXY | B62s | | | 1676 |
| HBV | 95 | 19 | POL | 376 | RLWDFSQF | XLXXXXXF | B62s | 20.0122 | | 1677 |
| HBV | 80 | 16 | POL | 615 | RPIDWKVCORI | XPXXXXXXXXI | B62s | | | 1678 |
| HBV | 90 | 18 | NUC | 56 | RQAILCWGELM | XQXXXXXXXXM | B62s | | | 1679 |
| HBV | 90 | 18 | NUC | 98 | RQLLWFHI | XQXXXXXI | B62s | | | 1680 |
| HBV | 75 | 15 | POL | 818 | RVHFASPLHV | XVXXXXXXXV | B62s | 1.0576 | | 1681 |
| HBV | 100 | 20 | POL | 357 | RVTGGVFLV | XVXXXXXXV | B62s | 1.0181 | | 1682 |
| HBV | 100 | 20 | POL | 49 | SIPWTHKV | XIXXXXXV | B62s | | | 1683 |
| HBV | 100 | 20 | POL | 49 | SIPWTHKVGNF | XIXXXXXXXXF | B62s | | | 1684 |
| HBV | 95 | 19 | ENV | 194 | SLDSWWTSLNF | XLXXXXXXXXF | B62s | | | 1685 |
| HBV | 95 | 19 | POL | 416 | SLDVSAAF | XLXXXXXF | B62s | | | 1686 |
| HBV | 95 | 19 | POL | 416 | SLDVSAAFY | XLXXXXXXY | B62s | 1.0186 | * | 1687 |
| HBV | 100 | 20 | ENV | 337 | SLLVPFVQW | XLXXXXXW | B62s | | | 1688 |
| HBV | 100 | 20 | ENV | 337 | SLLVPFVQWF | XLXXXXXXXF | B62s | | | 1689 |
| HBV | 95 | 19 | ENV | 337 | SLLVPFVQWFV | XLXXXXXXXXV | B62s | | | 1690 |
| HBV | 75 | 15 | POL | 581 | SLNFMGYV | XLXXXXXV | B62s | | | 1691 |
| HBV | 75 | 15 | POL | 581 | SLNFMGYVI | XLXXXXXXI | B62s | 3.0011 | | 1692 |
| HBV | 95 | 19 | X | 54 | SLRGLPVCAF | XLXXXXXXXF | B62s | 20.0259 | | 1693 |
| HBV | 95 | 19 | POL | 511 | SPFILAQF | XPXXXXXF | B62s | 19.0012 | * | 1694 |
| HBV | 100 | 20 | NUC | 49 | SPHHTALRQAI | XPXXXXXXXXI | B62s | 26.0567 | * | 1695 |
| HBV | 75 | 15 | ENV | 350 | SPTVWLSV | XPXXXXXV | B62s | | | 1696 |
| HBV | 75 | 15 | ENV | 350 | SPTVWLSVI | XPXXXXXXI | B62s | 1308.16 | | 1697 |
| HBV | 75 | 15 | ENV | 350 | SPTVWLSVIW | XPXXXXXXXW | B62s | 1308.17 | | 1698 |
| HBV | 75 | 15 | ENV | 350 | SPTVWLSVIWM | XPXXXXXXXXM | B62s | | | 1699 |
| HBV | 75 | 15 | ENV | 17 | SVPNPLGF | XVXXXXXF | B62s | | | 1700 |
| HBV | 80 | 16 | ENV | 330 | SVRFSWLSLLV | XVXXXXXXXXV | B62s | | | 1701 |
| HBV | 90 | 18 | POL | 739 | SWLSRKY | XVXXXXXY | B62s | 26.0029 | | 1702 |
| HBV | 85 | 17 | POL | 739 | SVVLSRKYTSF | XVXXXXXXXXF | B62s | | | 1703 |
| HBV | 90 | 18 | ENV | 190 | TIPQSLDSW | XIXXXXXXW | B62s | | | 1704 |

TABLE XIV-continued

HBV B62 SUPER MOTIF

| Source | Conservancy | Freq | Protein | Position | Sequence | String | Supermotif | Peptide | | Filed SEQ ID NO: |
|---|---|---|---|---|---|---|---|---|---|---|
| HBV | 90 | 18 | ENV | 190 | TIPQSLDSWW | XIXXXXXXXW | B62s | | | 1705 |
| HBV | 100 | 20 | NUC | 142 | TLPETTVV | XLXXXXXV | B62s | | | 1706 |
| HBV | 100 | 20 | POL | 150 | TLWKAGILY | XLXXXXXXY | B62s | 1.0177 | * | 1707 |
| HBV | 90 | 18 | POL | 354 | TPARVTGGV | XPXXXXXXV | B62s | 15.0033 | * | 1708 |
| HBV | 90 | 18 | POL | 35 | TPARVTGGVF | XPXXXXXXXF | B62s | 15.0214 | * | 1709 |
| HBV | 75 | 15 | ENV | 57 | TPPHGGLLGW | XPXXXXXXXW | B62s | 1308.04 | | 1710 |
| HBV | 75 | 15 | POL | 691 | TPTGWGLAI | XPXXXXXXI | B62s | | | 1711 |
| HBV | 95 | 19 | POL | 636 | TQCGVPALM | XQXXXXXXM | B62s | | | 1712 |
| HBV | 80 | 16 | NUC | 16 | TVQASKLCLGW | XVXXXXXXXXW | B62s | | | 1713 |
| HBV | 75 | 15 | ENV | 352 | TVWLSVIW | XVXXXXXW | B62s | | | 1714 |
| HBV | 75 | 15 | ENV | 352 | TVWLSVIWM | XVXXXXXXM | B62s | 3.0035 | | 1715 |
| HBV | 90 | 18 | X | 133 | VLGGCRHKLV | XLXXXXXXXV | B62s | 1.0589 | | 1716 |
| HBV | 95 | 19 | ENV | 259 | VLLDYQGM | XLXXXXXM | B62s | 17.0107 | | 1717 |
| HBV | 90 | 18 | ENV | 259 | VLLDYQGMLPV | XLXXXXXXXXV | B62s | 1147.14 | * | 1718 |
| HBV | 85 | 17 | POL | 741 | VLSRKYTSF | XLXXXXXXF | B62s | | | 1719 |
| HBV | 85 | 17 | POL | 741 | VLSRKYTSFPW | XLXXXXXXXXW | B62s | | | 1720 |
| HBV | 95 | 19 | ENV | 340 | VPFVQWFV | XPXXXXXV | B62s | 19.0006 | * | 1721 |
| HBV | 80 | 16 | NUC | 17 | VQASKLCLGW | XQXXXXXXXW | B62s | | | 1722 |
| HBV | 95 | 19 | ENV | 343 | VQWFVGLSPTV | XQXXXXXXXXV | B62s | | | 1723 |
| HBV | 90 | 18 | POL | 542 | VVLGAKSV | XVXXXXXV | B62s | | | 1724 |
| HBV | 80 | 16 | POL | 759 | WILRGTSF | XIXXXXXF | B62s | | | 1725 |
| HBV | 80 | 16 | POL | 759 | WILRGTSFV | XIXXXXXXV | B62s | 1.0204 | * | 1726 |
| HBV | 80 | 16 | POL | 759 | WILRGTSFVY | XIXXXXXXXY | B62s | 1.0572 | | 1727 |
| HBV | 80 | 16 | POL | 759 | WILRGTSFVYV | XIXXXXXXXXV | B62s | | | 1728 |
| HBV | 95 | 19 | NUC | 125 | WIRTPPAY | XIXXXXXY | B62s | 26.0031 | | 1729 |
| HBV | 80 | 16 | POL | 751 | WLLGCAANW | XLXXXXXXW | B62s | | | 1730 |
| HBV | 80 | 16 | POL | 751 | WLLGCAANWI | XLXXXXXXXI | B62s | Chisari | | 1731 |
| HBV | 95 | 19 | POL | 414 | WLSLDVSAAF | XLXXXXXXXF | B62s | | | 1732 |
| HBV | 95 | 19 | POL | 414 | WLSLDVSAAFY | XLXXXXXXXXY | B62s | 26.0551 | | 1733 |
| HBV | 100 | 20 | ENV | 335 | WLSLLVPF | XLXXXXXF | B62s | | | 1734 |
| HBV | 100 | 20 | ENV | 335 | WLSLLVPFV | XLXXXXXXV | B62s | 1.0838 | * | 1735 |
| HBV | 100 | 20 | ENV | 335 | WLSLLVPFVQW | XLXXXXXXXXW | B62s | | | 1736 |
| HBV | 85 | 17 | NUC | 26 | WLWGMDIDPY | XLXXXXXXXY | B62s | 1.0774 | * | 1737 |
| HBV | 95 | 19 | ENV | 237 | WMCLRRFI | XMXXXXXI | B62s | | | 1738 |
| HBV | 95 | 19 | ENV | 237 | WMCLRRFII | XMXXXXXI | B62s | 3.0031 | * | 1739 |
| HBV | 95 | 19 | ENV | 237 | WMCLRRFIIF | XMXXXXXXF | B62s | 20.0266 | | 1740 |
| HBV | 85 | 17 | ENV | 359 | WMMyWGPSL | XMXXXXXXXY | B62s | 1.0901 | * | 1741 |
| HBV | 100 | 20 | POL | 147 | YLHTLWKAGI | XLXXXXXXI | B62s | 7.0066 | | 1742 |

TABLE XIV-continued

HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 100 | 20 | POL | 122 | YLPLDKGI | XLXXXXXI | B62s | | | 1743 |
| HBV | 100 | 20 | POL | 122 | YLPLDKGIKPY | XLXXXXXXXXY | B62s | 26.0553 | | 1744 |
| HBV | 90 | 18 | NUC | 118 | YLVSFGVW | XLXXXXXW | B62s | | | 1745 |
| HBV | 90 | 16 | NUC | 118 | YLVSFGVWI | XLXXXXXXI | B62s | 3.0007 | * | 1746 |
| HBV | 95 | 19 | POL | 640 | YPALMPLY | XPXXXXXY | B62s | 19.0014 | * | 1747 |
| HBV | 95 | 19 | POL | 640 | YPALMPLYACI | XPXXXXXXXXI | B62s | 26.0570 | | 1748 |
| | | | | 242 | | | | | | |

TABLE XV

HBV A01 Motif (With Binding Information)

| Conservancy | Frequency | Protein | 1st Pos | Sequence | P2 | C-term | Peptide | Filed | A*0101 | SEQ ID NO: |
|---|---|---|---|---|---|---|---|---|---|---|
| 80 | 16 | ENV | 119 | AMQWNSTTF | M | F | | | | 1749 |
| 90 | 16 | POL | 748 | DNSVVLSRKY | N | Y | 20.0255 | | 0.0001 | 1750 |
| 95 | 19 | POL | 642 | FAAPFTQCGY | A | Y | 20.0254 | * | 0.0680 | 1751 |
| 85 | 17 | POL | 590 | GYSLNFMGY | Y | Y | 2.0058 | | | 1752 |
| 100 | 20 | POL | 149 | HTLWKAGILY | T | Y | 1069.04 | * | 0.1100 | 1753 |
| 95 | 19 | POL | 664 | KQAFTFSPTY | Q | Y | 20.0256 | | 0.0001 | 1754 |
| 85 | 17 | NUC | 30 | LLDTASALY | L | Y | 1069.01 | * | 12.0000 | 1755 |
| 95 | 19 | POL | 415 | LSLDVSAAFY | S | Y | 1090.07 | * | 0.0150 | 1756 |
| 85 | 17 | ENV | 360 | MMWYWGPSLY | M | Y | 1039.01 | * | 0.0810 | 1757 |
| 75 | 15 | X | 103 | MSTTDLEAY | S | Y | 2.0126 | * | 0.8500 | 1758 |
| 90 | 18 | POL | 738 | NSVVLSRKY | S | Y | 2.0123 | | 0.0005 | 1759 |
| 100 | 20 | POL | 124 | PLDKGIKPY | L | Y | 1147.12 | * | | 1760 |
| 100 | 20 | POL | 124 | PLDKGIKPYY | L | Y | 1069.03 | * | 0.1700 | 1761 |
| 85 | 17 | POL | 797 | PTTGRTSLY | T | Y | 1090.09 | * | 0.2100 | 1762 |
| 100 | 20 | POL | 165 | SASFCGSPY | A | Y | | | | 1763 |
| 95 | 19 | POL | 416 | SLDVSAAFY | L | Y | 1069.02 | * | 5.2000 | 1764 |
| | | | | 16 | | | | | | |

TABLE XVI

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 85 | 17 | POL | 721 | AACFARSR | A03/A11 | A03 | A | R | 26.0003 | | 0.0004 | 0.0003 | 1765 |
| 95 | 19 | POL | 643 | AAPFTQCGY | A03/A11 | A03 | A | Y | | | | | 1766 |
| 95 | 19 | POL | 540 | APPHCLAFSY | A03/A11 | A03 | F | Y | | | | | 1767 |
| 95 | 19 | X | 62 | AFSSAGPCA | A03/A11 | A03 | F | A | | | | | 1768 |
| 95 | 19 | POL | 866 | AFTFSPTYK | A03/A11 | A03 | F | K | 20.0130 | * | 0.2600 | 0.0400 | 1769 |
| 95 | 19 | POL | 666 | AFTFSPTYKA | A03/A11 | A03 | F | A | | | | | 1770 |
| 95 | 19 | POL | 18 | AGFLEEFLPR | A03/A11 | A03 | G | R | 20.0265 | | 0.0004 | 0.0002 | 1771 |
| 95 | 19 | POL | 521 | AICSVVRR | A03/A11 | A03 | I | R | 26.0004 | | -0.0002 | 0.0003 | 1772 |
| 95 | 19 | POL | 532 | AICSVVRRAF | A03/A11 | A03 | I | F | | | | | 1773 |
| 90 | 18 | POL | 772 | ALNPADDPSR | A03/A11 | A03 | L | R | 1.1090 | | 0.0003 | 0.0001 | 1774 |
| 85 | 17 | X | 70 | ALRFTSAR | A03/A11 | A03 | L | R | 26.0005 | | 0.0047 | 0.0009 | 1775 |
| 80 | 16 | ENV | 119 | AMQWNSTTF | A03/A11 | A03 | M | F | | | | | 1776 |
| 80 | 16 | ENV | 119 | AMQWNSTTF | A03/ | A03 | M | F | | | | | 1777 |
| 80 | 16 | ENV | 119 | AMQWNSTTFH | A03/A11 | A03 | M | H | | | | | 1778 |
| 80 | 16 | POL | 822 | ASPLHVAWR | A03/A11 | A03 | S | R | | | | | 1779 |
| 75 | 15 | ENV | 84 | ASTNRCSGR | A03/A11 | A03 | S | R | 1150.60 | | 0.0009 | 0.0002 | 1780 |
| 80 | 16 | POL | 755 | CAANWILR | A03/A11 | A03 | A | R | | | | | 1781 |
| 85 | 17 | X | 69 | CALRFTSAR | A03/A11 | A03 | A | R | 26.0149 | * | 0.0034 | 0.0230 | 1782 |
| 85 | 17 | POL | 734 | CFARSRSGA | A03/A11 | A03 | F | A | | | | | 1783 |
| 75 | 15 | POL | 618 | CFRKLPVNR | A03/A11 | A03 | F | R | | | | | 1784 |
| 95 | 19 | POL | 649 | CGYPALMPLY | A03/A11 | A03 | G | Y | | | | | 1785 |
| 100 | 20 | EVN | 323 | CIPIPSSWAF | A03/A11 | A03 | I | F | | | | | 1786 |
| 90 | 18 | X | 17 | CLRPVGAESR | A03/A11 | A03 | L | R | 1.1093 | | 0.0011 | 0.0001 | 1787 |
| 75 | 15 | ENV | 239 | CLRRHFIFLF | A03/A11 | A03 | L | F | | | | | 1788 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 100 | 20 | NUC | 48 | CSPHHTALR | A03/A11 | A03 | S | R | 5.0055 | * | 0.0029 | 0.0001 | 1789 |
| 95 | 19 | POL | 534 | CSVVRRAFPH | A03/A11 | A03 | S | H | | | | | 1790 |
| 85 | 17 | NUC | 58 | DLLDTASALY | A03/A11 | A03 | L | Y | 1.0519 | * | 0.0001 | 0.0001 | 1791 |
| 85 | 17 | NUC | 29 | DLLDTASALYR | A03/A11 | A03 | L | R | 26.0530 | | 0.0042 | -0.0003 | 1792 |
| 95 | 19 | ENV | 207 | DSWWTSLNF | A03/A11 | A03 | S | F | 20.0120 | | 0.0006 | 0.0002 | 1793 |
| 85 | 17 | NUC | 32 | DTASALYR | A03/A11 | A03 | T | R | 26.0006 | | 0.0004 | -0.0002 | 1794 |
| 95 | 19 | POL | 17 | EAGPLEEELPR | A03/A11 | A03 | A | R | 26.0531 | | -0.0009 | -0.0003 | 1795 |
| 90 | 18 | POL | 718 | ELLAACFAR | A03/A11 | A03 | L | R | 1.0988 | | 0.0002 | 0.0004 | 1796 |
| 85 | 17 | POL | 718 | ELLAACFARSR | A03/A11 | A03 | L | R | 26.0532 | | 0.0062 | 0.0016 | 1797 |
| 95 | 19 | NUC | 43 | ELLSFLPSDF | A03/A11 | A03 | L | F | | | | | 1798 |
| 95 | 19 | NUC | 72 | ESPEHCSPH | A03/A11 | A03 | S | H | | | | | 1799 |
| 95 | 19 | NUC | 72 | ESPEHCSPHH | A03/A11 | A03 | S | H | | | | | 1800 |
| 95 | 19 | NUC | 174 | ETTVVRRR | A03/A11 | A03 | T | R | 26.0007 | | 0.0003 | -0.0002 | 1801 |
| 80 | 16 | NUC | 174 | ETTVVRRRGR | A03/A11 | A03 | T | R | 1.1073 | | 0.0003 | 0.0001 | 1802 |
| 95 | 19 | POL | 642 | FAAPFTQCGY | A01/A03/A11 | A03 | A | Y | 20.0254 | * | | | 1803 |
| 80 | 16 | POL | 821 | FASPLHVAWR | A03/A11 | A03 | A | R | | | | | 1804 |
| 90 | 18 | ENV | 24 | FFPDHQLDPA | A03/A11 | A03 | F | A | | | | | 1805 |
| 75 | 15 | NUC | 139 | FGRETVLEY | A03/A11 | A03 | G | Y | | | | | 1806 |
| 75 | 15 | POL | 255 | FGVEPSGSGH | A03/A11 | A03 | G | H | | | | | 1807 |
| 80 | 16 | ENV | 248 | FILLLCLIF | A03/A11 | A03 | I | F | | | | | 1808 |
| 90 | 18 | X | 63 | FSSAGPCALR | A03/A11 | A03 | S | R | | | | | 1809 |
| 100 | 20 | ENV | 344 | FSWLSLLVPF | A03/A11 | A03 | S | F | 20.0263 | | 0.0004 | 0.0002 | 1810 |
| 95 | 19 | POL | 656 | FTFSPTYK | A03/A11 | A03 | T | K | 1147.19 | * | 0.0100 | 0.0100 | 1811 |
| 95 | 19 | POL | 867 | FTFSPTYKAF | A03/A11 | A03 | T | F | 20.0262 | | 0.0004 | 0.0006 | 1812 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 95 | 19 | POL | 518 | FTSAICSVVR | A03/A11 | A03 | T | R | 1.1085 | | 0.0003 | 0.0003 | 1813 |
| 95 | 19 | POL | 518 | FTSAICSVVRR | A03/A11 | A03 | T | R | 26.0533 | | 0.0065 | 0.0092 | 1814 |
| 90 | 18 | X | 132 | FVLGGCRHK | A03/A11 | A03 | V | K | 1090.03 | * | 0.0430 | 0.0090 | 1815 |
| 80 | 16 | POL | 765 | GCAANWILR | A03/A11 | A03 | C | R | | | | | 1816 |
| 75 | 15 | POL | 587 | GIHLNPNK | A03/A11 | A03 | I | K | | | | | 1817 |
| 75 | 15 | POL | 567 | GIHLNPNKTK | A03/A11 | A03 | I | K | 1.0563 | | 0.0025 | 0.0011 | 1818 |
| 76 | 15 | POL | 567 | GIHLNPNKTKR | A03/A11 | A03 | I | R | | | | | 1819 |
| 95 | 19 | POL | 638 | GLLGFAAPF | A03/A11 | A03 | L | F | 20.0124 | | 0.0006 | 0.0002 | 1820 |
| 95 | 19 | POL | 520 | GLSPFLLAQF | A03/A11 | A03 | L | F | | | | | 1821 |
| 85 | 17 | NUC | 29 | GMDIDPYK | A03/A11 | A03 | M | K | 26.0009 | | 0.0006 | 0.0004 | 1822 |
| 85 | 17 | NUC | 29 | GMDIDPYKEF | A03/A24 | A03 | M | F | 26.0372 | | -0.0003 | -0.0002 | 1823 |
| 90 | 18 | POL | 735 | GTDNSVVLSR | A03/A11 | A03 | T | R | 1090.04 | * | 0.0010 | 0.0420 | 1824 |
| 90 | 18 | POL | 735 | GTDNSVVLSRK | A03/A11 | A03 | T | K | 1147.17 | | 0.0140 | 0.5600 | 1825 |
| 80 | 16 | POL | 258 | GVEPSGSGH | A03/A11 | A03 | V | H | | | | | 1826 |
| 100 | 20 | POL | 372 | GVFLVDKNPH | A03/A11 | A03 | V | H | | | | | 1827 |
| 95 | 19 | NUC | 152 | GVWIRTPPAY | A03/A11 | A03 | V | Y | 1.0525 | * | 0.0047 | 0.0002 | 1828 |
| 95 | 19 | NUC | 123 | GVVIRTPPAYR | A03/A11 | A03 | V | R | 26.0535 | | 0.1900 | 0.1700 | 1829 |
| 100 | 20 | NUC | 78 | HCSPHHTALR | A03/A11 | A03 | C | R | | | | | 1830 |
| 80 | 16 | POL | 831 | HFASPLHVA | A03/A11 | A03 | F | A | | | | | 1831 |
| 90 | 18 | NUC | 104 | HISCLTFGR | A03/A11 | A03 | I | R | 1069.18 | * | 0.0160 | 0.0065 | 1832 |
| 75 | 15 | POL | 569 | HLNPNKTK | A03/A11 | A03 | L | K | | | | | 1833 |
| 75 | 15 | POL | 569 | HLNPNKTKR | A03/A11 | A03 | L | H | 1.0983 | | 0.0025 | 0.0001 | 1834 |
| 85 | 17 | POL | 728 | HTAELLAACF | A03/A11 | A03 | T | F | | | | | 1835 |
| 100 | 20 | POL | 149 | HTLWKAGILYK | A03/A11 | A03 | T | K | 1147.16 | * | 0.5400 | 0.4400 | 1836 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 95 | 19 | POL | 533 | ICSVVRRAF | A03/A11 | A03 | C | F | | | | | 1837 |
| 95 | 19 | ENV | 266 | IFLLVLLDY | A03/A11 | A03 | F | Y | | | | | 1838 |
| 80 | 16 | POL | 771 | ILRGTSFVY | A03/A11 | A03 | L | Y | 1.0205 | * | 0.0440 | 00002 | 1839 |
| 90 | 18 | NUC | 105 | ISCLTFGR | A03/A11 | A03 | S | R | 26.0010 | | 0.0004 | 0.0002 | 1840 |
| 100 | 20 | POL | 153 | KAGILYKR | A03/A11 | A03 | A | R | 26.0011 | | 0.0002 | -0.0002 | 1841 |
| 75 | 15 | POL | 108 | KLIMPARFY | A03/A11 | A03 | L | Y | 1.0171 | | | | 1842 |
| 80 | 16 | POL | 610 | KLPVNRPIDWK | A03/A11 | A03 | L | K | | | | | 1843 |
| 75 | 15 | X | 130 | KVFVLGGCR | A03/A11 | A03 | V | R | 1.0993 | * | 0.0420 | 0.0820 | 1844 |
| 75 | 15 | X | 130 | KVFVLGGCRH | A03/A11 | A03 | V | H | | | | | 1845 |
| 95 | 19 | POL | 55 | KVGNFTGLY | A03/A11 | A03 | V | Y | 1142.05 | * | 0.2100 | 0.0170 | 1846 |
| 85 | 17 | POL | 720 | LAACFARSR | A03/A11 | A03 | A | R | 20.0129 | | 0.0058 | 0.0065 | 1847 |
| 100 | 20 | POL | 125 | LDKGIKPYY | A03/A24 | A03 | D | Y | | | | | 1848 |
| 95 | 19 | ENV | 206 | LDSWWTSLNF | A03/A11 | A03 | D | F | | | | | 1849 |
| 85 | 17 | NUC | 60 | LDTASALYR | A03/A11 | A03 | D | R | 26.0151 | | 0.0004 | -0.0002 | 1850 |
| 95 | 19 | POL | 428 | LDVSAAFYH | A03/A11 | A03 | D | H | | | | | 1851 |
| 80 | 16 | EVN | 247 | LFILLLCLIF | A03/A11 | A03 | F | F | | | | | 1852 |
| 80 | 16 | ENV | 247 | LFILLLCLIF | A03/A11 | A03 | F | F | | | | | 1853 |
| 80 | 16 | ENV | 764 | LGCAANWILR | A03/A11 | A03 | G | R | | | | | 1854 |
| 75 | 15 | POL | 577 | LGHLNPNK | A03/A11 | A03 | G | K | | | | | 1855 |
| 95 | 19 | ENV | 265 | LIFLLVLLDY | A03/A11 | A03 | I | Y | 1.0899 | | 0.0022 | 0.0004 | 1856 |
| 90 | 18 | POL | 719 | LLAACFAR | A03/A11 | A03 | L | R | 26.0012 | | 0.0024 | 0.0003 | 1857 |
| 85 | 17 | POL | 719 | LLAACFARSR | A03/A11 | A03 | L | R | | | | | 1858 |
| 85 | 17 | NUC | 30 | LLDTASALYR | A03/A11 | A03 | L | R | 1.1070 | | 0.0050 | 0.0002 | 1859 |
| 80 | 16 | POL | 752 | LLGCAANWILR | A03/A11 | A03 | L | R | | | | | 1860 |

TABLE XVI-continued

HBV A03 and A11 Motif (With binding information)

| Conservancy | Frequency | Protein | 1st Pos | Sequence | Motif |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 95 | 19 | POL | 45 | NLNVSIPWTH | A03/A11 | A03 | L | H | | | | | 1885 |
| 95 | 19 | POL | 45 | NLNVSIPWTHK | A03/A11 | A03 | L | K | 26.0538 | | -0.0009 | 0.0005 | 1886 |
| 75 | 15 | ENV | 15 | NLSVPNPLGF | A03/A11 | A03 | L | F | | | | | 1887 |
| 75 | 15 | ENV | 215 | NSQSPTSNH | A03/A11 | A03 | S | H | | | | | 1888 |
| 90 | 18 | POL | 738 | NSVVLSRK | A03/A11 | A03 | S | K | 26.0015 | | 0.0006 | 0.0010 | 1889 |
| 100 | 20 | POL | 47 | NVSIPWTHK | A03/A11 | A03 | V | K | 1069.16 | * | 0.0820 | 0.0570 | 1890 |
| 90 | 18 | POL | 775 | PADDPSAGR | A03/A11 | A03 | A | R | 1150.35 | | 0.0008 | 0.0002 | 1891 |
| 80 | 16 | X | 11 | PARDVLCLR | A03/A11 | A03 | A | R | 1150.36 | | 0.0002 | 0.0002 | 1892 |
| 90 | 18 | POL | 385 | PARVTGGVF | A03/A11 | A03 | A | F | | | | | 1893 |
| 75 | 15 | EVN | 83 | PASTNRQSGR | A03/A11 | A03 | A | R | | | | | 1894 |
| 85 | 17 | X | 68 | PCALRFTSAR | A03/A11 | A03 | C | R | | | | | 1895 |
| 90 | 18 | ENV | 26 | PDHQLDPAF | A03/A11 | A03 | D | F | | | | | 1896 |
| 95 | 19 | POL | 523 | PFLLAQFTSA | A03/A11 | A03 | F | A | | | | | 1897 |
| 95 | 19 | POL | 645 | PFTQCGYPA | A03/A11 | A03 | F | A | | | | | 1898 |
| 100 | 20 | ENV | 244 | PGYRWMCLR | A03/A11 | A03 | G | R | 1.0964 | | 0.0008 | 0.0005 | 1899 |
| 95 | 19 | ENV | 244 | PGYRWMCLRR | A03/A11 | A03 | G | R | 1.1068 | | 0.0048 | 0.0001 | 1900 |
| 90 | 18 | POL | 616 | PIDWKVCQR | A03/A11 | A03 | I | R | 1.0985 | | 0.0002 | 0.0005 | 1901 |
| 100 | 20 | ENV | 391 | PIFFCLWVY | A03/A11 | A03 | I | Y | 1.0843 | | 0.0011 | 0.0002 | 1902 |
| 80 | 16 | POL | 496 | PIILGFRK | A03/A11 | A03 | I | K | | | | | 1903 |
| 95 | 19 | POL | 20 | PLEEELPR | A03/A11 | A03 | L | R | 26.0016 | | 0.0002 | -0.0002 | 1904 |
| 100 | 20 | POL | 438 | PLHPAAMPH | A03/A11 | A03 | L | H | 20.0128 | | 0.0012 | 0.0002 | 1905 |
| 95 | 19 | ENV | 174 | PLLYLQAGF | A03/A11 | A03 | L | F | | | | | 1906 |
| 95 | 19 | ENV | 174 | PLLVQAGFF | A03/A11 | A03 | L | F | | | | | 1907 |
| 100 | 20 | POL | 2 | PLSYQHFR | A03/A11 | A03 | L | R | 26.0017 | | -0.0002 | -0.0002 | 1908 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 75 | 15 | POL | 2 | PLSYQHFRK | A03/A11 | A03 | L | K | 1.0161 | | 0.0011 | 0.0031 | 1909 |
| 85 | 17 | POL | 98 | PLTVNEKR | A03/A11 | A03 | L | R | 26.0018 | | 0.0002 | -0.0002 | 1910 |
| 85 | 17 | POL | 98 | PLTVNEKRR | A03/A11 | A03 | L | R | 1.0974 | | 0.0008 | 0.0005 | 1911 |
| 80 | 16 | POL | 516 | PMGVGLSPF | A03/A11 | A03 | M | F | | | | | 1912 |
| 80 | 16 | POL | 516 | PMGVGLSPF | A03/A24 | A03 | M | F | | | | | 1913 |
| 90 | 18 | X | 20 | PVGAESRGR | A03/A11 | A03 | V | R | 1.0990 | | 0.0002 | 0.0005 | 1914 |
| 85 | 17 | POL | 612 | PVNRPIDWK | A03/A11 | A03 | V | K | 1142.06 | * | 0.0310 | 0.1400 | 1915 |
| 95 | 19 | POL | 665 | QAFTFSPTY | A03/A11 | A03 | A | V | 20.0127 | | 0.0030 | 0.0017 | 1916 |
| 95 | 19 | POL | 654 | QAFTFSPTYK | A03/A11 | A03 | A | K | 1090.10 | * | 0.0450 | 0.5400 | 1917 |
| 80 | 16 | EVN | 179 | QAGFFLLTR | A03/A11 | A03 | A | R | | | | | 1918 |
| 80 | 16 | ENV | 118 | QAMQWNSTTF | A03/A11 | A03 | A | F | | | | | 1919 |
| 75 | 15 | NUC | 169 | QSPRFFFSQSR | A03/A11 | A03 | S | R | 28.0839 | | | | 1920 |
| 80 | 16 | POL | 189 | QSSGILSR | A03/A11 | A03 | S | R | | | | | 1921 |
| 95 | 19 | POL | 539 | RAFPHCLAF | A03/A11 | A03 | A | F | 20.0125 | | 0.0015 | 0.0007 | 1922 |
| 75 | 15 | POL | 106 | RLKLIMPAR | A03/A11 | A03 | L | R | 1.0975 | * | 0.0950 | 0.0002 | 1923 |
| 75 | 15 | POL | 106 | RLKLIMPARF | A03/A11 | A03 | L | F | | | | | 1924 |
| 75 | 15 | X | 128 | RLKVFVLGGCR | A03/A11 | A03 | L | R | | | | | 1925 |
| 95 | 19 | POL | 387 | RLVVDFSCF | A03/A11 | A03 | L | F | 20.0122 | | 0.0006 | 0.0002 | 1926 |
| 75 | 15 | POL | 376 | RLWDPSQFSR | A03/A11 | A03 | L | R | 26.0539 | * | 0.2800 | 3.8000 | 1927 |
| 95 | 19 | NUC | 183 | RSPRRRTPSPR | A03/A11 | A03 | S | A | 26.0540 | | -0.0007 | -0.0003 | 1928 |
| 75 | 15 | NUC | 167 | RSQSPRRR | A03/A11 | A03 | S | R | | | | | 1929 |
| 75 | 15 | NUC | 187 | RSQSPRRRR | A03/A11 | A03 | S | R | | | | | 1930 |
| 95 | 19 | NUC | 188 | RTPSPRRR | A03/A11 | A03 | T | R | 26.0019 | * | -0.0002 | -0.0002 | 1931 |
| 95 | 19 | NUC | 188 | RTPSPRRRR | A03/A11 | A03 | T | R | 1.0971 | | 0.0054 | 0.0005 | 1932 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 80 | 18 | POL | 829 | RVHFASPLH | A03/A11 | A03 | V | H | 1147.18 | | 0.0190 | | 1933 |
| 100 | 20 | POL | 357 | RVTGGVFLVDK | A03/A11 | A03 | V | K | | * | -0.0002 | 0.0290 | 1934 |
| 90 | 18 | X | 65 | SAGPCALR | A03/A11 | A03 | A | R | 26.0020 | | -0.0002 | 0.0020 | 1935 |
| 90 | 18 | X | 65 | SAGPCALRF | A03/A11 | A03 | A | F | 26.0152 | | -0.0003 | 0.0004 | 1936 |
| 95 | 19 | POL | 520 | SAICSVVR | A03/A11 | A03 | A | R | 26.0021 | | -0.0002 | 0.0071 | 1937 |
| 95 | 19 | POL | 520 | SAICSVVRR | A03/A11 | A03 | A | R | 1090.11 | * | 0.0058 | 0.2100 | 1938 |
| 90 | 18 | POL | 771 | SALNPADDPSR | A03/A11 | A03 | A | R | 26.0542 | | -0.0004 | -0.0003 | 1939 |
| 100 | 20 | POL | 165 | SASFCGSPY | A01/A03/ | A03 | A | Y | | * | | | 1940 |
| 75 | 15 | POL | 759 | SFPWLLGCA | A03/A11 | A03 | F | A | | | | | 1941 |
| 75 | 15 | POL | 769 | SFPWLLGCAA | A03/A11 | A03 | F | A | | | | | 1942 |
| 95 | 19 | POL | 427 | SLDVSAAFYH | A03/A11 | A03 | L | H | | | | | 1943 |
| 75 | 15 | POL | 565 | SLGHLNPNK | A03/A11 | A03 | L | K | 28.0758 | * | | | 1944 |
| 100 | 20 | ENV | 348 | SLLVPFVQWF | A03/A11 | A03 | L | F | | | | | 1945 |
| 95 | 19 | X | 54 | SLRGLPVCAF | A03/A11 | A03 | L | F | 20.0259 | | 0.0004 | 0.0002 | 1946 |
| 90 | 18 | X | 64 | SSAGPCALR | A03/A11 | A03 | S | R | 26.0153 | * | 0.0080 | 0.1400 | 1947 |
| 90 | 18 | X | 64 | SSAGPCALRF | A03/A11 | A03 | S | F | 26.0374 | | -0.0003 | -0.0002 | 1948 |
| 95 | 19 | NUC | 170 | STLPETTVVR | A03/A11 | A03 | T | R | 1069.21 | * | 0.0007 | 0.0600 | 1949 |
| 95 | 19 | NUC | 170 | STLPETTVVRR | A03/A11 | A03 | T | R | 1083.01 | * | 0.0150 | 1.4000 | 1950 |
| 80 | 16 | ENV | 85 | STNRQSGR | A03/A11 | A03 | T | R | | | | | 1951 |
| 75 | 15 | X | 104 | STTDLEAYF | A03/A11 | A03 | T | F | | | | | 1952 |
| 75 | 15 | X | 104 | STTDLEAYFK | A03/A11 | A03 | T | K | 1.0584 | * | 0.0066 | 2.7000 | 1953 |
| 95 | 19 | POL | 535 | SVVRRAFPH | A03/A11 | A03 | V | H | 20.0131 | | 0.1100 | 0.6100 | 1954 |
| 85 | 17 | POL | 727 | TAELLAACF | A03/A11 | A03 | A | F | | | | | 1955 |
| 85 | 17 | POL | 716 | TAELLAACFAR | A03/A11 | A03 | A | R | 26.0544 | | 0.0006 | 0.0023 | 1956 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 90 | 18 | POL | 747 | TDNSVVLSR | A03/A11 | A03 | D | R | | | | | 1957 |
| 90 | 18 | POL | 747 | TDNSVVLSRK | A03/A11 | A03 | D | K | 20.0264 | | 0.0006 | 0.0017 | 1958 |
| 75 | 15 | NUC | 138 | TFGRETVLEY | A03/A11 | A03 | F | Y | | | | | 1959 |
| 95 | 19 | POL | 688 | TFSPTYKAF | A03/A24 | A03 | F | F | 5.0064 | | | | 1960 |
| 100 | 20 | POL | 370 | TGGVFLVDK | A03/A11 | A03 | G | K | 20.0133 | | 0.0007 | 0.0061 | 1961 |
| 95 | 19 | NUC | 171 | TLPETTVVR | A03/A11 | A03 | L | R | 1.0969 | | 0.0008 | 0.0002 | 1962 |
| 95 | 19 | NUC | 171 | TLPETTVVRR | A03/A11 | A03 | L | R | 1069.22 | * | 0.0007 | 0.0230 | 1963 |
| 95 | 19 | NUC | 171 | TLPETTVVRRR | A03/A11 | A03 | L | R | 26.0545 | * | 0.0005 | 0.0160 | 1964 |
| 95 | 19 | NUC | 150 | TLWKAGILY | A03/A11 | A03 | L | Y | 1099.03 | * | 0.1300 | 0.0008 | 1965 |
| 100 | 20 | NUC | 150 | TLWKAGILYK | A03/A11 | A03 | L | K | 1069.15 | * | 5.3000 | 0.3600 | 1966 |
| 100 | 20 | NUC | 150 | TLWKAGILYKR | A03/A11 | A03 | L | R | 26.0546 | | 0.0082 | 0.0095 | 1967 |
| 95 | 19 | POL | 519 | TSAICSVVR | A03/A11 | A03 | S | R | 5.0057 | | 0.0005 | 0.0008 | 1968 |
| 95 | 19 | POL | 519 | TSAICSVVAR | A03/A11 | A03 | S | R | 1142.08 | * | 0.0018 | 0.0006 | 1969 |
| 75 | 15 | POL | 756 | TSFPWLLGCA | A03/A11 | A03 | S | A | | | | | 1970 |
| 80 | 16 | POL | 775 | TSFVYVPSA | A03/A11 | A03 | S | A | | | | | 1971 |
| 75 | 15 | X | 105 | TTDLEAYFK | A03/A11 | A03 | T | K | 1.0215 | * | 0.0006 | 0.9200 | 1972 |
| 75 | 15 | EVN | 278 | TTSTGPCK | A03/A11 | A03 | T | K | | | | | 1973 |
| 80 | 16 | NUC | 175 | TTVVRRRGR | A03/A11 | A03 | T | R | 1.0970 | | 0.0008 | 0.0005 | 1974 |
| 80 | 16 | NUC | 176 | TVVRRRGR | A03/A11 | A03 | V | R | 3.0324 | | 0.0003 | 0.0001 | 1975 |
| 80 | 16 | NUC | 176 | TVVRRRGRSPR | A03/A11 | A03 | V | R | 28.0837 | | | | 1976 |
| 100 | 20 | POL | 373 | VFLVDKNPH | A03/A11 | A03 | F | H | | | | | 1977 |
| 80 | 16 | X | 131 | VFVLGGCRH | A03/A11 | A03 | F | H | | | | | 1978 |
| 75 | 15 | X | 131 | VFVLGGCRHK | A03/A11 | A03 | F | K | | | | | 1979 |
| 95 | 19 | POL | 637 | VGLLGFAAPF | A03/A11 | A03 | G | F | | | | | 1980 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 85 | 17 | POL | 96 | VGPLTVNEK | A03/A11 | A03 | G | K | 20.0132 | | 0.0007 | 0.0078 | 1981 |
| 85 | 17 | POL | 96 | VGPLTVNEKR | A03/A11 | A03 | G | R | | | | | 1982 |
| 95 | 19 | POL | 554 | VLGAKSVQH | A03/A11 | A03 | L | H | | | | | 1983 |
| 90 | 18 | X | 133 | VGGCRHK | A03/A11 | A03 | L | K | 26.0022 | | 0.0150 | 0.0002 | 1984 |
| 80 | 16 | ENV | 177 | VLQAGFFLLTR | A03/A11 | A03 | L | R | | | | | 1985 |
| 85 | 17 | POL | 752 | VLSRKYTSF | A03/A11 | A03 | L | F | | | | | 1986 |
| 90 | 18 | NUC | 120 | VSFGWWR | A03/A11 | A03 | S | R | 26.0023 | | 0.0040 | 0.0290 | 1987 |
| 100 | 20 | POL | 48 | VSIPWTHK | A03/A11 | A03 | S | K | 26.0024 | | 0.0130 | 0.0170 | 1988 |
| 100 | 20 | POL | 358 | VTGGVFLVDK | A03/A11 | A03 | T | K | 1069.17 | | 0.0390 | 0.0920 | 1989 |
| 100 | 20 | POL | 378 | VVDFSQFSR | A03/A11 | A03 | V | R | 1069.19 | | 0.0015 | 0.0750 | 1990 |
| 90 | 18 | POL | 553 | VVLGAKSVQH | A03/A11 | A03 | V | H | | | | | 1991 |
| 85 | 17 | POL | 751 | VVLSRKYTSF | A03/A11 | A03 | V | F | 20.0261 | * | 0.0004 | 0.0002 | 1992 |
| 80 | 16 | NUC | 177 | VVRRRGRSPR | A03/A11 | A03 | V | R | 1.1074 | * | 0.0027 | 0.0001 | 1993 |
| 80 | 16 | NUC | 177 | VVRRRGRSPRR | A03/A11 | A03 | V | R | 28.0838 | * | | | 1994 |
| 90 | 18 | NUC | 131 | WFHISCLTF | A03/A11 | A03 | F | F | 13.0073 | * | | | 1995 |
| 90 | 18 | NUC | 131 | WFHISCLTF | A03/A24 | A03 | F | F | 13.0073 | * | | | 1996 |
| 85 | 17 | NUC | 28 | WGMDIDPYK | A03/A11 | A03 | G | K | 26.0154 | | -0.0003 | 0.0006 | 1997 |
| 85 | 17 | POL | 589 | WGYSLNFMGY | A03/A11 | A03 | G | Y | | | | | 1998 |
| 80 | 16 | POL | 770 | WILRGTSFVY | A03/A11 | A03 | I | Y | 1.0572 | | 0.0076 | 0.0011 | 1999 |
| 95 | 19 | NUC | 125 | WIRTPPAYR | A03/A11 | A03 | I | R | 1.0968 | | 0.0008 | 0.0005 | 2000 |
| 90 | 18 | POL | 314 | WLQFRNSK | A03/A11 | A03 | L | K | 26.0025 | | -0.0002 | 0.0005 | 2001 |
| 95 | 19 | POL | 425 | WLSLDVSAAF | A03/A11 | A03 | L | F | | | | | 2002 |
| 85 | 17 | NUC | 26 | WLWGMDIDPY | A03/A11 | A03 | L | Y | 1.0774 | * | 0.0002 | 0.0002 | 2003 |
| 85 | 17 | NUC | 26 | WLWGMDIDPYK | A03/A11 | A03 | L | K | 26.0547 | | 0.0030 | 0.0013 | 2004 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 95 | 19 | ENV | 248 | WMCLRRFIIF | A03/A11 | A03 | M | F | 20.0266 | | 0.0004 | 0.0011 | 2005 |
| 95 | 19 | ENV | 248 | WMCLRRRIIF | A03/A24 | A03 | M | F | 20.0266 | | 0.0004 | 0.0011 | 2006 |
| 100 | 20 | POL | 122 | YLPLDKGIK | A03/A11 | A03 | L | K | 1.0173 | | 0.0001 | 0.0001 | 2007 |
| 90 | 18 | NUC | 118 | YLVSFGVWIR | A03/A11 | A03 | L | R | 1090.13 | * | 0.0005 | 0.0002 | 2008 |
| 90 | 18 | POL | 538 | YMDDVVLGAK | A03/A11 | A03 | M | K | 1090.15 | * | 0.0330 | 0.0043 | 2009 |
| 80 | 16 | POL | 504 | YSHPILGF | A03/A11 | A03 | S | F | | | | | 2010 |
| 80 | 16 | POL | 493 | YSHPILGFR | A03/A11 | A03 | S | R | | | | | 2011 |
| 80 | 16 | POL | 493 | YSHPIILGFRK | A03/A11 | A03 | S | K | | | | | 2012 |
| | | | | 248 | | | | | | | | | |

TABLE XVII

HBV A24 Motif With Binding Information

| Conservancy | Frequency | Protein | Position | Sequence | P2 | C-term | Peptide | Filed | A*2401 | SEQ ID NO: |
|---|---|---|---|---|---|---|---|---|---|---|
| 95 | 19 | X | 62 | AFSSAGPCAL | F | L | 5.0118 | | 0.0012 | 2013 |
| 90 | 18 | POL | 535 | AFSYMDDVVL | F | L | 13.0130 | | 0.0009 | 2014 |
| 80 | 16 | ENV | 108 | AMQWNSTTF | M | F | | | | 2015 |
| 100 | 20 | NUC | 131 | AYRPPNAPI | Y | I | 1090.02 | * | 0.0310 | 2016 |
| 100 | 20 | NUC | 131 | AYRPPNAPIL | Y | L | 1069.24 | * | 0.0042 | 2017 |
| 90 | 18 | NUC | 117 | EYLVSFGVW | Y | W | 26.0150 | | | 2018 |
| 90 | 18 | NUC | 117 | EYLVSFGVWI | Y | I | 17.0426 | * | | 2019 |
| 80 | 16 | ENV | 182 | FFLLTRILTI | F | I | | | | 2020 |
| 80 | 16 | ENV | 181 | GFFLLTRIL | F | L | | | | 2021 |
| 75 | 15 | ENV | 170 | GFLGPLLVL | F | L | | | | 2022 |
| 85 | 17 | NUC | 29 | GMDIDPYKEF | M | F | 26.0372 | | | 2023 |
| 85 | 17 | ENV | 65 | GWSPQAQGI | W | I | 20.0134 | | 0.0024 | 2024 |
| 85 | 17 | ENV | 65 | GWSPQAQGIL | W | L | 20.0268 | | 0.0003 | 2025 |
| 95 | 19 | ENV | 234 | GYRWMCLRRF | Y | F | 1069.25 | * | 0.0007 | 2026 |
| 80 | 16 | POL | 820 | HFASPLHVAW | F | W | | | | 2027 |
| 100 | 20 | ENV | 381 | IFFCLWVYI | F | I | 5.0058 | | 0.0087 | 2028 |
| 80 | 16 | ENV | 245 | IFLFILLLCL | F | L | | | | 2029 |
| 95 | 19 | POL | 395 | KFAVPNLQSL | F | L | 5.0114 | | 0.0020 | 2030 |
| 100 | 20 | POL | 121 | KYLPLDKGI | Y | I | | | | 2031 |
| 85 | 17 | POL | 745 | KYTSFPWLL | Y | L | 1069.23 | * | 5.3000 | 2032 |
| 80 | 16 | ENV | 247 | LFILLLCLI | F | I | | | | 2033 |
| 80 | 16 | ENV | 247 | LFILLLCLIF | F | F | | | | 2034 |
| 85 | 17 | NUC | 101 | LWFHISCLTF | W | F | 26.0373 | | | 2035 |
| 80 | 16 | POL | 492 | LYSHPIILGF | Y | F | 2.0181 | * | 1.1000 | 2036 |
| 95 | 19 | POL | 561 | NFLLSLGIHL | F | L | 5.0115 | | 0.0099 | 2037 |
| 80 | 16 | POL | 758 | NWILRGTSF | W | F | | | | 2038 |
| 95 | 19 | POL | 634 | PFTQCGYPAL | F | L | 5.0116 | | 0.0002 | 2039 |
| 95 | 19 | ENV | 341 | PFVQWFVGL | F | L | 5.0059 | | 0.0003 | 2040 |
| 80 | 16 | POL | 505 | PMGVGLSPF | M | F | | | | 2041 |
| 80 | 16 | POL | 750 | PWLLGCAANW | W | W | | | | 2042 |
| 100 | 20 | POL | 51 | PWTHKVGNF | W | F | 20.0138 | * | 0.0290 | 2043 |
| 75 | 15 | ENV | 242 | RFIIFLFIL | F | L | | | | 2044 |
| 75 | 15 | ENV | 242 | RFIIFLFILL | F | L | | | | 2045 |
| 95 | 19 | ENV | 236 | RWMCLRRFI | W | I | 20.0135 | * | 0.0710 | 2046 |
| 95 | 19 | ENV | 236 | RWMCLRRFII | W | I | 20.0269 | * | 1.1000 | 2047 |
| 100 | 20 | POL | 167 | SFCGSPYSW | F | W | 20.0139 | * | 0.0710 | 2048 |
| 80 | 16 | POL | 765 | SFVYVPSAL | F | L | | | | 2049 |
| 100 | 20 | ENV | 334 | SWLSLLVPF | W | F | 20.0136 | * | 0.3900 | 2050 |

TABLE XVII-continued

HBV A24 Motif With Binding Information

| Conservancy | Frequency | Protein | Position | Sequence | P2 | C-term | Peptide | Filed | A*2401 | SEQ ID NO: |
|---|---|---|---|---|---|---|---|---|---|---|
| 95 | 19 | POL | 392 | SWPKFAVPNL | W | L | 20.0271 | * | 5.6000 | 2051 |
| 95 | 19 | ENV | 197 | SWWTSLNFL | W | L | 20.0137 | * | 0.3800 | 2052 |
| 75 | 15 | POL | 4 | SYQHFFKLL | Y | L | 2.0042 | | 0.0051 | 2053 |
| 75 | 15 | POL | 4 | SYQHFRKLLL | Y | L | 2.0173 | * | 0.0660 | 2054 |
| 95 | 19 | POL | 657 | TFSPTYKAF | F | F | 5.0064 | | 0.0060 | 2055 |
| 95 | 19 | POL | 657 | TFSPTYKAFL | F | L | 5.0117 | | 0.0043 | 2056 |
| 95 | 19 | POL | 686 | VFADATPTGW | F | W | 20.0272 | * | 0.0180 | 2057 |
| 90 | 18 | NUC | 102 | WFHISCLTF | F | F | 13.0073 | * | 0.0300 | 2058 |
| 95 | 19 | ENV | 345 | WFVGLSPTVW | F | W | 20.0270 | * | 0.0120 | 2059 |
| 95 | 19 | ENV | 237 | WMCLRRFIIF | M | F | 20.0266 | | 0.0013 | 2060 |

48

TABLE XVIII

DR SUPER MOTIF (With binding information)

| SEQ ID NO: | Sequence | Peptide | DR1 | DR2w2B1 | DR2w2b1 | DR3 | DR4w4 | DR4w15 | DR5w11 | DR5w12 | DR6w19 | DR7 | DR8w2 | DR9 | DRW53 |
|---|---|---|---|---|---|---|---|---|---|---|---|---|---|---|---|
| 2061 | AANWILRGTSFVYVP | 1298.07 | 0.0920 | 0.0240 | 0.0061 | 0.0023 | 0.0510 | 0.0250 | 0.0140 | 0.3700 | 0.0250 | 0.5800 | 0.2500 | 0.2700 | |
| 2062 | AEDLNLGNLNVSIPW | 1186.01 | 0.0001 | | −0.0005 | | −0.0007 | | −0.0002 | | | −0.0003 | | | 0.0170 |
| 2063 | AELLAACFARSRSGA | | | | | | | | | | | | | | |
| 2064 | AFSYMDDVVLGAKSV | 1186.02 | 0.0027 | 0.0420 | −0.0005 | 0.00130 | 2.9000 | | 0.0006 | | | −0.0003 | | | −0.0005 |
| 2065 | AGFFLLTRILTIPQS | 1280.06 | 4.6000 | | 0.0190 | 0.0040 | 5.3000 | 0.1500 | 3.6000 | 0.0700 | 0.3700 | 3.1000 | 0.2600 | 1.3000 | |
| 2066 | AGPLEEELPRLADEG | 35.0091 | | | | 0.0022 | | | | | | | | | |
| 2067 | AKLIGTDNSVVLSRK | | | | | | | | | | | | | | |
| 2068 | ANWILRGTSFVYVPS | | | | | | | | | | | | | | |
| 2069 | ARDVLCLRPVGAESR | | | | | | | | | | | | | | |
| 2070 | ASALYREALESPEHC | | | | | | | | | | | | | | |
| 2071 | ASKLCLGWLWGMDID | 1186.03 | 0.0002 | | −0.0005 | | 0.0017 | | −0.0002 | | | 0.0013 | | | 0.0010 |
| 2072 | CLIFLLVLLDYQGML | | | | | | | | | | | | | | |
| 2073 | CLTFGRETVLEYLVS | | | | | | | | | | | | | | |
| 2074 | CPGYRWMCLRRFIIF | | | | | | | | | | | | | | |
| 2075 | CPTVQASKLCLGWLW | | | | | | | | | | | | | | |
| 2076 | CQVGADATPTGWGLA | | | | | | | | | | | | | | |
| 2077 | CSVVRRAPPHCLAFS | 1186.04 | 0.1000 | 0.1024 | 0.0770 | 0.0032 | 0.0016 | −0.0022 | 0.0008 | −0.0013 | 0.0540 | 0.0590 | 0.0250 | 1.2000 | 0.0460 |
| 2078 | CTCIPIPSSWAFARF | | | | | | | | | | | | | | |
| 2079 | CWWLQFRNSKPCSDY | | | | | | | | | | | | | | |
| 2080 | DDVVLGAKSVCHLES | | | | | | | | | | | | | | |
| 2081 | DEGLNRRVAEDLNLG | | | | | | | | | | | | | | |
| 2082 | DLNLGNLNVSIPWTH | 1280.07 | 0.0038 | | | | 0.0240 | | | | | 0.0010 | | | |
| 2083 | DVVLGAKSVQHLESL | | | | | | | | | | | | | | |
| 2084 | DWKVCQRIVGLLGFA | 1186.05 | 0.0120 | | −0.0026 | | 0.0030 | | 0.2500 | | | 0.0018 | | | 0.0130 |
| 2085 | EIRLKVFVLGGCRHK | | | | | | | | | | | | | | |
| 2086 | ESRLVVDFSQFSRGN | 35.0096 | 0.0007 | | | 2.6000 | | | | | | | | | |

TABLE XVIII-continued

DR_SUPER_MOTIF (With binding information)

| SEQ ID NO | Sequence | Peptide | DR1 | DR2w2B1 | DR2w2b1 | DR3 | DR4w4 | DR4w15 | DR5w11 | DR5w12 | DR6w19 | DR7 | DR8w2 | DR9 | DRW53 |
|---|---|---|---|---|---|---|---|---|---|---|---|---|---|---|---|
| 2087 | FFLLTRILTIPQSLD | F064.01 | | | | | | | | | | | | | |
| 2088 | FGVWIRTPPAYRPPN | | | | | | | | | | | | | | |
| 2089 | FIIFLFILLCLIFL | | | | | | | | | | | | | | |
| 2090 | FLFILLLCLIFLLVL | | | | | | | | | | | | | | |
| 2091 | FPWLLGCAANWILRG | | | | | | | | | | | | | | |
| 2092 | FRKLPVNRPIDWKVC | | | | | | | | | | | | | | |
| 2093 | FSWLSLLVPFVQWFV | | | | | | | | | | | | | | |
| 2094 | FSYMDDVVLGAKSVQ | | | | | | | | | | | | | | |
| 2095 | FVQWFVGLSPTVWLS | | | 0.0035 | 0.0160 | -0.0013 | 0.0130 | | | 0.0072 | 0.0021 | 0.0190 | 0.0690 | 0.0180 | 0.0410 | 0.0044 |
| 2096 | GAHLSLRGLPVCAFS | 1186.07 | 0.7800 | 0.0042 | -0.0041 | 0.0011 | | 0.0025 | | | 0.0077 | | | 0.0150 |
| 2097 | GFFLLTRILTIPQSL | 1280.08 | 0.4300 | 0.0150 | 0.0110 | | 3.1000 | 0.4500 | 2.3000 | | 0.0780 | 3.5000 | 1.6000 | 0.5500 | |
| 2098 | GIHLNPKTKRWGYS | | | | | | | | | | | | | | |
| 2099 | GLPVCAFSSAGPCAL | | | | | | | | | | | | | | |
| 2100 | GLYFPAGGSSSGTVN | | | | | | | | | | | | | | |
| 2101 | GTNLSVPNPLGFFPD | | | | | | | | | | | | | | |
| 2102 | GTSFVYVPSALNPAD | 1280.09 | 0.3500 | 0.0140 | 0.0500 | -0.0006 | 0.3800 | 0.4100 | 0.0470 | -0.0001 | 0.0001 | 0.2700 | 0.0610 | 0.3400 | |
| 2103 | GVFLVDKNPHNTTES | | | | | | | | | | | | | | |
| 2104 | GVGLSPFLLAQFTSA | | | | | | | | | | | | | | |
| 2105 | GVWIRTPPAYRPPNA | 27.0280 | 0.3700 | 0.0420 | 7.2000 | 0.0120 | 3.4000 | 0.5700 | 0.4800 | 0.0140 | -0.0004 | 0.2200 | 0.5300 | 0.0450 | |
| 2106 | HGGLLGWSPQAQGIL | | | | | | | | | | | | | | |
| 2107 | HLPLHPAAMPHLLVG | | | | | | | | | | | | | | |
| 2108 | HLSLRGLPVCAFSSA | 1280.10 | 1.3000 | | | | | 0.0028 | | | | | 0.0130 | | |
| 2109 | HTALRQAILCWGELM | | | | | | | | | | | | | | |
| 2110 | HTLWKAGILYKRETT | | | | | | | | | | | | | | |

TABLE XVIII-continued

DR_SUPER_MOTIF (With binding information)

| SEQ ID NO | Sequence | Peptide | DR1 | DR2w2B1 | DR2w2b1 | DR3 | DR4w4 | DR4w15 | DR5w11 | DR5w12 | DR6w19 | DR7 | DR8w2 | DR9 | DRW53 |
|---|---|---|---|---|---|---|---|---|---|---|---|---|---|---|---|
| 2111 | IFLFILLLCLIFLLV | 1280.11 | 0.0005 | | | | 0.0041 | | | | | 0.0018 | | | |
| 2112 | IIFLFILLLCLIFLL | 1280.12 | | | | | | | | | | | | | |
| 2113 | ILGFRKIPMGVGLSP | | | | | | | | | | | | | | |
| 2114 | ILLLCLIFLLVLLDY | F107.01 | 0.0026 | | 0.0069 | | 0.0320 | | 0.0018 | | | 0.0047 | | | |
| 2115 | IRDLLDTASALYREA | | | | | | | | | | | | | | |
| 2116 | IRQLLWFHISCLTFG | | | | | | | | | | | | | | |
| 2117 | IVGLLGFAAPFTQCG | 1186.09 | 0.0200 | | -0.0005 | | -0.0007 | | | | | 0.0009 | | | 0.0067 |
| 2118 | IWMMYWGPSLYNIL | | | | | | | | | | | | | | |
| 2119 | KFAVPNLQSLTNLLS | 1280.13 | 0.0180 | 0.0005 | -0.0003 | | 0.1300 | | 0.0043 | | 0.0088 | -0.0003 | | 0.0056 | |
| 2120 | KIPMGVGLSPFLLAQ | | | | | | | | | | | | | | |
| 2121 | KLHLYSHPIILGFRK | | | | | | | | | | | | | | |
| 2122 | KQAFTFSPTYKAFLC | 1298.06 | 0.5300 | 0.2400 | 0.1400 | 0.0090 | 1.1000 | 0.2200 | 0.2400 | 0.0024 | 0.0200 | 0.3300 | 0.1200 | 0.5400 | |
| 2123 | KQCFRKLPVNRPIDW | 1298.04 | 1.5000 | 0.0022 | 0.0210 | -0.0006 | 1.2000 | 0.8500 | 0.0130 | 0.0043 | 0.4000 | 0.0580 | 0.0250 | | |
| 2124 | KRRLKLIMPARFYPN | | | | | | | | | | | | | | |
| 2125 | LAQFTSAICSVVRRA | 1186.10 | 0.0120 | 0.0065 | 0.1500 | -0.0009 | 0.0150 | 0.0280 | 0.0076 | 0.0091 | 0.0010 | 0.0280 | 0.0150 | 0.0880 | 0.0190 |
| 2126 | LCLIFLLVLLDYQGM | F107.02 | 0.0016 | | 0.0060 | 0.0200 | 0.0230 | | 0.0017 | | | 0.0044 | | | |
| 2127 | LCQVFADATPTGWGL | 1280.14 | 0.0020 | | | | 0.9600 | | | | | 0.0013 | | | |
| 2128 | LEYLVSFGVWIRTPP | | | | | | | | | | | | | | |
| 2129 | LFILLCLIFLLVLL | | | | | | | | | | | | | | |
| 2130 | LGFFPDHQLDPAFGA | | | | | | | | | | | | | | |
| 2131 | LGNLNVSIPWTHKVG | | | | | | | | | | | | | | |
| 2132 | LGPLLVLQAGFFLLT | | | | | | | | | | | | | | |
| 2133 | LGWLWGMDIDPYKEF | 1186.12 | 0.0004 | | 0.0006 | 0.0200 | 0.0280 | | -0.0002 | | 0.0002 | 0.0004 | | | 0.0430 |
| 2134 | LHLYSHPIILGFRKI | 1280.15 | 0.0220 | 0.0340 | 0.0400 | 0.0040 | 0.6800 | 0.1600 | 0.0410 | 0.0310 | 0.0002 | 0.0006 | 0.0610 | 0.0490 | |

TABLE XVIII-continued

DR_SUPER_MOTIF (With binding information)

| SEQ ID NO: | Sequence | Peptide | DR1 | DR2w2B1 | DR2w2b1 | DR3 | DR4w4 | DR4w15 | DR5w11 | DR5w12 | DR6w19 | DR7 | DR8w2 | DR9 | DRW53 |
|---|---|---|---|---|---|---|---|---|---|---|---|---|---|---|---|
| 2135 | LHTLWKAGILYKRET | | | | | | | | | | | | | | |
| 2136 | LKVFVLGGCRHKLVC | | | | | | | | | | | | | | |
| 2137 | LLCLIFLLVLLDYQG | | | | | | | | | | | | | | |
| 2138 | LLDYQGMLPVCPLIP | | | | | | | | | | | | | | |
| 2139 | LLGFAAPFTQCGYPA | | | | | | | | | | | | | | |
| 2140 | LLWFHISCLTFGRET | | | | | | | | | | | | | | |
| 2141 | LPKVLHKRTLGLSAM | | | | | | | | | | | | | | |
| 2142 | LPLLPIFFCLWVYIZ | | | | | | | | | | | | | | |
| 2143 | LQSLTNLLSSNLSWL | F107.03 | 2.5000 | 0.4400 | 0.0200 | -0.0013 | 4.8000 | 0.8100 | 0.0680 | 0.7500 | 0.0260 | 0.1500 | 0.0880 | 0.1100 | 0.0200 |
| 2144 | LSAMSTTDLEAYFKD | | | | | | | | | | | | | | |
| 2145 | LSTLPETTVRRRGR | | | | | | | | | | | | | | |
| 2146 | LSWLSLDVSAAFYHI | | | | | | | | | | | | | | |
| 2147 | LTNLLSSNLSWLSLD | 1186.14 | 0.0010 | | 0.0083 | | 0.0160 | | 0.0013 | | 0.0019 | | | | |
| 2148 | LVLLDYQGMLPVCPL | 1280.17 | 0.0034 | | | | -0.0013 | | | | | 0.0011 | | | |
| 2149 | LVPFVQWFVGLSPTV | 1186.15 | 0.0130 | 0.6900 | 0.0140 | -0.0013 | 0.1500 | 1.4000 | 0.3800 | 0.6600 | 0.0018 | 0.0092 | 0.6600 | 2.5000 | 2.6000 |
| 2150 | MQLFHLCLIISCSCP | | | | | | | | | | | | | | |
| 2151 | NAPILSTLPETTVVR | 1186.16 | 0.0009 | | 0.0009 | | -0.0007 | | -0.0002 | | | 0.0005 | | | |
| 2152 | NLNVSIPWTHKVGNF | 1186.17 | 0.0001 | | -0.0005 | -0.0041 | -0.0007 | | -0.0002 | | | 0.0005 | | | 0.0009 |
| 2153 | NLSWLSLDVSAAFYH | 1186.18 | 0.1400 | 0.0003 | -0.0005 | 1.3000 | 0.2900 | | 0.0033 | 0.0022 | 0.0330 | 0.0041 | 0.0150 | 0.0620 | 2.4000 |
| 2154 | NRPIDWKVCQRIVGL | | | | | | | | | | | | | | |
| 2155 | PAAMPHLLVGSSGLS | | | | | | | | | | | | | | |
| 2156 | PDRVHFASPLHVAWR | 1298.08 | 0.0510 | 0.0290 | 0.0008 | | 0.0008 | 0.0054 | 0.0008 | | 0.0190 | 0.0810 | 0.0035 | 0.2400 | |
| 2157 | PFLLAQFTSAICSVV | F107.04 | 0.1800 | 0.0270 | 0.0042 | -0.0013 | 0.0800 | 0.1200 | 0.0120 | 0.0016 | 0.0800 | 0.0770 | 0.0580 | 0.0590 | |
| 2158 | PHCLAFSYMDDVVLG | | | | | | | | | | | | | | |

TABLE XVIII-continued

DR SUPER MOTIF (With binding information)

| SEQ ID NO: | Sequence | Peptide | DR1 | DR2w2B1 | DR2w2b1 | DR3 | DR4w4 | DR4w15 | DR5w11 | DR5w12 | DR6w19 | DR7 | DR8w2 | DR9 | DRW53 |
|---|---|---|---|---|---|---|---|---|---|---|---|---|---|---|---|
| 2159 | PIILGFRKIPMGVGL | | | | | | | | | | | | | | |
| 2160 | PLPIHTAELLAACFA | 1280.18 | 0.0046 | | | | 0.0490 | | | | | -0.0003 | | | 0.0015 |
| 2161 | PPAYRPPNAPILSTL | 1186.20 | 0.0056 | | -0.0005 | | 0.0038 | | 0.0022 | | | 0.0024 | | | |
| 2162 | PQAMQWNSTTFHQTL | 1298.01 | 0.0012 | | | | 0.0300 | | | | | 0.1200 | | | |
| 2163 | PQSLDSWWTSLNFLG | | | | | | | | | | | | | | |
| 2164 | QCGYPALMPLYACIQ | 1186.21 | 0.0062 | | 0.0018 | | 0.0068 | | 0.0023 | | | 0.0006 | | | |
| 2165 | QLLWFHISCLTFGRE | | | | | | | | | | | | | | |
| 2166 | QQYVGPLTVNEKRRL | | | | | | | | | | | | | | |
| 2167 | QWFVGLSPTVWLSVI | | | | | | | | | | | | | | |
| 2168 | RDLLDTASALYREAL | 1280.19 | 0.0001 | | | | 0.0092 | | | | | 0.0770 | | | |
| 2169 | RDVLCLRPVGAESRG | | | | | | | | | | | | | | |
| 2170 | RFIIFLFILLLCLIF | | | | | | | | | | | | | | |
| 2171 | RFSWLSLLVPFVQWF | 1186.22 | 0.0430 | | 0.0009 | | -0.0007 | | 0.0002 | | | 0.0005 | | | 0.0031 |
| 2172 | RPGLCQVFADATPTG | | | | | | | | | | | | | | |
| 2173 | RQLIWFHISCLTFGR | 1186.23 | 0.0002 | | 0.0009 | | 0.0140 | | 0.0011 | | | 0.0061 | | | 0.0096 |
| 2174 | RRAFPHCLAPSYMDD | F107.05 | 0.0010 | | 0.0010 | | -0.0009 | | 0.0010 | | | 0.0017 | | | |
| 2175 | RRFIFLFILLLCLI | | | | | | | | | | | | | | |
| 2176 | RRSFGVEPSGSGHID | | | | | | | | | | | | | | |
| 2177 | RVSWPKFAVPNLQSL | | | | | | | | | | | | | | |
| 2178 | RWGYSLNFMGYVIGS | | | | | | | | | | | | | | |
| 2179 | SFGVWIRTPPAYRPP | 1186.25 | 0.0094 | | 0.4300 | -0.0009 | 0.0780 | 0.0630 | 0.0260 | 0.0071 | 0.0002 | 0.0240 | 0.2500 | 0.0800 | 0.0016 |
| 2180 | SFPWLLGCAANWILR | | | | | | | | | | | | | | |
| 2181 | SFVVVPSALNPADDP | | | | | | | | | | | | | | |
| 2182 | SGFLGPLLVLQAGFF | | | | | | | | | | | | | | |

TABLE XVIII-continued

DR SUPER MOTIF (with binding information)

| SEQ ID NO | Sequence | Peptide | DR1 | DR2w2B1 | DR2w2b1 | DR3 | DR4w4 | DR4w15 | DR5w11 | DR5w12 | DR6w19 | DR7 | DR8w2 | DR9 | DRw53 |
|---|---|---|---|---|---|---|---|---|---|---|---|---|---|---|---|
| 2183 | SPFLLAQFTSAICSV | 1186.26 | 0.1200 | 0.0200 | 0.0085 | -0.0013 | 0.0740 | 0.0190 | -0.0002 | -0.0013 | 0.0540 | 0.0330 | 0.0014 | 0.0380 | 0.2000 |
| 2184 | SSNLSWLSLDVSAAF | 1186.27 | 0.1400 | 0.0030 | -0.0005 | 1.5000 | 0.2700 | | 0.0046 | 0.0180 | 0.1000 | 0.0039 | 0.0460 | 0.0110 | 6.2000 |
| 2185 | SVELLSFLPSDFFPS | | | | | | | | | | | | | | |
| 2186 | SVRFSWLSLLVPFVQ | 1280.20 | 0.9000 | | | | 0.0099 | | | | | 0.0037 | | | |
| 2187 | SVVLSRKYTSFPWLL | 27.0282 | 0.0005 | | 0.0057 | 0.2100 | -0.0016 | | 0.5300 | | | 0.0130 | | | |
| 2188 | TNFLLSLGIHLINPK | 1298.03 | 3.5000 | 0.0410 | 0.1200 | | 0.0220 | 0.0360 | 0.0053 | | 0.0160 | 0.2200 | 0.0032 | 0.3800 | |
| 2189 | TNLLSSNLSWLSLDV | 1186.26 | 0.0016 | | -0.0005 | | 0.1300 | | 0.0006 | | | 0.0019 | | | 0.0410 |
| 2190 | TRILTIPQSLDSWWT | | | | | | | | | | | | | | |
| 2191 | TSFVVPSALNPADD | | | | | | | | | | | | | | |
| 2192 | TSGFLGPLLVLQAGF | | | | | | | | | | | | | | |
| 2193 | VAPLPIHTAELLAAC | | | | | | | | | | | | | | |
| 2194 | VCAFSSAGPCALRFT | 1186.29 | 0.2100 | | 0.2600 | | 0.0023 | | 0.0003 | | | 0.0200 | | | 0.0150 |
| 2195 | VELLSFLPSDFFPSI | | | | | | | | | | | | | | |
| 2196 | VGLLGFAAPTQCGY | 1280.21 | 0.0470 | 0.3100 | 0.0008 | | -0.0014 | | -0.0004 | | -0.0001 | 0.0014 | | 0.5700 | |
| 2197 | VGNFTGLYSSTVPVF | 1298.02 | 1.7000 | 0.0100 | 0.0016 | | 0.0140 | 0.1700 | 0.0035 | | 0.0580 | 0.5600 | 0.0044 | 0.3100 | |
| 2198 | VLCLRPVGAESRGRP | | | | | | | | | | | | | | |
| 2199 | VQWFVGLSPTVWLSV | | | | | | | | | | | | | | |
| 2200 | WASVRFSWLSLLVPF | | | | | | | | | | | | | | |
| 2201 | WLSLDVSAAFYHIPL | | | | | | | | | | | | | | |
| 2202 | WLSLLVPFVQWFVGL | | | | | | | | | | | | | | |
| 2203 | WMCLRRFIIFLFILL | | | | | | | | | | | | | | |
| 2204 | WPKFAVPNLQSLTNL | 1186.30 | 0.0007 | | 0.0013 | | 0.0023 | | 0.0002 | | | 0.0008 | | | 0.0180 |
| 2205 | YPALMPLYACIQSKQ | 1298.05 | 0.2400 | | | | 0.0014 | | | | | 0.0011 | | | |

145

TABLE XIX

HBV DR3 MOTIF PEPTIDES WITH BINDING DATA

| Total Conservancy | Total | Core Convervancy | Core Freq. | Pro-tein | Posi-tion | Core Sequence | Core SEQ ID NO: | Sequence | SEQ ID NO: | Peptide | Filed | Binding Data DR3 | Motif |
|---|---|---|---|---|---|---|---|---|---|---|---|---|---|
| 90.00 | 18 | 90.00 | 18 | POL | 535 | YMDDVVLGA | 2228 | AFSYMDDVVLGAKSV | 2206 | 1186.02 | | 0.0130 | DR3 |
| 55.00 | 11 | 95.00 | 19 | POL | 655 | FSPTYKAFL | 2229 | AFTFSPTYKAFLCKQ | 2207 | 35.0099 | | 0.0035 | DR3 |
| 65.00 | 13 | 90.00 | 18 | POL | 18 | LEEELPRLA | 2230 | AGPLEEELPRLADEG | 2208 | 35.0091 | | 0.0022 | DR3 |
| 65.00 | 13 | 80.00 | 16 | POL | 731 | IGTDNSVVL | 2231 | AKLIGTDNSVVLSRK | 2209 | | | | DR3 |
| 85.00 | 17 | 85.00 | 17 | NUC | 34 | LYREALESP | 2232 | ASALYREALESPEHC | 2210 | | | | DR3 |
| 70.00 | 14 | 75.00 | 15 | NUC | 136 | FGRETVLEY | 2233 | CLTFGRETVLEYLVS | 2211 | | | | DR3 |
| 90.00 | 18 | 90.00 | 18 | x | 48 | AHLSLRGLP | 2234 | DHGAHLSLRGLPVCA | 2212 | | | | DR3 |
| 85.00 | 17 | 90.00 | 18 | POL | 737 | VVLSRKYTS | 2235 | DNSVVLSRKYTSFPW | 2213 | | | | DR3 |
| 45.00 | 9 | 100.00 | 20 | POL | 374 | LVVDFSQFS | 2236 | ESRLVVDFSQFSRGN | 2214 | 35.0096 | * | 2.6000 | DR3 |
| 5.00 | 1 | 75.00 | 1 | ENV | 172 | AVLDPRVRG | 2237 | FHQAVLDPRVRGLYL | 2215 | | | | DR3 |
| 90.00 | 18 | 95.00 | 19 | ENV | 256 | VLLDYQGML | 2238 | FLLVLLDYQGMLPVC | 2216 | 35.009 | | 0.0170 | DR3 |
| 55.00 | 11 | 100.00 | 20 | POL | 360 | FLVDKNPHN | 2239 | GGVFLVDKNPHNTTE | 2217 | 35.0095 | | 0.0790 | DR3 |
| 95.00 | 19 | 95.00 | 19 | POL | 683 | VFADATPTG | 2240 | LCQVFADATPTGWGL | 2218 | 1280.14 | | 0.0000 | DR3 |
| 35.00 | 7 | 95.00 | 19 | X | 18 | VGAESRGRP | 2241 | LRPVGAESRGRPVSG | 2219 | 35.0101 | | -0.0017 | DR3 |
| 55.00 | 11 | 95.00 | 19 | POL | 412 | LSLDVSAAF | 2242 | LSWLSLDVSAAFYHI | 2220 | | | | DR3 |
| 45.00 | 9 | 85.00 | 17 | NUC | 27 | MDIDPYKEF | 2243 | LWGMDIDPYKEFGAS | 2221 | | | | DR3 |
| 85.00 | 17 | 100.00 | 20 | POL | 34 | VAEDLNLGN | 2244 | NRRVAEDLNLGNLNV | 2222 | 35.0092 | | 0.1400 | DR3 |
| 100.00 | 20 | 100.00 | 20 | POL | 47 | IPWTHKVGN | 2245 | NVSIPWTHKVGNFTG | 2223 | | | | DR3 |
| 45.00 | 9 | 95.00 | 19 | ENV | 10 | FFPDHQLDP | 2246 | PLGFFPDHQLDPAFG | 2224 | | | | DR3 |
| 30.00 | 6 | 75.00 | 15 | POL | 241 | FGVEPSGSG | 2247 | RRSFGVEPSGSGHID | 2225 | | | | DR3 |
| 100.00 | 20 | 100.00 | 20 | POL | 120 | LPLDKGIKP | 2248 | TKYLPLDKGIKPYYP | 2226 | 35.0094 | | -0.0017 | DR3 |
| 60.00 | 12 | 85.00 | 17 | POL | 96 | LTVNEKRRL | 2249 | VGPLTVNEKRRLKLI | 2227 | 35.0093 | * | 2.2000 | DR3 |
| | | | | | | 22 | | 22 | | | | | |

TABLE XX

Population coverage with combined HLA Supertypes

| HLA-SUPERTYPES | PHENOTYPIC FREQUENCY | | | | | |
|---|---|---|---|---|---|---|
| | Caucasian | N.A. Black | Japanese | Chinese | Hispanic | Average |
| A2, A3, B7 | 83.0 | 86.1 | 87.5 | 88.4 | 86.3 | 86.2 |
| A2, A3, B7, A24, B44, A1 | 99.5 | 98.1 | 100.0 | 99.5 | 99.4 | 99.3 |
| A2, A3, B7, A24, B44, A1, B27, B62, B58 | 99.9 | 99.6 | 100.0 | 99.8 | 99.9 | 99.8 |

TABLE XXI

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| | ALFKDWEEL | | | | | | | | | 2250 |
| 9 | ALMPLYACV | L2.IV9 | N | Y | N | N | N | 1 | A | 2251 |
| | ALMPLYASI | | | | | | | | | 2252 |
| 9 | ALMPLYAXI | | N | Y | N | N | N | | A | 2253 |
| 10 | ALPSDFFPSV | | N | Y | N | N | N | No | A | 2254 |
| | ALPSDFFPSV-NH2 | | | | | | | | | 2255 |
| | ALSLIVNLL | | | | | | | | | 2256 |
| 9 | AMTFSPTYK | | N | N | Y | N | N | | A | 2257 |
| | ATVELLSFLPSDFFPSV-NH2 | | | | | | | | | 2258 |
| 10 | CILLLCLIFL | | N | Y | N | N | N | No | A | 2259 |
| 11 | CILLLCLIFLL | | N | Y | N | N | N | No | A | 2260 |
| 9 | DPFRGRLGL | | N | N | N | N | Y | | A | 2261 |
| 9 | DPSRGRLGI | | N | N | N | N | Y | | A | 2262 |
| | ELLSFLPSDFFPSV-NH2 | | | | | | | | | 2263 |
| 10 | FAPSDFFPSV | LA2.V10 | N | Y | N | N | N | Rev | A | 2264 |
| 10 | FILLLXLIFL | | N | Y | N | N | N | | A | 2265 |
| 10 | FLASDFFPSV | | N | Y | N | N | N | No | A | 2266 |
| 10 | FLGLSPTVWV | VL2.LV1 | N | Y | N | N | N | 1 | A | 2267 |
| 10 | FLKSDFFPSV | | N | Y | N | N | N | No | A | 2268 |
| 10 | FLLAQFTSAV | L2.IV10 | N | Y | N | N | N | 1 | A | 2269 |
| 9 | FLLAQFTSV | L2.AV9 | N | Y | N | N | N | 1 | A | 2270 |
| 9 | FLLPIFFCL | | N | Y | N | N | N | No | A | 2271 |
| 9 | FLLSLGIHV | L2.LV9 | N | Y | N | N | N | 1 | A | 2272 |
| 9 | FLLTRILTV | L2.IV9 | N | Y | N | N | N | 1 | A | 2273 |
| 9 | FLLTRILYI | | N | Y | N | N | N | | A | 2274 |
| 9 | FLLTYILTI | | N | Y | N | N | N | | A | 2275 |
| 10 | FLMSDYFPSV | | N | Y | N | N | N | No | A | 2276 |
| 9 | FLMSYFPSV | | N | Y | N | N | N | No | A | 2277 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 10 | FLPADFFPSI | L2.SA4 | N | Y | N | N | N | Rev | A | 2278 |
| 10 | FLPADFFPSV | | N | Y | N | N | N | No | A | 2279 |
| 10 | FLPDDFFPSA | L2.SD4 | N | Y | N | N | N | Rev | A | 2280 |
| 10 | FLPDDFFPSV | | N | Y | N | N | N | No | A | 2281 |
| 10 | FLPNDFFPSA | L2.SN4 | N | Y | N | N | N | Rev | A | 2282 |
| 10 | FLPNDFFPSV | | N | Y | N | N | N | No | A | 2283 |
| 10 | FLPS(X)YFPSV | | N | N | N | N | N | | A | 2284 |
| 10 | FLPSAFFPSV | | N | Y | N | N | N | No | A | 2285 |
| 10 | FLPSD(X)FPSV | | N | N | N | N | N | | A | 2286 |
| 10 | FLPSDAFPSV | | N | Y | N | N | N | No | A | 2287 |
| 10 | FLPSDFAPSV | | N | Y | N | N | N | No | A | 2288 |
| | FLPSDFF-NH2 | | | | | | | | | 2289 |
| 10 | FLPSDFFASV | | N | Y | N | N | N | No | A | 2290 |
| 10 | FLPSDFFKSV | | N | Y | N | N | N | No | A | 2291 |
| 8 | FLPSDFFP | | N | N | N | N | N | | A | 2292 |
| | FLPSDFFP-NH2 | | | | | | | | | 2293 |
| 10 | FLPSDFFPAV | | N | Y | N | N | N | No | A | 2294 |
| 10 | FLPSDFFPKV | | N | Y | N | N | N | No | A | 2295 |
| 9 | FLPSDFFPS | | N | N | N | N | N | | A | 2296 |
| | FLPSDFFPS-NH2 | | | | | | | | | 2297 |
| 10 | FLPSDFFPSA | LV.VA10 | N | Y | N | N | N | Rev | A | 2298 |
| 10 | FLPSDFFPSI | LV.VI10 | N | Y | N | N | N | Rev | A | 2299 |
| | FLPSDFFPSV(CONH2) | | | | | | | | | 2300 |
| | FLPSDFFPSV-NH2 | | | | | | | | | 2301 |
| 11 | FLPSDFFPSVR | | N | N | Y | N | N | | A | 2302 |
| | FLPSDFFPSVR-NH2 | | | | | | | | | 2303 |
| 12 | FLPSDFFPSVRD | | N | N | N | N | N | | A | 2304 |
| 10 | FLPSDFYPSV | | N | Y | N | N | N | No | A | 2305 |
| 11 | FLPSDLLPSVR | | N | N | Y | N | N | | A | 2306 |
| 10 | FLPSDYFPSV | | N | Y | N | N | N | No | A | 2307 |
| 10 | FLPSEFFPSV | | N | Y | N | N | N | No | A | 2308 |
| 9 | FLPSYFPSA | L2.FY5. | N | Y | N | N | N | Rev3 | A | 2309 |
| 9 | FLPSYFPSV | L2.FY5. | N | Y | N | N | N | 3 | A | 2310 |
| 10 | FLPSZFFPSV | | N | Y | N | N | N | No | A | 2311 |
| 10 | FLPSZFFPSV | | N | Y | N | N | N | No | A | 2312 |
| 10 | FLPVDFFPSI | L2.SV4. | N | Y | N | N | N | Rev | A | 2313 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 10 | FLPVDFFPSV | | N | Y | N | N | N | No | A | 2314 |
| | FLSKQYLNL | | | | | | | | | 2315 |
| 9 | FLYTRILTI | | N | Y | N | N | N | | A | 2316 |
| 8 | FMFSPTYK | | N | N | Y | N | N | | A | 2317 |
| 10 | FMLLLCLIFL | IM2.L10 | N | Y | N | N | N | 1 | A | 2318 |
| 10 | FMPSDFFPSV | LM2.V1 | N | Y | N | N | N | 1 | A | 2319 |
| 8 | FPAAMPHL | | N | N | N | N | Y | | A | 2320 |
| 9 | FPAAMPHLL | | N | N | N | N | Y | | A | 2321 |
| 10 | FPAAMPHLLV | | N | N | N | N | Y | | A | 2322 |
| 9 | FPALMPLYA | | N | N | N | N | Y | | A | 2323 |
| 10 | FPARVTGGVF | | N | N | N | N | Y | | A | 2324 |
| 10 | FPCALRFTSA | | N | N | N | N | Y | | A | 2325 |
| 9 | FPFCLAFSY | | N | N | N | N | Y | | A | 2326 |
| 10 | FPFCLAFSYM | | N | N | N | N | Y | | A | 2327 |
| 9 | FPHCLAFAL | | N | N | N | N | Y | | A | 2328 |
| 9 | FPHCLAFAY | | N | N | N | N | Y | | A | 2329 |
| 9 | FPHCLAFSA | | N | N | N | N | Y | | A | 2330 |
| 9 | FPHCLAFSI | | N | N | N | N | Y | | A | 2331 |
| 9 | FPHCLAFSL | | N | N | N | N | Y | | A | 2332 |
| 10 | FPHCLAFSYI | | N | N | N | N | Y | | A | 2333 |
| 10 | FPHXLAFSYM | | N | N | N | N | Y | | A | 2334 |
| 9 | FPIPSSWAF | | N | N | N | N | Y | | A | 2335 |
| 9 | FPSRGRLGL | | N | N | N | N | Y | | A | 2336 |
| 9 | FPVCAFSSA | | N | N | N | N | Y | | A | 2337 |
| 9 | FPVCLAFSY | | N | N | N | N | Y | | A | 2338 |
| 10 | FQPSDYFPSV | | N | N | N | N | Y | Rev | A | 2339 |
| 8 | FVFSPTYK | | N | N | Y | N | N | | A | 2340 |
| 9 | FVLGGXRHK | | N | N | Y | N | N | | A | 2341 |
| 9 | GLCQVGADV | L2.AV9 | N | Y | N | N | N | 1 | A | 2342 |
| 9 | GLLGWSPQV | L2.AV9 | N | Y | N | N | N | 1 | A | 2343 |
| 9 | GLWIRTIPPV | VL2.AV9 | N | Y | N | N | N | 1 | A | 2344 |
| 9 | GLXQFADA | | N | Y | N | N | N | | A | 2345 |
| 10 | GMDNSVVLSR | | N | N | Y | N | N | | A | 2346 |
| 11 | GMDNSVVLSRK | | N | N | Y | N | N | | A | 2347 |
| 10 | GPCALRFTSI | | N | N | N | N | Y | | A | 2348 |
| 10 | GPFALRFTSA | | N | N | N | N | Y | | A | 2349 |
| 10 | GPXALRFTSA | | N | N | N | N | Y | | A | 2350 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 10 | GTFNSVVLSR | | N | N | Y | N | N | | A | 2351 |
| 11 | GTFNSVVLSRK | | N | N | Y | N | N | | A | 2352 |
| 10 | GVDNSVVLSR | | N | N | Y | N | N | | A | 2353 |
| 11 | GVDNSVVLSRK | | N | N | Y | N | N | | A | 2354 |
| 10 | GYRWMXLRRF | | N | N | N | Y | N | | A | 2355 |
| 9 | HISXLTFGR | | N | N | Y | N | N | | A | 2356 |
| 10 | HMLWKAGILY | | Y | N | Y | N | N | | A | 2357 |
| 11 | HMLWKAGILYK | | N | N | Y | N | N | | A | 2358 |
| 8 | HPAAMPHI | | N | N | N | N | Y | | A | 2359 |
| 9 | HPAAMPHLI | | N | N | N | N | Y | | A | 2360 |
| 10 | HPAAMPHLLI | | N | N | N | N | Y | | A | 2361 |
| 8 | HPFAMPHL | | N | N | N | N | Y | | A | 2362 |
| 9 | HPFAMPHLL | | N | N | N | N | Y | | A | 2363 |
| 10 | HPFAMPHLLV | | N | N | N | N | Y | | A | 2364 |
| 10 | HTLWKAGILK | | N | N | Y | N | N | | A | 2365 |
| 10 | HTLWKAGILR | | N | N | Y | N | N | | A | 2366 |
| 10 | HVLWKAGILY | | N | N | Y | N | N | | A | 2367 |
| 11 | HVLWKAGILYK | | N | N | Y | N | N | | A | 2368 |
| | IIKKSEQFV | | | | | | | | | 2369 |
| 9 | ILGLLGFAV | VL2.AV9 | N | Y | N | N | N | 1 | A | 2370 |
| 10 | ILLLCLIFLV | L2.LV10 | N | Y | N | N | N | 1 | A | 2371 |
| 9 | ILLLXLIFL | | N | Y | N | N | N | | A | 2372 |
| 10 | ILLLXLIFLL | | N | Y | N | N | N | | A | 2373 |
| 9 | IPFPSSWAF | | N | N | N | N | Y | | A | 2374 |
| 9 | IPILSSWAF | | N | N | N | N | Y | | A | 2375 |
| 9 | IPIPMSWAF | | N | N | N | N | Y | | A | 2376 |
| 9 | IPIPSSWAI | | N | N | N | N | Y | | A | 2377 |
| 9 | IPITSSWAF | | N | N | N | N | Y | | A | 2378 |
| | KIKESFRKL | | N | N | N | N | Y | | A | 2379 |
| 9 | KLFLYSHPI | | N | Y | N | N | N | No | A | 2380 |
| 9 | KLHLYSHPV | L2.IV9 | N | Y | N | N | N | 1 | A | 2381 |
| 9 | KVGNFTGLK | | N | N | Y | N | N | | A | 2382 |
| 9 | KVGNFTGLR | | N | N | Y | N | N | | A | 2383 |
| 9 | LLAQFTSAV | L2.IV9 | N | Y | N | N | N | 1 | A | 2384 |
| 10 | LLFYQGMLPV | | N | Y | N | N | N | No | A | 2385 |
| | LLGSAANWI | | | | | | | | | 2386 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 10 | LLGXAANWIL | | N | Y | N | N | N | | A | 2387 |
| 9 | LLLXLIFLL | | N | Y | N | N | N | | A | 2388 |
| 10 | LLLXLIFLLV | | N | Y | N | N | N | | A | 2389 |
| 10 | LLLYQGMLPV | | N | Y | N | N | N | No | A | 2390 |
| 9 | LLPFVQWFV | VL2.V9 | N | Y | N | N | N | 1 | A | 2391 |
| 10 | LLPIFFXLWV | | N | Y | N | N | N | | A | 2392 |
| | LLSFLPSDFFPSV-NH2 | | | | | | | | | 2393 |
| 9 | LLSSNLSWV | L2.LV9 | N | Y | N | N | N | 1 | A | 2394 |
| 10 | LLVLQAGFFV | L2.LV10 | N | Y | N | N | N | 1 | A | 2395 |
| 9 | LLXLIFLLV | | N | Y | N | N | N | | A | 2396 |
| 10 | LMLLDYQGMV | VM2.LV | N | Y | N | N | N | 1 | A | 2397 |
| 10 | LMLQAGFFLV | VM2.LV | N | Y | N | N | N | 1 | A | 2398 |
| 9 | LMPFVQWFV | VM2.V9 | N | Y | N | N | N | 1 | A | 2399 |
| 9 | LPFCAFSSA | | N | N | N | N | Y | | A | 2400 |
| 8 | LPIFFCLI | | N | N | N | N | Y | | A | 2401 |
| 9 | LPIFFCLWI | | N | N | N | N | Y | | A | 2402 |
| 9 | LPIHTAELI | | N | N | N | N | Y | | A | 2403 |
| 11 | LPIHTAELLAI | | N | N | N | N | Y | | A | 2404 |
| | LPSDFFPSV-NH2 | | | | | | | | | 2405 |
| 9 | LPVCAFSSI | | N | N | N | N | Y | | A | 2406 |
| 9 | LPVXAFSSA | | N | N | N | N | Y | | A | 2407 |
| 12 | LSFLPSDFFPSV | | N | N | N | N | N | | A | 2408 |
| | LSFLPSDFFPSV-NH2 | | | | | | | | | 2409 |
| 10 | MMWYWGPSLK | | N | N | Y | N | N | | A | 2410 |
| 10 | MMWYWGPSLR | | N | N | Y | N | N | | A | 2411 |
| 9 | MMWYWGPSV | M2.LV9 | N | Y | N | N | N | 1 | A | 2412 |
| 8 | MPLSYCHI | | N | N | N | N | Y | | A | 2413 |
| 9 | NLGNLNVSV | L2.IV9 | N | Y | N | N | Y | 1 | A | 2414 |
| | NLNNLNVSI | | | | | | | | | 2415 |
| 9 | NMGLKYRQL | | N | Y | N | Y | N | No | A | 2416 |
| 11 | NPLGFFPDHQI | | N | N | N | N | Y | | A | 2417 |
| 9 | PLLPIFFCV | L2.LV9 | N | Y | N | N | N | 1 | A | 2418 |
| 9 | PLLPIFFXL | | N | Y | N | N | N | | A | 2419 |
| 8 | PSDFFPSV | | N | N | N | N | N | | A | 2420 |
| | PSDFFPSV-NH2 | | | | | | | | | 2421 |
| 10 | QLLWFHSXL | | N | Y | N | N | N | | A | 2422 |
| 10 | QMFTFSPTYK | | N | N | Y | N | N | | A | 2423 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 10 | QVFTFSPTYK | | N | N | Y | N | N | | A | 2424 |
| | RIPRTPRSV | | | | | | | | | 2425 |
| 9 | RLSWPKFAV | VL2.V9 | N | Y | N | N | N | 1 | A | 2426 |
| 9 | RLTGGVFLV | VL2.V9 | N | Y | N | N | N | 1 | A | 2427 |
| 9 | RMLTIPQSV | IM2.LV9 | N | Y | N | N | N | 1 | A | 2428 |
| 9 | RMTGGVFLV | VM2.V9 | N | Y | N | N | N | 1 | A | 2429 |
| 9 | RMYLHTLWK | | N | N | Y | N | N | | A | 2430 |
| 9 | RVYLHTLWK | | N | N | Y | N | N | | A | 2431 |
| 9 | SAIXSVVRR | | N | N | Y | N | N | | A | 2432 |
| 11 | SFLPSDFFPSV | | N | N | N | N | N | | A | 2433 |
| | SFLPSDFFPV-NH2 | | | | | | | | | 2434 |
| 9 | SLDSWWTSV | L2.LV9 | N | Y | N | N | N | 1 | A | 2435 |
| | SLNFLGGTTV(NH2) | L2.LV9 | N | Y | N | N | N | 1 | A | 2436 |
| 9 | SMICSVVRR | | N | N | Y | N | Y | | A | 2437 |
| 10 | SMLPETTVVR | | N | N | Y | N | N | | A | 2438 |
| 11 | SMLPETTVVRR | | N | N | Y | N | N | | A | 2439 |
| 10 | SMLSPFLPLY | IM2.LV1 | N | Y | N | N | N | 1 | A | 2440 |
| 8 | SPFLLAQI | | N | N | N | N | Y | | A | 2441 |
| 11 | STLPETYVVRR | | N | N | Y | N | N | | A | 2442 |
| 9 | SVICSVVRR | | N | N | Y | N | N | | A | 2443 |
| 10 | SVLPETTVVR | | N | N | Y | N | N | | A | 2444 |
| 11 | SVLPETTVVRR | | N | N | Y | N | N | | A | 2445 |
| 9 | SVNRPIDWK | | N | N | Y | N | N | | A | 2446 |
| 9 | SVVRRAFPK | | N | N | Y | N | N | | A | 2447 |
| 9 | SVVRRAFPR | | N | N | Y | N | N | | A | 2448 |
| 9 | TLWKAGILK | | N | N | Y | N | N | | A | 2449 |
| 9 | TLWKAGILR | | N | N | Y | N | N | | A | 2450 |
| 10 | TMPETTVVRR | | N | N | Y | N | N | | A | 2451 |
| 9 | TMWKAGILY | | Y | N | Y | N | N | | A | 2452 |
| 10 | TMWKAGILYK | | N | N | Y | N | N | | A | 2453 |
| 10 | TPARVTGGVI | | N | N | N | N | Y | | A | 2454 |
| 10 | TPFRVTGGVF | | N | N | N | N | Y | | A | 2455 |
| 10 | TSAIXSVVRR | | N | N | Y | N | N | | A | 2456 |
| | TVELLSFLPSDFFPSV-NH2 | | | | | | | | | 2457 |
| 10 | TVPETTVVRR | | N | N | Y | N | N | | A | 2458 |
| 9 | TVWKAGILY | | N | N | Y | N | N | | A | 2459 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 10 | TVWKAGILYK | | N | N | Y | N | N | | A | 2460 |
| | VELLSFLPSDFFPSV-NH2 | | | | | | | | | 2461 |
| | VLEYLVSFGV(NH2) | | | | | | | | | 2462 |
| | VLGGSRHKL | | | | | | | | | 2463 |
| 9 | VLLDYQGMV | L2.LV9 | N | Y | N | N | N | 1 | A | 2464 |
| 9 | VLQAGFFLV | L2.LV9 | N | Y | N | N | N | 1 | A | 2465 |
| 10 | VMGGVFLVDK | | N | N | Y | N | N | | A | 2466 |
| 10 | VPFVQWFVGI | | N | N | N | N | Y | | A | 2467 |
| 8 | VPSALNPI | | N | N | N | N | Y | | A | 2468 |
| 9 | VVFFSQFSR | | N | N | Y | N | N | | A | 2469 |
| 10 | VVGGVFLVDK | | N | N | Y | N | N | | A | 2470 |
| 9 | WLLRGTSFV | IL2.V9 | N | Y | N | N | N | 1 | A | 2471 |
| 10 | YLFTLWKAGI | | N | Y | N | N | N | No | A | 2472 |
| 10 | YLHTLWKAGV | L2.IV10 | N | Y | N | N | N | 1 | A | 2473 |
| 10 | YLLTLWKAGI | | N | Y | N | N | N | No | A | 2474 |
| 9 | YLLTRILTI | | N | Y | N | N | N | | A | 2475 |
| 9 | YLPSALNPV | VL2.AV9 | N | Y | N | N | N | 1 | A | 2476 |
| 10 | YLPSDFFPSV | | N | Y | N | N | N | No | A | 2477 |
| 9 | YMDDVVLGV | M2.AV9 | N | Y | N | N | N | 1 | A | 2478 |
| 9 | YMFDVVLGA | | N | Y | N | N | N | No | A | 2479 |
| 10 | YMFDVVLGAK | | N | N | Y | N | N | | A | 2480 |
| 10 | YNMGLKFRQL | | N | N | N | N | N | | A | 2481 |
| 8 | YPALMPLI | | N | N | N | N | N | | A | 2482 |
| 9 | YPALMPLYI | | N | N | N | N | Y | | A | 2483 |
| 9 | YPFLMPLYA | | N | N | N | N | Y | | A | 2484 |
| 12 | YSFLPSDFFPSV | | N | N | N | N | N | | A | 2485 |

237

TABLE XXII

Discreet substitutions improve the B7 supertype binding capacity and degeneracy of peptide ligands.

| | | | | | | | | | | Binding (IC$_{50}$ nM) | | | | | |
|---|---|---|---|---|---|---|---|---|---|---|---|---|---|---|---|
| Source | 1 | 2 | 3 | 4 | 5 | 6 | 7 | 8 | 9 | B*0701 | B*3501 | B*5101 | B*5301 | B*5401 | x-rxn | SEQ ID NO: |
| HBV ENV 313 | I | P | I | P | S | S | | A | F | 42 | 2.6 | 2.3 | 12 | 2970 | 4 | 2505 |
| | F | P | I | P | S | S | | A | F | 24 | 1.2 | 305 | 1.7 | 105 | 5 | 2506 |
| | I | P | I | P | S | S | | A | I | 31 | 54 | 15 | 24 | 7.7 | 5 | 2507 |
| HBV POL 541 | F | P | H | C | L | A | F | S | Y | — | 14 | 83 | 17 | 503 | 3 | 2508 |
| | F | P | H | C | L | A | F | A | L | 25 | 2.7 | 28 | 5.0 | 24 | 5 | 2509 |
| | F | P | H | C | L | A | F | S | L | 74 | 2.4 | 4.5 | 15 | 7.7 | 5 | 2510 |

TABLE XXII-continued

Discreet substitutions improve the B7 supertype binding capacity and degeneracy of peptide ligands.

| Source | 1 | 2 | 3 | 4 | 5 | 6 | 7 | 8 | 9 | B*0701 | B*3501 | B*5101 | B*5301 | B*5401 | x-rxn | SEQ ID NO: |
|---|---|---|---|---|---|---|---|---|---|---|---|---|---|---|---|---|
|  | F | P | F | C | L | A | F | S | Y | — | 6.5 | 27 | 4.8 | 5.1 | 4 | 2511 |
|  | F | P | H | C | L | A | F | S | I | 675 | 29 | 6.3 | 3.8 | 1.0 | 4 | 2512 |
|  | F | P | H | C | L | A | F | S | A | 3667 | 6.5 | 250 | 137 | 0.6 | 4 | 2513 |
| HCV Core 168 | L | P | G | C | S | F | S | I | F | 28 | 90 | 100 | 114 | 6897 | 4 | 2514 |
|  | F | P | G | C | S | F | S | I | F | 19 | 1.6 | 132 | 3.2 | 67 | 5 | 2515 |
| MAGE2 170 | V | P | I | S | H | L | Y | I | L | 22 | 171 | 96 | 238 | 3175 | 4 | 2516 |
|  | F | P | I | S | H | L | Y | I | L | 16 | 7.3 | 6.4 | 7.0 | 28 | 5 | 2517 |
| MAGE3 196 |  | P | K | A | G | L | L | I | I | 940 | 5039 | 393 | 90 | 248 | 3 | 2518 |
|  | F | P | K | A | G | L | L | I | I | 162 | 1303 | 5.8 | 60 | 150 | 4 | 2519 |
|  |  | P | F | A | G | L | L | I | I | 229 | 1.0 | 0.9 | 2.3 | 0.27 | 5 | 2520 |

TABLE XXIII

Sets of preferred epitopes restricted by class I and class II molecules can be selected for inclusion in an HBV-specific vaccine. Table XXIII lists as a matter of example one such set of epitopes.

| Peptide | Sequence | Protein | restriction | SEQ ID NO: |
|---|---|---|---|---|
| A) Class I restricted epitopes | | | | |
| 924.07 | FLPSDFFPSV | core 18 | A2 | 2521 |
| 777.03 | FLLTRILTI | env 183 | A2 | 2522 |
| 927.15 | ALMPLYACI | pol 642 | A2 | 2523 |
| 1013.01 | WLSLLVPFV | env 335 | A2 | 2524 |
| 1090.14 | YMDDVVLGA | pol 538 | A2/A1 | 2525 |
| 1168.02 | GLSRYVARL | pol 455 | A2 | 2526 |
| 927.11 | FLLSLGIHL | pol 562 | A2 | 2527 |
| 1069.10 | LLPIFFCLWV | env 378 | A2 | 2528 |
| 1069.06 | LLVPFVQWFV | env 338 | A2 | 2529 |
| 1147.16 | HTLWKAGILYK | pol 149 | A3/A1 | 2530 |
| 1083.01 | STLPETTVVRR | core 141 | A3 | 2531 |
| 1069.16 | NVSIPWTHK | pol 47 | A3 | 2532 |
| 1069.20 | LVVDFSQFSR | pol 388 | A3 | 2533 |
| 1090.10 | QAFTFSPTYK | pol 665 | A3 | 2534 |
| 1090.11 | SAICSVVRR | pol 531 | A3 | 2535 |
| 1142.05 | KVGNFTGLY | pol 629 | A3/A1 | 2536 |
| 1147.05 | FPHCLAFSYM | pol 530 | B7 | 2537 |
| 988.05 | LPSDFFPSV | core 19 | B7 | 2538 |
| 1145.04 | IPIPSSWAF | env 313 | B7 | 2539 |
| 1147.02 | HPAAMPHLL | pol 429 | B7 | 2540 |
| 26.0570 | YPALMPLYACI | pol 640 | B7 | 2541 |
| 1147.04 | TPARVTGGVF | pol 354 | B7 | 2542 |
| 1.0519 | DLLDTASALY | core 419 | A1 | 2543 |
| 2.0239 | LSLDVSAAFY | pol 1000 | A1 | 2544 |
| 1039.06 | WMMWYWGPSLY | env 359 | A1 | 2545 |
| 20.0269 | RWMCLRRFII | env 236 | A24 | 2546 |
| 20.0136 | SWLSLLVPF | env 334 | A24 | 2547 |
| 20.0137 | SWWTSLNFL | env 197 | A24 | 2548 |
| 13.0129 | EYLVSFGVWI | core 117 | A24 | 2549 |
| 1090.02 | AYRPPNAPI | core 131 | A24 | 2550 |
| 13.0073 | WFHISCLTF | core 102 | A24 | 2551 |
| 20.0271 | SWPKFAVPNL | pol 392 | A24 | 2552 |
| 1069.23 | KYTSFPWLL | pol 745 | A24 | 2553 |
| 2.0181 | LYSHPIILGF | pol 492 | A24 | 2554 |
| B) Class II restricted epitopes | | | | |
| F107.03 | LQSLTNLLSSNLSWL | pol 412 | DR super-motif | 2555 |
| 1298.06 | KQAFTFSPTYKAFLC | pol 664 |  | 2556 |
| 1280.06 | AGFFLLTRILTIPQS | env 180 |  | 2557 |
| 1280.09 | GTSFVYVPSALNPAD | pol 774 |  | 2558 |
| 6CF-08 | VSFGVWIRTPPAYRPP-NAPI | core 120 |  | 2559 |
| 27.0281 | RHYLHTLWKAGILYK | pol 145 |  | 2560 |
| 1186.15 | LVPFVQWFVGLSPTV | env 339 |  | 2561 |
| 1280.15 | LHLYSHPIILGFRKI | pol 501 |  | 2562 |

TABLE XXIII-continued

Sets of preferred epitopes restricted by class I and class II molecules can be selected for inclusion in an HBV-specific vaccine. Table XXIII lists as a matter of example one such set of epitopes.

| Peptide | Sequence | Protein | restric-tion | SEQ ID NO: |
|---|---|---|---|---|
| F107.04 | PFLLAQFTSAICSVV | pol 523 | | 2563 |
| 1298.04 | KQCFRKLPVNRPIDW | pol 618 | | 2564 |
| 1298.07 | AANWILRGTSFVYVP | pol 767 | | 2565 |
| 857.02 | PHHTALRQAILCWGEL-MTLA | core 50 | | 2566 |
| 1280.14 | LCQVFADATPTGWGL | pol 694 | DR3 motif | 2567 |
| 35.0096 | ESRLVVDFSQFSRGN | pol 385 | | 2568 |
| 35.0093 | VGPLTVNEKRRLKLI | pol 96 | | 2569 |
| 1186.27 | SSNLSWLSLDVSAAF | pol 420 | | 2570 |
| 1186.18 | NLSWLSLDVSAAFYH | pol 442 | | 2571 |

What is claimed is:

1. An isolated peptide consisting of the oligopeptide LWF-HISCLTF (SEQ ID NO:879).

2. A composition comprising the peptide of claim 1 and a carrier.

3. A composition comprising the peptide of claim 1 and a pharmaceutically acceptable carrier.

4. A composition comprising the peptide of claim 1 and a liposome.

5. A composition comprising the peptide of claim 1, wherein the peptide is admixed with at least one other peptide comprising a helper T lymphocyte (HTL) epitope or is joined to at least one other peptide consisting of an HTL epitope.

* * * * *